US011413310B2

(12) United States Patent
Albertson et al.

(10) Patent No.: US 11,413,310 B2
(45) Date of Patent: Aug. 16, 2022

(54) ARTICLES OF MANUFACTURE AND METHODS FOR TREATMENT USING ADOPTIVE CELL THERAPY

(71) Applicant: Juno Therapeutics, Inc., Seattle, WA (US)

(72) Inventors: Tina Albertson, Seattle, WA (US); Brian Christin, Seattle, WA (US); Jacob Randolph Garcia, Seattle, WA (US); Christopher Glen Ramsborg, Seattle, WA (US); Claire L. Sutherland, Seattle, WA (US); Clinton Weber, Seattle, WA (US); Rachel K. Yost, Seattle, WA (US); Mark J. Gilbert, Seattle, WA (US); He Li, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 223 days.

(21) Appl. No.: 16/616,938

(22) PCT Filed: Jun. 1, 2018

(86) PCT No.: PCT/US2018/035755
§ 371 (c)(1),
(2) Date: Nov. 25, 2019

(87) PCT Pub. No.: WO2018/223101
PCT Pub. Date: Dec. 6, 2018

(65) Prior Publication Data
US 2020/0147136 A1    May 14, 2020

Related U.S. Application Data

(60) Provisional application No. 62/614,957, filed on Jan. 8, 2018, provisional application No. 62/596,764, filed on Dec. 8, 2017, provisional application No. 62/593,871, filed on Dec. 1, 2017, provisional application No. 62/580,425, filed on Nov. 1, 2017, provisional application No. 62/549,938, filed on Aug. 24, 2017, provisional application No. 62/527,000, filed on Jun. 29, 2017, provisional application No. 62/521,366, filed on Jun. 16, 2017, provisional application No. 62/515,530, filed on Jun. 5, 2017, provisional application No. 62/514,774, filed on Jun. 2, 2017.

(51) Int. Cl.
*A61K 35/17*    (2015.01)
*A61P 35/00*    (2006.01)
*C07K 14/73*    (2006.01)
*C07K 14/705*   (2006.01)

(52) U.S. Cl.
CPC .............. *A61K 35/17* (2013.01); *A61P 35/00* (2018.01); *C07K 14/70514* (2013.01); *C07K 14/70517* (2013.01)

(58) Field of Classification Search
CPC ..................................................... A61K 35/17
See application file for complete search history.

(56) References Cited

U.S. PATENT DOCUMENTS

| 3,799,934 | A | 3/1974 | Vater |
|-----------|---|--------|-------|
| 4,452,773 | A | 6/1984 | Molday |
| 4,690,915 | A | 9/1987 | Rosenberg |
| 4,795,698 | A | 1/1989 | Owen |
| 5,087,616 | A | 2/1992 | Myers |
| 5,200,084 | A | 4/1993 | Liberti |
| 5,219,740 | A | 6/1993 | Miller |
| 5,424,297 | A | 6/1995 | Rubio |
| 5,504,090 | A | 4/1996 | Neely |
| 5,527,814 | A | 6/1996 | Louvel |
| 5,545,627 | A | 8/1996 | Jacobson |
| 5,565,566 | A | 10/1996 | Olsson |
| 5,591,827 | A | 1/1997 | Brakenhoff |
| 5,635,517 | A | 6/1997 | Muller |
| 5,670,501 | A | 9/1997 | Peck |
| 5,712,291 | A | 1/1998 | D'Amato |
| 5,786,360 | A | 7/1998 | Neely |

(Continued)

FOREIGN PATENT DOCUMENTS

| EP | 0090505 B1 | 8/1990 |
|----|------------|--------|
| EP | 0452342 B1 | 11/1994 |

(Continued)

OTHER PUBLICATIONS

Avdic et al. (American Society for Microbiology Journal of Virology. vol. 90, Issue 8, Apr. 15, 2016; pp. 3819-3827) (Year: 2016).*
Sommermeyer et al. (Leukemia (2016) 30, 492-500; doi: 10.1038/leu.2015.247) (Year: 2016).*
U.S. Appl. No. 17/297,771, filed Nov. 29, 2019, by Albertson et al. (Copy not provided). (Copy not submitted herewith pursuant to the waiver of 37 C.F. R. § 1 98(a)(2)(iii) issued by the Office on Sep. 21, 2004).
U.S. Appl. No. 17/297,831, filed Nov. 29, 2019, by Gillenwater et al. (Copy not provided). (Copy not submitted herewith pursuant to the waiver of 37 C.F. R. § 1.98(a)(2)(iii) issued by the Office on Sep. 21, 2004).

(Continued)

*Primary Examiner* — Scott Long
(74) *Attorney, Agent, or Firm* — Morrison and Foerster LLP

(57) ABSTRACT

Provided are adoptive cell therapy methods involving the administration of doses of cells for treating disease and conditions, including certain B cell malignancies. The cells generally express recombinant receptors such as chimeric antigen receptors (CARs). In some embodiments, the methods are for treating subjects with non-Hodgkin lymphoma (NHL). In some embodiments, the methods are for treating subjects with relapsed or refractory NHL. Also provided are articles of manufacture and prophylactic treatments in connection with adoptive therapy methods.

55 Claims, 55 Drawing Sheets
Specification includes a Sequence Listing.

(56) References Cited

U.S. PATENT DOCUMENTS

| | | |
|---|---|---|
| 5,798,368 A | 8/1998 | Muller |
| 5,861,405 A | 1/1999 | Jacobson |
| 5,981,524 A | 11/1999 | Peck |
| 6,040,177 A | 3/2000 | Riddell |
| 6,066,642 A | 5/2000 | Jacobson |
| 6,111,090 A | 8/2000 | Gorman |
| 6,117,998 A | 9/2000 | Neely |
| 6,207,453 B1 | 3/2001 | Maass |
| 6,232,297 B1 | 5/2001 | Linden |
| 6,281,230 B1 | 8/2001 | Muller |
| 6,313,131 B1 | 11/2001 | Lawyer |
| 6,316,471 B1 | 11/2001 | Muller |
| 6,322,771 B1 | 11/2001 | Linden |
| 6,326,390 B1 | 12/2001 | Leung |
| 6,335,349 B1 | 1/2002 | Muller |
| 6,380,239 B1 | 4/2002 | Muller |
| 6,395,754 B1 | 5/2002 | Muller |
| 6,403,613 B1 | 6/2002 | Man |
| 6,410,319 B1 | 6/2002 | Raubitschek |
| 6,451,995 B1 | 9/2002 | Cheung |
| 6,458,810 B1 | 10/2002 | Muller |
| 6,476,052 B1 | 11/2002 | Muller |
| 7,025,962 B1 | 4/2006 | Gorman |
| 7,070,995 B2 | 7/2006 | Jensen |
| 7,091,353 B2 | 8/2006 | Robarge |
| 7,132,255 B2 | 11/2006 | Blumberg |
| 7,141,575 B2 | 11/2006 | Gillespie |
| 7,244,759 B2 | 7/2007 | Muller |
| 7,265,209 B2 | 9/2007 | Jensen |
| 7,320,991 B2 | 1/2008 | Figg |
| 7,354,762 B2 | 4/2008 | Jensen |
| 7,405,219 B2 | 7/2008 | Gillespie |
| 7,446,179 B2 | 11/2008 | Jensen |
| 7,446,190 B2 | 11/2008 | Sadelain |
| 7,446,191 B2 | 11/2008 | Jensen |
| 7,514,444 B2 | 4/2009 | Honigberg |
| 7,618,632 B2 | 11/2009 | Collins |
| 7,812,135 B2 | 10/2010 | Smith |
| 7,893,075 B2 | 2/2011 | Zhang |
| 7,943,743 B2 | 5/2011 | Korman |
| 8,008,309 B2 | 8/2011 | Honigberg |
| 8,008,449 B2 | 8/2011 | Korman |
| 8,080,554 B2 | 12/2011 | Sitkovsky |
| 8,124,084 B2 | 2/2012 | Lefrancois |
| 8,247,425 B2 | 8/2012 | Bazhina |
| 8,324,353 B2 | 12/2012 | Jensen |
| 8,339,645 B2 | 12/2012 | Nakawaki |
| 8,354,509 B2 | 1/2013 | Carven |
| 8,388,967 B2 | 3/2013 | Smith |
| 8,389,282 B2 | 3/2013 | Sadelain |
| 8,399,514 B2 | 3/2013 | Lukashev |
| 8,399,645 B2 | 3/2013 | Campana |
| 8,476,284 B2 | 7/2013 | Honigberg |
| 8,497,118 B2 | 7/2013 | Jensen |
| 8,497,277 B2 | 7/2013 | Honigberg |
| 8,562,991 B2 | 10/2013 | Igawa |
| 8,586,023 B2 | 11/2013 | Shiku |
| 8,591,886 B2 | 11/2013 | Ponath |
| 8,609,089 B2 | 12/2013 | Langermann |
| 8,697,711 B2 | 4/2014 | Honigberg |
| 8,703,780 B2 | 4/2014 | Honigberg |
| 8,716,301 B2 | 5/2014 | Sitkovsky |
| 8,716,315 B2 | 5/2014 | Figg |
| 8,735,403 B2 | 5/2014 | Honigberg |
| 8,754,090 B2 | 6/2014 | Buggy |
| 8,754,091 B2 | 6/2014 | Honigberg |
| 8,802,374 B2 | 8/2014 | Jensen |
| 8,822,647 B2 | 9/2014 | Jensen |
| 8,883,500 B2 | 11/2014 | Sitkovsky |
| 8,911,993 B2 | 12/2014 | June |
| 8,957,079 B2 | 2/2015 | Honigberg |
| 8,987,279 B2 | 3/2015 | Bamford |
| 8,999,999 B2 | 4/2015 | Buggy |
| 9,125,889 B2 | 9/2015 | Buggy |
| 9,181,257 B2 | 11/2015 | Honigberg |
| 9,296,753 B2 | 3/2016 | Smyth |
| 2002/0045643 A1 | 4/2002 | Muller |
| 2002/0131960 A1 | 9/2002 | Sadelain |
| 2003/0045552 A1 | 3/2003 | Robarge |
| 2004/0047858 A1 | 3/2004 | Blumberg |
| 2007/0116690 A1 | 5/2007 | Yang |
| 2009/0082299 A1 | 3/2009 | Felber |
| 2010/0028330 A1 | 2/2010 | Collins |
| 2010/0190755 A1 | 7/2010 | Abato |
| 2010/0247521 A1 | 9/2010 | Jones |
| 2011/0003380 A1 | 1/2011 | Miltenyi |
| 2011/0044998 A1 | 2/2011 | Bedian |
| 2011/0081311 A1 | 4/2011 | Pavlakis |
| 2012/0039906 A1 | 2/2012 | Olive |
| 2012/0114649 A1 | 5/2012 | Langermann |
| 2012/0141413 A1 | 6/2012 | Pavlakis |
| 2012/0177598 A1 | 7/2012 | Lefrancois |
| 2013/0149337 A1 | 6/2013 | Cooper |
| 2013/0156774 A1 | 6/2013 | Kuchroo |
| 2013/0287748 A1 | 10/2013 | June |
| 2014/0056922 A1 | 2/2014 | Sitkovsky |
| 2014/0065141 A1 | 3/2014 | Daniel |
| 2014/0271618 A1 | 9/2014 | Markel |
| 2014/0271635 A1 | 9/2014 | Brogdon |
| 2014/0377240 A1 | 12/2014 | Sitkovsky |
| 2015/0119267 A1 | 4/2015 | Joyce |
| 2015/0210769 A1 | 7/2015 | Freeman |
| 2015/0218274 A1 | 8/2015 | Sabatos-peyton |
| 2015/0259420 A1 | 9/2015 | Triebel |
| 2015/0283178 A1 | 10/2015 | June |
| 2016/0032248 A1 | 2/2016 | Short |
| 2016/0122782 A1* | 5/2016 | Crisman ............... A61K 35/17 435/456 |
| 2016/0206656 A1 | 7/2016 | Gilbert |
| 2016/0313300 A1 | 10/2016 | Trotter |
| 2016/0362472 A1 | 12/2016 | Bitter |
| 2017/0051035 A1 | 2/2017 | Payne |
| 2021/0128616 A1 | 5/2021 | Dave et al. |
| 2021/0198372 A1 | 7/2021 | Albertson et al. |

FOREIGN PATENT DOCUMENTS

| | | |
|---|---|---|
| EP | 1866339 B1 | 5/2013 |
| EP | 1947183 B1 | 7/2013 |
| EP | 2537416 B1 | 11/2014 |
| EP | 2277543 | 12/2015 |
| WO | WO9208796 A1 | 5/1992 |
| WO | WO9428143 A1 | 12/1994 |
| WO | WO9613593 A2 | 5/1996 |
| WO | WO9618105 A1 | 6/1996 |
| WO | WO9803502 A1 | 1/1998 |
| WO | WO9854170 A1 | 12/1998 |
| WO | WO9918129 A1 | 4/1999 |
| WO | WO9920758 A1 | 4/1999 |
| WO | WO9940196 A1 | 8/1999 |
| WO | WO9952552 A1 | 10/1999 |
| WO | WO9960120 A2 | 11/1999 |
| WO | WO0014257 A1 | 3/2000 |
| WO | WO 2020/113194 | 6/2000 |
| WO | WO0103720 A2 | 1/2001 |
| WO | WO02055083 A1 | 7/2002 |
| WO | WO02059106 A1 | 8/2002 |
| WO | WO02068414 A2 | 9/2002 |
| WO | WO2003020763 A2 | 3/2003 |
| WO | WO2004033685 A1 | 4/2004 |
| WO | WO2005007190 A1 | 1/2005 |
| WO | WO2005055808 A2 | 6/2005 |
| WO | WO2005115451 A2 | 12/2005 |
| WO | WO2006000830 A2 | 1/2006 |
| WO | WO2006009755 A2 | 1/2006 |
| WO | WO2006083289 A2 | 8/2006 |
| WO | WO2006121168 A1 | 11/2006 |
| WO | WO2007005874 A2 | 1/2007 |
| WO | WO2007133822 A1 | 11/2007 |
| WO | WO2008154252 A1 | 12/2008 |
| WO | WO2008147482 A2 | 4/2009 |
| WO | WO2009072003 A2 | 6/2009 |
| WO | WO2009099553 A2 | 8/2009 |
| WO | WO2009101611 A1 | 8/2009 |

(56) References Cited

FOREIGN PATENT DOCUMENTS

| | | |
|---|---|---|
| WO | WO2009114335 A2 | 9/2009 |
| WO | WO2010003118 A1 | 1/2010 |
| WO | WO2010019570 A2 | 2/2010 |
| WO | WO2010027827 A2 | 3/2010 |
| WO | WO2010033140 A2 | 3/2010 |
| WO | WO2010077634 A1 | 7/2010 |
| WO | WO2010125571 A1 | 11/2010 |
| WO | WO2011028683 A1 | 3/2011 |
| WO | WO2011044186 A1 | 4/2011 |
| WO | WO2011051726 A2 | 5/2011 |
| WO | WO2011066342 A2 | 6/2011 |
| WO | WO2011090754 A1 | 7/2011 |
| WO | WO2012129514 A1 | 9/2012 |
| WO | WO2013006490 A2 | 1/2013 |
| WO | WO2013039954 A1 | 3/2013 |
| WO | WO2013054331 A1 | 4/2013 |
| WO | WO2013071154 A1 | 5/2013 |
| WO | WO2013082366 A1 | 6/2013 |
| WO | WO2013123061 A1 | 8/2013 |
| WO | WO2013126726 A1 | 8/2013 |
| WO | WO2013166321 A1 | 11/2013 |
| WO | WO2014001802 A1 | 1/2014 |
| WO | WO2014022332 A1 | 2/2014 |
| WO | WO2014031687 A1 | 2/2014 |
| WO | WO2014055668 A1 | 4/2014 |
| WO | WO2014059251 A1 | 4/2014 |
| WO | WO2014190273 A9 | 1/2015 |
| WO | WO2015079417 A1 | 6/2015 |
| WO | WO2015095895 A1 | 6/2015 |
| WO | WO 2015/157384 | 10/2015 |
| WO | WO 2016/019300 | 2/2016 |
| WO | WO 2016/033570 | 3/2016 |
| WO | WO2016172606 A1 | 10/2016 |
| WO | WO2016191756 A1 | 12/2016 |
| WO | WO 2019/109053 | 6/2019 |
| WO | WO 2019/113559 | 6/2019 |
| WO | WO 2020/113188 | 6/2020 |

OTHER PUBLICATIONS

Abramson et al., "Lisocabtagene maraleucel for patients with relapsed or refractory Targe B-cell lymphomas (Transcend NHL 001): a multicentre seamless design study," Lancet (2020) 396(10254):839-52.

SEER "Surveillance, Epidemiology, and End Results (SEER) Cancer Statistics Factsheets: Non-Hodgkin Lymphoma," (2017); retrieved May 2017, from https://seer.cancer.gov/statfacts/html/nhl.html.

Siddiqi et al., "Long-Term Follow-up of Patients with Relapsed/Refractory Chronic Lymphocytic Leukemia/Small Lymphocytic Lymphoma Treated with Lisocabtagene Maraleucel in the Phase 1 Monotherapy Cohort of Transcend CLL 004, Including High-Risk and Ibrutinib-Treated Patients," ASH Annual Meeting and Exposition, Dec. 5-8, 2020; Abstract 546.

US 8,252,592, 01/1970, Sadelain, Michel (withdrawn).
US 8,450,329, 09/2009, Ren, Pingda (withdrawn).

"JCAR015 in ALL: A Root-Cause Investigation," Cancer Discov. (2018) 8(1):4-5.

"Juno's Investigational CAR T Cell Product Candidates JCAR014 and JCAR018 Demonstrate Encouraging Clinical Responses in Patients with B-Cell Cancers" http://www.businesswire.com/news/home/20151206005065/en/Juno%E2%80%99s-Investigational-CAR-Cell-Product-Candidates-JCAR014.

Abramson et al., "Anti-CD19 CAR T Cells in CNS Diffuse Large-B-Cell Lymphoma," N Engl J Med. Aug. 24, 2017;377 (8):783-784.

Abramson et al., "CR rates in relapsed/refractory (R/R) aggressive B-NHL treated with the CD19-directed CAR T-cell product JCAR017 (Transcend NHL 001)," J. Clin. Oncol. (2017) 35 (15): 7513 Abstract.

Abramson et al., "High Durable CR Rates in R/R Aggressive B-NHL Treated with JCAR017 (Transcend NHL 001): Defined Composition CD19-Directed CAR T Cell Product Allows for Dose Finding and Definition of Pivotal Cohort," Presented Dec. 7, 2017 at ASH 2017.

Abramson et al., "High Durable CR Rates in Relapsed/Refractory (R/R) Aggressive BNHL treated with the CD-19Directed CAR T Cell Product JCAR017 (Transcend NHL 001): Defined Composition Allows for Dose-Finding and Definition of Pivotal Cohort," Blood (2017) 130:581.

Abramson et al., "Transcend NHL 001: Immunotherapy with the CD19-directed CAR T-cell Product JCAR017 Results in High Complete Response Rates in Relapsed or Refractory B-Cell Non-Hodgkin Lymphoma," Blood (2016) 128(22): 4192.

Abramson et al., "Transcend NHL 001: Immunotherapy with the CD19-directed CAR T-cell Product JCAR017 Results in High Complete Response Rates in Relapsed or Refractory B-Cell Non-Hodgkin Lymphoma," Poster 4192 presented Dec. 3, 2016 at ASH 2016.

Abramson et al., "Updated safety and long term clinical outcomes in Transcend NHL 001, pivotal trial of isocabtagene maraleucel (JCAR017) in R/R aggressive NHL," J Clin Oncol (2018) 36(15): 7505.

Actemra (tocilizumab) prescribing information. South San Francisco, CA: Genentech, Inc. 2017.

Actemra (tocilizumab) Summary of Product Characteristics. (2013). Retrieved Feb. 15, 2018, from http://www.ema.europa.eu/docs/en_GB/document_library/EPAR_-_Product_Information/human/000955/WC500054890.pdf.

Allard et al., "Targeting CD73 Enhances the Antitumor Activity of Anti-PD-1 and Anti-CTLA-4 mAbs," Clin Cancer Res (2013) 19(20):5626-5635.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Annaloro et al., "Severe fludarabine neurotoxicity after reduced intensity conditioning regimen to allogeneic hematopoietic stem cell transplantation: a case report," Clin. Case Rep. (2015) 3(7): 650-55.

Aukema et al., "Double-hit B-cell Lymphomas," Blood (2011) 117(8), 2319-2331.

Barret et al., "Interleukin 6 Is Not Made by Chimeric Antigen Receptor T Cells and Does Not Impact Their Function," Abstract 654. Presented at ASH 58th Annual Meeting San Diego, CA (Dec. 3-6, 2016).

Barrett et al., "Chimeric antigen receptor therapy for cancer," Annu Rev Med. (2014);65:333-47.

Basu et al., "Use of a novel hemoadsorption device for cytokine removal as adjuvant therapy in a patient with septic shock with multi-organ dysfunction: A case study," Indian J Crit Care Med (2014) 18(12):822-824.

Beavis et al., "Blockade of A2A receptors potently suppresses the metastasis of CD73+ tumors," PNAS (2013) 110 (36):14711-14716.

Berger et al., "Phase I safety and pharmacokinetic study of CT-011, a humanized antibody interacting with PD-1, in patients with advanced hematologic malignancies," Clin Cancer Res (2008) 14(10): 3044-3051.

Bertilaccio et al., "Low-Dose Lenalidomide Improves CAR-Based Immunotherapy in CLL by Reverting T-Cell Defects In Vivo," Blood (2013) 122:4171.

Bhojwani et al., "Methotrexate-induced neurotoxicity and leukoencephalopathy in childhood acute lymphoblastic leukemia," J. Clin. Oncol (2014) 32(9):949-59.

Bishop et al., "Long-term outcomes of adults with acute lymphoblastic leukemia after autologous or unrelated donor bone marrow transplantation: a comparative analysis by the National Marrow Donor Program and Center for International Blood and Marrow Transplant Research," Bone Marrow Transplant (2008) 41(7):635-642.

Blank et al., "Contribution of the PD-L1/PD-1 Pathway to T-cell Exhaustion: An Update on Implications for Chronic Infections and Tumor Evasion," Cancer Immunol Immunother (2007) 56(5): 739-745.

Blincyto (blinatumomab) prescribing information. Thousand Oaks, CA: Amgen Inc. 2014.

(56) References Cited

OTHER PUBLICATIONS

Boris-Lawrie et al., "Recent advances in retrovirus vector technology," Cur. Opin. Genet. Develop. (1993) 3:102-109.
Brahmer et al., "Safety and Activity of anti-PD-L1 Antibody in Patients With Advanced Cancer," N Engl J Med (2012) 366(26): 2455-2465.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brentjens et al., "Safety and persistence of adoptively transferred autologous CD19-targeted T cells in patients with relapsed or chemotherapy refractory B-cell leukemias," Blood (2011) 118(18):4817-4828.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Butovsky et al., "Targeting miR-155 restores abnormal microglia and attenuates disease in SOD1 mice," Ann Neurol (2015) 77(1):75-99.
Carceller et al., "Response Assessment in Paediatric Phase I Trials According to RECIST Guidelines: Survival Outcomes, Patterns of Progression and Relevance of Changes in Tumour Measurements," Pediatr Blood Cancer. (2016) 63(8):1400-1406.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Carroll et al., "Targeting the molecular basis for tumour hypoxia," Expert Rev Mol Med (2005) 7(6):1-16.
Cavaletti et al., "Chemotherapy-induced peripheral neurotoxicity," Nature Reviews Neurology (2010) 6, 657-666.
Cavalieri et al., "Human T lymphocytes transduced by lentiviral vectors in the absence of TCR activation maintain an intact immune competence," Blood (2003) 102(2): 497-505.
Cheadle et al., "Chimeric antigen receptors for T-cell based therapy," Methods Mol Biol. (2012);907:645-66.
Chervin et al., "Engineering higher affinity T cell receptors using a T cell display system," J Immunol Methods, (2008)339(2):175-84.
Cheson et al., "Neurotoxicity of purine analogs: a review," J. Clin.Oncol. (1994) 12(10): 2216-28.
Cheson et al., "Recommendations for initial evaluation, staging, and response assessment of Hodgkin and non-Hodgkin lymphoma: the Lugano classification," J Clin Oncol (2014) 20(27):3059-3068.
Cheson, "Staging and response assessment in lymphomas: the new Lugano classification," Chin Clin Oncol (2015) 4(1):5.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Chong et al., "Chimeric Antigen Receptor Modified T Cells Directed Against CD19 (CTL019) in Patients with Poor Prognosis, Relapsed or Refractory CD 19+ Follicular Lymphoma: Prolonged Remissions Relative to Antecedent Therapy," Blood (2016) 128(22):1100.
Chothia et al., "The outline structure of the T-cell alpha beta receptor," EMBO J. (1988) 7(12):3745-3755.
Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.
Clinical Trial Study Record No. NCT02315612. Updated Nov. 10, 2015. Accessed Feb. 8, 2016.
Collins et al., "Chemical approaches to targeted protein degradation through modulation of the ubiquitin-proteasome pathway," Biochem J. (2017) 474(7): 1127-1147.

Conway et al., "Inhibition of colony-stimulating-factor-1 signaling in vivo with the orally bioavailable cFMS kinase inhibitor GW2580," Proc Natl Acad Sci U.S.A (2005) 102(44):16078-16083.
Cooper et al., "T-cell clones can be rendered specific for CD19: toward the selective augmentation of the graft-versus-B-lineage leukemia effect," Blood (2003) 101:1637-1644.
Corazzelli et al., "Long-term results of gemcitabine plus oxaliplatin with and without rituximab as salvage treatment for transplant-ineligible patients with refractory/relapsing B-cell lymphoma," Cancer Chemother Pharmacol (2009) 64 (5): 907-16.
Couzin et al., "Gene therapy. As Gelsinger case ends, gene therapy suffers another blow," Science (2005) 307 (5712):1028.
Cronstein et al., "Adenosine modulates the generation of superoxide anion by stimulated human neutrophils via interaction with a specific cell surface receptor," Ann N Y Acad Sci (1985) 451:291-301.
Cronstein et al., "Engagement of adenosine receptors inhibits hydrogen peroxide (H2O2-) release by activated human neutrophils," Clin Immunol Immunopathol (1987) 42(1):76-85.
Crump et al., "Gemcitabine, dexamethasone, and cisplatin in patients with recurrent or refractory aggressive histology B-cell non-Hodgkin lymphoma: a Phase II study by the National Cancer Institute of Canada Clinical Trials Group (NCIC-CTG)," Cancer (2004) 101(8): 1835-1842.
Crump et al., "Outcomes in Refractory Diffuse Large B-cell Lymphoma: Results From the International SCHOLAR-1 Study," Blood (2017) 130 16): 1800-1808.
Culpin et al., "Prognostic significance of immunohistochemistrybased markers and algorithms in immunochemotherapy-treated diffuse large B cell lymphoma patients," Histopathology (2013) 63(6): 788-801.
Cunningham et al., "Rituximab plus cyclophosphamide, doxorubicin, vincristine, and prednisolone in patients with newly diagnosed diffuse large B-cell non-Hodgkin lymphoma: a phase 3 comparison of dose intensification with 14-day versus 21-day cycles," Lancet (2013) 381(9880): 1817-1826.
Dagher et al., "Colony-stimulating factor 1 receptor inhibition prevents microglial plaque association and improves cognition in 3xTg-AD mice," J Neuroinflammation (2015) 12 Article No. 139.
Dang et al., "Randomized, phase 3 trial of inotuzumab ozogamicin plus rituximab versus chemotherapy plus rituximab for relapsed/refractory aggressive B-cell non-Hodgkin lymphoma," Br J Haematol (2018) 182(4); 583-586.
Davila et al., "CD19 CAR-targeted T cells induce long-term remission and B Cell Aplasia in an immunocompetent mouse model of B cell acute lymphoblastic leukemia," PLoS ONE (2013) 8(4):e61338.
Davila et al., "Efficacy and toxicity management of 19-28z CAR T cell therapy in B cell acute lymphoblastic leukemia," Sci Transl Med (2014) 6:224ra25.
Davila et al., "How do CARs work?: Early insights from recent clinical studies targeting CD19," Oncoimmunology (2012) 1(9):1577-1583.
De Felipe, "Skipping the co-expression problem: the new 2A "CHYSEL" technology," Genet Vaccines Ther (2004) Sep. 13;2(1):13.
De Felipe, "Targeting of proteins derived from self-processing polyproteins containing multiple signal sequences," Traffic (2004) 5(8):616-626.
Dobber et al., "The in vivo effects of neutralizing antibodies against IFN-gamma, IL-4, or IL-10 on the humoral immune response in young and aged mice," Cell Immunol (1995)160(2):185-192.
Donahue et al., "Helper virus induced T cell lymphoma in nonhuman primates after retroviral mediated gene transfer," J Exp Med (1992) 176(4): 1125-1135.
Dutcher et al., "High dose interleukin-2 (Aldesleukin)—expert consensus on best management practices—2014," Journal for ImmunoTherapy of Cancer (2014) 2:26.
Eisenhauer, E.A. et al. (2009) "New response evaluation criteria in solid tumors: Revised RECIST guideline (version 1.1)." Eur. J. Cancer 45: 228-247.
El Gnaoui et al., "Rituximab, gemcitabine and oxaliplatin: an effective salvage regimen for patients with relapsed or refractory B-cell lymphoma not candidates for high-dose therapy," Ann Oncol (2007) 18(8): 1363-1868.

(56) References Cited

OTHER PUBLICATIONS

Fecteau et al., "Lenalidomide inhibits the proliferation of CLL cells via a cereblon/p21WAF1/Cip1-dependent mechanism independent of functional p53," Blood (2014) 124:1637-1644.

Federal Drug Administration, "Supplemental Guidance on Testing for Replication Competent Retrovirus in Retroviral Vector Based Gene Therapy Products and During Follow-up of Patients in Clinical Trials Using Retroviral Vectors," (2000).

Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.

Finger et al., "The Human PD-1 Gene: Complete cDNA, Genomic Organization, and Developmentally Regulated Expression in B Cell Progenitors," Gene (1997) 197(1-2): 177-187.

Fleischmann et al., "Safety of extended treatment with anakinra in patients with rheumatoid arthritis," Ann Rheum Dis (2006) 65(8):1006-1012.

Fludarabine Phosphate for Injection prescribing information. Schaumburg, IL: SAGENT Pharmaceuticals. 2014.

Foon et al., "Immunologic Classification of Leukemia and Lymphoma," Blood (1986) 68(1): 1-31.

Fred Hutchinson Cancer Research Center: "Laboratory Treated T Cells in Treating Patients With Relapsed or Refratory Chronic Lymphocytic Leukemia, Non-Hodgkin Lymphoma, or Acute Lymphoblastic Leukemia", ClinicalTrials.gov Identifier: NCT01865617, Retrieved from the Internet: URL:http://clinicaltrials gov/show/NCT01865617 [retrieved on Aug. 26, 2014].

Frey et al., "Cytokine release syndrome with novel therapeutics for acute lymphoblastic leukemia," Hematology Am Soc Hematol Educ Program (2016) 2016(1): 567-572.

Frey, "Optimizing Chimeric Antigen Receptor (CAR) T Cell Therapy for Adult Patients with Relapsed or Refractory Acute Lymphoblastic Leukemia," J. Clin. Oncol. (2016) 34(15 supp):7002.

Friedberg, "Double-hit diffuse large B-cell lymphoma," J Clin Oncol (2012) 30(28):3439-3443.

Fu et al., "Addition of rituximab to standard chemotherapy improves the survival of both the germinal center B-cell-like and non-germinal center b-cell-like subtypes of diffuse large b-cell lymphoma," J Clin Oncol (2008) 26(28): 4587-4594.

Gardner et al. "CD19 CAR-T Cell Products of Defined CD4:CD8 Composition and Transgene Expression Show Prolonged Persistence and Durable MRD-Negative Remission in Pediatric and Young Adult B-Cell ALL" Presented at ASH. 2016 Blood (2016) 128:219.

Gardner et al., "CD19 CAR-T Cell Products of Defined CD4:CD8 Composition and Transgene Expression Show Prolonged Persistence and Durable MRD-Negative Remission in Pediatric and Young Adult B-Cell ALL," Presented at ASH, San Diego, CA on Dec. 3, 2016. Presentation. 15 pages.

Gardner et al., "Intent to treat leukemia remission by CD19CAR T cells of defined formulation and dose in children and young adults," Blood (2017) 129(25):3322-3331.

Garfall et al., "Posterior Reversible Encephalopathy Syndrome (PRES) after Infusion of Anti-Bcma CAR T cells (CART-BCMA) for Multiple Myeloma: Successful Treatment with Cyclophosphamide," Blood (2016) Dec.; 128(22): 5702.

Gauthier et al., "Factors associated with duration of response after CD19-specific CAR-T cell therapy for refractory/relapsed B-cell non-Hodgkin lymphoma," J Clin Oncol (2018) 36(15 suppl.): 7567.

Gildener-Leapman et al., "Promising systemic immunotherapies in head and neck squamous cell carcinoma," Oral Oncol (2013) 49(12):1089-1096.

Godin et al., "Microfluidics and photonics for Bio-System-on-a-Chip: a review of advancements in technology towards a microfluidic flow cytometry chip," J Biophoton. (2008) 1(5):355-376.

Gokbuget et al., "Adult patients with acute lymphoblastic leukemia and molecular failure display a poor prognosis and are candidates for stem cell transplantation and targeted therapies," Blood (2012) 120(9):1868-1876.

Gokbuget et al., "Blinatumomab vs historical standard therapy of adult relapsed/refractory acute lymphoblastic leukemia," Blood Cancer J (2016) 6(9):e473.

Gong et al., "An Antagonist of Monocyte Chemoattractant Protein 1 (MCP-1) Inhibits Arthritis in the MRL-Ipr Mouse Model," J Exp Med (1997) 186(1):131-137.

Gopal et al.,"Efficacy and safety of gemcitabine, carboplatin, dexamethasone, and rituximab in patients with relapsed/refractory lymphoma: a prospective multi-center phase II study by the Puget Sound Oncology Consortium," Leuk Lymphoma (2010) 51(8): 1523-1529.

Grupp et al., "Analysis of a Global Registration Trial of the Efficacy and Safety of CTL019 in Pediatric and Young Adults with Relapsed/Refractory Acute Lymphoblastic Leukemia (ALL)," Blood (2016) 128(22) :221.

Grupp et al., "Chimeric antigen receptor-modified T cells for acute lymphoid leukemia," N. Engl. J. Med. (2013) 368:1509-1518.

Gust et al., "Endothelial Activation and Blood-Brain Barrier Disruption in Neurotoxicity after Adoptive Immunotherapy with CD19 CAR-T Cells," Cancer Discovery (2017) 7(12): 1404-1419.

Hacein-Bey-Abina et al., "LMO2-associated clonal T cell proliferation in two patients after gene therpay for SCID-X1," Science (2003) 302(5644); 415-419.

Haegel et al., "TG3003, an immunomodulatory anti-CD115 mAb targeting m2-macrophage polarization in the tumor microenvironment," Cancer Res AACR (2015) Abstract 288.

Hallek, M. et al.( Jun. 15, 2008). "Guidelines for the Diagnosis and Treatment of Chronic Lymphocytic Leukemia: A Report From the International Workshop on Chronic Lymphocytic Leukemia Updating the National Cancer Institute-Working Group 1996 Guidelines," Blood 111:(12):5446-5456 and Errata, Blood, (Dec. 15, 2008). 112(13) 5259.

Hannum et al., "Interleukin-1 receptor antagonist activity of a human interleukin-1 inhibitor," Nature (1990) 343:336-340.

Hausler et al., "Anti-CD39 and anti-CD73 antibodies A1 and 7G2 improve targeted therapy in ovarian cancer by blocking adenosine-dependent immune evasion," Am J transl Res (2014) 6(2):129-139.

Hay et al., "Chimeric antigen receptor (CAR) T cells: Lessons learned from targeting of CD19 in B-cell malignancies," Drugs (2017) 77(3): 237-245.

Hay et al., "Factors impacting disease-free survival in adult B cell B-ALL patients achieving MRD-negative CR after CD19 CAR-T cells," J Clin Oncol (2018) 36(15 suppl.):7005.

Hay et al., "Kinetics and Biomarkers of Severe Cytokine Release Syndrome After CD19 Chimeric Antigen Receptor-Modified T-cell Therapy," Blood (2017) 130(21): 2295-2306.

Heipel et al., "Pharmacokinetic, Pharmacodynamic and Blood Analytes Associated with Clinical response and Safety in Relapsed/Refractory Aggressive B-NHL Patients Treated with JCAR017," Blood (2017) 130 (Suppl 1): 2835.

Heipel et al., "Pharmacokinetic, Pharmacodynamic and Blood Analytes Associated with Clinical response and Safety in Relapsed/Refractory Aggressive B-NHL Patients Treated with JCAR017," Poster 2835 presented Dec. 9, 2017 at ASH 2017.

Henig et al., "Hematopoietic stem cell transplantation-50 years of evolution and future perspectives," Rambam Maimonides Med J (2014) 5(4):e0028.

Hermans et al., "The VITAL assay: a versatile fluorometric technique for assessing CTL- and NKT-mediated cytotoxicity against multiple targets in vitro and in vivo," J. Immunological Methods (2004) 285(1): 25-40.

Hershfield, "PEG-ADA: an alternative to haploidentical bone marrow transplantation and an adjunct to gene therapy for adenosine deaminase deficiency," Hum Mutat (1995) 5(2):107-112.

Hoing et al., "Discovery of inhibitors of microglial neurotoxicity acting through multiple mechanisms using a stem-cell-based phenotypic assay," Cell Stem Cell (2012) 11(5):620-632.

Holler et al., "In vitro evolution of a T cell receptor with high affinity for peptide/MHC," Proc Natl Acad Sci USA, (2000) 97(10):5387-92.

Hollyman et al., "Manufacturing Validation of Biologically Functional T Cells Targeted to CD19 Antigen for Autologous Adoptive Cell Therapy." Journal of Immunotherapy. 2009. 32(2):169-180.

(56) References Cited

OTHER PUBLICATIONS

Hu et al., "Predominant cerebral cytokine release syndrome in CD19-directed chimeric antigen receptor-modified T cell therapy," J Hematol Oncol (2016) 9(1): 70.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res. (2013) Jun. 15;19(12):3153-3164.
Hunter et al., "Neutralizing anti-IL-10 antibody blocks the protective effect of tapeworm infection in a murine model of chemically induced colitis," J Immunol (2005) 174(11):7368-7375.
Jain et al., "Impact of BCR-ABL transcript type on outcome in patients with chronic-phase CML treated with tyrosine kinase inhibitors," Blood (2016) 127(10): 1269-1275.
Juno Therapeutics,"Juno Therapeutics to Highlight New Advances in CD19- and BCMA-Targeted CAR T Therapy at ASH," News release published Nov. 1, 2017.
Janeway et al., Immunobiology: The Immune System in Health and Disease, 3rd ED., Current Biology Publications (1997), p. 4:33.
Jin et al., "CD73 on tumor cells impairs antitumor T-cell responses: a novel mechanism of tumor-induced immune suppression," Cancer Res (2010) 70(6):2245-2255.
Johnson et al., "Imaging for Staging and Response Assessment in Lymphoma," Radiology (2015) 276(2):323-338.
Johnston, "Biolistic transformation: microbes to mice," Nature (1990) 346:776-777.
Jores et al., "Resolution of hypervariable regions in T-cell receptor beta chains by a modified Wu-Kabat index of amino acid diversity," Proc Natl Acad Sci U S A. (1990) 87(23):9138-9142.
Juno Corporate Presentation. Retrieved on http://ir.junotherapeutics.com. Retrieved on Jan. 2018.
Juno Corporate Presentation. Retrieved on http://ir.junotherapeutics.com. Retrieved on Sep. 2017.
Kantarjian et al., "Blinatumomab versus Chemotherapy for Advanced Acute Lymphoblastic Leukemia," N Engl J Med (2017) 376(9): 836-847.
Kantarjian et al., "Inotuzumab Ozogamicin versus StandardTherapy for Acute Lymphoblastic Leukemia," N Engl J Med (2016) 375(8): 740-753.
Kawamura et al., "Effects of angiopoietin-1 on hemorrhagic transformation and cerebral edema after tissue plasminogen activator treatment for ischemic stroke in rats," PLoS One (2014) 9(6): e98639.
Kawano et al., "Cryopreservation of mobilized blood stem cells at a higher cell concentration without the use of a programmed freezer," Ann. Hematol. (2004) 83(1): 50-54.
Kivisakk et al., "Natalizumab treatment is associated with peripheral sequestration of proinflammatory T cells," Neurology (2009) 72(22):1922-1930.
Klebanoff et al., "Sorting through subsets: which T-cell populations mediate highly effective adoptive immunotherapy?," J Immunother. (2012) 35(9): 651-660.
Kochenderfer et al., "Anti-CD19 CAR T Cells Administered after Low-Dose Chemotherapy Can Induce Remissions of Chemotherapy-Refractory Diffuse Large B-Cell Lymphoma," Blood (2014) 124(21): 550.
Kochenderfer et al., "B cell depletion and remissions of malignancy a long with cytokine associated toxicity in a clinical trial of anti-CD 19 chimeric-antigen receptor-transduced T cells," Blood (2012) 119(12):2709-2720.
Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol (2015) 33(6):540-549.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nat Rev Clin Oncol (2013) 10(5):267-276.
Kochenderfer, "Anti-CD19 chimeric antigen receptor T cells preceded by low-dose chemotherapy to induce remissions of advanced lymphoma," J. Clin. Oncol. (2017) 34:18 suppl.
Koste et al., "T-cell receptor transfer into human T cells with ecotropic retroviral vectors," Gene Therapy (2014) 21: 533-538.
Kotb et al., "Bacterial pyrogenic exotoxins as superantigens," Clinical Microbiology Reviews (1995) 8:411-426.
Kranick et al., "Aphasia as a Complication of CD19-Targeted Chimeric Antigen Receptor Immunotherapy," Annual Meeting of the American Academy of Neurology 2014; Philadelphia, PA.
Kuramitsu et al., "Lenalidomide enhances the function of chimeric antigen receptor T cells against the epidermal growth factor receptor variant III by enhancing immune synapses," Cancer Gene Therapy (2015) 22(10):487-495.
Kurucz et al., "A bacterially expressed single-chain Fv construct from the 2B4 T-cell receptor," PNAS (1993) 90 (9):3830-3834.
Lee et al., "Current concepts in the diagnosis and management of cytokine release syndrome," Blood. (2014) 124 (2):188-95.
Lee et al., "Long-Term Outcomes Following CD19 CAR T Cell Therapy for B-ALL Are Superior in Patients Receiving a Fludarabine/Cyclophosphamide Preparative Regimen and Post-CAR Hematopoietic Stem Cell Transplantation," Blood (2016) 128(22):218.
Lee et al., "T cells expressing CD19 chimeric antigen receptors for acute lymphoblastic leukaemia in children and yound adults: a phase 1 dose escalation trial," The Lancet (2015) 385(9967): 517-528.
Lefranc et al., "IMGT unique numbering for immunoglobulin and T cell receptor variable domains and Ig superfamily V-like domains," Dev Comp Immunol (2003) 27(1):55-77.
Leone et al., "A2aR antagonists: Next generation checkpoint blockade for cancer immunotherapy," Comput Struct Biotechnol J. (2015) 13:265-272.
Li et al. Identification of the earliest B lineage stage in mouse bone marrow, Immunity (1996) 5(6):527-535.
Li et al., "Directed evolution of human T-cell receptors with picomolar affinities by phage display", Nat Biotechnol. (2005) 23(3):349-354.
Li et al., "Murine leukemia induced by retroviral gene marking," Science (2002) 296(5567):497.
Li et al., "The regulated expression of B lineage associated genes during B ell differentiation in bone marrow and fetal liver," J Exp Med (1993) 178(3):951-960.
Li et al., "Thrombin induces the release of angiopoietin-1 from platelets," Thromb Haemost (2001) 85(2): 204-206.
Lim et al., "Anti-CD20 monoclonal antibodies: historical and future perspectives," Haematologica (2010) 95(1):135-143.
Ling et al., "B-cell and plasma cell antigens: new and previously defined clusters," Leucocyte typing III. (1987) 302-355.
Lipson et al., "Durable Cancer Regression Off-Treatment and Effective Reinduction Therapy With an anti-PD-1 Antibody," Clin Cancer Res (2013) 19(2): 462-468.
Liu et al., "Inclusion of Strep-tag II in design of antigen receptors for T-cell immunotherapy," Nat Biotechnol (2016) 34 (4):430-434.
Locke et al., "Primary Results from ZUMA-1: A Pivotal Trial of Axicabtagene Ciloleucel (Axi-cel; KTE-C19) in Patients with Refractory Aggressive Non-Hodgkin Lymphoma (NHL)," Cancer Research (2017) 77(13) Abstract CT019.
Locke et al., "Immune Signatures of Cytokine Release Syndrome and Neurologic Events in a Multicenter Registrational Trial (ZUMA-1) in Subjects with Refractory Non-Hodgkin Lymphoma Treated with Axicabtagene Ciloleucel (KTE-C19)," Cancer Research (2017) 77(13): Abstract CT020.
Lupton et al., "Dominant positive and negative selection using a hygromycin phosphotransferase-thymidine kinase fusion gene," Mol and Cell Biol (1991) 11(6):3374-3378.
Luznik et al., "HLA-haploidentical bone marrow transplantation for hematologic malignancies using nonmyeloablative conditioning and high-dose, posttransplantation cyclophosphamide," Biol Blood Marrow Transplant (2008) 14(6): 641-650.

(56) References Cited

OTHER PUBLICATIONS

Maloney et al., "Preliminary Safety Profile of the CD19-Directed Defined Composition CAR T Cell Product JCAR017 in Relapsed/Refractory Aggressive B-NHL Patients: Potential for Outpatient Administration," Blood (2017) 130 (Suppl 1):1552.
Maloney et al., "Preliminary Safety Profile of the CD19-Directed Defined Composition CAR T Cell Product JCAR017 in Relapsed/Refractory Aggressive B-NHL Patients: Potential for Outpatient Administration," presentation presented at ASH 2017. (Poster, 1552).
Manthey et al., "JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia," Mol Cancer Ther (2009) 8(11):3151-3161.
Manuri et al., "piggyBac transposon/transposase system to generate CD19-specific T cells for the treatment of B-lineage malignancies," Hum Gene Ther (2010) 21(4): 427-437.
Maude et al., "Efficacy of Humanized CD19-Targeted Chimeric Antigen Receptor (CAR)-Modified T Cells in Children and Young Adults with Relapsed/Refractory Acute Lymphoblastic Leukemia," Blood (2016) 128(22):217.
Maude et al., "Chimeric antigen receptor T cells for sustained remissions in leukemia," N Engl J Med. (2014) Oct. 16;371(16):1507-17.
Maude et al., "Efficacy and Safety of CTL019 in the First US Phase II Multicenter Trial in Pediatric Relapsed/Refractory Acute Lymphoblastic Leukemia: Results of an Interim Analysis," Blood (2016) 128(22):2801.
Maus et al., "Antibody-modified T cells: CARs take the front seat for hematologic malignancies," Blood (2014) 123 (17): 2625-2635.
McGarrity et al., "Patient monitoring and follow-up in lentiviral clinical trials," J Gene Medicine (2013) 15: 78-82.
Menzies et al., "New combinations and immunotherapies for melanoma: latest evidence and clinical utility," Ther Adv Med Oncol (2013) 5(5):278-285.
Mesa et al., "Ruxolitinib," Nature Reviews Drug Disovery (2012) 11(2):103-104.
Miller et al., "Improved retroviral vectors for gene transfer and expression," Biotechniques (1989) 7(9):980-982.
Miller et al., "Retrovirus packaging cells," Human Gene Therapy (1990) 1:5-14.
Millrine et al., "A Brighter Side to Thalidomide: Its Potential Use in Immunological Disorders," Trends Mol Med. Apr. 2017;23(4):348-361.
Modlich et al., "Leukemias following retroviral transfer of multidrug resistance 1 (MDR1) are driven by ombinatorial insertional mutagenesis," Blood (2005) 105(11): 4235-4246.
Monney et al., "Th1-specific cell surface protein Tim-3 regulates macrophage activation and severity of an autoimmune disease," Nature (2002) 415(6871):536-541.
Monsky et al. "Semi-Automated Volumetric Quantification of Tumor Necrosis in Soft Tissue Sarcoma Using Contrast Enhanced MRI," Anticancer Res. (2012) 32(11): 4951-4961.
Morgan, et al., "Cancer regression and neurological toxicity following anti-MAGE-A3 TCR gene therapy," J Immunother (2013) 36(2): 133-151.
Mounier et al., "Rituximab plus gemcitabine and oxaliplatin in patients with refractory/relapsed diffuse large B-cell lymphoma who are not candidates for high-dose therapy. A phase II Lymphoma Study Association trial," Haematologica (2013) 98(11):1726-1731.
Muller et al., "Amino-substituted thalidomide analogs: Potent inhibitors of TNF-a production," Bioorganic & Medicinal Chemistry Letters (1999) 9(11):1625-1630.
Nabhan et al., "Efficacy and safety of clofarabine in relapsed and/or refractory non-Hodgkin lymphoma, including rituximab-refractory patients," Cancer (2011) 117(7): 1490-1497.
National Comprehensive Cancer Network, "National Comprehensive Cancer Network Clinical Practice Guidelines in Oneology. B-cell Lymphomas, version 2.2018," (2018).

National Comprehensive Cancer Network, "Non-Hodgkin's Lymphomas Version 3.2016. National Comprehensive Cancer Network Clinical Practice Guidelines in Oncology," (2016).
Neepalu et al., "Chimeric antigen receptor T-cell therapy—assessment and management of toxicities," Nat Rev Clin Oncol (2018) 15(1):47-62.
Ngiow et al., "Anti-TIM3 Antibody Promotes T Cell IFN-γ-mediated Antitumor Immunity and Suppresses Established Tumors," Cancer Res (2011) 71(10): 3540-3551.
O'Brien et al., "High-dose vincristine sulfate liposome injection for advanced, relapsed, and refractory adult Philadelphia chromosome-negative acute lymphoblastic leukemia," J Clin Oncol (2013) 31(6): 676-683.
O'Brien et al., "Outcome of adults with acute lymphocytic leukemia after second salvage therapy," Cancer (2008) 113 (11): 3186-3191.
Ohmachi et al., "Multicenter phase II study of bendamustine plus rituximab in patients with relapsed or refractory diffuse large B-cell lymphoma," J Clin Oncol (2013) 31(17): 2103-2109.
Ohno et al., "A c-fms tyrosine kinase inhibitor, Ki20227, suppresses osteoclast differentiation and osteolytic bone destruction in a bone metastasis model," Mol Cancer Ther (2006) 5(11):2634-2643.
Ohta et al., "A2A adenosine receptor protects tumors from antitumor T cells," PNAS (2006) 103(35):13132-13137.
Oken et al., "Toxicity and response criteria of the Eastern Cooperative Oncology Group," Am J Clin Oncol (1982) 5 (6):649-655.
Olson et al., "Tumor gene signature associated with neurotoxicty in R/R B-ALL patients treated with JCAR015, a CD19-directed CAR T cell product candidate," J Clin Oncol (2018) 36(15 suppl.): 7007.
Oshima et al., "Immunomodulatory drugs (IMiDs)," Nihon Rinsho. (2014) 72(6): 1130-5. (Article in Japanese English abstract provided).
Otahal et al., "Lenalidomide enhances antitumor functions of chimeric antigen receptor modified T cells," Oncoimmunology (2015) 5(4):e1115940.
Ott et al., "CTLA-4 and PD-1/PD-L1 Blockade: New Immunotherapeutic Modalities with Durable Clinical Benefit in Melanoma Patients," Clin Cancer Res (2013) 19(19):5300.
Ozmen et al., "Mouse soluble IFN gamma receptor as IFN gamma inhibitor. Distribution, antigenicity, and activity after injection in mice," J Immunol (1993) 150(7):2698-2705.
Pardoll, "The blockade of immune checkpoints in cancer immunotherapy," Nature Reviews Cancer (2012) 12:252-264.
Parikh et al. "How we treat Richter syndrome," Blood (2014) 123:1647-1657.
Parizel et al., "Cerebral complications of murine monoclonal CD3 antibody (OKT3): CT and MR findings," AJNR Am J Neuroradiol (1997) 18(10): 1935-1938.
Park et al., "Baseline and early post-treatment clinical and laboratory factors associated with severe neurotoxicity following 19-28z CAR T cells in adult patients with relapsed B-ALL," Annual Meeting of the American Society of Clinical Oncology (2017), Chicago, IL. (ABS7024) J. Clin Onc (2017) 35(15 Supp) 7024.
Park et al., "CD-19-targeted CAR T-cell therapeutics for hematologic malignancies: interpreting clinical outcomes to date," Blood (2016) 127(26):3312-3320.
Park et al., "Impact of disease burden on long-term outcome of 19-28z CAR modified T cells in adult patients with relapsed B-ALL," J. Clin. Oncol. (2016) 34(no. 15_suppl):7003.
Park et al., "Treating cancer with genetically engineered T cells," Trends Biotechnol. (2011) 29(11): 550-557.
Park JH, "Managing Cytokine Release Syndrome.," Clinical Care Options Oncology (2017) retrieved from https://www.clinicaloptions.com/oncology/programs/managing-aes/modules/managing_crs.
Pinna et al., "Novel investigational adenosine A2A receptor antagonists for Parkinson's disease," Expert Opin Investig Drugs (2009) 18:1619-1631.
Ponomarev et al., "MicroRNA-124 promotes microglia quiescence and suppresses EAE by deactivating macrophages via the C/EBP-α-PU.1 pathway," Nat Med (2011) 17(1):64-70.
Ponticelli et al., "Neurological complications in kidney transplant recipients," J Nephrol (2005) 18(5): 521-528.

(56) References Cited

OTHER PUBLICATIONS

Porter et al., "Chimeric antigen receptor T cells persist and induce sustained remissions in relapsed refractory chronic lymphocytic leukemia," Sci Transl Med (2015) 7(303):303ra139.
Porter et al., "Randomized, Phase II Dose Optimization Study of Chimeric Antigen Receptor Modified T Cells Directed Against CD19 (CTL019) In Patients With Relapsed, Refractory CLL," Blood. (2013) Nov.;122(21):873, 3 pages. Retrieved from the Internet:URL:http://www.bloodjournal.org/content/122/21/873?sso-checked=true; [retrieved on Sep. 24, 2014].
Pryer et al., "MCS110: a monoclonal antibody with potent neutralizing activity against macrophage colony-stimulating factor for the treatment of tumor-induced osteolysis," AACR Annual Meeting (2009) Abstract #DDT02-2.
Pyonteck et al., "CSF-1R inhibition alters macrophage polarization and blocks glioma progression," Nat Med (2013) 19(10):1264-1272.
Radvanyi et al., "Antagonist Antibodies to PD-1 and B7-H1 (PD-L1) in the Treatment of Advanced Human Cancer-Letter," Clin Cancer Res (2013) 19(19): 5541.
Ramirez et al., "Prevention of Alzheimer's disease pathology by cannabinoids: neuroprotection mediated by blockade of microglial activation," J Neurosci (2005) 25(8):1904-1913.
Ramsborg et al., "JCAR017 Is a Defined Composition CAR T Cell Product with Product and Process Controls That Deliver Precise Doses of CD4 and CD8 CAR T Cell to Patients with NHL," Blood (2017) 130 (Suppl 1): 4471.
Ramsborg et al., "JCAR017 Is a Defined Composition CAR T Cell Product with Product and Process Controls That Deliver Precise Doses of CD4 and CD8 CAR T Cell to Patients with NHL," poster presentation 4471 presented at ASH on Dec. 11, 2017.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Ries et al., "Targeting tumor-associated macrophages with anti-CSF-1R antibody reveals a strategy for cancer therapy," Cancer Cell (2014) 25(6):846-859.
Robert et al., "What is the role of cytotoxic T lymphocyte-associated antigen 4 blockade in patients with metastatic melanoma?," Oncologist (2009) 14(8):848-861.
Roberts et al., "Inhibition by adenosine of reactive oxygen metabolite production by human polymorphonuclear leucocytes," Biochem J (1985) 227(2):669-674.
Rosenberg, et al., "Cell transfer immunotherapy for metastatic solid cancer-what clinicians need to know," Nat Rev Clin Oncol. (2011) 8(10):577-585.
Rothe et al., "Biosafety challenges for use of lentiviral vectors in gene therapy," Current Gene Ther (2013) 13(6): 453-468.
Rovida et al., "Colony-Stimulating Factor-1 Receptor in the Polarization of Macrophages: A Target for Turning Bad to Sood Ones?" J Clin Cell Immunol (2015) 6:379.
Ruella et al., "Kinase Inhibitor Ibrutinib Prevents Cytokine-Release Syndrome after Anti-CD19 Chimeric Antigen Receptor T Cells (CART) for B Cell Neoplasms," Abstract 2159. Presented at ASH 58th Annual Meeting San Diego, CA (Dec. 3-6, 2016).
Sadelain et al., "The basic principles of chimeric antigen receptor design," Cancer Discov. (2013) 3(4): 388-398.
Santomasso et al., "Biomarkers associated with neurotoxicity in adult patients with relapsed or refractory B-ALL (R/R B-ALL) treated with CD19 CAR T cells," J. Clin. Oncol. (2017) 35 (Supp. 15): 3019.
Sanz et al., "Nimodipine inhibits IL-1β release stimulated by amyloid β from microglia," Br J Pharmacol (2012) 167 (8):1702-1711.
Scarpa et al., "Characterization of recombinant helper retroviruses from Moloneybased vectors in ecotropic and amphotropic packaging cell lines," Virology (1991) 180:849-852.
Schlueter et al., "Specificity and binding properties of a single-chain T cell receptor," J Mol Biol. (1996) 256(5): 859-69.

Scholler et al., "Decade-long safety and function of retroviral-modified chimeric antigen receptor T cells," Sci Transl Med (2012) 4(132): 132ra153.
Schrier et al., "The effects of adenosine agonists on human neutrophil function," J Immunol (1986) 137 (10):3284-3289.
Schuler et al., SYFPEITHI, Database for Searching and T-Cell Epitope Prediction, in Immunoinformatics Methods in Molecular Biology, (2007) 409(1): 75-93.
Schuster et al., "Treatment with Chimeric Antigen Receptor Modified T Cells Directed Against CD19 (CTL019) Results in Durable Remissions in Patients with Relapsed or Refractory Diffuse Large B Cell Lymphomas of Germinal Center and Non-Germinal Center Origin, "Double Hit" Diffuse Large B Cell Lymphomas, and Transformed Follicular to Diffuse Large B Cell Lymphomas," Blood (2016) 128(22): 3026.
Seattle Children's Hospital, "A Pediatric and Young Adult Trial of Genetically Modified T Cells Directed Against CD 19 for Relapsed/Refractory CD19+ Leukemia," NCT02028455; first posted Jan. 7, 2014.
Shah et al., "High Rates of Minimal Residual Disease-Negative (MRD-) Complete Responses (CR) in Adult and Pediatric and Patients With Relapsed/Refractory Acute Lymphoblastic Leukemia (R/R ALL) Treated With KTE-C19 (Anti-CD19 Chimeric Antigen Receptor [CAR] T Cells): Preliminary Results of the ZUMA-3 and ZUMA-4 Trials," Blood (2016) 12(22): 2803.
Shahrara et al., "Inhibition of Monocyte Chemoattractant Protein-1 Ameliorates Rat Adjuvant-Induced Arthritis," J Imunol (2008) 180:3447-3456.
Sharma et al., "Efficient sleeping beauty DNA transposition from DNA minicircles," Molec Ther Nucl Acids (2013) 2: e74.
Shinohara et al., "Structure and Chromosomal Localization of the Human PD-1 Gene (PDCD1)," Genomics (1994) 23(3): 704-706.
Siddiqi et al., "Patient Characteristics and Pre-Infusion Biomakers of Inflammation Correlate with Clinical Outcomes after Treatment with the Defined Composition, CD19-Targeted CAR T Cell Product, JCAR017," ASH 2017 Oral Presentation, presented Dec. 9, 2017.
Siddiqi et al., "Patient Characteristics and Pre-Infusion Biomakers of Inflammation Correlate with Clinical Outcomes after Treatment with the Defined Composition, CD19-Targeted CAR T Cell Product, JCAR017," ASH 2017. Abstract 193.
Siegel, R.L. et al. (Jan.-Feb. 2015, e-pub. Jan. 5, 2015). "Cancer Statistics, 2015," CA Cancer J Clin. 65 (1):5-29.
Singh et al., "ProPred: prediction of HLA-DR binding sites," Bioinformatics. (2001) 17(12): 1236-1237.
Sitkovsky, M. et al. (Jul. 2014). "Hostile, Hypoxia-A2-Adenosinergic Tumor Biology as the Next Barrier to Overcome for Tumor Immunologists," Cancer Immunol. Res. 2(7):598-605, 15 pages.
Smith et al., "Abstract 4889: The highly specific CSF1R inhibitor DCC-3014 exhibits immunomodulatory and anti-invasive activities in cancer models," Cancer Research (2016) 76(14 Supplement):4889.
Sommermeyer et al., "Chimeric antigen receptor-modified T cells derived from defined CD8+ and Cd4+ subsets confer superior antitumor reactivity in vivo," Leukemia (2016) 30(2): 492-500.
Sommermeyer et al., "Fully human CD-19-specific chimeric antigen receptors for T-cell therapy," Leukemia (2017) 31(10): 2191-2199, doi: 10.1038/1eu.2017.57.
Soo Hoo et al., "Characterization of a single-chain T-cell receptor expressed in *Escherichia coli*," Proc Natl Acad Sci U S A. (1992) 89(10): 4759-4763.
Sorensen et al., "Performance status assessment in cancer patients. An inter-observer variability study," Br J Cancer (1993) 67(4):773-775.
Stamenkovic et al., "CD19, the earliest differentation antigen of the B cell lineage, bears three extracellular immunoglobulin-like domains and an Epstein-Barr virus-related cytoplasmic tail," J Exp Med (1988) 168(3): 1205-1210.
Sugita et al., "HLA-Haploidentical Peripheral Blood Stem Cell Transplantation with Post-Transplant Cyclophosphamide after Busulfan-Containing Reduced-Intensity Conditioning," Biol Blood Marrow Transplant (2015) 21(9):1646-1652.

(56) References Cited

OTHER PUBLICATIONS

Swanson et al., "Predicting Clinical Response and Safety of JCAR017 in B-NHL Patients: Potential Importance of Tumor Microenvironment Biomarkers and CAR T-Cell Tumor Infiltration," Blood (2017) 130 (Suppl 1): 194.
Swanson et al., "Predicting Clinical Response and Safety of JCAR017 in B-NHL Patients: Potential Importance of Tumor Microenvironment Biomarkers and CAR T-Cell Tumor Infiltration," oral presentation presented on Dec. 11, 2017 at ASH 2017. (Abs 194).
Swerdlow et al., "The 2016 Revision of the World Health Organization Classification of Lymphoid Neoplasms," Blood (2016) 127(20): 2375-2390.
Terakura et al., "Generation of CD19-chimeric antigen receptor modified CD8+ T cells derived from virus-specific central memory T cells," Blood (2012) 1:72-82.
Thall et al., "Practical Bayesian guidelines for Phase IIB clinical trials," Biometrics (1994) 50(2):337-349.
Themeli et al., "Generation of tumor-targeted human T lymphocytes from induced pluripotent stem cells for cancer therapy," Nat Biotechnol. (2013) 31(10): 928-933.
Thurston et al., "Angiopoietin-1 protects the adult vasculature against plasma leakage," Nat Med (2000) 6(4): 460-463.
Topalian, S.L. et al. (Jun. 28, 2012). "Safety, Activity, and Immune Correlates of Anti-PD-1 Antibody in Cancer," N. Engl. J. Med. 366(26):2443-2454, 19 pages.
Tsukahara et al., "CD19 target-engineered T-cells accumulate at tumor lesions in human B-cell lymphoma xenograll mouse models," Biochem Biophys Res Commun (2013) 438(1): 84-89.
Turtle and Maloney, "Clinical trials of CD19-targeted CAR-modified T cell therapy; a complex and varied landscape," Expert Rev Hematol (2016): 9(8); 719-721.
Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodepletion Imprives In Vivo Expansion and Persistence of CAR-T Cells and Clinical Outcomes," Blood (2015) 126:184.
Turtle et al., "CD19 CAR-T Cells (JCAR014) are Highly effective in Ibrutinib-Refractory High-Risk CLL," ASH oral presentation abstract 56, presented Dec. 3, 2016.
Turtle et al., "CD19 CAR-T Cells (JCAR014) are Highly effective in Ibrutinib-Refractory High-Risk CLL," Oral presentation ASH 2016 Abstract 56.
Turtle et al., "CD19 CAR-T cells of defined CD4+:CD8+ composition in adult B cell ALL patients," J Clin Invest. (2016) 126(6):2123-2138.
Turtle et al., "CD19-targeted chimeric antigen receptor-modified T cell immunotherapy for B cell malignancies," Clin Pharmacol Ther (2016) 10(3); 252-258.
Turtle et al., "Engineered T cells for anti-cancer therapy," Curr. Opin. Immunol. (2012) 24(5): 633-639.
Turtle et al., "High Rate of Durable Complete Response in ALL, NHL and CLL after Immunotherapy with Optimized Lymphodepletion and Defined Composition CD19 CAR-T cells (JCAR014)," 2016 ASCO meeting abstract 102.
Turtle et al., "Immunotherapy of non-Hodgkin's lymphoma with adefined ratio of CD8+ and CD4+ CD19-specific chimeric antigen receptor-modified T cells," Sci Trasl Med (2016) 8(355):355ra116.
Turtle et al., "Immunotherapy with CD19-specific chimeric antigen receptor (CAR)-modified T cells of defined subset composition," 2015 ASCO meeting abstract 3006, J. Clin. Oncol. (2015) 33:Suppl. Abstr 3006).
Twitter post; IMG_8293 image posted on twitter Jun. 29, 2017.
Twitter post; IMG_8294 image posted on twitter Jun. 29, 2017.
Twitter post; IMG_8296 image posted on twitter Jun. 29, 2017.
Twitter post; IMG_8297 image posted on twitter Jun. 29, 2017.
Vacirca et al., "Bendustamine combined with rituximab for patients with relapsed or refractory diffuse large B cell lymphoa," Ann Hematol (2013) 93(3): 403-409.
Valera et al., "Lenalidomide reduces microglial activation and behavioral deficits in a transgenic model of Parkinson's disease," J Neuroinflammation (2015) 12:93.
Van Den Nesie et al., "Outcome of Patients With Relapsed Diffuse Large B-cell Lymphoma Who Fail Second-Line Salvage Regimens in the International CORAL Study," Bone Marrow Transplant (2016) 51(1): 51-57.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Von Tresckow et al., "An Open-Label, Multicenter, Phase I/II Study of JNJ-40346527, a CSF-1R Inhibitor, in Patients with Relapsed or Refractory Hodgkin Lymphoma," Clin Cancer Res (2015) 21(8):1843-1850.
Wada et al., "Sequencing CTLA-4 blockade with cell-based immunotherapy for prostate cancer," J Transl Med (2013) 11:89.
Wadhwa et al., "Receptor mediated glycotargeting," J. Drug Targeting (1995) 3(2):111-127.
Wang et al., "A transgene-encoded cell surface polypeptide for selection, in vivo tracking, and ablation of engineered cells," Blood (2011) 118(5):1255-1263.
Wang et al., "Analysis of lentiviral vector integration in HIV+ study subjects receiving autologous infusions of gene modified CD4+ T cells," Mol Ther (2009) 17(5): 844-850.
Wang et al., "Oral lenalidomide with rituximab in relapsed or refractory diffuse large cell, follicular and transformed lymphoma: a phase II clinical trial," Leukemia (2013) 27(9): 1902-1909.
Wang et al., "Phenotypic and functional attributes of lentivirus-modified CD19-specific human CD8+ central memory T cells manufactured at clinical scale," J Immunother (2012) 35(9):689-701.
Weber, "Review: Anti-CTLA-4 Antibody Ipilimumab: Case Studies of Clinical Response and Immune-Related Adverse Events," The Oncologist (2007) 12(7):864-872.
Wiernik et al.,"Lenalidomide monotherapy in relapsed or refractory aggressive non-Hodgkin's lymphoma," J Clin Oncol (2008) 26(30):4952-4957.
Wilson et al., "Treatment strategies for aggressive lymphomas: what works?" Hematol Am Soc Hematol Educ Program (2013) 584-590.
Winter et al., "Dose-dependent Inhibition of Demyelination and Microglia Activation by IVIG," Ann Clin Transl Neurol (2016)3(11): 828-843.
Witzig et al., "An international phase II trial of a single-agent lenalidomide for relapsed or refractory aggressive B-cell non-Hodgkin's lymphoma," Ann Oncol (2011) 22(7): 1622-1627.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly folded T-cell receptor fragments in the periplasm of *Escherichia coli*. Influence of folding catalysts," J Mol Biol. (1994) 242(5): 655-69.
Xu et al., "Cytokine release syndrome in cancer immunotherapy with chimeric antigen receptor engineered T cells," Cancer Letters (2014) 343:172-78.
Xu et al., "Double-hit and Triple-Hit Lymphomas Arising From Follicular Lymphoma Following Acquisition of MYC: Report of Two Cases and Literature Review," Int J Clin Exp Pathol (2013) 6(4):788-794.
Yao et al., "Safety monitoring in clinical trials," Pharmaceutics (2013) 5(1): 94-106.
Younger et al., "Fibromyalgia symptoms are reduced by low-dose naltrexone: a pilot study," Pain Med (2009) 10 (4):663-672.
Yrjanheikki et al., "Tetracyclines inhibit microglial activation and are neuroprotective in global brain ischemia," PNAS (1998) 95(26):15769-15774.
Zhang et al., "CD73: a novel target for cancer immunotherapy," Cancer Res (2010) 70(16):6407-6411.
Zheng et al., "A novel anti-CEACAM5 monoclonal antibody, CC4, suppresses colorectal tumor growth and enhances NK cells-mediated tumor immunity," PLoS One (2011) 6(6):e21146.

(56) References Cited

OTHER PUBLICATIONS

Zheng et al., "Protein L: a novel reagent for the detection of chimeric antigen receptor (CAR) expression by flow cytometry," J Transl Med (2012) 10:29, 6 pages.

Ziepert et al., "Standard International prognostic index remains a valid predictor of outcome for patients with aggressive CD20+ B-cell lymphoma in the rituximab era," J Clin Oncol (2010) 28(14): 2373-2380.

Zuurbier et al., "Clinical Course of Cerebral Venous Thrombosis in Adult Acute Lymphoblastic Leukemia," J Stroke Cerebrovasc Dis (2015) 24(7): 1679-1684.

* cited by examiner

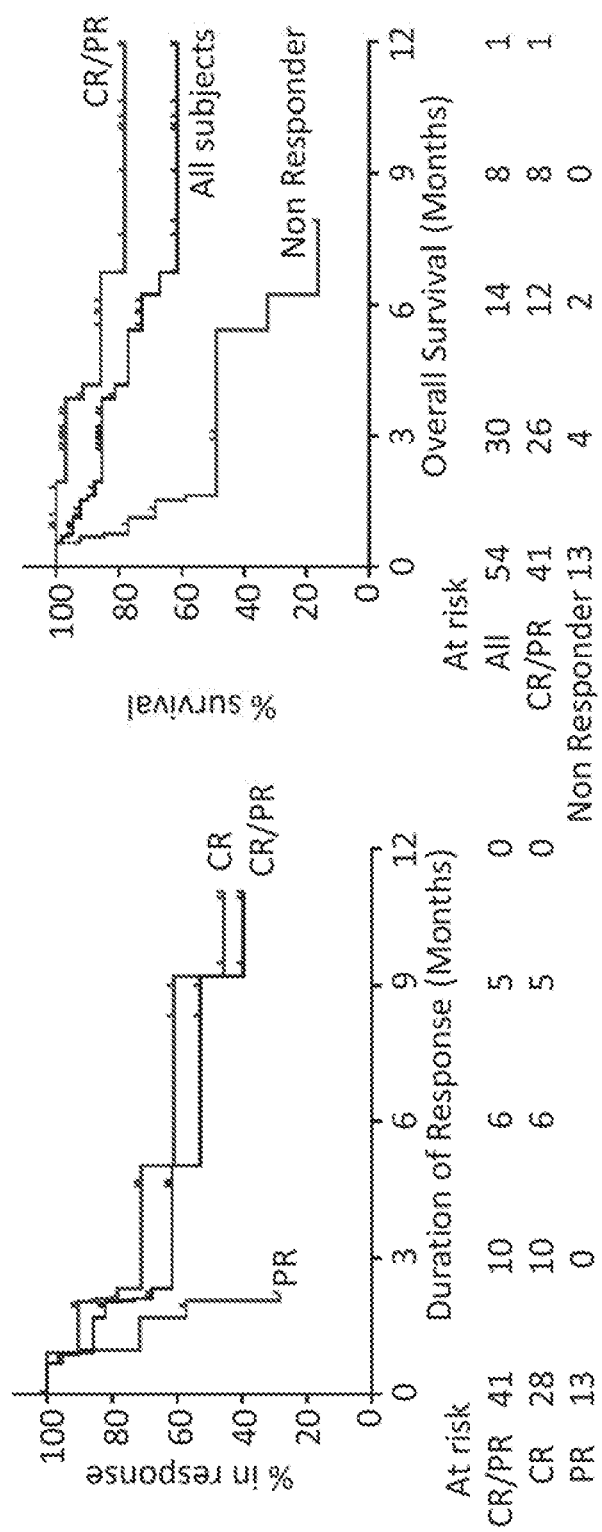
FIG. 4A FULL

CORE

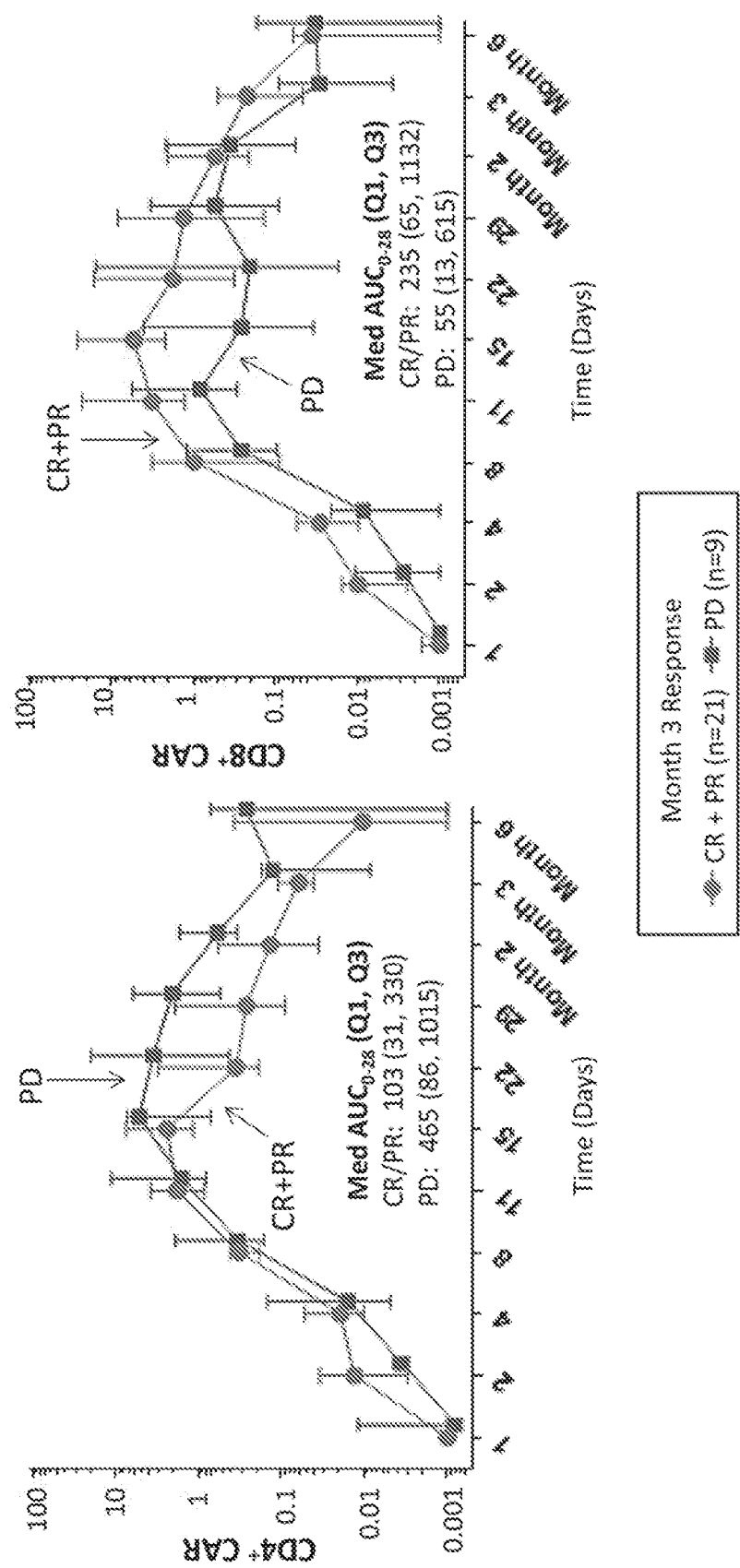

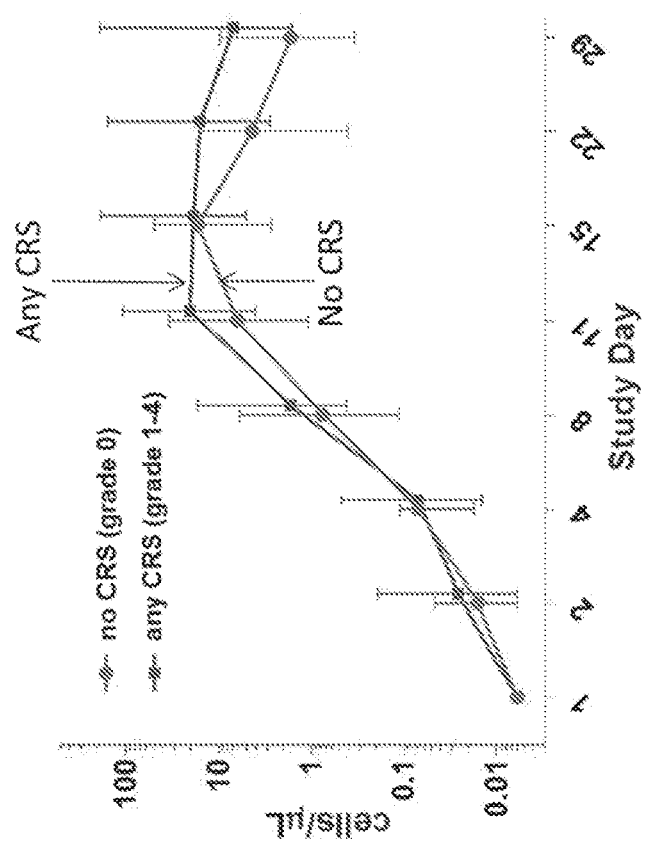
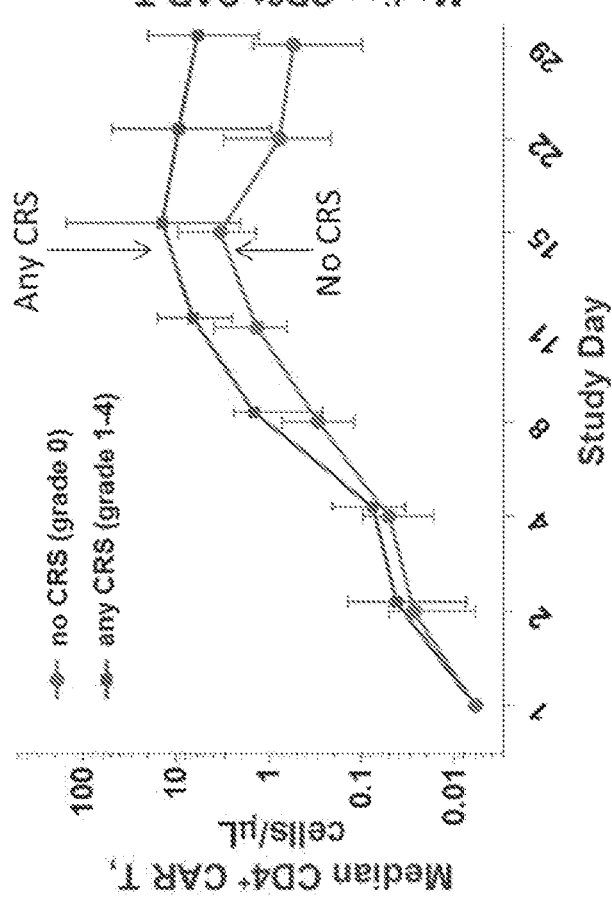
FIG. 12A
FIG. 12B

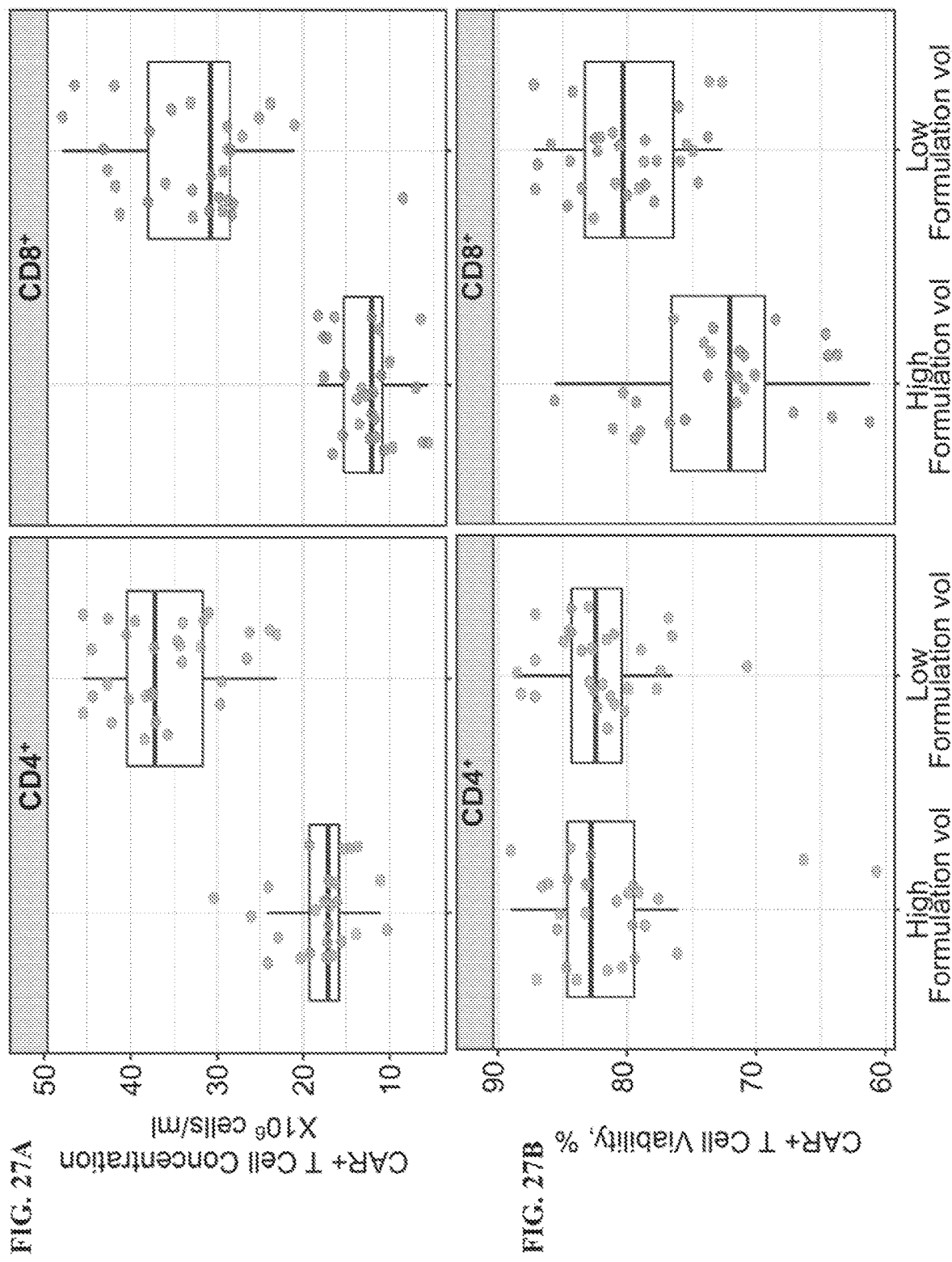

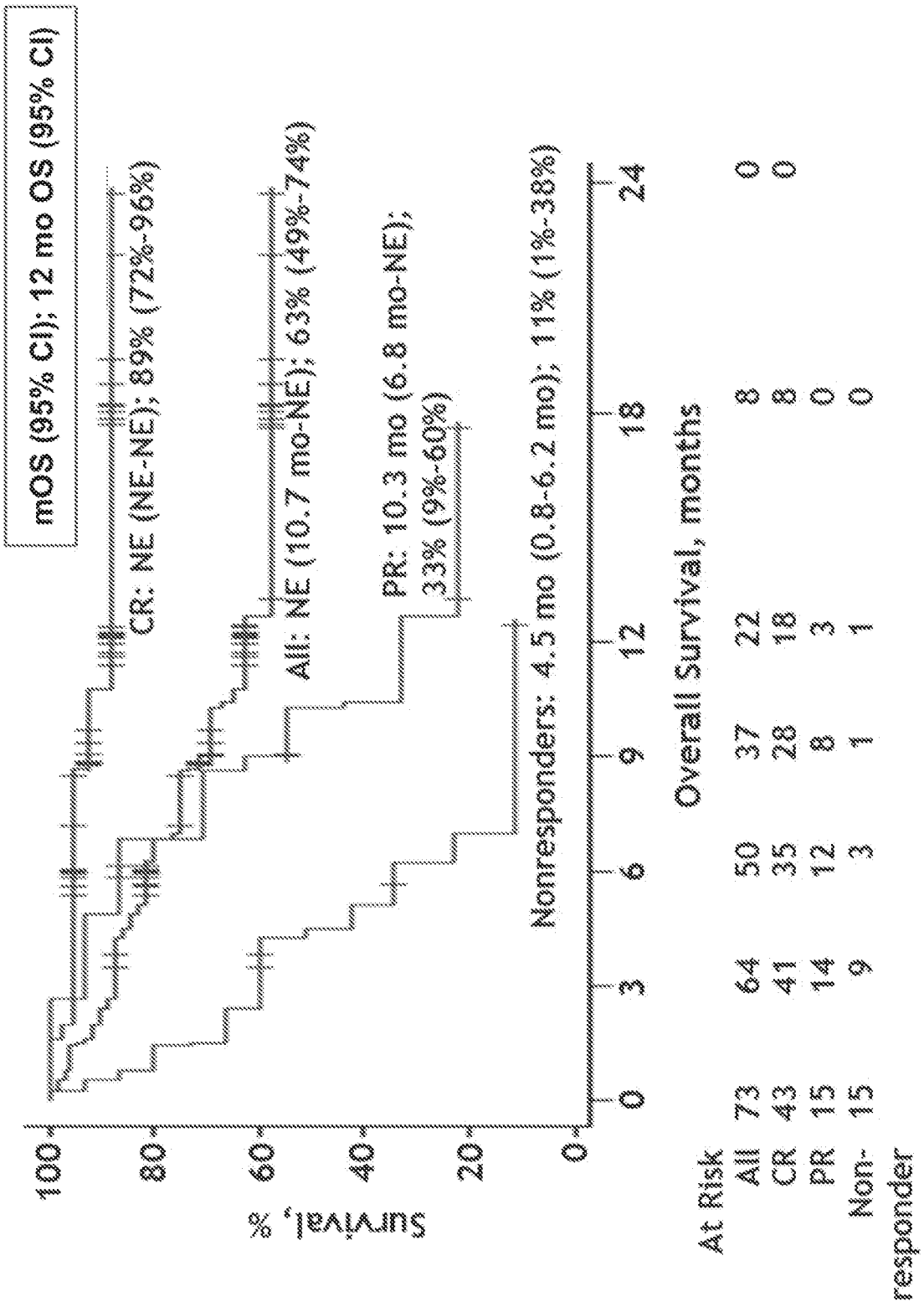

ARTICLES OF MANUFACTURE AND METHODS FOR TREATMENT USING ADOPTIVE CELL THERAPY

CROSS-REFERENCE TO RELATED APPLICATIONS

The application is a National Stage application under 35 U.S.C. § 371 of International Application No. PCT/US2018/035755, filed on Jun. 1, 2018, which claims priority from U.S. provisional application No. 62/514,774, filed Jun. 2, 2017, entitled "ARTICLES OF MANUFACTURE AND METHODS FOR TREATMENT USING ADOPTIVE CELL THERAPY," U.S. provisional application No. 62/515,530, filed Jun. 5, 2017, entitled "ARTICLES OF MANUFACTURE AND METHODS FOR TREATMENT USING ADOPTIVE CELL THERAPY," U.S. provisional application No. 62/521,366, filed Jun. 16, 2017, entitled "ARTICLES OF MANUFACTURE AND METHODS FOR TREATMENT USING ADOPTIVE CELL THERAPY," U.S. provisional application No. 62/527,000, filed Jun. 29, 2017, entitled "ARTICLES OF MANUFACTURE AND METHODS FOR TREATMENT USING ADOPTIVE CELL THERAPY," U.S. provisional application No. 62/549,938, filed Aug. 24, 2017, entitled "ARTICLES OF MANUFACTURE AND METHODS FOR TREATMENT USING ADOPTIVE CELL THERAPY," U.S. provisional application No. 62/580,425, filed Nov. 1, 2017, entitled "ARTICLES OF MANUFACTURE AND METHODS FOR TREATMENT USING ADOPTIVE CELL THERAPY," U.S. provisional application No. 62/593,871, filed Dec. 1, 2017, entitled "ARTICLES OF MANUFACTURE AND METHODS FOR TREATMENT USING ADOPTIVE CELL THERAPY," U.S. provisional application No. 62/596,764, filed Dec. 8, 2017, entitled "ARTICLES OF MANUFACTURE AND METHODS FOR TREATMENT USING ADOPTIVE CELL THERAPY," U.S. provisional application No. 62/614,957, filed Jan. 8, 2018, entitled "ARTICLES OF MANUFACTURE AND METHODS FOR TREATMENT USING ADOPTIVE CELL THERAPY," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042012100SeqList.txt, created Nov. 25, 2019, which is 35,524 bytes in size. The information in the electronic format of the Sequence Listing is incorporated by reference in its entirety.

FIELD

The present disclosure relates in some aspects to adoptive cell therapy involving the administration of doses of cells for treating subjects with disease and conditions such as certain B cell malignancies, and related methods, compositions, uses and articles of manufacture. The cells generally express recombinant receptors such as chimeric antigen receptors (CARs). In some embodiments, the disease or condition is a non-Hodgkin lymphoma (NHL), such as relapsed or refractory NHL or specific NHL subtype; in some embodiments, the subject is of a specific group or subset of NHL subjects, such as heavily pretreated or poor-prognosis subjects.

BACKGROUND

Various immunotherapy and/or cell therapy methods are available for treating diseases and conditions. For example, adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be beneficial in the treatment of cancer or other diseases or disorders. Improved approaches are needed. Provided are methods and uses that meet such needs.

SUMMARY

Provided herein are methods, uses, compositions, formulations and articles of manufacture for treating subjects having or suspected of having a disease or condition, such as a cancer or tumor, optionally a B cell malignancy such as NHL or ALL or CLL or a subtype thereof. The methods and other embodiments generally relate to administering to the subject T cells, generally engineered T cells, such as those expressing or containing a recombinant receptor such as a chimeric antigen receptor (CAR) or TCR.

In some embodiments, the dose of cells or cells administered in connection with any embodiments of the provided methods, compositions, articles of manufacture and uses, contains $CD4^+$ T cells or a subtype or phenotype thereof (such as engineered or recombinant receptor-expressing $CD4^+$ T cells) and/or $CD8^+$ T cells or a subtype thereof (such as an engineered or recombinant receptor-expressing $CD4^+$ cells). In some embodiments, the $CD8^+$ cells or subtype or phenotype are present at a particular dose or amount or number; in some embodiments the $CD4^+$ cells or subtype or phenotype are present at a particular dose or amount or number. In some embodiments, the $CD8^+$ cells or subtype or phenotype thereof and the $CD4^+$ cells or subtype or phenotype thereof, are present in the article or composition or combination, or are administered in the methods, at a defined ratio, such as at or about 1:1, or between at or about 1:3 and at or about 3:1. In some embodiments, the dose or administration contains or is of a particular amount or number of one population of the cells and the ratio is a defined ratio or is a naturally-occurring ratio, such as in the blood of the subject from which the cells are derived or ratio that occurs without selection or control for a particular ratio.

In some embodiments, the $CD4^+$ T cells (or subset thereof) and the $CD8^+$ T cells (or subset thereof), individually, contain a receptor that specifically binds to a target antigen expressed by the disease or condition, or a cell or tissue thereof, and/or that is associated with the disease or condition.

In some embodiments, the $CD4^+$ and $CD8^+$ cells are administered and/or formulated together, e.g. in a single formulation and/or from a single container.

In some embodiments, separate administrations are carried out of the $CD4^+$ and the $CD8^+$ cells in the dose, and/or separate formulations or containers are included, each individually enriched for the $CD4^+$ cells or the $CD4^+$ engineered cells (such as a formulation containing at least a certain percentage of, e.g., at least 80%, 85%, 90% or 95% or more of, $CD4^+$ cells and/or not comprising more than 10% or more than 5% $CD8^+$ T cells) and the $CD8^+$ Cells or the $CD8^+$ engineered cells (such as a formulation containing at least a certain percentage of, e.g., at least 80%, 85%, 90% or 95% or more of, CD8+ cells and/or not comprising more than 10% or more than 5% CD4+ T cells).

In some aspects, the administration comprises administering a plurality of separate compositions, said plurality of separate compositions comprising a first composition comprising one of the CD4+ T cells and the CD8+ T cells and a second composition comprising the other of the CD4+ T cells and the CD8+ T cells. In certain embodiments of any of the provided methods, the receptor contained by the CD4+ T cells and/or the receptor contained by the CD8+ T cells comprises T cells a recombinant receptor, and/or wherein the CD4+ T cells and/or the CD8+ T cells are genetically engineered to express the receptor.

In some embodiments of any of the provided embodiments, the administration of the first composition and the administration of the second composition are carried out on the same day, are carried out between about 0 and about 12 hours apart, between about 0 and about 6 hours apart or between about 0 and 2 hours apart; and/or the initiation of administration of the first composition and the initiation of administration of the second composition are carried out between about 1 minute and about 1 hour apart or between about 5 minutes and about 30 minutes apart. In certain embodiments of any of the provided methods, the first composition and second composition are administered no more than 2 hours, no more than 1 hour, no more than 30 minutes, no more than 15 minutes, no more than 10 minutes or no more than 5 minutes apart.

In certain embodiments of any of the provided embodiments, the first composition comprises the CD4+ T cells. In some embodiments of any of the provided methods, the first composition comprises the CD8+ T cells. In particular embodiments of any of the provided methods, the initiation of the administration of the first composition is carried out prior to the initiation of the administration of the second composition. In certain embodiments of any of the provided methods, the dose of cells comprises a defined ratio of CD4+ cells expressing a recombinant receptor to CD8+ cells expressing a recombinant receptor and/or of CD4+ cells to CD8+ cells, which ratio optionally is or is approximately 1:1 or is between approximately 1:3 and approximately 3:1; and/or the CD4+ T cells comprising the receptor in the one of the first and second compositions and the CD8+ T cells comprising the receptor in the other of the first and second compositions are present at a defined ratio, which ratio optionally is or is approximately 1:1 or is between approximately 1:3 and approximately 3:1; and/or the CD4+ T cells comprising the receptor and the CD8+ T cells comprising the receptor administered in the first and second compositions are present at a defined ratio, which ratio optionally is or is approximately 1:1 or is between approximately 1:3 and approximately 3:1. In some embodiments of any of the provided methods, the defined ratio is or is approximately 1:1. In particular embodiments of any of the provided methods, the dose of T cells is administered to the subject as a single dose or is administered only one time within a period of two weeks, one month, three months, six months, 1 year or more. In certain embodiments of any of the provided methods, the dose of T cells is administered as a double dose comprising a first dose of the T cells and a consecutive dose of the T cells, wherein one or both of the first dose and the second dose comprises administration of the plurality of compositions of T cells. In some embodiments of any of the provided methods, the consecutive dose is administered at a point in time that is at least or more than about 7 days or 14 days after and less than about 28 days after initiation of the administration of the first dose of cells.

In particular embodiments of any of the provided methods or embodiments, the dose of cells comprises between at or about $1 \times 10^5$ and at or about $5 \times 10^8$ total recombinant receptor-expressing T cells or total T cells, between at or about $1 \times 10^5$ and at or about $1 \times 10^8$ total recombinant receptor-expressing T cells or total T cells, between at or about $5 \times 10^5$ and at or about $1 \times 10^7$ total recombinant receptor-expressing T cells or total T cells, or from or from about $1 \times 10^6$ to $1 \times 10^7$ total recombinant receptor-expressing T cells or total T cells, each inclusive. In certain embodiments of any of the provided methods, the dose of T cells comprises the administration of no more than $1 \times 10^8$ total recombinant receptor-expressing T cells or total T cells, no more than $1 \times 10^7$ total recombinant receptor-expressing T cells or total T cells, no more than $0.5 \times 10^7$ total recombinant receptor-expressing T cells or total T cells, no more than $1 \times 10^6$ total recombinant receptor-expressing T cells or total T cells, no more than $0.5 \times 10^6$ total recombinant receptor-expressing T cells or total T cells. In some embodiments of any of the provided methods, the dose of T cells comprises between at or about $5 \times 10^7$ recombinant receptor-expressing T cells and $1 \times 10^8$ recombinant receptor-expressing T cells, each inclusive.

In particular embodiments of any of the provided methods, the recombinant receptor specifically binds to an antigen associated with the disease or condition or expressed in cells of the environment of a lesion associated with the disease or condition. In certain embodiments of any of the provided methods, the disease or condition is a cancer. In some embodiments of any of the provided methods, the disease or condition is a myeloma, leukemia or lymphoma. In particular embodiments of any of the provided methods, the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen. In certain embodiments of any of the provided methods, the antigen is CD19.

In some embodiments of any of the provided methods, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL). In particular embodiments of any of the provided methods, the disease or condition is NHL and the NHL is selected from the group consisting of aggressive NHL, diffuse large B cell lymphoma (DLBCL), NOS (not otherwise specified) (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

In some embodiments of any of the provided methods, the recombinant receptor includes an extracellular domain containing an antigen-binding domain. In some embodiments, the antigen-binding domain is or includes an antibody or an antibody fragment thereof, which optionally is a single chain fragment. In particular embodiments of any of the provided methods, the fragment includes antibody variable regions joined by a flexible linker. In some embodiments, the fragment includes an scFv. In some embodiments of any of the provided methods, the recombinant receptor also includes a spacer and/or a hinge region.

In certain embodiments of any of the provided methods, the recombinant receptor includes an intracellular signaling region. In some embodiments of any of the provided methods, the intracellular signaling region includes an intracellular signaling domain. In some embodiments of any of the provided methods, the intracellular signaling domain is or includes a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or includes an intracellular signaling domain of a CD3 chain, optionally a CD3-zeta (CD3) chain, or a signaling portion thereof.

In particular embodiments of any of the provided methods, the recombinant receptor also includes a transmembrane domain disposed between the extracellular domain and the intracellular signaling region.

In some embodiments of any of the provided methods, the intracellular signaling region also includes a costimulatory signaling region. In some embodiments, the costimulatory signaling region includes an intracellular signaling domain of a T cell costimulatory molecule or a signaling portion thereof. In certain embodiments of any of the provided methods, the costimulatory signaling region includes an intracellular signaling domain of a CD28, a 4-1BB or an ICOS or a signaling portion thereof. In some embodiments, the costimulatory signaling region is between the transmembrane domain and the intracellular signaling region.

In certain embodiments of any of the provided methods, the recombinant receptor is a chimeric antigen receptor (CAR), optionally wherein the recombinant receptor is a chimeric antigen receptor (CAR), optionally wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

In some embodiments, the articles of manufacture include a container such as a vial comprising a composition comprising CD4$^+$ T cells expressing a recombinant receptor, and instructions for administering, to a subject having a disease or condition, the composition of CD4$^+$ T cells as a plurality of compositions with a composition comprising CD8$^+$ T cells expressing a recombinant receptor or a unit dose of cells comprising all or a portion of the plurality of CD4$^+$ T cells and a composition comprising CD8$^+$ T cells expressing a recombinant receptor. In some embodiments, the article of manufacture includes a container such as a vial comprising a composition comprising CD8$^+$ T cells expressing a recombinant receptor, and instructions for administering, to a subject having a disease or condition, the composition of CD8$^+$ T cells as a plurality of compositions with a composition comprising CD4$^+$ T cells expressing a recombinant receptor or a unit dose of cells comprising all or a portion of the plurality of CD4$^+$ T cells and a composition comprising CD8$^+$ T cells expressing a recombinant receptor.

In some of any of the embodiments, the CAR comprises, in order, the CAR includes an scFv specific for the antigen, a transmembrane domain, a cytoplasmic signaling domain derived from a costimulatory molecule, which optionally is or comprises a 4-1BB, and a cytoplasmic signaling domain derived from a primary signaling ITAM-containing molecule, which optionally is or comprises a CD3zeta signaling domain and optionally further includes a spacer between the transmembrane domain and the scFv;

In some of any of the embodiments, the CAR includes, in order, an scFv specific for the antigen, a transmembrane domain, a cytoplasmic signaling domain derived from a costimulatory molecule, which optionally is or comprises a 4-1BB signaling domain, and a cytoplasmic signaling domain derived from a primary signaling ITAM-containing molecule, which optionally is a CD3zeta signaling domain.

In some of any of the embodiments, the CAR comprises or consists of, in order, an scFv specific for the antigen, a spacer, a transmembrane domain, a cytoplasmic signaling domain derived from a costimulatory molecule, which optionally is a 4-1BB signaling domain, and a cytoplasmic signaling domain derived from a primary signaling ITAM-containing molecule, which optionally is or comprises a CD3zeta signaling domain.

In some aspects, the spacer is a polypeptide spacer that (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) has or consists of the sequence of SEQ ID NO: 1, a sequence encoded by SEQ ID NO: 2, SEQ ID NO: 30, SEQ ID NO: 31, SEQ ID NO: 32, SEQ ID NO: 33, SEQ ID O:N 34, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine; and/or the costimulatory domain comprises SEQ ID NO: 12 or a variant thereof having at least 85%, 86%, 87%, 88%, 89%, 90%, 91%, 92%, 93%, 94%, 95%, 96%, 97%, 98%, 99% or more sequence identity thereto; and/or the primary signaling domain comprises SEQ ID NO: 13 or 14 or 15 or a variant thereof having at least 85%, 86%, 87%, 88%, 89%, 90%, 91%, 92%, 93%, 94%, 95%, 96%, 97%, 98%, 99% or more sequence identity thereto; and/or the scFv comprises a CDRL1 sequence of RASQDISKYLN (SEQ ID NO: 35), a CDRL2 sequence of SRLHSGV (SEQ ID NO: 36), and/or a CDRL3 sequence of GNTLPYTFG (SEQ ID NO: 37) and/or a CDRH1 sequence of DYGVS (SEQ ID NO: 38), a CDRH2 sequence of VIWGSETTYYN-SALKS (SEQ ID NO: 39), and/or a CDRH3 sequence of YAMDYWG (SEQ ID NO: 40) or wherein the scFv comprises a variable heavy chain region of FMC63 and a variable light chain region of FMC63 and/or a CDRL1 sequence of FMC63, a CDRL2 sequence of FMC63, a CDRL3 sequence of FMC63, a CDRH1 sequence of FMC63, a CDRH2 sequence of FMC63, and a CDRH3 sequence of FMC63 or binds to the same epitope as or competes for binding with any of the foregoing, and optionally wherein the scFv comprises, in order, a $V_H$, a linker, optionally comprising SEQ ID NO: 24, and a $V_L$, and/or the scFv comprises a flexible linker and/or comprises the amino acid sequence set forth as SEQ ID NO: 24.

In some embodiments, the spacer comprises or consists of SEQ ID NO: 1, the costimulatory domain comprises SEQ ID NO: 12 or variant thereof having at least 85%, 86%, 87%, 88%, 89%, 90%, 91%, 92%, 93%, 94%, 95%, 96%, 97%, 98%, 99% or more sequence identity thereto, the transmembrane domain is of CD28 or comprises SEQ ID NO: 9 or a variant thereof having at least 85%, 86%, 87%, 88%, 89%, 90%, 91%, 92%, 93%, 94%, 95%, 96%, 97%, 98%, 99% or more sequence identity thereto, the scFv contains the binding domain of or CDRs of or $V_H$ and $V_L$ of FMC63, the primary signaling domain contains SEQ ID NO: 13, 14, or 15, and/or a variant thereof having at least 85%, 86%, 87%, 88%, 89%, 90%, 91%, 92%, 93%, 94%, 95%, 96%, 97%, 98%, 99% or more sequence identity thereto.

In some embodiments, the spacer comprises or consists of SEQ ID NO: 30, the costimulatory domain comprises SEQ ID NO: 12 or variant thereof having at least 85%, 86%, 87%, 88%, 89%, 90%, 91%, 92%, 93%, 94%, 95%, 96%, 97%, 98%, 99% or more sequence identity thereto, the transmembrane domain is of CD28 or comprises SEQ ID NO: 9 or a variant thereof having at least 85%, 86%, 87%, 88%, 89%, 90%, 91%, 92%, 93%, 94%, 95%, 96%, 97%, 98%, 99% or more sequence identity thereto, the scFv contains the binding domain of or CDRs of or $V_H$ and $V_L$ of FMC63, the primary signaling domain contains SEQ ID NO: 13, 14, or 15, and/or a variant thereof having at least 85%, 86%, 87%, 88%, 89%, 90%, 91%, 92%, 93%, 94%, 95%, 96%, 97%, 98%, 99% or more sequence identity thereto.

In some embodiments, the spacer comprises or consists of SEQ ID NO: 31, the costimulatory domain comprises SEQ ID NO: 12 or variant thereof having at least 85%, 86%, 87%, 88%, 89%, 90%, 91%, 92%, 93%, 94%, 95%, 96%, 97%, 98%, 99% or more sequence identity thereto, the transmembrane domain is of CD28 or comprises SEQ ID NO: 9 or a variant thereof having at least 85%, 86%, 87%, 88%, 89%, 90%, 91%, 92%, 93%, 94%, 95%, 96%, 97%, 98%, 99% or more sequence identity thereto, the scFv contains the binding domain of or CDRs of or $V_H$ and $V_L$ of FMC63, the primary signaling domain contains SEQ ID NO: 13, 14, or 15, and/or a variant thereof having at least 85%, 86%, 87%, 88%, 89%, 90%, 91%, 92%, 93%, 94%, 95%, 96%, 97%, 98%, 99% or more sequence identity thereto.

In some embodiments, the spacer comprises or consists of SEQ ID NO: 33, the costimulatory domain comprises SEQ ID NO: 12 or variant thereof having at least 85%, 86%, 87%, 88%, 89%, 90%, 91%, 92%, 93%, 94%, 95%, 96%, 97%, 98%, 99% or more sequence identity thereto, the transmembrane domain is of CD28 or comprises SEQ ID NO: 9 or a variant thereof having at least 85%, 86%, 87%, 88%, 89%, 90%, 91%, 92%, 93%, 94%, 95%, 96%, 97%, 98%, 99% or more sequence identity thereto, the scFv contains the binding domain of or CDRs of or $V_H$ and $V_L$ of FMC63, the primary signaling domain contains SEQ ID NO: 13, 14, or 15, and/or a variant thereof having at least 85%, 86%, 87%, 88%, 89%, 90%, 91%, 92%, 93%, 94%, 95%, 96%, 97%, 98%, 99% or more sequence identity thereto.

In some embodiments, the spacer comprises or consists of SEQ ID NO: 34, the costimulatory domain comprises SEQ ID NO: 12 or variant thereof having at least 85%, 86%, 87%, 88%, 89%, 90%, 91%, 92%, 93%, 94%, 95%, 96%, 97%, 98%, 99% or more sequence identity thereto, the transmembrane domain is of CD28 or comprises SEQ ID NO: 9 or a variant thereof having at least 85%, 86%, 87%, 88%, 89%, 90%, 91%, 92%, 93%, 94%, 95%, 96%, 97%, 98%, 99% or more sequence identity thereto, the scFv contains the binding domain of or CDRs of or $V_H$ and $V_L$ of FMC63, the primary signaling domain contains SEQ ID NO: 13, 14, or 15, and/or a variant thereof having at least 85%, 86%, 87%, 88%, 89%, 90%, 91%, 92%, 93%, 94%, 95%, 96%, 97%, 98%, 99% or more sequence identity thereto.

In some embodiments of any of the provided articles of manufacture, the recombinant receptor expressed by the CD4$^+$ cells and the recombinant receptor expressed by the CD8$^+$ T cells is the same or different. In particular embodiments of any of the provided articles of manufacture, vial comprises greater than or greater than about $10 \times 10^6$ T cells or recombinant receptor-expressing T cells, greater than or greater than about $15 \times 10^6$ T cells or recombinant receptor-expressing T cells, greater than or greater than about $25 \times 10^6$ T cells or recombinant receptor-expressing T cell.

In certain embodiments of any of the provided articles of manufacture, the vial comprises between about 10 million cells per ml and about 70 million cells per ml, between about 10 million cells per ml and about 50 million cells per ml, between about 10 million cells per ml and about 25 million cells per ml, between about 10 million cells per ml and about 15 million cells per ml, 15 million cells per ml and about 70 million cells per ml, between about 15 million cells per ml and about 50 million cells per ml, between about 15 million cells per ml and about 25 million cells per ml, between about 25 million cells per ml and about 70 million cells per ml, between about 25 million cells per ml and about 50 million cells per ml, and between about 50 million cells per ml and about 70 million cells per ml. In some embodiments of any of the provided articles of manufacture, the composition further comprises a cryoprotectant and/or the article further includes instructions for thawing the composition prior to administration to the subject.

In some embodiments of any of the provided articles of manufacture, the compositions or plurality of compositions comprises a dose of cells comprising from or from about $2 \times 10^7$ to about $4 \times 10^7$ CD8$^+$ cells, such as about $2 \times 10^7$, $2.5 \times 10^7$, $3 \times 10^7$, $3.5 \times 10^7$, or $4 \times 10^7$ CD8$^+$ cells, and from or from about $2 \times 10^7$ to about $4 \times 10^7$ CD4$^+$ cells, such as about $2 \times 10^7$, $2.5 \times 10^7$, $3 \times 10^7$, $3.5 \times 10^7$, or $4 \times 10^7$ CD4$^+$ cells, each inclusive. In some embodiments, the compositions or plurality of compositions comprises a dose of cells comprising approximately $3 \times 10^7$ CD8$^+$ cells and $3.5 \times 10^7$ CD4$^+$ cells.

In particular embodiments of any of the provided articles of manufacture, the plurality of compositions of cells comprises a defined ratio of CD4$^+$ cells expressing the recombinant receptor to CD8$^+$ cells expressing the recombinant receptor and/or of CD4$^+$ cells to CD8$^+$ cells, which ratio optionally is approximately 1:1 or is between approximately 1:3 and approximately 3:1. In certain embodiments of any of the provided articles of manufacture, the defined ratio is or is approximately 1:1. In some embodiments of any of the provided articles of manufacture, the plurality of compositions, collectively, comprises a dose of cells comprising from or from about $1 \times 10^5$ to $5 \times 10^8$ total recombinant receptor-expressing T cells or total T cells, $1\times10^5$ to $1\times10^8$ total recombinant receptor-expressing T cells or total T cells, from or from about $5\times10^5$ to $1\times10^7$ total recombinant receptor-expressing T cells or total T cells, or from or from about $1\times10^6$ to $1\times10^7$ total recombinant receptor-expressing T cells or total T cells, each inclusive. In particular embodiments of any of the provided articles of manufacture, the plurality of compositions, collectively, comprises a dose of cells comprising no more than $1\times10^8$ total recombinant receptor-expressing T cells or total T cells, no more than $1\times10^7$ total recombinant receptor-expressing T cells or total T cells, no more than $0.5\times10^7$ total recombinant receptor-expressing T cells or total T cells, no more than $1\times10^6$ total recombinant receptor-expressing T cells or total T cells, no more than $0.5\times10^6$ total recombinant receptor-expressing T cells or total T cells. In certain embodiments of any of the provided articles of manufacture, the plurality of compositions, collectively, comprises a dose of cells comprising between at or about $5\times10^7$ recombinant receptor-expressing T cells and $1\times10^8$ recombinant receptor-expressing T cells, each inclusive.

In some embodiments of any of the provided articles of manufacture, the instructions specify administering the composition comprising the CD4$^+$ T cells and the composition comprising the CD8$^+$ T cells 0 to 12 hours apart, 0 to 6 hours apart or 0 to 2 hours apart. In particular embodiments of any of the provided articles of manufacture, the instructions specify administering the composition comprising the CD4$^+$ T cells and the composition comprising the CD8$^+$ T cells no more than 2 hours, no more than 1 hour, no more than 30 minutes, no more than 15 minutes, no more than 10 minutes or no more than 5 minutes apart. In certain embodiments of any of the provided articles of manufacture, the instructions specify administering the composition comprising the CD4$^+$ T cells prior to administering the composition comprising the CD8$^+$ cells. In some embodiments of any of the provided articles of manufacture, the instructions specify administering the composition comprising the CD8$^+$ T cells prior to administering the composition comprising the CD4$^+$ cells.

In particular embodiments of any of the provided articles of manufacture, the recombinant receptor specifically binds to an antigen associated with the disease or condition or expressed in cells of the environment of a lesion associated with the disease or condition. In certain embodiments of any of the provided articles of manufacture, the disease or condition is a cancer. In some embodiments of any of the provided articles of manufacture, the disease or condition is a myeloma, leukemia or lymphoma.

In particular embodiments of any of the provided articles of manufacture, the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAM), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen. In certain embodiments of any of the provided articles of manufacture, the antigen is CD19.

In some embodiments of any of the provided articles of manufacture, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL). In particular embodiments of any of the provided articles of manufacture, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

In certain embodiments of any of the provided articles of manufacture, the T cells are primary T cells obtained from a subject. In some embodiments of any of the provided articles of manufacture, the T cells are autologous to the subject. In particular embodiments of any of the provided articles of manufacture, the T cells are allogeneic to the subject.

In certain embodiments of any of the provided articles of manufacture, the recombinant receptor is or includes a functional non-TCR antigen receptor or a TCR or antigen-binding fragment thereof. In some embodiments, the recombinant receptor is a chimeric antigen receptor (CAR).

In particular embodiments any of the provided articles of manufacture, the recombinant receptor includes an extracellular domain containing an antigen-binding domain. In some embodiments, the antigen-binding domain is or includes an antibody or an antibody fragment thereof, which optionally is a single chain fragment. In some embodiments, the fragment includes antibody variable regions joined by a flexible linker. In some embodiments, the fragment includes an scFv.

In some embodiments any of the provided articles of manufacture or methods, the recombinant receptor also includes a spacer and/or a hinge region.

In certain embodiments any of the provided articles of manufacture or methods, the recombinant receptor includes an intracellular signaling region. In some embodiments, the intracellular signaling region includes an intracellular signaling domain. In some embodiments any of the provided articles of manufacture, the intracellular signaling domain is or includes a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or includes an intracellular signaling domain of a CD3 chain, optionally a CD3-zeta (CD3ζ) chain, or a signaling portion thereof.

In particular embodiments any of the provided articles of manufacture or methods, the recombinant receptor also includes a transmembrane domain disposed between the extracellular domain and the intracellular signaling region.

In some embodiments any of the provided articles of manufacture or methods, the intracellular signaling region also includes a costimulatory signaling region. In some embodiments, the costimulatory signaling region includes an intracellular signaling domain of a T cell costimulatory molecule or a signaling portion thereof. In some embodiments any of the provided articles of manufacture, the costimulatory signaling region includes an intracellular signaling domain of a CD28, a 4-1BB or an ICOS or a signaling portion thereof. In some embodiments, the costimulatory signaling region is between the transmembrane domain and the intracellular signaling region.

In some embodiments, the methods and articles are for or capable of treating a subject having non-Hodgkin lymphoma (NHL). In some aspects, the method involves, and/or the article of manufacture specifies or includes formulations capable of, administering to the subject a dose or plurality of T cells. In some aspects, the T cells comprising T cells such as CD8$^+$ T cells and/or CD4$^+$ T cells, expressing a chimeric antigen receptor (CAR) that specifically binds to a target antigen expressed by the NHL.

In some embodiments, the dose of T cells comprises between at or about $5 \times 10^7$ CAR-expressing T cells and $1 \times 10^8$ CAR-expressing T cells, inclusive; and the NHL comprises diffuse large B cell lymphoma (DLBCL), primary mediastinal large B cell lymphoma (PMBCL), NOS (de novo or transformed from indolent lymphoma), or follicular lymphoma Grade 3B and wherein the subject is or has been identified as having an Eastern Cooperative Oncology Group Performance Status (ECOG) status of 0 or 1.

In some embodiments of any of the provided embodiments, the methods further comprise identifying, or the article of manufacture includes information specifying, treatment of a subject having diffuse large B cell lymphoma (DLBCL), primary mediastinal large B cell lymphoma (PMBCL), NOS (de novo or transformed from indolent lymphoma), or follicular lymphoma Grade 3B having an ECOG status of 0 or 1. In some embodiments of any of the provided embodiments, the dose of T cells and/or the cells administered comprises a defined ratio of CD4$^+$ cells expressing the CAR to CD8$^+$ cells expressing the CAR and/or of CD4$^+$ cells to CD8$^+$ cells, which ratio optionally is approximately 1:1 or is between approximately 1:3 and approximately 3:1.

In some aspects, the embodiments are for treating a subject having non-Hodgkin lymphoma (NHL) and involve administering to the subject a dose of T cells comprising T cells expressing a chimeric antigen receptor (CAR) that specifically binds to a target antigen expressed by the NHL. In some aspects, the dose of T cells includes a defined ratio of CD4$^+$ cells expressing the CAR to CD8$^+$ cells expressing the CAR and/or of CD4$^+$ cells to CD8$^+$ cells, which ratio in some aspects is approximately or is 1:1. In some aspects, the NHL comprises diffuse large B cell lymphoma (DLBCL), primary mediastinal large B cell lymphoma (PMBCL), NOS (not otherwise specified) (de novo or transformed from indolent lymphoma), or follicular lymphoma Grade 3B.

In particular embodiments of any of the provided embodiments, the subject is or has been identified as or is specified as having an Eastern Cooperative Oncology Group Performance Status (ECOG) status of 0, 1 or 2. In certain embodiments of any of the provided embodiments, the subject is or has been identified as or is specified as having an ECOG status of 0 or 1.

In some embodiments of any of the provided embodiments, the methods and/or uses and/or administration of cells according to the articles of manufacture, achieve certain outcomes and/or are associated with certain reduced risks of toxicity, e.g., in the population of subjects treated according to the methods or according to information provided in the article of manufacture. In some aspects, at least 35%, at least 40% or at least 50% of subjects treated according to the method achieve a complete response (CR) and/or a durable CR; and/or at least 50%, at least 60% or at least 70% of the subjects treated according to the method achieve objective response (OR) and/or a durable OR. In particular embodiments of any of the provided methods, the response is durable for greater than 3 months or greater than 6 months. In some embodiments, at least 40%, at least 50%, at least 60%, at least 70% of the subjects who, at or prior to the administration of the dose of cells had or were identified to have a double/triple hit lymphoma or relapse, optionally relapse within 12 months, following administration of an autologous stem cell transplant (ASCT), achieved an OR, optionally wherein the OR is durable for at or greater than 3 months or at or greater than 6 months. In certain embodiments of any of the provided methods, greater than or greater than about 50% of the subjects treated according to the method do not exhibit a grade 3 or greater cytokine release syndrome (CRS) or a grade 3 or greater neurotoxicity. In some embodiments, such subjects do not exhibit early onset CRS and/or neurotoxicity.

Provided herein are methods of assessing likelihood of a response to a cell therapy, the methods involving: assessing the level, amount or concentration of one or more analyte in a biological sample, wherein the one or more analyte is selected from ferritin, LDH, CXCL10, G-CSF, and IL-10, wherein: the biological sample is from a subject that is a candidate for treatment with the cell therapy, said cell therapy comprising a dose of genetically engineered cells expressing a recombinant receptor; and the biological sample is obtained from the subject prior to administering the cell therapy and/or said biological sample does not comprise the recombinant receptor and/or said engineered cells; and comparing, individually, the level, amount or concentration of the analyte in the sample to a threshold level, thereby determining a likelihood that a subject will achieve a response to the cell therapy. In some embodiments, the methods also involve administering the cell therapy to the subject if the subject is likely to achieve a response.

Provided herein are methods of selecting a subject for treatment, the methods involving: assessing the level, amount or concentration of one or more analyte in a biological sample, wherein the one or more analyte is selected from ferritin, LDH, CXCL10, G-CSF, and IL-10, wherein: the biological sample is from a subject that is a candidate for treatment with the cell therapy, said cell therapy comprising a dose of genetically engineered cells expressing a recombinant receptor; and the biological sample is obtained from the subject prior to administering the cell therapy and/or said biological sample does not comprise the recombinant receptor and/or said engineered cells; and selecting a subject who is likely to respond to treatment based on the results of determining a likelihood that a subject will achieve a response to the cell therapy by comparing, individually, the level, amount or concentration of the analyte in the sample to a threshold level. In some embodiments, the methods also involve administering the cell therapy to the subject selected for treatment.

Provided herein are methods of treatment, the methods involving: selecting a subject who is likely to respond to treatment with a cell therapy based on the results of determining a likelihood that a subject will achieve a response to the cell therapy by comparing, individually, the level, amount or concentration of one or more analyte in a biological sample, wherein the one or more analyte is selected from ferritin, LDH, CXCL10, G-CSF, and IL-10, to a threshold level, wherein: the biological sample is from a subject that is a candidate for treatment with the cell therapy, said cell therapy comprising a dose of genetically engineered cells expressing a recombinant receptor; and the biological sample is obtained from the subject prior to administering the cell therapy and/or said biological sample does not comprise the recombinant receptor and/or said engineered cells; and administering the cell therapy to a subject selected for treatment.

In some embodiments, the subject is likely to achieve a response if the level, amount or concentration of one or more of the analyte is below a threshold level and the subject is not likely to achieve a response if the level, amount or concentration of one or more of the analyte is above a threshold level.

In some embodiments, the threshold level is within 25%, within 20%, within 15%, within 10% or within 5% and/or is within a standard deviation below the median or mean level, amount or concentration, or is or is about the median or mean level, amount or concentration, of the analyte in a biological sample obtained from a group of subjects prior to receiving a cell therapy, wherein each of the subjects of the group went on to achieve a response after administration of a recombinant-receptor-expressing therapeutic cell composition for treating the same disease or condition.

In some embodiments, the threshold level is within 25%, within 20%, within 15%, within 10% or within 5% and/or is within a standard deviation above the median or mean level, amount or concentration of the analyte in a biological sample obtained from a group of subjects prior to receiving a cell therapy, wherein each of the subjects of the group went on to exhibit stable disease (SD) and/or progressive disease (PD) after administration of a recombinant-receptor-expressing therapeutic cell composition for treating the same disease or condition.

In some embodiments, the response comprises objective response. In some embodiments, the objective response comprises complete response (CR) or partial response (PR).

Provided herein are methods of assessing likelihood of a durable response to a cell therapy, the methods involving: assessing the level, amount or concentration of one or more analyte in a biological sample, wherein the one or more analyte is selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, wherein: the biological sample is from a subject that is a candidate for treatment with the cell therapy, said cell therapy comprising a dose of genetically engineered cells expressing a recombinant receptor; and the biological sample is obtained from the subject prior to administering the cell therapy and/or said biological sample does not comprise the recombinant receptor and/or said engineered cells; and comparing, individually, the level, amount or concentration of the analyte in the sample to a threshold level, thereby determining a likelihood that a subject will achieve a durable response to the cell therapy.

In some embodiments, the methods also involve administering the cell therapy to the subject if the subject is likely to achieve a response.

Provided herein are methods of selecting a subject for treatment, the methods involving: assessing the level, amount or concentration of one or more analyte in a biological sample, wherein the one or more analyte is selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, wherein: the biological sample is from a subject that is a candidate for treatment with the cell therapy, said cell therapy comprising a dose of genetically engineered cells expressing a recombinant receptor; and the biological sample is obtained from the subject prior to administering the cell therapy and/or said biological sample does not comprise the recombinant receptor and/or said engineered cells; and selecting a subject who is likely to respond to treatment based on the results of determining a likelihood that a subject will achieve a durable response to the cell therapy by comparing, individually, the level, amount or concentration of the analyte in the sample to a threshold level. In some embodiments, the methods also involve administering the cell therapy to the subject selected for treatment.

Provided herein are methods of treatment, the methods involving: selecting a subject who is likely to respond to treatment with a cell therapy based on the results of determining a likelihood that a subject will achieve a durable response to the cell therapy by comparing, individually, the level, amount or concentration of one or more analyte in a biological sample to a threshold level, wherein the one or more analyte is selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, wherein: the biological sample is from a subject that is a candidate for treatment with the cell therapy, said cell therapy comprising a dose of genetically engineered cells expressing a recombinant receptor; and the biological sample is obtained from the subject prior to administering the cell therapy and/or said biological sample does not comprise the recombinant receptor and/or said engineered cells; and administering the cell therapy to a subject selected for treatment.

In some embodiments, the subject is likely to achieve a durable response if the level, amount or concentration one or more of the analyte is below a threshold level and the subject is not likely to achieve a durable response if the level, amount or concentration one or more of the analyte is above a threshold level.

In some embodiments, the threshold level is within 25%, within 20%, within 15%, within 10% or within 5% and/or is within a standard deviation below the median or mean level, amount or concentration, or is or is about the median or mean level, amount or concentration, of the analyte in a biological sample obtained from a group of subjects prior to receiving a cell therapy, wherein each of the subjects of the group went on to achieve a durable response after administration of a recombinant-receptor-expressing therapeutic cell composition for treating the same disease or condition.

In some embodiments, the threshold level is within 25%, within 20%, within 15%, within 11% or within 5% and/or is within a standard deviation above the median or mean level, amount or concentration of the analyte in a biological sample obtained from a group of subjects prior to receiving a cell therapy, wherein each of the subjects of the group did not achieve a durable response after administration of a recombinant-receptor-expressing therapeutic cell composition for treating the same disease or condition.

In some embodiments, the durable response comprises a complete response (CR) or partial response (PR) that is durable for at or greater than 3 months, 4 months, 5 months, or 6 months.

In some embodiments, the durable response comprises a CR or PR that is durable for at least 3 months.

Provided herein are methods of assessing the risk of developing a toxicity after administration of a cell therapy, the methods involving assessing the level, amount or concentration of one or more analyte in a biological sample from a subject or a volumetric measure of tumor burden in a subject, wherein the one or more analyte is selected from LDH, Ferritin, C-reactive protein (CRP), D-dimer (fibrin degradation product), IL-6, IL-8, IL-10, IL-15, IL-16 TNF-α, IFN-α2, MCP-1, MIP-1α and MIP-1β, wherein: the subject is a candidate for treatment with the cell therapy, said cell therapy optionally comprising a dose or composition of genetically engineered cells expressing a recombinant receptor; and the biological sample is obtained from the subject prior to administering the cell therapy and/or said biological sample does not comprise the recombinant receptor and/or said engineered cells; and comparing, individually, the level, amount or concentration of the analyte in the sample or the volumetric measure of tumor burden to a threshold level, thereby determining a risk of developing a toxicity after administration of the cell therapy.

Provided herein are methods of identifying a subject, the methods involving assessing the level, amount or concentration of one or more analyte in a biological sample from a subject or a volumetric measure of tumor burden in a subject, wherein the one or more analyte is selected from LDH, Ferritin, C-reactive protein (CRP), D-dimer (fibrin degradation product), IL-6, IL-8, IL-10, IL-15, IL-16 TNF-α, IFN-α2, MCP-1, MIP-1α and MIP-1β, wherein: the subject is a candidate for treatment with the cell therapy, said cell therapy optionally comprising a dose or composition of genetically engineered cells expressing a recombinant receptor; and the biological sample is obtained from the subject prior to administering the cell therapy and/or said biological sample does not comprise the recombinant receptor and/or said engineered cells; and identifying a subject who has a risk of developing a toxicity after administration of a cell therapy based by comparing, individually, the level, amount or concentration of the analyte in the sample or the volumetric measure of tumor burden to a threshold level.

Provided herein are methods of treatment, comprising assessing the level, amount or concentration of one or more analyte in a biological sample from a subject or a volumetric measure of tumor burden in the subject, wherein the one or more analyte is selected from LDH, Ferritin, C-reactive protein (CRP), D-dimer (fibrin degradation product), IL-6, IL-8, IL-10, IL-15, IL-16 TNF-α, IFN-α2, MCP-1, MIP-1α and MIP-1β, wherein: the subject is a candidate for treatment with the cell therapy, said cell therapy optionally comprising a dose or composition of genetically engineered cells expressing a recombinant receptor; and the biological sample is obtained from the subject prior to administering the cell therapy and/or said biological sample does not comprise the recombinant receptor and/or said engineered cells; and; and comparing, individually, the level, amount or concentration of the analyte in the sample or the volumetric measure of tumor burden to a threshold level, thereby determining a risk of developing a toxicity after administration of the cell therapy; and following or based on the results of the assessment, administering to the subject the cell therapy, and, optionally, an agent or other treatment capable of treating, preventing, delaying, reducing or attenuating the development or risk of development of a toxicity.

In some embodiments, the biological sample is a blood or plasma sample.

In some embodiments, the volumetric measure of tumor burden is a sum of product dimensions (SPD) or is a volumetric measurement based on CT and/or MM imaging or other imaging of body. In some embodiments, the volumetric measure of tumor burden is carried out prior to treatment, prior to apheresis, or prior to cell product manufacturing.

In some embodiments, the methods also involve monitoring the subject for symptoms of toxicity if the subject is administered a cell therapy and is identified as having a risk of developing a toxicity.

In some embodiments, the subject has a risk of developing a toxicity if the level, amount or concentration one or more of the analyte or the volumetric measure of tumor burden is above a threshold level and the subject has a low risk of developing a toxicity if the level, amount or concentration one or more of the analyte or the volumetric measure of tumor burden is below a threshold level.

In some embodiments, the threshold level is within 25%, within 20%, within 15%, within 10% or within 5% and/or is within a standard deviation above the median or mean level, amount or concentration, or is or is about the median or mean level, amount or concentration, of the analyte or the volumetric measure of tumor burden in a biological sample obtained from a group of subjects prior to receiving a cell therapy, wherein each of the subjects of the group went on not to develop any toxicity after receiving a recombinant-receptor-expressing therapeutic cell composition for treating the same disease or condition.

In some embodiments, the threshold level is within 25%, within 20%, within 15%, within 10% or within 5% and/or is within a standard deviation below the median or mean level, amount or concentration of the analyte or the volumetric measure of tumor burden in a biological sample obtained from a group of subjects prior to receiving a cell therapy, wherein each of the subjects of the group went on to develop a toxicity after receiving a recombinant-receptor-expressing therapeutic cell composition for treating the same disease or condition.

In some embodiments, the toxicity is neurotoxicity or CRS.

In some embodiments, the toxicity is grade 1 or higher neurotoxicity or CRS.

In some embodiments, the toxicity is severe neurotoxicity or is grade 2 or higher neurotoxicit, a grade 3 or higher neurotoxicity, at least prolonged grade 3 neurotoxicity or is at or above grade 4 or grade 5 neurotoxixity; or the toxicity is severe CRS or comprises grade 2 or higher or grade 3 or higher CRS.

In some embodiments, the toxicity is neurotoxicity and the volumetric measure of tumor burden is SPD and the one or more analyte is selected from LDH, IL-10, IL-15, IL-16, TNF-α and MIP-1β.

In some embodiments, the toxicity is neurotoxicity and one or more analytes is assessed and the analytes are selected from LDH, Ferritin, CRP, IL-6, IL-8, IL-10, TNF-α, IFN-α2, MCP-1 and MIP-1β.

In some embodiments, the toxicity is neurotoxicity and one or more analytes is assessed and the analytes are selected from IL-8, IL-10 and CXCL10.

In some embodiments, the neurotoxicity is severe neurotoxicity or grade 3 or higher neurotoxicity.

In some embodiments, toxicity is CRS and the one or more analyte or volumetric measure of tumor burden is selected from LDH, SPD, CRP, d-dimer, IL-6, IL-15, TNF-α and MIP-1α.

In some embodiments, the CRS is severe CRS or grade 3 or higher CRS.

In some embodiments, if the subject is identified as having a risk of developing a toxicity, administering to the subject: (1) an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject; and/or a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject a cell therapy in an in-patient setting and/or with admission to the hospital for one or more days, optionally wherein the cell therapy is otherwise to be administered to subjects on an outpatient basis or without admission to the hospital for one or more days.

In some embodiments, the agent or other treatment is an anti-IL-6 antibody or an anti-IL6 receptor antibody.

In some embodiments, the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

In some embodiments, the agent or other treatment is or comprises a steroid, optionally dexamethasone.

In some embodiments, a volumetric measure is assessed and the volumetric measure is SPD and the threshold level is or is about 30 $cm^2$, is or is about 40 $cm^2$, is or is about 50 $cm^2$, is or is about 60 $cm^2$, or is or is about 70 $cm^2$. In some embodiments, the volumetric measure is SPD and the threshold level is or is about 50 $cm^2$.

In some embodiments, the one or more analyte is or comprises LDH and the threshold level is or is about 300 units per liter, is or is about 400 units per liter, is or is about 500 units per liter or is or is about 600 units per liter. In some embodiments, the analyte is LDH and the threshold level is or is about 500 units per liter.

In some embodiments, the recombinant receptor specifically binds to an antigen associated with the disease or condition or expressed in cells of the environment of a lesion associated with the disease or condition. In some embodiments, the disease or condition is a cancer. In some embodiments, the disease or condition is a myeloma, leukemia or lymphoma. In some embodiments, the disease or condition is a B cell malignancy and/or is acute lymphoblastic leukemia (ALL), adult ALL, chronic lymphoblastic leukemia (CLL), non-Hodgkin lymphoma (NEIL), and Diffuse Large B-Cell Lymphoma (DLBCL).

In some embodiments, the recombinant receptor is a chimeric antigen receptor (CAR). In some embodiments, the engineered cells comprise T cells, optionally $CD4^+$ and/or $CD8^+$. In some embodiments, the T cells are primary T cells obtained from a subject or are autologous to the subject.

Provided herein are methods of treating a subject having non-Hodgkin lymphoma (NHL), the methods comprising administering to the subject a dose of T cells comprising T cells expressing a chimeric antigen receptor (CAR) that specifically binds to a target antigen expressed by the NHL, wherein: the dose of T cells comprises between at or about $5 \times 10^7$ recombinant receptor-expressing T cells and $1 \times 10^8$ recombinant receptor-expressing T cells, inclusive, said dose comprising a defined ratio of $CD4^+$ cells expressing the recombinant receptor to $CD8^+$ cells expressing the recombinant receptor and/or of $CD4^+$ cells to $CD8^+$ cells, which ratio is approximately or is 1:1; and the method results in (1) a complete response (CR) in at least 35%, at least 40% or at least 50% of subjects treated and/or objective response (OR) in at least 50%, at least 60% or at least 70% of subjects treated and (2) results in no more than 50% of subjects exhibiting a cytokine release syndrome (CRS) higher than grade 2 and/or a neurotoxicity higher than grade 2.

In some embodiments of any of the provided methods, at least 40%, at least 50%, at least 60%, at least 70% of the subjects who, at or prior to the administration of the dose of cells had or were identified to have a double/triple hit lymphoma (or high-grade B-cell lymphoma, with MYC and BCL2 and/or BCL6 rearrangements with DLBCL histology (double/triple hit)) or relapse following administration of an autologous stem cell transplant (ASCT), achieved an OR, optionally wherein the OR is durable for at or greater than 3 months or at or greater than 6 months.

In some embodiments of any of the provided methods, the CR or the OR is durable for greater than 3 months or greater than 6 months. In particular embodiments of any of the provided methods, greater than or greater than about 50% of the subjects treated according to the method do not exhibit any grade of cytokine release syndrome (CRS) or neurotoxicity.

In some embodiments, the CR or the OR is durable for greater than 3 months or greater than 6 months; at least 20%, at least 25%, at least 35%, at least 40% or at least 50% of subjects treated according to the method achieve a CR that is durable; at least 60%, 70%, 80%, 90%, or 95% of subjects treated with the method and who achieve a CR, remain in CR or remain in response or remain surviving for at or greater than 3 months or at or greater than 6 months or at or greater than 9 months; and/or wherein at least 60%, 70%, 80%, 90%, or 95% of subjects treated with the method who achieve a CR by one month and/or by three months remain in response, remain in CR, and/or survive or survive without progression, for greater at or greater than 3 months and/or at or greater than 6 months and/or at greater than nine months; and/or at least 50%, at least 60% or at least 70% of the subjects treated according to the method achieve objective response (OR) optionally wherein the OR is durable, or is durable in at least 60%, 70%, 80%, 90%, or 95% of subjects achieving the OR, for at or greater than 3 months or at or greater than 6 months; and/or wherein at least 60%, 70%, 80%, 90%, or 95% of subjects treated with the method and achieving an OR remain in response or surviving for greater at or greater than 3 months and/or at or greater than 6 months.

In some embodiments, at or prior to administration of the dose of cells, the subject is or has been identified as having a lymphoma associated with or involving central nervous system (CNS) involvement; and/or at least 70%, at least 80%, at least 90% or at least 95% of subjects treated according to the method who, at or prior to the administration of the dose of cells exhibited or were identified to exhibit a lymphoma with CNS involvement, achieved a resolution of the CNS disease.

Provided herein are methods of treating a subject, the method involving administering, to a subject that has a lymphoma a dose of T cells comprising T cells expressing a chimeric antigen receptor (CAR) that specifically binds to a target antigen expressed by the lymphoma, wherein the lymphoma in the subject is associated with or involves central nervous system (CNS) involvement. In some aspects, at or prior to the time of administration of the dose of cells, the subject comprises a brain lesion, optionally a temporal lobe brain lesion. In some examples, the lymphoma is a B cell malignancy. In some embodiments, the lymphoma is non-Hodgkin lymphoma (NHL).

In some of any such embodiments, at least 35%, at least 40% or at least 50% of subjects treated according to the method achieve a complete response (CR) or remission of CNS disease and/or achieve reduction in or clearance of CNS disease, optionally wherein the CR or remission or reduction or clearance of the CNS disease is durable, or is durable in at least 60%, 70%, 80%, 90%, or 95% of subjects achieving the CR, for at or greater than 3 months or at or greater than 6 months; and/or at least 60%, 70%, 80%, 90%, or 95% of subjects achieving a CR or remission or other reduction of CNS disease by one month and/or by three months remain in response, remain in remission, e.g., in CR, or remain showing signs of the reduction or remission, and/or survive or survive without progression, for greater at or greater than 3 months and/or at or greater than 6 months and/or at greater than nine months; and/or at least 50%, at least 60% or at least 70% of the subjects treated according to the method achieve objective response (OR) or remission of CNS disease optionally wherein the OR or remission of the CNS disease is durable, or is durable in at least 60%, 70%, 80%, 90%, or 95% of subjects achieving the OR, for at or greater than 3 months or at or greater than 6 months; and/or at least 60%, 70%, 80%, 90%, or 95% of subjects achieving the OR or remission of CNS disease remain in response or surviving for greater at or greater than 3 months and/or at or greater than 6 months; and/or the brain lesion is reduced in size or volume, optionally by greater than or greater than about 25%, 50%, 75% or more. In some aspects, reduction or remission or clearance of CNS disease is achieved without or without substantial signs or symptoms of a toxicity, such as a neurotoxicity such as severe neurotoxicity, e.g., neurotoxicity greater than grade 2 or greater than grade 3, and/or without toxicity caused by activation or presence of the cellular therapy cells in the brain of the subject, and/or is achieved without an increased level of the toxicity, as compared to a subject in which CNS disease remains and/or treated with the therapy but that does not exhibit CNS disease.

In some embodiments of any of the provided methods, greater than or greater than about 30%, 35%, 40%, or 50% of the subjects treated according to the method do not exhibit any grade of cytokine release syndrome (CRS) or neurotoxicity. In some embodiments of any of the provided methods, at least at or about 45%, 50%, 60%, 65%, 70%, 75%, 80%, 85%, 90%, or 95% of subjects treated according to the method do not exhibit early onset CRS or neurotoxicity and/or do not exhibit onset of CRS earlier than 3 days following initiation of the administration and/or do not exhibit onset of neurotoxicity earlier than 5 days following initiation of the administration and/or wherein the median onset of neurotoxicity among subjects treated according to the method is at or after the median peak of, or median time to resolution of, CRS in subjects treated according to the method and/or the median onset of neurotoxicity among subjects treated according to the method is greater than at or about 8, 9, 10, or 11 days.

In certain embodiments of any of the provided methods, prior to initiation of administration of the dose of cells, the subject has not been administered an agent or treatment to capable of treating, preventing, delaying, reducing or attenuating the development or risk of development of a toxicity.

In certain embodiments of any of the provided methods, the subject is not administered an agent or treatment for the treatment or prevention or reduction or attenuation of a neurotoxicity and/or a cytokine release syndrome or risk thereof, within a period of time following administration of the dose, which period of time is optionally at or about 1, 2, 3, 4, 5 days or is optionally at or about 6, 7, 8, 9, 10, 11 days or is optionally 1, 2, 3 or 4 weeks. In certain embodiments of any of the provided methods, the subject is not administered an agent or treatment for the treatment or prevention or reduction or attenuation of a neurotoxicity and/or a cytokine release syndrome or risk thereof, following administration of the dose, prior to or unless the subject exhibits a sign or symptom of the toxicity and/or prior to or unless the subject exhibits a sign or symptom of the toxicity other than a fever, optionally wherein the fever is not a sustained fever or the fever is or has been reduced or reduced by more than 1° C. after treatment with an antipyretic. In certain embodiments of any of the provided methods, the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

In some embodiments of any of the provided methods, prior to initiation of administration of the dose of cells, the subject has not been administered an anti-IL-6 or anti-IL-6R antibody, optionally tocilizumab or situximab, and/or has not been administered a steroid, optionally dexamethasone. In certain embodiments of any of the provided methods, the subject is not administered an anti-IL-6 or anti-IL-6R antibody, optionally tocilizumab or siltuximab, and/or has not been administered a steroid, optionally dexamethasone, within a period of time following administration of the dose, which period of time is optionally at or about 1, 2, 3, 4, 5 days or is optionally at or about 6, 7, 8, 9, 10, 11 days or is optionally 1, 2, 3 or 4 weeks. In certain embodiments of any of the provided methods, the subject is not administered an anti-IL-6 or anti-IL-6R antibody, optionally tocilizumab or siltuximab, and/or has not been administered a steroid, optionally dexamethasone, following administration of the cell dose, prior to, or unless, the subject exhibits a sign or symptom of a toxicity, optionally a neurotoxicity or CRS, and/or prior to, or unless, the subject exhibits a sign or symptom of a toxicity, optionally a neurotoxicity or CRS, other than a fever, optionally wherein the fever is not a sustained fever or the fever is or has been reduced or reduced by more than 1° C. after treatment with an antipyretic. In certain embodiments of any of the provided methods, the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

In some embodiments of any of the provided methods, the administration is carried out on an outpatient basis and/or without requiring admission to or an overnight stay at a hospital. In some embodiments of any of the provided methods, if the subject, who is or has been treated on an outpatient basis, exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

In particular embodiments of any of the provided methods, the NHL is selected from the group consisting of aggressive NHL, diffuse large B cell lymphoma (DLBCL), NOS (de novo and transformed from indolent), primary mediastinal large B cell lymphoma (PMBCL), mantle cell lymphoma (MCL), and/or follicular lymphoma (FL), optionally follicular lymphoma Grade 3B (FL3B). In certain embodiments of any of the provided methods, the NHL comprises diffuse large B cell lymphoma (DLBCL), primary mediastinal large B cell lymphoma (PMBCL), NOS (de novo or transformed from indolent lymphoma), or follicular lymphoma Grade 3B. In some examples, the NHL includes DLBCL. In some embodiments of any of the provided methods, the DLBCL is de novo or transformed from follicular lymphoma (FL) and/or does not comprise DLBCL transformed from MZL and CLL (Richter's).

In particular embodiments of any of the provided methods, the subject is or has been identified as having an Eastern Cooperative Oncology Group Performance Status (ECOG) status of 0, 1 or 2. In certain embodiments of any of the provided methods, the subject is or has been identified as having an ECOG status of 0 or 1. In some embodiments of any of the provided methods, at or immediately prior to the time of the administration of the dose of cells the subject has relapsed following remission after treatment with, or become refractory to, one or more prior therapies for the NHL, optionally one, two or three prior therapies other than another dose of cells expressing the CAR.

In some embodiments of any of the provided methods, at or prior to administration of the dose of cells, the subject is or has been identified as having a lymphoma associated with or involving central nervous system (CNS) involvement. In some embodiments of any of the provided methods, at least 70%, at least 80%, at least 90% or at least 95% of subjects treated according to the method who, at or prior to the administration of the dose of cells exhibited or were identified to exhibit a lymphoma with CNS involvement, achieved a resolution of the CNS disease.

In particular embodiments of any of the provided methods, at or prior to the administration of the dose of cells: the subject is or has been identified as having a double/triple hit lymphoma (or high-grade B-cell lymphoma, with MYC and BCL2 and/or BCL6 rearrangements with DLBCL histology (double/triple hit)); the subject is or has been identified as having a chemorefractory lymphoma, optionally a chemorefractory DLBCL; the subject has not achieved complete remission (CR) in response to a prior therapy; and/or the subject has relapsed within 1 year or less than 1 year after receiving an autologous stem cell transplant (ASCT).

In some embodiments of any of the provided methods, the method includes, prior to administration of the dose of cells, identifying or selecting a subject for the administration of the dose of cells that has a double/triple hit lymphoma (or high-grade B-cell lymphoma, with MYC and BCL2 and/or BCL6 rearrangements with DLBCL histology (double/triple hit)), a chemorefractory lymphoma, optionally a chemorefractory DLBCL, has not achieved complete remission (CR) in response to a prior therapy for treating the malignancy, optionally the NHL; and/or has relapsed within 1 year or less than 1 year after receiving an autologous stem cell transplant (ASCT); and/or has a lymphoma associated with or involving central nervous system (CNS) involvement.

In some embodiments of any of the provided methods, the method further includes administration of an additional therapeutic agent or therapy, optionally other than a cell therapy, optionally other than CAR+ T cell therapy. In some embodiments, the additional therapeutic agent or therapy is for treating the NHL or malignancy and/or increases the persistence, activity and/or efficacy of the dose of cells. In some embodiments, the additional therapeutic agent or therapy is administered if the subject does not exhibit a response, optionally does not exhibit a CR or OR, to the cell therapy within 1 month, within 2 months or within 3 months after administration of the dose of cells. In some embodiments, the additional therapeutic agent or therapy is administered to a subject: that is or has been identified to have stable or progressive disease (SD/PD) following treatment with a prior therapy, optionally a prior therapy with a chemotherapeutic agent, that is or has been identified with an Eastern Cooperative Oncology Group Performance Status (ECOG) status of 2, that is or has been identified as having a transformed follicular lymphoma (tFL) and/or that is or has been identified has having a DLBCL transformed from MZL and CLL. In some embodiments, prior to administration of the dose of cells or the additional therapeutic agent or therapy, the method includes identifying or selecting a subject for the administration of the dose of cells that has stable or progressive disease (SD/PD) following treatment with a prior therapy, optionally a prior therapy with a chemotherapeutic agent, an Eastern Cooperative Oncology Group Performance Status (ECOG) status of 2, a transformed follicular lymphoma (tFL) and/or a DLBCL transformed from MZL and CLL. In some of any of such embodiments, the additional therapeutic agent or therapy is administered prior to, with or at the same time and/or subsequent to initiation of administration of the dose of cells.

In certain embodiments of any of the provided methods, the CAR comprises an scFv specific for the antigen, a transmembrane domain, a cytoplasmic signaling domain derived from a costimulatory molecule, which optionally is a 4-1BB, and a cytoplasmic signaling domain derived from a primary signaling ITAM-containing molecule, which optionally is a CD3zeta. In some embodiments of any of the provided methods, the antigen is a B cell antigen, which optionally is CD19.

In particular embodiments of any of the provided methods, prior to the administration, the subject has been preconditioned with a lymphodepleting therapy comprising the administration of fludarabine and/or cyclophosphamide. Certain embodiments of any of the provided methods further comprise, immediately prior to the administration, administering a lymphodepleting therapy to the subject comprising the administration of fludarabine and/or cyclophosphamide. In some embodiments of any of the provided methods, the lymphodepleting therapy comprises administration of cyclophosphamide at about 200-400 mg/m$^2$, optionally at or about 300 mg/m$^2$, inclusive, and/or fludarabine at about 20-40 mg/m$^2$, optionally 30 mg/m$^2$, daily for 2-4 days, optionally for 3 days. In particular embodiments of any of the provided methods, the lymphodepleting therapy comprises administration of cyclophosphamide at or about 300 mg/m$^2$ and fludarabine at about 30 mg/m$^2$ daily for 3 days.

In certain embodiments of any of the provided methods, the administration of the cell dose and/or the lymphodepleting therapy is carried out via outpatient delivery. In some embodiments of any of the provided methods, the dose of cells is administered parenterally, optionally intravenously.

In particular embodiments of any of the provided methods: at least 40% or at least 50% of subjects treated according to the method achieve complete remission (CR), exhibit progression-free survival (PFS) and/or overall survival (OS) of greater than at or about 3 months, 6 months or 12 months; on average, subjects treated according to the method exhibit a median PFS or OS of greater than at or about 6 months, 12 months, or 18 months; and/or the subject exhibits PFS or OS following therapy for at least at or about 6, 12, 18 or more months. In certain embodiments of any of the provided methods, at or about 14 or 28 days after initiation of administration of the dose of cells, the number of CAR$^+$ T cells, optionally CAR$^+$ CD8$^+$ T cells and/or CAR$^+$ CD4$^+$ T cells, detectable in the blood of the subject, or in a majority of subjects so treated by the method, is greater than1 cells per greater than 5 cells per µL or greater than per 10 cells per µL.

In some embodiments of any of the provided methods, the T cells are primary T cells obtained from a subject. In particular embodiments of any of the provided methods, the T cells are autologous to the subject. In certain embodiments of any of the provided methods, the T cells are allogeneic to the subject. In some embodiments of any of the provided methods, the T cells comprise CD4$^+$ and CD8$^+$ T cells administered as a plurality of compositions, said plurality of compositions comprising administration of a first composition comprising the CD4$^+$ T cells or the CD8$^+$ T cells and administration of a second composition comprising the other of the CD4$^+$ T cells or the CD8$^+$ T cells.

In particular embodiments of any of the provided methods, the first composition and second composition are administered 0 to 12 hours apart, 0 to 6 hours apart or 0 to 2 hours apart. In certain embodiments of any of the provided methods, the first composition and second composition are administered no more than 2 hours, no more than 1 hour, no more than 30 minutes, no more than 15 minutes, no more than 10 minutes or no more than 5 minutes apart. In some embodiments of any of the provided methods, the first composition comprises the CD4$^+$ T cell. In particular embodiments of any of the provided methods, the first composition comprises the CD8$^+$ T cells. In certain embodiments of any of the provided methods, the first composition is administered prior to the second composition.

In some embodiments of any of the provided methods, the dose of T cells is administered to the subject as a single dose or is administered only one time within a period of two weeks, one month, three months, six months, 1 year or more. In particular embodiments of any of the provided methods, the dose of T cells is administered as a double dose comprising a first dose of the T cells and a consecutive dose of the T cells, wherein one or both of the first dose and the second dose comprises administration of the plurality of compositions of T cells. In certain embodiments of any of the provided methods, the consecutive dose is administered at a point in time that is at least or more than about 7 days or 14 days after and less than about 28 days after initiation of the administration of the first dose of cells.

Provided herein is an article of manufacture comprising a cell therapy comprising a dose or composition of genetically engineered cells expressing a chimeric antigen receptor (CAR), and instructions for administering the cell therapy, wherein the instructions specify: the dose of cells is to be administered to a subject having or identified to have non-Hodgkin lymphoma (NHL), the NHL selected from diffuse large B cell lymphoma (DLBCL), primary mediastinal large B cell lymphoma (PMBCL), NOS (de novo or transformed from indolent lymphoma), or follicular lymphoma Grade 3B, wherein the subject is or has been identified as having an Eastern Cooperative Oncology Group Performance Status (ECOG) status of 0 or 1; and the dose of T cells to be administered comprises between at or about 5×10$^7$ CAR-expressing T cells and 1×10$^8$ CAR-expressing T cells, inclusive. In some embodiments of any of the provided articles of manufacture, the instructions specify administering the dose of T cells at a defined ratio of CD4$^+$ cells expressing the CAR to CD8$^+$ cells expressing the CAR and/or of CD4$^+$ cells to CD8$^+$ cells, which ratio optionally is approximately 1:1 or is between approximately 1:3 and approximately 3:1.

Provided herein is an article of manufacture comprising a cell therapy comprising a dose or composition of genetically engineered cells expressing a chimeric antigen receptor (CAR), and instructions for administering the cell therapy, wherein the instructions specify: the dose of T cells is to be administered at a defined ratio of CD4$^+$ cells expressing the CAR to CD8$^+$ cells expressing the CAR and/or of CD4$^+$ cells to CD8$^+$ cells, which ratio is approximately or is 1:1; and the dose of cells is to be administered to a subject having or identified to have non-Hodgkin lymphoma (NHL), the NHL selected from diffuse large B cell lymphoma (DLBCL), primary mediastinal large B cell lymphoma (PMBCL), NOS (de novo or transformed from indolent lymphoma), or follicular lymphoma Grade 3B.

Provided herein is an article of manufacture comprising a cell therapy comprising a dose or composition of genetically engineered cells expressing a chimeric antigen receptor (CAR), and instructions for administering the cell therapy, wherein the instructions specify: the dose of cells is to be administered to a subject having or identified to have non-Hodgkin lymphoma (NHL), optionally an NHL selected from aggressive NHL, diffuse large B cell lymphoma (DLBCL), NOS (de novo and transformed from indolent), primary mediastinal large B cell lymphoma (PMBCL), mantle cell lymphoma (MCL), and/or follicular lymphoma (FL), optionally follicular lymphoma Grade 3B (FL3B), the dose of T cells to be administered comprises between at or about 5×10$^7$ CAR-expressing T cells and 1×10$^8$ CAR-expressing T cells, inclusive; and the dose of T cells is to be administered at a defined ratio of CD4$^+$ cells expressing the CAR to CD8$^+$ cells expressing the CAR and/or of CD4$^+$ cells to CD8$^+$ cells, which ratio is approximately or is 1:1.

In some embodiments of any of the provided articles of manufacture, the instructions further specify the dose of cells is to be administered to a subject that is or has been identified as having an Eastern Cooperative Oncology Group Performance Status (ECOG) status of 0, 1 or 2, optionally an ECOG status of 0 or 1. In certain embodiments of any of the provided articles of manufacture, the instructions specify that the administration is in a subject that has not received, immediately prior to the administration of the dose of cells or within or about 1 month of the dose of cells, an agent or treatment capable of treating, preventing, delaying, reducing or attenuating the development or risk of development of a toxicity. In some embodiments of any of the provided articles of manufacture, the agent is or comprises an anti-IL-6 or anti-IL-6R antibody, optionally tocilizumab or siltuximab, and/or a steroid, optionally dexamethasone. In particular embodiments of any of the provided articles of manufacture, the instructions specify the dose of cells is not for administration in a subject having DLBCL transformed from MZL and CLL (Richter's) and/or is for a subject having a DLBCL that is de novo or transformed from indolent disease. In some embodiments of any of the provided articles of manufacture, the instructions specify the subject does not have a DLBCL transformed from MZL and CLL (Richter's).

In some embodiments of any of the provided articles of manufacture, the instructions specify the administration of the cell therapy is for a subject that is or has been identified as having a double/triple hit lymphoma (or high-grade B-cell lymphoma, with MYC and BCL2 and/or BCL6 rearrangements with DLBCL histology (double/triple hit)), is or has been identified as having a chemorefractory lymphoma, optionally a chemorefractory DLBCL; and/or that has not achieved complete remission (CR) in response to a prior therapy. In certain embodiments of any of the provided articles of manufacture, the CAR comprises an scFv specific for the antigen, a transmembrane domain, a cytoplasmic signaling domain derived from a costimulatory molecule, which optionally is a 4-1BB, and a cytoplasmic signaling domain derived from a primary signaling ITAM-containing molecule, which optionally is a CD3zeta. In certain embodiments of any of the provided articles of manufacture, the antigen is a B cell antigen, which optionally is CD19.

Particular embodiments of any of the provided articles of manufacture further comprise instructions for use with, after or in connection with a lymphodepleting therapy, the lymphodepleting therapy optionally comprising fludarabine and/or cyclophosphamide. In certain embodiments of any of the provided articles of manufacture, the lymphodepleting therapy comprises administration of cyclophosphamide at about 200-400 mg/m$^2$, optionally at or about 300 mg/m$^2$, inclusive, and/or fludarabine at about 20-40 mg/m$^2$, optionally 30 mg/m$^2$, daily for 2-4 days, optionally for 3 days. In particular embodiments of any of the provided articles of manufacture, the lymphodepleting therapy comprises administration of cyclophosphamide at or about 300 mg/m$^2$ and fludarabine at about 30 mg/m$^2$ daily for 3 days.

In some embodiments of any of the provided articles of manufacture, the instructions further specify the administration of the cell therapy is to be or may be administered to the subject on an outpatient setting and/or without admission of the subject to the hospital overnight or for one or more consecutive days and/or is without admission of the subject to the hospital for one or more days. In certain embodiments of any of the provided articles of manufacture, the instructions further specify the cell therapy is for parenteral administration, optionally intravenous administration. In particular embodiments of any of the provided articles of manufacture, the cell therapy comprises primary T cells obtained from a subject. In some embodiments of any of the provided articles of manufacture, the T cells are autologous to the subject. In certain embodiments of any of the provided articles of manufacture, the T cells are allogeneic to the subject.

In particular embodiments of any of the provided articles of manufacture, the article of manufacture comprises a plurality of compositions of the cell therapy, the plurality of compositions comprising a first composition of genetically engineered cells comprising CD4$^+$ T cells or CD8$^+$ T cells, wherein the instructions specify the first composition is for use in with a second composition comprising the other of the CD4$^+$ T cells or the CD8$^+$ T cells, optionally wherein the cells of the first composition and cells of the same composition are from the same subject.

In some embodiments of any of the provided articles of manufacture, the instructions specify the first composition and second composition are to be administered at a defined ratio of CD4$^+$ cells expressing the recombinant receptor to CD8$^+$ cells expressing the recombinant receptor and/or of CD4$^+$ cells to CD8$^+$ cells, which ratio optionally is approximately 1:1 or is between approximately 1:3 and approximately 3:1. In certain embodiments of any of the provided articles of manufacture, the defined ratio is or is approximately 1:1. In particular embodiments of any of the provided articles of manufacture, the composition further comprises a cryoprotectant and/or the article further includes instructions for thawing the composition prior to administration to the subject.

In some embodiments of any of the provided articles of manufacture, the instructions specify administering the composition comprising the CD4$^+$ T cells and the composition comprising the CD8$^+$ T cells 0 to 12 hours apart, 0 to 6 hours apart or 0 to 2 hours apart. In certain embodiments of any of the provided articles of manufacture, the instructions specify administering the composition comprising the CD4$^+$ T cells and the composition comprising the CD8$^+$ T cells no more than 2 hours, no more than 1 hour, no more than 30 minutes, no more than 15 minutes, no more than 10 minutes or no more than 5 minutes apart. In particular embodiments of any of the provided articles of manufacture, the instructions specify administering the composition comprising the CD4$^+$ T cells prior to administering the composition comprising the CD8$^+$ cells. In some embodiments of any of the provided articles of manufacture, the instructions specify administering the composition comprising the CD8$^+$ T cells prior to administering the composition comprising the CD4$^+$ cells.

Provided herein are articles of manufacture comprising one or more reagent capable of detecting one or more analytes, and instructions for using the reagent to assay a biological sample from a subject that is a candidate for treatment, optionally with a cell therapy, said cell therapy optionally comprising a dose or composition of genetically engineered cells expressing a recombinant receptor, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perform, and D-dimer (fibrin degradation product).

Particular embodiments of any of the provided articles of manufacture further comprise the cell therapy and/or further comprising instructions for use with, prior to and/or in connection with treatment with the cell therapy. Certain embodiments of any of the provided articles of manufacture further comprise one or more agents or treatments for treating, preventing, delaying, reducing or attenuating the development or risk of development of a toxicity and/or instructions for the administration of one or more agents or treatments for treating, preventing, delaying, reducing or attenuating the development or risk of development of a toxicity in the subject.

In some embodiments of any of the provided articles of manufacture, the instructions further specify, if the level, amount or concentration of the analyte in the sample is at or above a threshold level for the analyte: administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In particular embodiments of any of the provided articles of manufacture, the instructions further specify, if the level, amount or concentration of the analyte is below a threshold level for the analyte, administering to the subject the cell therapy, optionally at a non-reduced dose, optionally on an outpatient basis or without admission to the hospital for one or more days.

In certain embodiments of any of the provided articles of manufacture, the instructions further specify administering the cell therapy to the subject and wherein the instructions further specify, if the level, amount or concentration of the analyte, is below a threshold level: the administration of the cell therapy does not comprise administering, prior to or concurrently with administering the cell therapy and/or prior to the development of a sign of symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

In some embodiments of any of the provided articles of manufacture, the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. Provided herein is an article of manufacture comprising a cell therapy, said cell therapy optionally comprising a dose or composition of genetically engineered cells expressing a recombinant receptor, and instructions for administering the cell therapy following or based on the results of an assessment, in a biological sample of the level, or amount or concentration of one or more analyte in a biological sample, said biological sample obtained from the subject prior to administering the cell therapy and/or said biological sample not comprising the recombinant receptor and/or said engineered cells, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product).

In particular embodiments of any of the provided articles of manufacture, said assessment comprises detection which optionally comprises contacting a reagent capable of directly or indirectly detecting the analyte with the biological sample and determining the level, amount or concentration of the analyte in the biological sample. Certain embodiments of any of the provided articles of manufacture further comprise the reagent and/or further comprising instructions for use with, prior to and/or in connection with the reagent for detecting the analyte. Some embodiments of any of the provided articles of manufacture further comprise one or more agents or treatments for treating, preventing, delaying, reducing or attenuating the development or a risk of development of a toxicity and/or instructions for the administration of one or more agents or treatments for treating, preventing, delaying, reducing or attenuating the development or risk of development of a toxicity in the subject.

In particular embodiments of any of the provided articles of manufacture, the instructions for administering the cell therapy specify, if the level, amount or concentration of the analyte in the sample, is at or above a threshold level: administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of administration of the therapeutic cell composition or the genetically engineered cells; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In certain embodiments of any of the provided articles of manufacture, the instructions for administering the cell therapy specify, if the level, amount or concentration of the analyte in the sample, is below a threshold level, administering to the subject the cell therapy, optionally at a non-reduced dose, optionally on an outpatient basis or without admission to the hospital for one or more days. In some embodiments of any of the provided articles of manufacture, the instructions further specify administering the cell therapy to the subject and wherein the instructions further specify, if the level, amount or concentration of the analyte is below a threshold level: not administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

In particular embodiments of any of the provided articles of manufacture, the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

Provided herein are articles of manufacture comprising an agent capable of treating, preventing, delaying, reducing or attenuating the development or risk of development of a toxicity, and instructions for administering the agent following or based on the results of an assessment in a biological sample of the level, amount or concentration of one or more analytes in a biological sample, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product). In certain embodiments of any of the provided articles of manufacture, said assessment comprises detection which optionally comprises contacting a reagent capable of directly or indirectly detecting the analyte with the biological sample and determining the level, amount or concentration of the analyte in the biological sample.

In some embodiments of any of the provided articles of manufacture, the instructions specify that the agent is to be administered i) prior to, (ii) within one, two, or three days of, (iii) concurrently with and/or (iv) at first fever following, the initiation of administration of the cell therapy to the subject and/or further comprises instructions for use with, prior to and/or in connection with treatment with the cell therapy. In particular embodiments of any of the provided articles of manufacture, said biological sample is obtained from the subject prior to administering the agent or cell therapy. In certain embodiments of any of the provided articles of manufacture, the reagent is a binding molecule that specifically binds to the marker or cells of the myeloid cell population. In some embodiments of any of the provided articles of manufacture, the reagent is an antibody or an antigen-binding fragment thereof. In particular embodiments of any of the provided articles of manufacture, the biological sample is or is obtained from a blood, plasma or serum sample. In certain embodiments of any of the provided articles of manufacture, comprising the reagent for detecting the analyte and/or further comprising instructions for use with, prior to and/or in connection with the reagent for detecting the analyte. Some embodiments of any of the provided articles of manufacture further comprise the cell therapy and/or further comprising instructions for use with, prior to and/or in connection with treatment with the cell therapy.

In particular embodiments of any of the provided articles of manufacture, the instructions for administering the agent specify, if the level, amount or concentration of the analyte in the sample, is at or above a threshold level administering to the subject the agent. In certain embodiments of any of the provided articles of manufacture, the instruction further specify administering a cell therapy to the subject, wherein administration of the agent is to be carried out (i) prior to, (ii) within one, two, or three days of, (iii) concurrently with and/or (iv) at first fever following, the initiation of administration of the cell therapy to the subject. In some embodiments of any of the provided articles of manufacture, the instructions for administering the agent specify, if the level, amount or concentration is below the threshold level administering to the subject the cell therapy, optionally. wherein the instructions specify the cell therapy is to be or may be administered to the subject on an outpatient setting and/or without admission of the subject to the hospital overnight or for one or more consecutive days and/or is without admission of the subject to the hospital for one or more days.

In particular embodiments of any of the provided articles of manufacture, the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. In certain embodiments of any of the provided articles of manufacture, assaying or assessing cells for the analyte is by an immunoassay.

In some embodiments of any of the provided articles of manufacture, the toxicity comprises neurotoxicity or cytokine release syndrome (CRS), optionally grade 1 or higher neurotoxicity or CRS. In particular embodiments of any of the provided articles of manufacture: the toxicity comprises severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or the toxicity comprises severe CRS and/or comprises grade 2 or higher or grade 3 or higher CRS. In certain embodiments of any of the provided articles of manufacture, the toxicity is associated with cerebral edema.

In some embodiments of any of the provided articles of manufacture, the agent or other treatment is or comprises one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function. In particular embodiments of any of the provided articles of manufacture, the antagonist or inhibitor is or comprises an agent selected from among an antibody or antigen-binding fragment, a small molecule, a protein or peptide and a nucleic acid. In certain embodiments of any of the provided articles of manufacture, the agent or other treatment is an anti-IL-6 antibody or an anti-IL6 receptor antibody.

In some embodiments of any of the provided articles of manufacture, the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. In particular embodiments of any of the provided articles of manufacture, the agent or other treatment is or comprises tocilizumab. In certain embodiments of any of the provided articles of manufacture, the agent or other treatment is or comprises siltuximab. In some embodiments of any of the provided articles of manufacture, the steroid is or comprises dexamethasone.

In particular embodiments of any of the provided articles of manufacture, the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124). In certain embodiments of any of the provided articles of manufacture, the agent capable of preventing, blocking or reducing microglial cell activation or function is a small molecule, peptide, protein, antibody or antigen-binding fragment thereof, an antibody mimetic, an aptamer, or a nucleic acid molecule.

In some embodiments of any of the provided articles of manufacture, the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003. In particular embodiments of any of the provided articles of manufacture, the agent is an inhibitor of colony stimulating factor 1 receptor (CSF1R). In certain embodiments of any of the provided articles of manufacture, the inhibitor is selected from: PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof; emactuzumab, IMC-CS4, FPA008, LY-3022855, AMG-820 and TG-3003 or is an antigen-binding fragment thereof; or a combination of any of the foregoing. In some embodiments of any of the provided articles of manufacture, the inhibitor is PLX-3397.

In certain embodiments of any of the provided articles of manufacture, the disease or condition is a cancer. In particular embodiments of any of the provided articles of manufacture, the disease or condition is a myeloma, leukemia or lymphoma. In some embodiments of any of the provided articles of manufacture, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

In certain embodiments of any of the provided articles of manufacture, the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAM), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen.

In particular embodiments of any of the provided articles of manufacture, the recombinant receptor is a T cell receptor or a functional non-T cell receptor. In some embodiments of any of the provided articles of manufacture, the recombinant receptor is a chimeric antigen receptor (CAR). In certain embodiments of any of the provided articles of manufacture, the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ζ) chain; and/or wherein the CAR further comprises a costimulatory signaling region, which optionally comprises a signaling domain of CD28 or 4-1BB.

In particular embodiments of any of the provided articles of manufacture, the engineered cells comprise T cells, optionally $CD4^+$ and/or $CD8^+$. In some embodiments of any of the provided articles of manufacture, the T cells are primary T cells obtained from a subject. In certain embodiments of any of the provided articles of manufacture, the dose that is not associated with risk of developing toxicity or severe toxicity is or comprises less than or less than about $5\times10^7$ total recombinant receptor-expressing cells, optionally $CAR^+$ cells, total T cells, or total peripheral blood mononuclear cells (PBMCs), such as less than or less than about $2.5\times10^7$, less than or less than about $1.0\times10^7$, less than or less than about $5.0\times10^6$, less than or less than about $1.0\times10^6$, less than or less than about $5.0\times10^5$, or less than or less than about $1\times10^5$ total recombinant receptor-expressing cells, optionally $CAR^+$ cells, total T cells, or total peripheral blood mononuclear cells (PBMCs). In particular embodiments of any of the provided articles of manufacture, the dose that is not associated with risk of developing toxicity or severe toxicity is or comprises from or from about $1\times10^5$ to $5\times10^7$ total recombinant receptor-expressing cells, optionally $CAR^+$ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10^7$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally $CAR^+$ cells, total T cells, or total peripheral blood mononuclear cells (PBMCs).

In certain embodiments of any of the provided articles of manufacture, the reagent is detectably labeled, optionally fluorescently labeled. In some embodiments of any of the provided articles of manufacture, the one or more analyte is LDH, ferritin, CRP, IL-6, IL-8, IL-10, TNF-alpha, IFN-alpha2, MCP-1 and MCP-1beta. In particular embodiments of any of the provided articles of manufacture, the one or more analyte is or comprises LDH.

Provided herein are methods of selecting a subject for treatment, the method comprising: (a) contacting a biological sample with one or more reagent capable of detecting or that is specific for one or more analyte, wherein the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product), wherein: the biological sample is from a subject that is a candidate for treatment with a cell therapy, said cell therapy optionally comprising a dose or composition of genetically engineered cells expressing a recombinant receptor; and the biological sample is obtained from the subject prior to administering the cell therapy and/or said biological sample does not comprise the recombinant receptor and/or said engineered cells; and (b) selecting a subject in which either: (i) the level, amount or concentration of the analyte in the samples at or above a threshold level, thereby identifying a subject that is at risk for developing a toxicity to the cell therapy; or (ii) the level, amount or concentration of the analyte is below a threshold level.

In certain embodiments of any of the provided methods: (a) a subject in (i) is selected for administering to the subject (1) an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject; and/or (c) a subject in (i) is selected for administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (b) a subject in (i) is selected for administering to the subject a cell therapy in an in-patient setting and/or with admission to the hospital for one or more days, optionally wherein the cell therapy is otherwise to be administered to subjects on an outpatient basis or without admission to the hospital for one or more days.

In some embodiments of any of the provided methods, a subject in (i) is selected, and the method further comprises: (a) administering to the subject (1) an agent or other treatment capable of treating, preventing, delaying, reducing or attenuating the development or risk of development of a toxicity and (2) the cell therapy, wherein administration of the agent is carried out (i) prior to, (ii) within one, two, or three days of, (iii) concurrently with and/or (iv) at first fever following, the initiation of administration of the cell therapy to the subject; and/or (b) administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (c) administering to the subject a cell therapy or a dose of genetically engineered cells of a cell therapy that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (d) administering to the subject a cell therapy in an in-patient setting and/or with admission to the hospital for one or more days, optionally wherein the cell therapy is otherwise to be administered to subjects on an outpatient basis or without admission to the hospital for one or more days.

In particular embodiments of any of the provided methods: (a) a subject in (ii) is selected for administering to the subject a cell therapy, optionally at a non-reduced dose, optionally on an outpatient basis or without admission to the hospital for one or more days; (b) a subject in (ii) is selected for administering to the subject a cell therapy, wherein the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or a subject in (ii) is selected for administering a cell therapy on an outpatient setting and/or without admission of the subject to the hospital overnight or for one or more consecutive days and/or is without admission of the subject to the hospital for one or more days.

In certain embodiments of any of the provided methods, a subject in (ii) is selected, and the method further comprises administering to the subject the cell therapy, optionally at a non-reduced dose, optionally on an outpatient basis or without admission to the hospital for one or more days. In some embodiments of any of the provided methods, a subject in (ii) is selected, and the method further comprises administering to the subject the cell therapy, wherein: the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

Provided herein is a method of treatment, comprising: (a) assaying a biological sample for the level, amount or concentration of one or more analyte, wherein the biological sample is from a subject that is a candidate for treatment, optionally with a cell therapy, said cell therapy optionally comprising a dose or composition of genetically engineered cells expressing a recombinant receptor for treating a disease or condition, wherein the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product); and (b) following or based on the results of the assay, administering to the subject the cell therapy, and, optionally, an agent or other treatment capable of treating, preventing, delaying, reducing or attenuating the development or risk of development of a toxicity.

Provided herein is a method of treatment, comprising, following or based on the results of an assay, of a biological sample from a subject, for the level, amount or concentration of one or more analyte, administering to the subject (i) a cell therapy, optionally comprising a dose or composition of genetically engineered expressing a recombinant receptor for treating a disease or condition, and, optionally, (ii) an agent or other treatment capable of treating, preventing, delaying, reducing or attenuating the development or risk of development of a toxicity, wherein: the biological sample is obtained from the subject prior to administering the cell therapy; and the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product).

In particular embodiments of any of the provided methods, said assaying comprises detection which optionally comprises contacting a reagent capable of directly or indirectly detecting the analyte with the biological sample and determining the level, amount or concentration of the analyte in the biological sample. In certain embodiments of any of the provided methods, if the level, amount or concentration of the analyte in the sample, is at or above a threshold level: administering to the subject the agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

In some embodiments of any of the provided methods, if the level, amount or concentration of the analyte, is at or above a threshold level: the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

In particular embodiments of any of the provided methods, administering, to a subject, an agent or other treatment capable of treating, preventing, delaying, reducing or attenuating the development or risk of development of a toxicity, wherein: the subject is a candidate for treatment optionally with a cell therapy, said cell therapy optionally comprising a dose or composition of genetically engineered cells expressing a recombinant receptor for treating a disease or condition; and the subject has been identified as at risk for developing a toxicity following or based on the results of an assay, of a biological sample from a subject, for the level, amount or concentration of one or more analyte, said biological sample obtained from the subject prior to administering the cell therapy and/or said biological sample not comprising the recombinant receptor and/or said engineered cells, wherein the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product).

In certain embodiments of any of the provided methods, said assay comprises detection which optionally comprises contacting a reagent capable of directly or indirectly detecting the analye with the biological sample and determining the level, amount or concentration of the analyte in the biological sample. In some embodiments of any of the provided methods, the agent is administered to the subject if the level, amount or concentration of the analyte in the sample is at or above a threshold level.

In particular embodiments of any of the provided methods, the agent is administered (i) prior to, (ii) within one, two, or three days of, (iii) concurrently with and/or (iv) at first fever following, the initiation of administration of the cell therapy to the subject. In certain embodiments of any of the provided methods, the threshold level is within 25%, within 20%, within 15%, within 10% or within 5% of the average percent or number, and/or is within a standard deviation of the average percent or number, of cells surface positive for the myeloid marker in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

In particular embodiments of any of the provided methods, the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition. In certain embodiments of any of the provided methods, the reagent is a binding molecule that specifically binds to the marker or cells of the myeloid cell population. In some embodiments of any of the provided methods, the reagent is an antibody or an antigen-binding fragment thereof. In particular embodiments of any of the provided methods, the biological sample is or is obtained from a blood, plasma or serum sample. In certain embodiments of any of the provided methods, assaying or assessing cells the analyte comprises an immunoassay.

In some embodiments of any of the provided methods, the toxicity comprises neurotoxicity or cytokine release syndrome (CRS), optionally grade 1 or higher neurotoxicity or CRS. In particular embodiments of any of the provided methods: the toxicity comprises severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or the toxicity comprises severe CRS and/or comprises grade 2 or higher or grade 3 or higher CRS. In certain embodiments of any of the provided methods, the toxicity is associated with cerebral edema.

In some embodiments of any of the provided methods, the agent or other treatment is or comprises one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function. In particular embodiments of any of the provided methods, the antagonist or inhibitor is or comprises an agent selected from among an antibody or antigen-binding fragment, a small molecule, a protein or peptide and a nucleic acid.

In certain embodiments of any of the provided methods, the agent or other treatment is an anti-IL-6 antibody or an anti-IL6 receptor antibody. In some embodiments of any of the provided methods, the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. In particular embodiments of any of the provided methods, the agent or other treatment is or comprises tocilizumab. In certain embodiments of any of the provided methods, the agent or other treatment is or comprises siltuximab.

In some embodiments of any of the provided methods, the steroid is or comprises dexamethasone. In particular embodiments of any of the provided methods, the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124).

In certain embodiments of any of the provided methods, the agent capable of preventing, blocking or reducing microglial cell activation or function is a small molecule, peptide, protein, antibody or antigen-binding fragment thereof, an antibody mimetic, an aptamer, or a nucleic acid molecule. In some embodiments of any of the provided methods, the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

In particular embodiments of any of the provided methods, the agent is an inhibitor of colony stimulating factor 1 receptor (CSF1R). In certain embodiments of any of the provided methods, the inhibitor is selected from: PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof; emactuzumab, IMC-CS4, FPA008, LY-3022855, AMG-820 and TG-3003 or is an antigen-binding fragment thereof; or a combination of any of the foregoing.

In some embodiments of any of the provided methods, the inhibitor is PLX-3397. In particular embodiments of any of the provided methods, the recombinant receptor specifically binds to an antigen associated with the disease or condition or expressed in cells of the environment of a lesion associated with the disease or condition. In certain embodiments of any of the provided methods, the disease or condition is a cancer. In some embodiments of any of the provided methods, the disease or condition is a myeloma, leukemia or lymphoma. In particular embodiments of any of the provided methods, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

In certain embodiments of any of the provided methods, the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen.

In some embodiments of any of the provided methods, the recombinant receptor is a T cell receptor or a functional non-T cell receptor. In particular embodiments of any of the provided methods, the recombinant receptor is a chimeric antigen receptor (CAR). In certain embodiments of any of the provided methods, the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

In some embodiments of any of the provided methods, the engineered cells comprise T cells, optionally $CD4^+$ and/or $CD8^+$. In particular embodiments of any of the provided methods, the T cells are primary T cells obtained from a subject. In certain embodiments of any of the provided methods, the cell therapy comprises the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive.

In some embodiments of any of the provided methods, the cell therapy comprises the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

In particular embodiments of any of the provided methods, the dose that is not associated with risk of developing toxicity or severe toxicity is or comprises less than or less than about $5\times10^7$ total recombinant receptor-expressing cells, optionally $CAR^+$ cells, total T cells, or total peripheral blood mononuclear cells (PBMCs), such as less than or less than about $2.5\times10^7$, less than or less than about $1.0\times10^7$, less than or less than about $5.0\times10^6$, less than or less than about $1.0\times10^6$, less than or less than about $5.0\times10^5$, or less than or less than about $1\times10^5$ total recombinant receptor-expressing cells, optionally $CAR^+$ cells, total T cells, or total peripheral blood mononuclear cells (PBMCs).

In certain embodiments of any of the provided methods, the dose that is not associated with risk of developing toxicity or severe toxicity is or comprises from or from about $1\times10^5$ to $5\times10^7$ total recombinant receptor-expressing cells, optionally $CAR^+$ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10^7$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally CAR$^+$ cells, total T cells, or total peripheral blood mononuclear cells (PBMCs). In some embodiments of any of the provided methods, the engineered cells are autologous to the subject. In particular embodiments of any of the provided methods, the engineered cells are allogeneic to the subject. In certain embodiments of any of the provided methods, the reagent is detectably labeled, optionally fluorescently labeled.

In some embodiments, the instructions provide information about a threshold level, individually for each of the one or more analytes, that is indicative of whether a subject is likely to exhibit a response to treatment with the cell therapy. In some embodiments, the instructions provide information about a threshold level, individually for each of the one or more analytes, that is indicative of whether a subject is likely to exhibit a durable response following administration of the cell therapy. In some embodiments, the instructions provide information about a threshold level, individually for each of the one or more analytes, that is indicative of whether a subject is likely to exhibit a toxicity following administration of the cell therapy.

BRIEF DESCRIPTION OF THE DRAWINGS

FIG. 4A and FIG. 4B show the duration of response (CR/PR, CR or PR) and overall survival in the full and core cohort of subjects.

FIG. 5B shows the pharmacokinetics of the CAR$^+$ T cells in peripheral blood at various time points post-treatment between responders and nonresponders.

FIG. 10A) and maximum serum concentration (C$_{max}$; CAR$^+$ cells/μL, blood; FIG. 10B) of CD4$^+$ and CD8$^+$ CAR$^+$ cells in subject subgroups with diffuse large B-cell lymphoma de novo or transformed from indolent lymphoma (DLBCL, NOS; N=27), transformed follicular lymphoma (tFL; N=10), DLBCL transformed from marginal zone lymphoma or chronic lymphocytic leukemia (tMZL/tCLL; N=4), or mantle cell lymphoma (MCL; N-5), who have received CAR-expressing T cells at DL1.

FIG. 11A) and maximum serum concentration (C$_{max}$; CAR$^+$ cells/μL, blood; FIG. 11B) of CD3$^+$, CD4$^+$ and CD8$^+$ CAR$^+$ cells in subjects who have received CAR$^+$ cells at DL1 or DL2.

FIGS. 12A-12D depict the median (±quartiles) number of CAR-expressing CD4$^+$ and CD8$^+$ CAR$^+$ cells/μL, blood over time, in subjects that developed cytokine release syndrome (any CRS) compared to subjects that have not developed CRS (no CRS) (CD4$^+$: FIG. 12A; CD8$^+$: FIG. 12B) or in subjects that developed neurotoxicity (any NT) compared to subjects that have not developed NT (no NT) (CD4$^+$: FIG. 12C; CD8$^+$: FIG. 12D).

FIGS. 27A-27C show box plots displaying the concentration (FIG. 27A), viability (FIG. 27B), and frequency of caspase-3 negative (FIG. 27C) CD4$^+$ and CD8$^+$ CAR$^+$ T cells in therapeutic cell compositions of a high or low formulation volume.

FIGS. 31C and 31D depict the overall survival for the full cohort (FIG. 31C) and the core cohort (FIG. 31D), for subjects who achieved CR, PR, all subjects that showed a response, non-responders, and all treated subjects. NE, not estimable.

DETAILED DESCRIPTION

Figure 1:
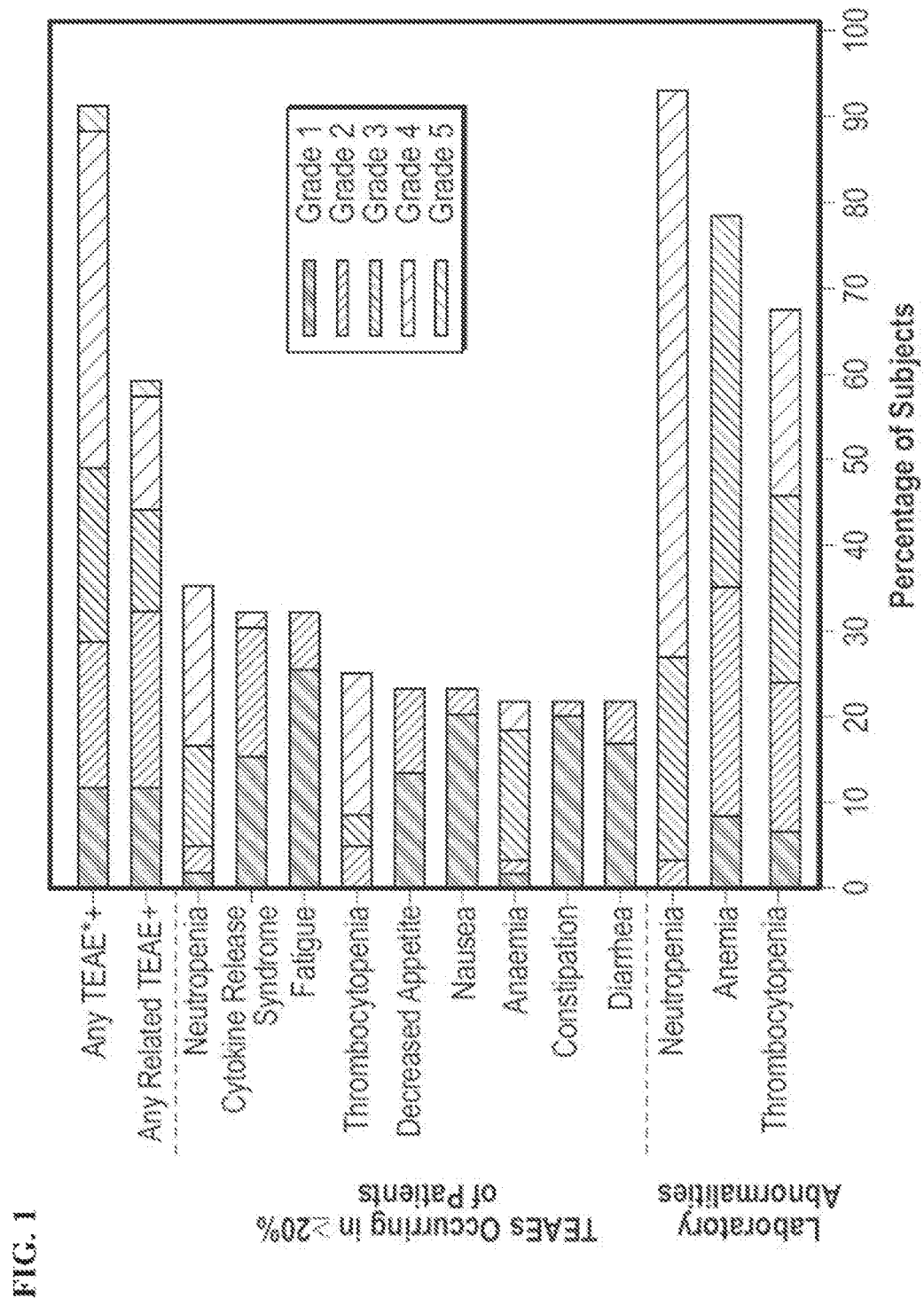
FIG. 1 shows the percentage of subjects who experienced laboratory abnormalities and treatment-emergent adverse events (TEAEs) that occurred in ≥20% of subjects. *: One Grade 5 AE of multi-organ failure unrelated to study treatment and due to progression of lymphoma; †: One Grade 5 AE of diffuse alveolar damage, investigator assessed as related to fludarabine, cyclophosphamide, and CAR T cell therapy, occurred on day 23 in a subject who refused mechanical ventilation for progressive respiratory failure while neutropenic on growth factors and broad spectrum antibiotics and antifungals

I. Methods and Uses of Cell Therapy with Genetically Engineered Cells

Provided are methods and uses of engineered cells (e.g., T cells) and/or compositions thereof, for the treatment of subjects having a disease or condition, which generally is or includes a cancer or a tumor, such as a leukemia or a lymphoma, most particularly a non-Hodgkin lymphoma (NHL). In some aspects, the methods and uses provide for or achieve improved response and/or more durable responses or efficacy and/or a reduced risk of toxicity or other side effects, e.g., in particular groups of subjects treated, as compared to certain alternative methods. In some embodiments, the methods are advantageous by virtue of the administration of specified numbers or relative numbers of the engineered cells, the administration of defined ratios of particular types of the cells, treatment of particular patient populations, such as those having a particular risk profile, staging, and/or prior treatment history, and/or combinations thereof. Also provided are methods that include assessing particular parameters, e.g., expression of specific biomarkers or analytes, that can be correlated with development of toxicity, and methods for treatment, e.g., intervention therapy, to prevent and/or ameliorate toxicities. Also provided are methods that involve assessing particular parameters, e.g., expression of specific biomarkers or analytes, that can be correlated with an outcome, such as a therapeutic outcome, including a response, such as a complete response (CR) or a partial response (PR), optionally durable response, such as a response that is durable for at least 3 months, 6 months or more; or a safety outcome, such as a development of a toxicity, for example, neurotoxicity or CRS, after administration of an immunotherapy and/or cell therapy. Also provided are methods to assess the likelihood of response and/or likelihood of risk of toxicity, based on assessment of the parameters, such as expression of biomarkers or analytes. Also provided are compositions for use in cell therapy. Also provided are articles of manufacture and kits, e.g., for use in the methods provided herein. In some embodiments, the articles of manufacture and kits optionally contain instructions for using, according to the methods provided herein.

In some embodiments, the methods and uses include administering to the subject cells expressing genetically engineered (recombinant) cell surface receptors in adoptive cell therapy, which generally are chimeric receptors such as chimeric antigen receptors (CARs), recognizing an antigen expressed by, associated with and/or specific to the leukemia or lymphoma and/or cell type from which it is derived. The cells are generally administered in a composition formulated for administration; the methods generally involve administering one or more doses of the cells to the subject, which dose(s) may include a particular number or relative number of cells or of the engineered cells, and/or a defined ratio or compositions of two or more sub-types within the composition, such as CD4 vs. CD8 T cells.

In some embodiments, the cells, populations, and compositions are administered to a subject having the particular disease or condition to be treated, e.g., via adoptive cell therapy, such as adoptive T cell therapy. In some embodiments, the methods involve treating a subject having a lymphoma or a leukemia, such as a non-Hodgkin lymphoma (NHL) with a dose of antigen receptor-expressing cells (e.g. CAR-expressing cells).

In some embodiments, the provided methods involve treating a specific group or subset of subjects, e.g., subjects identified as having high-risk disease, e.g., high-risk NHL. In some aspects, the methods treat subjects having a form of aggressive and/or poor prognosis B-cell non-Hodgkin lymphoma (NHL), such as NHL that has relapsed or is refractory (R/R) to standard therapy has a poor prognosis. In some cases, the overall response rate (ORR; also known in some cases as objective response rate) to available therapies, to a standard of care, or to a reference therapy for the disease and/or patient population for which the therapy is indicated, is less than 40% and/or the complete response (CR; also known in some cases as complete remission) is less than 20%. In some embodiments, in chemorefractory DLBCL, the ORR with a reference or available treatment or standard-of-care therapy is about 26% and the CR rate is about 8% (Crump et al. Outomes in refractory aggressive diffuse large B-cell lymphoma (DLBCL): Results from the international SCHOLAR study. ASCO 2016 [Abstract 7516]). In some aspects, the provided methods, compositions, uses and articles of manufacture achieve improved and superior responses to available therapies.

In some embodiments, the methods, uses and articles of manufacture involve, or are used for treatment of subjects involving, selecting or identifying a particular group or subset of subjects, e.g., based on specific types of disease, diagnostic criteria, prior treatments and/or response to prior treatments. In some embodiments, the methods involve treating a subject having relapsed following remission after treatment with, or become refractory to, one or more prior therapies; or a subject that has relapsed or is refractory (R/R) to one or more prior therapies, e.g., one or more lines of standard therapy. In some embodiments, the methods involve treating subjects having diffuse large B-cell lymphoma (DLBCL), not otherwise specified (NOS; de novo and transformed from indolent), primary mediastinal B-cell lymphoma (PMBCL) or follicular lymphoma, such as follicular lymphoma grade 3B (FL3B). In some embodiments, the methods involve treating a subject that has an Eastern Cooperative Oncology Group Performance Status (ECOG) of 0-1 or 0-2. In some embodiments, the methods treat a poor-prognosis population or of DLBCL patients or subject thereof that generally responds poorly to therapies or particular reference therapies, such as one having one or more, such as two or three, chromosomal translocations (such as so-called "double-hit" or "triple-hit" lymphoma; having translocations MYC/8q24 loci, usually in combination with the t(14; 18) (q32; q21) bcl-2 gene or/and BCL6/3q27 chromosomal translocation; see, e.g., Xu et al. (2013) Int J Clin Exp Pathol. 6(4): 788-794), and/or one having relapsed, optionally relapsed within 12 months, following administration of an autologous stem cell transplant (ASCT), and/or one having been deemed chemorefractory.

In some aspects, the provided embodiments are based on observations that the provided methods can be used to achieve a high response rate with high durability, compared to certain available methods for cell therapy, without an increased risk of toxicity. In some embodiments, the provided methods permit prolonged persistence of adoptively transferred cells for cell therapy, and/or low rate of developing toxicity in the subject. In some embodiments, the methods can be used to select subjects for treatment with cell therapy that are likely or more likely to respond to the therapy and/or to determine appropriate doses or dosing regime for higher response rate and/or more durable response, while minimizing the risk of toxicity. Such methods can inform rational strategies to facilitate the safe and effective clinical application of adoptive cell therapy, such as CAR-T cell therapy.

In some embodiments, the antigen receptor (e.g. CAR) specifically binds to a target antigen associated with the disease or condition, such as associated with NHL. In some embodiments, the antigen associated with the disease or disorder is selected from CD20, CD19, CD22, ROR1, CD45, CD21, CD5, CD33, Igkappa, Iglambda, CD79a, CD79b or CD30.

In some embodiments, the methods include administration of the cells or a composition containing the cells to a subject, tissue, or cell, such as one having, at risk for, or suspected of having the disease, condition or disorder. In some embodiments, the subject is the subject is an adult. In some embodiments, the subject is over at or about 30, 40, 50, 60, or 70 years of age.

In some embodiments, the methods include administration of cells to a subject selected or identified as having a certain prognosis or risk of NHL. Non-Hodgkin lymphoma (NHL) is a can be a variable disease. Some subjects with NHL may survive without treatment while others may require immediate intervention. In some cases, subjects with NHL may be classified into groups that may inform disease prognosis and/or recommended treatment strategy. In some cases, these groups may be "low risk," "intermediate risk," "high risk," and/or "very high risk" and patients may be classified as such depending on a number of factors including, but not limited to, genetic abnormalities and/or morphological or physical characteristics. In some embodiments, subjects treated in accord with the methods, and/or with the articles of manufacture or compositions, are classified or identified based on the risk of NHL. In some embodiments, the subject is one that has high risk NHL.

In some embodiments, the subject has been previously treated with a therapy or a therapeutic agent targeting the disease or condition, e.g., NHL, prior to administration of the cells expressing the recombinant receptor. In some embodiments, the subject has been previously treated with a hematopoietic stem cell transplantation (HSCT), e.g., allogeneic HSCT or autogeneic HSCT. In some embodiments, the subject has had poor prognosis after treatment with standard therapy and/or has failed one or more lines of previous therapy. In some embodiments, the subject has been treated or has previously received at least or about at least or about 1, 2, 3, or 4 other therapies for treating the NHL other than a lymphodepleting therapy and/or the dose of cells expressing the antigen receptor. In some embodiments, the subject has been previously treated with chemotherapy or radiation therapy. In some aspects, the subject is refractory or non-responsive to the other therapy or therapeutic agent. In some embodiments, the subject has persistent or relapsed disease, e.g., following treatment with another therapy or therapeutic intervention, including chemotherapy or radiation.

In some embodiments, the subject is one that is eligible for a transplant, such as is eligible for a hematopoietic stem cell transplantation (HSCT), e.g., allogeneic HSCT. In some such embodiments, the subject has not previously received a transplant, despite being eligible, prior to administration of the engineered cells (e.g. CAR-T cells) or a composition containing the cells to the subject as provided herein.

In some embodiments, the subject is one that is not eligible for a transplant, such as is not eligible for a hematopoietic stem cell transplantation (HSCT), e.g., allogeneic HSCT. In some embodiments, such a subject is administered the engineered cells (e.g. CAR-T cells) or a composition containing the cells according to the provided embodiments herein.

In some embodiments, the methods include administration of cells to a subject selected or identified as having high-risk NHL. In some embodiments, the subject exhibits one or more cytogenetic abnormalities, such as associated with high-risk NHL. In some embodiments, the subject is selected or identified based on having a disease or condition characterized or determined to be aggressive NHL, diffuse large B cell lymphoma (DLBCL), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL). In particular embodiments, the subject to be treated using the methods provided herein include subjects with aggressive NHL, in particular, with diffuse large B-cell lymphoma (DLBCL), not otherwise specified (NOS; de novo and transformed from indolent), primary mediastinal B-cell lymphoma (PMBCL) or follicular lymphoma grade 3B (FL3B). In some embodiments, the subject has poor performance status. In some aspects, the population to be treated includes subjects having an Eastern Cooperative Oncology Group Performance Status (ECOG) that is anywhere from 0-2. In other aspects of any of the embodiments, the subjects to be treated included ECOG 0-1 or do not include ECOG 2 subjects. In some aspects of any of the embodiments, the subjects to be treated have failed two or more prior therapies. In some embodiments, the subject does not have DLBCL transformed from marginal zone lymphoma (MZL) and chronic lymphocytic leukemia (CLL; Richter's). In some embodiments, a subject with CLL can exhibit Richter's syndrome (RS), defined as the transformation of CLL into an aggressive lymphoma, most commonly diffuse large B-cell lymphoma (DLBCL) (see, e.g., Parikh et al. Blood 2014 123:1647-1657). In some embodiments, the subject has mantle cell lymphoma (MCL). In some embodiments, the subject has features that correlate with poor overall survival. In some embodiments, the subject has never achieved a complete response (CR), never received autologous stem cell transplant (ASCT), refractory to 1 or more second line therapy, has primary refractory disease, and/or has an ECOG performance score of 2.

In some embodiments, the subject to be treated includes a group of subjects with diffuse large B-cell lymphoma (DLBCL), de novo or transformed from indolent lymphoma (NOS), primary mediastinal large b-cell lymphoma (PMBCL), and follicular lymphoma grade 3b (FL3B) after failure of 2 lines of therapy, and ECOG score of 0-2, and the subject may optionally have previously been treated with allogeneic stem cell transplantation (SCT). In some embodiments, such subject group can be referred to as the "full cohort." In some embodiments, the subject is selected for treatment with adoptive cell therapy, if the subject meets said criteria. In some embodiments, within said group ("full cohort"), the subject is not selected for treatment or excluded from treatment, if the subject has a poor performance status (e.g. ECOG 2) and/or has DLBCL transformed from marginal zone lymphomas (MZL) and chronic lymphocytic leukemia (CLL, Richter's). Thus, in some embodiments, the subject is selected for treatment if the subject has subjects with diffuse large B-cell lymphoma (DLBCL), de novo or transformed from indolent lymphoma (NOS), primary mediastinal large b-cell lymphoma (PMBCL), and follicular lymphoma grade 3b (FL3B) after failure of 2 lines of therapy, and ECOG score of 0 or 1, and the subject may optionally have previously been treated with allogeneic stem cell transplantation (SCT) but does not have DLBCL transformed from marginal zone lymphomas (MZL) and chronic lymphocytic leukemia (CLL, Richter's). In some embodiments, such subject group can be referred to as the "core cohort." In some embodiments, the subject to be treated is subjects in the "core cohort."

In some aspects, the provided embodiments are based on observations that certain subject population, for example, the "core cohort" subjects who have been administered a certain dose of the cell therapy, show an overall response rate (ORR) of more than 80%, with a complete response (CR) rate of more than 55%, with high durability, e.g., response that is maintained over a longer period of time, e.g., more than 3 months, with a 3-month ORR of over 65%, and a 3-month CR rate of approximately 50%. In particular, the provided observations indicated that the 3-month ORR was high in subjects with two or three chromosomal translocations ("double-hit" or "triple-hit" lymphoma; having translocations MYC/8q24 loci, usually in combination with the t(14; 18) (q32; q21) bcl-2 gene or/and BCL6/3q27 chromosomal translocation; see, e.g., Xu et al. (2013) Int J Clin Exp Pathol. 6(4): 788-794), primary-refractory lymphomas, chemorefractory DLBCL, and subjects who have never previously achieved CR.

In some aspects, provided are compositions, methods and uses for administration of a defined composition of the cell therapy, at particular doses, that are associated with a high response rate and/or high durability of response, and low levels and/or incidence of toxicity. In some embodiments, the composition or dose administered is a flat and/or fixed dose, such as a precise flat dose, of cells and/or of one or more cells having a particular phenotype, such as a particular number of such cells or a number that is within a particular range and/or degree of variability or variance as compared to a target number. In some embodiments, the composition or dose administered contains a defined ratio of $CD4^+$ and $CD8^+$ cells (e.g., 1:1 ratio of $CD4^+$:$CD8^+$ $CAR^+$ T cells) and/or contains a ratio that is within a certain degree of variability from such ratio, such as no more than ±10%, such as no more than ±8%, such as a degree of variability or variance of no more than ±10%, such as no more than ±8%. In some embodiments, the $CD4^+$ and $CD8^+$ cells are individually formulated and administered. In some embodiments, the administered cells exhibit consistent activity and/or function, e.g., cytokine production, apoptosis and/or expansion. In some embodiments, the provided compositions exhibit highly consistent and defined activity, and low variability between cells, e.g., in terms of cell number, cell function and/or cell activity, in the composition or between preparations. In some embodiments, the consistency in activity and/or function, e.g., low variability between preparations of compositions, allows improved efficacy and/or safety. In some embodiments, administration of the defined compositions resulted in low product variability and low toxicity, e.g., CRS or neurotoxicity, compared to administration of cell compositions with high heterogeneity. In some embodiments, the defined, consistent composition also exhibits consistent cell expansion. Such consistency can facilitate the identification of dose, therapeutic window, evaluation of dose reponse and identification of factors of the subject that may correlate with safety or toxicity outcomes.

In some embodiments, in a certain cohort of subjects receiving a single infusion of a particular dose level, a durable response rate after 6 months of greater than 60% can be achieved. In some embodiments, the subjects in some cohorts can achieve an overall response rate (ORR, in some cases also known as objective response rate) of more than 80%, a complete response (CR) rate of more than 60% and/or a high durable CR rate at 6 months. In some embodiments, subjects receiving a defined dose show improved safety outcomes, e.g., more than two-thirds of the subjects that do not exhibit any CRS or NT. In some aspects, the rate of severe CRS or severe NT is low. In some embodiments, a higher exposure (e.g., $C_{max}$ and $AUC_{0-28}$) observed with a particular defined dose, does not associate with increased toxicity, e.g., CRS or NT. In some embodiments, particular factors of the subject, e.g., certain biomarkers, can be used to predict the risk of toxicity. In some embodiments, the provided embodiments can be used to achieve high response rate with low risk of toxicity.

In some embodiments, no more than 25%, no more than 20%, no more than 15%, no more than 10% or no more than 5% of subjects treated using the provided compositions, articles of manufacture, kits, methods and uses are administered an agent (e.g. tocilizumab and/or dexamethasone) to ameliorate, treat or prevent a toxicity, either prior to or subsequent to administration of the cell therapy. In some embodiments, the subject is not administered any prophylaxis treatment prior to receiving the engineered cells (e.g. CAR-T cells).

In some embodiments, the provided embodiments provide an advantage, e.g., permits administration of the cell therapy on an outpatient basis. In some embodiments, the administration of the cell therapy, e.g. dose of T cells in accord with the provided embodiments, can be performed on an outpatient basis or does not require admission to the subject to the hospital, such as admission to the hospital requiring an overnight stay. In some embodiments, such outpatient administration can allow increased access and decreased costs, while maintaining a high, durable response rate with low toxicity. In some aspects, outpatient treatment can be advantageous for patients who already are otherwise immunocompromised by prior treatments, e.g. post-lympodepletion, and are at a greater risk for exposures at a hospital stay or in an in-patient setting. In some aspects, outpatient treatments also increases options for treatment for subjects who may not have access to in-patient, hospital settings, or transplant centers, thereby expanding access to the treatment. In some embodiments, subjects treated on an outpatient basis using the provided compositions, articles of manufacture, kits, methods and uses remain in outpatient for at least 3 days or a certain percentage of subjects, e.g. at least 60%, at least 70%, at least 80%, at least 85%, at least 90% or at least 95%, of subjects so treated remain in outpatient for at least 3 days. In some aspects, the subjects remain in outpatient for at least 4 days, 5 days, 6 days, 7 days, 8 days or more. In some embodiments, subjects treated using the provided compositions, articles of manufacture, kits, methods and uses show a reduction in the duration of hospital stay, e.g., of at least 10%, at least 15%, at least 20%, at least 25%, at least 30%, at least 35% or at least 40%, compared to subjects treated with other compositions, articles of manufacture, kits, methods and uses.

In some embodiments, the methods, cells and compositions can provide high rate of durable response to subjects across a range of patient characteristics and/or tumor burden. In some embodiments, the methods, cells and compositions can provide high rate of durable response to high risk patients with poor prognosis, with a reduced risk of adverse effects or toxicities. In some embodiments, the methods and uses provide for or achieve a higher response rate and/or more durable responses or efficacy and/or a reduced risk of toxicity or other side effects that can be associated with cell therapy, such as neurotoxicity (NT) or cytokine release syndrome (CRS). In some aspects, the provided observations indicated a low rate of severe NT (sNT) or severe CRS (sCRS), and a high rate of patients without any toxicities, e.g., NT or CRS.

In some embodiments, at least 35%, at least 40%, at least 50%, at least 55%, at least 60%, at least 65%, at least 70%, or at least 75% or more of the subjects treated according to the provided methods, and/or with the provided articles of manufacture or compositions, achieve a complete response (CR). In some embodiments, at least 50%, at least 60%, at least 70%, at least 80%, or at least 90% of the subjects treated according to the provided methods, and/or with the provided articles of manufacture or compositions, achieve an objective response (OR). In some embodiments, at least 60%, at least 70%, at least 80%, at least 90%, at least 95% or more of the subjects treated according to the provided methods, and/or with the provided articles of manufacture or compositions, achieve a CR or OR by one month, by two months or by three months.

In some embodiments, by three months, four months, five months, six months or more after initiation of administration of the cell therapy, at least 60%, at least 70%, at least 80%, at least 90%, at least 95% or more of the subjects treated according to the provided methods, and/or with the provided articles of manufacture or compositions, remain in response, such as remain in CR or OR. In some embodiments, such response, such as CR or OR, is durable for at least three months, four months, five months, six months, seven months, eight months or nine months, such as in at least or about at least 60%, at least 70%, at least 80%, at least 90%, at least 95% or more of the subjects treated according to the provided methods or in such subjects who achieve a CR by one month or by three months. In some embodiments, at least 60%, at least 70%, at least 80%, at least 90%, at least 95% or more of the subjects treated according to the provided methods, and/or with the provided articles of manufacture or compositions, or such subjects who achieve a CR by one month or by three months, survive or survive without progression for greater than or greater than about three months, four months, five months, six months, seven months, eight months or nine months.

In some embodiments, the resulting response observed in such subjects by the treatment in accord with the provided methods, and/or with the provided articles of manufacture or compositions, is associated with or results in a low risk of any toxicity or a low risk of severe toxicity in a majority of the subjects treated. In some embodiments, greater than or greater than about 30%, 35%, 40%, 50%, 55%, 60% or more of the subjects treated according to the provided methods and/or with the provided articles of manufacture or compositions do not exhibit any grade of CRS or any grade of neurotoxicity (NT). In some embodiments, greater than or greater than about 50%, 60%, 70%, 80% or more of the subjects treated according to the provided methods and/or with the provided articles of manufacture or compositions do not exhibit severe CRS or grade 3 or higher CRS. In some embodiments, greater than or greater than about 50%, 60%, 70%, 80% or more of the subjects treated according to the provided methods, and/or with the provided articles of manufacture or compositions, do not exhibit severe neurotoxicity or grade 3 or higher neurotoxicity, such as grade 4 or 5 neurotoxicity.

In some embodiments, at least at or about 45%, 50%, 60%, 65%, 70%, 75%, 80%, 85%, 90%, or 95% of subjects treated according to the method and/or with the provided articles of manufacture or compositions do not exhibit early onset CRS or neurotoxicity and/or do not exhibit onset of CRS earlier than 1 day, 2 days, 3 days or 4 days following initiation of the administration. In some embodiments, at least at or about 45%, 50%, 60%, 65%, 70%, 75%, 80%, 85%, 90%, or 95% of subjects treated according to the methods, and/or with the provided articles of manufacture or compositions, do not exhibit onset of neurotoxicity earlier than 3 days, 4 days, 5 days, six days or 7 days following initiation of the administration. In some aspects, the median onset of neurotoxicity among subjects treated according to the methods, and/or with the provided articles of manufacture or compositions, is at or after the median peak of, or median time to resolution of, CRS in subjects treated according to the method. In some cases, the median onset of neurotoxicity among subjects treated according to the method is greater than at or about 8, 9, 10, or 11 days.

In some embodiments, such results are observed following administration of from or from about $5 \times 10^7$ to $1.5 \times 10^8$, such as $5 \times 10^7$ to $1 \times 10^8$ total recombinant receptor-expressing T cells, such as a dose of T cells including $CD4^+$ and $CD8^+$ T cells administered at a defined ratio as described herein, e.g. at or about a 1:1 ratio, and/or at a precise or flat or fixed number of $CAR^+$ T cells, or precise or flat or fixed number of a particular type of $CAR^+$ T cells such as $CD4^+$ $CAR^+$ T cells and/or $CD8^+$ $CAR^+$ T cells, and/or a number of any of such cells that is within a specified degree of variance, such as no more than, + or − (plus or minus, in some cases indicated as ±), 5, 6, 7, 8, 9, 10, 11, 12, 13, 14, or 15% as compared to such precise or flat or fixed number. In some embodiments, such flat or fixed number of cells is at or about $2.5 \times 10^7$, $5 \times 10^7$, $10 \times 10^7$, $15 \times 10^7$ or $20 \times 10^7$, e.g., of total $CAR^+$ T cells or of $CD8^+$ and/or $CD4^+$ $CAR^+$ T cells. In some embodiments, the number of cells in the dose includes or consists of or consists essentially of $5 \times 10^7$ $CD4^+$ $CAR^+$ T cells (optionally $2.5 \times 10^7$ $CD4^+$ $CAR^+$ T cells and $2.5 \times 10^7$ $CD8^+$ $CAR^+$ T cells); in some embodiments, it includes or consists of or consists essentially of $10 \times 10^7$ $CAR^+$ T cells (optionally $5 \times 10^7$ $CD4^+$ $CAR^+$ T cells and $5 \times 10^7$ $CD8^+$ $CAR^+$ T cells). In some aspects, the number of cells administered, is within a certain degree of variance of such numbers in the aforementioned embodiments, such as within plus or minus (±) 5, 6, 7, 8, 9, or 10%, such as within plus or minus 8%, as compared to such number(s) of cells. In some aspects, the dose is within a range in which a correlation is observed (optionally a linear relationship) between the number of such cells (e.g., of total $CAR^+$ T cells or of $CD8^+$ and/or $CD4^+$ $CAR^+$ T cells) and one or more outcomes indicative of therapeutic response, or duration thereof (e.g., likelihood of achieving a remission, a complete remission, and/or a particular duration of remission) and/or duration of any of the foregoing. In some aspects, it is found that the higher dose of cells administered can result in greater response without or without substantially impacting or affecting the incidence or risk of toxicity (e.g. CRS or neurotoxicity), or degree of incidence or risk of toxicity, in the subject e.g. severe CRS or severe neurotoxicity.

In some aspects, the provided methods can achieve a high or a particular rate of response (such as a rate of response among a population as assessed after a certain period post-administration, such as three months or six months), e.g., ORR (such as a 6-month or 3-month ORR) of 40% or more, 45% or more, 50% or more, 55% or more, 60% or more, 65% or more, 70% or more, 75% or 80% or 81%, 82%, 83%, 84% or 85% or more and CR rate (such as a 6-month or 3-month CR rate) of 30% or more, 35% or more, 40% or more, 45% or more, 50% or more, 55% or more, 60% or more, 65% or more, 70% or more, 71%, 72%, 73% or more or approximately 75% or more, which also is durable such as for a particular period of time or at least a particular period of time, e.g., is sustained for more than 1, 3 or 6 months or more or 9 months or more after initiation of therapy. In some embodiments, such rates of response and durability are received following only a single administration or dose of such therapy. Treatment of such subjects by the provided methods, and/or with the provided articles of manufacture or compositions, in some embodiments, also result in the subjects achieving the high rate of response, yet not exhibiting higher incidence of developing toxicities, such as neurotoxicity or CRS, even at a higher cell dosage. In some embodiments, about or greater than 50%, 55% or 60% of subjects achieving such responses do not develop any grade of toxicity, such as any grade of CRS and/or neurotoxicity.

Thus, in some embodiments, the provided methods, articles of manufacture and/or compositions, can offer advantages over other available methods or solutions or approaches for treatment such as for adoptive cell therapy. In particular, among the provided embodiments are those that offer an advantage for subjects with high-risk NHL, by achieving a durable response at a high rate, with reduced incidence of toxicities or side effects.

A. Method of Treatment

Provided herein are methods of treatment that involve administering engineered cells or compositions containing engineered cells, such as engineered T cells. Also provided are methods and uses of engineered cells (e.g., T cells) and/or compositions thereof, including methods for the treatment of subjects having a disease or condition such as a leukemia or a lymphoma, e.g., a non-Hodgkin lymphoma (NHL), that involves administration of the engineered cells and/or compositions thereof. In some embodiments, the provided methods and uses can achieve improved response and/or more durable responses or efficacy and/or a reduced risk of toxicity or other side effects, e.g., in particular groups of subjects treated, as compared to certain alternative methods. In some aspects, also provided are methods of administering engineered cells or compositions containing engineered cells, such as engineered T cells, to a subject, such as a subject that has a disease or disorder. In some aspects, also provided are uses of engineered cells or compositions containing engineered cells, such as engineered T cells for treatment of a disease or disorder. In some aspects, also provided are uses of engineered cells or compositions containing engineered cells, such as engineered T cells for the manufacture of a medicament for the treatment of a disease or disorder. In some aspects, also provided are methods of administering engineered cells or compositions containing engineered cells, such as engineered T cells, for use in treatment of a disease or disorder, or for administration to a subject having a disease or disorder. In some aspects, the uses of the engineered cells or compositions containing engineered cells, such as engineered T cells are in accord with any of the methods described herein.

General methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CIVIL), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

In some embodiments, NHL can be staged based on the Lugano classification (see, e.g., Cheson et al., (2014) JCO 32(27):3059-3067; Cheson, B. D. (2015) Chin Clin Oncol 4(1):5). In some cases, the stages are described by Roman numerals I through IV (1-4), and limited stage (I or II) lymphomas that affect an organ outside the lymph system (an extranodal organ) are indicated by an E. Stage I represents involvement in one node or a group of adjacent nodes, or a single extranodal lesions without nodal involvement (IE). Stage 2 represents involvement in two or more nodal groups on the same side of the diaphragm or stage I or II by nodal extent with limited contiguous extranodal involvement (IIE). Stage III represents involvement in nodes on both sides of the diaphragm or nodes above the diaphragm with spleen involvement. Stage IV represents involvement in additional non-contiguous extralymphatic involvement. In addition, "bulky disease" can be used to describe large tumors in the chest, in particular for stage II. The extent of disease is determined by positron emission tomography (PET)-computed tomography (CT) for avid lymphomas, and CT for non-avid histologies.

In some embodiments, the Eastern Cooperative Oncology Group (ECOG) performance status indicator can be used to assess or select subjects for treatment, e.g., subjects who have had poor performance from prior therapies (see, e.g., Oken et al. (1982) Am J Clin Oncol. 5:649-655). The ECOG Scale of Performance Status describes a patient's level of functioning in terms of their ability to care for themselves, daily activity, and physical ability (e.g., walking, working, etc.). In some embodiments, an ECOG performance status of 0 indicates that a subject can perform normal activity. In some aspects, subjects with an ECOG performance status of 1 exhibit some restriction in physical activity but the subject is fully ambulatory. In some aspects, patients with an ECOG performance status of 2 is more than 50% ambulatory. In some cases, the subject with an ECOG performance status of 2 may also be capable of selfcare; see e.g., Sorensen et al., (1993) Br J Cancer 67(4) 773-775. The criteria reflective of the ECOG performance status are described in Table 1 below:

TABLE 1

ECOG Performance Status Criteria

| Grade | ECOG performance status |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

In some embodiments, the subject has or has been identified as having as having a double/triple hit lymphoma or a lymphoma of the double/triple hit molecular subtypes. In some embodiments, the lymphoma is a double hit lymphoma characterized by the presence of MYC (myelocytomatosis oncogene), BCL2 (B-cell lymphoma 2), and/or BCL6 (B-cell lymphoma 6) gene rearrangements (e.g., translocations). In some embodiments, the gene rearrangement affects the MYC/8q24 locus in combination with another gene rearrangement. For example, the other gene rearrangement includes t(14;18)(q32;q21) involving BCL2. In some embodiments, the gene rearrangements affect the MYC/8q24 locus in combination with BCL6/3q27. In some embodiments, the lymphoma is a triple hit lymphoma characterized by the presence of MYC, BCL2, and BCL6 gene rearrangements; see, e.g., Aukema et al., (2011) Blood 117:2319-2331. In some aspects of such embodiments the subject is ECOG 0-1 or does not have or is not suspected or characterized as having DLBCL transformed from MZL or CLL. In aspects, the therapy is indicated for such subjects and/or the instructions indicate administration to a subject within such population. In some embodiments, based on the 2016 WHO criteria (Swerdlow et al., (2016) Blood 127(20): 2375-2390), double/triple hit lymphoma can be considered high-grade B-cell lymphoma, with MYC and BCL2 and/or BCL6 rearrangements with DLBCL histology (double/triple hit).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another or additional therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some embodiments, the additional therapeutic agent is any interventions or agents described herein, such as any interventions or agents descried that can ameliorate symptoms of toxicity described herein, for example, in Section II. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m² of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m²) of cyclophosphamide and 3 to 5 doses of 25 mg/m² fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known. See, for instance, Wadwa et al., J. Drug Targeting 3: 1 1 1 (1995), and U.S. Pat. No. 5,087,616. In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

B. Dosing

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of cells is a flat dose of cells or fixed dose of cells such that the dose of cells is not tied to or based on the body surface area or weight of a subject.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of $CD3^+$ or $CD8^+$, in some cases also recombinant receptor-expressing (e.g. $CAR^P$) cells. In some embodiments, the cell therapy comprises administration of a dose comprising a number of cell from or from about $1\times10^5$ to $5\times10^8$ $CD3^+$ or $CD8^+$ total T cells or $CD3^+$ or $CD8^+$ recombinant receptor-expressing cells, from or from about $5\times10^5$ to $1\times10^7$ $CD3^+$ or $CD8^+$ total T cells or $CD3^+$ or $CD8^+$ recombinant receptor-expressing cells, or from or from about $1\times10^6$ to $1\times10^7$ $CD3^+$ or $CD8^+$ total T cells or $CD3^+$ or $CD8^+$ recombinant receptor-expressing cells, each inclusive. In some embodiments, the cell therapy comprises administration of a dose comprising a number of cell from or from about $1\times10^5$ to $5\times10^8$ total $CD3^+/CAR^+$ or $CD8^+/CAR^+$ cells, from or from about $5\times10^5$ to $1\times10^7$ total $CD3^+/CAR^+$ or $CD8^+/CAR^+$ cells, or from or from about $1\times10^6$ to $1\times10^7$ total $CD3^+/CAR^+$ or $CD8^+/CAR^+$ cells, each inclusive.

In some embodiments, the dose of T cells comprises: at or about $5\times10^7$ recombinant receptor-expressing T cells or at or about $2.5\times10^7$ recombinant receptor-expressing $CD8^+$ T cells. In some embodiments, the dose of T cells comprises: at or about $1\times10^8$ recombinant receptor-expressing T cells or at or about $5\times10^7$ recombinant receptor-expressing $CD8^+$ T cells. In some embodiments, the dose of T cells comprises: at or about $1.5\times10^8$ recombinant receptor-expressing T cells or at or about $0.75\times10^8$ recombinant receptor-expressing $CD8^+$ T cells.

In some embodiments, the T cells of the dose include $CD4^+$ T cells, $CD8^+$ T cells or $CD4^+$ and $CD8^+$ T cells.

In some embodiments, for example, where the subject is human, the $CD8^+$ T cells of the dose, including in a dose including $CD4^+$ and $CD8^+$ T cells, includes between about $1\times10^6$ and $5\times10^8$ total recombinant receptor (e.g., CAR)-expressing $CD8^+$ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing $CD8^+$ T cells, $1\times10^7$ to $2.5\times10^7$ total recombinant receptor-expressing $CD8^+$ T cells, from or from about $1\times10^7$ to $0.75\times10^8$ total recombinant receptor-expressing $CD8^+$ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing $CD8^+$ T cells.

In some embodiments, for example, where the subject is a human, the dose includes fewer than about $2\times10^8$ $1\times10^8$ total recombinant receptor (e.g., CAR)-expressing cells, T cells, or peripheral blood mononuclear cells (PBMCs), e.g., in the range of about $1\times10^6$ to $2\times10^8$ or $1\times10^6$ to $1\times10^8$ such cells, such as $2\times10^6$, $5\times10^6$, $1\times10^7$, $5\times10^7$, $1\times10^8$ or $1.5\times10^8$ total such cells, or the range between any two of the foregoing values. In some embodiments, where the subject is a human, the dose includes between about $1\times10^6$ and $3\times10^8$ total recombinant receptor (e.g., CAR)-expressing cells, e.g., in the range of about $1\times10^7$ to $2\times10^8$ such cells, such as $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^5$ to $5\times10^8$ total recombinant receptor-expressing T cells or total T cells, $1\times10^5$ to $1.5\times10^8$ total recombinant receptor-expressing T cells or total T cells, $1\times10^5$ to $1\times10^8$ total recombinant receptor-expressing T cells or total T cells, from or from about $5\times10^5$ to $1\times10^7$ total recombinant receptor-expressing T cells or total T cells, or from or from about $1\times10^6$ to $1\times10^7$ total recombinant receptor-expressing T cells or total T cells, each inclusive.

In some embodiments, the T cells of the dose include $CD4^+$ T cells, $CD8^+$ T cells or $CD4^+$ and $CD8^+$ T cells.

In some embodiments, for example, where the subject is human, the $CD8^+$ T cells of the dose, including in a dose including $CD4^+$ and $CD8^+$ T cells, includes between about $1 \times 10^6$ and $1 \times 10^8$ total recombinant receptor (e.g., CAR)-expressing CD8$^+$ cells, e.g., in the range of about $5 \times 10^6$ to $1 \times 10^8$ such cells, such cells $1 \times 10^7$, $2.5 \times 10^7$, $5 \times 10^7$, $7.5 \times 10^7$ or $1 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to $0.75 \times 10^8$ total recombinant receptor-expressing CD8$^+$ T cells, $1 \times 10^7$ to $2.5 \times 10^7$ total recombinant receptor-expressing CD8$^+$ T cells, from or from about $1 \times 10^7$ to $0.75 \times 10^8$ total recombinant receptor-expressing CD8$^+$ T cells, each inclusive. In some embodiments, the dose of cells comprises the administration of or about $1 \times 10^7$, $2.5 \times 10^7$, $5 \times 10^7$ $7.5 \times 10^7$ or $1 \times 10^8$ total recombinant receptor-expressing CD8$^+$ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8$^+$ and CD4$^+$ T cells, respectively, and/or CD8$^+$- and CD4$^+$-enriched populations, respectively, e.g., CD4$^+$ and/or CD8$^+$ T cells each individually including cells genetically engineered to express the recombinant receptor. In some embodiments, the administration of the dose comprises administration of a first composition comprising a dose of CD8$^+$ T cells or a dose of CD4$^+$ T cells and administration of a second composition comprising the other of the dose of CD4$^+$ T cells and the CD8$^+$ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4$^+$ T cells. In some composition, the first composition, e.g., first composition of the dose, comprises CD8$^+$ T cells. In some embodiments, the first composition is administered prior to the second composition.

In some embodiments, the dose or composition of cells includes a defined or target ratio of CD4$^+$ cells expressing a recombinant receptor to CD8$^+$ cells expressing a recombinant receptor and/or of CD4$^+$ cells to CD8$^+$ cells, which ratio optionally is approximately 1:1 or is between approximately 1:3 and approximately 3:1, such as approximately 1:1. In some aspects, the administration of a composition or dose with the target or desired ratio of different cell populations (such as CD4$^+$:CD8$^+$ ratio or CAR$^+$CD4$^+$:CAR$^+$CD8$^+$ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or antitumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the $CD4^+$ to $CD8^+$ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of $CD4^+$ cells and/or a desired dose of $CD8^+$ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as $CD4^+$ and $CD8^+$ cells or sub-types. In some aspects, the desired ratio can be a specific ratio or can be a range of ratios. for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

C. Response, Efficacy and Survival

In some embodiments, the administration effectively treats the subject despite the subject having become resistant to another therapy. In some embodiments, at least 30%, at least 35%, at least 40% or at least 50% of subjects treated according to the method achieve complete remission (CR); and/or at least about 40%, at least about 50%, at least about 60% or at least about 70% of the subjects treated according to the method achieve an objective response (OR). In some embodiments, at least or about at least 50% of subjects, at least or about at least 60% of the subjects, at least or about at least 70% of the subjects, at least or about at least 80% of the subjects or at least or about at least 90% of the subjects treated according to the method achieve CR and/or achieve an objective response (OR). In some embodiments, criteria assessed for effective treatment includes overall response rate (ORR; also known in some cases as objective response rate), complete response (CR; also known in some cases as complete response), duration of response (DOR) progression-free survival (PFS), and/or overall survival (OS).

In some embodiments, at least 40% or at least 50% of subjects treated according to the methods provided herein achieve complete remission (CR; also known in some cases as complete response), exhibit progression-free survival (PFS) and/or overall survival (OS) of greater than at or about 3 months, 6 months or 12 months or greater than 13 months or approximately 14 months; on average, subjects treated according to the method exhibit a median PFS or OS of greater than at or about 6 months, 12 months, or 18 months; and/or the subject exhibits PFS or OS following therapy for at least at or about 6, 12, 18 or more months or longer.

In some aspects, response rates in subjects, such as subjects with NHL, are based on the Lugano criteria. (Cheson et al., (2014) JCO 32(27):3059-3067; Johnson et al., (2015) Radiology 2:323-338; Cheson, B. D. (2015) Chin Clin Oncol 4(1):5). In some aspects, response assessment utilizes any of clinical, hematologic, and/or molecular methods. In some aspects, response assessed using the Lugano criteria involves the use of positron emission tomography (PET)-computed tomography (CT) and/or CT as appropriate. PET-CT evaluations may further comprise the use of fluorodeoxyglucose (FDG) for FDG-avid lymphomas. In some aspects, where PET-CT will be used to assess response in FDG-avid histologies, a 5-point scale may be used. In some respects, the 5-point scale comprises the following criteria: 1, no uptake above background; 2, uptake ≤mediastinum; 3, uptake >mediastinum but ≤liver; 4, uptake moderately >liver; 5, uptake markedly higher than liver and/or new lesions; X, new areas of uptake unlikely to be related to lymphoma.

In some aspects, a complete response as described using the Lugano criteria involves a complete metabolic response and a complete radiologic response at various measureable sites. In some aspects, these sites include lymph nodes and extralymphatic sites, wherein a CR is described as a score of 1, 2, or 3 with or without a residual mass on the 5-point scale, when PET-CT is used. In some aspects, in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic uptake. In some aspects, response is assessed in the lymph nodes using CT, wherein a CR is described as no extralymphatic sites of disease and target nodes/nodal masses must regress to ≤1.5 cm in longest transverse diameter of a lesion (LDi). Further sites of assessment include the bone marrow wherein PET-CT-based assessment should indicate a lack of evidence of FDG-avid disease in marrow and a CT-based assessment should indicate a normal morphology, which if indeterminate should be IHC negative. Further sites may include assessment of organ enlargement, which should regress to normal. In some aspects, nonmeasured lesions and new lesions are assessed, which in the case of CR should be absent (Cheson et al., (2014) JCO 32(27): 3059-3067; Johnson et al., (2015) Radiology 2:323-338; Cheson, B. D. (2015) Chin Clin Oncol 4(1):5).

In some aspects, a partial response (PR; also known in some cases as partial remission) as described using the Lugano criteria involves a partial metabolic and/or radiological response at various measureable sites. In some aspects, these sites include lymph nodes and extralymphatic sites, wherein a PR is described as a score of 4 or 5 with reduced uptake compared with baseline and residual mass(es) of any size, when PET-CT is used. At interim, such findings can indicate responding disease. At the end of treatment, such findings can indicate residual disease. In some aspects, response is assessed in the lymph nodes using CT, wherein a PR is described as ≥50% decrease in SPD of up to 6 target measureable nodes and extranodal sites. If a lesion is too small to measure on CT, 5 mm×5 mm is assigned as the default value; if the lesion is no longer visible, the value is 0 mm×0 mm; for a node >5 mm×5 mm, but smaller than normal, actual measurements are used for calculation. Further sites of assessment include the bone marrow wherein PET-CT-based assessment should indicate residual uptake higher than uptake in normal marrow but reduced compared with baseline (diffuse uptake compatible with reactive changes from chemotherapy allowed). In some aspects, if there are persistent focal changes in the marrow in the context of a nodal response, consideration should be given to further evaluation with MRI or biopsy, or an interval scan. In some aspects, further sites may include assessment of organ enlargement, where the spleen must have regressed by >50% in length beyond normal. In some aspects, nonmeasured lesions and new lesions are assessed, which in the case of PR should be absent/normal, regressed, but no increase. No response/stable disease (SD) or progressive disease (PD) can also be measured using PET-CT and/or CT based assessments. (Cheson et al., (2014) JCO 32(27):3059-3067; Johnson et al., (2015) Radiology 2:323-338; Cheson, B. D. (2015) Chin Clin Oncol 4(1):5).

In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR; also known in some cases as overall response rate) is described as the proportion of patients who achieved CR or PR. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the measure of duration of response (DOR) includes the time from documentation of tumor response to disease progression. In some embodiments, the parameter for assessing response can include durable response, e.g., response that persists after a period of time from initiation of therapy. In some embodiments, durable response is indicated by the response rate at approximately 1, 2, 3, 4, 5, 6, 7, 8, 9, 10, 11, 12, 18 or 24 months after initiation of therapy. In some embodiments, the response is durable for greater than 3 months or greater than 6 months.

In some aspects, the RECIST criteria is used to determine objective tumor response; in some aspects, in solid tumors. (Eisenhauer et al., European Journal of Cancer 45 (2009) 228-247.) In some aspects, the RECIST criteria is used to determine objective tumor response for target lesions. In some respects, a complete response as determined using RECIST criteria is described as the disappearance of all target lesions and any pathological lymph nodes (whether target or non-target) must have reduction in short axis to <10 mm. In other aspects, a partial response as determined using RECIST criteria is described as at least a 30% decrease in the sum of diameters of target lesions, taking as reference the baseline sum diameters. In other aspects, progressive disease (PD) is described as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (in some aspects the appearance of one or more new lesions is also considered progression). In other aspects, stable disease (SD) is described as neither sufficient shrinkage to qualify for PR nor sufficient increase to qualify for PD, taking as reference the smallest sum diameters while on study.

In some aspects, the administration in accord with the provided methods, and/or with the provided articles of manufacture or compositions, generally reduces or prevents the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor, the number or extent of metastases and/or the percentage of blast cells present in the bone marrow.

In some embodiments, a subject has leukemia. The extent of disease burden can be determined by assessment of residual leukemia in blood or bone marrow.

In some aspects, response rates in subjects, such as subjects with CLL, are based on the International Workshop on Chronic Lymphocytic Leukemia (IWCLL) response criteria (Hallek, et al., Blood 2008, Jun. 15; 111(12): 5446-5456). In some aspects, these criteria are described as follows: complete remission (CR; also known in some cases as complete response), which in some aspects requires the absence of peripheral blood clonal lymphocytes by immunophenotyping, absence of lymphadenopathy, absence of hepatomegaly or splenomegaly, absence of constitutional symptoms and satisfactory blood counts; complete remission with incomplete marrow recovery (CRi), which in some aspects is described as CR above, but without normal blood counts; partial remission (PR; also known in some cases as partial response), which in some aspects is described as ≥50% fall in lymphocyte count, ≥50% reduction in lymphadenopathy or ≥50% reduction in liver or spleen, together with improvement in peripheral blood counts; progressive disease (PD), which in some aspects is described as ≥50% rise in lymphocyte count to >5×10$^9$/L, ≥50% increase in lymphadenopathy, ≥50% increase in liver or spleen size, Richter's transformation, or new cytopenias due to CLL; and stable disease, which in some aspects is described as not meeting criteria for CR, CRi, PR or PD.

In some embodiments, the subjects exhibits a CR or OR if, within 1 month of the administration of the dose of cells, lymph nodes in the subject are less than at or about 20 mm in size, less than at or about 10 mm in size or less than at or about 10 mm in size.

In some embodiments, an index clone of the CLL is not detected in the bone marrow of the subject (or in the bone marrow of greater than 50%, 60%, 70%, 80%, 90% or more of the subjects treated according to the methods. In some embodiments, an index clone of the CLL is assessed by IgH deep sequencing. In some embodiments, the index clone is not detected at a time that is at or about or at least at or about 1, 2, 3, 4, 5, 6, 12, 18 or 24 months following the administration of the cells.

In some embodiments, a subject exhibits morphologic disease if there are greater than or equal to 5% blasts in the bone marrow, for example, as detected by light microscopy, such as greater than or equal to 10% blasts in the bone marrow, greater than or equal to 20% blasts in the bone marrow, greater than or equal to 30% blasts in the bone marrow, greater than or equal to 40% blasts in the bone marrow or greater than or equal to 50% blasts in the bone marrow. In some embodiments, a subject exhibits complete or clinical remission if there are less than 5% blasts in the bone marrow.

In some embodiments, a subject has leukemia. The extent of disease burden can be determined by assessment of residual leukemia in blood or bone marrow.

In some embodiments, a subject exhibits morphologic disease if there are greater than or equal to 5% blasts in the bone marrow, for example, as detected by light microscopy, such as greater than or equal to 10% blasts in the bone marrow, greater than or equal to 20% blasts in the bone marrow, greater than or equal to 30% blasts in the bone marrow, greater than or equal to 40% blasts in the bone marrow or greater than or equal to 50% blasts in the bone marrow. In some embodiments, a subject exhibits complete or clinical remission if there are less than 5% blasts in the bone marrow.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD⁻, such that, in some cases, no leukemia cells are able to be detected in the subject using PCR or flow cytometry techniques.

In some embodiments, an index clone of the leukemia, e.g. CLL, is not detected in the bone marrow of the subject (or in the bone marrow of greater than 50%, 60%, 70%, 80%, 90% or more of the subjects treated according to the methods. In some embodiments, an index clone of the leukemia, e.g. CLL, is assessed by IGH deep sequencing. In some embodiments, the index clone is not detected at a time that is at or about or at least at or about 1, 2, 3, 4, 5, 6, 12, 18 or 24 months following the administration of the cells.

In some aspects MRD is detected by flow cytometry. Flow cytometry can be used to monitor bone marrow and peripheral blood samples for cancer cells. In particular aspects, flow cytometry is used to detect or monitor the presence of cancer cells in bone marrow. In some aspects, multiparameter immunological detection by flow cytometry is used to detect cancer cells (see for example, Coustan-Smith et al., (1998) Lancet 351:550-554). In some aspects, multiparameter immunological detection by mass cytometry is used to detect cancer cells. In some examples, 1, 2, 3, 4, 5, 6, 7, 8, 9, 10, 11, 12, 13, 14, 15, 20, 25, 30, 35, 40, 45 or 50 parameters can be used to detect cancer cells. The antigens used for detection are selected based on the cancer being detected (Foon and Todd (1986) Blood 68:1-31).

In some examples, bone marrow is harvested by bone marrow aspirates or bone marrow biopsies, and lymphocytes are isolated for analysis. Monoclonal and/or polyclonal antibodies conjugated to a fluorochrome (e.g., fluorescein isothiocyanate (FITC), phycoerythrin, peridinin chlorophyll protein, or biotin) can be used to detect epitopes, such as terminal deoxynucleotidyl transferase (TdT), CD3, CD10, CD11c, CD13, CD14, CD33, CD19, CD20, CD21, CD22, CD23, CD34, CD45, CD56, CD79b, IgM, and/or KORSA3544, on isolated lymphocytes. Labeled cells can then be detected using flow cytometry, such as multiparameter flow cytometry, or mass cytometry, to detect multiple epitopes.

Lymphoid cells can be identified and gated based on a light-scatter dot plot and then secondarily gated to identify cell populations expressing the immunophenotypic features of interest. Exemplary epitopes are set forth in Table 2 below. Other immunologic classification of leukemias and lymphomas are provided by Foon and Todd (Blood (1986) 68(1): 1-31). In some aspects, flow cytometric assessment of MRD can be achieved by quantifying live lymphocytes bearing one or more CLL immunophenotypes (e.g., low forward/side scatter; $CD3^{neg}$; $CD5^+$; $CD14^{neg}$; $CD19^+$; $CD23^+$; $CD45^+$; $CD56^{neg}$).

TABLE 2

Exemplary Immnunophenotype and Cytogentics Characteristics

| Disease | Immunophenotype | Cytogenetics |
|---|---|---|
| Chronic Lymphocytic Leukemia (CLL) | Pan-B+; CD5+; CD23+; CD79b/CD22 weak; FMC7−; sIg weak | Trisomy12<br>del(13)(q14.3)<br>del 11q22-q23<br>del 17p13 (p53)<br>t(11; 14)(q13; q32) BCL1/IgH rearrangement<br>t(14; 19)(q32; q13)<br>IgH deletion (14q32)<br>del(6q)<br>+8q24<br>+3<br>+18<br>del 6q21 |
| Small lymphocytic lymphoma (SLL) | Pan-B+; CD5+; CD23+; CD10−; sIgM+ faint | del(6)(q21-23) |
| Lymphoplasmacytic lymphoma | Pan-B+; CD5−; CD10−; cyIgM+ | t(9; 14)(p13; q32) PAX5/IgH |
| Follicle centre cell lymphoma | Pan-B+; CD10+/−; CD5−; sIg+ | t(14; 18)(q32; q21)/BCL2 Rearr |
| Diffuse large cell lymphoma | CD19+; CD22+; CD10−/+; SIg+ | t(14; 18) and p53 mutations<br>t(3; V)(q27; V)/BCL6 Rearr<br>variants c-MYC Rearr |
| Burkitt's lymphoma | Pan-B+; TdT−; CD10+; CD5−; sIgM+ | t(8; 14)(q24; q32) or variants/c-MYC Rearr |
| Burkitt-like lymphoma | Pan-B+; TdT−; CD10−/+ CD5−; sIg+ | t(8; 14) or variants<br>t(8; 14)+ t(14; 18) |
| Mantle cell lymphoma | Pan-B+; CD5+; CD23−; CD10−/+; sIgM+ bright | t(11; 14)(q13; q32)/BCL1 Rearr |

TABLE 2-continued

Exemplary Immnunophenotype and Cytogentics Characteristics

| Disease | Immunophenotype | Cytogenetics |
| --- | --- | --- |
| Marginal zone B-cell lymphoma (MZBCL) | pan-B+; CD5−/+; CD10−; CD23−; CD11c+/−; cyIg+ (40% of the cells), sIgM+ bright; sIgD− | t(11; 18)(q21; q21)/PI2/MLT fusion: Extra-nodal low-grade MALT lymphoma; indolent disease<br>t(1; 14)(p21; q32): Extra-nodal MALT lymphoma<br>del(7)(q22-31): Splenic MZBCL/+3q: Nodal, extra-nodal and splenic MZBCL |

+positive in >90% of the cases
+/−positive in more than 50% of the cases
−/+positive in less than 50% of cases
−positive in <10% of the cases
Pan-B markers: e.g., CD19, CD20, CD79a
sIG: surface immunoglobulins
cyIg: cytoplasmic immunoglobulins In some aspects, deep sequencing of the immunoglobulin heavy chain (IGH) locus of harvested B cells can be used to detect minimal residual disease (MRD). Clonal presence of a particular IgG rearrangement can provide a marker to detect the presence of B cell malignancies, such as CLL or NHL and/or residual presence of malignant cells thereof. In some aspects cells such as a population containing or suspected of containing B cells are harvested and isolated from blood. In some aspects, cells are harvested and isolated from bone marrow, e.g., from bone marrow aspirates or bone marrow biopsies and/or from other biological samples. In some aspects, polymerase chain reaction (PCR) amplification of the complementarity determining region 3 (CDR3) is achieved using primers to highly conserved sequences within the V and J regions of the gene locus, which may be used to identify clonal populations of cells for purposes of assessing minimal residual disease. Other methods for detecting clonal populations, such as single cell sequencing approaches, including those providing information regarding number of cells of a particular lineage and/or expressing a particular variable chain such as variable heavy chain or binding site thereof, such as a clonal population, may be used. In some aspects, the IGH DNA is amplified using a degenerate primers or primers recognizing regions of variable chains shared among different cell clones, such as those recognizing consensus V and degenerate consensus J region of the IGH sequence. An exemplary sequence of the V region is ACACGGCCTCGTGTATTACTGT (SEQ ID NO: 57). An exemplary degenerate consensus sequence of the J region is ACCTGAGGAGACGGTGACC (SEQ ID NO: 58).

The PCR product or sequencing result in some aspects is specific to the rearranged allele and serves as a clonal marker for MRD detection. Following PCR amplification of the CDR3 region, PCR products can be sequenced to yield patient-specific oligonucleotides constructed as probes for allele-specific PCR for sensitive detection of MRD following treatment of B-cell malignancies with CAR-T cell therapy, e.g. CD19 CAR-T cell therapy. In examples where a PCR product is not generated using the consensus primers, V region family-specific primers for the framework region 1 can be used instead.

In some aspects, persistence of PCR-detectable tumor cells such as cells of the B cell malignancy such as the NHL or CLL, such as detectable IGH sequences corresponding to the malignant or clonal IGH sequences, after treatment is associated with increased risk of relapse. In some aspects, patients who are negative for malignant IGH sequences following treatment (in some aspects, even in the context of other criteria indicating progressive disease or only a partial response, such as persistence of enlarged lymph nodes or other criteria that may in some contexts be associated with disease or lack of complete response) may be deemed to have increased likelihood of PFS or to enter into CR or durable CR or prolonged survival, compared to patients with persistent malignant IGH sequences. In some embodiments, such prognostic and staging determinations are particularly relevant for treatments in which clearance of malignant cells is observed within a short period of time following administration of the therapy, e.g., in comparison to resolution of other clinical symptoms such as lymph node size or other staging criteria. For example, in some such aspects, absence of detectable IGH or minimal residual disease in a sample such as the bone marrow may be a preferred readout for response or likelihood of response or durability thereof, as compared to other available staging or prognostic approaches. In some aspects, results from MRD, e.g., IGH deep sequencing information, may inform further intervention or lack thereof. For example, the methods and other provided embodiments in some contexts provide that a subject deemed negative for malignant IGH may in some aspects be not further treated or not be further administered a dose of the therapy provided, or that the subject be administered a lower or reduced dose. Conversely, it may be provided or specified that a subject exhibiting MRD via IGH deep sequencing be further treated, e.g., with the therapy initially administered at a similar or higher dose or with a further treatment. In some aspects, the disease or condition persists following administration of the first dose and/or administration of the first dose is not sufficient to eradicate the disease or condition in the subject.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative dosing regimen, such as one in which the subject receives one or more alternative therapeutic agents and/or one in which the subject does not receive a dose of cells and/or a lymphodepleting agent in accord with the provided methods, and/or with the provided articles of manufacture or compositions. In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, the event-free survival rate or overall survival rate of the subject is improved by the methods, as compared with other methods, for example, methods in which the subject receives one or more alternative therapeutic agents and/or one in which the subject does not receive a dose of cells and/or a lymphodepleting agent in accord with the provided methods, and/or with the provided articles of manufacture or compositions. For example, in some embodiments, event-free survival rate or probability for subjects treated by the methods at 6 months following the dose is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods, for example, methods in which the subject receives one or more alternative therapeutic agents and/or one in which the subject does not receive a dose of cells and/or a lymphodepleting agent in accord with the provided methods, and/or with the provided articles of manufacture or compositions. For example, in some embodiments, the probability of relapse at 6 months following the first dose is less than about 80%, less than about 70%, less than about 60%, less than about 50%, less than about 40%, less than about 30%, less than about 20%, or less than about 10%.

In some cases, the pharmacokinetics of administered cells, e.g., adoptively transferred cells are determined to assess the availability, e.g., bioavailability of the administered cells. Methods for determining the pharmacokinetics of adoptively transferred cells may include drawing peripheral blood from subjects that have been administered engineered cells, and determining the number or ratio of the engineered cells in the peripheral blood. Approaches for selecting and/or isolating cells may include use of chimeric antigen receptor (CAR)-specific antibodies (e.g., Brentjens et al., Sci. Transl. Med. 2013 March; 5(177): 177ra38) Protein L (Zheng et al., J. Transl. Med. 2012 February; 10:29), epitope tags, such as Strep-Tag sequences, introduced directly into specific sites in the CAR, whereby binding reagents for Strep-Tag are used to directly assess the CAR (Liu et al. (2016) Nature Biotechnology, 34:430; international patent application Pub. No. WO2015095895) and monoclonal antibodies that specifically bind to a CAR polypeptide (see international patent application Pub. No. WO2014190273). Extrinsic marker genes may in some cases be utilized in connection with engineered cell therapies to permit detection or selection of cells and, in some cases, also to promote cell suicide. A truncated epidermal growth factor receptor (EGFRt) in some cases can be co-expressed with a transgene of interest (a CAR or TCR) in transduced cells (see e.g. U.S. Pat. No. 8,802,374). EGFRt may contain an epitope recognized by the antibody cetuximab (Erbitux®) or other therapeutic anti-EGFR antibody or binding molecule, which can be used to identify or select cells that have been engineered with the EGFRt construct and another recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434).

In some embodiments, the number of $CAR^+$ T cells in a biological sample obtained from the patient, e.g., blood, can be determined at a period of time after administration of the cell therapy, e.g., to determine the pharmacokinetics of the cells. In some embodiments, number of $CAR^+$ T cells, optionally $CAR^+$ $CD8^+$ T cells and/or $CAR^+$ $CD4^+$ T cells, detectable in the blood of the subject, or in a majority of subjects so treated by the method, is greater than 1 cells per µL, greater than 5 cells per µL or greater than per 10 cells per µL.

D. Toxicity

In some embodiments, the provided methods are designed to or include features that result in a lower rate and/or lower degree of toxicity, toxic outcome or symptom, toxicity-promoting profile, factor, or property, such as a symptom or outcome associated with or indicative of cytokine release syndrome (CRS) or neurotoxicity, for example, compared to administration of an alternative cell therapy, such as an alternative $CAR^+$ T cell composition and/or an alternative dosing of cells, e.g. a dosing of cells that is not administered at a defined ratio.

In some embodiments, the provided methods do not result in a high rate or likelihood of toxicity or toxic outcomes, or reduces the rate or likelihood of toxicity or toxic outcomes, such as neurotoxicity (NT), cytokine release syndrome (CRS), such as compared to certain other cell therapies. In some embodiments, the methods do not result in, or do not increase the risk of, severe NT (sNT), severe CRS (sCRS), macrophage activation syndrome, tumor lysis syndrome, fever of at least at or about 38 degrees Celsius for three or more days and a plasma level of CRP of at least at or about 20 mg/dL. In some embodiments, greater than or greater than about 30%, 35%, 40%, 50%, 55%, 60% or more of the subjects treated according to the provided methods do not exhibit any grade of CRS or any grade of neurotoxcity. In some embodiments, no more than 50% of subjects treated (e.g. at least 60%, at least 70%, at least 80%, at least 90% or more of the subjects treated) exhibit a cytokine release syndrome (CRS) higher than grade 2 and/or a neurotoxicity higher than grade 2. In some embodiments, at least 50% of subjects treated according to the method (e.g. at least 60%, at least 70%, at least 80%, at least 90% or more of the subjects treated) do not exhibit a severe toxic outcome (e.g. severe CRS or severe neurotoxicity), such as do notexhibit grade 3 or higher neurotoxicity and/or does not exhibit severe CRS, or does not do so within a certain period of time following the treatment, such as within a week, two weeks, or one month of the administration of the cells. In some embodiments, parameters assessed to determine certain toxicities include adverse events (AEs), dose-limiting toxicities (DLTs), CRS and NT.

Administration of adoptive T cell therapy, such as treatment with T cells expressing chimeric antigen receptors, can induce toxic effects or outcomes such as cytokine release syndrome and neurotoxicity. In some examples, such effects or outcomes parallel high levels of circulating cytokines, which may underlie the observed toxicity.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

CRS may be treated using anti-inflammatory therapy such as an anti-IL-6 therapy, e.g., anti-IL-6 antibody, e.g., tocilizumab, or antibiotics or other agents as described. Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly. Other exemplary signs or symptoms associated with CRS include hemodynamic instability, febrile neutropenia, increase in serum C-reactive protein (CRP), changes in coagulation parameters (for example, international normalized ratio (INR), prothrombin time (PTI) and/or fibrinogen), changes in cardiac and other organ function, and/or absolute neutrophil count (ANC).

In some embodiments, outcomes associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures).

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

In some embodiments, the CRS-associated serum factors or CRS-related outcomes include inflammatory cytokines and/or chemokines, including interferon gamma (IFN-γ), TNF-a, IL-1β, IL-2, IL-6, IL-7, IL-8, IL-10, IL-12, sIL-2Rα, granulocyte macrophage colony stimulating factor (GM-CSF), macrophage inflammatory protein (MIP)-1, tumor necrosis factor alpha (TNFα), IL-6, and IL-10, IL-1(3, IL-8, IL-2, MIP-1, Flt-3L, fracktalkine, and/or IL-5. In some embodiments, the factor or outcome includes C reactive protein (CRP). In addition to being an early and easily measurable risk factor for CRS, CRP also is a marker for cell expansion. In some embodiments, subjects that are measured to have high levels of CRP, such as ≥15 mg/dL, have CRS. In some embodiments, subjects that are measured to have high levels of CRP do not have CRS. In some embodiments, a measure of CRS includes a measure of CRP and another factor indicative of CRS.

In some embodiments, one or more inflammatory cytokines or chemokines are monitored before, during, or after CAR treatment. In some aspects, the one or more cytokines or chemokines include IFN-γ, TNF-α, IL-2, IL-1β, IL-6, IL-7, IL-8, IL-10, IL-12, sIL-2Rα, granulocyte macrophage colony stimulating factor (GM-CSF), or macrophage inflammatory protein (MIP). In some embodiments, IFN-γ, TNF-α, and IL-6 are monitored.

CRS criteria that appear to correlate with the onset of CRS to predict which patients are more likely to be at risk for developing sCRS have been developed (see Davila et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 3 below.

TABLE 3

Exemplary Grading Criteria for CRS

| Grade | Description of Symptoms |
| --- | --- |
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention:<br>Oxygen requirement <40%, or<br>Hypotension responsive to fluids or low dose of a single vasopressor, or<br>Grade 2 organ toxicity (by CTCAE v4.0) |
| 3<br>Severe | Require and respond to aggressive intervention:<br>Oxygen requirement ≥40%, or<br>Hypotension requiring high dose of a single vasopressor (e.g., norepinephrine ≥20 μg/kg/min, dopamine ≥10 μg/kg/min, phenylephrine ≥200 μg/kg/min, or epinephrine ≥10 μg/kg/min), or<br>Hypotension requiring multiple vasopressors (e.g., vasopressin + one of the above agents, or combination vasopressors equivalent to ≥20 μg/kg/min norepinephrine), or<br>Grade 3 organ toxicity or Grade 4 transaminitis (by CTCAE v4.0) |
| 4<br>Life-threatening | Life-threatening:<br>Requirement for ventilator support, or<br>Grade 4 organ toxicity (excluding transaminitis) |
| 5<br>Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater, such as set forth in Table 3.

In some embodiments, outcomes associated with severe CRS or grade 3 CRS or greater, such as grade 4 or greater, include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures). In some embodiments, severe CRS includes CRS that requires management or care in the intensive care unit (ICU).

In some embodiments, the CRS, such as severe CRS, encompasses a combination of (1) persistent fever (fever of at least 38 degrees Celsius for at least three days) and (2) a serum level of CRP of at least at or about 20 mg/dL. In some embodiments, the CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

The method of measuring or detecting the various outcomes may be specified.

In some aspects, the toxic outcome is or is associated with neurotoxicity. In some embodiments, symptoms associated with a clinical risk of neurotoxicity include confusion, delirium, aphasia, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute—Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1)

symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 4.

TABLE 4

Exemplary Grading Criteria for neurotoxicity

| Grade | Description of Symptoms |
|---|---|
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the methods reduce symptoms associated with CRS or neurotoxicity compared to other methods. In some aspects, the provided methods reduce symptoms, outcomes or factors associated with CRS, including symptoms, outcomes or factors associated with severe CRS or grade 3 or higher CRS, compared to other methods. For example, subjects treated according to the present methods may lack detectable and/or have reduced symptoms, outcomes or factors of CRS, e.g. severe CRS or grade 3 or higher CRS, such as any described, e.g. set forth in Table 3. In some embodiments, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the present methods may have reduced symptoms associated with peripheral motor neuropathy, peripheral sensory neuropathy, dysethesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, the toxicity outcome is a dose-limiting toxicity (DLT). In some embodiments, the toxic outcome is a dose-limiting toxicity. In some embodiments, the toxic outcome is the absence of a dose-limiting toxicity. In some embodiments, a dose-limiting toxicity (DLT) is defined as any grade 3 or higher toxicity as assessed by any known or published guidelines for assessing the particular toxicity, such as any described above and including the National Cancer Institute (NCI) Common Terminology Criteria for Adverse Events (CTCAE) version 4.0.

In some embodiments, the low rate, risk or likelihood of developing a toxicity, e.g. CRS or neurotoxicity or severe CRS or neurotoxicity, e.g. grade 3 or higher CRS or neurotoxicity, observed with administering a dose of T cells in accord with the provided methods, and/or with the provided articles of manufacture or compositions, permits administration of the cell therapy on an outpatient basis. In some embodiments, the administration of the cell therapy, e.g. dose of T cells (e.g. CAR$^+$ T cells) in accord with the provided methods, and/or with the provided articles of manufacture or compositions, is performed on an outpatient basis or does not require admission to the subject to the hospital, such as admission to the hospital requiring an overnight stay.

In some aspects, subjects administered the cell therapy, e.g. dose of T cells (e.g. CAR$^+$ T cells) in accord with the provided methods, and/or with the provided articles of manufacture or compositions, including subjects treated on an outpatient basis, are not administered an intervention for treating any toxicity prior to or with administration of the cell dose, unless or until the subject exhibits a sign or symptom of a toxicity, such as of a neurotoxicity or CRS. Exemplary agents for treating, delaying, attenuating or ameliorating a toxicity are described in Section II.

In some embodiments, if a subject administered the cell therapy, e.g. dose of T cells (e.g. CAR$^+$ T cells), including subjects treated on an outpatient basis, exhibits a fever the subject is given or is instructed to receive or administer a treatment to reduce the fever. In some embodiments, the fever in the subject is characterized as a body temperature of the subject that is (or is measured at) at or above a certain threshold temperature or level. In some aspects, the threshold temperature is that associated with at least a low-grade fever, with at least a moderate fever, and/or with at least a high-grade fever. In some embodiments, the threshold temperature is a particular temperature or range. For example, the threshold temperature may be at or about or at least at or about 38, 39, 40, 41, or 42 degrees Celsius, and/or may be a range of at or about 38 degrees Celsius to at or about 39 degrees Celsius, a range of at or about 39 degrees Celsius to at or about 40 degrees Celsius, a range of at or about 40 degrees Celsius to at or about 41 degrees, or a range of at or about 41 degrees Celsius to at or about 42 degrees Celsius.

In some embodiments, the treatment designed to reduce fever includes treatment with an antipyretic. An antipyretic may include any agent, e.g., compound, composition, or ingredient, that reduces fever, such as one of any number of agents known to have antipyretic effects, such as NSAIDs (such as ibuprofen, naproxen, ketoprofen, and nimesulide), salicylates, such as aspirin, choline salicylate, magnesium salicylate, and sodium salicylate, paracetamol, acetaminophen, Metamizole, Nabumetone, Phenaxone, antipyrine, febrifuges. In some embodiments, the antipyretic is acetaminophen. In some embodiments, acetaminophen can be administered at a dose of 12.5 mg/kg orally or intravenously up to every four hours. In some embodiments, it is or comprises ibuprofen or aspirin.

In some embodiments, if the fever is a sustained fever, the subject is administered an alternative treatment for treating the toxicity, such as any described in Section II below. For subjects treated on an outpatient basis, the subject is instructed to return to the hospital if the subject has and/or is determined to or to have a sustained fever. In some embodiments, the subject has, and/or is determined to or considered to have, a sustained fever if he or she exhibits a fever at or above the relevant threshold temperature, and where the fever or body temperature of the subject is not reduced, or is not reduced by or by more than a specified amount (e.g., by more than 1° C., and generally does not fluctuate by about, or by more than about, 0.5° C., 0.4° C., 0.3° C., or 0.2° C.), following a specified treatment, such as a treatment designed to reduce fever such as treatment with an antipyreticm, e.g. NSAID or salicylates, e.g. ibuprofen, acetaminophen or aspirin. For example, a subject is considered to have a sustained fever if he or she exhibits or is determined to exhibit a fever of at least at or about 38 or 39 degrees Celsius, which is not reduced by or is not reduced by more than at or about 0.5° C., 0.4° C., 0.3° C., or 0.2° C., or by at or about 1%, 2%, 3%, 4%, or 5%, over a period of 6 hours, over a period of 8 hours, or over a period of 12 hours, or over a period of 24 hours, even following treatment with the antipyretic such as acetaminophen. In some embodiments, the dosage of the antipyretic is a dosage ordinarily effective in such as subject to reduce fever or fever of a particular type such as fever associated with a bacterial or viral infection, e.g., a localized or systemic infection.

In some embodiments, the subject has, and/or is determined to or considered to have, a sustained fever if he or she exhibits a fever at or above the relevant threshold temperature, and where the fever or body temperature of the subject does not fluctuate by about, or by more than about, 1° C., and generally does not fluctuate by about, or by more than about, 0.5° C., 0.4° C., 0.3° C., or 0.2° C. Such absence of fluctuation above or at a certain amount generally is measured over a given period of time (such as over a 24-hour, 12-hour, 8-hour, 6-hour, 3-hour, or 1-hour period of time, which may be measured from the first sign of fever or the first temperature above the indicated threshold). For example, in some embodiments, a subject is considered to or is determined to exhibit sustained fever if he or she exhibits a fever of at least at or about or at least at or about 38 or 39 degrees Celsius, which does not fluctuate in temperature by more than at or about 0.5° C., 0.4° C., 0.3° C., or 0.2° C., over a period of 6 hours, over a period of 8 hours, or over a period of 12 hours, or over a period of 24 hours.

In some embodiments, the fever is a sustained fever; in some aspects, the subject is treated at a time at which a subject has been determined to have a sustained fever, such as within one, two, three, four, five six, or fewer hours of such determination or of the first such determination following the initial therapy having the potential to induce the toxicity, such as the cell therapy, such as dose of T cells, e.g. CAR$^+$ T cells.

In some embodiments, one or more interventions or agents for treating the toxicity, such as a toxicity-targeting therapies, is administered at a time at which or immediately after which the subject is determined to or confirmed to (such as is first determined or confirmed to) exhibit sustained fever, for example, as measured according to any of the aforementioned embodiments. In some embodiments, the one or more toxicity-targeting therapies is administered within a certain period of time of such confirmation or determination, such as within 30 minutes, 1 hour, 2 hours, 3 hours, 4 hours, 6 hours, or 8 hours thereof.

E. Biomarkers, Analytes or Parameters

Among the provided methods are methods of assessing a risk for developing toxicity associated with cell therapy in a subject that involves assessing or detecting biomarkers (e.g., analytes) or parameters that are associated with the toxicity, e.g., neurotoxicity, such as severe neurotoxicity, and/or CRS, such as severe CRS. Also among the provided methods are methods of assessing the likelihood of response to a cell therapy in a subject that involves assessing or detecting biomarkers (e.g., analytes) or parameters that are associated with a response outcome, such as objective response (OR), including complete response (CR) and partial response (PR). In some embodiments, the associate response outcome includes durable response, such as a response that is durable for 3 months, 6 months, 9 months 12 months or more, after the initial response.

In some embodiments, the methods involve assessing or detecting the presence or absence of one or a panel of biomarkers (e.g. analytes) and/or parameters (e.g. concentration, amount, level or activity) associated with one or a panel of biomarkers (e.g. analytes). In some cases, the methods can include comparing the one or more parameters to a particular reference value, such as a threshold level (also called "threshold value" herein), e.g., those associated with a risk for developing toxicity or those associated with a particular response, such as OR, CR or PR, or durable response, such as a response that is durable for 3 months, 6 months, 9 months 12 months or more, after the initial response. In some embodiments, the methods also involve selecting subjects for treatment with a cell therapy based on the assessment of the presence or absence of the biomarker and/or comparison of the biomarkers to a reference value or threshold level of the biomarker. In some embodiments, the methods also involve administering an agent or a therapy that can treat, prevent, delay and/or attenuate development of the toxicity, e.g., based on the assessment of the presence or absence of the biomarker and/or comparison of the biomarkers to a reference value or threshold level of the biomarker.

In some embodiments, the methods involve assessing the likelihood of response of the subject or the risk of development of a toxicity, after administration of a cell therapy. In some embodiments, the methods involve assessing the level, amount or concentration of one or more analyte in a biological sample, wherein the biological sample is from a subject that is a candidate for treatment with the cell therapy, said cell therapy optionally comprising a dose or composition of genetically engineered cells expressing a recombinant receptor; and the biological sample is obtained from the subject prior to administering the cell therapy and/or said biological sample does not comprise the recombinant receptor and/or said engineered cells. In some aspects, the methods involve comparing, individually, the level, amount or concentration of the analyte in the sample to a threshold level, thereby determining a risk of developing a toxicity after administration of the cell therapy. In some aspects, the comparisons can be used to determine the likelihood of response of the subject or the risk of development of a toxicity, after administration of a cell therapy.

In some embodiments, the methods also involve selecting subjects for treatment with an a cell therapy, such as a particular dose of cell therapy, including administration of a particular dose of cell therapy such as those described herein, e.g., in Section I.A and I.B, based on the assessment of the presence or absence of the biomarker and/or comparison of the biomarkers to a reference value or threshold level of the biomarker. In some embodiments, the methods also involve selecting subjects for treatment with an additional agent, such as an agent or other treatment capable of treating, preventing, delaying, reducing or attenuating the development or risk of development of a toxicity, based on the assessment of the presence or absence of the biomarker and/or comparison of the biomarkers to a reference value or threshold level of the biomarker.

In some embodiments, the parameter is or includes attributes, factors, characteristic of the patient and/or the disease or condition. In some embodiments, the parameter is a parameter related to tumor burden, e.g., a measurement of tumor burden. In some aspects, the methods also involve further monitoring the subject for possible symptoms of toxicity based on the risk of toxicity determined by assessment of the presence or absence of the biomarker and/or comparison of the biomarkers to a reference value or threshold level of the biomarker. In some aspects, a biological sample, e.g., blood sample or tissue sample from the subject, can be obtained for detecting the presence or absence of a biomarker (e.g. analyte), such as for detecting or measuring a parameter (e.g. concentration, amount, level or activity) of the biomarker and/or assessing the presence of a biomarker, for analysis, correlation and/or detection of particular outcomes and/or toxicities. In some embodiments, certain physiological or biological parameters associated with a biomarker, including expression of biomarkers and/or clinical and laboratory parameters, can be assessed, from a biological sample, e.g., blood, from subjects before or after administration of the cell therapy. In some embodiments, expression biomarkers or analytes and/or clinical and laboratory parameters, can be assessed from a biological sample, e.g., blood, from subjects before administration of the cell therapy (pre-treatment). In some embodiments, expression biomarkers or analytes and/or clinical and laboratory parameters, can be assessed from a biological sample, e.g., blood, from subjects after administration of the cell therapy (post-treatment). In some embodiments, the concentration, amount, level or activity of biomarkers (e.g., analytes) and/or clinical and laboratory parameters can be assessed at one or more time points before or after administration of the cell therapy. In some embodiments, the peak concentration, amount, level or activity of biomarkers (e.g., analytes) and/or clinical and laboratory parameters during a specified period of time can also be determined.

In some embodiments, a biomarker or an analyte is an objectively measurable characteristic or a molecule expressed by or in a biological sample, including cells, that can be indicative of or associated with a particular state or phenomenon, such as a biological process, a therapeutic outcome, a cell phenotype or a diseased state. In some aspects, a biomarker or an analyte or parameters associated with a biomarker or an analyte can be measured or detected. For example, the presence or absence of expression of a biomarker or analyte, can be detected. In some aspects, the parameters such as concentration, amount, level or activity of the biomarker or analyte can be measured or detected. In some embodiments, the presence, absence, expression, concentration, amount, level and/or activity of the biomarker can be associated with, correlated to, indicative of and/or predictive of particular states, such as particular therapeutic outcomes or state of the subject. In some aspects, the presence, absence, expression, concentration, amount, level and/or activity of the biomarker or analyte, such as any described herein, can be used to assess the likelihood of a particular outcome or state, such as a particular therapeutic outcome, including response outcome or toxicity outcome. In some embodiments, exemplary biomarkers include cytokines, cell surface molecules, chemokines, receptors, soluble receptors, soluble serum proteins and/or degradation products. In some embodiments, biomarkers or analytes can also include particular attributes, factors, characteristic of the patient and/or the disease or condition or factors indicative of the state of the patient and/or the disease or condition of the patient (including disease burden), and/or clinical or laboratory parameters.

In some embodiments, the biomarkers can be used singly or in combination with other biomarkers, such as in a panel of biomarkers. In some embodiments, expression of particular biomarkers can be correlated to particular outcomes or toxicities, e.g., development of neurotoxicity. In some embodiments, biomarkers (e.g. analytes), including parameters thereof, that can be assessed include Lactate dehydrogenase (LDH), ferritin, C-reactive protein (CRP), Interleukin-6 (IL-6), IL-7, IL-8, IL-10, IL-15, IL-16, tumor necrosis factor alpha (TNF-α), interferon alpha 2 (IFN-α2), monocyte chemoattractant protein-1 (MCP-1), macrophage inflammatory protein 1 alpha (MIP-1a), macrophage inflammatory protein 1 beta (MIP-1β), Eotaxin, Granulocyte-colony stimulating factor (G-CSF), IL-1 receptor alpha (IL-1Rα), IL-1(3, IFN-γ-Inducible Protein 10 (IP-10), perforin, and D-dimer (fibrin degradation product). In some embodiments, the biomarkers (e.g. analytes), including parameters thereof, include LDH, ferritin, CRP, IL-6, IL-8, IL-10, TNF-α, IFN-α2, MCP-1 and MIP-1β. In some embodiments, the biomarkers (e.g. analytes), including parameters thereof, include ferritin, CRP, D-dimer, IL-6, IL-15, TNF-α and MIP-1α. In some embodiments, the biomarkers (e.g. analytes), including parameters thereof, include ferritin, CRP, IL-10, IL-15, IL-16, TNF-α, or MIP-1β.

In some embodiments, the methods include detecting the presence or absence of one or more biomarkers, such as a parameter (e.g. concentration, amount, level or activity) associated with one or more biomarkers, in which the one or more biomarkers are selected from among Lactate dehydrogenase (LDH), ferritin, C-reactive protein (CRP), Interleukin-6 (IL-6), IL-7, IL-8, IL-10, IL-15, IL-16, tumor necrosis factor alpha (TNF-α), interferon alpha 2 (IFN-α2), monocyte chemoattractant protein-1 (MCP-1), macrophage inflammatory protein 1 alpha (MIP-1a), macrophage inflammatory protein 1 beta (MIP-1β), Eotaxin, Granulocyte-colony stimulating factor (G-CSF), IL-1 receptor alpha (IL-1Rα), IL-1β, IFN-γ-Inducible Protein 10 (IP-10), perforin, and D-dimer (fibrin degradation product).

In some embodiments, the parameter that is assessed is or includes attributes, factors, characteristic of the patient and/or the disease or condition, and/or expression of biomarkers. In some embodiments, the parameter is or includes one or more factors indicative of the state of the patient and/or the disease or condition of the patient. In some embodiments, the parameter is indicative of tumor burden. In some embodiments, the factor indicative of tumor burden is a volumetric measure of tumor(s). In some embodiments, the volumetric measure is a measure of the lesion(s), such as the tumor size, tumor diameter, tumor volume, tumor mass, tumor load or bulk, tumor-related edema, tumor-related necrosis, and/or number or extent of metastases. In some embodiments, the volumetric measure of tumor is a bidimensional measure. For example, in some embodiments, the area of lesion(s) are calculated as the product of the longest diameter and the longest perpendicular diameter of all measurable tumors. In some cases, the volumetric measure of tumor is a unidimensional measure. In some cases, the size of measurable lesions is assessed as the longest diameter. In some embodiments, the sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR) is measured.

Exemplary methods for measuring and assessing tumor burden include those described in, e.g., Carceller et al., Pediatr Blood Cancer. (2016) 63(8):1400-1406 and Eisenhauer et al., Eur J Cancer. (2009) 45(2):228-247. In some embodiments, the volumetric is a sum of the products of diameters (SPD) measured by determining the sum of the products of the largest perpendicular diameters of all measurable tumors. In some aspects, the tumor or lesion are measured in one dimension with the longest diameter (LD) and/or by determining the sum of longest tumor diameters (SLD) of all measurable lesions. In some embodiments, the volumetric measure of tumor is a volumetric quantification of tumor necrosis, such as necrosis volume and/or necrosis-tumor ratio (NTR), see Monsky et al., Anticancer Res. (2012) 32(11): 4951-4961. In some aspects, the volumetric measure of tumor is a volumetric quantification of tumor-related edema, such as peritumoral edema (PTE) and/or edema-tumor ratio (ETR). In some embodiments, measuring can be performed using imaging techniques such as computed tomography (CT), positron emission tomography (PET), and/or magnetic resonance imaging (Mill) of the subject.

In some embodiments, the volumetric measure of tumor is determined at a screening session, such as a routine assessment or blood draw to confirm and/or identify the condition or disease in the subject.

In some embodiments, the presence or absence and/or a parameter of one or more biomarkers (e.g. analytes) is assessed from a biological sample. In some aspects, the biological sample is a bodily fluid or a tissue. In some such embodiments, the biological sample, e.g., bodily fluid, is or contains whole blood, serum or plasma.

In some embodiments, the presence or absence and/or a parameter of one or more biomarkers (e.g. analytes) is assessed prior to administration of the cell therapy (e.g., pre-infusion), e.g., obtained up to 2 days, up to 7 days, up to 14 days, up to 21 days, up to 28 days, up to 35 days or up to 40 days prior to initiation of the administration of the engineered cells. In some embodiments, the biological sample is obtained from the subject prior to administration of the cell therapy (e.g., pre-infusion), e.g., obtained up to 2 days, up to 7 days, up to 14 days, up to 21 days, up to 28 days, up to 35 days or up to 40 days prior to initiation of the administration of the engineered cells.

In some embodiments, the biological sample is an apheresis or leukaphresis sample. In some embodiments, the or absence and/or a parameter of one or more biomarkers (e.g. analytes) is assessed or the biological sample is obtained after administration of the cell therapy. In some embodiments, the reagents can be used prior to the administration of the cell therapy or after the administration of cell therapy, for diagnostic purposes, to identify subjects and/or to assess treatment outcomes and/or toxicities.

In some embodiments, measuring the value of the one or more biomarkers comprises performing an in vitro assay. In some aspects, the in vitro assay is an immunoassay, an aptamer-based assay, a histological or cytological assay, or an mRNA expression level assay. In some embodiments, the values of the one or more biomarkers are measured by an enzyme-linked immunosorbent assay (ELISA), immunoblotting, immunoprecipitation, radioimmunoassay (MA), immunostaining, a flow cytometry assay, surface plasmon resonance (SPR), a chemiluminescence assay, a lateral flow immunoassay, an inhibition assay or an avidity assay. In some cases, the value of at least one of the one or more biomarkers is determined using a binding reagent that specifically binds to at least one biomarker. In some aspects, the binding reagent is an antibody or antigen-binding fragment thereof, an aptamer or a nucleic acid probe.

In some embodiments, measuring the value of the one or more biomarkers (e.g., analytes) comprises contacting a reagent capable of directly or indirectly detecting the analyte with the biological sample and determining the presence or absence, level, amount or concentration of the analyte in the biological sample. In some embodiments, the one or more biomarker (e.g. analyte) is lactate dehydrogenase (LDH), ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product). In some embodiments, the one or more biomarker (e.g. analyte) is LDH, ferritin, CRP, IL-6, IL-8, IL-10, TNF-alpha, IFN-alpha2, MCP-1 and MIP-1beta. In some embodiments, the one or more biomarker (e.g. analyte) is or includes LDH.

In some aspects, the reagent is a binding molecule that specifically binds to the analyte. For example, in some embodiments, the reagent is an antibody or an antigen-binding fragment thereof. In some embodiments, the reagent is or includes a substrate or binding partner of the analyte.

In some embodiments, the presence, absence or parameter (e.g. level, amount, concentration and/or other measure) of LDH is detected or determined in a sample. Various methods of detecting or determining LDH are known. For example, an assay which measures LDH conversion of lactate to pyruvate through $NAD^+$ reduction to NADH can be used to detect LDH in the sample. In some embodiments, the sample is contacted with lactate in the presence of coenzyme NAD which, as a measure of LDH in the sample, results in NADH that is then oxidized in the presence of an electron transfer agent. In some embodiments, the NADH interacts with a probe or dye precursor that is detectable by measuring absorption in a visible light range. In some examples, diaphorase uses the NADH to reduce tetrazolium salt (INT) to a red formazan product and the product is measured. Therefore, in some embodiments, the amount of colored product formed is directly proportional to the LDH activity in the sample.

In some embodiments, the methods involve comparing, individually, the level, amount or concentration of the analyte in the sample to a threshold level, thereby determining a risk of developing a toxicity after administration of the cell therapy, or thereby determining a likelihood that a subject will achieve a response to the cell therapy. In some aspects, the exemplary threshold levels can be determined based on the mean or median values and values within a range or standard deviation of the mean or median values of the level, amount or concentration of the analyte in a biological sample obtained from a group of subjects prior to receiving a cell therapy, wherein each of the subjects of the group went on to exhibit a particular outcome, such as a particular therapeutic outcome, including either exhibiting a response or not exhibiting a response; or either developing a toxicity or not developing a toxicity. In some embodiments, particular aspects of determining threshold values include those described below in Sections I.E.1 and I.E.2.

1. Exemplary Biomarkers, Analytes or Parameters Associated with Response Outcomes In some embodiments, the analyte or biomarker is associated with, correlated to, indicative of and/or predictive of a particular outcome, such as a particular response outcome, such as an objective response (OR) a complete response (CR) or a partial response (PR), or durable response, such as an OR or CR or a PR that is durable at 3, 6, 9 months or more. In some embodiments, lower or reduced levels or increased levels of one or more of such biomarkers (e.g, analytes), such as compared to a reference value or threshold level, can be associated with the a response, such as an OR, CR or PR, or any response outcomes described herein, e.g., in Section I.C, optionally a durable response, such as a response that is durable for at least 3 months, 6 months or more.

In some embodiments, the analyte or biomarker is associated with, correlated to, indicative of and/or predictive of a particular outcome, such as a particular response or durable response outcome, in a subject that has been administered a cell therapy, such as with a composition containing genetically engineered cells. In some embodiments, the presence, expression, level, amount or concentration of one or more analyte in a biological sample obtained from a subject prior to the administration of cell therapy, can be associated with, correlated to, indicative of and/or predictive of a particular outcome, such as a particular response or durable response outcome. In some embodiments, presence, expression, level, amount or concentration of particular biomarkers can be correlated to a particular response or durable response outcome. In some embodiments, the response outcome can be any response outcomes described herein, e.g., in Section I.C.

In some embodiments, the methods include comparing, individually, the level, amount or concentration of the analyte in the sample to a threshold level, thereby determining a likelihood that a subject will achieve a response to the cell therapy. In some embodiments, the methods include selecting a subject who is likely to respond to treatment based on the results of determining a likelihood that a subject will achieve a response to the cell therapy by comparing, individually, the level, amount or concentration of the analyte in the sample to a threshold level. In some embodiments, the methods also include administering the cell therapy to the subject selected for treatment. In some embodiments, if the subject is determined as not likely to achieve a response or a durable response, further comprising administering an additional therapeutic agent to the subject.

In some embodiments, the biomarkers (e.g., analytes) include those associated with a response outcome, and/or a durable response. In some embodiments, the biomarkers (e.g. analytes), including parameters thereof, include LDH, ferritin, CRP, D-dimer, Serum Amyloid A1 (SAA-1), IL-6, IL-10, IL-15, IL-16, TNF-α, IFN-γ, MIP-1α and C-X-C motif chemokine 10 (CXCL10).

In some aspects, exemplary analytes or biomarkers that can be assessed or analyzed with respect to assessment of likelihood of response after administration of a cell therapy include one or more analyte selected from ferritin, LDH, CXCL10, G-CSF, and IL-10. In some embodiments, for any of the foregoing analytes or biomarkers, the subject is likely to achieve a response if the level, amount or concentration one or more of the analyte is below a threshold level and the subject is not likely to achieve a response if the level, amount or concentration one or more of the analyte is above a threshold level. In some embodiments, the response is or comprises objective response. In some embodiments, the objective response is or comprises complete response (CR) or partial response (PR). In some aspects, reduced levels of ferritin, LDH, CXCL10, G-CSF, and IL-10, in a biological sample from a subject obtained prior to administration of a cell therapy (pre-treatment), can be associated with achieving objective response, including complete response (CR) or partial response (PR).

In some embodiments, the threshold level is within 25%, within 20%, within 15%, within 10% or within 5% and/or is within a standard deviation below the median or mean level, amount or concentration of ferritin, LDH, CXCL10, G-CSF, or IL-10 in a biological sample obtained from a group of subjects prior to receiving a cell therapy, wherein each of the subjects of the group went on to achieve a response after administration of a recombinant-receptor-expressing therapeutic cell composition for treating the same disease or condition. In some embodiments, the threshold level is within 25%, within 20%, within 15%, within 10% or within 5% and/or is within a standard deviation above the median or mean level, amount or concentration of ferritin, LDH, CXCL10, G-CSF, or IL-10 in a biological sample obtained from a group of subjects prior to receiving a cell therapy, wherein each of the subjects of the group went on to exhibit stable disease (SD) and/or progressive disease (PD) after administration of a recombinant-receptor-expressing therapeutic cell composition for treating the same disease or condition.

In some aspects, exemplary analytes or biomarkers that can be assessed or analyzed with respect to assessment of likelihood of durable response after administration of a cell therapy include one or more analyte selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β. In some embodiments, for any of the foregoing analytes or biomarkers, the subject is likely to achieve a durable response if the level, amount or concentration one or more of the analyte is below a threshold level and the subject is not likely to achieve a durable response if the level, amount or concentration one or more of the analyte is above a threshold level. In some embodiments, the durable response is or comprises a complete response (CR) or partial response (PR) that is durable for at or greater than 3 months, 4 months, 5 months, or 6 months. In some embodiments, the durable response is or comprises a CR or PR that is durable for at least 3 months. In some aspects, reduced levels of LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, in a biological sample from a subject obtained prior to administration of a cell therapy (pre-treatment), can be associated with achieving durable response, such as a CR or PR that is durable for at least 3 months.

In some embodiments, the threshold level is within 25%, within 20%, within 15%, within 11% or within 5% and/or is within a standard deviation below the median or mean level, amount or concentration of LDH, ferritin, CRP, D-dimer, SAA-1, IL-6, IL-10, IL-15, IL-16, TNF-α, IFN-γ, MIP-1α, CXCL-10, IL-8, MCP-1 or MIP-1β in a biological sample obtained from a group of subjects prior to receiving a cell therapy, wherein each of the subjects of the group went on to achieve a durable response after administration of a recombinant-receptor-expressing therapeutic cell composition for treating the same disease or condition.

In some embodiments, the threshold level is within 25%, within 20%, within 15%, within 11% or within 5% and/or is within a standard deviation above the median or mean level, amount or concentration of LDH, ferritin, CRP, D-dimer, SAA-1, IL-6, IL-10, IL-15, IL-16, TNF-α, IFN-γ, MIP-1α, CXCL-10, IL-8, MCP-1 or MIP-1β in a biological sample obtained from a group of subjects prior to receiving a cell therapy, wherein each of the subjects of the group did not achieve a durable response after administration of a recombinant-receptor-expressing therapeutic cell composition for treating the same disease or condition.

In some embodiments, the response is durable response, such as a CR or PR that is durable for at least 3 months.

In some embodiments, the threshold level for LDH is at or at about or below or below about 600 U/L, 500 U/L, 400 U/L, 300 U/L or 200 U/L.

In some embodiments, exemplary threshold level for ferritin is at or at about or below or below about 1000 μg/L, 900 μg/L, 800 μg/L, 700 μg/L, 600 μg/L, 500 μg/L, 400 μg/L, 300 μg/L or 200 μg/L.

In some embodiments, exemplary threshold level for CRP is at or at about or below or below about 20 mg/L, 19 mg/L, 18 mg/L, 17 mg/L, 16 mg/L, 15 mg/L, 14 mg/L, 13 mg/L, 12 mg/L, 11 mg/L, 10 mg/L, 9 mg/L, 8 mg/L, 7 mg/L, 6 mg/L or 5 mg/L.

In some embodiments, exemplary threshold level for D-dimer is at or at about or below or below about 1000 μg/L, 900 μg/L, 800 μg/L, 700 μg/L, 600 μg/L, 500 μg/L, 400 μg/L, 300 μg/L or 200 μg/L.

In some embodiments, exemplary threshold level for SAA-1 is at or at about or below or below about 100 mg/L, 90 mg/L, 80 mg/L, 70 mg/L, 60 mg/L, 50 mg/L, 40 mg/L, 30 mg/L or 20 mg/L.

In some embodiments, exemplary threshold level for IL-6 is at or at about or below or below about 6 pg/mL, 5 pg/mL, 4 pg/mL, 3 pg/mL or 2 pg/mL.

In some embodiments, exemplary threshold level for IL-10 is at or at about or below or below about 2 pg/mL, 1 pg/mL, 0.9 pg/mL, 0.8 pg/mL, 0.7 pg/mL, 0.6 pg/mL or 0.5 pg/mL.

In some embodiments, exemplary threshold level for IL-15 is at or at about or below or below about 7 pg/mL, 6 pg/mL, 5 pg/mL, 4 pg/mL or 3 pg/mL.

In some embodiments, exemplary threshold level for IL-16 is at or at about or below or below about 1000 pg/mL, 900 pg/mL, 800 pg/mL, 700 pg/mL or 600 pg/mL.

In some embodiments, exemplary threshold level for TNF-α is at or at about or below or below about 10 pg/mL, 9 pg/mL, 8 pg/mL, 7 pg/mL or 6 pg/mL.

In some embodiments, exemplary threshold level for IFN-γ is at or at about or below or below about 30 pg/mL, 20 pg/mL, 10 pg/mL, 9 pg/mL, 8 pg/mL or 7 pg/mL;

In some embodiments, exemplary threshold level for MIP-1α is at or at about or below or below about 40 pg/mL, 30 pg/mL or 20 pg/mL; and/or In some embodiments, exemplary threshold level for CXCL-10 is at or at about or below or below about 1500 pg/mL, 1000 pg/mL, 900 pg/mL, 800 pg/mL, 700 pg/mL, 600 pg/mL or 500 pg/mL.

In some aspects, exemplary analytes or biomarkers that can be assessed or analyzed with respect to assessment of likelihood of durable response after administration of a cell therapy include one or more analyte selected from ferritin, CRP, LDH, CXCL10, IL-8, IL-10, IL-15, MCP-1, MIP-1β and TNF-α. In some embodiments, for any of the foregoing analytes or biomarkers, the subject is likely to achieve a durable response if the level, amount or concentration one or more of the analyte is below a threshold level and the subject is not likely to achieve a durable response if the level, amount or concentration one or more of the analyte is above a threshold level. In some embodiments, the durable response is or comprises a complete response (CR) or partial response (PR) that is durable for at or greater than 3 months, 4 months, 5 months, or 6 months. In some embodiments, the durable response is or comprises a CR or PR that is durable for at least 3 months. In some aspects, reduced levels of ferritin, CRP, LDH, CXCL10, IL-8, IL-10, IL-15, MCP-1, MIP-1β and TNF-α, in a biological sample from a subject obtained prior to administration of a cell therapy (pre-treatment), can be associated with achieving durable response, such as a CR or PR that is durable for at least 3 months.

In some embodiments, the threshold level is within 25%, within 20%, within 15%, within 11% or within 5% and/or is within a standard deviation below the median or mean level, amount or concentration of ferritin, CRP, LDH, CXCL10, IL-8, IL-10, IL-15, MCP-1, MIP-1β or TNF-α in a biological sample obtained from a group of subjects prior to receiving a cell therapy, wherein each of the subjects of the group went on to achieve a durable response after administration of a recombinant-receptor-expressing therapeutic cell composition for treating the same disease or condition.

In some embodiments, the threshold level is within 25%, within 20%, within 15%, within 11% or within 5% and/or is within a standard deviation above the median or mean level, amount or concentration of ferritin, CRP, LDH, CXCL10, IL-8, IL-10, IL-15, MCP-1, MIP-1β or TNF-α in a biological sample obtained from a group of subjects prior to receiving a cell therapy, wherein each of the subjects of the group did not achieve a durable response after administration of a recombinant-receptor-expressing therapeutic cell composition for treating the same disease or condition.

In some aspects, exemplary analytes or biomarkers that can be assessed or analyzed with respect to assessment of likelihood of durable response after administration of a cell therapy include one or more analyte selected from hemoglobin and albumin. In some embodiments, for any of the foregoing analytes or biomarkers, the subject is likely to achieve a durable response if the level, amount or concentration one or more of the analyte is above a threshold level and the subject is not likely to achieve a durable response if the level, amount or concentration one or more of the analyte is below a threshold level. In some embodiments, the durable response is or comprises a complete response (CR) or partial response (PR) that is durable for at or greater than 3 months, 4 months, 5 months, or 6 months. In some embodiments, the durable response is or comprises a CR or PR that is durable for at least 3 months. In some aspects, elevated levels of hemoglobin and albumin, in a biological sample from a subject obtained prior to administration of a cell therapy (pre-treatment), can be associated with achieving durable response, such as a CR or PR that is durable for at least 3 months.

In some embodiments, the threshold level is within 25%, within 20%, within 15%, within 11% or within 5% and/or is within a standard deviation above the median or mean level, amount or concentration of hemoglobin or albumin in a biological sample obtained from a group of subjects prior to receiving a cell therapy, wherein each of the subjects of the group went on to achieve a durable response after administration of a recombinant-receptor-expressing therapeutic cell composition for treating the same disease or condition.

In some embodiments, the threshold level is within 25%, within 20%, within 15%, within 11% or within 5% and/or is within a standard deviation below the median or mean level, amount or concentration of hemoglobin or albumin in a biological sample obtained from a group of subjects prior to receiving a cell therapy, wherein each of the subjects of the group did not achieve a durable response after administration of a recombinant-receptor-expressing therapeutic cell composition for treating the same disease or condition.

2. Exemplary Biomarkers, Analytes or Parameters Associated with Toxicity Outcomes In some embodiments, the analyte or biomarker is associated with, correlated to, indicative of and/or predictive of a particular outcome, such as development of a toxicity, in a subject that has been administered a cell therapy, such as with a composition containing genetically engineered cells. In some embodiments, the presence, expression, level, amount or concentration of one or more analyte in a biological sample obtained from a subject prior to the administration of cell therapy, can be associated with, correlated to, indicative of and/or predictive of a particular outcome, such as development of a toxicity, such as any toxicity outcomes described herein, e.g., in Section I.D. In some embodiments, presence, expression, level, amount or concentration of particular biomarkers can be correlated to particular outcomes or toxicities, e.g., development of NT or CRS. In some embodiments, the toxicity is a toxicity potentially associated with cell therapy, such as any described herein, for example, in Section I.D. In some embodiments, the toxicity is neurotoxicity (NT) or cytokine release syndrome (CRS). In some embodiments, the toxicity is a severe NT or severe CRS. In some embodiments, the toxicity is grade 2 or higher NT or grade 2 or higher CRS. In some embodiments, the toxicity is grade 3 or higher NT or grade 3 or higher CRS.

In some embodiments, the methods include comparing, individually, the level, amount or concentration of the analyte in the sample to a threshold level, thereby determining a risk of developing a toxicity after administration of the cell therapy. In some embodiments, the methods include identifying a subject who has a risk of developing a toxicity after administration of a cell therapy based by comparing, individually, the level, amount or concentration of the analyte in the sample to a threshold level. In some embodiments, the methods also include following or based on the results of the assessment, administering to the subject the cell therapy, and, optionally, an agent or other treatment capable of treating, preventing, delaying, reducing or attenuating the development or risk of development of a toxicity. In some embodiments, the methods also involve monitoring the subject for symptoms of toxicity if the subject is administered a cell therapy and is identified as having a risk of developing a toxicity.

In some embodiments, if the subject is identified as having a risk of developing a toxicity, one or more of the following steps can be performed can be administered to the subject: (a) (1) an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject; and/or (b) administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (c) administering to the subject a cell therapy in an in-patient setting and/or with admission to the hospital for one or more days, optionally wherein the cell therapy is otherwise to be administered to subjects on an outpatient basis or without admission to the hospital for one or more days.

In some embodiments, biomarkers or analytes, including parameters thereof, that can be assessed include Lactate dehydrogenase (LDH), ferritin, C-reactive protein (CRP), Interleukin-6 (IL-6), IL-7, IL-8, IL-10, IL-15, IL-16, tumor necrosis factor alpha (TNF-α), interferon alpha 2 (IFN-α2), monocyte chemoattractant protein-1 (MCP-1), macrophage inflammatory protein 1 alpha (MIP-1a), macrophage inflammatory protein 1 beta (MIP-1β), Eotaxin, Granulocyte-colony stimulating factor (G-CSF), IL-1 receptor alpha (IL-1Rα), IL-1β, IFN-γ-Inducible Protein 10 (IP-10), perforin, and D-dimer (fibrin degradation product). In some embodiments, the biomarkers (e.g. analytes), including parameters thereof, include LDH, ferritin, CRP, IL-6, IL-8, IL-10, TNF-α, IFN-α2, MCP-1 and MIP-1β. In some embodiments, the biomarkers (e.g. analytes), including parameters thereof, include ferritin, CRP, D-dimer, IL-6, IL-15, TNF-α and MIP-1α. In some embodiments, the biomarkers (e.g. analytes), including parameters thereof, include ferritin, CRP, IL-10, IL-15, IL-16, TNF-α, or MIP-1β. In some embodiments, elevated levels or increased levels of one or more of such biomarkers (e.g, biomarkers), such as compared to a reference value or threshold level, can be associated with the development of neurotoxcity, e.g. severe neurotoxicity or grade 3 or higher or grade 4 or 5 neurotoxicity. In some embodiments, elevated levels or increased levels of one or more of such biomarkers (e.g, analytes), such as compared to a reference value or threshold level, can be associated with the development of neurotoxcity, e.g. severe neurotoxicity or grade 3 or higher or grade 4 or 5 neurotoxicity.

In some aspects, exemplary analytes or biomarkers that can be assessed or analyzed with respect to assessment of the risk of developing a toxicity after administration of a cell therapy include one or more analyte selected from LDH, Ferritin, C-reactive protein (CRP), IL-6, IL-8, IL-10, TNF-α, IFN-α2, MCP-1 and MIP-1β. In some embodiments, for any of the foregoing analytes or biomarkers, the subject has a risk of developing a toxicity if the level, amount or concentration one or more of the analyte is above a threshold level and the subject has a low risk of developing a toxicity if the level, amount or concentration one or more of the analyte is below a threshold level. In some embodiments, the toxicity is neurotoxicity. In some aspects, elevated levels of LDH, Ferritin, C-reactive protein (CRP), IL-6, IL-8, IL-10, TNF-α, IFN-α2, MCP-1 and MIP-1β, in a biological sample from a subject obtained prior to administration of a cell therapy (pre-treatment), can be associated with a higher risk of developing a neurotoxicity.

In some embodiments, the threshold level is within 25%, within 20%, within 15%, within 30% or within 5% and/or is within a standard deviation above the median or mean level, amount or concentration of LDH, Ferritin, C-reactive protein (CRP), IL-6, IL-8, IL-10, TNF-α, IFN-α2, MCP-1 or MIP-1β in a biological sample obtained from a group of subjects prior to receiving a cell therapy, wherein each of the subjects of the group went on not develop any toxicity after receiving a recombinant-receptor-expressing therapeutic cell composition for treating the same disease or condition.

In some embodiments, the threshold level is within 25%, within 20%, within 15%, within 30% or within 5% and/or is within a standard deviation below the median or mean level, amount or concentration of LDH, Ferritin, C-reactive protein (CRP), IL-6, IL-8, IL-10, TNF-α, IFN-α2, MCP-1 or MIP-1β in a biological sample obtained from a group of subjects prior to receiving a cell therapy, wherein each of the subjects of the group went on to develop a toxicity after receiving a recombinant-receptor-expressing therapeutic cell composition for treating the same disease or condition. In some embodiments, the toxicity is neurotoxicity.

In some embodiments, exemplary threshold level for LDH is at or at about or above about 300 U/L, 400 U/L, 500 U/L, 600 U/L or 700 U/L.

In some embodiments, exemplary threshold level for Ferritin is at or at about or above or above about 500 ng/mL, 600 ng/mL, 700 ng/mL, 800 ng/mL, 900 ng/mL, 1000 ng/mL or 1500 ng/mL.

In some embodiments, exemplary threshold level for CRP is at or at about or above or above about 20 mg/L, 30 mg/L, 40 mg/L, 50 mg/L, 60 mg/L, 70 mg/L or 80 mg/L.

In some embodiments, exemplary threshold level for IL-6 is at or at about or above or above about 5 pg/mL, 6 pg/mL, 7 pg/mL, 8 pg/mL, 9 pg/mL, 10 pg/mL, 20 pg/mL or 30 pg/mL.

In some embodiments, exemplary threshold level for IL-8 is at or at about or above or above about 8 pg/mL, 9 pg/mL, 10 pg/mL, 20 pg/mL or 30 pg/mL.

In some embodiments, exemplary threshold level for IL-10 is at or at about or above or above about 20 pg/mL, 30 pg/mL, 40 pg/mL, 50 pg/mL, 60 pg/mL or 70 pg/mL.

In some embodiments, exemplary threshold level for TNF-α is at or at about or above or above about 20 pg/mL or 30 pg/mL.

In some embodiments, exemplary threshold level for IFN-α2 is at or at about or above or above about 40 pg/mL, 50 pg/mL, 60 pg/mL, 70 pg/mL or 80 pg/mL.

In some embodiments, exemplary threshold level for MCP-1; and/or is at or at about or above or above about 200 pg/mL or 300 pg/mL.

In some embodiments, exemplary threshold level for MIP-1β is at or at about or above or above about 40 pg/mL, 50 pg/mL, 60 pg/mL, 70 pg/mL or 80 pg/mL.

In some aspects, exemplary analytes or biomarkers that can be assessed or analyzed with respect to assessment of the risk of developing a toxicity after administration of a cell therapy include one or more analyte selected from IL-8, IL-10 and CXCL10. In some embodiments, for any of the foregoing analytes or biomarkers, the subject has a risk of developing a toxicity if the level, amount or concentration one or more of the analyte is above a threshold level and the subject has a low risk of developing a toxicity if the level, amount or concentration one or more of the analyte is below a threshold level. In some embodiments, the toxicity is neurotoxicity. In some embodiments, the toxicity is severe neurotoxicity or a grade 3 or higher neurotoxicity. In some aspects, elevated levels of IL-8, IL-10 and CXCL10, in a biological sample from a subject obtained prior to administration of a cell therapy (pre-treatment), can be associated with a higher risk of developing a neurotoxicity, or a severe neurotoxicity or a grade 3 or higher neurotoxicity.

In some embodiments, the threshold level is within 25%, within 20%, within 15%, within 30% or within 5% and/or is within a standard deviation above the median or mean level, amount or concentration of IL-8, IL-10 or CXCL10 in a biological sample obtained from a group of subjects prior to receiving a cell therapy, wherein each of the subjects of the group went on not develop any toxicity after receiving a recombinant-receptor-expressing therapeutic cell composition for treating the same disease or condition.

In some embodiments, the threshold level is within 25%, within 20%, within 15%, within 30% or within 5% and/or is within a standard deviation below the median or mean level, amount or concentration of IL-8, IL-10 or CXCL10 in a biological sample obtained from a group of subjects prior to receiving a cell therapy, wherein each of the subjects of the group went on to develop a toxicity after receiving a recombinant-receptor-expressing therapeutic cell composition for treating the same disease or condition.

In some aspects, exemplary analytes or biomarkers or a volumetric measure of tumor burden that can be assessed or analyzed with respect to assessment of the risk of developing a toxicity after administration of a cell therapy include one or more analyte or volumetric measure of tumor burden selected from a sum of the products of diameters (SPD), LDH, Ferritin, C-reactive protein (CRP), D-dimer (fibrin degradation product), IL-6, IL-10, IL-15, IL-16 TNF-α, MIP-1α and MIP-1β. In some embodiments, for any of the foregoing analytes or biomarkers or volumetric measure of tumor burden, the subject has a risk of developing a toxicity if the level, amount or concentration one or more of the analyte or the volumetric measure of tumor burden is above a threshold level and the subject has a low risk of developing a toxicity if the level, amount or concentration one or more of the analyte or the volumetric measure of tumor burden is below a threshold level. In some embodiments, the toxicity is neurotoxicity. In some aspects, elevated levels or measure of a sum of the products of diameters (SPD), LDH, Ferritin, C-reactive protein (CRP), D-dimer (fibrin degradation product), IL-6, IL-10, IL-15, IL-16 TNF-α, MIP-1α and MIP-1β, in a biological sample from a subject obtained prior to administration of a cell therapy (pre-treatment), can be associated with a higher risk of developing a neurotoxicity (NT) or a cytokine release syndrome (CRS).

In some embodiments, the one or more analyte or volumetric measure of tumor burden selected from LDH, SPD, IL-10, IL-15, IL-16, TNF-α and MIP-1β, and the toxicity is neurotoxicity In some embodiments, the one or more analyte or volumetric measure of tumor burden selected from LDH, SPD, CRP, d-dimer, IL-6, IL-15, TNF-α and MIP-1α, and the toxicity is CRS. In some aspects, elevated levels or measure of LDH, SPD, IL-10, IL-15, IL-16, TNF-α and MIP-1β, in a biological sample from a subject obtained prior to administration of a cell therapy (pre-treatment), can be associated with a higher risk of developing a neurotoxicity (NT). In some aspects, elevated levels or measure of LDH, SPD, CRP, d-dimer, IL-6, IL-15, TNF-α and MIP-1α, in a biological sample from a subject obtained prior to administration of a cell therapy (pre-treatment), can be associated with a higher risk of developing a cytokine release syndrome (CRS).

In some embodiments, the threshold level is within 25%, within 20%, within 15%, within 32% or within 5% and/or is within a standard deviation above the median or mean level, amount or concentration of LDH, Ferritin, C-reactive protein (CRP), D-dimer (fibrin degradation product), IL-6, IL-10, IL-15, IL-16 TNF-α, MIP-1α or MIP-1β, or the median or mean volumetric measure of tumor burden of a sum of the products of diameters (SPD), in a biological sample obtained from a group of subjects prior to receiving a cell therapy, wherein each of the subjects of the group went on not develop any toxicity after receiving a recombinant-receptor-expressing therapeutic cell composition for treating the same disease or condition.

In some embodiments, the threshold level is within 25%, within 20%, within 15%, within 32% or within 5% and/or is within a standard deviation below the median or mean level, amount or concentration of LDH, Ferritin, C-reactive protein (CRP), D-dimer (fibrin degradation product), IL-6, IL-10, IL-15, IL-16 TNF-α, MIP-1α or MIP-1β, or the median or mean volumetric measure of tumor burden of a sum of the products of diameters (SPD), in a biological sample obtained from a group of subjects prior to receiving a cell therapy, wherein each of the subjects of the group went on to develop a toxicity after receiving a recombinant-receptor-expressing therapeutic cell composition for treating the same disease or condition.

In some embodiments, the toxicity is neurotoxicity and exemplary threshold level for LDH is at or at about or above or above about 300 U/L, 400 U/L, 500 U/L or 600 U/L.

In some embodiments, the toxicity is neurotoxicity and exemplary threshold level for SPD is at or at about or above or above about 30 cm$^2$, 40 cm$^2$, 50 cm$^2$, 60 cm$^2$, 70 cm$^2$, 80 cm$^2$ or 90 cm$^2$.

In some embodiments, the toxicity is neurotoxicity and exemplary threshold level for IL-10 is at or at about or above or above about 0.8 pg/mL, 0.9 pg/mL, 1 pg/mL, 2 pg/mL, 3 pg/mL or 4 pg/mL.

In some embodiments, the toxicity is neurotoxicity and exemplary threshold level for IL-15 is at or at about or above or above about 3 pg/mL, 4 pg/mL, 5 pg/mL, 6 pg/mL or 7 pg/mL.

In some embodiments, the toxicity is neurotoxicity and exemplary threshold level for IL-16 is at or at about or above or above about 600 pg/mL, 700 pg/mL, 800 pg/mL, 900 pg/mL or 1000 pg/mL.

In some embodiments, the toxicity is neurotoxicity and exemplary threshold level for TNF-α is at or at about or above or above about 6 pg/mL, 7 pg/mL, 8 pg/mL, 9 pg/mL or 10 pg/mL.

In some embodiments, the toxicity is neurotoxicity and exemplary threshold level for MIP-1β is at or at about or above or above about 70 pg/mL, 80 pg/mL, 90 pg/mL or 100 pg/mL.

In some embodiments, the toxicity is CRS and exemplary threshold level for LDH is at or at about or above or above about 300 U/L, 400 U/L, 500 U/L or 600 U/L.

In some embodiments, the toxicity is CRS the and threshold level for SPD is at or at about or above or above about 20 cm$^2$, 30 cm$^2$, 40 cm$^2$ or 50 cm$^2$.

In some embodiments, the toxicity is CRS and exemplary threshold level for ferritin is at or at about or above or above about 300 ng/mL, 400 ng/mL, 500 ng/mL, 600 ng/mL, 700 ng/mL, 800 ng/mL, 900 ng/mL or 1000 ng/mL.

In some embodiments, the toxicity is CRS and exemplary threshold level for CRP is at or at about or above or above about 20 mg/L, 30 mg/L or 40 mg/L.

In some embodiments, the toxicity is CRS and exemplary threshold level for d-dimer is at or at about or above or above about 300 pg/mL, 400 pg/mL, 500 pg/mL, 600 pg/mL, 700 pg/mL, 800 pg/mL, 900 pg/mL or 1000 pg/mL.

In some embodiments, the toxicity is CRS and exemplary threshold level for IL-6 is at or at about or above or above about 2 pg/mL, 3 pg/mL, 4 pg/mL, 5 pg/mL, 6 pg/mL, 7 pg/mL, 8 pg/mL or 9 pg/mL.

In some embodiments, the toxicity is CRS and exemplary threshold level for IL-15 is at or at about or above or above about 3 pg/mL, 4 pg/mL, 5 pg/mL, 6 pg/mL, 7 pg/mL, 8 pg/mL, 9 pg/mL or 10 pg/mL.

In some embodiments, the toxicity is CRS and exemplary threshold level for TNF-α is at or at about or above or above about 7 pg/mL, 8 pg/mL, 9 pg/mL, 10 pg/mL or 15 pg/mL.

In some embodiments, the toxicity is CRS and exemplary threshold level for MIP-1α is at or at about or above or above about 20 pg/mL, 30 pg/mL or 40 pg/mL.

In some embodiments, the biomarker is LDH and in some cases, development of toxicity, e.g., CRS or NT, is correlated with the LDH value that is above a threshold value. In some embodiments, the inflammatory marker is LDH and the threshold value is or is about 300 units per liter, is or is about 400 units per liter, is or is about 500 units per liter or is or is about 600 units per liter.

In some embodiments, if the level, amount or concentration of the biomarker (e.g., analyte) in the sample is at or above a threshold level of the analyte, an agent or other treatment capable of treating, preventing, delaying, reducing or attenuating the development or risk of development of a toxicity is administered to the subject prior to, within one, two, or three days of, concurrently with and/or at first fever following, the initiation of administration of the cell therapy to the subject. Exemplary agents or interventions for use in connection with the provided methods to treat, prevent, delay, reduce or attenuate the risk of developing toxicity are described in Section II.

In some cases, if the level, amount of concentration of the biomarker in the sample is at or above a threshold level, the cell therapy is administered to the subject at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy. In some cases, if the level, amount of concentration of the biomarker in the sample is at or above a threshold level, the cell therapy is administered to the subject in an in-patient setting and/or with admission to the hospital for one or more days, optionally wherein the cell therapy is otherwise to be administered to subjects on an outpatient basis or without admission to the hospital for one or more days.

In some embodiments, if the level, amount or concentration of the biomarker (e.g., analyte) is below a threshold level for the analyte, the cell therapy is administered to the subject, optionally at a non-reduced dose. In some cases, the cells therapy is optionally administered on an outpatient basis or without admission to the hospital for one or more days. In some embodiments, if the level, amount or concentration of the analyte, is below a threshold level, the administration of the cell therapy does not include administering, prior to or concurrently with administering the cell therapy and/or prior to the development of a sign of symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

In some aspects of the provided methods, a subject is determined to be at risk of developing toxicity (e.g. neurotoxcity, such as severe neurotoxicity or grade 3 or higher neurotoxcity, e.g. grade 4 or 5 neurotoxicity and/or CRS, such as severe CRS or grade 3 or higher CRS) by a comparison of the parameter (e.g. concentration, amount, level or activity) of the biomarker (e.g. analyte) or, individually, each of the biomarkers (e.g. analytes) to a reference value, such as threshold level, of the corresponding parameter for the biomarker or each biomarker. In some embodiments, the comparison indicates whether the subject is or is not at risk for developing toxicity, e.g., neurotoxicity such as severe neurotoxicity or grade 3 or higher neurotoxcity, e.g. grade 4 or 5 neurotoxicity and/or CRS, such as severe CRS or grade 3 or higher CRS, and/or indicates a degree of risk for developing said toxicity. In some embodiments, the reference value is one that is a threshold level or cut-off at which there is a good predictive value (e.g. accuracy, sensitivity and/or specificity) that such toxicity will occur or is likely to occur either alone or in combination with one or more biomarkers in the panel. In some cases, such reference value, e.g. threshold level, can be or is predetermined or known prior to performing the method, such as from a plurality of subjects previously treated with a cell therapy and assessed for the correlation of the parameter of the biomarker or, individually, each of the biomarkers in a panel to the presence of a toxic outcome (e.g. the presence of neurotoxicity such as severe neurotoxicity or grade 3 or higher neurotoxcity, e.g. grade 4 or 5 neurotoxicity and/or CRS, such as severe CRS or grade 3 or higher CRS).

In some embodiments, a parameter of a biomarker (e.g. LDH, ferritin, CRP, IL-6, IL-8, IL-10, TNF-α, IFN-α2, MCP-1 and MIP-1β) that is higher or greater than the reference value, e.g. threshold level, of the corresponding parameter is associated with a positive prediction of a risk of toxicity (alone or in conjunction with assessment of the other biomarkers in the panel). In some embodiments, a parameter of a biomarker that is equal to or lower than the reference value, e.g. threshold level, of the corresponding parameter is associated with a negative prediction of a risk of toxicity (alone or in conjunction with assessment of the other biomarkers in the panel).

In some embodiments, the threshold level is determined based on the level, amount, concentration or other measure of the biomarker (e.g. analyte) in the sample positive for the biomarker. In some aspects, the threshold level is within 25%, within 20%, within 15%, within 10% or within 5% of the average level, amount or concentration or measure, and/or is within a standard deviation of the average level, amount or concentration or measure, of the analyte or parameter in a biological sample obtained from a group of subjects prior to receiving a recombinant receptor-expressing therapeutic cell composition, wherein each of the subjects of the group went on to develop a toxicity, e.g. neurotoxicity such as severe neurotoxicity or grade 3 or higher neurotoxcity, e.g. grade 4 or 5 neurotoxicity and/or CRS, such as severe CRS or grade 3 or higher CRS, after receiving a recombinant-receptor-expressing therapeutic cell composition for treating the same disease or condition.

In some embodiments of any of the provided methods, the biomarker (e.g. analyte) correlates to and/or is predictive of the risk of developing severe neurotoxicity, such as severe neurotoxicity or grade 3 or higher neurotoxicity, e.g. grade 4 or 5 neurotoxicity and/or severe CRS or grade 3 or higher CRS. In some embodiments, the threshold level is within 25%, within 20%, within 15%, within 10% or within 5% of the average level, amount or concentration or measure, and/or is within a standard deviation of the average level, amount or concentration or measure, of the analyte or parameter in a biological sample obtained from a group of subjects prior to receiving a recombinant receptor-expressing therapeutic cell composition, wherein each of the subjects of the group went on to develop severe neurotoxicity or grade 3 or higher neurotoxcity, e.g. grade 4 or 5 neurotoxicity and/or severe CRS or grade 3 or higher CRS, after receiving a recombinant-receptor-expressing therapeutic cell composition for treating the same disease or condition.

In some embodiments, the volumetric measure is SPD and in some cases, development of toxicity, e.g., CRS or NT, is correlated with the SPD value that is above a threshold value. In some embodiments, the volumetric measure is SPD, and the threshold value is or is about 30 cm$^2$, is or is about 40 cm$^2$, is or is about 50 cm$^2$, is or is about 60 cm$^2$, or is or is about 70 cm$^2$. In some embodiments, the volumetric measure is SPD and the threshold value is or is about 30 cm$^2$, is or is about 40 cm$^2$, is or is about 50 cm$^2$, is or is about 60 cm$^2$, or is or is about 70 cm$^2$.

In some embodiments, the parameter, including volumetric tumor measurements or is associated with response to the cell therapy, and/or a risk for developing toxicity, e.g., CRS or neurotoxicity (NT).

In some embodiments, the volumetric measure is SPD and the threshold level is or is about 30 cm$^2$, is or is about 40 cm$^2$, is or is about 50 cm$^2$, is or is about 60 cm$^2$, or is or is about 70 cm$^2$. In some embodiments, the volumetric measure is SPD and the threshold level is or is about 50 cm$^2$.

In some embodiments, the analyte is LDH and the threshold level is or is about 300 units per liter (U/L), is or is about 400 U/L, is or is about 500 U/L or is or is about 600 U/L. In some embodiments, the analyte is LDH and the threshold level is or is about 500 U/L.

In some embodiments, the parameter or biomarker is LDH. In some embodiments, the biomarker is LDH and the threshold value is 500 U/L or higher. In some embodiments, the parameter or biomarker is SPD. In some embodiments, the parameter is SPD, and the threshold value is or is about 50 cm$^2$ or higher. In some embodiments, biomarker or parameters are SPD and LDH, and the threshold values are SPD of 50 cm$^2$ or higher and LDH of 500 U/L or higher. In some embodiments, the biomarkers or parameters are associated with increased risk of developing CRS or NT.

In some embodiments, a measurement of the parameter or marker that is above the threshold value, e.g., SPD of 50 cm$^2$ or higher and LDH of 500 U/L or higher, are associated with an approximately 2-, 3-, 4-, 5-, 6-, 7-, 8-, 9-, 10-fold or more increased risk of developing CRS or NT, such as any grade CRS or NT. In some embodiments, a measurement of the parameter or marker that is below the threshold value, e.g., SPD of lower than 500 cm$^2$ and LDH of lower than 500 U/L, are associated with an approximately 2-, 3-, 4-, 5-, 6-, 7-, 8-, 9-, 10-fold or more decreased risk of developing CRS or NT, such as any grade CRS or NT.

In some embodiments, the biomarkers (e.g., analytes), include those associated with increased pharmacokinetic (PK) parameters of the cell, e.g., increased maximum serum concentration of cell ($C_{max}$) or increased exposure (e.g., area under the curve (AUC)). In some embodiments, the biomarkers (e.g. analytes), including parameters thereof, include IL-7, IL-15, MIP-1α and TNF-α.

In some embodiments, the parameter is a parameter related to tumor burden, e.g., a measurement of tumor burden. In some aspects, the methods also involve further monitoring the subject for possible symptoms of toxicity based on the risk of toxicity determined by assessment of the presence or absence of the biomarker and/or comparison of the biomarkers to a reference value or threshold level of the biomarker.

II. Interventions or Agents that Treat or Ameliorate Symptoms of Toxicity

In some embodiments, the provided methods and articles of manufacture can be used in connection with, or involve or include, one or more agents or treatments for treating, preventing, delaying, or attenuating the development of a toxicity. In some examples, the agent or other treatment capable of treating, preventing, delaying, or attenuating the development of a toxicity is administered prior to and/or concurrently with administration of a therapeutic cell composition comprising the genetically engineered cells.

In some embodiments, the agent, e.g., a toxicity-targeting agent, or treatment capable of treating, preventing, delaying, or attenuating the development of a toxicity is a steroid, is an antagonist or inhibitor of a cytokine receptor, such as IL-6 receptor, CD122 receptor (IL-2Rbeta receptor), or CCR2, or is an inhibitor of a cytokine, such as IL-6, MCP-1, IL-10, IFN-γ, IL-8, or IL-18. In some embodiments, the agent is an agonist of a cytokine receptor and/or cytokine, such as TGF-β. In some embodiments, the agent, e.g., agonist, antagonist or inhibitor, is an antibody or antigen-binding fragment, a small molecule, a protein or peptide, or a nucleic acid.

In some embodiments, a fluid bolus can be employed as an intervention, such as to treat hypotension associated with CRS. In some embodiments, the target hematocrit levels are >24%. In some embodiments, the intervention includes the use of absorbent resin technology with blood or plasma filtration. In some cases, the intervention includes dialysis, plasmapheresis, or similar technologies. In some embodiments, vassopressors or acetaminophen can be employed.

In some embodiments, the agent can be administered sequentially, intermittently, or at the same time as or in the same composition as the therapy, such as cells for adoptive cell therapy. For example, the agent can be administered before, during, simultaneously with, or after administration of the immunotherapy and/or cell therapy.

In some embodiments, the agent is administered at a time as described herein and in accord with the provided methods, and/or with the provided articles of manufacture or compositions. In some embodiments, the toxicity-targeting agent is administered at a time that is within, such as less than or no more than, 3, 4, 5, 6, 7, 8, 9 or 10 days after initiation of the immunotherapy and/or cell therapy. In some embodiments, the toxicity-targeting agent is administered within or within about 1 day, 2 days or 3 days after initiation of administration of the immunotherapy and/or cell therapy.

In some embodiments, the agent, e.g., toxicity-targeting agent, is administered to a subject after initiation of administration of the immunotherapy and/or cell therapy at a time at which the subject does not exhibit grade 2 or higher CRS or grade 2 or higher neurotoxicity. In some aspects, the toxicity-targeting agent is administered after initiation of administration of the immunotherapy and/or cell therapy at a time at which the subject does not exhibit severe CRS or severe neurotoxicity. Thus, between initiation of administration of the immunotherapy and/or cell therapy and the toxicity-targeting agent, the subject is one that does not exhibit grade 2 or higher CRS, such as severe CRS, and/or does not exhibit grade 2 or higher neurotoxicity, such as severe neurotoxicity.

Non-limiting examples of interventions for treating or ameliorating a toxicity, such as severe CRS (sCRS), are described in Table 5. In some embodiments, the intervention includes tocilizumab or other toxicity-targeting agent as described, which can be at a time in which there is a sustained or persistent fever of greater than or about 38° C. or greater than or greater than about 39° C. in the subject. In some embodiments, the fever is sustained in the subject for more than 10 hours, more than 12 hours, more than 16 hours, or more than 24 hours before intervention.

TABLE 5

Exemplary Interventions.

| Symptoms related to CRS | Suggested Intervention |
|---|---|
| Fever of ≥38.3° C. | Acetaminophen (12.5 mg/kg) PO/IV up to every four hours |
| Persistent fever of ≥39° C. for 10 hours that is unresponsive to acetaminophen | Tocilizumab (8-12 mg/kg) IV |
| Persistent fever of ≥39° C. after tocilizumab | Dexamethasone 5-10 mg IV/PO up to every 6-12 hours with continued fevers |
| Recurrence of symptoms 48 hours after initial dose of tocilizumab | Tocilizumab (8-12 mg/kg) IV |
| Hypotension | Fluid bolus, target hematocrit >24% |
| Persistent/recurrent hypotension after initial fluid bolus (within 6 hours) | Tocilizumab (8-12 mg/kg) IV |
| Use of low dose pressors for hypotension for longer than 12 hours | Dexamethasone 5-10 mg IV/PO up to every 6 hours with continued use of pressors |
| Initiation of higher dose pressors or addition of a second pressor for hypotension | Dexamethasone 5-10 mg IV/PO up to every 6 hours with continued use of pressors |
| Initiation of oxygen supplementation | Tocilizumab (8-12 mg/kg) IV |
| Increasing respiratory support with concern for impending intubation | Dexamethasone 5-10 mg IV/PO up to every 6 hours with continued use of pressors |
| Recurrence/Persistence of symptoms for which tocilizumab was given ≥48 hours after initial dose was administered | Tocilizumab (8-12 mg/kg) IV |

In some cases, the agent or therapy or intervention, e.g., toxicity-targeting agent, is administered alone or is administered as part of a composition or formulation, such as a pharmaceutical composition or formulation, as described herein. Thus, the agent alone or as part of a pharmaceutical composition can be administered intravenously or orally, or by any other acceptable known route of administration or as described herein.

In some embodiments, the dosage of agent or the frequency of administration of the agent in a dosage regimen is reduced compared to the dosage of the agent or its frequency in a method in which a subject is treated with the agent after grade 2 or higher CRS or neurotoxicity, such as after severe, e.g., grade 3 or higher, CRS or after severe, e.g., grade 3 or higher neurotoxicity, has developed or been diagnosed (e.g. after physical signs or symptoms of grade 3 or higher CRS or neurotoxicity has manifested). In some embodiments, the dosage of agent or the frequency of administration of the agent in a dosage regimen is reduced compared to the dosage of the agent or its frequency in a method in which a subject is treated for CRS or neurotoxicity greater than 3 days, 4 days, 5 days, 6 days, 1 week, 2 weeks, three weeks, or more after administration of the immunotherapy and/or cell therapy. In some embodiments, the dosage is reduced by greater than or greater than about 1.2-fold, 1.5-fold, 2-fold, 3-fold, 4-fold, 5-fold, 6-fold, 7-fold, 8-fold, 9-fold, 10-fold or more. In some embodiments, the dosage is reduced by greater than or about 10%, 20%, 30%, 40%, 50%, 60%, 70%, 80%, 90%, or more. In some embodiments, the frequency of dosing is reduced, such as the number of daily doses is reduced or the number of days of dosing is reduced.

A. Steroid

In some embodiments, the agent, e.g., toxicity-targeting agent, that treats and/or that prevents, delays, or attenuates the development of or risk for developing a toxicity to an immunotherapy and/or a cell therapy, is a steroid, e.g., corticosteroid. Corticosteroids typically include glucocorticoids and mineralocorticoids.

Any corticosteroid, e.g., glucocorticoid, can be used in the methods provided herein. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemi succinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemi succinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980).

In some examples, the glucocorticoid is selected from among cortisones, dexamethasones, hydrocortisones, methylprednisolones, prednisolones and prednisones. In a particular example, the glucocorticoid is dexamethasone.

In some embodiments, the agent is a corticosteroid and is administered in an amount that is therapeutically effective to treat, ameliorate or reduce one or more symptoms of a toxicity to an immunotherapy and/or a cell therapy, such as CRS or neurotoxicity. In some embodiments, indicators of improvement or successful treatment include determination of the failure to manifest a relevant score on toxicity grading scale (e.g. CRS or neurotoxicity grading scale), such as a score of less than 3, or a change in grading or severity on the grading scale as discussed herein, such as a change from a score of 4 to a score of 3, or a change from a score of 4 to a score of 2, 1 or 0.

In some aspects, the corticosteroid is provided in a therapeutically effective dose. Therapeutically effective concentration can be determined empirically by testing in known in vitro or in vivo (e.g. animal model) systems. For example, the amount of a selected corticosteroid to be administered to ameliorate symptoms or adverse effects of a toxicity to an immunotherapy and/or a cell therapy, such as CRS or neurotoxicity, can be determined by standard clinical techniques. In addition, animal models can be employed to help identify optimal dosage ranges. The precise dosage, which can be determined empirically, can depend on the particular therapeutic preparation, the regime and dosing schedule, the route of administration and the seriousness of the disease.

The corticosteroid can be administered in any amount that is effective to ameliorate one or more symptoms associated with the toxicity, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid can be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

The corticosteroid, or glucocorticoid, for example dexamethasone, can be administered orally (tablets, liquid or liquid concentrate), PO, intravenously (IV), intramuscularly or by any other known route or route described herein (e.g., with respect to pharmaceutical formulations). In some aspects, the corticosteroid is administered as a bolus, and in other aspects it may be administered over a period of time.

In some aspects, the glucocorticoid can be administered over a period of more than one day, such as over two days, over 3 days, or over 4 or more days. In some embodiments, the corticosteroid can be administered one per day, twice per day, or three times or more per day. For example, the corticosteroid, e.g., dexamethasone, may in some examples be administered at 10 mg (or equivalent) IV twice a day for three days.

In some embodiments, the dosage of corticosteroid, e.g., glucocorticoid, is administered in successively lower dosages per treatment. Hence, in some such treatment regimes, the dose of corticosteroid is tapered. For example, the corticosteroid may be administered at an initial dose (or equivalent dose, such as with reference to dexamethasone) of 4 mg, and upon each successive administration the dose may be lowered, such that the dose is 3 mg for the next administration, 2 mg for the next administration, and 1 mg for the next administration Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Table 6 shows equivalence in terms of potency for various glucocorticoids and routes of administration. Equivalent potency in clinical dosing is well known. Information relating to equivalent steroid dosing (in a non-chronotherapeutic manner) may be found in the British National Formulary (BNF) 37, March 1999.

TABLE 6

| Glucocorticoid administration | |
|---|---|
| Glucocorticoid (Route) | Equivalency Potency |
| Hydrocortisone (IV or PO) | 20 |
| Prednisone | 5 |
| Prednisolone (IV or PO) | 5 |
| Methylprednisolone sodium succinate (IV) | 4 |
| Dexamethasone (IV or PO) | 0.5-0.75 |

Thus, in some embodiments, the steroid is administered in an equivalent dosage amount of from or from about 1.0 mg to 20 mg dexamethasone per day, such as 1.0 mg to 15 mg dexamethasone per day, 1.0 mg to 10 mg dexamethasone per day, 2.0 mg to 8 mg dexamethasone per day, or 2.0 mg to 6.0 mg dexamethasone per day, each inclusive. In some cases, the steroid is administered in an equivalent dose of at or about 4 mg or at or about 8 mg dexamethasone per day.

In some embodiments, the steroid is administered if fever persists after treatment with tocilizumab. For example, in some embodiments, dexamethasone is administered orally or intravenously at a dosage of 5-10 mg up to every 6-12 hours with continued fevers. In some embodiments, tocilizumab is administered concurrently with or subsequent to oxygen supplementation.

B. Microglial Cell Inhibitor

In some embodiments, the inhibitor in the combination therapy is an inhibitor of a microglial cell activity. In some embodiments, the administration of the inhibitor modulates the activity of microglia. In some embodiments, the inhibitor is an antagonist that inhibits the activity of a signaling pathway in microglia. In some embodiments, the microglia inhibitor affects microglial homeostasis, survival, and/or proliferation. In some embodiments, the inhibitor targets the CSF1R signaling pathway. In some embodiments, the inhibitor is an inhibitor of CSF1R. In some embodiments, the inhibitor is a small molecule. In some cases, the inhibitor is an antibody.

In some aspects, administration of the inhibitor results in one or more effects selected from an alteration in microglial homeostasis and viability, a decrease or blockade of microglial cell proliferation, a reduction or elimination of microglial cells, a reduction in microglial activation, a reduction in nitric oxide production from microglia, a reduction in nitric oxide synthase activity in microglia, or protection of motor neurons affected by microglial activation. In some embodiments, the agent alters the level of a serum or blood biomarker of CSF1R inhibition, or a decrease in the level of urinary collagen type 1 cross-linked N-telopeptide (NTX) compared to at a time just prior to initiation of the administration of the inhibitor. In some embodiments, the administration of the agent transiently inhibits the activity of microglia activity and/or wherein the inhibition of microglia activity is not permanent. In some embodiments, the administration of the agent transiently inhibits the activity of CSF1R and/or wherein the inhibition of CSF1R activity is not permanent.

In some embodiments, the agent that reduces microglial cell activity is a small molecule, peptide, protein, antibody or antigen-binding fragment thereof, an antibody mimetic, an aptamer, or a nucleic acid molecule. In some embodiments, the method involves administration of an inhibitor of microglia activity. In some embodiments, the agent is an antagonist that inhibits the activity of a signaling pathway in microglia. In some embodiments, the agent that reduces microglial cell activity affects microglial homeostasis, survival, and/or proliferation.

In some embodiments, the agent that reduces microglial cell activation is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155), upregulates microRNA-124 (miR-124), inhibits nitric oxide production in microglia, inhibits nitric oxide synthase, or activates the transcription factor NRF2 (also called nuclear factor (erythroid-derived 2)-like 2, or NFE2L2).

In some embodiments, the agent that reduces microglial cell activity targets CSF1 (also called macrophage colony-stimulating factor MCSF). In some embodiments, the agent that reduces microglial cell activity affects MCSF-stimulated phosphorylation of the M-CSF receptor (Pryer et al. *Proc Am Assoc Cancer Res*, AACR Abstract nr DDT02-2 (2009)). In some cases, the agent that reduces microglial cell activity is MCS110 (international patent application publication number WO2014001802; Clinical Trial Study Record Nos.: A1 NCT00757757; NCT02807844; NCT02435680; NCT01643850).

In some embodiments, the agent that reduces microglial cell activity is a small molecule that targets the CSF1 pathway. In some embodiments, the agent is a small molecule that binds CSF1R. In some embodiments, the agent is a small molecule which inhibits CSF1R kinase activity by competing with ATP binding to CSF1R kinase. In some embodiments, the agent is a small molecule which inhibits the activation of the CFS1R receptor. In some cases, the binding of the CSF-1 ligand to the CSF1R is inhibited. In some embodiments, the agent that reduces microglial cell activity is any of the inhibitors described in US Patent Application Publication Number US20160032248.

In some embodiments, the agent is a small molecule inhibitor selected from PLX-3397, PLX7486, JNJ- 40346527, JNJ28312141, ARRY-382, PLX73086 (AC-708), DCC-3014, AZD6495, GW2580, Ki20227, BLZ945, PLX647, PLX5622. In some embodiments, the agent is any of the inhibitors described in Conway et al., *Proc Natl Acad Sci USA*, 102(44):16078-83 (2005); Dagher et al., *Journal of Neuroinflammation*, 12:139 (2015); Ohno et al., *Mol Cancer Ther.* 5(11):2634-43 (2006); von Tresckow et al. *Clin Cancer Res.*, 21(8) (2015); Manthey et al. *Mol Cancer Ther.* (8(11):3151-61 (2009); Pyonteck et al., *Nat Med.* 19(10): 1264-1272 (2013); Haegel et al., *Cancer Res* AACR Abstract nr 288 (2015); Smith et al., Cancer Res AACR Abstract nr 4889 (2016); Clinical Trial Study Record Nos.: NCT01525602; NCT02734433; NCT02777710; NCT01804530; NCT01597739; NCT01572519; NCT01054014; NCT01316822; NCT02880371; NCT02673736; international patent application publication numbers WO2008063888A2, WO2006009755A2, US patent application publication numbers US20110044998, US 2014/0065141, and US 2015/0119267.

In some embodiments, the agent that reduces microglial cell activity is 4-((2-(((1R,2R)-2-hydroxycyclohexyl) amino)benzo[d]thiazol-6-yl)oxy)-N-methylpicolinamide (BLZ945) or a pharmaceutically acceptable salt thereof or derivatives thereof. In some embodiments, the agent is the following compound:

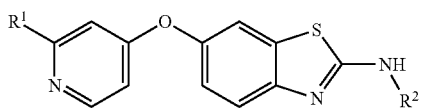

wherein R1 is an alkyl pyrazole or an alkyl carboxamide, and R2 is a hydroxycycloalkyl or a pharmaceutically acceptable salt thereof.

In some embodiments, the agent that reduces microglial cell activity is 5-((5-chloro-1H-pyrrolo[2,3-b]pyridin-3-yl) methyl)-N-((6-(trifluoromethyl)pyridin-3-yl)methyl)pyridin-2-amine, N-[5-[(5-Chloro-1H-pyrrolo[2,3-b]pyridin-3-yl)methyl]-2-pyridinyl]-6-(trifluoromethyl)-3-pyridinemethanamine) (PLX 3397) or a pharmaceutically acceptable salt thereof or derivatives thereof. In some embodiments, the agent is 5-(1H-Pyrrolo[2,3-b]pyridin-3-ylmethyl)-N-[[4-(trifluoromethyl)phenyl]methyl]-2-pyridinamine dihydrochloride (PLX647) or a pharmaceutically acceptable salt thereof or derivatives thereof. In some embodiments, the agent that reduces microglial cell activity is the following compound:

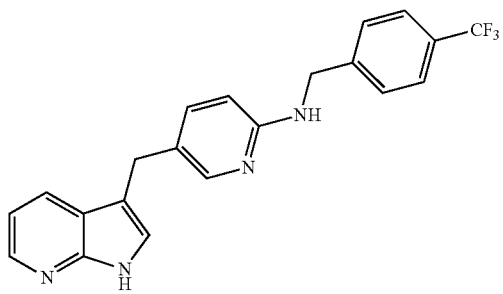 [SMILES: FC(F)(F)c1ccc(CNc2ccc(Cc3c[nH]c4ncccc34)cn2)cc1]

or a pharmaceutically acceptable salt thereof. In some embodiments, the agent that reduces microglial cell activity is the following compound:

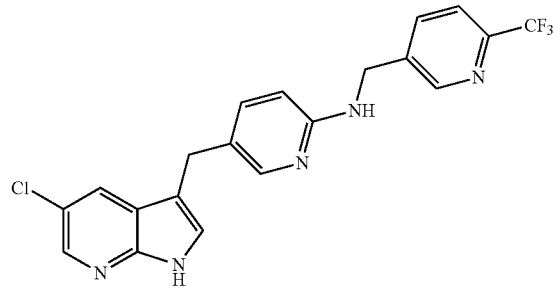 [SMILES: FC(F)(F)c1ccc(CNc2ccc(Cc3c[nH]c4ncc(Cl)cc34)cn2)cn1]

or a pharmaceutically acceptable salt thereof. In some embodiments, the agent is any of the inhibitors described in U.S. Pat. No. 7,893,075.

In some embodiments, the agent that reduces microglial cell activity is 4-cyano-N-[2-(1-cyclohexen-1-yl)-4-[1-[(dimethylamino)acetyl]-4-piperidinyl]phenyl]-1H-imidazole-2-carboxamide monohydrochloride (JNJ28312141) or a pharmaceutically acceptable salt thereof or derivatives thereof. In some embodiments, the agent is the following compound:

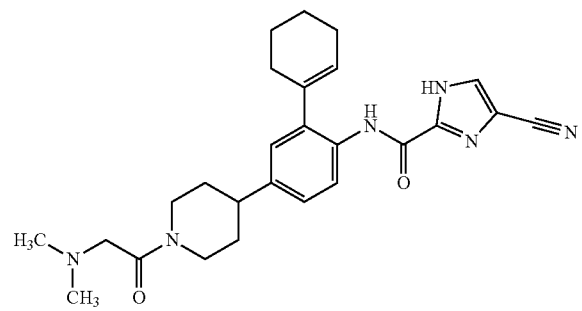 [SMILES: CN(C)CC(=O)N1CCC(c2ccc(NC(=O)c3nc(C#N)c[nH]3)c(C3=CCCCC3)c2)CC1]

or a pharmaceutically acceptable salt thereof. In some embodiments, the agent is any of the inhibitors described in U.S. Pat. No. 7,645,755.

In some embodiments, the agent that reduces microglial cell activity is 1H-Imidazole-2-carboxamide, 5-cyano-N-(2-(4,4-dimethyl-1-cyclohexen-1-yl)-6-(tetrahydro-2,2,6,6-tetramethyl-2H-pyran-4-yl)-3-pyridinyl)-, 4-Cyano-1H-imidazole-2-carboxylic acid N-(2-(4,4-dimethylcyclohex-1-enyl)-6-(2,2,6,6-tetramethyltetrahydropyran-4-yl)pyridin-3-yl)amide, 4-Cyano-N-(2-(4,4-dimethylcyclohex-1-en-1-yl)-6-(2,2,6,6-tetramethyl-tetrahydro-2H-pyran-4-yl)pyridin-3-yl)-1H-imidazole-2-carboxamide (JNJ-40346527) or a pharmaceutically acceptable salt thereof or derivatives thereof. In some embodiments, the agent is the following compound:

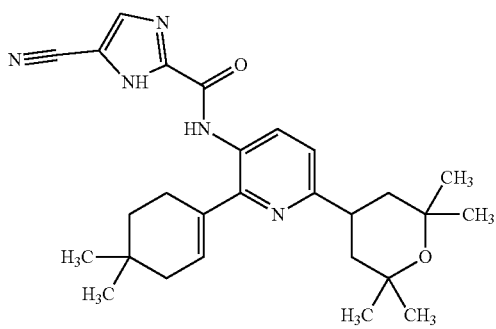 [SMILES: CC1(C)CC=C(c2nc(C3CC(C)(C)OC(C)(C)C3)ccc2NC(=O)c2ncc(C#N)[nH]2)CC1]

or a pharmaceutically acceptable salt thereof.

In another embodiment, the agent that reduces microglial cell activity is 5-(3-Methoxy-4-((4-methoxybenzyl)oxy) benzyl)pyrimidine-2,4-diamine (GW2580) or a pharmaceutically acceptable salt thereof or derivatives thereof. In some embodiments, the agent is the following compound:

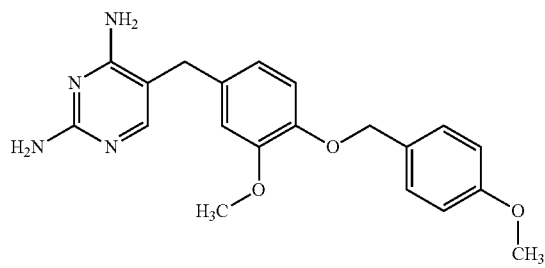 [SMILES: COc1ccc(COc2ccc(Cc3cnc(N)nc3N)cc2OC)cc1]

or a pharmaceutically acceptable salt thereof (international patent application publication number WO2009099553).

In some embodiments, the agent that reduces microglial cell activity is 4-(2,4-difluoroanilino)-7-ethoxy-6-(4-methylpiperazin-1-yl)quinoline-3-carboxamide (AZD6495) or a pharmaceutically acceptable salt thereof or derivatives thereof. In some embodiments, the agent is the following compound:

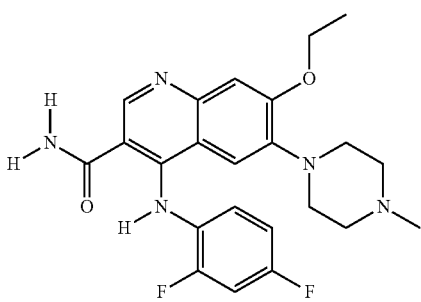 [SMILES: CCOc1cc2ncc(C(N)=O)c(Nc3ccc(F)cc3F)c2cc1N1CCN(C)CC1]

or a pharmaceutically acceptable salt thereof.

In some embodiments, the agent that reduces microglial cell activity is N-{4-[(6,7-dimethoxy-4-quinolyl)oxy]-2-methoxyphenyl}-N0-[1-(1,3-thiazole-2-yl)ethyl]urea (Ki20227) or a pharmaceutically acceptable salt thereof or derivatives thereof. In some embodiments, the agent is the following compound:

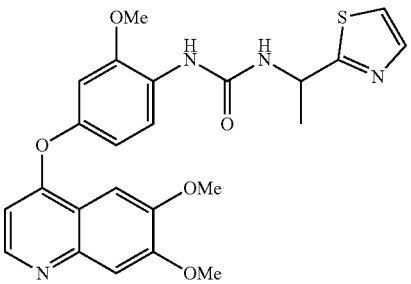 [SMILES: COc1cc(Oc2ccnc3cc(OC)c(OC)cc23)ccc1NC(=O)NC(C)c1nccs1]

or a pharmaceutically acceptable salt thereof.

In some embodiments, the agent that reduces microglial cell activation is an antibody that targets the CSF1 pathway. In some embodiments, the agent is an antibody that binds CSF1R. In some embodiments, the anti-CSF1R antibody blocks CSF1R dimerization. In some embodiments, the anti-CSF1R antibody blocks the CSF1R dimerization interface that is formed by domains D4 and D5 (Ries et al. Cancer Cell 25(6):846-59 (2014)). In some cases, the agent is selected from emactuzumab (RG7155; R05509554), Cabiralizumab (FPA-008), LY-3022855 (IMC-CS4), AMG-820, TG-3003, MCS110, H27K15, 12-2D6, 2-4A5 (Rovida and Sbarba, J Clin Cell Immunol.6:6 (2015); Clinical Trial Study Record Nos.: NCT02760797; NCT01494688; NCT02323191; NCT01962337; NCT02471716; NCT02526017; NCT01346358; NCT02265536; NCT01444404; NCT02713529, NCT00757757; NCT02807844; NCT02435680; NCT01643850).

In some embodiments, the agent that reduces microglial cell activation is a tetracycline antibiotic. For example, the agent affects IL-1b, IL-6, TNF-α, or iNOS concentration in microglia cells (Yrjänheikki et al. PNAS 95(26): 15769-15774 (1998); Clinical Trial Study Record No: NCT01120899). In some embodiments, the agent is an opioid antagonist (Younger et al. Pain Med. 10(4):663-672 (2009.) In some embodiments, the agent reduces glutamatergic neurotransmission (U.S. Pat. No. 5,527,814). In some embodiments, the agent modulates NFkB signaling (Valera et al J. Neuroinflammation 12:93 (2015); Clinical Trial Study Record No: NCT00231140). In some embodiments, the agent targets cannabinoid receptors (Ramirez et al. J. Neurosci 25(8):1904-13(2005)). In some embodiments, the agent is selected from minocycline, naloxone, riluzole, lenalidomide, and a cannabinoid (optionally WIN55 or 212-2).

Nitric oxide production from microglia is believed, in some cases, to result in or increase neurotoxicity. In some embodiments, the agent modulates or inhibitis nitric oxide production from microglia. In some embodiments, the agent inhibits nitric oxide synthase (NOS). In some embodiments, the NOS inhibitor is Ronopterin (VAS-203), also known as 4-amino-tetrahydrobiopterin (4-ABH4). In some embodiments, the NOS inhibitor is cindunistat, A-84643, ONO-1714, L-NOARG, NCX-456, VAS-2381, GW-273629, NXN-462, CKD-712, KD-7040, or guanidinoethyldisulfide. In some embodiments, the agent is any of the inhibitors described in Ming et al., Cell Stem Cell. 2012 Nov. 2; 11(5):620-32.

In some embodiments, the agent blocks T cell trafficking, such as to the central nervous system. In some embodiments, blocking T cell trafficking can reduce or prevent immune cells from crossing blood vessel walls into the central nervous system, including crossing the blood-brain barrier. In some cases, activated antigen-specific T cells produce proinflammatory cytokines, including IFN-γ and TNF, upon reactivation in the CNS, leading to activation of resident cells such as microglia and astrocytes. See Kivisäkk et al., Neurology. 2009 Jun. 2; 72(22): 1922-1930. Thus, in some embodiments, sequestering activated T cells from microglial cells, such as by blocking trafficking and/or inhibiting the ability of such cells to cross the blood-brain barrier, can reduce or eliminate microglial activation. In some embodiments, the agent inhibits adhesion molecules on immune cells, including T cells. In some embodiments, the agent inhibits an integrin. In some embodiments, the integrin is alpha-4 integrin. In some embodiments, the agent is natalizumab (Tysabri®). In some embodiments, the agent modulates a cell surface receptor. In some embodiments, the agent modulates the sphingosine-1-phosphate (S1P) receptor, such as S1PR1 or S1PR5. In some embodiments, the agent causes the internalization of a cellular receptor, such as a sphingosine-1-phosphate (S1P) receptor, such as S1PR1 or S1PR5. In some embodiments, the agent is fingolimod (Gilenya®) or ozanimod (RPC-1063).

The transcription factor NRF2 is believed to regulate the anti-oxidant response, for example, by turning on genes that contain a cis-acting element in their promoter region. An example of such an element includes an antioxidant response element (ARE). In some embodiments, the agent activates NRF2. In some embodiments, activating NRF2 in microglial cells reduces the microglial cells' responsiveness to IFN and LPS. In some embodiments, activating NRF2 inhibits, slows, or reduces demyelination, axonal loss, neuronal death, and/or oligodendrocyte death. In some embodiments, the agent upregulates the cellular cytoprotective pathway regulated by NRF2. In some embodiments, the agent that activates NRF2 is dimethyl fumarate (Tecfidera®). In some embodiments, the agent is any of the inhibitors described in U.S. Pat. No. 8,399,514. In some embodiments, the agent is any of the inhibitors described in Ming et al., Cell Stem Cell. 2012 Nov. 2; 11(5):620-32.

In some embodiments, the agent that reduces microglial cell activation is (4S,4aS,5aR,12a5)-4,7-bis(dimethylamino)-3,10,12,12a-tetrahydroxy-1,11-dioxo-1,4,4a,5,5a,6,11,12a-octahydrotetracene-2-carboxamide (Minocycline) or a pharmaceutically acceptable salt thereof or derivatives thereof. In some embodiments, the agent is any of the compounds described in US patent application publication number US20100190755. In some embodiments, the agent is the following compound:

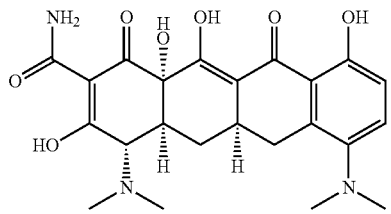 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

In some embodiments, the agent that reduces microglial cell activation is 3-(7-amino-3-oxo-1H-isoindol-2-yl)piperidine-2,6-dione (lenalidomide) or a pharmaceutically acceptable salt thereof or derivatives thereof. In some embodiments, the agent is the following compound:

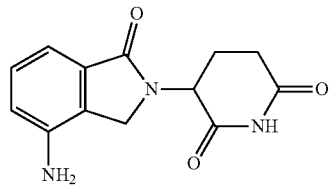 [SMILES: Nc1cccc2c1CN(C1CCC(=O)NC1=O)C2=O]

or a pharmaceutically acceptable salt thereof.

In some embodiments, the agent that reduces microglial cell activation is 4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one (naloxone) or a pharmaceutically acceptable salt thereof or derivatives thereof. In some embodiments, the agent is any of the compounds described in U.S. Pat. No. 8,247,425. In some embodiments, the agent is the following compound:

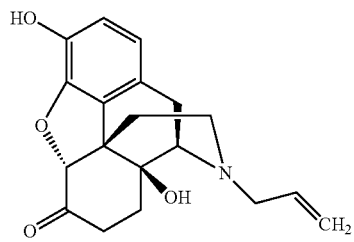 [SMILES: C=CCN1CC[C@]23c4c5ccc(O)c4O[C@H]2C(=O)CC[C@@]3(O)[C@H]1C5]

or a pharmaceutically acceptable salt thereof.

In some embodiments, the agent that reduces microglial cell activation is 2-amino-6-(trifluoromethoxy)benzothiazole, 6-(trifluoromethoxy)benzo[d]thiazol-2-amine, or 6-(trifluoromethoxy)-1,3-benzothiazol-2-amine (riluzole) or a pharmaceutically acceptable salt thereof or derivatives thereof as described in US patent number US5527814. In some embodiments, the agent is the following compound:

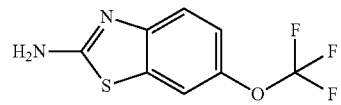

or a pharmaceutically acceptable salt thereof.

In some embodiments, the agent that reduces microglial cell activation is a modulator of a signaling pathway in microglia. In some cases, the agent reduces microglia singling. In some embodiments, the agent is a GM-CSF (CSF2) inhibitor. In other embodiments, the agent that reduces microglial cell activation is an ion channel blocker. In some specific embodiments, the agent is a calcium channel blocker. For example, in some specific examples, the agent is a dihydropyridine calcium channel blocker. In some embodiments, the agent is a microRNA inhibitor. For example, the agent targets miR-155. In some embodiments, the agent that reduces microglial cell activation is selected from MOR103, Nimodipine, IVIg, and LNA-anti-miR-155 (Butoxsky et al. *Ann Neurol.*, 77(1):75-99 (2015) and Sanz et al., *Br J Pharmacol.* 167(8): 1702-1711 (2012); Winter et al., *Ann Clin and Transl Neurol.* 2328-9503 (2016); Clinical Trial Study Record Nos.: NCT01517282, NCT00750867).

In some embodiments, the agent that reduces microglial cell activation is 3-(2-methoxyethyl) 5-propan-2-yl 2,6-dimethyl-4-(3-nitrophenyl)-1,4-dihydropyridine-3,5-dicarboxylate (nimodipine) or a pharmaceutically acceptable salt thereof or derivatives thereof. In some embodiments, the agent is any of the inhibitors described in U.S. Pat. No. 3,799,934. In some embodiments, the agent is the following compound:

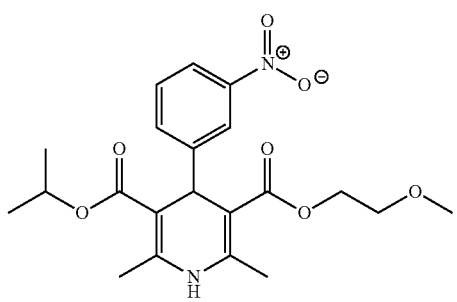 [SMILES: COCCOC(=O)C1=C(C)NC(C)=C(C(=O)OC(C)C)C1c1cccc([N+](=O)[O-])c1]

or a pharmaceutically acceptable salt thereof.

In some cases, the agent that reduces microglial cell activation is administered in a form that only affects to central nervous system and/or does not affect tumor-associated macrophages. In some embodiments, the agent promotes microglia quiescence but does not eliminate or reduce the number of microglia. In some embodiments, the method involves inhibiting microglia activity specifically in the brain such as described in Ponomarev et al., Nature Medicine, (1):64-70 (2011)

Exemplary agents that reduce microglial cell activation, and exemplary dosing regimens for administering such agents, are set forth in Table 7 below.

TABLE 7

Exemplary microglia inhibitors and dosage regimens

| Exemplary Inhibitor | Type of Molecule | Molecular Target(s) | Exemplary Dosing Regimen(s) |
|---|---|---|---|
| Pexidartinib (PLX3397) | small molecule | CSF1R; c-Kit; FLT3 | 200 mg tablets, twice daily for 28 days; Administer daily as split dose regimen, five dose-levels possible in dose escalation part: 400 mg 5 days on 2 days off (intermittent schedule), 400 mg, 600 mg, 800 mg or 1000 mg; 1000 mg/day for 2 weeks then 800 mg/day for 22 weeks |
| Emactuzumab (RG1755; RO5509554) | monoclonal antibody | CSF1R | 100-3000 mg once every 2 weeks |
| Cabiralizumab (FPA-008) | antibody | CSF1R | Intravenous infusion over 30 minutes every 2 weeks |
| LY-3022855 (IMC-CS4) | monoclonal antibody | CSF1R | 1.25 mg/kg intravenous delivery every 2 weeks for 6 weeks |
| JNJ-40346527 | small molecule | CSF1R | 100 mg twice daily for 12 weeks; 100-1000 mg capsule daily |
| MCS110 | antibody | MCSF (CSF1) | Up to 4 doses of 10 mg/kg MCS110 administered intravenously once every 4 weeks starting at Day 1 |
| MOR103 | antibody | GM-CSF | 6 doses of 0.5-2.0 mg/kg over 70 days |
| IVIg | immunoglobulin | Unknown | Intravenous infusion of 0.4 g/kg each month for 6 months |
| Minocyline | small molecule | broad spectrum antibiotic: IL-1b; IL-6, TNF-a; iNOS | Oral dose of 100 mg of minocycline twice daily for 24 months |
| Naloxone | small molecule | Opioid receptors | 4.5 mg naltrexone hydrochloride capsules once/day for 8 weeks |
| Lenalidomide/ thalidomide | small molecule | NFkB signaling | 100-400 mg daily |
| Riluzole | small molecule | Glutamate release by microglia | 50 mg twice daily |
| Cannabinoids/ cannabidiol (e.g. WIN55, 212-2) | small molecule | cannabinoid receptors | Orally 10 mg/kg/day for 6 weeks (average of 700 mg/day) |
| Dimethyl fumarate (Tecfidera ®). | small molecule | Nrf2 signaling | Starting dose of 120 mg taken orally twice/day for 7 days. Dose increased to 240 mg taken orally twice/day thereafter |
| natalizumab (Tysabri ®) | antibody | alpha-4 integrin | 300 mg infused intravenously over one hour, every four weeks |
| fingolimod (Gilenya ®) | small molecule | S1P receptors, including S1PR1 | 0.5 mg orally once-daily |
| ozanimod (RPC-1063) | small molecule | S1PR1 and S1PR5 | 0.25 mg, 0.5 mg, or 1 mg once daily |

C. Other Agents (e.g. Cytokine Targeting Agents)

In some embodiments, the agent, e.g. toxicity-targeting agent, that treats or ameliorates symptoms of a toxicity of immunotherapy and/or a cell therapy, such as CRS or neurotoxicity, is one that targets a cytokine, e.g., is an antagonist or inhibitor of a cytokine, such as transforming growth factor beta (TGF-beta), interleukin 6 (IL-6), interleukin 10 (IL-10), IL-2, MIP1β (CCL4), TNF alpha, IL-1, interferon gamma (IFN-gamma), or monocyte chemoattractant protein-1 (MCP-1). In some embodiments, the agent that treats or ameliorates symptoms of a toxicity of an immunotherapy and/or a cell therapy, such as CRS or neurotoxicity, is one that targets (e.g. inhibits or is an antagonist of) a cytokine receptor, such as IL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1β receptor (e.g., CCR5), TNF alpha receptor (e.g., TNFR1), IL-1 receptor (IL1-Rα/IL-1Rβ), or IL-10 receptor (IL-10R).

The amount of a selected agent that treats or ameliorates symptoms of a toxicity of an immunotherapy and/or a cell therapy, such as CRS or neurotoxicity to be administered to ameliorate symptoms or adverse effects of a toxicity to an immunotherapy and/or a cell therapy, such as CRS or neurotoxicity, can be determined by standard clinical techniques. Exemplary adverse events include, but are not limited to, an increase in alanine aminotransferase, an increase in aspartate aminotransferase, chills, febrile neutropenia, headache, hypotension, left ventricular dysfunction, encephalopathy, hydrocephalus, seizure, and/or tremor.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg.

In some embodiments, the agent is administered from or from about 0.5 mg/kg to 100 mg/kg, such as from or from about 1 mg/kg to 50 mg/kg, 1 mg/kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive. In some aspects, the agent is administered in a dosage amount of at least or at least about or about 1 mg/kg, 2 mg/kg, 4 mg/kg, 6 mg/kg, 8 mg/kg, 10 mg/kg or more. In some embodiments, the agent is administered at a dose of 4 mg/kg or 8 mg/kg.

In some embodiments, the agent is administered by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the amount of the agent is administered about or approximately twice daily, daily, every other day, three times a week, weekly, every other week or once a month.

In some embodiments, the agent is administered as part of a composition or formulation, such as a pharmaceutical composition or formulation as described below. Thus, in some cases, the composition comprising the agent is administered as described below. In other aspects, the agent is administered alone and may be administered by any known acceptable route of administration or by one described herein, such as with respect to compositions and pharmaceutical formulations.

In some embodiments, the agent that treats or ameliorates symptoms of a toxicity of the immunotherapy and/or cell therapy, such as CRS or neurotoxicity, is an antibody or antigen binding fragment. In some embodiments, the agent is tocilizumab, siltuximab, sarilumab, olokizumab (CDP6038), elsilimomab, ALD518/BMS-945429, sirukumab (CNTO 136), CPSI-2634, ARGX-109, FE301, or FM101.

In some embodiments, the agent is an antagonist or inhibitor of IL-6 or the IL-6 receptor (IL-6R). In some aspects, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-IL-6 antibody, such as siltuximab, elsilimomab, ALD518/BMS-945429, sirukumab (CNTO 136), CPSI-2634, ARGX-109, FE301, FM101, or olokizumab (CDP6038). In some aspects, the agent may neutralize IL-6 activity by inhibiting the ligand-receptor interactions. The feasibility of this general type of approach has been demonstrated with a natural occurring receptor antagonist for interleukin-1. See Harmurn, C. H. et al., Nature (1990) 343:336-340. In some aspects, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, the agent is tocilizumab. In some embodiments, tocilizumab is administered as an early intervention in accord with the provided methods, and/or with the provided articles of manufacture or compositions, at a dosage of from or from about 1 mg/kg to 12 mg/kg, such as at or about 4 mg/kg, 8 mg/kg, or 10 mg/kg. In some embodiments, tocilizumab is administered by intravenous infusion. In some embodiments, tocilizumab is administered for a persistent fever of greater than 39° C. lasting 10 hours that is unresponsive to acetaminophen. In some embodiments, a second administration of tocilizumab is provided if symptoms recur after 48 hours of the initial dose.

In some embodiments, the agent is an agonist or stimulator of TGF-β or a TGF-β receptor (e.g., TGF-β receptor I, II, or III). In some aspects, the agent is an antibody that increases TGF-β activity, such as an antibody or antigen-binding fragment that binds to TGF-β or one of its receptors. In some embodiments, the agent that is an agonist or stimulator of TGF-β and/or its receptor is a small molecule, a protein or peptide, or a nucleic acid.

In some embodiments, the agent is an antagonist or inhibitor of MCP-1 (CCL2) or a MCP-1 receptor (e.g., MCP-1 receptor CCR2 or CCR4). In some aspects, the agent is an antibody that neutralizes MCP-1 activity, such as an antibody or antigen-binding fragment that binds to MCP-1 or one of its receptors (CCR2 or CCR4). In some embodiments, the MCP-1 antagonist or inhibitor is any described in Gong et al. J Exp Med. 1997 Jul. 7; 186(1): 131-137 or Shahrara et al. J Immunol 2008; 180:3447-3456. In some embodiments, the agent that is an antagonist or inhibitor of MCP-1 and/or its receptor (CCR2 or CCR4) is a small molecule, a protein or peptide, or a nucleic acid.

In some embodiments, the agent is an antagonist or inhibitor of IFN-γ or an IFN-γ receptor (IFNGR). In some aspects, the agent is an antibody that neutralizes IFN-γ activity, such as an antibody or antigen-binding fragment that binds to IFN-γ or its receptor (IFNGR). In some aspects, the IFN-gamma neutralizing antibody is any described in Dobber et al. Cell Immunol. 1995 February; 160(2):185-92 or Ozmen et al. J Immunol. 1993 Apr. 1; 150(7):2698-705. In some embodiments, the agent that is an antagonist or inhibitor of IFN-γ/IFNGR is a small molecule, a protein or peptide, or a nucleic acid.

In some embodiments, the agent is an antagonist or inhibitor of IL-10 or the IL-10 receptor (IL-10R). In some aspects, the agent is an antibody that neutralizes IL-10 activity, such as an antibody or antigen-binding fragment that binds to IL-10 or IL-10R. In some aspects, the IL-10 neutralizing antibody is any described in Dobber et al. Cell Immunol. 1995 February; 160(2):185-92 or Hunter et al. J Immunol. 2005 Jun. 1; 174(11):7368-75. In some embodiments, the agent that is an antagonist or inhibitor of IL-10/IL-10R is a small molecule, a protein or peptide, or a nucleic acid.

In some embodiments, the agent is an antagonist or inhibitor of IL-1 or the IL-1 receptor (IL-1R). In some aspects, the agent is an IL-1 receptor antagonist, which is a modified form of IL-1R, such as anakinra (see, e.g., Fleischmann et al., (2006) Annals of the rheumatic diseases. 65(8):1006-12). In some aspects, the agent is an antibody that neutralizes IL-1 activity, such as an antibody or antigen-binding fragment that binds to IL-1 or IL-1R, such as canakinumab (see also EP 2277543). In some embodiments, the agent that is an antagonist or inhibitor of IL-1/IL-1R is a small molecule, a protein or peptide, or a nucleic acid.

In some embodiments, the agent is an antagonist or inhibitor of a tumor necrosis factor (TNF) or a tumor necrosis factor receptor (TNFR). In some aspects, the agent is an antibody that blocks TNF activity, such as an antibody or antigen-binding fragment that binds to a TNF, such as TNFα, or its receptor (TNFR, e.g., TNFRp55 or TNFRp75). In some aspects, the agent is selected from among infliximab, adalimumab, certolizumab pegol, golimumab and etanercept. In some embodiments, the agent that is an antagonist or inhibitor of TNF/TNFR is a small molecule, a protein or peptide, or a nucleic acid. In some embodiments, the agent is a small molecule that affects TNF, such as lenalidomide (see, e.g., Muller et al. (1999) Bioorganic & Medicinal Chemistry Letters. 9 (11):1625).

In some embodiments, the agent is an antagonist or inhibitor of signaling through the Janus kinase (JAK) and two Signal Transducer and Activator of Transcription (STAT) signaling cascade. JAK/STAT proteins are common components of cytokine and cytokine receptor signaling. In some embodiments, the agent that is an antagonist or inhibitor of JAK/STAT, such as ruxolitinib (see, e.g., Mesa et al. (2012) Nature Reviews Drug Discovery. 11(2):103-104), tofacitinib (also known as Xeljanz, Jakvinus tasocitinib and CP-690550), Baricitinib (also known as LY-3009104, INCB-28050), Filgotinib (G-146034, GLPG-0634), Gandotinib (LY-2784544), Lestaurtinib (CEP-701), Momelotinib (GS-0387, CYT-387), Pacritinib (SB1518), and Upadacitinib (ABT-494). In some embodiments, the agent is a small molecule, a protein or peptide, or a nucleic acid.

In some embodiments, the agent is a kinase inhibitor. In some embodiments, the agent is an inhibitor of Bruton's tyrosine kinase (BTK). In some embodiments, the inhibitor is or comprises ibrutinib or acalabrutinib (see, e.g., Barrett et al., ASH 58$^{th}$ Annual Meeting San Diego, Calif. Dec. 3-6, 2016, Abstract 654; Ruella et al., ASH 58$^{th}$ Annual Meeting San Diego, Calif. Dec. 3-6, 2016, Abstract 2159). In some embodiments, the agent is an inhibitor as described in U.S. Pat. Nos. 7,514,444; 8,008,309; 8,476,284; 8,497,277; 8,697,711; 8,703,780; 8,735,403; 8,754,090; 8,754,091; 8,957,079; 8,999,999; 9,125,889; 9,181,257; or 9,296,753.

In some embodiments, a device, such as absorbent resin technology with blood or plasma filtration, can be used to reduce cytokine levels. In some embodiments, the device used to reduce cytokine levels is a physical cytokine absorber, such as an extracorporeal cytokine absorber. In some embodiments, a physical cytokine absorber can be used to eliminate cytokines from the bloodstream in an ex vivo, extracorporeal manner. In some embodiments, the agent is a porous polymer. In some embodiments, the agent is CytoSorb (see, e.g., Basu et al. Indian J Crit Care Med. (2014) 18(12): 822-824).

III. Recombinant Antigen Receptors Expressed by the Cells

In some embodiments, the cells for use in or administered in connection with the provided methods contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8$^+$ or CD4$^+$ cells are enriched or selected. Among the compositions are pharmaceutical compositions and formulations for administration, such as for adoptive cell therapy. Also provided are therapeutic methods for administering the cells and compositions to subjects, e.g., patients, in accord with the provided methods, and/or with the provided articles of manufacture or compositions.

In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

A. Chimeric Antigen Receptors (CARs)

In some embodiments of the provided methods and uses, chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is a stimulating or an activating intracellular domain portion, such as a T cell stimulating or activating domain, providing a primary activation signal or a primary signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen targeted by the receptor is or comprises selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). *Leucocyte typing III*. 302). The FMC63 antibody comprises CDRH1 and H2 set forth in SEQ ID NOS: 38, 39 respectively, and CDRH3 set forth in SEQ ID NOS: 40 or 54 and CDRL1 set forth in SEQ ID NOS: 35 and CDR L2 36 or 55 and CDR L3 sequences 37 or 56. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the svFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region of FMC63 set forth in SEQ ID NO:41 and a variable light chain region of FMC63 set forth in SEQ ID NO:42. In some embodiments, the variable heavy and variable light chain are connected by a linker. In some embodiments, the linker is set forth in SEQ ID NO:24. In some embodiments, the scFv comprises, in order, a $V_H$, a linker, and a $V_L$. In some embodiments, the scFv comprises, in order, a $V_L$, a linker, and a $V_H$. In some embodiments, the svFc is encoded by a sequence of nucleotides set forth in SEQ ID NO:25 or a sequence that exhibits at least 85%, 86%, 87%, 88%, 89%, 90%, 91%, 92%, 93%, 94%, 95%, 96%, 97%, 98%, or 99% sequence identity to SEQ ID NO:25. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). The SJ25C1 antibody comprises CDRH1, H2 and H3 set forth in SEQ ID NOS: 47-49, respectively, and CDRL1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing the CDRL1 sequence of SEQ ID NO:44, a CDRL2 sequence of SEQ ID NO: 45, and a CDRL3 sequence of SEQ ID NO:46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region of SJ25C1 set forth in SEQ ID NO:50 and a variable light chain region of SJ25C1 set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv.

In some embodiments, the antibody portion of the recombinant receptor, e.g., CAR, further includes at least a portion of an immunoglobulin constant region, such as a hinge region, e.g., an IgG4 hinge region, and/or a $C_H1/C_L$ and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include, but are not limited to, those described in Hudecek et al. (2013) *Clin. Cancer Res.*, 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5. In some embodiments, the spacer has the sequence set forth in SEQ ID NOS: 26-34. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 26-34.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein.

In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CDtransmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. An exemplary T2A linker sequence comprises the sequence of amino acids set forth in SEQ ID NO: 6 or 17 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. Nos. 7,446,190 or 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO: 4. In some embodiments, the spacer is an Ig hinge, e.g., an IgG4 hinge, linked to a $C_H3$ domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 17, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

B. T Cell Receptors (TCRs)

In some embodiments, engineered cells, such as T cells, used in connection with the provided methods, uses, articles of manufacture or compositions are cells that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or C$_β$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4$^+$ or CD8$^+$ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPredl (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MEW class I binding sites, such models include, but are not limited to, ProPred1 (described in more detail in Singh and Raghava, ProPred: prediction of HLA-DR binding sites. BIOINFOR- MATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wüfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)$_5$-P- wherein P is proline, G is glycine and S is serine (SEQ ID NO:28). In some embodiments, the linker has the sequence GSADDAKKDAAKKDGKS (SEQ ID NO:29)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector. Genetically Engineered Cells and Methods of Producing Cells In some embodiments, the provided methods involve administering to a subject having a disease or condition cells expressing a recombinant antigen receptor. Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

C. Chimeric Auto-Antibody Receptors (CAARs)

In some embodiments, among the recombinant receptor expressed by the engineered cells used in connection with the provided methods, uses, articles of manufacture and compositions is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

D. Multi-Targeting

In some embodiments, the cells used in connection with the provided methods, uses, articles of manufacture and compositions include cells employing multi-targeting strategies, such as expression of two or more genetically engineered receptors on the cell, each recognizing the same of a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine*, 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating or stimulatory signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains or regions of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

E. Vectors and Methods for Genetic Engineering

In some embodiments, engineered cells, such as T cells, used in connection with the provided methods, uses, articles of manufacture or compositions are cells have been genetically engineered to express a recombinant receptor, e.g., a CAR or a TCR described herein. In some embodiments, the cells are engineered by introduction, delivery or transfer of nucleic acid sequences that encode the recombinant receptor and/or other molecules.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

F. Cells and Preparation of Cells for Genetic Engineering

In some embodiments, cells, such as T cells, used in connection with the provided methods, uses, articles of manufacture or compositions are cells have been genetically engineered to express a recombinant receptor, e.g., a CAR or a TCR described herein. In some embodiments, the engineered cells are used in the context of cell therapy, e.g., adoptive cell therapy. In some embodiments, the engineered cells are immune cells. In some embodiments, the engineered cells are T cells, such as CD4+ or CD8+ T cells.

In some embodiments, the nucleic acids, such as nucleic acids encoding a recombinant receptor, are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-$CD3$/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{O4}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^- CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_CM$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood.1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood.1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific $CD4^+$ and/or $CD8^+$ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

IV. Compositions and Formulations

In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods or uses, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

V. Combination Therapy

In some embodiments of the methods, articles of manufacture, uses or compositions, the cell therapy, e.g. dose of T cells (e.g. CAR$^+$ T cells) is administered to subjects in combination with an additional therapeutic agent or therapy, generally other than the cell therapy or another cell therapy, such as other than a CAR$^+$ T cell therapy. In some embodiments, the cell therapy, e.g. dose of genetically engineered T cells, such as CAR$^+$ T cells, in the provided methods or uses, and/or with the articles of manufacture or compositions, is administered as part of a combination treatment or combination therapy, such as simultaneously with, sequentially with or intermittently with, in any order, one or more additional therapeutic intervention. In some embodiments, the one or more additional therapeutic intervention includes any agent or treatment for treating or preventing the disease or condition, such as the B cell malignancy, e.g. NHL, and/or any agent or treatment to increase the efficacy, persistence, and/or activity of the engineered cell therapy.

In some embodiments, an additional therapeutic agent or therapy is administered to subjects who are or are likely to be or who are predicted to be poor responders and/or who do not, are likely not to and/or who are predicted not to respond or do not respond within a certain time and/or to a certain extent to treatment with the cell therapy, e.g. dose of T cells (e.g. CAR$^+$ T cells). In some embodiments, the additional therapeutic agent is administered to subjects who do not or are not likely to or are not predicted to exhibit a complete response or overall response, such as within 1 month, within two months or within three months after initiation of administration of the cell therapy. In some embodiments, the additional therapeutic agent is administered to subjects who exhibit or are likely to exhibit or who are predicted to exhibit progressive disease (PD), such as within 1 month, two months or three months, following administration of the cell therapy. In some embodiments, a subject is likely or predicted not to exhibit a response or a certain response based on a plurality of similarly situated subjects so treated or previously treated with the cell therapy.

In some embodiments, it is observed that a subject that may or that is more likely to exhibit a poor response to cell therapy, e.g. dose of T cells (e.g. CAR$^+$ T cells) includes a subject with NHL that is or has been identified to have stable or progressive disease (SD/PD) following treatment with a prior therapy, optionally a prior therapy with a chemotherapeutic agent, that is or has been identified with an Eastern Cooperative Oncology Group Performance Status (ECOG) status of 2, that is or has been identified as having a transformed follicular lymphoma (tFL), or that is or has been identified has having a DLBCL transformed from MZL and CLL. In some embodiments, the provided methods include selecting a subject that is or is likely to exhibit a poor response to a cell therapy when the cell therapy is administered alone, and administering the cell therapy in combination with an additional agent or therapy, such as any as described. In some embodiments, the a subject for treatment in the provided combination therapy methods is a subject that is selected as having a B cell malignancy, such as NHL, and that has stable or progressive disease (SD/PD) following treatment with a prior therapy, optionally a prior therapy with a chemotherapeutic agent, that has an Eastern Cooperative Oncology Group Performance Status (ECOG) status of 2, that has a transformed follicular lymphoma (tFL), or that has a DLBCL transformed from MZL and CLL. In some embodiments, the additional agent or therapy can be administered prior to, concomitantly with or at the same time and/or subsequently to initiation of administration of the cell therapy, e.g. dose of T cells (e.g. CAR$^+$ T cells).

In certain embodiments, it is found that the pharmacokinetics (PK) of the cell therapy in the blood of subjects following administration of the cell therapy is similar or not substantially different between subjects that respond (e.g. exhibit a CR or OR) versus do not respond (e.g. exhibit PD) to the cell therapy. In some embodiments, such observations indicate that the cell therapy has or is expanding in the subject but may not exhibit optimal efficacy.

In some contexts, optimal efficacy of a cell therapy can depend on the ability of the administered cells to recognize and bind to a target, e.g., target antigen, to traffic, to localize to and successfully enter appropriate sites within the subject, tumors, and environments thereof. In some contexts, optimal efficacy can depend on the ability of the administered cells to become activated, expand, to exert various effector functions, including cytotoxic killing and secretion of various factors such as cytokines, to persist, including long-term, to differentiate, transition or engage in reprogramming into certain phenotypic states (such as long-lived memory, less-differentiated, and effector states), to avoid or reduce immunosuppressive conditions in the local microenvironment of a disease, to provide effective and robust recall responses following clearance and re-exposure to target ligand or antigen, and avoid or reduce exhaustion, anergy, peripheral tolerance, terminal differentiation, and/or differentiation into a suppressive state.

In some aspects, the efficacy of the immunotherapy, e.g., T cell therapy, may be limited by the immunosuppressive activity or factors present in the local microenvironment of the disease or disorder, e.g., the TME. In some aspects, the TME contains or produces factors or conditions that can suppress the activity, function, proliferation, survival and/or persistence of T cells administered for T cell therapy.

In some embodiments, administration of an additional agent or therapy, prior to, concomitantly with or at the same time and/or subsequently to initiation of administration of the cell therapy, e.g. dose of T cells (e.g. CAR$^+$ T cells) can result in improved activity, efficacy and/or persistence of the cell therapy and/or improve responses of the treated subject. In some embodiments, the additional agent for combination treatment or combination therapy enhances, boosts and/or promotes the efficacy and/or safety of the therapeutic effect of the cell therapy, e.g. engineered T cell therapy, such as CAR$^+$ T cells. In some embodiments, the additional agent enhances or improves the efficacy, survival or persistence of the administered cells, e.g., cells expressing the recombinant receptor, e.g. CAR.

In some embodiments, the additional agent of therapy is an antibody or a cytotoxic or therapeutic agent, e.g., a chemotherapeutic agent. In some embodiments, the one or more additional agents for treatment or therapy is an immunomodulatory agent, immune checkpoint inhibitor, adenosine pathway or adenosine receptor antagonist or agonist and kinase inhibitors. In some embodiments, the combination treatment or combination therapy includes an additional treatment, such as a surgical treatment, transplant, and/or radiation therapy.

In some embodiments, the additional agent is selected from among a protein phosphatase inhibitor, a kinase inhibitor, a cytokine, an immunomodulator, or an agent that decreases the level or activity of a regulatory T (Treg) cell. In some embodiments, the additional agent enhances safety, by virtue of reducing or ameliorating adverse effects of the administered cell therapy. In some embodiments, the additional agent can treat the same disease, condition or a comorbidity. In some embodiments, the additional agent can ameliorate, reduce or eliminate one or more toxicities, adverse effects or side effects that are associated with administration of the cells, e.g., CAR-expressing cells.

In some embodiments, the additional therapy, treatment or agent includes chemotherapy, radiation therapy, surgery, transplantation, adoptive cell therapy, antibodies, cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, immune checkpoint inhibitors, antibiotics, angiogenesis inhibitors, metabolic modulators or other therapeutic agents or any combination thereof. In some embodiments, the additional agent is a protein, a peptide, a nucleic acid, a small molecule agent, a cell, a toxin, a lipid, a carbohydrate or combinations thereof, or any other type of therapeutic agent, e.g. radiation. In some embodiments, the additional therapy, agent or treatment includes surgery, chemotherapy, radiation therapy, transplantation, administration of cells expressing a recombinant receptor, e.g., CAR, kinase inhibitor, immune checkpoint inhibitor, mTOR pathway inhibitor, immunosuppressive agents, immunomodulators, antibodies, immunoablative agents, antibodies and/or antigen binding fragments thereof, antibody conjugates, other antibody therapies, cytotoxins, steroids, cytokines, peptide vaccines, hormone therapy, antimetabolites, metabolic modulators, drugs that inhibit either the calcium dependent phosphatase calcineurin or the p70S6 kinase FK506) or inhibit the p70S6 kinase, alkylating agents, anthracyclines, *vinca* alkaloids, proteosome inhibitors, GITR agonists, protein tyrosine phosphatase inhibitors, protein kinase inhibitors, an oncolytic virus, and/or other types of immunotherapy. In some embodiments, the additional agent or treatment is bone marrow transplantation, T cell ablative therapy using chemotherapy agents such as, fludarabine, external-beam radiation therapy (XRT), cyclophosphamide, and/or antibody therapy.

In some embodiments, the additional agent is a kinase inhibitor, e.g., an inhibitor of Bruton's tyrosine kinase (Btk), e.g., ibrutinib. In some embodiments, the additional agent is an adenosine pathway or adenosine receptor antagonist or agonist. In some embodiments, the additional agent is an immunomodulator such as thalidomide or a thalidomide derivative (e.g., lenalidomide). In some embodiments, the additional therapy, agent or treatment is a cytotoxic or chemotherapy agent, a biologic therapy (e.g., antibody, e.g., monoclonal antibody, or cellular therapy), or an inhibitor (e.g., kinase inhibitor).

In some embodiments, the additional agent is a chemotherapeutic agent. Exemplary chemotherapeutic agents include an anthracycline (e.g., doxorubicin, such as liposomal doxorubicin); a vinca alkaloid (e.g., vinblastine, vincristine, vindesine, vinorelbine); an alkylating agent (e.g., cyclophosphamide, decarbazine, melphalan, ifosfamide, temozolomide); an immune cell antibody (e.g., alemtuzamab, gemtuzumab, rituximab, tositumomab); an antimetabolite (including, e.g., folic acid antagonists, pyrimidine analogs, purine analogs and adenosine deaminase inhibitors such as fludarabine); a TNFR glucocorticoid induced TNFR related protein (GITR) agonist; a proteasome inhibitor (e.g., aclacinomycin A, gliotoxin or bortezomib); an immunomodulatory such as thalidomide or a thalidomide derivative (e.g., lenalidomide).

In some embodiments, the additional agent is an immunomodulatory agent. In some embodiments, the combination therapy includes an immunomodulatory agent that can stimulate, amplify and/or otherwise enhance an anti-tumor immune response, e.g. anti-tumor immune response from the administered engineered cells, such as by inhibiting immunosuppressive signaling or enhancing immunostimulant signaling. In some embodiments, the immunomodulatory agent is a peptide, protein or is a small molecule. In some embodiments, the protein can be a fusion protein or a recombinant protein. In some embodiments, the immunomodulatory agent binds to an immunologic target, such as a cell surface receptor expressed on immune cells, such a T cells, B cells or antigen-presenting cells. For example, in some embodiments, the immunomodulatory agent is an antibody or antigen-binding antibody fragment, a fusion protein, a small molecule or a polypeptide. In some embodiments, the binding molecules, recombinant receptors, cells and/or compositions are administered in combination with an additional agent that is an antibody or an antigen-binding fragment thereof, such as a monoclonal antibody.

In some embodiments, the immunomodulatory agent blocks, inhibits or counteracts a component of the immune checkpoint pathway. The immune system has multiple inhibitory pathways that are involved in maintaining self-tolerance and for modulating immune responses. Tumors can use certain immune-checkpoint pathways as a major mechanism of immune resistance, particularly against T cells that are specific for tumor antigens (Pardoll (2012) Nature Reviews Cancer 12:252-264), e.g., engineered cells such as CAR-expressing cells. Because many such immune checkpoints are initiated by ligand-receptor interactions, they can be readily blocked by antibodies against the ligands and/or their receptors. In contrast to the majority of anti-cancer agents, checkpoint inhibitors do not necessarily target tumor cells directly, but rather target lymphocyte receptors or their ligands in order to enhance the endogenous antitumor activity of the immune system.

In some embodiments, the additional agent is an immunomodulatory agent that is an antagonist molecule or is an immune checkpoint inhibitor capable of inhibiting or blocking a function of a molecule, or signaling pathway, involving an immune checkpoint molecule. In some embodiments, the immune checkpoint molecule or pathway is PD-1, PD-L1, PD-L2, CTLA-4, LAG-3, TIM3, VISTA, adenosine 2A Receptor (A2AR), or adenosine or a pathway involving any of the foregoing. In certain embodiments, antagonistic molecules blocking an immune checkpoint pathway, such as small molecules, nucleic acid inhibitors (e.g., RNAi) or antibody molecules, are becoming promising avenues of immunotherapy for cancer and other diseases.

In some embodiments, the immune checkpoint inhibitor is a molecule that totally or partially reduces, inhibits, interferes with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors, ligands and/or receptor-ligand interaction. In some embodiments, modulation, enhancement and/or stimulation of particular receptors can overcome immune checkpoint pathway components. Illustrative immune checkpoint molecules that may be targeted for blocking, inhibition, modulation, enhancement and/or stimulation include, but are not limited to, PD-1 (CD279), PD-L1 (CD274, B7-H1), PDL2 (CD273, B7-DC), CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8$^+$ (αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and a transforming growth factor receptor (TGFR; e.g., TGFR beta). Immune checkpoint inhibitors include antibodies, or antigen binding fragments thereof, or other binding proteins, that bind to and block or inhibit and/or enhance or stimulate the activity of one or more of any of the said molecules.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary of immunomodulatory antibodies include, but are not limited to, Daclizumab (Zenapax), Bevacizumab (Avastin®), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MMNRP1685A or an antibody-binding fragment thereof. Other exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon.gamma., CAS 951209-71-5, available from IRX Therapeutics).

In some embodiments, the additional agent that is administered in accord with the provided methods, and/or with the provided articles of manufacture or compositions, is an agent that binds to and/or inhibits Programmed cell death 1 (PD-1). PD-1 is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197: 177-87; Pardoll (2012) Nature Reviews Cancer 12:252-264). The major role of PD-1 is to limit the activity of T cells in peripheral tissues during inflammation in response to infection, as well as to limit autoimmunity. PD-1 expression is induced in activated T cells and binding of PD-1 to one of its endogenous ligands acts to inhibit T-cell activation by inhibiting stimulatory kinases. PD-1 also acts to inhibit the TCR "stop signal". PD-1 is highly expressed on Treg cells and may increase their proliferation in the presence of ligand (Pardoll (2012) Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck), nivolumab (also referred to as Opdivo, BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are described in U.S. Pat. No. 8,008,449 and WO2006/121168. Pidilizumab (CT-011; Cure Tech) is a humanized IgGlk monoclonal antibody that binds to PD-1. Pidilizumab and other humanized anti-PD-1 monoclonal antibodies are described in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are described in U.S. Pat. No. 8,354,509 and WO2009/114335. Other anti-PD-1 antibodies include AMP 514 (Amplimmune), among others, e.g., anti-PD-1 antibodies described in U.S. Pat. No. 8,609,089, US 2010028330, US 20120114649 and/or US 20150210769. AMP-224 (B7-DCIg; Amplimmune; e.g., described in WO2010/027827 and WO2011/066342), is a PD-L2 Fc fusion soluble receptor that blocks the interaction between PD-1 and B7-H1.

In some embodiments, the additional agent that is administered in accord with the provided methods, and/or with the provided articles of manufacture or compositions, is an agent that binds to or inhibits PD-L1 (also known as CD274 and B7-H1) and/or PD-L2 (also known as CD273 and B7-DC). PD-L1 and PD-L2 are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8$^+$ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., 2012, N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Genentech), BMS-935559 (Bristol-Myers Squibb) and MSB0010718C. MEDI4736 (Medimmune) is a human monoclonal antibody that binds to PD-L1, and inhibits interaction of the ligand with PD-1. MDPL3280A (Genentech/Roche) is a human Fc optimized IgG1 monoclonal antibody that binds to PD-L1. MDPL3280A and other human monoclonal antibodies to PD-L1 are described in U.S. Pat. No. 7,943,743 and U.S Publication No. 20120039906. Other anti-PD-L1 binding agents include YW243.55.570 (see WO2010/077634) and MDX-1105 (also referred to as BMS-936559, and, e.g., anti-PD-L1 binding agents described in WO2007/005874).

In some embodiments, the additional agent that is administered in accord with the provided methods, and/or with the provided articles of manufacture or compositions, is an agent that is an inhibitor of Cytotoxic T-lymphocyte-associated antigen (CTLA-4), also known as CD152, or binds to CTLA-4. CTLA-4 is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity. Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll (2012) Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response. In some cases, tumors may actually increase in size after treatment initiation, before a reduction is seen (Pardoll (2012) Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89).

In some embodiments, the additional agent that is administered in accord with the provided methods, and/or with the provided articles of manufacture or compositions, is an agent that bind to and/or inhibits Lymphocyte activation gene-3 (LAG-3), also known as CD223. LAG-3 is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MEW class II receptor, which is substantially expressed on melanoma-infiltrating T cells including those endowed with potent immune-suppressive activity. Exemplary anti-LAG-3 antibodies include BMS-986016 (Bristol-Myers Squib), which is a monoclonal antibody that targets LAG-3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG-3 and Ig that binds to MEW class II molecules and activates antigen presenting cells (APC). Other antibodies are described, e.g., in WO2010/019570 and US 2015/0259420.

In some embodiments, the additional agent that is administered in accord with the provided methods, and/or with the provided articles of manufacture or compositions, is an agent that bins to and/or inhibits T-cell immunoglobulin domain and mucin domain-3 (TIM-3). TIM-3 was initially identified on activated Thl cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present. In some embodiments, antibodies, antibody fragments, small molecules, or peptide inhibitors that target TIM-3 can bind to the IgV domain of TIM-3 to inhibit interaction with its ligands. Exemplary antibodies and peptides that inhibit TIM-3 are described in US 2015/0218274, WO2013/006490 and US 2010/0247521. Other anti-TIM-3 antibodies include humanized versions of RMT3-23 (Ngiow et al., 2011, Cancer Res, 71:3540-3551), and clone 8B.2C12 (Monney et al., 2002, Nature, 415:536-541). Bi-specific antibodies that inhibit TIM-3 and PD-1 are described in US 2013/0156774.

In some embodiments, the additional agent that is administered in accord with the provided methods, and/or with the provided articles of manufacture or compositions, is an agent that is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. (2011) 6(6): e21146, or crossreacts with CEACAM-1 and CEACAM-5 as described in, e.g., WO 2013/054331 and US 2014/0271618.

In some embodiments, the additional agent that is administered in accord with the provided methods, and/or with the provided articles of manufacture or compositions, is an agent that binds to and/or inhibits 4-1BB, also known as CD137. 4-1BB is a transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

In some embodiments, the additional agent that is administered in accord with the provided methods, and/or with the provided articles of manufacture or compositions, is an agent that binds to and/or inhibits Tumor necrosis factor receptor superfamily, member 4 (TNFRSF4), also known as OX40 and CD134. TNFRSF4 is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the additional agent that is administered in accord with the provided methods, and/or with the provided articles of manufacture or compositions, is an agent or a molecule that decreases the regulatory T cell (Treg) population. Methods that decrease the number of (e.g., deplete) Treg cells are known in the art and include, e.g., CD25 depletion, cyclophosphamide administration, and modulating Glucocorticoid-induced TNFR family related gene (GITR) function. GITR is a member of the TNFR superfamily that is upregulated on activated T cells, which enhances the immune system. Reducing the number of Treg cells in a subject prior to apheresis or prior to administration of engineered cells, e.g., CAR-expressing cells, can reduce the number of unwanted immune cells (e.g., Tregs) in the tumor microenvironment and reduces the subject's risk of relapse. In some embodiments, the additional agent includes a molecule targeting GITR and/or modulating GITR functions, such as a GITR agonist and/or a GITR antibody that depletes regulatory T cells (Tregs). In some embodiments, the additional agent includes cyclophosphamide. In some embodiments, the GITR binding molecule and/or molecule modulating GITR function (e.g., GITR agonist and/or Treg depleting GITR antibodies) is administered prior to the engineered cells, e.g., CAR-expressing cells. For example, in some embodiments, the GITR agonist can be administered prior to apheresis of the cells. In some embodiments, cyclophosphamide is administered to the subject prior to administration (e.g., infusion or re-infusion) of the engineered cells, e.g., CAR-expressing cells or prior to apheresis of the cells. In some embodiments, cyclophosphamide and an anti-GITR antibody are administered to the subject prior to administration (e.g., infusion or re-infusion) of the engineered cells, e.g., CAR-expressing cells or prior to apheresis of the cells.

In some embodiments, the additional agent that is administered in accord with the provided methods, and/or with the provided articles of manufacture or compositions, is an agent that is a GITR agonist. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B 1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B 1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726. An exemplary anti-GITR antibody is TRX518.

In some embodiments, the additional agent that is administered in accord with the provided methods, and/or with the provided articles of manufacture or compositions, enhances tumor infiltration or transmigration of the administered cells, e.g., CAR-expressing cells. For example, in some embodiments, the additional agent stimulates CD40, such as CD40L, e.g., recombinant human CD40L. Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893. In some embodiments, the additional agent that enhances tumor infiltration includes tyrosine kinase inhibitor sunitnib, heparanase, and/or chemokine receptors such as CCR2, CCR4, and CCR7.

In some embodiments, the additional agent that is administered in accord with the provided methods, and/or with the provided articles of manufacture or compositions, is an immunomodulatory agent that is a structural or functional analog or derivative of thalidomide and/or an inhibitor of E3 ubiquitin ligase. In some embodiments, the immunomodulatory agent binds to cereblon (CRBN). In some embodiments, the immunomodulatory agent binds to the CRBN E3 ubiquitin-ligase complex. In some embodiments, the immunomodulatory agent binds to CRBN and the CRBN E3 ubiquitin-ligase complex. In some embodiments, the immunomodulatory agent up-regulates the protein or gene expression of CRBN. In some aspects, CRBN is the substrate adaptor for the CRL4$^{CRBN}$ E3 ubiquitin ligase, and modulates the specificity of the enzyme. In some embodiments, binding to CRB or the CRBN E3 ubiquitin ligase complex inhibits E3 ubiquitin ligase activity. In some embodiments, the immunomodulatory agent induces the ubiqutination of KZF1 (Ikaros) and IKZF3 (Aiolos) and/or induces degradation of IKZF1 (Ikaros) and IKZF3 (Aiolos). In some embodiments, the immunomodulatory agent induces the ubiquitination of casein kinase 1A1 (CK1α) by the CRL4$^{CRBN}$ E3 ubiquitin ligase. In some embodiments, the ubiquitination of CK1α results in CK1α degradation.

In some embodiments, the immunomodulatory agent is an inhibitor of the Ikaros (IKZF1) transcription factor. In some embodiments, the immunomodulatory agent enhances ubiquitination of Ikaros. In some embodiments, the immunomodulatory agent enhances the degradation of Ikaros. In some embodiments, the immunomodulatory agent down-regulates the protein or gene expression of Ikaros. In some embodiments, administration of the immunomodulatory agent causes a decrease in Ikaros protein levels.

In some embodiments, the immunomodulatory agent is an inhibitor of the Aiolos (IKZF3) transcription factor. In some embodiments, the immunomodulatory agent enhances ubiquitination of Aiolos. In some embodiments, the immunomodulatory agent enhances the degradation of Aiolos. In some embodiments, the immunomodulatory agent down-regulates the protein or gene expression of Aiolos. In some embodiments, administration of the immunomodulatory agent causes a decrease in Aiolos protein levels.

In some embodiments, the immunomodulatory agent is an inhibitor of both the Ikaros (IKZF1) and Aiolos (IKZF3) transcription factors. In some embodiments, the immunomodulatory agent enhances ubiquitination of both Ikaros and Aiolos. In some embodiments, the immunomodulatory agent enhances the degradation of both Ikaros and Aiolos. In some embodiments, the immunomodulatory agent enhances ubiquitination and degradation of both Ikaros and Aiolos. In some embodiments, administration of the immunomodulatory agent causes both Aiolos protein levels. and Ikaros protein levels to decrease.

In some embodiments, the immunomodulatory agent is a selective cytokine inhibitory drug (SelCID). In some embodiments, the immunomodulatory agent inhibits the activity of phosphodiesterase-4 (PDE4). In some embodiments, the immunomodulatory agent suppresses the enzymatic activity of the CDC25 phosphatases. In some embodiments, the immunomodulatory agent alters the intracellular trafficking of CDC25 phosphatases.

In some embodiments, the immunomodulatory agent is thalidomide (2-(2,6-dioxopiperidin-3-yl)-1H-isoindole-1,3 (2H)-dione) or an analog or derivative of thalidomide. In certain embodiments, a thalidomide derivative includes structural variants of thalidomide that have a similar biological activity. Exemplary thalidomide derivatives include, but are not limited to lenalidomide (REVLIMMUNOMODULATORY COMPOUND™; Celgene Corporation), pomalidomide (also known as ACTIMMUNOMODULATORY COMPOUND™ or POMALYST™ (Celgene Corporation)), CC-1088, CDC-501, and CDC-801, and the compounds disclosed in U.S. Pat. Nos. 5,712,291; 7,320, 991; and 8,716,315; U.S. Appl. No. 2016/0313300; and PCT Pub. Nos. WO 2002/068414 and WO 2008/154252.

In some embodiments, the immunomodulatory agent is 1-oxo- and 1,3 dioxo-2-(2,6-dioxopiperldin-3-yl) isoindolines substituted with amino in the benzo ring as described in U.S. Pat. No. 5,635,517 which is incorporated herein by reference.

In some embodiments, the immunomodulatory agent is a compound of the following formula:

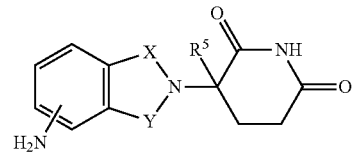

wherein one of X and Y is —C(O)— and the other of X and Y is —C(O)— or —CH$_2$—, and R$^5$ is hydrogen or lower alkyl, or a pharmaceutically acceptable salt thereof. In some embodiments, X is —C(O)— and Y is —CH$_2$—. In some embodiments, both X and Y are —C(O)—. In some embodiments, R$^5$ is hydrogen. In other embodiments, R$^5$ is methyl.

In some embodiments, the immunomodulatory compound is a compound that belongs to a class of substituted 2-(2, 6-dioxopiperidin-3-yl)phthalimmunomodulatory compounds and substituted 2-(2,6-dioxopiperldin-3-yl)-1-oxoisoindoles, such as those described in U.S. Pat. Nos. 6,281, 230; 6,316,471; 6,335,349; and 6,476,052, and International Patent Application No. PCT/US97/13375 (International Publication No. WO 98/03502), each of which is incorporated herein by reference.

In some embodiments, the immunomodulatory agent is a compound of the following formula:

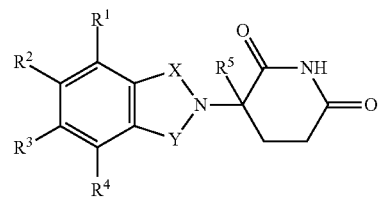

wherein
one of X and Y is —C(O)— and the other of X and Y is —C(O)— or —CH$_2$—;
(1) each of R$^1$, R$^2$, R$^3$, and R$^4$ are independently halo, alkyl of 1 to 4 carbon atoms, or alkoxy or 1 to 4 carbon atoms, or
(2) one of R$^1$, R$^3$, R$^4$, and R$^5$ is —NHR$^a$ and the remaining of R$^1$, R$^2$, R$^3$, and R$^4$ is are hydrogen, wherein leis hydrogen or alkyl of 1 to 8 carbon atoms;
R$^5$ is hydrogen or alkyl of 1 to 8 carbon atoms, benzyl, or halo;
provided that R$^5$ is other than hydrogen if X and Y are —C(O)— and (i) each of R$^1$, R$^2$, R$^3$, and R$^4$ is fluoro; or (ii) one of R$^1$, R$^2$, R$^3$, and R$^4$ is amino;
or a pharmaceutically acceptable salt thereof.

In some embodiments, the immunomodulatory agent is a compound that belongs to a class of isoindole-immunomodulatory compounds disclosed in U.S. Pat. No. 7,091, 353, U.S. Patent Publication No. 2003/0045552, and International Application No. PCT/USOI/50401 (International Publication No. WO02/059106), each of which are incorporated herein by reference. For example, in some embodiments, the immunomodulatory agent is [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2, 3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl) methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl) methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl} (butylamino)carboxamide; N-{[2-(2,6-dioxo(3-piperidyl))-1,3-dioxoisoindolin-4-yl]methyl}(octylamino)carboxamide; or N-{[2-(2,6-dioxo(3-piperidyl))-1,3-dioxoisoindolin-4-yl] methyl}(benzylamino)carboxamide.

In some embodiments, the immunomodulatory agent is a compound that belongs to a class of isoindole-immunomodulatory compounds disclosed in U.S. Patent Application Publication Nos. 2002/0045643, International Publication No. WO 98/54170, and U.S. Pat. No. 6,395,754, each of which is incorporated herein by reference. In some embodiments, the immunomodulatory agent is a tetra substituted 2-(2,6-dioxopiperdin-3-yl)-1-oxoisoindolines described in U.S. Pat. No. 5,798,368, which is incorporated herein by reference. In some embodiments, the immunomodulatory agent is 1-oxo and 1,3-dioxo-2-(2,6-dioxopiperidin-3-yl) isoindolines disclosed in U.S. Pat. No. 6,403,613, which is incorporated herein by reference. In some embodiments the immunomodulatory agent is a 1-oxo or 1,3-dioxoisoindoline substituted in the 4- or 5-position of the indoline ring as described in U.S. Pat. Nos. 6,380,239 and 7,244,759, both of which are incorporated herein by reference.

In some embodiments, the immunomodulatory agent is 2-(4-amino-1-oxo-1,3-dihydro-isoindol-2-yl)-4-carbamoyl-butyric acid or 4-(4-amino-1-oxo-1,3-dihydro-isoindol-2-yl)-4-carbamoyl-butyric acid. In some embodiments, the immunomodulatory compound is 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, or 2-{4-[(furan-2-yl-methyl)-amino]-1,3-dioxo-1,3-dihydro-isoindol-2-yl}-pentanedioic acid.

In some embodiments, the immunomodulatory agent is a isoindoline-1-one or isoindoline-1,3-dione substituted in the 2-position with 2,6-dioxo-3-hydroxypiperidin-5-yl as described in U.S. Pat. No. 6,458,810, which is incorporated herein by reference. In some embodiments, the immunomodulatory compound is 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof. In some embodiments, the immunomodulatory compound is 3-[4-(4-morpholin-4-ylmethyl-benzyloxy)-1-oxo-1,3-dihydro-isoindol-2-yl]-piperidine-2,6-dione.

In some embodiments, the immunomodulatory agent is as described in Oshima, K. et al., *Nihon Rinsho.*, 72(6):1130-5 (2014); Millrine, D. et al., *Trends Mot Med.*, 23(4):348-364 (2017); and Collins, et al., Biochem 1, 474(7):1127-1147 (2017).

In some embodiments, the immunomodulatory agent is lenalidomide, pomalidomide, avadomide, a stereoisomer of lenalidomide, pomalidomide, avadomide or a pharmaceutically acceptable salt, solvate, hydrate, co-crystal, clathrate, or polymorph thereof. In some embodiments, the immunomodulatory compound is lenalidomide, a stereoisomer of lenalidomide or a pharmaceutically acceptable salt, solvate, hydrate, co-crystal, clathrate, or polymorph thereof. In some embodiments, the immunomodulatory compound is lenalidomide, or ((RS)-3-(4-Amino-1-oxo-1,3-dihydro-2H-isoindol-2-yl)piperidine-2,6-dione).

In some embodiments, the additional agent includes thalidomide drugs or analogs thereof and/or derivatives thereof, such as lenalidomide, pomalidomide or apremilast. See, e.g., Bertilaccio et al., Blood (2013) 122:4171, Otahal et al., Oncoimmunology (2016) 5(4):e1115940; Fecteau et al., Blood (2014) 124(10):1637-1644 and Kuramitsu et al., Cancer Gene Therapy (2015) 22:487-495). Lenalidomide ((RS)-3-(4-Amino-1-oxo-1,3-dihydro-2H-isoindol-2-yl)piperidine-2,6-dione; also known as Revlimid) is a synthetic derivative of thalidomide, and has multiple immunomodulatory effects, including enforcement of immune synapse formation between T cell and antigen presenting cells (APCs). For example, in some cases, lenalidomide modulates T cell responses and results in increased interleukin (IL)-2 production in $CD4^+$ and $CD8^+$ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. Lenalidomide can also induce malignant B cells to express higher levels of immunostimulatory molecules such as CD80, CD86, HLA-DR, CD95, and CD40 (Fecteau et al., Blood (2014) 124(10): 1637-1644). In some embodiments, lenalidomide is administered at a dosage of from about 1 mg to about 20 mg daily, e.g., from about 1 mg to about 10 mg, from about 2.5 mg to about 7.5 mg, from about 5 mg to about 15 mg, such as about 5 mg, 10 mg, 15 mg or 20 mg daily. In some embodiments, lenalidomide is administered at a dose of from about 10 μg/kg to 5 mg/kg, e.g., about 100 μg/kg to about 2 mg/kg, about 200 μg/kg to about 1 mg/kg, about 400 μg/kg to about 600 μg/kg, such as about 500 μg/kg.

In some embodiments, the additional agent that is administered in accord with the provided methods, and/or with the provided articles of manufacture or compositions, is is a B-cell inhibitor. In some embodiments, the additional agent is one or more B-cell inhibitors selected from among inhibitors of CD10, CD19, CD20, CD22, CD34, CD123, CD79a, CD79b, CD179b, FLT-3, or ROR1, or a combination thereof. In some embodiments, the B-cell inhibitor is an antibody (e.g., a mono- or bispecific antibody) or an antigen binding fragment thereof. In some embodiments, the additional agent is an engineered cell expressing recombinant receptors that target B-cell targets, e.g., CD10, CD19, CD20, CD22, CD34, CD123, CD79a, CD79b, CD179b, FLT-3, or ROR1.

In some embodiments, the additional agent that is administered in accord with the provided methods, and/or with the provided articles of manufacture or compositions, is a CD20 inhibitor, e.g., an anti-CD20 antibody (e.g., an anti-CD20 mono- or bi-specific antibody) or a fragment thereof. Exemplary anti-CD20 antibodies include but are not limited to rituximab, ofatumumab, ocrelizumab (also known as GA101 or R05072759), veltuzumab, obinutuzumab, TRU-015 (Trubion Pharmaceuticals), ocaratuzumab (also known as AME-133v or ocaratuzumab), and Pro131921 (Genentech). See, e.g., Lim et al. Haematologica. (2010) 95(1):135-43. In some embodiments, the anti-CD20 antibody comprises rituximab. Rituximab is a chimeric mouse/human monoclonal antibody IgG1 kappa that binds to CD20 and causes cytolysis of a CD20 expressing cell. In some embodiments, the additional agent includes rituximab. In some embodiments, the CD20 inhibitor is a small molecule.

In some embodiments, the additional agent that is administered in accord with the provided methods, and/or with the provided articles of manufacture or compositions, is a CD22 inhibitor, e.g., an anti-CD22 antibody (e.g., an anti-CD22 mono- or bi-specific antibody) or a fragment thereof. Exemplary anti-CD22 antibodies include epratuzumab and RFB4. In some embodiments, the CD22 inhibitor is a small molecule. In some embodiments, the antibody is a monospecific antibody, optionally conjugated to a second agent such as a chemotherapeutic agent. For instance, in some embodiments, the antibody is an anti-CD22 monoclonal antibody-MMAE conjugate (e.g., DCDT2980S). In some embodiments, the antibody is an scFv of an anti-CD22 antibody, e.g., an scFv of antibody RFB4. In some embodiments, the scFv is fused to all of or a fragment of *Pseudomonas* exotoxin-A (e.g., BL22). In some embodiments, the scFv is fused to all of or a fragment of (e.g., a 38 kDa fragment of) *Pseudomonas* exotoxin-A (e.g., moxetumomab pasudotox). In some embodiments, the anti-CD22 antibody is an anti-CD19/CD22 bispecific antibody, optionally conjugated to a toxin. For instance, in some embodiments, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In some embodiments, the bispecific portion (e.g., anti-CD 19/anti-CD22) is linked to a toxin such as deglycosylated ricin A chain (e.g., Combotox).

In some embodiments, the additional agent that is administered in accord with the provided methods, and/or with the provided articles of manufacture or compositions, is a cytokine or is an agent that induces increased expression of a cytokine in the tumor microenvironment. Cytokines have important functions related to T cell expansion, differentiation, survival, and homeostasis. Cytokines that can be administered to the subject receiving the combination therapy in the provided methods or uses, recombinant receptors, cells and/or compositions provided herein include one or more of IL-2, IL-4, IL-7, IL-9, IL-15, IL-18, and IL-21. In some embodiments, the cytokine administered is IL-7, IL-15, or IL-21, or a combination thereof. In some embodiments, administration of the cytokine to the subject that has sub-optimal response to the administration of the engineered cells, e.g., CAR-expressing cells improves efficacy and/or anti-tumor activity of the administered cells, e.g., CAR-expressing cells.

In some embodiments, the additional agent that is administered in accord with the provided methods, and/or with the provided articles of manufacture or compositions, is a cytokine, such as a protein that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immunomodulatory agent is a cytokine and the cytokine is IL-4, TNF-α, GM-CSF or IL-2.

In some embodiments, the additional agent that is administered in accord with the provided methods, and/or with the provided articles of manufacture or compositions, includes an interleukin-15 (IL-15) polypeptide, an interleukin-15 receptor alpha (IL-15Ra) polypeptide, or combination thereof, e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311. In some embodiments, the immunomodulatory agent can contain one or more cytokines. For example, the interleukin can include leukocyte interleukin injection (Multikine), which is a combination of natural cytokines.

In some embodiments, the additional agent that is administered in accord with the provided methods, and/or with the provided articles of manufacture or compositions, is a modulator of adenosine levels and/or an adenosine pathway component. Adenosine can function as an immunomodulatory agent in the body. For example, adenosine and some adenosine analogs that non-selectively activate adenosine receptor subtypes decrease neutrophil production of inflammatory oxidative products (Cronstein et al., Ann. N.Y. Acad. Sci. 451:291, 1985; Roberts et al., Biochem. J., 227:669, 1985; Schrier et al., J. Immunol. 137:3284, 1986; Cronstein et al., Clinical Immunol. Immunopath. 42:76, 1987). In some cases, concentration of extracellular adenosine or adenosine analogs can increase in specific environments, e.g., tumor microenvironment (TME). In some cases, adenosine or adenosine analog signaling depends on hypoxia or factors involved in hypoxia or its regulation, e.g., hypoxia inducible factor (HIF). In some embodiments, increase in adenosine signaling can increase in intracellular cAMP and cAMP-dependent protein kinase that results in inhibition of proinflammatory cytokine production, and can lead to the synthesis of immunosuppressive molecules and development of Tregs (Sitkovsky et al., Cancer Immunol Res (2014) 2(7):598-605). In some embodiments, the additional agent can reduce or reverse immunosuppressive effects of adenosine, adenosine analogs and/or adenosine signaling. In some embodiments, the additional agent can reduce or reverse hypoxia-driven A2-adenosinergic T cell immunosuppression. In some embodiments, the additional agent is selected from among antagonists of adenosine receptors, extracellular adenosine-degrading agents, inhibitors of adenosine generation by CD39/CD73 ectoenzymes, and inhibitors of hypoxia-HIF-1α signaling. In some embodiments, the additional agent is an adenosine receptor antagonist or agonist.

In some embodiments, the additional agent that is administered in accord with the provided methods, and/or with the provided articles of manufacture or compositions, is an agent that inhibits the activity and/or an amount of an adenosine receptor. Particular embodiments contemplate that inhibition or reduction of extracellular adenosine or the adenosine receptor by virtue of an inhibitor of extracellular adenosine (such as an agent that prevents the formation of, degrades, renders inactive, and/or decreases extracellular adenosine), and/or an adenosine receptor inhibitor (such as an adenosine receptor antagonist) can enhance immune response, such as a macrophage, neutrophil, granulocyte, dendritic cell, T- and/or B cell-mediated response. In addition, inhibitors of the Gs protein mediated cAMP dependent intracellular pathway and inhibitors of the adenosine receptor-triggered Gi protein mediated intracellular pathways, can also increase acute and chronic inflammation.

In some embodiments, the additional agent that is administered in accord with the provided methods, and/or with the provided articles of manufacture or compositions, is an adenosine receptor antagonist or agonist, e.g., an antagonist or agonist of one or more of the adenosine receptors A2a, A2b, A1, and A3. A1 and A3 inhibit, and A2a and A2b stimulate, respectively, adenylate cyclase activity. Certain adenosine receptors, such as A2a, A2b, and A3, can suppress or reduce the immune response during inflammation. Thus, antagonizing immunosuppressive adenosine receptors can augment, boost or enhance immune response, e.g., immune response from administered cells, e.g., CAR-expressing T cells. In some embodiments, the additional agent inhibits the production of extracellular adenosine and adenosine-triggered signaling through adenosine receptors. For example, enhancement of an immune response, local tissue inflammation, and targeted tissue destruction can be enhanced by inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors.

In some embodiments, the additional agent that is administered in accord with the provided methods, and/or with the provided articles of manufacture or compositions, is an adenosine receptor antagonist. In some embodiments, the antagonist is small molecule or chemical compound of an adenosine receptor, such as the A2a, A2b, or A3 receptor. In some embodiments, the antagonist is a peptide, or a pepidomimetic, that binds the adenosine receptor but does not trigger a Gi protein dependent intracellular pathway. Examples of such antagonists are described in U.S. Pat. Nos. 5,565,566; 5,545,627, 5,981,524; 5,861,405; 6,066,642; 6,326,390; 5,670,501; 6,117,998; 6,232,297; 5,786,360; 5,424,297; 6,313,131, 5,504,090; and 6,322,771.

In some embodiments, the additional agent is an A2 receptor (A2R) antagonist, such as an A2a antagonist. Exemplary A2R antagonists include, but are not limited to, KW6002 (istradefyline), SCH58261, caffeine, paraxanthine, 3,7-dimethyl-1-propargylxanthine (DMPX), 8-(m-chlorostyryl) caffeine (CSC), MSX-2, MSX-3, MSX-4, CGS-15943, ZM-241385, SCH-442416, preladenant, vipadenant (BII014), V2006, ST-1535, SYN-115, PSB-1115, ZM241365, FSPTP, and an inhibitory nucleic acid targeting A2R expression, e.g., siRNA or shRNA, or any antibodies or antigen-binding fragment thereof that targets an A2R. In some embodiments, the additional agent is an A2R antagonist described in, e.g., Ohta et al., Proc Natl Acad Sci USA (2006) 103:13132-13137; Jin et al., Cancer Res. (2010) 70(6):2245-2255; Leone et al., Computational and Structural Biotechnology Journal (2015) 13:265-272; Beavis et al., Proc Natl Acad Sci USA (2013) 110:14711-14716; and Pinna, A., Expert Opin Investig Drugs (2009) 18:1619-1631; Sitkovsky et al., Cancer Immunol Res (2014) 2(7):598-605; U.S. Pat. Nos. 8,080,554; 8,716,301; US 20140056922; WO2008/147482; U.S. Pat. No. 8,883,500; US 20140377240; WO02/055083; U.S. Pat. Nos. 7,141,575; 7,405,219; 8,883,500; 8,450,329 and 8,987,279).

In particular embodiments, an adenosine receptor antagonist that is an antisense molecule, inhibitory nucleic acid molecule (e.g., small inhibitory RNA (siRNA)) or catalytic nucleic acid molecule (e.g. a ribozyme) that specifically binds mRNA encoding an adenosine receptor. In some embodiments, the antisense molecule, inhibitory nucleic acid molecule or catalytic nucleic acid molecule binds nucleic acids encoding A2a, A2b, or A3. In some embodiments, an antisense molecule, inhibitory nucleic acid molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway. In some embodiments, the additional agent includes dominant negative mutant form of an adenosine receptor, such as A2a, A2b, or A3.

In some embodiments, the additional agent that is administered in accord with the provided methods, and/or with the provided articles of manufacture or compositions, is an agent that inhibits extracellular adenosine. Agents that inhibit extracellular adenosine include agents that render extracellular adenosine non-functional (or decrease such function), such as a substance that modifies the structure of adenosine to inhibit the ability of adenosine to signal through adenosine receptors. In some embodiments, the additional agent is an extracellular adenosine-generating or adenosine-degrading enzyme, a modified form thereof or a modulator thereof. For example, in some embodiments, the additional agent is an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation.

In some embodiments, the additional agent is an adenosine deaminase (ADA) or a modified form thereof, e.g., recombinant ADA and/or polyethylene glycol-modified ADA (ADA-PEG), which can inhibit local tissue accumulation of extracellular adenosine. ADA-PEG has been used in treatment of patients with ADA SCID (Hershfield (1995)

Hum Mutat. 5:107). In some embodiments, an agent that inhibits extracellular adenosine includes agents that prevent or decrease formation of extracellular adenosine, and/or prevent or decrease the accumulation of extracellular adenosine, thereby abolishing, or substantially decreasing, the immunosuppressive effects of adenosine. In some embodiments, the additional agent specifically inhibits enzymes and proteins that are involved in regulation of synthesis and/or secretion of pro-inflammatory molecules, including modulators of nuclear transcription factors. Suppression of adenosine receptor expression or expression of the Gs protein- or Gi protein-dependent intracellular pathway, or the cAMP dependent intracellular pathway, can result in an increase/enhancement of immune response.

In some embodiments, the additional agent can target ectoenzymes that generate or produce extracellular adenosine. In some embodiments, the additional agent targets CD39 and CD73 ectoenzymes, which function in tandem to generate extracellular adenosine. CD39 (also called ecto-nucleoside triphosphate diphosphohydrolase) converts extracellular ATP (or ADP) to 5'AMP. Subsequently, CD73 (also called 5'nucleotidase) converts 5'AMP to adenosine. The activity of CD39 is reversible by the actions of NDP kinase and adenylate kinase, whereas the activity of CD73 is irreversible. CD39 and CD73 are expressed on tumor stromal cells, including endothelial cells and Tregs, and also on many cancer cells. For example, the expression of CD39 and CD73 on endothelial cells is increased under the hypoxic conditions of the tumor microenvironment. Tumor hypoxia can result from inadequate blood supply and disorganized tumor vasculature, impairing delivery of oxygen (Carroll and Ashcroft (2005), Expert. Rev. Mol. Med. 7(6): 1-16). Hypoxia also inhibits adenylate kinase (AK), which converts adenosine to AMP, leading to very high extracellular adenosine concentration. Thus, adenosine is released at high concentrations in response to hypoxia, which is a condition that frequently occurs the tumor microenvironment (TME), in or around solid tumors. In some embodiments, the additional agent is one or more of anti-CD39 antibody or antigen binding fragment thereof, anti-CD73 antibody or antigen binding fragment thereof, e.g., MEDI9447 or TY/23, α-β-methylene-adenosine diphosphate (ADP), ARL 67156, POM-3, IPH52 (see, e.g., Allard et al. Clin Cancer Res (2013) 19(20):5626-5635; Hausler et al., Am J Transl Res (2014) 6(2):129-139; Zhang, B., Cancer Res. (2010) 70(16):6407-6411).

In some embodiments, the additional agent that is administered in accord with the provided methods, and/or with the provided articles of manufacture or compositions, is a chemotherapeutic agent (sometimes referred to as a cytotoxic agent). In particular embodiments, the chemotherapeutic agent is any agent known to those of skill in the art to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. In particular embodiments, chemotherapeutic drugs include alkylating agents, anthracyclines, cytoskeletal disruptors (taxanes), epothilones, histone deacetylase inhibitors, topoisomerase inhibitors, topoisomerase II inhibitors, kinase inhibitors, nucleotide analogs and precursor analogs, peptide antibiotics, platinum-based agents, and vinca alkaloids and derivatives.

Chemotherapeutic agents may include, but are not limited to, abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, the additional agent is an inhibitor of hypoxia inducible factor 1 alpha (HIF-1α) signaling. Exemplary inhibitors of HIF-1α include digoxin, acriflavine, sirtuin-7 and ganetespib.

In some embodiments, the additional agent includes a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor, e.g., an SHP-2 inhibitor described herein.

In some embodiments, the additional agent is a kinase inhibitor. Kinase inhibitors, such as a CDK4 kinase inhibitor, a BTK kinase inhibitor, a MNK kinase inhibitor, or a DGK kinase inhibitor, can regulate the constitutively active survival pathways that exist in tumor cells and/or modulate the function of immune cells. In some embodiments, the kinase inhibitor is a Bruton's tyrosine kinase (BTK) inhibitor, e.g., ibrutinib. In some embodiments, the kinase inhibitor is a phosphatidylinositol-4,5-bisphosphate 3-kinase (PI3K) inhibitor. In some embodiments, the kinase inhibitor is a CDK4 inhibitor, e.g., a CDK4/6 inhibitor. In some embodiments, the kinase inhibitor is an mTOR inhibitor, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor. In some embodiments, the kinase inhibitor is an MNK inhibitor, or a dual PI3K/mTOR inhibitor. In some embodiments, other exemplary kinase inhibitors include the AKT inhibitor perifosine, the mTOR inhibitor temsirolimus, the Src kinase inhibitors dasatinib and fostamatinib, the JAK2 inhibitors pacritinib and ruxolitinib, the PKCβ inhibitors enzastaurin and bryostatin, and the AAK inhibitor alisertib.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In some embodiments, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (1-[(3R)-3-[4-Amino-3-(4-phenoxyphenyl)-1H-pyrazolo[3,4-d]pyrimidin-1-yl]piperidin-1-yl] prop-2-en-1-one; also known as PCI-32765). In some embodiments, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In some embodiments, 1, 2, 3, 4, 5, 6, 7, 8, 9, 10, 11, 12 or more cycles of ibrutinib are administered. In some embodiments, the BTK inhibitor is a BTK inhibitor described in International Application WO 2015/079417.

In some embodiments, the kinase inhibitor is a PI3K inhibitor. PI3K is central to the PI3K/Akt/mTOR pathway involved in cell cycle regulation and lymphoma survival. Exemplary PI3K inhibitor includes idelalisib (PI3Kδ inhibitor). In some embodiments, the additional agent is idelalisib and rituximab.

In some embodiments, the additional agent is an inhibitor of mammalian target of rapamycin (mTOR). In some embodiments, the kinase inhibitor is an mTOR inhibitor selected from temsirolimus; ridaforolimus (also known as AP23573 and MK8669); everolimus (RAD001); rapamycin (AY22989); simapimod; AZD8055; PF04691502; SF1126; and XL765. In some embodiments, the additional agent is an inhibitor of mitogen-activated protein kinase (MAPK), such as vemurafenib, dabrafenib, and trametinib.

In some embodiments, the additional agent is an agent that regulates pro- or anti-apoptotic proteins. In some embodiments, the additional agent includes a B-cell lymphoma 2 (BCL-2) inhibitor (e.g., venetoclax, also called ABT-199 or GDC-0199; or ABT-737). Venetoclax is a small molecule (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) that inhibits the anti-apoptotic protein, BCL-2. Other agents that modulate pro- or anti-apoptotic protein include BCL-2 inhibitor ABT-737, navitoclax (ABT-263); Mcl-1 siRNA or Mcl-1 inhibitor retinoid N-(4-hydroxyphenyl) retinamide (4-HPR) for maximal efficacy. In some embodiments, the additional agent provides a pro-apoptotic stimuli, such as recombinant tumor necrosis factor-related apoptosis-inducing ligand (TRAIL), which can activate the apoptosis pathway by binding to TRAIL death receptors DR-4 and DR-5 on tumor cell surface, or TRAIL-R2 agonistic antibodies.

In some embodiments, the additional agent includes a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. In some embodiments, the additional agent includes a hypomethylating agent, e.g., a DNA methyltransferase inhibitor, e.g., azacitidine or decitabine.

In another embodiment, the additional therapy is a transplantation, e.g., allogeneic stem cell transplant.

In some embodiments, the additional therapy is a lymphodepleting therapy. In some embodiments, lymphodepletion is performed on a subject, e.g., prior to administering engineered cells, e.g., CAR-expressing cells. In some embodiments, the lymphodepletion comprises administering one or more of melphalan, Cytoxan, cyclophosphamide, and fludarabine. In some embodiments, a lymphodepleting chemotherapy is administered to the subject prior to, concurrently with, or after administration (e.g., infusion) of engineered cells, e.g., CAR-expressing cells. In an example, the lymphodepleting chemotherapy is administered to the subject prior to administration of engineered cells, e.g., CAR-expressing cells.

In some embodiments, the additional agent is an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Other exemplary combination therapy, treatment and/or agents include anti-allergenic agents, anti-emetics, analgesics and adjunct therapies. In some embodiments, the additional agent includes cytoprotective agents, such as neuroprotectants, free-radical scavengers, cardioprotectors, anthracycline extravasation neutralizers and nutrients.

In some embodiments, an antibody used as an additional agent is conjugated or otherwise bound to a therapeutic agent, e.g., a chemotherapeutic agent (e.g., Cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein. In some embodiments, the additional agent is an antibody-drug conjugate.

Any of the additional agents described herein can be prepared and administered as a combination therapy described in the provided methods, uses, articles of manufacture or compositions, such as in pharmaceutical compositions comprising one or more agents of the combination therapy and a pharmaceutically acceptable carrier, such as any described herein. In some embodiments, the combination therapy in the provided methods, uses, articles of manufacture or compositions can be administered simultaneously, concurrently or sequentially, in any order with the additional agents, therapy or treatment, wherein such administration provides therapeutically effective levels each of the agents in the body of the subject. In some embodiments, the additional agent can be co-administered with the combination therapy in the provided methods, uses, articles of manufacture or compositions, for example, as part of the same pharmaceutical composition or using the same method of delivery. In some embodiments, the additional agent is administered simultaneously with the cell therapy, e.g. dose of engineered T cells (e.g. CAR$^+$ T cells), but in separate compositions. In some embodiments, the additional agent is incubated with the engineered cell, e.g., CAR-expressing cells, prior to administration of the cells.

In some examples, the one or more additional agents are administered subsequent to or prior to the administration of the cell therapy, e.g. dose of engineered T cells (e.g. CAR$^+$ T cells), separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one or more additional agents are administered multiple times. In some embodiments, the additional agent is administered prior to the cell therapy, e.g. dose of engineered T cells (CAR+ T cells) in the provided methods, uses, articles of manufacture or compositions, e.g., two weeks, 12 days, 10 days, 8 days, one week, 6 days, 5 days, 4 days, 3 days, 2 days or 1 day before the administration. In some embodiments, the additional agent is administered after the cell therapy, e.g. dose of engineered T cells (e.g. CAR+ T cells) in the provided methods, uses, articles of manufacture or compositions, e.g., two weeks, 12 days, 10 days, 8 days, one week, 6 days, 5 days, 4 days, 3 days, 2 days or 1 day after the administration.

The dose of the additional agent can be any therapeutically effective amount, e.g., any dose amount described herein, and the appropriate dosage of the additional agent may depend on the type of disease to be treated, the type, dose and/or frequency of the binding molecule, recombinant receptor, cell and/or composition administered, the severity and course of the disease, previous therapy, the patient's clinical history and response to cell therapy, e.g. dose of engineered T cells (CAR+ T cells), and the discretion of the attending physician.

VI. Articles of Manufacture and Kits

Also provided are articles of manufacture and kits containing engineered cells expressing a recombinant receptor or compositions thereof, and optionally instructions for use, for example, instructions for administering, according to the provided methods.

In some embodiments, provided are articles of manufacture and/or kits that include a composition comprising a therapeutically effective amount of any of the engineered cells described herein, and instructions for administering, to a subject for treating a disease or condition. In some embodiments, the instructions can specify some or all of the elements of the methods provided herein. In some embodiments, the instructions specify particular instructions for administration of the cells for cell therapy, e.g., doses, timing, selection and/or identification of subjects for administration and conditions for administration. In some embodiments, the articles of manufacture and/or kits further include one or more additional agents for therapy, e.g., lymphodepleting therapy and/or combination therapy, such as any described herein and optionally further includes instructions for administering the additional agent for therapy. In some embodiments, the articles of manufacture and/or kits further comprise an agent for lymphodepleting therapy, and optionally further includes instructions for administering the lymphodepleting therapy. In some embodiments, the instructions can be included as a label or package insert accompanying the compositions for administration.

In some embodiments, the instructions specify the criteria for selection or identification of subjects for therapy. In some embodiments, such criteria include subjects having NHL or sub-type thereof and/or a high-risk NHL. In some embodiments, the instructions specify that the subjects to be treated include subjects having a disease or condition characterized or determined to be aggressive NHL, diffuse large B cell lymphoma (DLBCL), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL). In particular embodiments, the subject to be treated include subjects with aggressive NHL, in particular, with diffuse large B-cell lymphoma (DLBCL), not otherwise specified (NOS) and in some aspects including de novo and transformed from indolent). In some aspects, the subject or population to be treated may include and/or further include subjects with primary mediastinal B-cell lymphoma (PMBCL) or follicular lymphoma grade 3B (FL3B). In some embodiments, the subject or population to be treated include those subjects having poor performance status. In some aspects, the population to be treated includes, e.g., subjects having an Eastern Cooperative Oncology Group Performance Status (ECOG) that is anywhere from 0-2. In other aspects of any of the embodiments, the subjects to be treated include ECOG 0-1 or do not include ECOG2 subjects. In some embodiments, of any of the embodiments, the subjects to be treated have failed two or more prior therapies. In some embodiments, the subject does not have DLBCL transformed from marginal zone lymphoma (MZL) and chronic lymphocytic leukemia (CLL; Richter's) and/or has a DLBCL characterized as de novo or transformed from an indolent disease. In some embodiments, the subject has mantle cell lymphoma (MCL). In some embodiments, the instructions specify the administration of the cell therapy is for a subject that is or has been identified as having a double/triple hit lymphoma (or high-grade B-cell lymphoma, with MYC and BCL2 and/or BCL6 rearrangements with DLBCL histology) has been identified as having a chemorefractory lymphoma, (e.g., chemorefractory DLBCL) and/or that has not achieved complete remission (CR) in response to a prior therapy.

In some embodiments, the instructions specify the dose of cells to be administered. For example, in some embodiments, the dose specified in the instructions include a total recombinant receptor (e.g., CAR)-expressing cells between about $1 \times 10^6$ and $3 \times 10^8$, e.g., in the range of about $1 \times 10^7$ to $2 \times 10^8$ such cells, such as $1 \times 10^7$, $5 \times 10^7$, $1 \times 10^8$ or $1.5 \times 10^8$ total such cells, or the range between any two of the foregoing values. In some embodiments, the patient is administered multiple doses, and each of the doses or the total dose can be within any of the foregoing values.

In some embodiments, the article of manufacture or kit comprises a container, optionally a vial comprising a plurality of CD4+ T cells expressing a recombinant receptor, and a container, optionally a vial comprising a plurality of CD8+ T cells expressing a recombinant receptor. In some embodiments, the article of manufacture or kit comprises a container, optionally a vial comprising a plurality of CD4+ T cells expressing a recombinant receptor, and further comprises, in the same container, a plurality of CD8+ T cells expressing a recombinant receptor. In some embodiments, a cryoprotectant is included with the cells. In some aspects the container is a bag.

In some embodiments, the container such as the vial comprises greater than or greater than about $10 \times 10^6$ T cells or recombinant receptor-expressing T cells, greater than or greater than about $15 \times 10^6$ T cells or recombinant receptor-expressing T cells, greater than or greater than about $25 \times 10^6$ T cells or recombinant receptor-expressing T cell. In some aspects, the vial comprises between about 10 million cells per ml and about 70 million cells per ml, between about 10 million cells per ml and about 50 million cells per ml, between about 10 million cells per ml and about 25 million cells per ml, between about 10 million cells per ml and about 15 million cells per ml, 15 million cells per ml and about 70 million cells per ml, between about 15 million cells per ml and about 50 million cells per ml, between about 15 million cells per ml and about 25 million cells per ml, between about 25 million cells per ml and about 70 million cells per ml, between about 25 million cells per ml and about 50 million cells per ml, and between about 50 million cells per ml and about 70 million cells per ml.

In some embodiments, the plurality of vials or plurality of cells or unit dose of cells specified for administration, collectively, comprises a dose of cells comprising from or from about $1\times10^5$ to $5\times10^8$ total recombinant receptor-expressing T cells or total T cells, $1\times10^5$ to $1\times10^8$ total recombinant receptor-expressing T cells or total T cells, from or from about $5\times10^5$ to $1\times10^7$ total recombinant receptor-expressing T cells or total T cells, or from or from about $1\times10^6$ to $1\times10^7$ total recombinant receptor-expressing T cells or total T cells, each inclusive. In some aspects, the article comprises one or more unit dose of the CD4$^+$ and CD8$^+$ cells or of the CD$^{4+}$ receptor$^+$ cells and CD8$^+$ receptor$^+$ cells, wherein the unit dose comprises between at or about $1\times10^7$ and at or about $2\times10^8$ recombinant receptor-expressing T cells, between at or about $5\times10^7$ and at or about $1.5\times10^8$ recombinant receptor-expressing T cells, at or about $5\times10^7$ recombinant receptor-expressing T cells, at or about $1\times10^8$ recombinant receptor-expressing T cells, or at or about $1.5\times10^8$ recombinant receptor-expressing T cells, optionally wherein the information in the article specifies administration of one or of a plurality of unit doses and/or a volume corresponding to such one or plurality of unit doses. In some cases, the article comprises one or more unit doses of the CD8$^+$ cells, wherein the dose comprises between at or about $5\times10^6$ and at or about $1\times10^8$ recombinant receptor-expressing CD8$^+$ T cells, the dose comprises between at or about $1\times10^7$ and at or about $0.75\times10^8$ recombinant receptor-expressing CD8$^+$ T cells, the dose comprises at or about $2.5\times10^7$ recombinant receptor-expressing CD8$^+$ T cells, or the dose comprises at or about $5\times10^7$ recombinant receptor-expressing CD8$^+$ T cells, or the dose comprises at or about $0.75\times10^8$ recombinant receptor-expressing CD8$^+$ T cells, optionally wherein the information in the article specifies administration of one or of a plurality of unit doses and/or a volume corresponding to such one or plurality of unit doses. In some embodiments, the cells in the article, collectively, comprise a dose of cells comprising no more than $1\times10^8$ total recombinant receptor-expressing T cells or total T cells, no more than $1\times10^7$ total recombinant receptor-expressing T cells or total T cells, no more than $0.5\times10^7$ total recombinant receptor-expressing T cells or total T cells, no more than $1\times10^6$ total recombinant receptor-expressing T cells or total T cells, no more than $0.5\times10^6$ total recombinant receptor-expressing T cells or total T cells.

In some embodiments, each vial or the plurality of vials or plurality of cells or unit dose of cells specified for administration, collectively, comprises a flat dose of cells or fixed dose of cells such that the dose of cells is not tied to or based on the body surface area or weight of a subject.

In some embodiments, a unit dose of a cell is or comprises the number or amount of cells, such as engineered T cells, that can be administered to a subject or a patient in a single dose.

In some embodiments, each vial or the plurality of vials or plurality of cells or unit dose of cells specified for administration, collectively, comprises a dose that includes fewer than about $5\times10^8$ total recombinant receptor (e.g., CAR)-expressing cells, T cells, or peripheral blood mononuclear cells (PBMCs), e.g., in the range of about $1\times10^6$ to $5\times10^8$ such cells, such as $2\times10^6$, $5\times10^6$, $1\times10^7$, $5\times10^7$, $1\times10^8$, or $5\times10^8$ total such cells, or the range between any two of the foregoing values.

In some embodiments, each vial or the plurality of vials or plurality of cells or unit dose of cells specified for administration, collectively, comprises a dose of genetically engineered cells comprising from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, each vial or the plurality of vials or plurality of cells or unit dose of cells specified for administration, collectively, comprises a dose of genetically engineered cells comprising at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the instructions for administration of a dose of engineered cell specify administering a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about 1×10$^5$ total recombinant receptor-expressing cells, total T cells, or total peripheral blood mononuclear cells (PBMCs), such at least or at least 1×10$^6$, at least or at least about 1×10$^7$, at least or at least about 1×10$^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about 1×10$^5$ to 5×10$^8$ CD3+ or CD8+ total T cells or CD3+ or CD8+ recombinant receptor-expressing cells, from or from about 5×10$^5$ to 1×10$^7$ CD3+ or CD8+ total T cells or CD3+ or CD8+ recombinant receptor-expressing cells, or from or from about 1×10$^6$ to 1×10$^7$ CD3+ or CD8+ total T cells or CD3+ or CD8+recombinant receptor-expressing cells, each inclusive. In some embodiments, the cell therapy comprises administration of a dose comprising a number of cell from or from about 1×10$^5$ to 5×10$^8$ total CD3+/CAR+ or CD8+/CAR+ cells, from or from about 5×10$^5$ to 1×10$^7$ total CD3+/CAR+ or CD8+/CAR+ cells, or from or from about 1×10$^6$ to 1×10$^7$ total CD3+/CAR+ or CD8+/CAR+ cells, each inclusive.

In some embodiments, the instructions can specify dosage regimen and timing of the administration. For example, in some embodiments, the instructions can specify administering to the subject multiple doses, e.g., two or more doses, of the cells. In some embodiments, the instructions specify the timing of the multiple doses, e.g., the second dose being administered approximately 4, 5, 6, 7, 8, 9, 10, 11, 12, 13, 14, 15, 16, 17, 18, 19, 20 or 21 days after the first dose; and/or the dosage amount in each dose.

In some embodiments, the article of manufacture or kit comprises a plurality of CD4$^+$ T cells expressing a recombinant receptor, and instructions for administering, to a subject having a disease or condition, all or a portion of the plurality of CD4$^+$ T cells and further administering CD8$^+$ T cells expressing a recombinant receptor. In some embodiments, the instructions specify administering the CD4$^+$ T cells prior to administering the CD8$^+$ cells. In some cases, the instructions specify administering the CD8$^+$ T cells prior to administering the CD4$^+$ cells. In some embodiments, the article of manufacture or kit comprises a plurality of CD8$^+$ T cells expressing a recombinant receptor, and instructions for administering, to a subject having a disease or condition, all or a portion of the plurality of CD8$^+$ T cells and CD4$^+$ T cells expressing a recombinant receptor. In some embodiments, the instructions specify dosage regimen and timing of the administration of the cells.

In some aspects, the instructions specify administering all or a portion of the CD4$^+$ T cells and the all or a portion of the CD8$^+$ T cells 0 to 12 hours apart, 0 to 6 hours apart or 0 to 2 hours apart. In some cases, the instructions specify administering the CD4$^+$ T cells and the CD8$^+$ T cells no more than 2 hours, no more than 1 hour, no more than 30 minutes, no more than 15 minutes, no more than 10 minutes or no more than 5 minutes apart.

In some embodiments, the instructions specify the dose or number of cells or cell type(s) and/or a ratio of cell types, e.g., individual populations or sub-types, such as the CD4$^+$ to CD8$^+$ ratio. In some embodiments, the populations or sub-types of cells, such as CD8$^+$ and CD4$^+$ T cells. For example, in some embodiments, the instructions specify that the cells are administered at or within a tolerated range of an output ratio of multiple cell populations or sub-types, such as CD4$^+$ and CD8$^+$ cells or sub-types, of between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, the articles of manufacture and/or kits further include one or more additional agents for therapy, e.g., lymphodepleting therapy and/or combination therapy, as described herein, and optionally instructions for administering the additional agents. In some examples, the articles of manufacture may further contain one or more therapeutic agents. In some embodiments, the therapeutic agent is an immunomodulatory agent, a cytotoxic agent, an anti-cancer agent or a radiotherapeutic.

In some embodiments, the articles of manufacture and/or kits further include one or more agents or treatments for treating, preventing, delaying, reducing or attenuating the development or risk of development of a toxicity and/or instructions for the administration of one or more agents or treatments for treating, preventing, delaying, reducing or attenuating the development or risk of development of a toxicity in the subject. In some embodiments, the agent is or comprises an anti-IL-6 antibody or anti-IL-6 receptor antibody. For example, in some embodiments, the agent or treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. For example, in some embodiments, the agent or treatment is or comprises one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1f3, CCR5, TNFalpha, TNFR1, IL-1, and IL-1Ralpha/IL-1beta; or an agent capable of preventing, blocking or reducing microglial cell activity or function.

In some embodiments, the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a CB$_2$ receptor and/or is a CB$_2$ agonist, a phosphodiesterase inhibitor, inhibits microRNA-155 (miR-155) or upregulates microRNA-124 (miR-124). In some cases, the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl) pyrimidine-2,4-diamine (GW2580), AZD6495, Ki20227, BLZ945, emactuzumab, IMC-CS4, FPA008, LY-3022855, AMG-820 and TG-3003. In some embodiments, the agent is an inhibitor of colony stimulating factor 1 receptor (CSF1R). For example, the agent PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof; emactuzumab, IMC-CS4, FPA008, LY-3022855, AMG-820 and TG-3003 or is an antigen-binding fragment thereof, or a combination of any of the foregoing.

In some embodiments, the articles of manufacture and/or kits further include one or more reagents for assaying biological samples, e.g., biological samples from subjects who are candidates for administration or who have been administered the therapy, and optionally instructions for use of the reagents or assays. In some embodiments, the biological sample is or is obtained from a blood, plasma or serum sample In some embodiments, the reagents can be used prior to the administration of the cell therapy or after the administration of cell therapy, for diagnostic purposes, to identify subjects and/or to assess treatment outcomes and/or toxicities. For example, in some embodiments, the article of manufacture and/or kits further contain reagents for measuring the level of particular biomarkers, e.g., cytokines or analytes, that are associated with toxicity, and instructions for measuring. In some embodiments, the reagents include components for performing an in vitro assay to measure the biomarkers (e.g. analytes), such as an immunoassay, an aptamer-based assay, a histological or cytological assay, or an mRNA expression level assay. In some embodiments, the in vitro assay is selected from among an enzyme linked immunosorbent assay (ELISA), immunoblotting, immunoprecipitation, radioimmunoassay (MA), immunostaining, flow cytometry assay, surface plasmon resonance (SPR), chemiluminescence assay, lateral flow immunoassay, inhibition assay and avidity assay. In some aspects, the reagent is a binding reagent that specifically binds the biomarkers (e.g. analytes). In some cases, the binding reagent is an antibody or antigen-binding fragment thereof, an aptamer or a nucleic acid probe.

In some embodiments, the articles of manufacture and/or kits comprise one or more reagent capable of detecting one or more analytes, and instructions for using the reagent to assay a biological sample from a subject that is a candidate for treatment, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product). In some embodiments, instructions for assaying presence or absence, level, amount, or concentration of an analyte in the subject compared to a threshold level of the analyte is also included.

In some embodiments, the instructions are included which specify, if the level, amount or concentration of the analyte in the sample is at or above a threshold level for the analyte, administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject. In some cases, the instructions specify that if the level, amount or concentration of the analyte in the sample is at or above a threshold level for the analyte, the cell therapy is administered to the subject at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy. In some cases, the instructions specify that if the level, amount or concentration of the analyte in the sample is at or above a threshold level for the analyte, the cell therapy is administered in an in-patient setting and/or with admission to the hospital for one or more days, optionally wherein the cell therapy is otherwise to be administered to subjects on an outpatient basis or without admission to the hospital for one or more days.

In some embodiments, the instructions for administering the cell therapy specify, if the level, amount or concentration of the analyte in the sample, is below a threshold level, administering to the subject the cell therapy, optionally at a non-reduced dose, optionally on an outpatient basis or without admission to the hospital for one or more days. In some embodiments, the instructions for administering the cell therapy specify, if the level, amount or concentration of the analyte in the sample, is below a threshold level, prior to or concurrently with administering the cell therapy and/or prior to the development of a sign or symptom of a toxicity other than fever, an agent or treatment capable of treating, preventing, delaying, or attenuating the development of the toxicity is not administered to the subject. In some aspects, the instructions for administering the cell therapy specify that if the level, amount or concentration of the analyte in the sample, is below a threshold level, the administration of the cell therapy is to be or may be administered to the subject on an outpatient setting and/or without admission of the subject to the hospital overnight or for one or more consecutive days and/or is without admission of the subject to the hospital for one or more days.

The articles of manufacture and/or kits may further include a cell therapy and/or further include instructions for use with, prior to and/or in connection with treatment with the cell therapy. In some embodiments, the instructions are included for administering the agent and the instructions specify if the level, amount or concentration of the analyte in the sample, is at or above a threshold level administering to the subject the agent. In some aspects, the instructions further specify administering a cell therapy to the subject, wherein administration of the agent is to be carried out (i) prior to, (ii) within one, two, or three days of, (iii) concurrently with and/or (iv) at first fever following, the initiation of administration of the cell therapy to the subject.

The articles of manufacture and/or kits may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may include (a) a first container with a composition contained therein, wherein the composition includes engineered cells expressing a recombinant receptor; and (b) a second container with a composition contained therein, wherein the composition includes the second agent. In some embodiments, the article of manufacture may include (a) a first container with a first composition contained therein, wherein the composition includes a subtype of engineered cells expressing a recombinant receptor; and (b) a second container with a composition contained therein, wherein the composition includes a different subtype of engineered cells expressing a recombinant receptor. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

VII. Exemplary Embodiments

Among the provided embodiments are:

1. A method of treating a subject having or suspected of having a disease or condition, the method comprising administering to the subject a dose of $CD4^+$ and $CD8^+$ T cells, each of the $CD4^+$ and the $CD8^+$ T cells, individually, comprising a receptor that specifically binds to a target antigen expressed by the disease or condition or a cell or tissue thereof and/or that is associated with the disease or condition, wherein the administration comprises administering a plurality of separate compositions, the plurality of separate compositions comprising a first composition comprising one of the $CD4^+$ T cells and the $CD8^+$ T cells and administration of a second composition comprising the other of the $CD4^+$ T cells and the $CD8^+$ T cells.

2. The method of embodiment 1, wherein the receptor comprised by the $CD4^+$ T cells and/or the receptor comprised by the $CD8^+$ T cells comprises a recombinant receptor and/or wherein the $CD4^+$ T cells and/or the $CD8^+$ T cells are genetically engineered to express the receptor.

3. The method of embodiment 1 or embodiment 2, wherein:
the administration of the first composition and the administration of the second composition are carried out on the same day, are carried out between about 0 and about 12 hours apart, between about 0 and about 6 hours apart or between about 0 to 2 hours apart; or
the initiation of administration of the first composition and the initiation of administration of the second composition are carried out between about 1 minute and about 1 hour apart or between about 5 minutes and about 30 minutes apart.

4. The method of any of embodiments 1-3, wherein the first composition and second composition are administered no more than 2 hours, no more than 1 hour, no more than 30 minutes, no more than 15 minutes, no more than 10 minutes or no more than 5 minutes apart.

5. The method of any of embodiments 1-4, wherein the first composition comprises the $CD4^+$ T cells.

6. The method of any of embodiments 1-5, wherein the first composition comprises the $CD8^+$ T cells.

7. The method of any of embodiments 1-6, wherein the initiation of the administration of the first composition is carried out prior to the initiation of the administration of the second composition.

8. The method of any of embodiments 1-7, wherein:
the dose of cells comprises a defined ratio of $CD4^+$ cells expressing a recombinant receptor to $CD8^+$ cells expressing a recombinant receptor and/or of $CD4^+$ cells to $CD8^+$ cells, which ratio optionally is or is approximately 1:1 or is between approximately 1:3 and approximately 3:1; and/or
the $CD4^+$ T cells comprising the receptor in the one of the first and second compositions and the $CD8^+$ T cells comprising the receptor in the other of the first and second compositions are present at a defined ratio, which ratio optionally is or is approximately 1:1 or is between approximately 1:3 and approximately 3:1; and/or
the $CD4^+$ T cells comprising the receptor and the $CD8^+$ T cells comprising the receptor administered in the first and second compositions are present at a defined ratio, which ratio optionally is or is approximately 1:1 or is between approximately 1:3 and approximately 3:1.

9. The method of embodiment 8, wherein the defined ratio is or is approximately 1:1.

10. The method of any of embodiments 1-9, wherein the dose of T cells is administered to the subject as a single dose or is administered only one time within a period of two weeks, one month, three months, six months, 1 year or more.

11. The method of any of embodiments 1-9, wherein the dose of T cells is administered as a double dose comprising a first dose of the T cells and a consecutive dose of the T cells, wherein one or both of the first dose and the second dose comprises administration of the plurality of composition of T cells.

12. The method of embodiment 11, wherein the consecutive dose is administered at a point in time that is at least or more than about 7 days or 14 days after and less than about 28 days after initiation of the administration of the first dose of cells.

13. The method of any of embodiments 1-12, wherein:
the dose of cells comprises between at or about $1 \times 10^5$ and at or about $5 \times 10^8$ total recombinant receptor-expressing T cells or total T cells, between at or about $1 \times 10^5$ and at or about $1 \times 10^8$ total recombinant receptor-expressing T cells or total T cells, between at or about $5 \times 10^5$ and at or about $1 \times 10^7$ total recombinant receptor-expressing T cells or total T cells, or between at or about $1 \times 10^6$ and at or about $1 \times 10^7$ total recombinant receptor-expressing T cells or total T cells, each inclusive.

14. The method of any of embodiments 1-13, wherein the dose of T cells comprises the administration of no more than $1 \times 10^8$ total recombinant receptor-expressing T cells or total T cells, no more than $1 \times 10^7$ total recombinant receptor-expressing T cells or total T cells, no more than $0.5 \times 10^7$ total recombinant receptor-expressing T cells or total T cells, no more than $1 \times 10^6$ total recombinant receptor-expressing T cells or total T cells, no more than $0.5 \times 10^6$ total recombinant receptor-expressing T cells or total T cells.

15. The method of any of embodiments 1-14, wherein the dose of $CD4^+$ and $CD8^+$ T cells comprises:
between at or about $5 \times 10^7$ recombinant receptor-expressing T cells and at or about $1 \times 10^8$ recombinant receptor-expressing T cells, each inclusive;
between at or about $1 \times 10^7$ and at or about $2 \times 10^8$ recombinant receptor-expressing T cells;
between at or about $5 \times 10^7$ and at or about $1.5 \times 10^8$ recombinant receptor-expressing T cells
at or about $5 \times 10^7$ recombinant receptor-expressing T cells; or
at or about $1 \times 10^8$ recombinant receptor-expressing T cells; or
the dose comprises at or about $1.5 \times 10^8$ recombinant receptor-expressing T cells;
between at or about $5 \times 10^6$ and at or about $1 \times 10^8$ recombinant receptor-expressing $CD8^+$ T cells;
between at or about $1 \times 10^7$ and at or about $0.75 \times 10^8$ recombinant receptor-expressing $CD8^+$ T cells;
at or about $2.5 \times 10^7$ recombinant receptor-expressing $CD8^+$ T cells;
at or about $5 \times 10^7$ recombinant receptor-expressing $CD8^+$ T cells; and/or
at or about $0.75 \times 10^8$ recombinant receptor-expressing $CD8^+$ T cells.

16. The method of any of embodiments 1-15, wherein the recombinant receptor specifically binds to an antigen associated with the disease or condition or expressed in cells of the environment of a lesion associated with the disease or condition.

17. The method of any of embodiments 1-16, wherein the disease or condition is a cancer.

18. The method of any of embodiments 1-17, wherein the disease or condition is a myeloma, leukemia or lymphoma.

19. The method of any of embodiments 1-18, wherein the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen.

20. The method of any of embodiments 1-19, wherein the antigen is CD19.

21. The method of any of embodiments 1-20, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

22. The method of any of embodiments 1-21, wherein the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

23. The method of any of embodiments 1-22, wherein the recombinant receptor is a chimeric antigen receptor (CAR), optionally wherein the recombinant receptor is a chimeric antigen receptor (CAR), optionally wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

24. An article of manufacture, comprising (1) a vial comprising a composition comprising a plurality of CD4$^+$ T cells expressing a recombinant receptor, and (2) instructions for administering, to a subject having a disease or condition:

a unit dose of cells of the composition, the unit dose comprising all or a portion of the plurality of CD4$^+$ T cells, and a unit dose of a composition comprising CD8$^+$ T cells expressing a recombinant receptor, wherein the vial does not comprise the unit dose of the composition comprising CD8+ T cells expressing the recombinant receptor.

25. An article of manufacture, comprising (1) a vial comprising a composition comprising a plurality of CD8$^+$ T cells expressing a recombinant receptor, and (2) instructions for administering, to a subject having a disease or condition:

a unit dose of cells of the composition, the unit dose comprising all or a portion of the plurality of CD8$^+$ T cells, and a unit dose of a composition comprising CD4$^+$ T cells expressing a recombinant receptor, wherein the vial does not comprise the unit dose of the composition comprising CD4+ T cells expressing the recombinant receptor.

26. The article of manufacture of embodiment 24 or embodiment 25, wherein:

the recombinant receptor expressed by the CD4$^+$ cells and the recombinant receptor expressed by the CD8$^+$ T cells is the same;

the recombinant receptor expressed by the CD4$^+$ cells and the recombinant receptor expressed by the CD8$^+$ T cells is different; or the recombinant receptor expressed by the CD4$^+$ cells and the recombinant receptor expressed by the CD8$^+$ T cells binds to the same antigen, which is expressed by or associated with the disease or condition or cell or tissue thereof.

27. The article of manufacture of any of embodiments 24-26, wherein the vial comprises greater than or greater than about $10 \times 10^6$ T cells or recombinant receptor-expressing T cells, greater than or greater than about $15 \times 10^6$ T cells or recombinant receptor-expressing T cells, greater than or greater than about $25 \times 10^6$ T cells or recombinant receptor-expressing T cell.

28. The article of manufacture of any of embodiments 24-27, wherein the vial comprises between about 10 million cells per mL and about 70 million cells per mL, between about 10 million cells per mL and about 50 million cells per mL, between about 10 million cells per mL and about 25 million cells per mL, between about 10 million cells per mL and about 15 million cells per mL, 15 million cells per mL and about 70 million cells per mL, between about 15 million cells per mL and about 50 million cells per mL, between about 15 million cells per mL and about 25 million cells per mL, between about 25 million cells per mL and about 70 million cells per mL, between about 25 million cells per mL and about 50 million cells per mL, and between about 50 million cells per mL and about 70 million cells per mL.

29. The article of manufacture of any of embodiments 24-28, wherein the composition further comprise(s) a cryoprotectant and/or the article further includes instructions for thawing the composition prior to administration to the subject.

30. The article of manufacture of any of embodiments 24-29, wherein:

the plurality of CD4$^+$ cells expressing the recombinant receptor and the plurality of CD8$^+$ cells expressing the recombinant receptor in the article, and/or the CD4$^+$ cells and the CD8$^+$ cells in the vial, are present at a defined ratio, which optionally is at or is approximately 1:1 or is between approximately 1:3 and approximately 3:1; and/or the article further comprises information or instructions specifying the administration of the plurality of cells at a defined ratio of cells of the plurality of CD4$^+$ cells expressing the recombinant receptor and cells of the plurality of CD8+ cells expressing the recombinant receptor, and/or the CD4+ cells and the CD8+ cells, which ratio is optionally is at or is approximately 1:1 or is between approximately 1:3 and approximately 3:1; and/or the article further comprises information or instructions specifying the administration of formulations in the vials at a defined volumetric or weight-based ratio, which optionally is at or about 1:1 and/or between at or about 3:1 and at or about 1:3, by volume or weight, and/or optionally corresponds to a ratio of CD4+ cells expressing the recombinant receptor to CD8+ cells expressing the recombinant receptor, and/or CD4+ cells to CD8+ cells, which ratio is optionally is at or is approximately 1:1 or is between approximately 1:3 and approximately 3:1.

31. The article of manufacture of embodiment 30, wherein the defined ratio is or is approximately 1:1.

32. The article of manufacture of any of embodiments 24-31, wherein the plurality of vials or plurality of cells or unit dose of cells specified for administration, collectively, comprises a dose of cells comprising from or from about $1 \times 10^5$ to $5 \times 10^8$ total recombinant receptor-expressing T cells or total T cells, $1 \times 10^5$ to $1 \times 10^8$ total recombinant receptor-expressing T cells or total T cells, from or from about $5 \times 10^5$ to $1 \times 10^7$ total recombinant receptor-expressing T cells or total T cells, or from or from about $1 \times 10^6$ to $1 \times 10^7$ total recombinant receptor-expressing T cells or total T cells, each inclusive;

the article comprises one or more unit dose of the CD4+ and CD8+ cells or of the CD4+ receptor+ cells and CD8+ receptor+ cells, wherein the unit dose comprises between at or about $1 \times 10^7$ and at or about $2 \times 10^8$ recombinant receptor-expressing T cells, between at or about $5 \times 10^7$ and at or about $1.5 \times 10^8$ recombinant receptor-expressing T cells, at or about $5 \times 10^7$ recombinant receptor-expressing T cells, at or about $1 \times 10^8$ recombinant receptor-expressing T cells, or at or about $1.5 \times 10^8$ recombinant receptor-expressing T cells, optionally wherein the information in the article specifies administration of one or of a plurality of unit doses and/or a volume corresponding to such one or plurality of unit doses;

the article comprises one or more unit doses of the CD8+ cells, wherein the dose comprises between at or about $5 \times 10^6$ and at or about $1 \times 10^8$ recombinant receptor-expressing CD8+ T cells, the dose comprises between at or about $1 \times 10^7$ and at or about $0.75 \times 10^8$ recombinant receptor-expressing CD8+ T cells, the dose comprises at or about $2.5 \times 10^7$ recombinant receptor-expressing CD8+ T cells, or the dose comprises at or about $5 \times 10^7$ recombinant receptor-expressing CD8+ T cells, or the dose comprises at or about $0.75 \times 10^8$ recombinant receptor-expressing CD8+ T cells, optionally wherein the information in the article specifies administration of one or of a plurality of unit doses and/or a volume corresponding to such one or plurality of unit doses.

33. The article of manufacture of any of embodiments 24-32, wherein the cells in the article, collectively, comprise a dose of cells comprising no more than $1 \times 10^8$ total recombinant receptor-expressing T cells or total T cells, no more than $1 \times 10^7$ total recombinant receptor-expressing T cells or total T cells, no more than $0.5 \times 10^7$ total recombinant receptor-expressing T cells or total T cells, no more than $1 \times 10^6$ total recombinant receptor-expressing T cells or total T cells, no more than $0.5 \times 10^6$ total recombinant receptor-expressing T cells or total T cells.

34. The article of manufacture of any of embodiments 24-33, wherein the plurality of containers, collectively, comprises a dose of cells comprising:

between at or about $5 \times 10^7$ recombinant receptor-expressing T cells and $1 \times 10^8$ recombinant receptor-expressing T cells, each inclusive;
between at or about $1 \times 10^7$ and at or about $2 \times 10^8$ recombinant receptor-expressing T cells;
between at or about $5 \times 10^7$ and at or about $1.5 \times 10^8$ recombinant receptor-expressing T cells;
at or about $5 \times 10^7$ recombinant receptor-expressing T cells;
at or about $1 \times 10^8$ recombinant receptor-expressing T cells;
at or about $1.5 \times 10^8$ recombinant receptor-expressing T cells;
between at or about $5 \times 10^6$ and at or about $1 \times 10^8$ recombinant receptor-expressing CD8+ T cells;
between at or about $1 \times 10^7$ and at or about $0.75 \times 10^8$ recombinant receptor-expressing CD8+ T cells;
at or about $2.5 \times 10^7$ recombinant receptor-expressing CD8+ T cells;
at or about $5 \times 10^7$ recombinant receptor-expressing CD8+ T cells; or
at or about $0.75 \times 10^8$ recombinant receptor-expressing CD8+ T cells.

35. The article of manufacture of any of embodiments 24-34, wherein the instructions specify administering all or a portion of the CD4+ T cells and the all or a portion of the CD8+ T cells 0 to 12 hours apart, 0 to 6 hours apart or 0 to 2 hours apart.

36. The article of manufacture of any of embodiments 24-34, wherein the instructions specify administering the CD4+ T cells and the CD8+ T cells no more than 2 hours, no more than 1 hour, no more than 30 minutes, no more than 15 minutes, no more than 10 minutes or no more than 5 minutes apart.

37. The article of manufacture of any of embodiments 24-36, wherein the instructions specify administering the CD4+ T cells prior to administering the CD8+ cells.

38. The article of manufacture of any of embodiments 24-36, wherein the instructions specify administering the CD8+ T cells prior to administering the CD4+ Cells.

39. The article of manufacture of any of embodiments 24-38, wherein the recombinant receptor specifically binds to an antigen associated with the disease or condition or expressed in cells of the environment of a lesion associated with the disease or condition.

40. The article of manufacture of any of embodiments 24-39, wherein the disease or condition is a cancer.

41. The article of manufacture of any of embodiments 24-40, wherein the disease or condition is a myeloma, leukemia or lymphoma.

42. The article of manufacture of any of embodiments 24-41, wherein the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAM), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen.

43. The article of manufacture of any of embodiments 24-42, wherein the antigen is CD19.

44. The article of manufacture of any of embodiments 24-43, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

45. The article of manufacture of any of embodiments 24-44, wherein the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

46. The article of manufacture of any of embodiments 24-45, wherein the T cells are primary T cells obtained from a subject.

47. The article of manufacture of any of embodiments 24-46, wherein the T cells are autologous to the subject.

48. The article of manufacture of any of embodiments 24-46, wherein the T cells are allogeneic to the subject.

49. A method of treating a subject having or suspected of having a B cell malignancy, optionally a non-Hodgkin lymphoma (NHL), the method comprising administering to the subject a dose of T cells comprising T cells expressing a chimeric antigen receptor (CAR) that specifically binds to a target antigen expressed by the NHL, wherein:
the dose of T cells comprises between at or about $2.5 \times 10^7$ CAR-expressing T cells and $2 \times 10^8$ CAR-expressing T cells, inclusive, optionally between at or about $5 \times 10^7$ CAR-expressing T cells and at or about $1 \times 10^8$ CAR-expressing T cells, inclusive; and the malignancy, optionally the NHL, comprises diffuse large B cell lymphoma (DLBCL), primary mediastinal large B cell lymphoma (PMBCL), NOS (de novo or transformed from indolent lymphoma), or follicular lymphoma Grade 3B and wherein the subject is or has been identified as having an Eastern Cooperative Oncology Group Performance Status (ECOG) status of 0 or 1, optionally wherein the method further comprises identifying the subject as having diffuse large B cell lymphoma (DLBCL), primary mediastinal large B cell lymphoma (PMBCL), NOS (de novo or transformed from indolent lymphoma), or follicular lymphoma Grade 3B having an ECOG status of 0 or 1.

50. The method of embodiment 49, wherein the dose of T cells comprises a defined ratio of CD4$^+$ cells expressing the CAR to CD8$^+$ cells expressing the CAR and/or of CD4$^+$ cells to CD8$^+$ cells, which ratio optionally is approximately 1:1 or is between approximately 1:3 and approximately 3:1.

51. A method of treating a subject having non-Hodgkin lymphoma (NHL), the method comprising administering to the subject a dose of T cells comprising T cells expressing a chimeric antigen receptor (CAR) that specifically binds to a target antigen expressed by the NHL, the dose of T cells comprising a defined ratio of CD4$^+$ cells expressing the CAR to CD8$^+$ cells expressing the CAR and/or of CD4$^+$ cells to CD8$^+$ cells, which ratio is approximately or is 1:1, wherein the NHL comprises diffuse large B cell lymphoma (DLBCL), primary mediastinal large B cell lymphoma (PMBCL), NOS (de novo or transformed from indolent lymphoma), or follicular lymphoma Grade 3B.

52. The method of embodiment 51, wherein the subject is or has been identified as having an Eastern Cooperative Oncology Group Performance Status (ECOG) status of 0, 1 or 2.

53. The method of embodiment 51 or embodiment 52, wherein the subject is or has been identified as having an ECOG status of 0 or 1.

54. The method of any of embodiments 49-53, wherein:
at least 35%, at least 40% or at least 50% of subjects treated according to the method achieve a complete response (CR), optionally wherein the CR is durable, or is durable in at least 60%, 70%, 80%, 90%, or 95% of subjects achieving the CR, for at or greater than 3 months or at or greater than 6 months; and/or
at least 60%, 70%, 80%, 90%, or 95% of subjects achieving a CR by one month and/or by three months remain in response, remain in CR, and/or survive or survive without progression, for greater at or greater than 3 months and/or at or greater than 6 months and/or at greater than nine months; and/or
at least 50%, at least 60% or at least 70% of the subjects treated according to the method achieve objective response (OR) optionally wherein the OR is durable, or is durable in at least 60%, 70%, 80%, 90%, or 95% of subjects achieving the OR, for at or greater than 3 months or at or greater than 6 months; and/or
at least 60%, 70%, 80%, 90%, or 95% of subjects achieving the OR remain in response or surviving for greater at or greater than 3 months and/or at or greater than 6 months; and/or
at least 40%, at least 50%, at least 60%, at least 70% of the subjects who, at or prior to the administration of the dose of cells had or were identified to have a double/triple hit lymphoma or relapse, optionally relapse within 12 months, following administration of an autologous stem cell transplant (ASCT), achieved an OR, optionally wherein the OR is durable for at or greater than 3 months or at or greater than 6 months.

55. The method of any of embodiments 49-54, wherein:
the cells are autologous to the subject and no minimum absolute lymphocyte count (ALC) for apheresis is required and/or specified for production of the therapy; and/or
the cells are produced by a process which, for at least 90%, 91%, 92%, 93%, 94%, 95%, 96%, 97%, 98%, 99%, or 100% of subjects having the disease or condition or of the selected population of subjects, is capable of generating a cell product for administration and outcomes according to the method.

56. The method of any of embodiment 49-55, wherein:
greater than or greater than about 50%, about 60%, about 70%, or about 80% of the subjects treated according to the method do not exhibit a grade 3 or greater cytokine release syndrome (CRS) and/or do not exhibit a grade 3 or greater neurotoxicity and/or greater than 40% or 50% or 55% do not exhibit any neurotoxicity or CRS.

57. A method of treating a subject having non-Hodgkin lymphoma (NHL), the method comprising administering to the subject a dose of T cells comprising T cells expressing a chimeric antigen receptor (CAR) that specifically binds to a target antigen expressed by the NHL, wherein:

the dose of T cells comprises between at or about $5\times10^7$ recombinant receptor-expressing T cells and $1\times10^8$ recombinant receptor-expressing T cells, inclusive, said dose comprising a defined ratio of CD4$^+$ cells expressing the recombinant receptor to CD8$^+$ cells expressing the recombinant receptor and/or of CD4$^+$ cells to CD8$^+$ cells, which ratio is approximately or is 1:1; and the method results in (1) a complete response (CR) in at least 35%, at least 40% or at least 50% of subjects treated and/or objective response (OR) in at least 50%, at least 60% or at least 70% of subjects treated and (2) results in no more than 50% of subjects exhibiting a cytokine release syndrome (CRS) higher than grade 2 and/or a neurotoxicity higher than grade 2.

58. The method of embodiment 57, wherein at least 40%, at least 50%, at least 60%, at least 70% of the subjects who, at or prior to the administration of the dose of cells had or were identified to have a double/triple hit lymphoma or relapse following administration of an autologous stem cell transplant (ASCT), achieved an OR, optionally wherein the OR is durable for at or greater than 3 months or at or greater than 6 months.

59. The method of embodiment 57, wherein:

the CR or the OR is durable for greater than 3 months or greater than 6 months; and/or at least 20%, at least 25%, at least 35%, at least 40% or at least 50% of subjects treated according to the method achieve a CR that is durable; and/or at least 60%, 70%, 80%, 90%, or 95% of subjects treated with the method and who achieve a CR, remain in CR or remain in response or remain surviving for at or greater than 3 months or at or greater than 6 months or at or greater than 9 months; and/or at least 60%, 70%, 80%, 90%, or 95% of subjects treated with the method who achieve a CR by one month and/or by three months remain in response, remain in CR, and/or survive or survive without progression, for greater at or greater than 3 months and/or at or greater than 6 months and/or at or greater than nine months; and/or at least 50%, at least 60% or at least 70% of the subjects treated according to the method achieve objective response (OR) optionally wherein the OR is durable, or is durable in at least 60%, 70%, 80%, 90%, or 95% of subjects achieving the OR, for at or greater than 3 months or at or greater than 6 months; and/or at least 60%, 70%, 80%, 90%, or 95% of subjects treated with the method and achieving an OR remain in response or surviving for greater at or greater than 3 months and/or at or greater than 6 months.

60. The method of any of embodiments 49-59, wherein:

at or prior to administration of the dose of cells, the subject is or has been identified as having a lymphoma associated with or involving central nervous system (CNS) involvement; and/or at least 70%, at least 80%, at least 90% or at least 95% of subjects treated according to the method who, at or prior to the administration of the dose of cells exhibited or were identified to exhibit a lymphoma with CNS involvement, achieved a resolution of the CNS disease.

61. A method of treating a subject, the method comprising administering, to a subject that has a lymphoma, a dose of T cells comprising T cells expressing a chimeric antigen receptor (CAR) that specifically binds to a target antigen expressed by the lymphoma, wherein the lymphoma in the subject is associated with or involves central nervous system (CNS) involvement.

62. The method of embodiment 60 or embodiment 61, wherein, at or prior to the time of administration of the dose of cells, the subject comprises a brain lesion, optionally a temporal lobe brain lesion.

63. The method of embodiment 62, wherein the lymphoma is a B cell malignancy.

64. The method of embodiment 61 or embodiment 62, wherein the lymphoma is non-Hodgkin lymphoma (NHL).

65. The method of any of embodiments 60-64, wherein:

at least 35%, at least 40% or at least 50% of subjects treated according to the method achieve a complete response (CR) or remission of CNS disease, optionally wherein the CR or remission of the CNS disease is durable, or is durable in at least 60%, 70%, 80%, 90%, or 95% of subjects achieving the CR, for at or greater than 3 months or at or greater than 6 months; and/or at least 60%, 70%, 80%, 90%, or 95% of subjects achieving a CR or remission of CNS disease by one month and/or by three months remain in response, remain in CR, and/or survive or survive without progression, for greater at or greater than 3 months and/or at or greater than 6 months and/or at greater than nine months; and/or at least 50%, at least 60% or at least 70% of the subjects treated according to the method achieve objective response (OR) or remission of CNS disease optionally wherein the OR or remission of the CNS disease is durable, or is durable in at least 60%, 70%, 80%, 90%, or 95% of subjects achieving the OR, for at or greater than 3 months or at or greater than 6 months; and/or at least 60%, 70%, 80%, 90%, or 95% of subjects achieving the OR or remission of CNS disease remain in response or surviving for greater at or greater than 3 months and/or at or greater than 6 months; and/or the brain lesion is reduced in size or volume, optionally by greater than or greater than about 25%, 50%, 75% or more; and/or reduction or remission or clearance of CNS disease is achieved, optionally is achieved in at least 35%, at least 40% or at least 50% of subjects treated according to the method.

66. The method of any of embodiments 49-65, wherein:

greater than or greater than about 30%, 35%, 40%, or 50% of the subjects treated according to the method do not exhibit any grade of cytokine release syndrome (CRS) or neurotoxicity; and/or at least at or about 45%, 50%, 60%, 65%, 70%, 75%, 80%, 85%, 90%, or 95% of subjects treated according to the method do not exhibit early onset CRS or neurotoxicity and/or do not exhibit onset of CRS earlier than 3 days following initiation of the administration and/or do not exhibit onset of neurotoxicity earlier than 5 days following initiation of the administration and/or wherein the median onset of neurotoxicity among subjects treated according to the method is at or after the median peak of, or median time to resolution of, CRS in subjects treated according to the method and/or the median onset of neurotoxicity among subjects treated according to the method is greater than at or about 8, 9, 10, or 11 days.

67. The method of any of embodiments 49-66, wherein:

prior to initiation of administration of the dose of cells, the subject has not been administered an agent or treatment capable of treating, preventing, delaying, reducing or attenuating the development or risk of development of a toxicity; and/or the subject is not administered an agent or treatment for the treatment or prevention or reduction or attenuation of a neurotoxicity and/or a cytokine release syndrome or risk thereof, within a period of time following administration of the dose, which period of time is optionally at or about 1, 2, 3, 4, 5 days, or is optionally at or about 6, 7, 8, 9, 10, 11 days, or is optionally 1, 2, 3 or 4 weeks; and/or the subject is not administered an agent or treatment for the treatment or prevention or reduction or attenuation of a neurotoxicity and/or a cytokine release syndrome or risk thereof, following administration of the dose, prior to or unless the subject exhibits a sign or symptom of the toxicity and/or prior to or unless the subject exhibits a sign or symptom of the toxicity other than a fever, optionally wherein the fever is not a sustained fever or the fever is or has been reduced or reduced by more than 1° C. after treatment with an antipyretic; and/or the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

68. The method of any of embodiments 49-67, wherein:

prior to initiation of administration of the dose of cells, the subject has not been administered an anti-IL-6 or anti-IL-6R antibody, optionally tocilizumab or siltuximab, and/or has not been administered a steroid, optionally dexamethasone; and/or the subject is not administered an anti-IL-6 or anti-IL-6R antibody, optionally tocilizumab or siltuximab, and/or has not been administered a steroid, optionally dexamethasone, within a period of time following administration of the dose, which period of time is optionally at or about 1, 2, 3, 4, 5 days, or is optionally at or about 6, 7, 8, 9, 10, 11 days, or is optionally 1, 2, 3 or 4 weeks; and/or the subject is not administered an anti-IL-6 or anti-IL-6R antibody, optionally tocilizumab or siltuximab, and/or has not been administered a steroid, optionally dexamethasone, following administration of the cell dose, prior to, or unless, the subject exhibits a sign or symptom of a toxicity, optionally a neurotoxicity or CRS, and/or prior to, or unless, the subject exhibits a sign or symptom of a toxicity, optionally a neurotoxicity or CRS, other than a fever, optionally wherein the fever is not a sustained fever or the fever is or has been reduced or reduced by more than 1° C. after treatment with an antipyretic; and/or the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

69. The method of any of embodiments 49-67, wherein:

the administration is carried out on an outpatient basis and/or without requiring admission to or an overnight stay at a hospital; and if the subject exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

70. The method of any of embodiments 49-60 and 64-69, wherein the NHL is selected from the group consisting of aggressive NHL, diffuse large B cell lymphoma (DLBCL), NOS (de novo and transformed from indolent), primary mediastinal large B cell lymphoma (PMBCL), mantle cell lymphoma (MCL), and/or follicular lymphoma (FL), optionally follicular lymphoma Grade 3B (FL3B).

71. The method of any of embodiments 49-60 and 64-70, wherein the NHL comprises diffuse large B cell lymphoma (DLBCL), primary mediastinal large B cell lymphoma (PMBCL), NOS (de novo or transformed from indolent lymphoma), or follicular lymphoma Grade 3B.

72. The method of any of embodiments 49-60 and 64-71, wherein the NHL comprises DLBCL.

73. The method of any of embodiments 49-60 and 70-72, wherein the DLBCL does not comprise DLBCL transformed from MZL and CLL (Richter's) and/or the subject administered the dose of cells has a DLBCL characterized as de novo or transformed from indolent and/or does not comprise a DLBCL transformed from MZL and CLL.

74. The method of any of embodiments 49-60 and 64-73, wherein the NHL does not comprise PMBCL and/or the subject administered the dose of cells does not comprise PMBCL.

75. The method of any of embodiments 57-73, wherein the subject is or has been identified as having an Eastern Cooperative Oncology Group Performance Status (ECOG) status of 0, 1 or 2.

76. The method of any of embodiments 49-75, wherein the subject is or has been identified as having an ECOG status of 0 or 1.

77. The method of any of embodiments 49-76, wherein, at or immediately prior to the time of the administration of the dose of cells the subject has relapsed following remission after treatment with, or become refractory to, one or more prior therapies for the NHL, optionally one, two or three prior therapies other than another dose of cells expressing the CAR.

78. The method of any of embodiments 49-77, wherein, at or prior to the administration of the dose of cells:

the subject is or has been identified as having a double/triple hit lymphoma; and/or the subject is or has been identified as having a chemorefractory lymphoma, optionally a chemorefractory DLBCL; and/or the subject has not achieved complete remission (CR) in response to a prior therapy; and/or the subject has relapsed within 1 year or less than 1 year after receiving an autologous stem cell transplant (ASCT).

79. The method of any of embodiments 49-78, comprising, prior to administration of the dose of cells, identifying or selecting a subject for the administration of the dose of cells that has:

a double/triple hit lymphoma;

a chemorefractory lymphoma, optionally a chemorefractory DLBCL;

not achieved complete remission (CR) in response to a prior therapy for treating the malignancy, optionally the NHL; and/or has relapsed within 1 year or less than 1 year after receiving an autologous stem cell transplant (ASCT); and/or has a lymphoma associated with or involving central nervous system (CNS) involvement.

80. The method of any of embodiments 49-79, further comprising administration of an additional therapeutic agent or therapy, optionally other than a cell therapy, optionally other than CAR+ T cell therapy.

81. The method of embodiment 80, wherein the additional therapeutic agent or therapy is for treating the NHL or malignancy and/or increases the persistence, activity and/or efficacy of the dose of cells.

82. The method of embodiment 80 or embodiment 81, wherein the additional therapeutic agent or therapy is administered if the subject does not exhibit a response, optionally does not exhibit a CR or OR, to the cell therapy within 1 month, within 2 months or within 3 months after administration of the dose of cells.

83. The method of embodiment 80 or embodiment 81, wherein the additional therapeutic agent or therapy is administered to a subject:
that is or has been identified to have stable or progressive disease (SD/PD) following treatment with a prior therapy, optionally a prior therapy with a chemotherapeutic agent;
that is or has been identified with an Eastern Cooperative Oncology Group Performance Status (ECOG) status of 2;
that is or has been identified as having a transformed follicular lymphoma (tFL); or
that is or has been identified has having a DLBCL transformed from MZL and CLL.

84. The method of any of embodiments 80-83, comprising, prior to administration of the dose of cells or the additional therapeutic agent or therapy, identifying or selecting a subject for the administration of the dose of cells that has:
stable or progressive disease (SD/PD) following treatment with a prior therapy, optionally a prior therapy with a chemotherapeutic agent;
an Eastern Cooperative Oncology Group Performance Status (ECOG) status of 2;
a transformed follicular lymphoma (tFL); or
a DLBCL transformed from MZL and CLL.

85. The method of any of embodiments 80-84, wherein the additional therapeutic agent or therapy is administered prior to, with or at the same time and/or subsequent to initiation of administration of the dose of cells.

86. The method of any of embodiments 49-85, wherein:
the CAR comprises an scFv specific for the antigen, a transmembrane domain, a cytoplasmic signaling domain derived from a costimulatory molecule, which optionally is or comprises a 4-1BB, and a cytoplasmic signaling domain derived from a primary signaling ITAM-containing molecule, which optionally is or comprises a CD3zeta signaling domain and optionally further comprises a spacer between the transmembrane domain and the scFv;
the CAR comprises, in order, an scFv specific for the antigen, a transmembrane domain, a cytoplasmic signaling domain derived from a costimulatory molecule, which optionally is or comprises a 4-1BB signaling domain, and a cytoplasmic signaling domain derived from a primary signaling ITAM-containing molecule, which optionally is a CD3zeta signaling domain; or
the CAR comprises, in order, an scFv specific for the antigen, a spacer, a transmembrane domain, a cytoplasmic signaling domain derived from a costimulatory molecule, which optionally is a 4-1BB signaling domain, and a cytoplasmic signaling domain derived from a primary signaling ITAM-containing molecule, which optionally is or comprises a CD3zeta signaling domain; and wherein:
the spacer is optionally a polypeptide spacer that (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) has or consists of the sequence of SEQ ID NO: 1, a sequence encoded by SEQ ID NO: 2, SEQ ID NO: 30, SEQ ID NO: 31, SEQ ID NO: 32, SEQ ID NO: 33, SEQ ID NO: 34, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine; and/or
the costimulatory domain comprises SEQ ID NO: 12 or a variant thereof having at least 85%, 86%, 87%, 88%, 89%, 90%, 91%, 92%, 93%, 94%, 95%, 96%, 97%, 98%, 99% or more sequence identity thereto; and/or
the primary signaling domain comprises SEQ ID NO: 13 or 14 or 15 having at least 85%, 86%, 87%, 88%, 89%, 90%, 91%, 92%, 93%, 94%, 95%, 96%, 97%, 98%, 99% or more sequence identity thereto; and/or
the scFv comprises a CDRL1 sequence of RASQDISKYLN (SEQ ID NO: 35), a CDRL2 sequence of SRLHSGV (SEQ ID NO: 36), and/or a CDRL3 sequence of GNTLPYTFG (SEQ ID NO: 37) and/or a CDRH1 sequence of DYGVS (SEQ ID NO: 38), a CDRH2 sequence of VIWGSETTYYNSALKS (SEQ ID NO: 39), and/or a CDRH3 sequence of YAMDYWG (SEQ ID NO: 40) or wherein the scFv comprises a variable heavy chain region of FMC63 and a variable light chain region of FMC63 and/or a CDRL1 sequence of FMC63, a CDRL2 sequence of FMC63, a CDRL3 sequence of FMC63, a CDRH1 sequence of FMC63, a CDRH2 sequence of FMC63, and a CDRH3 sequence of FMC63 or binds to the same epitope as or competes for binding with any of the foregoing, and optionally wherein the scFv comprises, in order, a $V_H$, a linker, optionally comprising SEQ ID NO: 24, and a $V_L$, and/or the scFv comprises a flexible linker and/or comprises the amino acid sequence set forth as SEQ ID NO: 24.

87. The method of any of embodiments 49-86, wherein the antigen is a B cell antigen, which optionally is CD19.

88. The method of any of embodiments 1-23 and 49-87, wherein, prior to the administration, the subject has been preconditioned with a lymphodepleting therapy comprising the administration of fludarabine and/or cyclophosphamide.

89. The method of any of embodiments 1-23 and 49-88, further comprising, immediately prior to the administration, administering a lymphodepleting therapy to the subject comprising the administration of fludarabine and/or cyclophosphamide.

90. The method of embodiment 88 or embodiment 89, wherein the lymphodepleting therapy comprises administration of cyclophosphamide at about 200-400 mg/m$^2$, optionally at or about 300 mg/m$^2$, inclusive, and/or fludarabine at about 20-40 mg/m$^2$, optionally 30 mg/m$^2$, daily for 2-4 days, optionally for 3 days, or wherein the lymphodepleting therapy comprises administration of cyclophosphamide at about 500 mg/m$^2$.

91. The method of embodiment 88 or embodiment 89, wherein:
the lymphodepleting therapy comprises administration of cyclophosphamide at or about 300 mg/m$^2$ and fludarabine at about 30 mg/m$^2$ daily for 3 days; and/or the lymphodepleting therapy comprises administration of cyclophosphamide at or about 500 mg/m² and fludarabine at about 30 mg/m² daily for 3 days.

92. The method of any of embodiments 49-91, wherein the administration of the cell dose and/or the lymphodepleting therapy is carried out via outpatient delivery, optionally unless or until the subject exhibits a sustained fever or a fever that is or has not been reduced or not reduced by more than 1° C. after treatment with an antipyretic.

93. The method of embodiment 92, wherein if the subject exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

94. The method of any of embodiments 49-92, wherein the dose of cells is administered parenterally, optionally intravenously.

95. The method of any of embodiments 49-94, wherein:
at least 40% or at least 50% of subjects treated according to the method achieve complete remission (CR), exhibit progression-free survival (PFS) and/or overall survival (OS) of greater than at or about 3 months, 6 months or 12 months;
on average, subjects treated according to the method exhibit a median PFS or OS of greater than at or about 6 months, 12 months, or 18 months; and/or
the subject exhibits PFS or OS following therapy for at least at or about 6, 12, 18 or more months.

96. The method of any of embodiments 1-23 and 49-95, wherein, at or about 14 or 28 days after initiation of administration of the dose of cells, the number of CAR⁺ T cells, optionally CAR⁺ CD8⁺ T cells and/or CAR⁺ CD4⁺ T cells, detectable in the blood of the subject, or in a majority of subjects so treated by the method, is greater than 1 cells per greater than 5 cells per µL or greater than per 10 cells per µL.

97. The method of any of embodiments 1-23 and 49-96, wherein the T cells are primary T cells obtained from a subject.

98. The method of any of embodiments 1-23 and 49-97, wherein the T cells are autologous to the subject.

99. The method of any of embodiments 1-23 and 49-97, wherein the T cells are allogeneic to the subject.

100. The method of any of embodiments 49-99, wherein the T cells comprise CD4⁺ T cells expressing the CAR and CD8⁺ T cells expressing the CAR and the administration comprises administering a plurality of separate compositions, said plurality of separate compositions comprising a first composition comprising one of the CD4⁺ T cells and the CD8⁺ T cells and the second composition comprising the other of the CD4⁺ T cells or the CD8⁺ T cells.

101. The method of embodiment 100, wherein:
the first composition and second composition are administered 0 to 12 hours apart, 0 to 6 hours apart or 0 to 2 hours apart or wherein the administration of the first composition and the administration of the second composition are carried out on the same day, are carried out between about 0 and about 12 hours apart, between about 0 and about 6 hours apart or between about 0 and 2 hours apart; and/or
the initiation of administration of the first composition and the initiation of administration of the second composition are carried out between about 1 minute and about 1 hour apart or between about 5 minutes and about 30 minutes apart.

102. The method of embodiment 100 or embodiment 101, wherein the first composition and second composition are administered no more than 2 hours, no more than 1 hour, no more than 30 minutes, no more than 15 minutes, no more than 10 minutes or no more than 5 minutes apart.

103. The method of any of embodiments 100-102, wherein the first composition comprises the CD4⁺ T cells.

104. The method of any of embodiments 100-102, wherein the first composition comprises the CD8⁺ T cells.

105. The method of any of embodiments 100-104, wherein the first composition is administered prior to the second composition.

106. The method of any of embodiments 49-105, wherein the dose of T cells is administered to the subject as a single dose or is administered only one time within a period of two weeks, one month, three months, six months, 1 year or more.

107. The method of any of embodiments 49-106, wherein the dose of T cells is administered as a double dose comprising a first dose of the T cells and a consecutive dose of the T cells, wherein one or both of the first dose and the second dose comprises administration of the plurality of compositions of T cells.

108. The method of embodiment 107, wherein the consecutive dose is administered at a point in time that is at least or more than about 7 days or 14 days after and less than about 28 days after initiation of the administration of the first dose of cells.

109. A method of assessing likelihood of a response to a cell therapy, the method comprising:
(a) assessing the level, amount or concentration of one or more analyte in a biological sample, wherein the one or more analyte is selected from ferritin, LDH, CXCL10, G-CSF, and IL-10, wherein:
the biological sample is from a subject that is a candidate for treatment with the cell therapy, said cell therapy comprising a dose of genetically engineered cells expressing a recombinant receptor; and
the biological sample is obtained from the subject prior to administering the cell therapy and/or said biological sample does not comprise the recombinant receptor and/or said engineered cells; and
(b) comparing, individually, the level, amount or concentration of the analyte in the sample to a threshold level, thereby determining a likelihood that a subject will achieve a response to the cell therapy.

110. The method of embodiment 109, further comprising administering the cell therapy to the subject if the subject is likely to achieve a response.

111. A method of selecting a subject for treatment, the method comprising:
(a) assessing the level, amount or concentration of one or more analyte in a biological sample, wherein the one or more analyte is selected from ferritin, LDH, CXCL10, G-CSF, and IL-10, wherein:
the biological sample is from a subject that is a candidate for treatment with the cell therapy, said cell therapy comprising a dose of genetically engineered cells expressing a recombinant receptor; and
the biological sample is obtained from the subject prior to administering the cell therapy and/or said biological sample does not comprise the recombinant receptor and/or said engineered cells; and
(b) selecting a subject who is likely to respond to treatment based on the results of determining a likelihood that a subject will achieve a response to the cell therapy by comparing, individually, the level, amount or concentration of the analyte in the sample to a threshold level.

112. The method of embodiment 111, further comprising administering the cell therapy to the subject selected for treatment.

113. A method of treatment, the method comprising:
(a) selecting a subject who is likely to respond to treatment with a cell therapy based on the results of determining a likelihood that a subject will achieve a response to the cell therapy by comparing, individually, the level, amount or concentration of one or more analyte in a biological sample, wherein the one or more analyte is selected from ferritin, LDH, CXCL10, G-CSF, and IL-10, to a threshold level, wherein:
the biological sample is from a subject that is a candidate for treatment with the cell therapy, said cell therapy comprising a dose of genetically engineered cells expressing a recombinant receptor; and
the biological sample is obtained from the subject prior to administering the cell therapy and/or said biological sample does not comprise the recombinant receptor and/or said engineered cells; and
(b) administering the cell therapy to a subject selected for treatment.

114. The method of any of embodiments 109-113, wherein:
the subject is likely to achieve a response if the level, amount or concentration of one or more of the analyte is below a threshold level and the subject is not likely to achieve a response if the level, amount or concentration of one or more of the analyte is above a threshold level.

115. The method of any of embodiments 109-114, wherein the threshold level is within 25%, within 20%, within 15%, within 10% or within 5% and/or is within a standard deviation below the median or mean level, amount or concentration, or is or is about the median or mean level, amount or concentration, of the analyte in a biological sample obtained from a group of subjects prior to receiving a cell therapy, wherein each of the subjects of the group went on to achieve a response after administration of a recombinant-receptor-expressing therapeutic cell composition for treating the same disease or condition.

116. The method of any of embodiments 109-114, wherein the threshold level is within 25%, within 20%, within 15%, within 10% or within 5% and/or is within a standard deviation above the median or mean level, amount or concentration of the analyte in a biological sample obtained from a group of subjects prior to receiving a cell therapy, wherein each of the subjects of the group went on to exhibit stable disease (SD) and/or progressive disease (PD) after administration of a recombinant-receptor-expressing therapeutic cell composition for treating the same disease or condition.

117. The method of any of embodiments 109-116, wherein the response comprises objective response.

118. The method of embodiment 117, wherein the objective response comprises complete response (CR) or partial response (PR).

119. A method of assessing likelihood of a durable response to a cell therapy, the method comprising:
(a) assessing the level, amount or concentration of one or more analyte in a biological sample, wherein the one or more analyte is selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, wherein:
the biological sample is from a subject that is a candidate for treatment with the cell therapy, said cell therapy comprising a dose of genetically engineered cells expressing a recombinant receptor; and
the biological sample is obtained from the subject prior to administering the cell therapy and/or said biological sample does not comprise the recombinant receptor and/or said engineered cells; and
(b) comparing, individually, the level, amount or concentration of the analyte in the sample to a threshold level, thereby determining a likelihood that a subject will achieve a durable response to the cell therapy.

120. The method of embodiment 119, further comprising administering the cell therapy to the subject if the subject is likely to achieve a response.

121. A method of selecting a subject for treatment, the method comprising:
(a) assessing the level, amount or concentration of one or more analyte in a biological sample, wherein the one or more analyte is selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, wherein:
the biological sample is from a subject that is a candidate for treatment with the cell therapy, said cell therapy comprising a dose of genetically engineered cells expressing a recombinant receptor; and
the biological sample is obtained from the subject prior to administering the cell therapy and/or said biological sample does not comprise the recombinant receptor and/or said engineered cells; and
(b) selecting a subject who is likely to respond to treatment based on the results of determining a likelihood that a subject will achieve a durable response to the cell therapy by comparing, individually, the level, amount or concentration of the analyte in the sample to a threshold level.

122. The method of embodiment 121, further comprising administering the cell therapy to the subject selected for treatment.

123. A method of treatment, the method comprising:
(a) selecting a subject who is likely to respond to treatment with a cell therapy based on the results of determining a likelihood that a subject will achieve a durable response to the cell therapy by comparing, individually, the level, amount or concentration of one or more analyte in a biological sample to a threshold level, wherein the one or more analyte is selected from LDH, ferritin, CRP, D-dimer, SAA-1, IL-6, IL-10, IL-15, IL-16, TNF-α, IFN-γ, MIP-1α, CXCL-10, IL-8, MCP-1 and MIP-1β, wherein:
the biological sample is from a subject that is a candidate for treatment with the cell therapy, said cell therapy comprising a dose of genetically engineered cells expressing a recombinant receptor; and
the biological sample is obtained from the subject prior to administering the cell therapy and/or said biological sample does not comprise the recombinant receptor and/or said engineered cells; and
(b) administering the cell therapy to a subject selected for treatment.

124. The method of any of embodiments 120-123, wherein:
the subject is likely to achieve a durable response if the level, amount or concentration one or more of the analyte is below a threshold level and the subject is not likely to achieve a durable response if the level, amount or concentration one or more of the analyte is above a threshold level.

125. The method of any of embodiments 120-124, wherein the threshold level is within 25%, within 20%, within 15%, within 10% or within 5% and/or is within a standard deviation below the median or mean level, amount or concentration, or is or is about the median or mean level, amount or concentration, of the analyte in a biological sample obtained from a group of subjects prior to receiving a cell therapy, wherein each of the subjects of the group went on to achieve a durable response after administration of a recombinant-receptor-expressing therapeutic cell composition for treating the same disease or condition.

126. The method of any of embodiments 120-124, wherein the threshold level is within 25%, within 20%, within 15%, within 11% or within 5% and/or is within a standard deviation above the median or mean level, amount or concentration of the analyte in a biological sample obtained from a group of subjects prior to receiving a cell therapy, wherein each of the subjects of the group did not achieve a durable response after administration of a recombinant-receptor-expressing therapeutic cell composition for treating the same disease or condition.

127. The method of any of embodiments 120-126, wherein the durable response comprises a complete response (CR) or partial response (PR) that is durable for at or greater than 3 months, 4 months, 5 months, or 6 months.

128. The method of any of embodiments 120-127, wherein the durable response comprises a CR or PR that is durable for at least 3 months.

129. A method of assessing the risk of developing a toxicity after administration of a cell therapy, the method comprising:
(a) assessing the level, amount or concentration of one or more analyte in a biological sample from a subject or a volumetric measure of tumor burden in a subject, wherein the one or more analyte is selected from LDH, Ferritin, C-reactive protein (CRP), D-dimer (fibrin degradation product), IL-6, IL-8, IL-10, IL-15, IL-16 TNF-α, IFN-α2, MCP-1, MIP-1α and MIP-1β, wherein:
the subject is a candidate for treatment with the cell therapy, said cell therapy optionally comprising a dose or composition of genetically engineered cells expressing a recombinant receptor; and
the biological sample is obtained from the subject prior to administering the cell therapy and/or said biological sample does not comprise the recombinant receptor and/or said engineered cells; and
(b) comparing, individually, the level, amount or concentration of the analyte in the sample or the volumetric measure of tumor burden to a threshold level, thereby determining a risk of developing a toxicity after administration of the cell therapy.

130. A method of identifying a subject, the method comprising:
(a) assessing the level, amount or concentration of one or more analyte in a biological sample from a subject or a volumetric measure of tumor burden in a subject, wherein the one or more analyte is selected from LDH, Ferritin, C-reactive protein (CRP), D-dimer (fibrin degradation product), IL-6, IL-8, IL-10, IL-15, IL-16 TNF-α, IFN-α2, MCP-1, MIP-1α and MIP-1β, wherein:
the subject is a candidate for treatment with the cell therapy, said cell therapy optionally comprising a dose or composition of genetically engineered cells expressing a recombinant receptor; and
the biological sample is obtained from the subject prior to administering the cell therapy and/or said biological sample does not comprise the recombinant receptor and/or said engineered cells; and
(b) identifying a subject who has a risk of developing a toxicity after administration of a cell therapy based by comparing, individually, the level, amount or concentration of the analyte in the sample or the volumetric measure of tumor burden to a threshold level.

131. A method of treatment, comprising:
(a) assessing the level, amount or concentration of one or more analyte in a biological sample from a subject or a volumetric measure of tumor burden in the subject, wherein the one or more analyte is selected from LDH, Ferritin, C-reactive protein (CRP), D-dimer (fibrin degradation product), IL-6, IL-8, IL-10, IL-15, IL-16 TNF-α, IFN-α2, MCP-1, MIP-1α and MIP-1β, wherein:
the subject is a candidate for treatment with the cell therapy, said cell therapy optionally comprising a dose or composition of genetically engineered cells expressing a recombinant receptor; and
the biological sample is obtained from the subject prior to administering the cell therapy and/or said biological sample does not comprise the recombinant receptor and/or said engineered cells; and; and
(b) comparing, individually, the level, amount or concentration of the analyte in the sample or the volumetric measure of tumor burden to a threshold level, thereby determining a risk of developing a toxicity after administration of the cell therapy; and
(c) following or based on the results of the assessment, administering to the subject the cell therapy, and, optionally, an agent or other treatment capable of treating, preventing, delaying, reducing or attenuating the development or risk of development of a toxicity.

132. The method of any of embodiments 129-131, wherein the biological sample is a blood or plasma sample.

133. The method of any of embodiments 129-132, wherein the volumetric measure of tumor burden is a sum of product dimensions (SPD) or is a volumetric measurement based on CT and/or MRI imaging or other imaging of body.

134. The method of embodiment 133, wherein the volumetric measure of tumor burden is carried out prior to treatment, prior to apheresis, or prior to cell product manufacturing.

135. The method of any of embodiments 129-134, further comprising monitoring the subject for symptoms of toxicity if the subject is administered a cell therapy and is identified as having a risk of developing a toxicity.

136. The method of any of embodiments 129-135, wherein:
the subject has a risk of developing a toxicity if the level, amount or concentration one or more of the analyte or the volumetric measure of tumor burden is above a threshold level and the subject has a low risk of developing a toxicity if the level, amount or concentration one or more of the analyte or the volumetric measure of tumor burden is below a threshold level.

137. The method of any of embodiments 129-136, wherein the threshold level is within 25%, within 20%, within 15%, within 10% or within 5% and/or is within a standard deviation above the median or mean level, amount or concentration, or is or is about the median or mean level, amount or concentration, of the analyte or the volumetric measure of tumor burden in a biological sample obtained from a group of subjects prior to receiving a cell therapy, wherein each of the subjects of the group went on not to develop any toxicity after receiving a recombinant-receptor-expressing therapeutic cell composition for treating the same disease or condition.

138. The method of any of embodiments 129-137, wherein the threshold level is within 25%, within 20%, within 15%, within 10% or within 5% and/or is within a standard deviation below the median or mean level, amount or concentration of the analyte or the volumetric measure of tumor burden in a biological sample obtained from a group of subjects prior to receiving a cell therapy, wherein each of the subjects of the group went on to develop a toxicity after receiving a recombinant-receptor-expressing therapeutic cell composition for treating the same disease or condition.

139. The method of any of embodiments 129-138, wherein the toxicity is neurotoxicity or CRS.

140. The method of any of embodiments 129-139, wherein the toxicity is grade 1 or higher neurotoxicity or CRS.

141. The method of any of embodiments 129-140, wherein:
the toxicity is severe neurotoxicity or is grade 2 or higher neurotoxicit, a grade 3 or higher neurotoxicity, at least prolonged grade 3 neurotoxicity or is at or above grade 4 or grade 5 neurotoxixity; or
the toxicity is severe CRS or comprises grade 2 or higher or grade 3 or higher CRS.

142. The method of any of embodiments 129-141, wherein the toxicity is neurotoxicity and the volumetric measure of tumor burden is SPD and the one or more analyte is selected from LDH, IL-10, IL-15, IL-16, TNF-α and MIP-1β.

143. The method of any of embodiments 129-141, wherein the toxicity is neurotoxicity and one or more analytes is assessed and the analytes are selected from LDH, Ferritin, CRP, IL-6, IL-8, IL-10, TNF-α, IFN-α2, MCP-1 and MIP-1β.

144. The method of any of embodiments 129-141, wherein the toxicity is neurotoxicity and one or more analytes is assessed and the analytes are selected from IL-8, IL-10 and CXCL10.

145. The method of embodiment 144, wherein the neurotoxicity is severe neurotoxicity or grade 3 or higher neurotoxicity.

146. The method of any of embodiments 129-141, wherein toxicity is CRS and the one or more analyte or volumetric measure of tumor burden is selected from LDH, SPD, CRP, d-dimer, IL-6, IL-15, TNF-α and MIP-1α.

147. The method of embodiment 146, wherein the CRS is severe CRS or grade 3 or higher CRS.

148. The method of any of embodiments 129-147, wherein if the subject is identified as having a risk of developing a toxicity, administering to the subject:
(a) (1) an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject; and/or
(b) a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or
(c) administering to the subject a cell therapy in an in-patient setting and/or with admission to the hospital for one or more days, optionally wherein the cell therapy is otherwise to be administered to subjects on an outpatient basis or without admission to the hospital for one or more days.

149. The method of embodiment 148, wherein the agent or other treatment is an anti-IL-6 antibody or an anti-IL6 receptor antibody.

150. The method of embodiment 149, wherein the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

151. The method of embodiment 148, wherein the agent or other treatment is or comprises a steroid, optionally dexamethasone.

152. The method of any of embodiments 129-142 and 148-151, wherein a volumetric measure is assessed and the volumetric measure is SPD and the threshold level is or is about 30 cm$^2$, is or is about 40 cm$^2$, is or is about 50 cm$^2$, is or is about 60 cm$^2$, or is or is about 70 cm$^2$.

153. The method of embodiment 152, wherein the volumetric measure is SPD and the threshold level is or is about 50 cm$^2$.

154. The method of any of embodiments 129-151, wherein the one or more analyte is or comprises LDH and the threshold level is or is about 300 units per liter, is or is about 400 units per liter, is or is about 500 units per liter or is or is about 600 units per liter.

155. The method of any of embodiments 154, wherein the analyte is LDH and the threshold level is or is about 500 units per liter.

156. The method of any of embodiments 109-155, wherein the recombinant receptor specifically binds to an antigen associated with the disease or condition or expressed in cells of the environment of a lesion associated with the disease or condition.

157. The method of any of embodiments 109-156, wherein the disease or condition is a cancer.

158. The method of any of embodiments 109-157, wherein the disease or condition is a myeloma, leukemia or lymphoma.

159. The method of any of embodiments 109-158, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

160. The method of any of embodiments 109-159, wherein the recombinant receptor is a chimeric antigen receptor (CAR).

161. The method of any of embodiments 109-160, wherein the engineered cells comprise T cells, optionally CD4$^+$ and/or CD8$^+$.

162. The method of embodiment 161, wherein the T cells are primary T cells obtained from a subject or are autologous to the subject.

163. A method of selecting a subject for treatment, the method comprising:
(a) contacting a biological sample with one or more reagent capable of detecting or that is specific for one or more analyte, wherein the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product),
wherein:
the biological sample is from a subject that is a candidate for treatment with a cell therapy, said cell therapy optionally comprising a dose or composition of genetically engineered cells expressing a recombinant receptor; and the biological sample is obtained from the subject prior to administering the cell therapy and/or said biological sample does not comprise the recombinant receptor and/or said engineered cells; and (b) selecting a subject in which either:

(i) the level, amount or concentration of the analyte in the sample is at or above a threshold level, thereby identifying a subject that is at risk for developing a toxicity to the cell therapy; or (ii) the level, amount or concentration of the analyte is below a threshold level.

164. The method of embodiment 163, wherein:

(a) a subject in (i) is selected for administering to the subject (1) an agent or other treatment capable of treating, preventing, delaying, reducing or attenuating the development or risk of development of a toxicity and (2) the cell therapy, wherein administration of the agent is to be administered (i) prior to, (ii) within one, two, or three days of, (iii) concurrently with and/or (iv) at first fever following, the initiation of administration of the cell therapy to the subject; and/or (b) a subject in (i) is selected for administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (c) a subject in (i) is selected for administering to the subject a cell therapy in an in-patient setting and/or with admission to the hospital for one or more days, optionally wherein the cell therapy is otherwise to be administered to subjects on an outpatient basis or without admission to the hospital for one or more days.

165. The method of embodiment 163 or embodiment 164, wherein a subject in (i) is selected, and the method further comprises:

(a) administering to the subject (1) an agent or other treatment capable of treating, preventing, delaying, reducing or attenuating the development or risk of development of a toxicity and (2) the cell therapy, wherein administration of the agent is carried out (i) prior to, (ii) within one, two, or three days of, (iii) concurrently with and/or (iv) at first fever following, the initiation of administration of the cell therapy to the subject; and/or (b) administering to the subject a cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (c) administering to the subject a cell therapy or a dose of genetically engineered cells of a cell therapy that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or (d) administering to the subject a cell therapy in an in-patient setting and/or with admission to the hospital for one or more days, optionally wherein the cell therapy is otherwise to be administered to subjects on an outpatient basis or without admission to the hospital for one or more days.

166. The method of embodiment 163 or embodiment 164, wherein:

(a) a subject in (ii) is selected for administering to the subject a cell therapy, optionally at a non-reduced dose, optionally on an outpatient basis or without admission to the hospital for one or more days;

(b) a subject in (ii) is selected for administering to the subject a cell therapy, wherein the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or (c) a subject in (ii) is selected for administering a cell therapy on an outpatient setting and/or without admission of the subject to the hospital overnight or for one or more consecutive days and/or is without admission of the subject to the hospital for one or more days.

167. The method of embodiment 163, 164 or 166, wherein a subject in (ii) is selected, and the method further comprises administering to the subject the cell therapy, optionally at a non-reduced dose, optionally on an outpatient basis or without admission to the hospital for one or more days.

168. The method of any of embodiments 163, 164, 166 and 167, wherein a subject in (ii) is selected, and the method further comprises administering to the subject the cell therapy, wherein:

the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

169. A method of treatment, comprising:

(a) assaying a biological sample for the level, amount or concentration of one or more analyte, wherein the biological sample is from a subject that is a candidate for treatment, optionally with a cell therapy, said cell therapy optionally comprising a dose or composition of genetically engineered cells expressing a recombinant receptor for treating a disease or condition, wherein the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product); and (b) following or based on the results of the assay, administering to the subject the cell therapy, and, optionally, an agent or other treatment capable of treating, preventing, delaying, reducing or attenuating the development or risk of development of a toxicity.

170. A method of treatment of a subject having or suspected of having a disease or condition, the method comprising:

(1) administering to the subject a cell therapy comprising a dose or composition of genetically engineered expressing a recombinant receptor for treating or that specifically recognizes the disease or condition, and, optionally, (2) further administering to the subject an agent or other treatment capable of treating, preventing, delaying, reducing or attenuating the development or risk of development of a toxicity, wherein:

the administration is carried out following, or is carried out in a manner based on the results of, assessment of one or more pre-treatment parameters, wherein:

(a) the one or more pre-treatment parameters comprise a parameter associated or correlated with, or that is a surrogate for, burden of the disease or condition in the subject, which parameters optionally comprise one or more analytes and/or one or more volumetric or other body measurement, (b) the assessment of the one or more pre-treatment parameters comprises assessment of an amount or level of, in a biological sample that is or is from a sample obtained from the subject, a level, amount or concentration of one or more analyte, the biological sample is obtained from the subject prior to administering the cell therapy, wherein the sample is obtained from the subject prior to the administration of the cell therapy and, optionally, prior to apheresis or prior to manufacture of cells for administration, and/or the one or more analyte is associated with disease burden and/or the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product); and/or (c) the assessment of the one or more pre-treatment parameters optionally comprises assessment of a volumetric measurement of the disease or condition in the subject, which optionally is a measurement obtained by imaging, optionally a sum of product dimensions (SPD) result, or other volumetric measurement(s), optionally based on CT and/or MRI imaging or other imaging of the body, carried out prior to treatment and optionally prior to apheresis or manufacturing of cells.

171. The method of embodiment 170, wherein said assessment of one or more pre-treatment parameters comprises the assaying of one or more analytes, which comprises detection which optionally comprises contacting a reagent capable of directly or indirectly detecting the analyte(s) with the biological sample and determining the level, amount or concentration of the analyte(s) in the biological sample.

172. The method of embodiment 170 or embodiment 171, wherein the assessment of one or more pre-treatment parameters comprises (A) assessment of, in a biological sample that is or is from a sample obtained from the subject prior to treatment and/or prior to apheresis or cell processing, a level, amount or concentration of one or more analytes, optionally associated with disease burden, and (B) assessment of a volumetric measure of disease burden, wherein the measure of disease burden optionally is a sum of product dimensions (SPD) result, or other volumetric measurement(s), optionally based on CT and/or MM imaging or other imaging of the body and/or is carried out prior to treatment, prior to apheresis, or prior to cell product manufacturing.

173. The method of any of embodiments 169-172, wherein, if the level, amount or concentration and/or measure, or combination thereof, resulting from or obtained via the pre-treatment assessment, is at or above a threshold level:

the administering comprises the further administering to the subject the agent or other treatment capable of treating, preventing, delaying, reducing or attenuating the development or risk of development of a toxicity, optionally wherein said further administering is carried out (i) prior to, (ii) within one, two, or three days of, or within four five or six days of, (iii) concurrently with and/or (iv) at first fever following, the initiation of administration of the cell therapy to the subject; and/or the cell therapy administered to the subject is administered (A) at a reduced dose as compared to if the level, amount or concentration and/or measure, or combination thereof is below the threshold level, or (B) at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy, or (C) at a dose reduced compared to the maximum tolerated dose or the approved dose or maximum approved dose, for use in subjects having the disease or condition or for treatment of the disease or condition; and/or the administering to the subject of the cell therapy is carried out or is specified to be carried out in an in-patient setting and/or with admission to the hospital for one or more days, optionally wherein the cell therapy is otherwise, if the level, amount, concentration, measure or combination is below the threshold or is not assessed, to be administered to subjects on an outpatient basis or without admission to the hospital for one or more days or overnight.

174. The method of any of embodiments 169-173, wherein, if the level, amount or concentration and/or measure, or combination thereof, resulting from or obtained via the pre-treatment assessment, is below a threshold level:

the administration of the cell therapy does not comprise administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be, or may be, administered to the subject on an outpatient setting and/or without admission of the subject to the hospital overnight or for one or more consecutive days and/or is without admission of the subject to the hospital for one or more days; and/or the cell therapy administered to the subject is administered (A) at a dose, optionally an amount of T cells or engineered T cells or T cells of a specified phenotype, that is higher than that that would be administered if the level, amount or concentration and/or measure, or combination thereof were at or above the threshold level, or (B) at a dose, optionally an amount of T cells or engineered T cells or T cells of a specified phenotype, that is or is about the maximum tolerated dose or the maximum dose, approved for use to treat subjects having the disease or condition.

175. A method of prophylactic treatment, comprising administering, to a subject, an agent or other treatment capable of treating, preventing, delaying, reducing or attenuating the development or risk of development of a toxicity, wherein:

the subject is a candidate for treatment optionally with a cell therapy, said cell therapy optionally comprising a dose or composition of genetically engineered cells expressing a recombinant receptor for treating a disease or condition; and the subject has been identified as at risk for developing a toxicity following or based on an assessment of one or more pre-treatment parameters, wherein:

(a) the one or more pre-treatment parameters comprise a parameter associated or correlated with, or that is a surrogate for, burden of the disease or condition in the subject, which parameters optionally comprise one or more analytes and/or one or more volumetric or other body measurement, or (b) the assessment of the one or more pre-treatment parameters comprises assessment of an amount or level of, in a biological sample that is or is from a sample obtained from the subject, a level, amount or concentration of one or more analytes in a biological sample obtained from or from a sample from a subject, for the level, amount or concentration of one or more analyte, said biological sample obtained from the subject prior to administering the cell therapy and/or said biological sample not comprising the recombinant receptor and/or said engineered cells, wherein:

(i) the one or more pre-treatment parameters comprise a parameter associated or correlated with, or that is a surrogate for, burden of the disease or condition in the subject, which parameters optionally comprise one or more analytes and/or one or more volumetric or other body measurement, (ii) the assessment of the one or more pre-treatment parameters comprises assessment of an amount or level of, in a biological sample that is or is from a sample obtained from the subject, a level, amount or concentration of one or more analyte, the biological sample is obtained from the subject prior to administering the cell therapy, wherein the sample is obtained from the subject prior to the administration of the cell therapy and, optionally, prior to apheresis or prior to manufacture of cells for administration, and/or the one or more analyte is associated with disease burden and/or the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product); and/or (ii) the assessment of the one or more pre-treatment parameters optionally comprises assessment of a volumetric measurement of the disease or condition in the subject, which optionally is a measurement obtained by imaging, optionally a sum of product dimensions (SPD) result, or other volumetric measurement(s), optionally based on CT and/or MRI imaging or other imaging of the body, carried out prior to treatment and optionally prior to apheresis or manufacturing of cells; or wherein the one or more analyte is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perform, and D-dimer (fibrin degradation product).

176. The method of embodiment 175, wherein said assay comprises detection which optionally comprises contacting a reagent capable of directly or indirectly detecting the analyte with the biological sample and determining the level, amount or concentration of the analyte in the biological sample, and/or wherein the agent is administered to the subject if the level, amount or concentration of the analyte in the sample is at or above a threshold level and optionally wherein the agent is administered (i) prior to, (ii) within one, two, or three days of, (iii) concurrently with and/or (iv) at first fever following, the initiation of administration of the cell therapy to the subject.

177. The method of embodiment 175 or embodiment 176, wherein the assessment of one or more pre-treatment parameters comprises (A) assessment of, in a biological sample that is or is from a sample obtained from the subject prior to treatment and/or prior to apheresis or cell processing, a level, amount or concentration of one or more analytes, optionally associated with disease burden, and (B) assessment of a volumetric measure of disease burden, wherein the measure of disease burden optionally is a sum of product dimensions (SPD) result, or other volumetric measurement(s), optionally based on CT and/or MM imaging or other imaging of the body and/or is carried out prior to treatment, prior to apheresis, or prior to cell product manufacturing.

178. The method of any of embodiments 169-177, wherein the threshold level is within 25%, within 20%, within 15%, within 10% or within 5% of the average level, amount or concentration or measure, and/or is within a standard deviation of the average level, amount or concentration or measure, of the analyte or parameter in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

179. The method of any of embodiments 169-178, wherein the reagent is a binding molecule that specifically binds to the analyte.

180. The method of any of embodiments 169-179, wherein the reagent is an antibody or an antigen-binding fragment thereof.

181. The method of any of embodiments 169-180, wherein the biological sample is or is obtained from a blood, plasma or serum sample.

182. The method of any of embodiments 169-181, wherein assaying or assessing cells the analyte comprises an immunoassay.

183. The method of any of embodiments 169-182, wherein the toxicity comprises neurotoxicity or cytokine release syndrome (CRS), optionally grade 1 or higher neurotoxicity or CRS.

184. The method of any of embodiments 169-183, wherein:

the toxicity comprises severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or the toxicity comprises severe CRS and/or comprises grade 2 or higher or grade 3 or higher CRS.

185. The method of any of embodiments 169-184, wherein the toxicity is associated with cerebral edema.

186. The method of any of embodiments 169-185, wherein the agent or other treatment is or comprises one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function.

187. The method of embodiment 186, wherein the antagonist or inhibitor is or comprises an agent selected from among an antibody or antigen-binding fragment, a small molecule, a protein or peptide and a nucleic acid.

188. The method of any of embodiments 169-187, wherein the agent or other treatment is an anti-IL-6 antibody or an anti-IL6 receptor antibody.

189. The method of any of embodiments 169-188, wherein the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

190. The method of any of embodiments 169-189, wherein the agent or other treatment is or comprises tocilizumab.

191. The method of any of embodiments 169-190, wherein the agent or other treatment is or comprises siltuximab.

192. The method of embodiment 186, wherein the steroid is or comprises dexamethasone.

193. The method of embodiment 186, wherein the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124).

194. The method of embodiment 193, wherein the agent capable of preventing, blocking or reducing microglial cell activation or function is a small molecule, peptide, protein, antibody or antigen-binding fragment thereof, an antibody mimetic, an aptamer, or a nucleic acid molecule.

195. The method of embodiment 193 or embodiment 194, wherein the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCS110, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

196. The method of any of embodiments 193-195, wherein the agent is an inhibitor of colony stimulating factor 1 receptor (CSF1R).

197. The method of any of embodiments 193-196, wherein the agent is selected from: PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof;
emactuzumab, IMC-CS4, FPA008, LY-3022855, AMG-820 and TG-3003 or is an antigen-binding fragment thereof; or a combination of any of the foregoing.

198. The method of any of embodiments 193-197, wherein the inhibitor is PLX-3397.

199. The method of any of embodiments 1-23 and 109-198, wherein the recombinant receptor specifically binds to an antigen associated with the disease or condition or expressed in cells of the environment of a lesion associated with the disease or condition.

200. The method of any of embodiments 1-23 and 109-199, wherein the disease or condition is a cancer.

201. The method of any of embodiments 1-23 and 109-200, wherein the disease or condition is a myeloma, leukemia or lymphoma.

202. The method of any of embodiments 1-23 and 109-201, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

203. The method of any of embodiments 1-23 and 109-202, wherein the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAM), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC 16, P SCA, NKG2D, NY-ESO-1, MART-1, gp 100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD13 8, G Protein Coupled Receptor 5D (GPCR5D), or a pathogen-specific antigen.

204. The method of any of embodiments 1-23 and 109-203, wherein the recombinant receptor is a T cell receptor or a functional non-T cell receptor.

205. The method of any of embodiments 1-23 and 109-204, wherein the recombinant receptor is a chimeric antigen receptor (CAR).

206. The method of embodiment 205, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

207. The method of any of embodiments 1-23 and 109-206, wherein the engineered cells comprise T cells, optionally $CD4^+$ and/or $CD8^+$.

208. The method of embodiment 207, wherein the T cells are primary T cells obtained from a subject.

209. The method of any of embodiments 1-23 and 109-208, wherein the cell therapy comprises the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive.

210. The method of any of embodiments 1-23 and 109-209, wherein the cell therapy comprises the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

211. The method of any of embodiments 109-210, wherein the dose that is not associated with risk of developing toxicity or severe toxicity is or comprises less than or less than about $5\times10^7$ total recombinant receptor-expressing cells, optionally CAR$^+$ cells, total T cells, or total peripheral blood mononuclear cells (PBMCs), such as less than or less than about $2.5\times10^7$, less than or less than about $1.0\times10^7$, less than or less than about $5.0\times10^6$, less than or less than about $1.0\times10^6$, less than or less than about $5.0\times10^5$, or less than or less than about $1\times10^5$ total recombinant receptor-expressing cells, optionally CAR$^+$ cells, total T cells, or total peripheral blood mononuclear cells (PBMCs).

212. The method of any of embodiments 109-211, wherein the dose that is not associated with risk of developing toxicity or severe toxicity is or comprises from or from about $1\times10^5$ to $5\times10^7$ total recombinant receptor-expressing cells, optionally CAR$^+$ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10^7$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally CAR$^+$ cells, total T cells, or total peripheral blood mononuclear cells (PBMCs).

213. The method of any of embodiments 109-212, wherein the engineered cells are autologous to the subject.

214. The method of any of embodiments 109-213, wherein the engineered cells are allogeneic to the subject.

215. The method of any of embodiments 109-214, wherein the reagent is detectably labeled, optionally fluorescently labeled.

216. The method of any of embodiments 163-215, wherein the one or more analyte is LDH, ferritin, CRP, IL-6, IL-8, IL-10, TNF-alpha, IFN-alpha2, MCP-1 and MCP-1beta.

217. The method of any of embodiments 163-215, wherein the one or more analyte is selected from LDH, ferritin, CRP, IL-6, IL-8, IL-10, TNF-α, MCP-1 and MIP-1beta, and the toxicity is neurotoxicity.

218. The method of any of embodiments 163-215, wherein the one or more analyte is selected from IL-8 and IL-10 and the toxicity is neurotoxicity, optionally severe neurotoxicity or grade 3 or higher neurotoxicity.

219. The method of any of embodiments 163-215, wherein the one or more analyte is selected from among LDH, Ferritin, C-reactive protein (CRP), D-dimer (fibrin degradation product), IL-6, IL-10, IL-15, IL-16 TNF-α, MIP-1α and MIP-10 and the toxicity is CRS or neurotoxicity.

220. The method of any of embodiments 109-219, wherein the one or more analyte is or comprises LDH.

221. An article of manufacture comprising one or more dose of a cell therapy, each dose comprising cells expressing a chimeric antigen receptor (CAR), and instructions for administering the cell therapy, wherein the instructions specify that:

the dose of cells is to be administered to a subject having or identified to have non-Hodgkin lymphoma (NHL), the NHL selected from diffuse large B cell lymphoma (DLBCL), primary mediastinal large B cell lymphoma (PMBCL), NOS (de novo or transformed from indolent lymphoma), or follicular lymphoma Grade 3B, wherein the subject is or has been identified as having an Eastern Cooperative Oncology Group Performance Status (ECOG) status of 0 or 1; and the instructions specify administration of a number of T cells or of cells of a specified phenotype, or specify administration of an amount or volume of one or more formulations corresponding to or containing said specified number of cells, wherein the specified number of cells comprises between at or about $5\times10^7$ CAR-expressing T cells and $1\times10^8$ CAR-expressing T cells, inclusive, between at or about $5\times10^7$ CAR-expressing T cells and at or about $1.5\times10^8$ CAR-expressing T cells, at or about $5\times10^7$ CAR-expressing T cells, at or about $1\times10^8$ CAR-expressing T cells, or at or about $1.5\times10^8$ CAR-expressing T cells, between at or about $2.5\times10^7$ CD8$^+$ CAR-expressing T cells and at or about $5\times10^7$ CD8$^+$ CAR-expressing T cells, inclusive, between at or about $2.5\times10^7$ CAR-expressing T cells and at or about $0.75\times10^8$ CD8$^+$ CAR-expressing T cells, or at or about $2.5\times10^7$ CD8$^+$ CAR-expressing T cells, at or about $5\times10^7$ CAR-expressing T cells, or at or about $0.75\times10^8$ CD8$^+$ CAR-expressing T cells, or of viable populations of any of the foregoing.

222. The article of manufacture of embodiment 221, wherein the instructions specify administering the cell therapy at a defined ratio of CD4$^+$ cells expressing the CAR to CD8$^+$ cells, or specify administering amounts of volumes of the formulation(s) corresponding to such defined ratio, or comprises a formulation having the cells at such ratio or comprises the cells at such ratio expressing the CAR and/or of CD4$^+$ cells to CD8$^+$ cells, which ratio optionally is approximately 1:1 or is between approximately 1:3 and approximately 3:1.

223. An article of manufacture comprising a cell therapy, or one of a plurality of compositions of a cell therapy, comprising a dose or composition of genetically engineered cells expressing a chimeric antigen receptor (CAR), and instructions for administering the cell therapy, wherein the instructions specify:

the dose of T cells is to be administered at a defined ratio of CD4$^+$ cells expressing the CAR to CD8$^+$ cells expressing the CAR and/or of CD4$^+$ cells to CD8$^+$ cells, which ratio is approximately or is 1:1; and the dose of cells is to be administered to a subject having or identified to have non-Hodgkin lymphoma (NHL), the NHL selected from diffuse large B cell lymphoma (DLBCL), primary mediastinal large B cell lymphoma (PMBCL), NOS (de novo or transformed from indolent lymphoma), or follicular lymphoma Grade 3B.

224. An article of manufacture comprising a cell therapy, or one of a plurality of compositions of a cell therapy, comprising a dose or composition of genetically engineered cells expressing a chimeric antigen receptor (CAR), and instructions for administering the cell therapy, wherein the instructions specify:

the dose of cells is to be administered to a subject having or identified to have non-Hodgkin lymphoma (NHL), optionally an NHL selected from aggressive NHL, diffuse large B cell lymphoma (DLBCL), NOS (de novo and transformed from indolent), primary mediastinal large B cell lymphoma (PMBCL), mantle cell lymphoma (MCL), and/or follicular lymphoma (FL), optionally follicular lymphoma Grade 3B (FL3B);

the dose of T cells to be administered comprises between at or about $5\times10^7$ CAR-expressing T cells and $1\times10^8$ CAR-expressing T cells, inclusive; and the dose of T cells is to be administered at a defined ratio of CD4+ cells expressing the CAR to CD8+ cells expressing the CAR and/or of CD4+ cells to CD8+ cells, which ratio is approximately or is 1:1.

225. The article of manufacture of embodiment 222 or embodiment 223, wherein the instructions further specify the cell therapy is to be administered to a subject that is or has been identified as having an Eastern Cooperative Oncology Group Performance Status (ECOG) status of 0, 1 or 2 and/or that is or has been identified as having an ECOG status of 0 or 1.

226. The article of manufacture of any of embodiments 221-225, wherein:

the instructions specify that the administration is to a subject that has not received, immediately prior to the administration of the dose of cells or within or about 1 month of the dose of cells, an agent or treatment capable of treating, preventing, delaying, reducing or attenuating the development or risk of development of a toxicity; and/or the instructions do not specify that the administration to a subject who, prior to initiation of administration of the dose of cells, has been administered an anti-IL-6 or anti-IL-6R antibody, optionally tocilizumab or siltuximab, and/or has not been administered a steroid, optionally dexamethasone; and/or the instructions do not specify administering an agent that is an anti-IL-6 or anti-IL-6R antibody, optionally tocilizumab or siltuximab, a steroid, optionally dexamethasone, and/or an agent for the purpose of prophylactically reducing the risk of or treating CRS or neurotoxicity, and/or do not specify administering said agent within a period of time following administration of the dose of cells, which period of time is optionally at or about 1, 2, 3, 4, 5 days, or is optionally at or about 6, 7, 8, 9, 10, 11 days, or is optionally 1, 2, 3 or 4 weeks, and/or do not specify administering said agent prior to the subject exhibiting, or unless the subject exhibits, a sign or symptom of neurotoxicity and/or CRS, optionally other than a fever, optionally wherein the fever is not a sustained fever or the fever is or has been reduced or reduced by more than 1° C. after treatment with an antipyretic; and/or the instructions specify administration of the cell dose on an outpatient basis and/or without admitting the subject to a hospital and/or without an overnight stay at a hospital and/or without requiring admission to or an overnight stay at a hospital, optionally unless a risk factor specific to the subject or cells of the subject is otherwise identified in the instructions or information in the article or optionally unless or until the subject exhibits a sustained fever or a fever that is or has not been reduced or not reduced by more than 1° C. after treatment with an antipyretic.

227. The article of manufacture of embodiment 226, wherein the instructions further specify that if, after administration of the cell dose on an outpatient basis without requiring admission to or an overnight stay at a hospital, the subject exhibits a sustained fever or a fever that is or has not been reduced or not reduced by more than 1° C. after treatment with an antipyretic, the subject is to be admitted to the hospital or to an overnight stay at a hospital and/or is to be administered an agent or treatment for the treatment or prevention or reduction or attenuation of a neurotoxicity and/or a cytokine release syndrome or risk thereof.

228. The article of manufacture of embodiment 226 or embodiment 227, wherein the agent is or comprises an anti-IL-6 or anti-IL-6R antibody, optionally tocilizumab or siltuximab, and/or a steroid, optionally dexamethasone.

229. The article of manufacture of any of embodiments 221-228, wherein the instructions specify the subject has a DLBCL characterized as de novo or transformed from an indolent disease and/or does not have a DLBCL transformed from MZL and CLL (Richter's).

230. The article of manufacture of any of embodiments 221-229, wherein the instructions specify the subject does not have primary mediastinal large B cell lymphoma (PMBCL).

231. The article of manufacture of any of embodiments 221-230, wherein the instruction specify the administration of the cells is in a subject that is or has been identified as having a lymphoma associated with or involving central nervous system (CNS) involvement.

232. The article of manufacture of any of embodiments 221-231, wherein the instructions specify the administration of the cell therapy is for a subject that is or has been identified as having a double/triple hit lymphoma, is or has been identified as having a chemorefractory lymphoma, optionally a chemorefractory DLBCL; that has not achieved complete remission (CR) in response to a prior therapy; and/or has relapsed within 1 year or less than 1 year after receiving an autologous stem cell transplant (ASCT).

233. The article of manufacture of any of embodiments 221-232, wherein the instructions specify further administering to a subject an additional therapeutic agent or therapy, optionally other than a cell therapy, optionally other than a CAR+ T cell therapy.

234. The article of manufacture of embodiment 233, wherein the additional therapeutic agent or therapy is an agent for treating the NHL or malignancy and/or increases the persistence, activity and/or efficacy of the dose of cells.

235. The article of manufacture of embodiment 233 or embodiment 234, wherein the instructions specify administration of the additional therapeutic agent or therapy is in a subject that does not exhibit a response, optionally does not exhibit a CR or OR, to the cell therapy within 1 month, within 2 months or within 3 months after administration of the dose of cells.

236. The article of manufacture of any of embodiments 233-235, wherein the instructions specify the administration of the additional therapeutic agent or therapy is in a subject:

that is or has been identified to have stable or progressive disease (SD/PD) following treatment with a prior therapy, optionally a prior therapy with a chemotherapeutic agent;

that is or has been identified with an Eastern Cooperative Oncology Group Performance Status (ECOG) status of 2;

that is or has been identified as having a transformed follicular lymphoma (tFL); or that is or has been identified has having a DLBCL transformed from MZL and CLL.

237. The article of manufacture of any of embodiments 233-236, wherein the instructions specify the additional therapeutic agent or therapy is for administration prior to, with or at the same time and/or subsequent to initiation of administration of the dose of cells.

238. The article of manufacture of any of embodiments 221-237, wherein the CAR comprises an scFv specific for the antigen, a transmembrane domain, a cytoplasmic signaling domain derived from a costimulatory molecule, which optionally is a 4-1BB, and a cytoplasmic signaling domain derived from a primary signaling ITAM-containing molecule, which optionally is a CD3zeta.

239. The article of manufacture of any of embodiments 221-238, wherein the antigen is a B cell antigen, which optionally is CD19.

240. The article of manufacture of any of embodiments 221-239, further comprising instructions for use with, after or in connection with a lymphodepleting therapy, the lymphdepleting therapy optionally comprising fludarabine and/or cyclophosphamide.

241. The article of manufacture of embodiment 240, wherein the lymphodepleting therapy comprises administration of cyclophosphamide at about 200-400 mg/m$^2$, optionally at or about 300 mg/m$^2$, inclusive, and/or fludarabine at about 20-40 mg/m$^2$, optionally 30 mg/m$^2$, daily for 2-4 days, optionally for 3 days.

242. The article of manufacture of embodiment 240 or embodiment 241, wherein the lymphodepleting therapy comprises administration of cyclophosphamide at or about 300 mg/m$^2$ and fludarabine at about 30 mg/m$^2$ daily for 3 days.

243. The article of manufacture of any of embodiments 221-242, wherein the instructions further specify the administration of the cell therapy is to be or may be administered to the subject on an outpatient setting and/or without admission of the subject to the hospital overnight or for one or more consecutive days and/or is without admission of the subject to the hospital for one or more days, optionally unless or until the subject exhibits a sustained fever or a fever that is or has not been reduced or not reduced by more than 1° C. after treatment with an antipyretic.

244. The article of manufacture of embodiment 243, wherein if the subject exhibits a sustained fever or a fever that is or has not been reduced or not reduced by more than 1° C. after treatment with an antipyretic, the instructions further specify the subject is to be admitted to the hospital or to an overnight stay at a hospital and/or is to be administered an agent or treatment for the treatment or prevention or reduction or attenuation of a neurotoxicity and/or a cytokine release syndrome or risk thereof.

245. The article of manufacture of any of embodiments 221-244, wherein the instructions further specify the cell therapy is for parenteral administration, optionally intravenous administration.

246. The article of manufacture of any of embodiments 221-245, wherein the cell therapy comprises primary T cells obtained from a subject.

247. The article of manufacture of any of embodiments 221-246, wherein the T cells are autologous to the subject.

248. The article of manufacture of any of embodiments 221-246, wherein the T cells are allogeneic to the subject.

249. The article of manufacture of any of embodiments 221-248, wherein the article of manufacture comprises one of a plurality of compositions of the cell therapy comprising a first composition of genetically engineered cells comprising CD4$^+$ T cells or CD8$^+$ T cells, wherein the instructions specify the first composition is for use in with a second composition comprising the other of the CD4$^+$ T cells or the CD8$^+$ T cells, optionally wherein the cells of the first composition and cells of the same composition are from the same subject.

250. The article of manufacture of embodiment 249, wherein the instructions specify the first composition and second composition are to be administered at a defined ratio of CD4$^+$ cells expressing the recombinant receptor to CD8$^+$ cells expressing the recombinant receptor and/or of CD4$^+$ cells to CD8$^+$ cells, which ratio optionally is approximately 1:1 or is between approximately 1:3 and approximately 3:1.

251. The article of manufacture of embodiment 250, wherein the defined ratio is or is approximately 1:1.

252. The article of manufacture of any of embodiments 221-251, wherein the composition further comprises a cryoprotectant and/or the article further includes instructions for thawing the composition prior to administration to the subject.

253. The article of manufacture of any of embodiments 249-252, wherein the instructions specify administering the composition comprising the CD4$^+$ T cells and the composition comprising the CD8$^+$ T cells 0 to 12 hours apart, 0 to 6 hours apart or 0 to 2 hours apart.

254. The article of manufacture of any of embodiments 249-253, wherein the instructions specify administering the composition comprising the CD4$^+$ T cells and the composition comprising the CD8$^+$ T cells no more than 2 hours, no more than 1 hour, no more than 30 minutes, no more than 15 minutes, no more than 10 minutes or no more than 5 minutes apart.

255. The article of manufacture of any of embodiments 249-254, wherein the instructions specify administering the composition comprising the CD4$^+$ T cells prior to administering the composition comprising the CD8$^+$ cells.

256. The article of manufacture of any of embodiments 249-254, wherein the instructions specify administering the composition comprising the CD8$^+$ T cells prior to administering the composition comprising the CD4$^+$ cells.

257. An article of manufacture comprising one or more reagent capable of detecting one or more analytes, and instructions for using the reagent to assay a biological sample from a subject that is a candidate for treatment, optionally with a cell therapy, said cell therapy optionally comprising a dose or composition of genetically engineered cells expressing a recombinant receptor, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin and D-dimer (fibrin degradation product).

258. The article of manufacture of embodiment 257, further comprising the cell therapy and/or further comprising instructions for use with, prior to and/or in connection with treatment with the cell therapy.

259. The article of manufacture of embodiment 257 or embodiment 258, further comprising one or more agents or treatments for treating, preventing, delaying, reducing or attenuating the development or risk of development of a toxicity and/or instructions for the administration of one or more agents or treatments for treating, preventing, delaying, reducing or attenuating the development or risk of development of a toxicity in the subject.

260. The article of manufacture of any of embodiments 257-259, wherein the instructions further specify, if the level, amount or concentration of the analyte in the sample is at or above a threshold level for the analyte:

administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

261. The article of manufacture of any of embodiments 257-259, wherein the instructions further specify, if the level, amount or concentration of the analyte is below a threshold level for the analyte, administering to the subject the cell therapy, optionally at a non-reduced dose, optionally on an outpatient basis or without admission to the hospital for one or more days.

262. The article of manufacture of any of embodiments 257-261, wherein the instructions further specify administering the cell therapy to the subject and wherein the instructions further specify, if the level, amount or concentration of the analyte, is below a threshold level:

the administration of the cell therapy does not comprise administering, prior to or concurrently with administering the cell therapy and/or prior to the development of a sign of symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

263. The article of manufacture of any of embodiments 257-262, wherein the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

264. An article of manufacture comprising:

a cell therapy, said cell therapy optionally comprising a dose or composition of genetically engineered cells expressing a recombinant receptor, and instructions for administering the cell therapy following or based on the results of an assessment, in a biological sample of the level, or amount or concentration of one or more analyte in a biological sample, said biological sample obtained from the subject prior to administering the cell therapy and/or said biological sample not comprising the recombinant receptor and/or said engineered cells, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product).

265. The article of manufacture of embodiment 264, wherein said assessment comprises detection which optionally comprises contacting a reagent capable of directly or indirectly detecting the analyte with the biological sample and determining the level, amount or concentration of the analyte in the biological sample.

266. The article of manufacture of embodiment 265, further comprising the reagent and/or further comprising instructions for use with, prior to and/or in connection with the reagent for detecting the analyte.

267. The article of manufacture of any of embodiments 264-266, further comprising one or more agents or treatments for treating, preventing, delaying, reducing or attenuating the development or a risk of development of a toxicity and/or instructions for the administration of one or more agents or treatments for treating, preventing, delaying, reducing or attenuating the development or risk of development of a toxicity in the subject.

268. The article of manufacture of any of embodiments 264-267, wherein the instructions for administering the cell therapy specify, if the level, amount or concentration of the analyte in the sample, is at or above a threshold level:

administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of administration of the therapeutic cell composition or the genetically engineered cells; and/or administering to the subject the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or administering to the subject the cell therapy in an in-patient setting and/or with admission to the hospital for one or more days, optionally wherein the cell therapy is otherwise to be administered to subjects on an outpatient basis or without admission to the hospital for one or more days.

269. The article of manufacture of any of embodiments 264-268, wherein the instructions for administering the cell therapy specify, if the level, amount or concentration of the analyte in the sample, is below a threshold level, administering to the subject the cell therapy, optionally at a non-reduced dose, optionally on an outpatient basis or without admission to the hospital for one or more days.

270. The article of manufacture of any of embodiments 264-269, wherein the instructions further specify administering the cell therapy to the subject and wherein the instructions further specify, if the level, amount or concentration of the analyte is below a threshold level:

not administering, prior to or concurrently with administering the cell therapy and/or prior to the development of a sign or symptom of a toxicity other than fever, an agent or treatment capable of treating, preventing, delaying, or attenuating the development of the toxicity; and/or the administration of the cell therapy is to be or may be administered to the subject on an outpatient setting and/or without admission of the subject to the hospital overnight or for one or more consecutive days and/or is without admission of the subject to the hospital for one or more days.

271. The article of manufacture of any of embodiments 264-270, wherein the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

272. An article of manufacture comprising an agent capable of treating, preventing, delaying, reducing or attenuating the development or risk of development of a toxicity, and instructions for administering the agent following or based on the results of an assessment in a biological sample of the level, amount or concentration of one or more analytes in a biological sample, wherein the one or more analytes is selected from LDH, ferritin, CRP, IL-6, IL-7, IL-8, IL-10, IL-15, IL-16, TNF-alpha, IFN-gamma, MCP-1, MIP-1beta, eotaxin, G-CSF, IL-1Ralpha, IL-1Rbeta, IP-10, perforin, and D-dimer (fibrin degradation product).

273. The article of manufacture of embodiment 272, wherein said assessment comprises detection which optionally comprises contacting a reagent capable of directly or indirectly detecting the analyte with the biological sample and determining the level, amount or concentration of the analyte in the biological sample.

274. The article of manufacture of embodiment 272 or embodiment 273, wherein the instructions specify that the agent is to be administered i) prior to, (ii) within one, two, or three days of, (iii) concurrently with and/or (iv) at first fever following, the initiation of administration of the cell therapy to the subject and/or further comprises instructions for use with, prior to and/or in connection with treatment with the cell therapy.

275. The article of manufacture of any of embodiments 272-274, wherein said biological sample is obtained from the subject prior to administering the agent or cell therapy.

276. The article of manufacture of any of embodiments 257-275, wherein the reagent is a binding molecule that specifically binds to the analyte.

277. The article of manufacture of any of embodiments 257-276, wherein the reagent is an antibody or an antigen-binding fragment thereof 278. The article of manufacture of any of embodiments 257-277, wherein the biological sample is or is obtained from a blood, plasma or serum sample.

279. The article of manufacture of any of embodiments 272-278, further comprising the reagent for detecting the analyte and/or further comprising instructions for use with, prior to and/or in connection with the reagent for detecting the analyte.

280. The article of manufacture of any of embodiments 272-279, further comprising the cell therapy and/or further comprising instructions for use with, prior to and/or in connection with treatment with the cell therapy.

281. The article of manufacture of any of embodiments 272-280, wherein the instructions for administering the agent specify, if the level, amount or concentration of the analyte in the sample, is at or above a threshold level administering to the subject the agent.

282. The article of manufacture of embodiment 281, wherein the instruction further specify administering a cell therapy to the subject, wherein administration of the agent is to be carried out (i) prior to, (ii) within one, two, or three days of, (iii) concurrently with and/or (iv) at first fever following, the initiation of administration of the cell therapy to the subject.

283. The article of manufacture of any of embodiments 272-282, wherein the instructions for administering the agent specify, if the level, amount or concentration is below the threshold level administering to the subject the cell therapy, optionally wherein the instructions specify the cell therapy is to be or may be administered to the subject on an outpatient setting and/or without admission of the subject to the hospital overnight or for one or more consecutive days and/or is without admission of the subject to the hospital for one or more days.

284. The article of manufacture of any of embodiments 272-283, wherein the threshold level is within 25%, within 20%, within 15%, within 10% or within 5% of the average level, amount or concentration, and/or is within a standard deviation of the average level, amount or concentration, of the analyte in a biological sample obtained from a group of subjects prior to receiving a recombinant receptor-expressing therapeutic cell composition, wherein each of the subjects of the group went on to develop a toxicity after receiving a recombinant-receptor-expressing therapeutic cell composition for treating the same disease or condition.

285. The article of manufacture of any of embodiments 257-284, wherein assaying or assessing cells for the analyte is by an immunoassay.

286. The article of manufacture of any of embodiments 257-285, wherein the toxicity comprises neurotoxicity or cytokine release syndrome (CRS), optionally grade 1 or higher neurotoxicity or CRS.

287. The article of manufacture of any of embodiments 257-286, wherein:
the toxicity comprises severe neurotoxicity and/or comprises a grade 2 or higher neurotoxicity, a grade 3 or higher neurotoxicity, at least prolonged grade 3 neurotoxicity or is at or above grade 4 or grade 5 neurotoxicity; and/or
the toxicity comprises severe CRS and/or comprises grade 2 or higher or grade 3 or higher CRS.

288. The article of manufacture of any of embodiments 257-287, wherein the toxicity is associated with cerebral edema.

289. The article of manufacture of any of embodiments 257-288, wherein the agent or other treatment is or comprises one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function.

290. The article of manufacture of embodiment 289, wherein the antagonist or inhibitor is or comprises an agent selected from among an antibody or antigen-binding fragment, a small molecule, a protein or peptide and a nucleic acid.

291. The article of manufacture of any of embodiments 257-290, wherein the agent or other treatment is an anti-IL-6 antibody or an anti-IL6 receptor antibody.

292. The article of manufacture of any of embodiments 257-291, wherein the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

293. The article of manufacture of any of embodiments 257-292, wherein the agent or other treatment is or comprises tocilizumab.

294. The article of manufacture of any of embodiments 257-293, wherein the agent or other treatment is or comprises siltuximab.

295. The article of manufacture of embodiment 289, wherein the steroid is or comprises dexamethasone.

296. The article of manufacture of embodiment 289, wherein the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124).

297. The article of manufacture of embodiment 296, wherein the agent capable of preventing, blocking or reducing microglial cell activation or function is a small molecule, peptide, protein, antibody or antigen-binding fragment thereof, an antibody mimetic, an aptamer, or a nucleic acid molecule.

298. The article of manufacture of embodiment 296 or embodiment 297 wherein the agent is selected from minocycline, naloxone, nimodipine, Riluzole, MOR103, lenalidomide, a cannabinoid, optionally WIN55 or 212-2, intravenous immunoglobulin (IVIg), ibudilast, anti-miR-155 locked nucleic acid (LNA), MCS110, PLX-3297, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003.

299. The article of manufacture of any of embodiments 296-298, wherein the agent is an inhibitor of colony stimulating factor 1 receptor (CSF1R).

300. The article of manufacture of any of embodiments 296-299, wherein the inhibitor is selected from:
PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof;
emactuzumab, IMC-CS4, FPA008, LY-3022855, AMG-820 and TG-3003 or is an antigen-binding fragment thereof; or a combination of any of the foregoing.

301. The article of manufacture of any of embodiments 296-300, wherein the inhibitor is PLX-3397.

302. The article of manufacture of any of embodiments 24-48 and 257-301, wherein the recombinant receptor specifically binds to an antigen associated with the disease or condition or expressed in cells of the environment of a lesion associated with the disease or condition.

303. The article of manufacture of any of embodiments 24-48 and 257-302, wherein the disease or condition is a cancer.

304. The article of manufacture of any of embodiments 24-48 and 257-303, wherein the disease or condition is a myeloma, leukemia or lymphoma.

305. The article of manufacture of any of embodiments 24-48 and 257-304, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

306. The article of manufacture of any of embodiments 302-305, wherein the antigen is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAM), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, P SCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, G Protein Coupled Receptor 5D (GPCR5D), or a pathogen-specific antigen.

307. The article of manufacture of any of embodiments 24-48 and 257-306, wherein the recombinant receptor is a T cell receptor or a functional non-T cell receptor.

308. The article of manufacture of any of embodiments 24-48 and 257-307, wherein the recombinant receptor is a chimeric antigen receptor (CAR).

309. The article of manufacture of embodiment 308, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

310. The article of manufacture of any of embodiments 24-48 and 257-309, wherein the engineered cells comprise T cells, optionally CD4$^+$ and/or CD8$^+$.

311. The article of manufacture of embodiment 310, wherein the T cells are primary T cells obtained from a subject.

312. The article of manufacture of any of embodiments 257-311, wherein the dose that is not associated with risk of developing toxicity or severe toxicity is or comprises less than or less than about $5\times10^7$ total recombinant receptor-expressing cells, optionally CAR$^+$ cells, total T cells, or total peripheral blood mononuclear cells (PBMCs), such as less than or less than about $2.5\times10^7$, less than or less than about $1.0\times10^7$, less than or less than about $5.0\times10^6$, less than or less than about $1.0\times10^6$, less than or less than about $5.0\times10^5$, or less than or less than about $1\times10^5$ total recombinant receptor-expressing cells, optionally CAR$^+$ cells, total T cells, or total peripheral blood mononuclear cells (PBMCs).

313. The article of manufacture of any of embodiments 257-312, wherein the dose that is not associated with risk of developing toxicity or severe toxicity is or comprises from or from about $1\times10^5$ to $5\times10^7$ total recombinant receptor-expressing cells, optionally CAR$^+$ cells, total T cells, or total peripheral blood mononuclear cells (PBMCs), such as $1\times10^5$ to $2.5\times10^7$, $1\times10^5$ to $1.0\times10^7$, $1\times10^5$ to $5.0\times10^6$, $1\times10^5$ to $1.0\times10^6$, $1.0\times10^5$ to $5.0\times10^5$, $5.0\times10^5$ to $5\times10^7$, $5\times10^5$ to $2.5\times10^7$, $5\times10^5$ to $1.0\times10^7$, $5\times10^5$ to $5.0\times10^6$, $5\times10^5$ to $1.0\times10^6$, $1.0\times10^6$ to $5\times10^7$, $1\times10^6$ to $2.5\times10^7$, $1\times10^6$ to $1.0\times10^7$, $1\times10^6$ to $5.0\times10^6$, $5.0\times10^6$ to $5\times10^7$, $5\times10^6$ to $2.5\times10^7$, $5\times10^6$ to $1.0\times10^7$, $1.0\times10^7$ to $5\times10^7$, $1\times10^7$ to $2.5\times10^7$ or $2.5\times10^7$ to $5\times10^7$ total recombinant receptor-expressing cells, optionally CAR$^+$ cells, total T cells, or total peripheral blood mononuclear cells (PBMCs).

314. The article of manufacture of any of embodiments 257-313, wherein the reagent is detectably labeled, optionally fluorescently labeled.

315. The article of manufacture of any of embodiments 257-314, wherein the one or more analyte is LDH, ferritin, CRP, IL-6, IL-8, IL-10, TNF-alpha, IFN-alpha2, MCP-1 and MCP-1beta.

316. The article of manufacture of any of embodiments 257-315, wherein the one or more analyte is or comprises LDH.

317. The article of manufacture of any of embodiments 221-316, wherein:

the CAR comprises an scFv specific for the antigen, a transmembrane domain, a cytoplasmic signaling domain derived from a costimulatory molecule, which optionally is or comprises a 4-1BB, and a cytoplasmic signaling domain derived from a primary signaling ITAM-containing molecule, which optionally is or comprises a CD3zeta signaling domain and optionally further comprises a spacer between the transmembrane domain and the scFv;

the CAR comprises, in order, an scFv specific for the antigen, a transmembrane domain, a cytoplasmic signaling domain derived from a costimulatory molecule, which optionally is or comprises a 4-1BB signaling domain, and a cytoplasmic signaling domain derived from a primary signaling ITAM-containing molecule, which optionally is a CD3zeta signaling domain; or the CAR comprises, in order, an scFv specific for the antigen, a spacer, a transmembrane domain, a cytoplasmic signaling domain derived from a costimulatory molecule, which optionally is a 4-1BB signaling domain, and a cytoplasmic signaling domain derived from a primary signaling ITAM-containing molecule, which optionally is or comprises a CD3zeta signaling domain; and wherein:

the spacer is optionally a polypeptide spacer that (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) has or consists of the sequence of SEQ ID NO: 1, a sequence encoded by SEQ ID NO: 2, SEQ ID NO: 30, SEQ ID NO: 31, SEQ ID NO: 32, SEQ ID NO: 33, SEQ ID NO: 34, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine; and/or the costimulatory domain comprises SEQ ID NO: 12 or a variant thereof having at least 85%, 86%, 87%, 88%, 89%, 90%, 91%, 92%, 93%, 94%, 95%, 96%, 97%, 98%, 99% or more sequence identity thereto; and/or the primary signaling domain comprises SEQ ID NO: 13 or 14 or 15 having at least 85%, 86%, 87%, 88%, 89%, 90%, 91%, 92%, 93%, 94%, 95%, 96%, 97%, 98%, 99% or more sequence identity thereto; and/or the scFv comprises a CDRL1 sequence of RASQDISKYLN (SEQ ID NO: 35), a CDRL2 sequence of SRLHSGV (SEQ ID NO: 36), and/or a CDRL3 sequence of GNTLPYTFG (SEQ ID NO: 37) and/or a CDRH1 sequence of DYGVS (SEQ ID NO: 38), a CDRH2 sequence of VIWGSETTYYNSALKS (SEQ ID NO: 39), and/or a CDRH3 sequence of YAMDYWG (SEQ ID NO: 40) or wherein the scFv comprises a variable heavy chain region of FMC63 and a variable light chain region of FMC63 and/or a CDRL1 sequence of FMC63, a CDRL2 sequence of FMC63, a CDRL3 sequence of FMC63, a CDRH1 sequence of FMC63, a CDRH2 sequence of FMC63, and a CDRH3 sequence of FMC63 or binds to the same epitope as or competes for binding with any of the foregoing, and optionally wherein the scFv comprises, in order, a $V_H$, a linker, optionally comprising SEQ ID NO: 24, and a $V_L$, and/or the scFv comprises a flexible linker and/or comprises the amino acid sequence set forth as SEQ ID NO: 24.

318. The article of manufacture of any of claims 221-317, wherein the instructions provide information about a threshold level, individually for each of the one or more analytes, that is indicative of whether a subject is likely to exhibit a response to treatment with the cell therapy.

319. The article of manufacture of any of claims 221-317, wherein the instructions provide information about a threshold level, individually for each of the one or more analytes, that is indicative of whether a subject is likely to exhibit a durable response following administration of the cell therapy.

320. The article of manufacture of any of claims 221-317, wherein the instructions provide information about a threshold level, individually for each of the one or more analytes, that is indicative of whether a subject is likely to exhibit a toxicity following administration of the cell therapy.

VIII. Definitions

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated.

In some embodiments, sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Unless defined otherwise, all terms of art, notations and other technical and scientific terms or terminology used herein are intended to have the same meaning as is commonly understood to which the claimed subject matter pertains. In some cases, terms with commonly understood meanings are defined herein for clarity and/or for ready reference, and the inclusion of such definitions herein should not necessarily be construed to represent a substantial difference over what is generally understood.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

IX. Examples

The following examples are included for illustrative purposes only and are not intended to limit the scope of the invention.

Example 1: Administration of Anti-CD19 CAR-Expressing Cells to Subjects with Relapsed and Refractory Non-Hodgkin's Lymphoma (NHL)

A. Subjects and Treatment

Therapeutic CAR+ T cell compositions containing autologous T cells expressing a chimeric antigen-receptor (CAR) specific for CD19 were administered to subjects with B cell malignancies.

Example 1.A.1

Results are described in this Example 1.A.1 for evaluation through a particular time-point (1.A.1) in an ongoing clinical study administering such therapy to patients with B cell Malignancies. Specifically, a cohort (full cohort) of (at this time-point, fifty-five (55)) adult human subjects with relapsed or refractory (R/R) aggressive non-Hodgkin's lymphoma (NHL), including diffuse large B-cell lymphoma (DLBCL), de novo or transformed from indolent lymphoma (NOS), high-grade B-cell lymphoma, with MYC and BCL2 and/or BCL6 rearrangements with DLBCL histology (double/triple hit), DLBCL transformed from chronic lymphocytic leukemia (CLL) or marginal zone lymphomas (MZL), primary mediastinal large b-cell lymphoma (PMBCL), and follicular lymphoma grade 3b (FL3B) after failure of 2 lines of therapy. Among the subjects treated were those having Eastern Cooperative Oncology Group (ECOG) scores of between 0 and 2 (median follow-up 3.2 months). The full cohort did not include subjects with mantle cell lymphoma (MCL). No subjects were excluded based on prior allogeneic stem cell transplantation (SCT), secondary central nervous system (CNS) involvement or an ECOG score of 2, and there was no minimum absolute lymphocyte count (ALC) for apheresis required.

Outcomes were separately assessed for a core subset of subjects within the full cohort (subjects within the full cohort excluding those subjects with a poor performance status (ECOG 2), DLBCL transformed from marginal zone lymphomas (MZL) and/or chronic lymphocytic leukemia (CLL, Richter's), and subjects with primary mediastinal large b-cell lymphoma (PMBCL), and follicular lymphoma grade 3b (FL3B) (core cohort)). The core cohort includes subjects with DLBCL, NOS and transformed follicular lymphoma (tFL) or high grade B-cell lymphoma (double/triple hit) or high-grade B-cell lymphoma, with MYC and BCL2 and/or BCL6 rearrangements with DLBCL histology (double/triple hit) and with Eastern Cooperative Oncology Group performance status (ECOG PS) of 0 or 1 At the timepoint in Example 1.A.1, outcomes for 44 subjects within this core cohort were assessed.

The demographics and baseline characteristics of the full and core cohort subjects at the timepoint in Example 1.A.1 are set forth in Table E1.

TABLE E1

Demographics and Baseline Characteristics

| Characteristic | FULL N = 55 | CORE N = 44 |
|---|---|---|
| Median Age, years (range) | 61 (29-82) | 61 (29-82) |
| ≥65 years, n (%) | 22 (40) | 17 (39) |
| Male/Female, n (%) | 38/17 (69/31) | 28/16 (64/36) |
| Months from diagnosis, median (range) | 17 (3-259) | 20 (8-259) |
| B-NHL Subtype, n (%) | | |
| DLBCL, NOS | 40 (73) | 35 (80) |
| Transformed DLBCL | 14 (26) | 8 (18) |
| Follicular, Grade 3B | 1 (2) | 1 (2) |
| Molecular Subtype, n (%) | | |
| Double/triple hit | 15 (27) | 12 (27) |
| Double expressor | 6 (11) | 4 (9) |
| Patient Characteristics, n (%) | | |
| Chemorefractory† | 42 (76) | 34 (77) |
| ECOG 0-1 | 48 (87) | 44 (100) |
| ECOG 2 | 7 (13) | 0 |
| Prior lines of therapy, median (range) | 3 (1-11) | 3 (1-8) |
| <5 lines of therapy | 44 (80) | 37 (84) |
| Any HSCT | 27 (49) | 22 (50) |
| Allogeneic | 4 (7) | 3 (7) |
| Autologous | 24 (44) | 20 (45) |

*SD or PD to last chemo-containing regimen or relapse <12 months after autologous SCT The therapeutic T cell compositions administered had been generated by a process including immunoaffinity-based (e.g., immunomagnetic selection) enrichment of CD4+ and CD8+ cells from leukapheresis samples from the individual subjects to be treated. Isolated CD4+ and CD8+ T cells were separately activated and independently transduced with a viral vector (e.g., lentiviral vector) encoding an anti-CD19 CAR, followed by separate expansion and cryopreservation of the engineered cell populations in a low-volume. The CAR contained an anti-CD19 scFv derived from a murine antibody (variable region derived from FMC63, $V_L$-linker-$V_H$ orientation), an immunoglobulin-derived spacer, a transmembrane domain derived from CD28, a costimulatory region derived from 4-1BB, and a CD3-zeta intracellular signaling domain. The viral vector further contained sequences encoding a truncated receptor, which served as a surrogate marker for CAR expression; separated from the CAR sequence by a T2A ribosome skip sequence.

The cryopreserved cell compositions were thawed prior to intravenous administration. The therapeutic T cell dose was administered as a defined cell composition by administering a formulated CD4+ CAR+ cell population and a formulated CD8+ CAR+ population administered at a target ratio of approximately 1:1. Subjects were administered a single or double dose of CAR-expressing T cells (each single dose via separate infusions of CD4+ CAR-expressing T cells and CD8+ CAR-expressing T cells, respectively) as follows: a single dose of dose level 1 (DL-1) containing 5×10$^7$ total CAR-expressing T cells (n=30 for subjects assessed in Example 1.A.1), a double dose of DL1 in which each dose was administered approximately fourteen (14) days apart (n=6 for subjects assessed in Example 1.A.1, administered on day 1 and day 14, including one subject that inadvertently received two DL2 doses via the two-dose schedule, due to a dosing error), or a single dose of dose level 2 (DL-2) containing $1\times10^8$ total CAR-expressing T cells (n=18 for subjects assessed in Example 1.A.1). The target dose level and the numbers of T cell subsets for the administered compositions are set forth in Table E2.

TABLE E2

Target dose levels and number of T cell subsets for cell compositions containing anti-CD19 CAR T cells

| Dose level | Helper T cell ($T_H$) Dose (CD4$^+$CAR$^+$) | Cytotoxic T Cell ($T_C$) Dose (CD8$^+$CAR$^+$) | Total T Cell Dose (CD3$^+$ CAR$^+$) |
|---|---|---|---|
| 1 | $25 \times 10^6$ | $25 \times 10^6$ | $50 \times 10^6$ |
| 2 | $50 \times 10^6$ | $50 \times 10^6$ | $100 \times 10^6$ |

Beginning at prior to CAR$^+$ T cell infusion, subjects received a lymphodepleting chemotherapy with fludarabine (flu, 30 mg/m$^2$) and cyclophosphamide (Cy, 300 mg/m$^2$) for three (3) days. The subjects received CAR-expressing T cells 2-7 days after lymphodepletion.

Example 1.A.2

For Example 1.A.2, at a subsequent point in time in the clinical study described in this Example 1 above, results were analyzed. At this analysis time point in Example 1.A.2, 74 patients had been treated (51 male, 23 female). The subjects included sixty-nine (69) subjects in the full DLBCL cohort (including 67 DLBCL NOS (45 de novo, 14 transformed from FL, 8 transformed from CLL or MZL), 1 FL grade 3B, and 1 PMBCL), and 5 subjects in the MCL cohort. Among subjects in the full (DLBCL) cohort, median age was 61 yrs (range 26, 82), median prior therapies was 3 (range 1, 12), 46 (67%) were chemorefractory, 32 (46%) had any prior transplant, and at least 16 (23%) patients had double/triple hit lymphoma. Forty-nine (49) subjects in the core cohort were assessed at this timepoint in 1.A.2.

B. Safety

The presence or absence of treatment-emergent adverse events (TEAE) following administration of the CAR-T cell therapy was assessed. Subjects also were assessed and monitored for neurotoxicity (neurological complications including symptoms of confusion, aphasia, encephalopathy, myoclonus seizures, convulsions, lethargy, and/or altered mental status), graded on a 1-5 scale, according to the National Cancer Institute—Common Toxicity Criteria (CT-CAE) scale, version 4.03 (NCI-CTCAE v4.03). Common Toxicity Criteria (CTCAE) scale, version 4.03 (NCI-CT-CAE v4.03). See Common Terminology for Adverse Events (CTCAE) Version 4, U. S. Department of Health and Human Services, Published: May 28, 2009 (v4.03: Jun. 14, 2010); and Guido Cavaletti & Paola Marmiroli *Nature Reviews Neurology* 6, 657-666 (December 2010). Cytokine release syndrome (CRS) also was determined and monitored, graded based on severity. See Lee et al, Blood. 2014; 124(2):188-95. In some cases, adverse events data were reported and collected starting at lymphodepletion to 90 days after CAR$^+$ T cell administration.

Example 1.B.1

Example 1.B.1 describes results based on the analysis time-point in Example 1.A.1.

FIG. 1 depicts the percentage of such subjects who were observed to have experienced laboratory abnormalities and TEAEs, which occurred in ≥20% of subjects. In addition to the TEAEs shown in FIG. 1, the following event terms were observed at Grade 3-4 in ≥5% of patients: white blood cell count decreased (13.6%), encephalopathy (12%), hypertension (7%). Degree of toxicities observed were consistent between dose levels 1 and 2.

In 84% of the full cohort subjects in Example 1.B.1 analysis, severe (grade 3 or higher) cytokine release syndrome (CRS) and severe neurotoxicity were not observed. Additionally, it was observed that 60% of the full cohort subjects did not develop any grade of CRS or neurotoxicity. No differences in incidence of CRS, neurotoxicity (NT), sCRS, or severe neurotoxicity (sNT) were observed between dose levels. Table E3 summarizes the incidence of cytokine release syndrome (CRS) and neurotoxicity adverse events in patients 28 days after receiving at least one dose of CAR-T cells. As shown in Table E3, no sCRS (Grade 3-4) was observed in any subjects that received a single dose of DL2 or double dose of DL1. Severe neurotoxicity or severe CRS (grade 3-4) was observed in 16% (9/55) of the full cohort of subjects and in 18% (8/44) of the subjects in the core subset. 11% (n=6) of subjects received tocilizumab, 24% (n=13) of subjects received dexamethasone. Among the ECOG2 subjects within the full cohort, observed rates of CRS and neurotoxicity were 71% and 29%, respectively.

TABLE E3

Assessment of Presence or Absence of CRS and Neurotoxicity Adverse Events for Example 1.B.1

| | FULL | | | | |
|---|---|---|---|---|---|
| | All Dose Levels | DL1S | DL2S | DL1D† | CORE |
| Safety, N | 55 | 30 | 19 | 6 | 44 |
| sCRS or sNT, n (%) | 9 (16) | 6 (20) | 2 (11) | 1 (17) | 8 (18) |
| CRS or NT, n (%) | 22 (40) | 12 (40) | 7 (37) | 3 (50) | 15 (34) |
| CRS | | | | | |
| Grade 1-2, n (%) | 18 (33) | 10 (33) | 5 (26) | 3 (50) | 12 (27) |
| Grade 3-4, n (%) | 1 (2) | 1 (3) | 0 | 0 | 1 (2) |
| Neurotoxicity | | | | | |
| Grade 1-2, n (%) | 3 (6) | 1 (3) | 2 (11) | 0 | 2 (5) |
| Grade 3-4, n (%) | 9 (16) | 6 (20) | 2 (11) | 1 (17) | 8 (18) |

†Includes one patient treated at DL2 2-dose schedule due to dosing error

Figure 2:
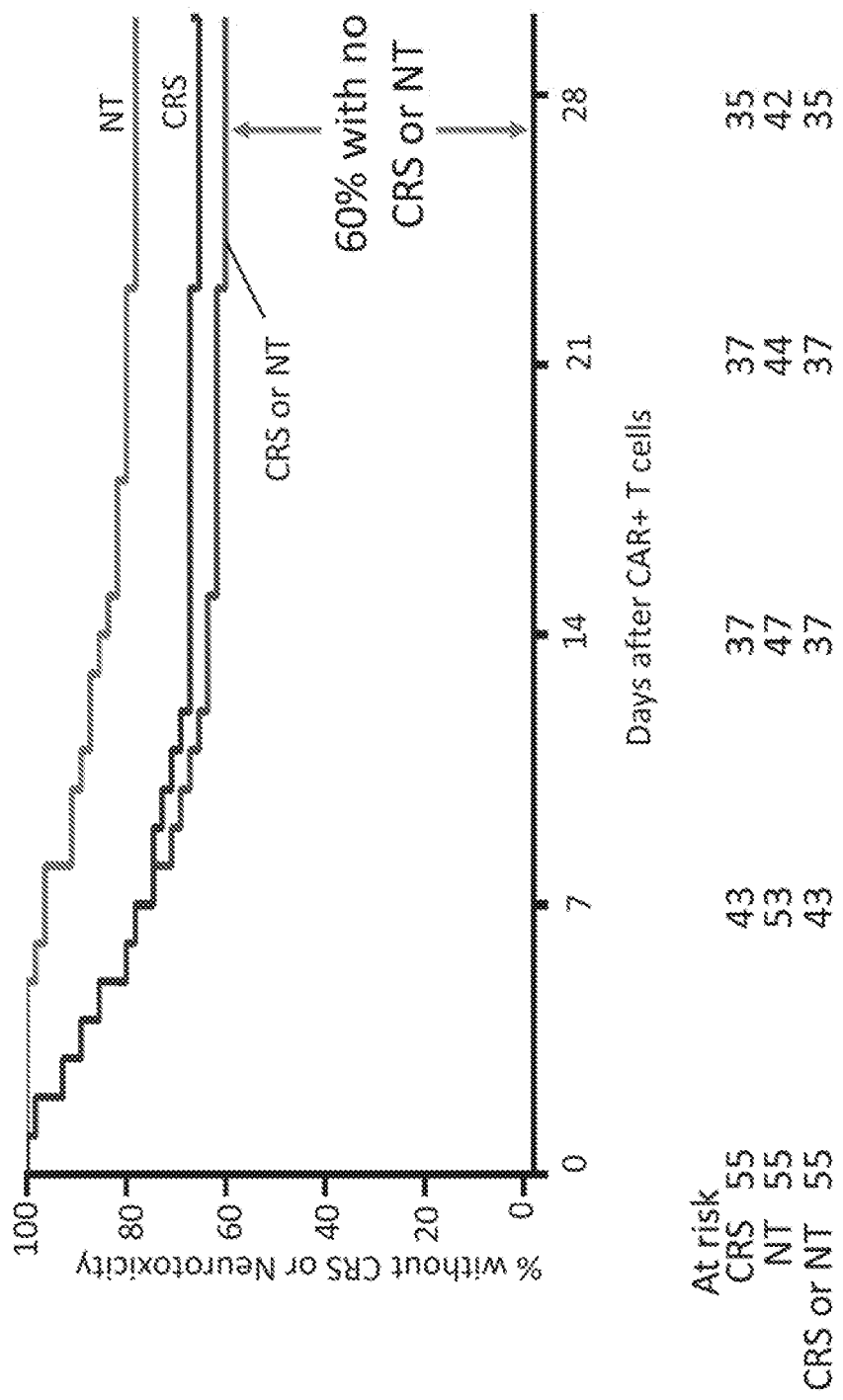
FIG. 2 is a Kaplan meier curve depicting observed time to onset of CRS and neurotoxicity.

FIG. 2 shows a Kaplan meier curve depicting observed time to onset of CRS and/or neurotoxicity for the analysis in 1.B.1. As shown, the observed median times to onset of CRS and to onset of neurotoxicity were 5 and 11 days, respectively, with only 11% of patients experiencing onset of CRS less than 72 hours after initiation of the administration of the cell therapy. The median time to resolution of CRS and neurotoxicity to Grade 1 or better was 5 and 7 days, respectively. The median time to complete resolution of CRS and neurotoxicity was 5 and 11 days, respectively. The results were consistent with a conclusion that there was a low rate of early onset of any CRS or neurotoxicity in the subjects.

Example 1.B.2

Example 1.B.2 describes assessment at the time-point in Example 1.B.2. Up to this time point, adverse event (AE) data were collected from lymphodepletion (LD) to 90 days post administration of CAR-expressing T cells. At the second time point, 69 subjects in the DLBCL cohort (full cohort) were evaluated for safety, 38 that had received DL1 single dose, 25 having received DL2 single dose, and 6 having recieved DL1 double dose schedule. The most common TEAEs other than CRS or NT included neutropenia (41%, 28/69), fatigue (30%, 21/69), thrombocytopenia (30%, 21/69), and anemia (26%, 18/69). One Grade 5 TEAE of diffuse alveolar damage was observed.

No acute infusional toxicity was observed, and the majority of subjects in the full cohort, 64% (44/69), were observed to have no CRS or NT, indicating that outpatient delivery of CAR-expressing T cells may be possible. Rates of CAR T cell-associated toxicities, including CRS and NT, did not differ between dose levels. Safety profile was observed to be similar across cohorts and dose levels. Among the 25 subjects in the full cohort (36%) who experienced any grade CRS or NT, 21 (30%) had CRS and 14 (20%) had NT. No subjects had Grade 3 CRS and only one (1%, 1/69) had Grade 4 CRS and required ICU care; the other 29% (20/69) had Grade 1-2 CRS. Of the 20% of subjects with NT, 6% (4/69) had Grade 1-2 and 14% (10/69) had Grade 3-4; 2 (3%) had seizure. No Grade 5 CRS or grade 5 NT was observed. No incidences of cerebral edema were observed. All CRS and NT events were resolved except one case of Grade 1 tremor, which was ongoing at the time of analysis. Median time to onset of first CRS and NT was 5 days (range 2, 12) and 10 days (range 5, 23), respectively. In the first 72 hours post infusion, no subjects were observed to have NT, and only 10% (7/69) were observed to have CRS (all Grade 1); NT was preceded by CRS in >70% of subjects. Overall, thirteen (13) subjects (19%) required intervention for CRS or NT with anti-cytokine therapy (tocilizumab alone 1 (1%), dexamethasone alone 6 (9%), or both 6 (9%)) and only one required any vasopressor support. Median doses of tocilizumab and dexamethasone were 1 and 6, respectively. Median CRS and NT duration was 5 days and 11 days, respectively. Analysis of the core cohort (n=49) also showed similar rates of CRS and NT.

In this assessment, low incidences and late onsets of CRS and/or NT were observed, at both dose levels, supported the feasibility of outpatient infusion, such as with hospital admission at the first sign of fever or fever lasting beyond a certain period of time. No Grade 5 CRS or grade 5 NT was observed, and all severe CRS and severe NT were resolved. Further, approximately 2 out of 3 patients had no CRS or NT, supporting that the cells can be administered on outpatient basis. At the time of assessment in 1.B.2, four subjects had been treated in the outpatient setting. Further, no meaningful differences in toxicity was observed in subjects receiving DL1 or DL2, indicating achievement of higher response rates without an increase risk of toxicity or safety concerns.

C. Response Outcomes following Treatment

Subjects were monitored for response, including by assessing tumor burden at 1, 3, 6, 7, 12, 18, and 24 months after administration ofthe CAR+ T cells.

Example 1.C.1

Example 1.C.1 describes results based on the analysis time-point in Example 1.A.1 and 1.B.1.

Response rates are listed in Table E4. High durable response rates were observed in the cohort of subjects, which included subjects heavily pretreated or, with poor prognosis and/or with relapsed or refractory disease. For subjects across all doses in the Core (n=44) cohort, the observed overall response rate (ORR) was 86% and the observed complete response (CR) rate was 59%. At three months for the core cohort, the overall response rate (ORR) was 66%; the three-month CR rate was 50% among the core cohort. In the core cohort, the 3 month ORR was 58% (11/19) at dose level 1 and 78% at dose level 2; the 3 month CR rate was 42% (8/19) for dose level 1 and 56% (5/9) for dose level 2, consistent with a suggested dose response effect on treatment outcome. Additionally, the results were consistent with a relationship between dose and durability of response.

TABLE E4

| | Response | | | | | | | |
|---|---|---|---|---|---|---|---|---|
| | FULL | | | | CORE | | | |
| | All Dose Levels | DL1S | DL2S | DL1D$^c$ | All Dose Levels | DL1S | DL2S | DL1D$^a$ |
| Best Overall Response, N$^a$ | 54 | 30 | 18 | 6 | 44 | 25 | 15 | 4 |
| ORR, % | 76 | 80 | 72 | 67 | 86 | 84 | 87 | 100 |
| (95% CI) | (62, 87) | (61, 92) | (47, 90) | (23, 96) | (73, 95) | (64, 95) | (60, 98) | (40, 100) |
| CR, % | 52 | 53 | 50 | 50 | 59 | 56 | 60 | 75 |
| (95% CI) | (38, 66) | (34, 72) | (26, 74) | (12, 88) | (43, 74) | (35, 76) | (32, 84) | (19, 99) |
| ≥3 mos f/u, n$^b$ | 41 | 24 | 11 | 6 | 32 | 19 | 9 | 4 |
| 3 mo ORR, % | 51 | 46 | 64 | 50 | 66 | 58 | 78 | 75 |
| (95% CI) | (35, 67) | (26, 67) | (31, 89) | (12, 88) | (47, 81) | (34, 80) | (40, 97) | (19, 99) |
| 3 mo CR, % | 39 | 33 | 46 | 50 | 50 | 42 | 56 | 75 |
| (95% CI) | (24, 56) | (16, 55) | (17, 77) | (12, 88) | (32, 68) | (20, 67) | (21, 86) | (19, 99) |

Figure 3A:
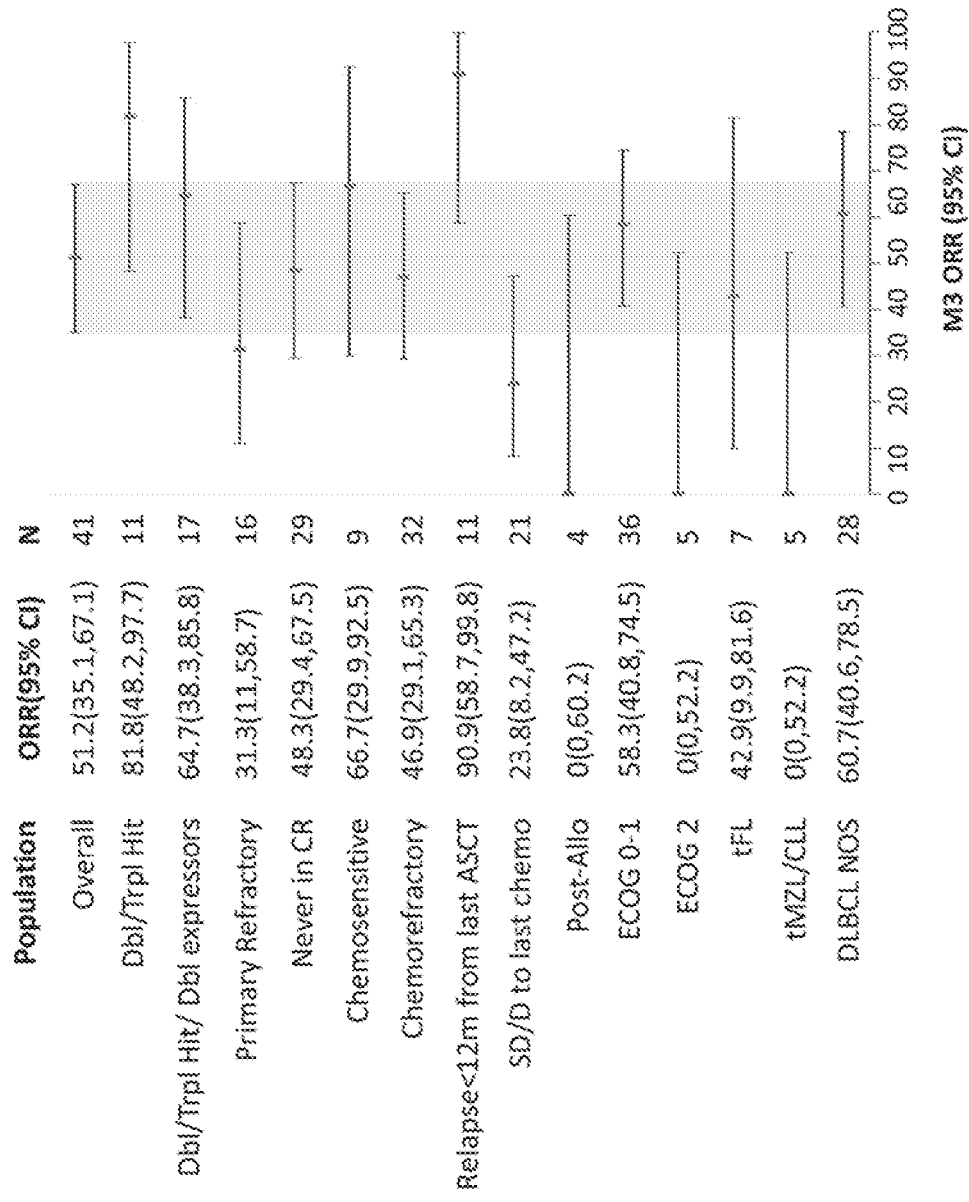
FIG. 3A and FIG. 3B depict 3 month objective response rates (ORR) among subgroups of treated subjects.
Figure 3B:
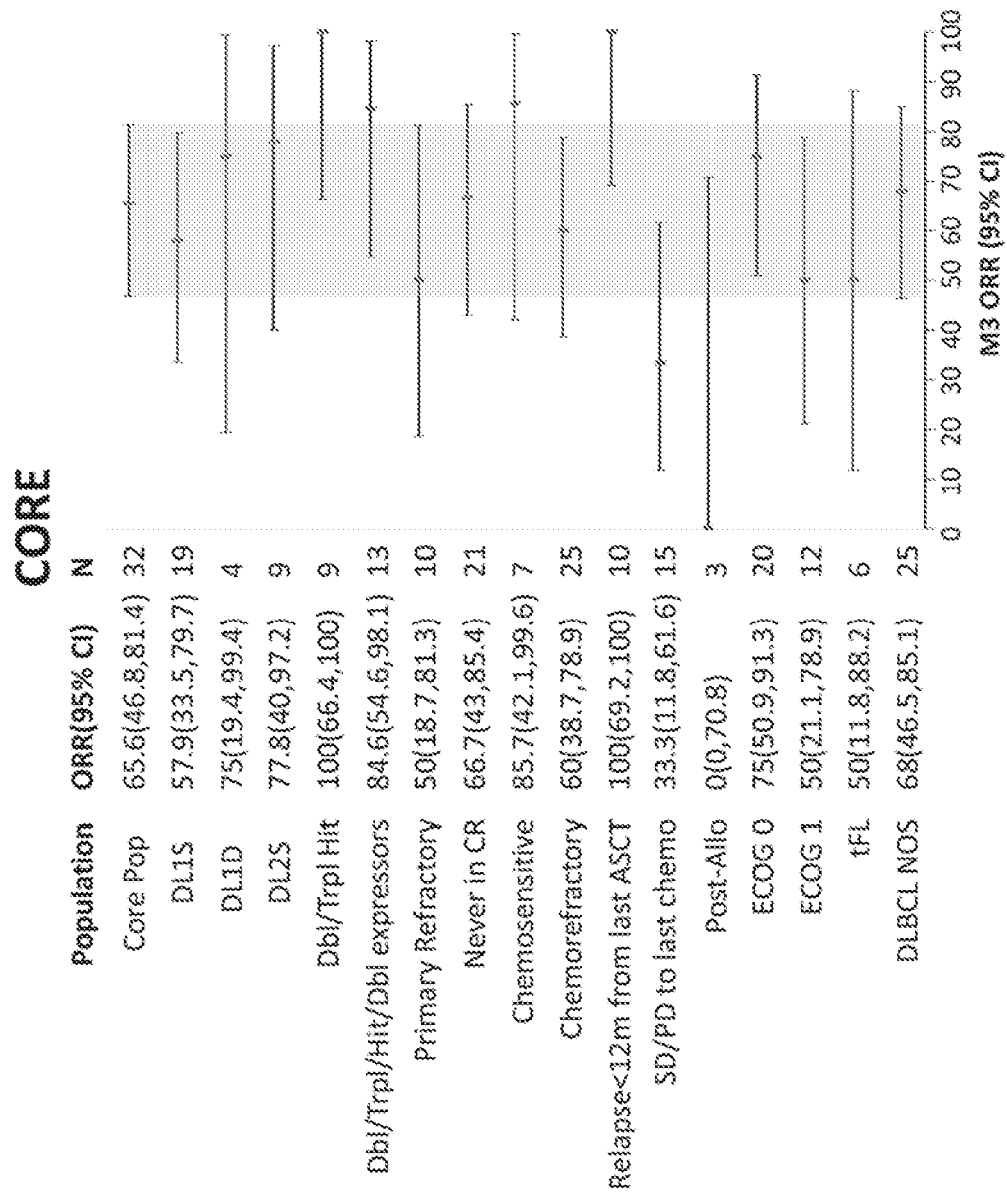

DL1S: DL1 1-dose schedule; DL2S: DL2 1-dose schedule; DL1D: DL1 2-dose schedule;
$^a$Included patients with event of PD, death, or 28 day restaging scans. Treated patients 28 days prior to data snapshot were not included.
$^b$The denominator is number of patients who received the CAR T-cell therapy ≥ 3 months ago, prior snapshot date with an efficacy assessment at Month 3 or prior assessment of PD or death.
$^c$Includes one patient treated at DL2 2-dose schedule due to dosing error Overall response rates among various subgroups of subjects in the full and core cohorts are shown in FIGS. 3A and 3B, respectively. In poor-risk DLBCL subgroups, response rates were generally high. An ORR of greater than 50% was observed at 3 months in patients with double/triple hit molecular subtype, that had primary refractory or chemorefractory DLBCL or that never before had achieved a CR. Complete resolution of CNS involvement by lymphoma was observed in 2 patients.

Among the subjects treated six months or greater prior to the particular time-point of the evaluation, of the ten (10) patients that had been in response at three months, 9 (90%) remained in response at six months. At the evaluation time-point, 97% of subjects in the core subset who had responded were alive and in follow-up, median follow-up time 3.2 months.

Figure 4B:
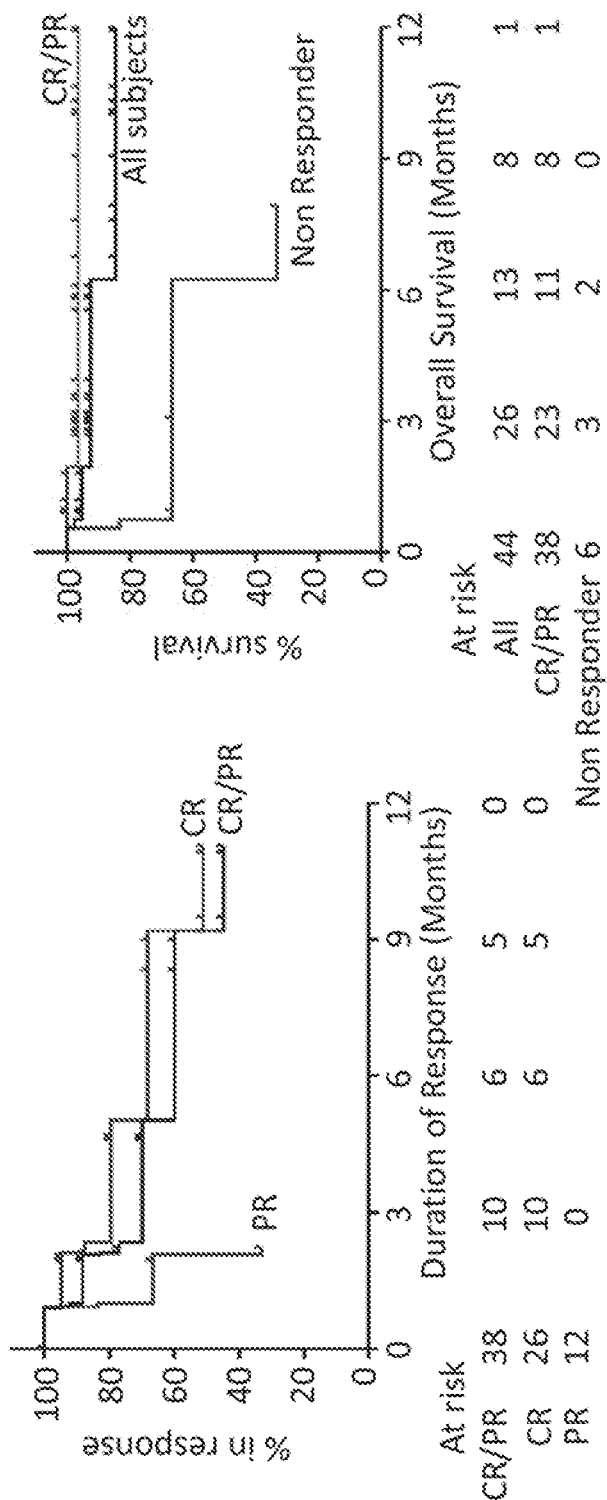

Results for the duration of response and overall survival (grouped by best overall response (non-responder, CR/PR, CR and/or PR)) are shown for full and core cohorts of subjects, in FIGS. 4A and 4B, respectively. As shown, prolonged survival was observed in responders, with increased durability of response in subjects with CRs. All patients in response at three months remained alive at the time of evaluation, although 5/6 subjects with poor performance status (ECOG 2) had expired.

Figure 8:
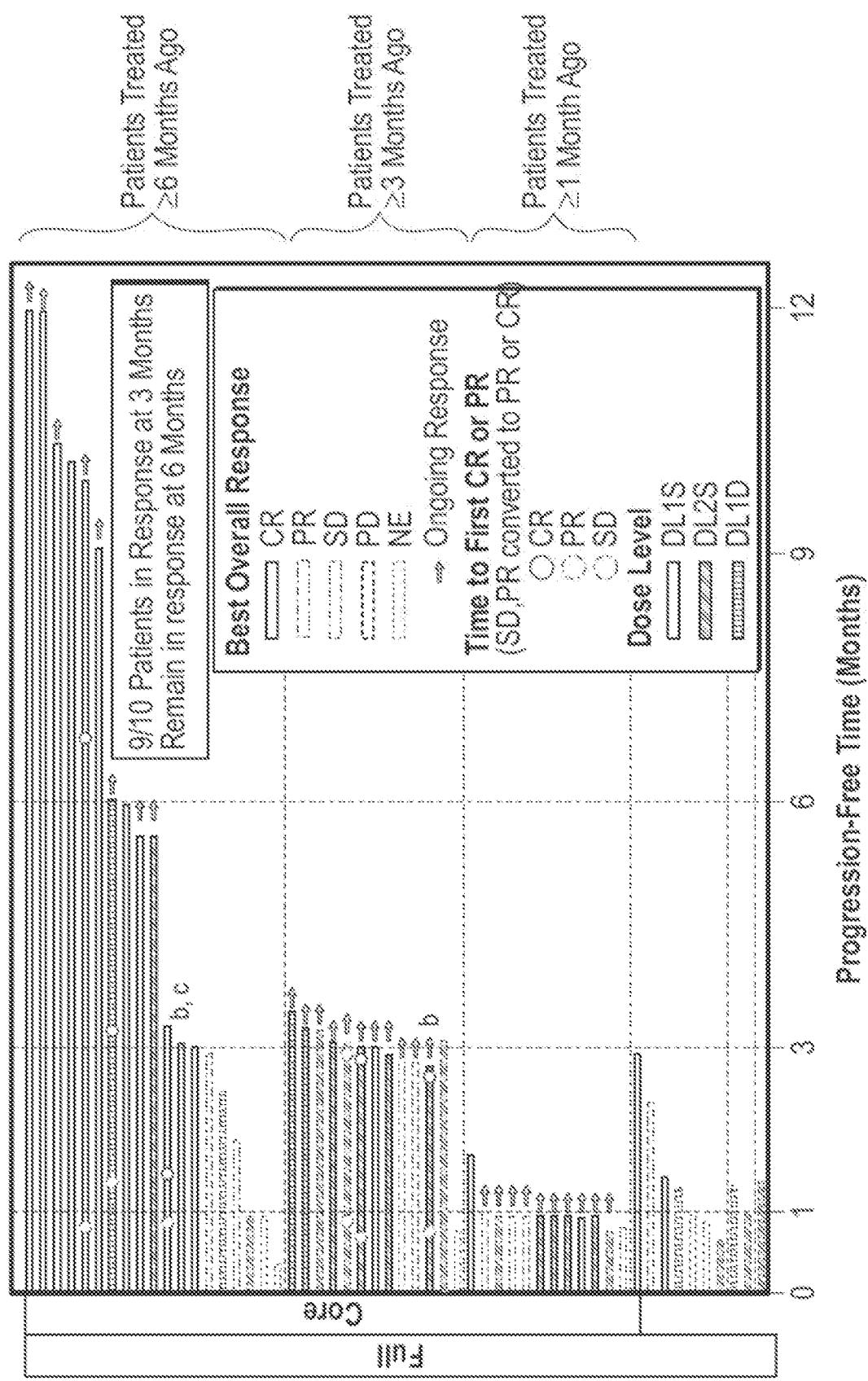
FIG. 8 shows a graph plotting progression-free time (months) and indicating best overall response and response durability, and individual clinical outcomes observed over time in individual subjects within a Full cohort and a Core cohort of NHL subjects treated with an anti-CD19 cell therapy containing CAR-T-expressing CD4$^+$ and CD8$^+$ T cells. $^a$: Patients achieved BOR at month 1 except where otherwise noted; $^b$: Complete resolution of CNS involvement by lymphoma observed in 2 patients; $^c$: One patient re-expanded after biopsy upon disease progression

FIG. 8 shows a graph plotting progression-free time (months) for individual subjects within the full and core cohorts. Each bar represents a single patient. Shading indicates best overall response (in each case, unless otherwise indicated, achieved at 1 month); texture indicates dose (solid=dose level 1, single dose; cross-hatched, dose-level 2, single dose; vertical hatched=dose level 1, two-dose). Horizontal arrows indicate an ongoing response. Certain individual subjects were initially assessed (e.g., at 1-month) as exhibiting stable disease (SD) or Partial Response (PR), and were later observed to have achieved a PR (e.g., conversion of SD to PR) or CR. In such cases, shading of the individual patient bar, as noted, indicates best overall response, and dots (same correspondence of shading to response achieved) along each individual subject bar, indicate when each SD, PR, and/or CR was observed to have occurred in the subject.

Figure 6A:
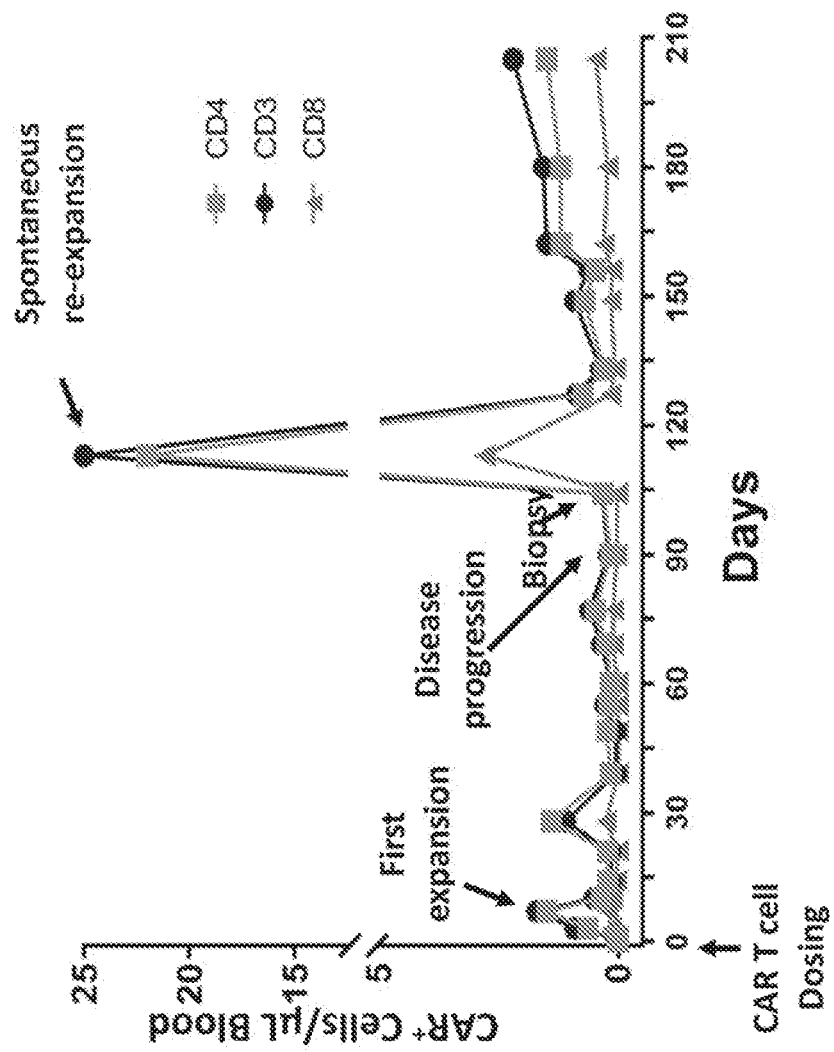
FIG. 6A shows the number of CD3$^+$/CAR$^+$, CD4$^+$/CAR$^+$, CD8$^+$/CAR$^+$ T cells in peripheral blood of a subject with chemorefractory transformed DLBCL measured at certain time points.
Figure 6C:
FIG. 6C is a post-treatment PET-CT image depicting resolution of the abnormality in FIG. 2B after treatment with anti-CD19 CAR$^+$ T cells.
Figure 6B:
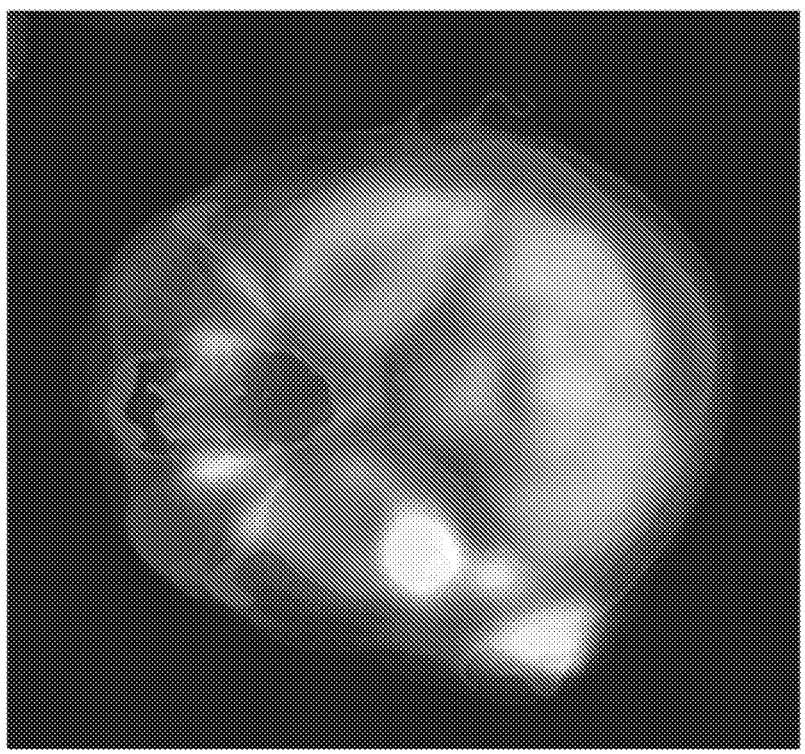
FIG. 6B depicts a pretreatment axial PET-CT image showing an intracranial abnormality in the right middle cranial foss and extensive abnormality in subcutaneous tissues in the right posterior auricular region.
Figure 6E:
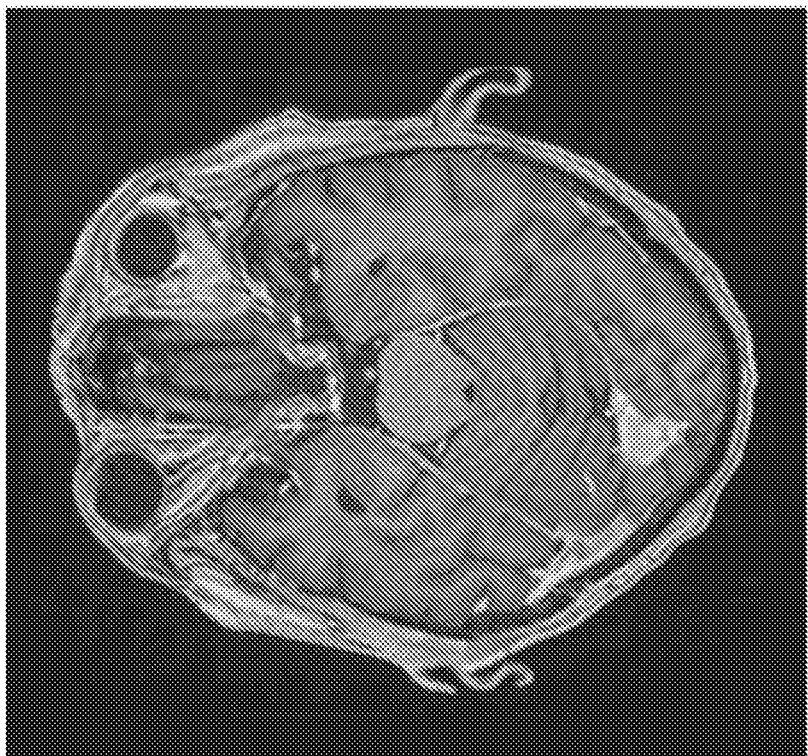
FIG. 6E is a post-treatment MRI image showing near-complete resolution of the enhancing mass.
Figure 6D:
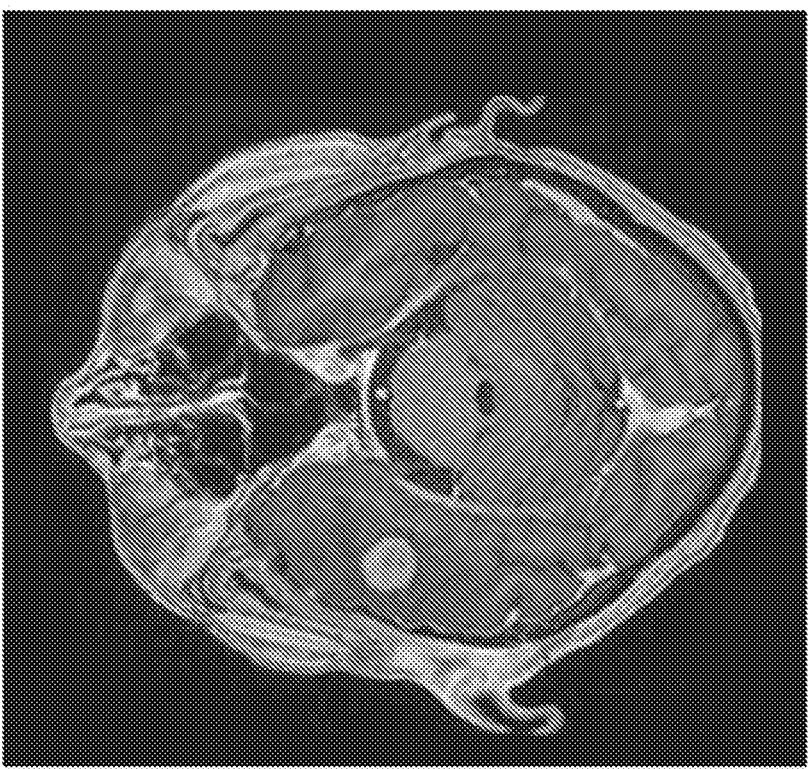
FIG. 6D is a pretreatment brain MRI (high-resolution T$_1$-weighted image with the use of contrast material; axial view) showing a homogeneously enhancing mass in the right middle cranial fossa.

Complete resolution of CNS involvement by lymphoma was observed in two patients. CAR$^+$ cells in one subject were observed to have expanded following biopsy after relapse. The subject who exhibited expansion following biopsy had chemorefractory transformed DLBCL (germinal center subtype with a BCL2 rearrangement and multiple copies of MYC and BCL6). The subject had been administered the CAR$^+$ T cells at DL-1 and the numbers of CD3$^+$/CAR$^+$, CD4$^+$/CAR$^+$, CD8$^+$/CAR$^+$ T cells in peripheral blood were measured at certain time points, are shown in FIG. 6A. The subject had previously been treated with, and was refractory to, five prior lines of therapy including dose-adjusted etoposide, doxorubicin, and cyclophosphamide with vincristine and prednisone plus rituximab (DA-EPOCH-R) and intermediate-intensity allogeneic stem-cell transplantation from an 8/8 HLA-matched unrelated donor. Following allogeneic stem cell transplantation and prior to receiving CAR$^+$ T cells, the subject showed 100% donor chimerism in all blood lineages, had ceased taking immunosuppressive therapy, and did not have graft versus host disease (GVHD). Prior to administration of CAR$^+$ T cells, the subject had a periauricular mass and temporal lobe lesion observed by positron-emission tomography and computed tomography (PET-CT) (FIG. 6B) and confirmed by magnetic resonance imaging (MRI) (FIG. 6D).

Figure 6G:
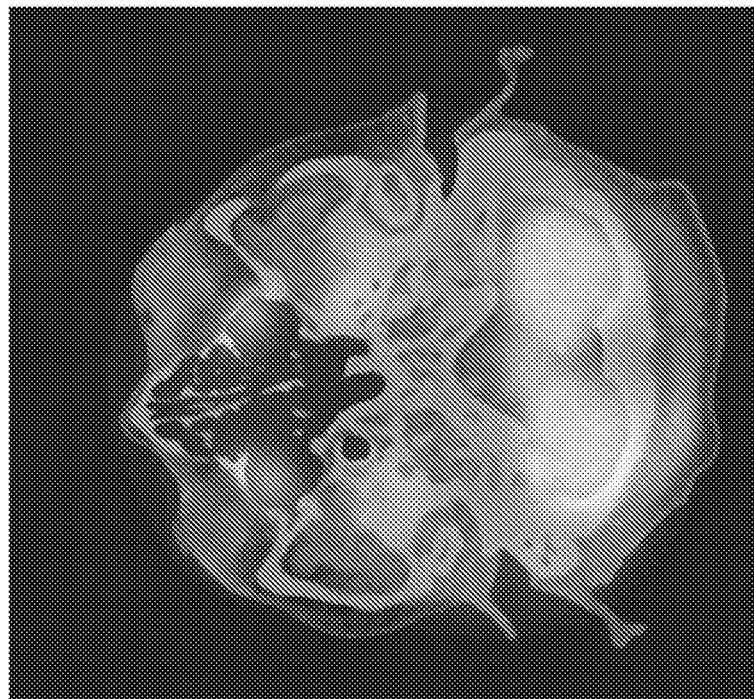
FIG. 6G is a PET-CT imaging showing resolution of the posterior auricular tumor after incisional biopsy and re-expansion of CAR$^+$ T cells.
Figure 6F:
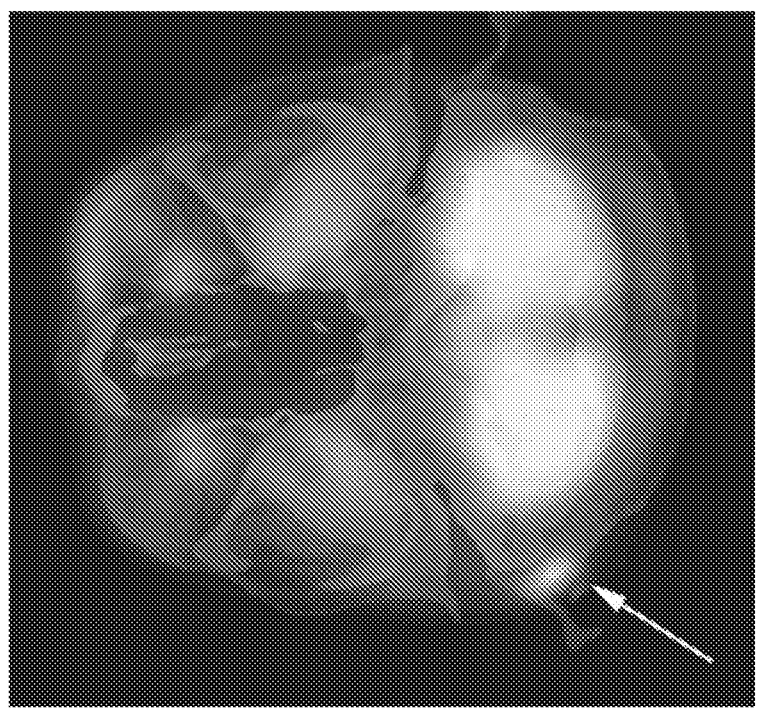
FIG. 6F is an axial PET-CT image at relapse showing right posteriour auricular tumor recurrence associated with intense uptake of $^{18}$F-flurodeoxyglucose (arrow).

After receiving anti-CD19 CAR-T cell treatment, the subject achieved CR 28 days post-infusion, as shown by PET-CT (FIG. 6C) and brain MRI (FIG. 6E), with no observed signs of neurotoxicity or CRS. Three months post-infusion of the CAR-T cells, relapse of the periauricular mass was noted in this subject (FIG. 6F), and an incisional biopsy was performed. As shown in FIG. 6A, following biopsy, the visible tumor receded with no further therapy. Pharmacokinetic analysis showed a marked re-expansion of the CAR$^+$ T cells in peripheral blood (to a level higher than initial expansion observed, with peak levels observed at about 113 days post-infusion) i, which coincided with tumor regression. The subject then went on to achieve a second CR, as confirmed by restaging PET-CT one month following the biopsy (FIG. 6G), and remained in CR at 6 months post CAR-T cell infusion. Further assessment of the subject showed that the CNS response was durable and the subject remained in CR at 12 months.

The results in the subject having received the biopsy followed by observed re-expansion of CAR$^+$ T cells are consistent with a conclusion that re-expansion and activation of CAR$^+$ T cells can be initiated in vivo following reduction or loss of functional or active CAR$^+$ T cells and/or relapse following anti-tumor response to CAR-T cell therapy. Further, following re-expansion in vivo late after initial CAR$^+$ T cell infusion, the CAR$^+$ T cells are able to re-exert anti-tumor activity. This result supports that CAR$^+$ T cell re-expansion and activation can be triggered in vivo and that methods of reactivating CAR$^+$ T cells, may further augment their efficacy.

The complete responses in the two DLBCL subjects with CNS involvement were observed without development of any grade of neurotoxicity. These results are consistent with the observation that CAR$^+$ T cells of embodiments provided herein are capable of readily accessing the CNS and exerting effector function to reduce or eliminate CNS tumors, without increasing or without substantially increasing risk of toxicity such as neurotoxicity. In other studies, among subjects having ALL treated with anti-CD19 CAR T cells, no clear correlation has been observed between incidence of neurotoxicity and the presence of CNS leukemia in the brain (which has been observed to respond to such CAR T cell therapy). Thus, whereas neurotoxicity can occur in some contexts following treatment with CAR-T therapies, such neurotoxicity may not necessarily be the result of target expression in the brain or activity of the CAR T cells in the CNS, and may not result from "on-target" toxicity by the CAR$^+$ T cells.

Example 1.C.2

Example 1.C.2 describes results based on the analysis time-point in Example 1.A.2 and 1.B.2.

Up to the time point in Example 1.C.2, 68 subjects in the full DLBCL cohort was evaluated for response. Overall or objective response (OR), 3-month, and 6-month objective response rates were 75% (51/68), 49% (27/55), and 40% (14/35), respectively. Complete response (CR) rate, 3-month CR rate, and 6-month CR rate were 56% (38/68), 40% (22/55), and 37% (13/35), respectively. A trend toward improved response rate at 3 months was observed in subjects treated at DL2 compared to DL1: 63% (12/19; 95% CI 38, 84) vs 40% (12/30; 95% CI 23, 59) for ORR with p=0.148, and 58% (11/19; 95% CI 34, 80) vs 27% (8/30; 95% CI: 12, 46) for CR with p=0.0385. Among 16 double/triple hit lymphoma subjects, ORR was 81%, and 3-month CR rate was 60%.

In the core cohort (n=49 for the time-point in Example 1.C.2), OR, 3-month, and 6-month OR rates were 84% (41/49), 65% (26/40), and 57% (13/23), respectively. CR rate, 3-month CR rate, and 6-month CR rate were 61% (30/49), 53% (21/40), and 52% (12/23), respectively. A similar trend in improved durable ORR and CR at 3 months at higher doses was observed. Specifically, for patients in the CORE cohort administered DL2, 3-month ORR was 80% (12/15; 95% CI 52, 96) and 3-month CR was 73% (11/15; 95% CI 45, 92), compared to 3-month ORR and CR rates of 52% (11/21; 95% CI 30, 74) and 33% (7/21; 95% CI 15, 57) in CORE cohort subjects administered DL1, with p=0.159 and p=0.0409 respectively. Among subjects in the CORE cohort having received DL2 and with 3-month follow-up (n=15), 3-month ORR was 80% and 3-month CR was 73%.

Median DOR in the full cohort and core cohorts at this time-point in 1.C.2 was 5.0 and 9.2 months, respectively; median duration of CR was 9.2 months in the full cohort. Median duration of CR had not been reached in the core cohort. Median overall survival (OS) was 13.7 months in the full cohort and had not been reached in the core cohort. 6-month OS was 75% in the full cohort, with median follow-up of 5.8 months. 6-month OS was 88% in the core cohort, with median follow up of 5.6 months.

D. Assessment of $CAR^+$ T cells in Blood

Figure 5A:
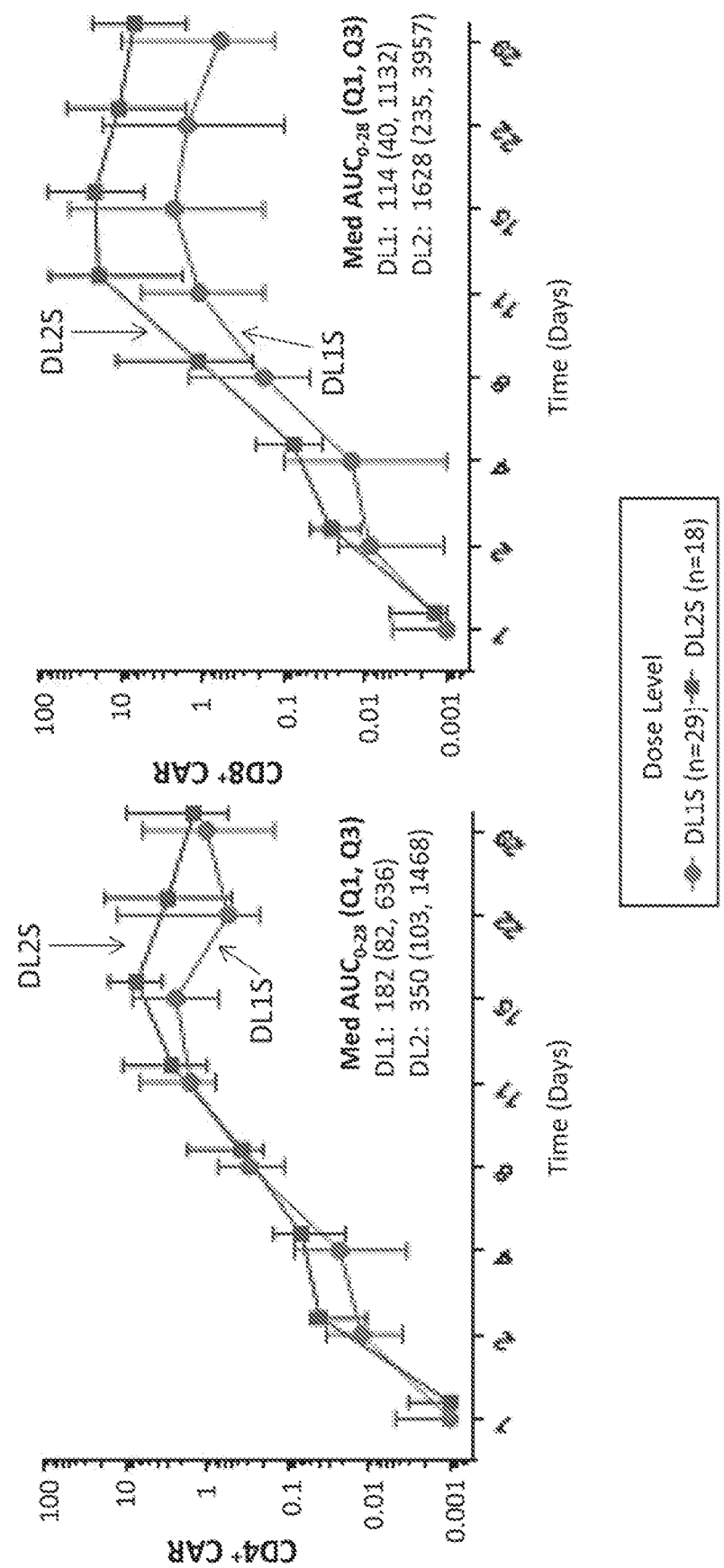
FIG. 5A shows the pharmacokinetics of the CAR$^+$ T cells in peripheral blood at various time points post-treatment at different dose levels.

Based on data from the time-point described in Example 1.A.1, 1.B.1 and 1.C.1, pharmacokinetic analysis was carried out to assess numbers of $CAR^+$ T cells in peripheral blood at various time points post-treatment. Results from the fifty-five (55) subjects assessed at the time-point in Example 1.A.1 in the DLBCL cohort and four (4) subjects (assessed at that same time-point) in the mantle cell lymphoma (MCL) cohort, as described in Example 2 below. were analyzed. Pharmacokinetics (PK) measurements were carried out using validated flow cytometry to detect a marker expressed in the CAR construct and quantitative PCR-based assays to detect the integration of the CAR construct. B cell aplasia was assessed by flow cytometry using anti-CD19 antibodies. As shown in FIG. 5A, $CD4^+$ and $CD8^+$ CAR-expressing cells, as measured by the number of cells/µL blood (median±quartiles) plotted on a log scale, were detected throughout the course of assessment at both administered dose levels. Subjects receiving DL2 relative to DL1 had higher median $C_{max}$ and median $AUC_{0-28}$ for $CD3^+/CAR^+$, $CD4^+/CAR^+$, and $CD8^+/CAR^+$ T cell subsets in peripheral blood ($AUC_{0-28}$: DL2 vs. DL1 was 1836 vs. 461, 350 vs. 182, and 1628 vs. 114, for $CD3^+$, $CD4^+$, and $CD8^+$, respectively; p<0.05 for $CD8^+$; $C_{max}$: DL2 vs. DL1 was 99.8 vs. 27.9, 15.1 vs. 5.2, and 73.1 vs. 5.5 cells/µL, respectively). Median time to maximum $CD3^+$ $CAR^+$ T cell expansion was 15 days (range 8-29) and did not differ between dose levels. $CD4^+$ and $CD8^+$ CAR-expressing T cells homed to the bone marrow at relatively similar levels.

An increased median area under the curve (AUC) ($CD8^+$ $CAR^+$ T cell numbers over time in the blood) was observed among subjects administered the higher dose level, as compared to the lower dose level, without an observed increase in toxicity. Higher peak $CD8^+/CAR^+$ T cell exposure was observed in responders (CR/PR) than non-responders (PD); persistence of cells over the time of assessment, including out to 3 and 6 months, was observed even in subjects whose disease had progressed (FIG. 5B). Median $C_{max}$ and median $AUC_{0-28}$ of $CD8^+$ $CAR^+$ T cells were higher in responding subjects and with durable response at month 3 ($CD8^+$ $C_{max}$ median=20.8 vs. 5.5; $CD8^+$ $AUC_{0-28}$ median=235 vs. 55 in CR/PR at Month 3 vs. PD at Month 3). Among subjects that were evaluated for CAR T cell persistence, 90% and 93% of 29 subjects had detectable $CD8^+$ and $CD4^+$ $CAR^+$ T cells, respectively, at month 3; 63% and 58% of 19 subjects had detectable $CD8^+$ and $CD4^+$ $CAR^+$ T cells, respectively, at month 6. At months 3 and 6, no statistically significant differences in the persistence of $CAR^+$ T cells were observed between subjects with durable response or relapse. $CAR^+$ T cells were detectable at time of relapse in 89% of 11 subjects with PK, even though B cell aplasia (<1 cell/µl) was demonstrated in nearly all subjects 97% (34/35) at month 3, and 100% (24/24) at month 6.

Higher $C_{max}$ and $AUC_{0-28}$ at DL2 as compared to DL1 was not observed to be associated with increased CRS or NT. For any NT or for >Grade 2 CRS, median AUCs of $CD4^+/CAR^+$ and $CD8^+/CAR^+$ T cells were 5 to 10 fold and 3 to 5 fold higher, respectively, than the median AUC for DL2. Higher disease burden and baseline levels of inflammatory cytokines was observed to be associated with higher peak levels of $CAR^+$ T cells, higher cytokine peak levels, and higher incidences of CRS and NT. The results were consistent with a conclusion that the higher Cmax and median $AUC_{0-28}$ at DL2 did not increase CRS or NT.

Figure 5C:
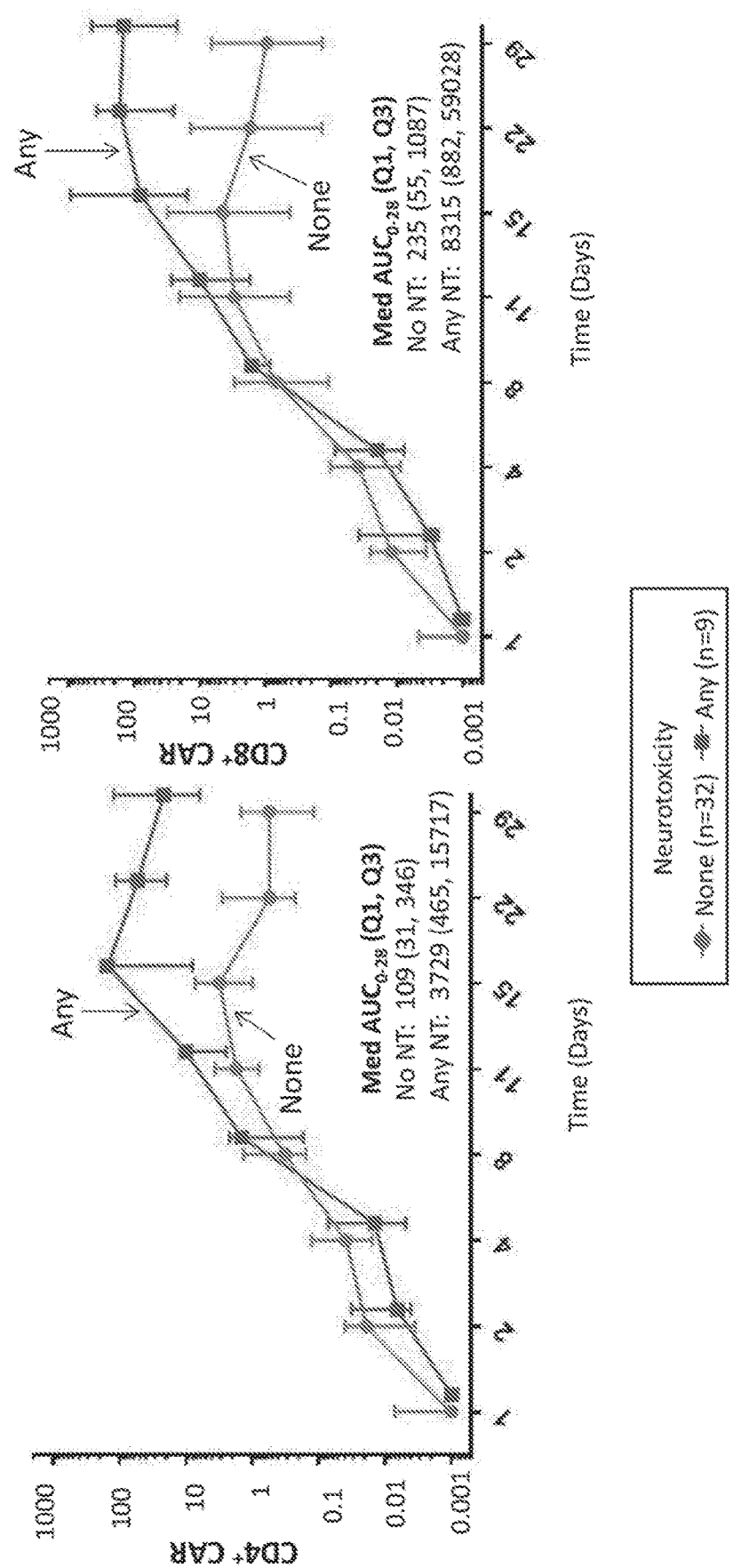
FIG. 5C shows the pharmacokinetics of the CAR$^+$ T cells in peripheral blood at various time points post-treatment in subjects that did or did not develop any neurotoxicity.

The results were consistent with a conclusion that treatment resulted in prolonged exposure and persistence of the engineered cells, even in subjects with poor responses. In some embodiments, combination approaches are used, such as administration of an immune checkpoint modulator or other immune modulatory agent, e.g., following relapse or disease progression, at a time at which engineered cells persist in the subject, e.g., as measured by levels of cells in peripheral blood. In some aspects, the cells, having persisted for a prolonged period, re-expand or become activated and/or exhibit anti-tumor function, following administration of the other agent or treatment. Higher median $CD4^+$ and $CD8^+$ $CAR^+$ T cell numbers were generally observed over time in blood of subjects who developed neurotoxicity (FIG. 5C). Results indicated that the $CAR^+$ T cells exhibited expansion and persistence, durability of response at 3 months that increased at higher dose levels, without increased toxicity. Results were observed that were consistent with a suggestion that high peak levels of $CAR^+$ T cells and cytokines in the blood may be associated with NT and CRS, and may be influenced by baseline subject factors. It was observed that $CAR^+$ T cells were present at the time of relapse, indicating that combination or retreatment approaches may provide certain advantages.

E. Blood Analytes and Neurotoxicity, CRS and Response

Various pre-treatment blood analytes, including cytokines, were measured in the serum of subjects (those assessed at the time-point in Example 1.A.1), prior to administration of the $CAR^+$ T cells. Cytokines were measured using a multiplex cytokine assay. Potential correlations to risk of developing neurotoxicity were assessed using statistical analysis based on univariate nonparametric tests.

Figure 7:
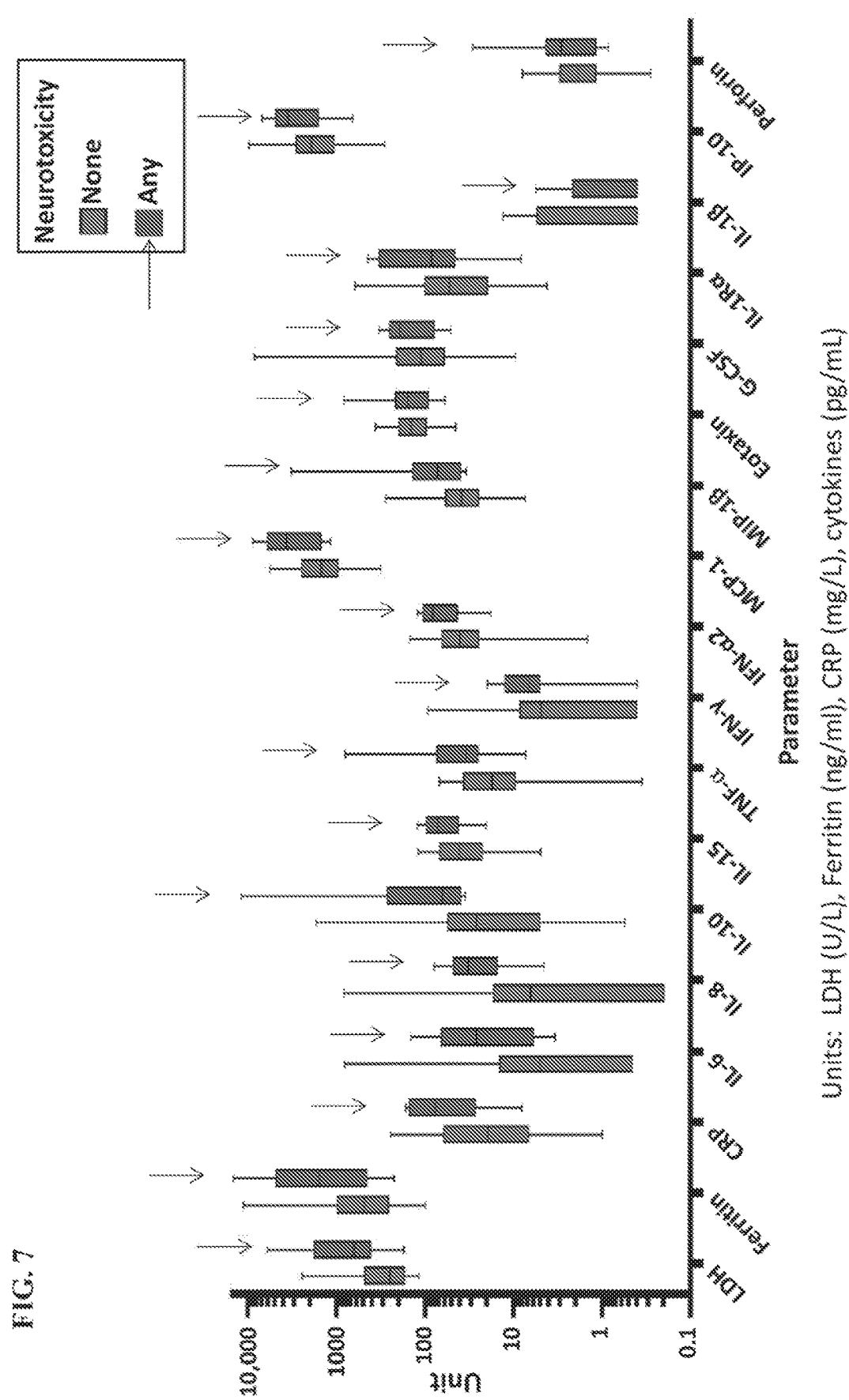
FIG. 7 shows levels of analytes measured in the serum of subjects prior to administration of the CAR$^+$ T cells and correlation to the development of neurotoxicity.

FIG. 7 shows median levels of the assessed analytes in units (LDH, U/L; ferritin, ng/mL; CRP, mg/L; cytokines, pg/mL) in subjects that did not develop a neurotoxicity versus subjects that did develop a neurotoxcity following $CAR^+$ T cell therapy. Levels of certain blood analytes, including LDH, Ferritin, CRP, IL-6, IL-8, IL-10, TNF-α, IFN-α2, MCP-1 and MIP-1β, were observed to be associated with level of risk of developing neurotoxicity (Wilcoxon p values <0.05, without multiplicity adjustment). In particular, the results were consistent with a conclusion that pre-treatment levels of LDH, which in some embodiments is a surrogate for disease burden, may be useful for potential neurotoxicity risk assessment and/or risk-adapted dosing or adjustment of treatment of certain subjects. In addition, tumor burden measured before administration of the CAR-T cell composition correlated (Spearman p values <0.05) with the risk of developing neurotoxicity. In some aspects, LDH levels may be assessed alone and/or in combination with another pre-treatment parameter, such as another measure or indicator of disease burden, such as a volumetric tumor measurement such as sum of product dimensions (SPD) or other CT-based or MM-based volumetric measurement of disease burden. In some aspects, one or more parameters indicative of disease burden are assessed, and in some contexts may indicate the presence, absence or degree of risk of developing neurotoxicity following the T cell therapy. In some aspects, the one or more parameters include LDH and/or a volumetric tumor measurement.

In an additional analysis, fifty-five (55) subjects in the DLBCL cohort at the time-point in Example 1.A.1, and four (4) subjects in the mantle cell lymphoma (MCL) described in Example 2 below were included in analysis for correlation with safety evaluations. In the 59 subjects evaluated for safety, CRS was observed in 32% (30% Grade 1-2, 0% Grade 3, 2% Grade 4); NT was observed in 20% (5% Grade 1-2, 10% Grade 3, 5% Grade 4). Dose level did not correlate with CRS or NT ($p=0.565$ and $p=1.00$, respectively). Subject factors that correlate with any grade CRS and NT were poorer performance status (e.g. ECOG Status 2) ($p=0.03$) and higher disease burden ($p<0.05$) as measured by the sum of the products of diameters (SPD) based on imaging results. Pre-CAR$^+$ T cell infusion clinical laboratory parameters and cytokine measurements for pre-CAR$^+$ T cell infusion that were observed to be associated with the occurrence of any grade NT included higher serum LDH, ferritin, and CRP, and higher plasma IL-6, IL-8, IL-10, TNF-α, IFN-α2, MCP-1, and MIP-10 ($p<0.05$ for each). Higher pre-CAR$^+$ T cell infusion plasma levels of IL-8, IL-10, and CXCL10 were also associated with Grade 3-4 NT ($p<0.05$ for each).

Of the 54 subjects in the DLBCL cohort that were evaluated for response, higher ECOG scores and DLBCL transformed from CLL or MZL correlated with lower durable response at month 3 ($p=0.02$ for both). Pre-CAR$^+$ T cell infusion parameters associated with best ORR included lower values of ferritin, LDH, CXCL10, G-CSF, and IL-10, and those associated with durable response at 3 months included lower ferritin, CRP, LDH, CXCL10, IL-8, IL-10, IL-15, MCP-1, TNF-α, and higher pre-CAR$^+$ T infusion hemoglobin and albumin ($p<0.05$ for each).

In some cases, the apheresis sample and CAR$^+$ T cell composition for administration was assessed and correlated with clinical outcomes. The results showed that T cell memory subsets and T cell functionality may correlate with certain clinical outcomes.

The results showed that certain baseline patient characteristics, including inflammatory state and high tumor burden prior to treatment, may be useful for the identification of patients at risk for increased toxicity following administration of CAR-expressing T cells. Low tumor burden and low inflammatory state were observed to be associated with improved toxicity profile and better durability of response. The results support that treating subjects earlier in the course of therapy and/or assessing a panel of clinical and laboratory biomarkers to risk stratify subjects for potential early intervention may mitigate the risk of toxicity and improve durability of response.

Example 2: Administration of Anti-CD19 CAR-Expressing Cells to Subjects with Mantle Cell Lymphoma (MCL)

Therapeutic CAR$^+$ T cell compositions containing autologous T cells expressing a chimeric antigen-receptor (CAR) specific for CD19, generated as described in Example 1, were administered to four (4) human subjects with mantle cell lymphoma (MCL) that had failed 1 line of therapy. The cryopreserved cell compositions were thawed prior to intravenous administration. The therapeutic T cell composition was administered as a defined composition cell product with formulated CD4$^+$ and CD8$^+$ populations of CAR$^+$ engineered T cells derived from the same subject administered at a target ratio of approximately 1:1. Subjects were administered a dose of CAR-expressing T cells (as a split dose of the CD4$^+$ and CD8$^+$ CAR-expressing T cells) at a single dose of dose level 1 (DL1) containing $5\times10^7$ CAR-expressing T cells. Beginning at three (3) days prior to CAR$^+$ T cell infusion, subjects received a lymphodepleting chemotherapy with fludarabine (flu, 30 mg/m$^2$) and cyclophosphamide (Cy, 300 mg/m$^2$).

Subjects were monitored for response and toxicities as described in Example 1. No CRS or neurotoxicity was observed in any of the subjects. Of the 4 subjects that were treated, two (2) subjects achieved PR (not durable) and two (2) patients had progressive disease.

Example 3: Further Assessment of Response, Safety, Pharmacokinetics, Pharmacodynamics and Blood Analytes in Subjects with Relapsed and Refractory Non-Hodgkin's Lymphoma (NHL) After Administration of Anti-CD19 CAR-Expressing Cells Response outcomes, safety outcomes, pharmacokinetic and pharmacodynamics parameters, and blood analytes were assessed in patients at a subsequent point in time in the clinical study described in Example 1 above.

A. Subjects and Treatment

The analysis at this time point presented in this example is based on assessment of a total of 91 subjects in the full DLBCL cohort (88 (65 from the CORE cohort) assessed for response and 91 (67 from the CORE cohort) assessed for safety) that had been administered the anti-CD19 CAR-expressing cells. The FULL cohort included DLBCL, NOS de novo and transformed from any indolent lymphoma, ECOG 0-2; the CORE cohort for analysis included subjects having DLBCL, NOS and transformed from follicular lymphoma (tFL) or high grade B-cell lymphoma and with Eastern Cooperative Oncology Group performance status (ECOG PS) of 0 or 1. Approximately 90% of treated patients in the CORE cohort had at least 1 poor-risk disease feature predictive of short median overall survival (OS) of 3-6 months, such as double/triple hit expressors, primary refractory disease, refractory to 2 or more lines of therapy, never achieved CR, or never received autologous stem cell transplant (ASCT). In some embodiments a cohort of subjects having Diffuse large B-cell lymphoma (DLBCL) not otherwise specified (NOS; de novo and transformed from follicular lymphoma tFL)) or high-grade B-cell lymphoma, with MYC and BCL2 and/or BCL6 rearrangements with DLBCL histology, and excluding subjects with ECOG score of 2 or subjects who have received prior hematopoietic stem cell transplantation (HSCT), are administered CAR-T compositions as provided herein. In some embodiments, subjects of the CORE cohort are administered anti-CD19 CAR$^+$ T cells at a single dose of DL2 ($1 \times 10^8$ total CAR-expressing T cells).

At this time point, a total of 140 subjects had been leukapheresed, of which 10 were awaiting manufactured composition, 2 had withdrawn before manufacturing, and 2 had compositions unavailable. Of another 18 subjects whose products were available, 4 were awaiting treatment, 4 had withdrawn, and 10 had developed progressive disease or had died. A total of 108 subjects had been administered the anti-CD19 CAR-expressing cells, of which 6 were not evaluable and 11 received non-conforming anti-CD19 CAR-expressing cells (compositions not necessarily meeting certain specifications but deemed to be safe for administration). Subjects had received DL1 (n=45), double dose of DL1 (n=6) or DL2 (n=40). Six (6) subjects with mantle cell lymphoma (MCL) had been administered CAR$^+$ cells at DL1 (five treated with conforming product, one treated with non-conforming product), and five (5) had completed 28 days of follow-up. One MCL subject had developed CRS, and none had received tocilizumab or dexamethasone. Product had been available for 98% of apheresed subjects (126/128) in the DLBCL cohort.

The subjects at this time-point included 5 patients that had been treated in the outpatient setting (including four (4) subjects treated with DL1, one (1) treated with DL2; four (4) of which were included in the CORE cohort). For subjects treated in the outpatient setting, median age was 57 years old (range 26-61), 3 had DLBCL, NOS, 1 had tFL, and 1 had PMBCL. All five (5) subjects had an ECOG scores of 0 or 1. Data on outpatient results included results for three (3) additional subjects that had been treated in the outpatient setting (total of eight (8) subjects) and whose data became available after the time point for the analysis in this Example.

The demographics and baseline characteristics of the full and core cohort subjects at the timepoint are set forth in Table E5.

TABLE E5

Patient Characteristics: DLBCL Cohort

| Characteristic | FULL (n = 91) | CORE (n = 67) |
|---|---|---|
| Median Age, years (range), | 61 (20-82) | 60 (20-82) |
| ≥65 years, n (%) | 34 (37) | 24 (36) |
| Male/Female, n (%) | 61/30 (67/33) | 46/21 (69/31) |
| B-NHL subtype, n (%) | | |
| DLBCL, NOS de novo | 59 (65) | 51 (76) |
| Transformed from FL (tFL) | 19 (21) | 16 (24) |
| Transformed from MZL (tMZL)/ CLL (tCLL) | 6 (7)/4 (4) | 0 |
| Follicular, Grade 3B/PMBCL | 1 (1)/2 (2) | 0 |
| Molecular subtype, n (%) | | |
| Double/triple hit [High grade B-cell lymphoma]$^a$ | 18 (20) | 16 (24) |
| Patient characteristics, n (%) | | |
| Chemorefractory$^b$ | 61 (67) | 44 (66) |
| ECOG PS 0-1/2 (pre-LD) | 81 (89)/10 (11) | 67 (100)/0 |
| IPI 3-5/Disease stage 3-4 | 38 (42)/70 (77) | 24 (36)/49 (73) |
| CNS involvement | 2 (2) | 2 (3) |
| Prior lines of therapy, median (range) | 3 (1-12) | 3 (1-8) |
| Never achieved CR | 47 (52) | 34 (51) |
| Any HSCT | 39 (43) | 28 (42) |
| Prior Autologous | 36 (40) | 28 (42) |
| Prior Allogeneic | 5 (5) | 0 |

HSCT, hematopoietic stem cell transplantation; LD, lymphodepletion.
$^a$At trial initiation, included in DLBCL, NOS histology; based on most recent WHO criteria (Swerdlow et al., (2016) Blood 127(20): 2375-2390), are now considered "high-grade B-cell lymphoma, with MYC and BCL2 and/or BCL6 rearrangements with DLBCL histology (double/triple hit).
$^b$SD or PD to last chemotherapy-containing regimen or relapse <12 months after autologous SCT.

B. Safety and Response Outcomes after Treatment

As shown in Table E6, the objective response rate (ORR) was 74%, including 52% subjects who showed a complete response (CR). The incidence of any grade of cytokine release syndrome (CRS) was 35%, with 1% severe CRS; and the incidence of any grade of neurotoxicity (NT) was 19%, with 1% severe NT.

TABLE E6

Response and Safety After CAR$^+$ Cell Administration

| | FULL | CORE | | |
|---|---|---|---|---|
| | All Dose Levels | All Dose Levels$^a$ | DL1S | DL2S |
| Best Overall Response (BOR), n$^b$ | 88 | 65 | 34 | 27 |
| ORR, % (95% CI) | 74 (63, 83) | 80 (68, 89) | 77 (59, 89) | 82 (62, 94) |
| CR, % (95% CI) | 52 (41, 63) | 55 (43, 68) | 47 (30, 65) | 63 (42, 81) |
| Safety, n$^c$ | 91 | 67 | 34 | 29 |
| Any CRS, % (95% CI) | 35 (25, 46) | 36 (24, 48) | 41 (25, 59) | 24 (10, 44) |
| sCRS(grade 3-4), % (95% CI) | 1 (0, 6) | 1 (0, 8) | 38 (0, 15) | 0 |
| Any NT, % (95% CI) | 19 (11, 28) | 21 (12, 33) | 24 (11, 41) | 17 (6, 36) |
| sNT (grade 3-4), % (95% CI) | 12 (6, 21) | 15 (7, 26) | 21 (9, 38) | 7 (1, 23) |

$^a$Four patients treated on DL1D (dose level 1, two-dose schedule) with similar outcomes.
$^b$Includes patients with event of PD, death, or 28-day restaging scans. One patient did not have restaging scans available.
$^c$Includes all subjects who have received at least one dose of conforming CAR-expressing cell product 28 days prior to data snapshot date or died.

As shown in Table E7, high rates of response and low severe toxicity was observed in the full DLBCL population.

TABLE E7

Response After CAR+ Cell Administration

|  | FULL | By Diagnosis | | | |
|---|---|---|---|---|---|
|  |  | DLBCL, NOS | tFL | tCLL/MZL | FL3B/PMBCL |
| BOR, n[a] | 88 | 57 | 19 | 10 | 2 |
| ORR, % (95% CI) | 74 (63, 83) | 74 (60, 85) | 84 (60, 97) | 50 (19, 81) | 100 (16, 100) |
| CR, % (95% CI) | 52 (41, 63) | 51 (37, 64) | 63 (38, 84) | 30 (7, 65) | 100 (16, 100) |
| Safety, n[b] | 91 | 59 | 19 | 10 | 3 |
| Any CRS, % (95% CI) | 35 (25, 46) | 34 (22, 47) | 42 (20, 67) | 20 (3, 56) | 67 (9, 99) |
| sCRS (grade 3-4),% (95% CI) | 1 (0, 6) | 2 (0, 9) | 0 | 0 | 0 |
| Any NT, % (95% CI) | 19 (11, 28) | 20 (11, 33) | 21 (6, 46) | 10 (0, 45) | 0 |
| sNT (grade 3-4), % (95% CI) | 12 (6, 21) | 14 (6, 25) | 11 (1, 33) | 10 (0, 45) | 0 |

[a]Includes patients with event of PD, death, or 28-day restaging scans. One patient did not have restaging scans available.
[b]Includes all subjects who have received at least one dose of conforming CAR+ expressing cells 28 days prior to data snapshot date or died.

As shown in Table E8, high rate of response and a dose-dependent response was observed in the CORE cohort of subjects.

TABLE E8

Durable Response After CAR+ Cell Administration

|  | Dose Levels[a] | DL1S | DL2S |
|---|---|---|---|
| BOR, n[b] | 65 | 34 | 27 |
| ORR (95% CI), % | 80 (68, 89) | 77 (59, 89) | 82 (62, 94) |
| CR (95% CI), % | 55 (43, 68) | 47 (30, 65) | 63 (42, 81) |
| ≥3-mo f/u, n[c] | 52 | 29 | 19 |
| 3-mo ORR (95% CI), % | 65 (51, 78) | 59 (39, 77) | 74 (49, 91) |
| 3-mo CR (95% CI), % | 54 (40, 68) | 41 (24, 61) | 68 (43, 87) |
| ≥6-mo f/u, n[d] | 38 | 20 | 14 |
| 6-mo ORR (95% CI), % | 47 (31, 64) | 40 (19, 64) | 50 (23, 77) |
| 6-mo CR (95% CI), % | 42 (26, 59) | 30 (12, 54) | 50 (23, 77) |

[a]Four patients (CORE) treated on DL1D with similar outcomes.
[b]Includes patients with event of PD, death, or 28-day restaging scans. One patient did not have restaging scans available.
[c]The denominator is number of patients who received CAR+ cells ≥3 months ago, prior to data snapshot date, with an efficacy assessment at month 3 or prior assessment of PD or death.
[d]The denominator is number of patients who received CAR+ cells ≥6 months ago, prior to data snapshot date, with an efficacy assessment at month 6 or prior assessment of PD or death.

Figure 22:
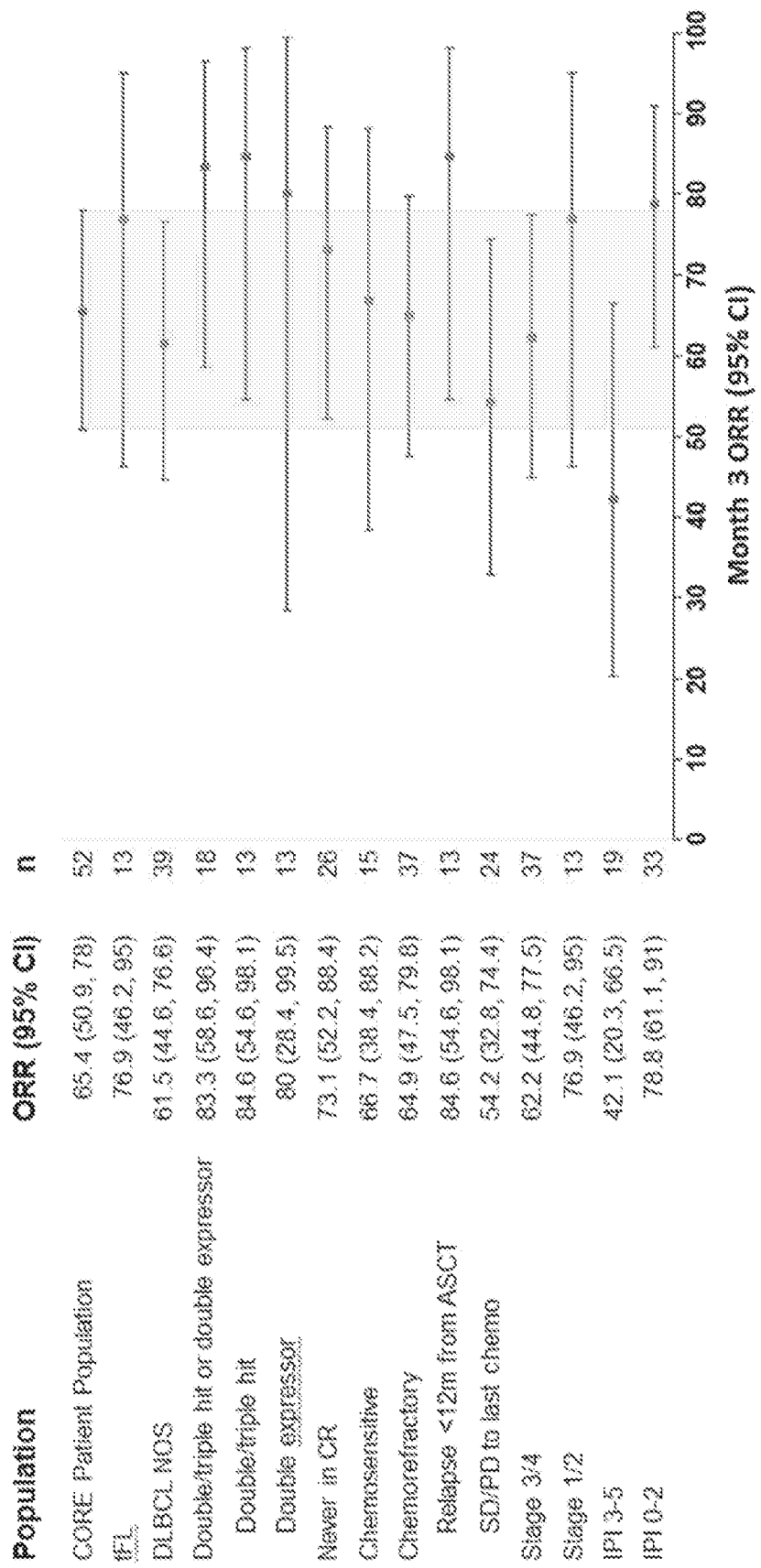
FIG. 22 depicts month 3 objective response rates (ORR) among subgroups of treated subjects, with the 95% confidence interval.
Figure 23A:
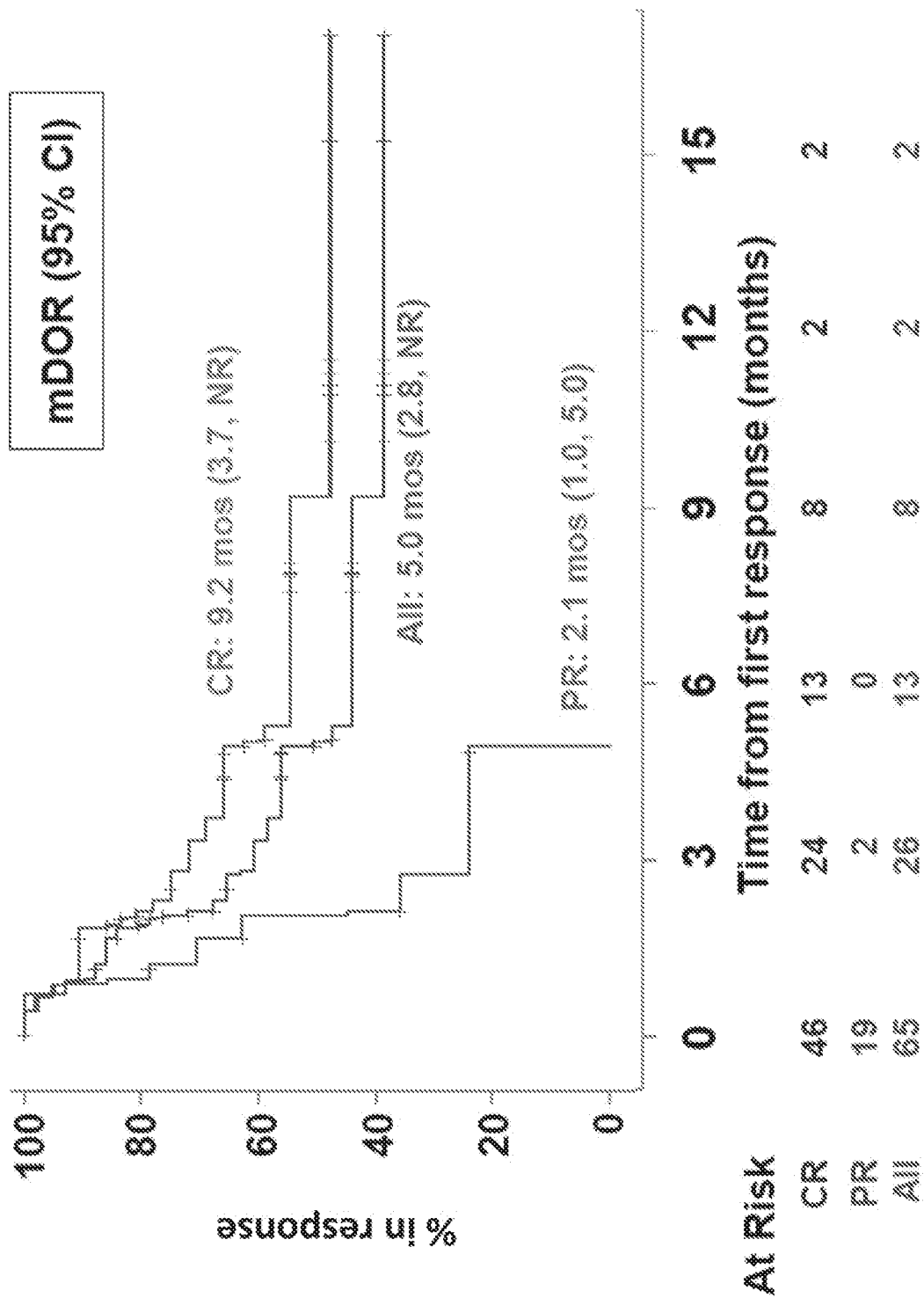
FIGS. 23A and 23B depict the duration of response (DOR) for the full cohort (FIG. 23A) and the core cohort (FIG. 23B)
Figure 23B:
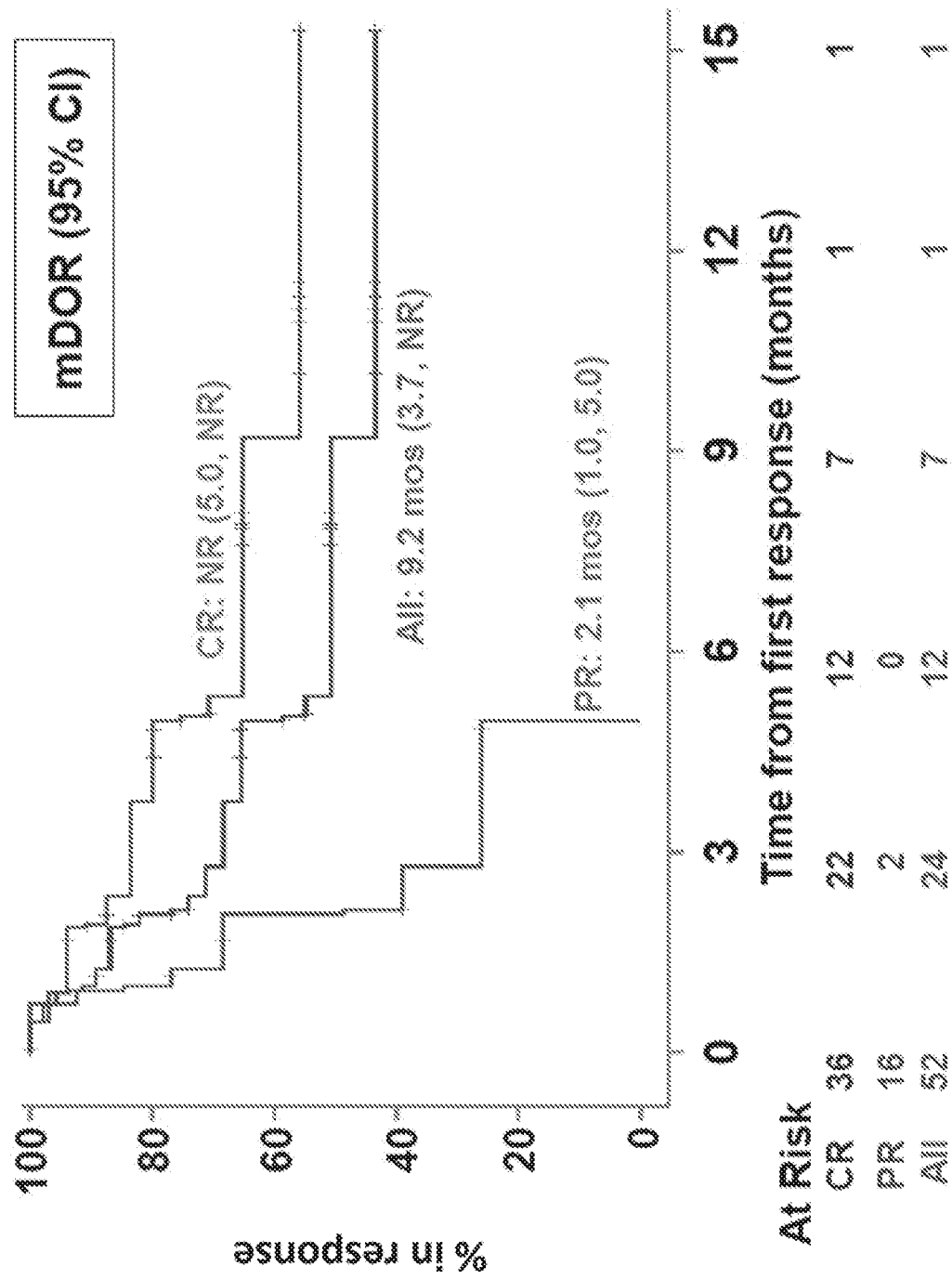
Figure 23C:
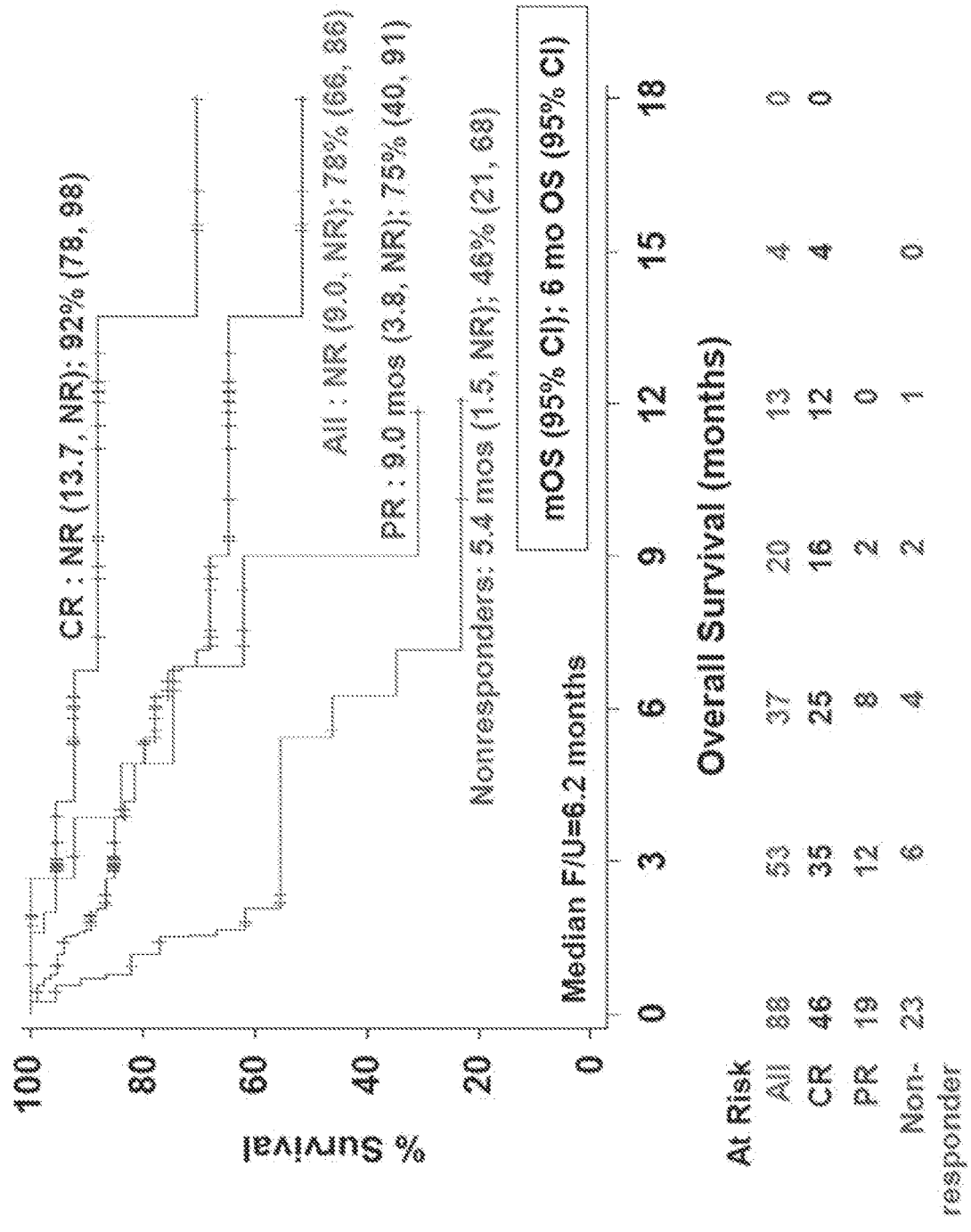
FIGS. 23C and 23D depict the overall survival for the full cohort (FIG. 23C) and the core cohort (FIG. 23D), for subjects who achieved CR, PR, all subjects that showed a response, non-responders, and all treated subjects. Median F/U was 6.3 months for duration of response.
Figure 23D:
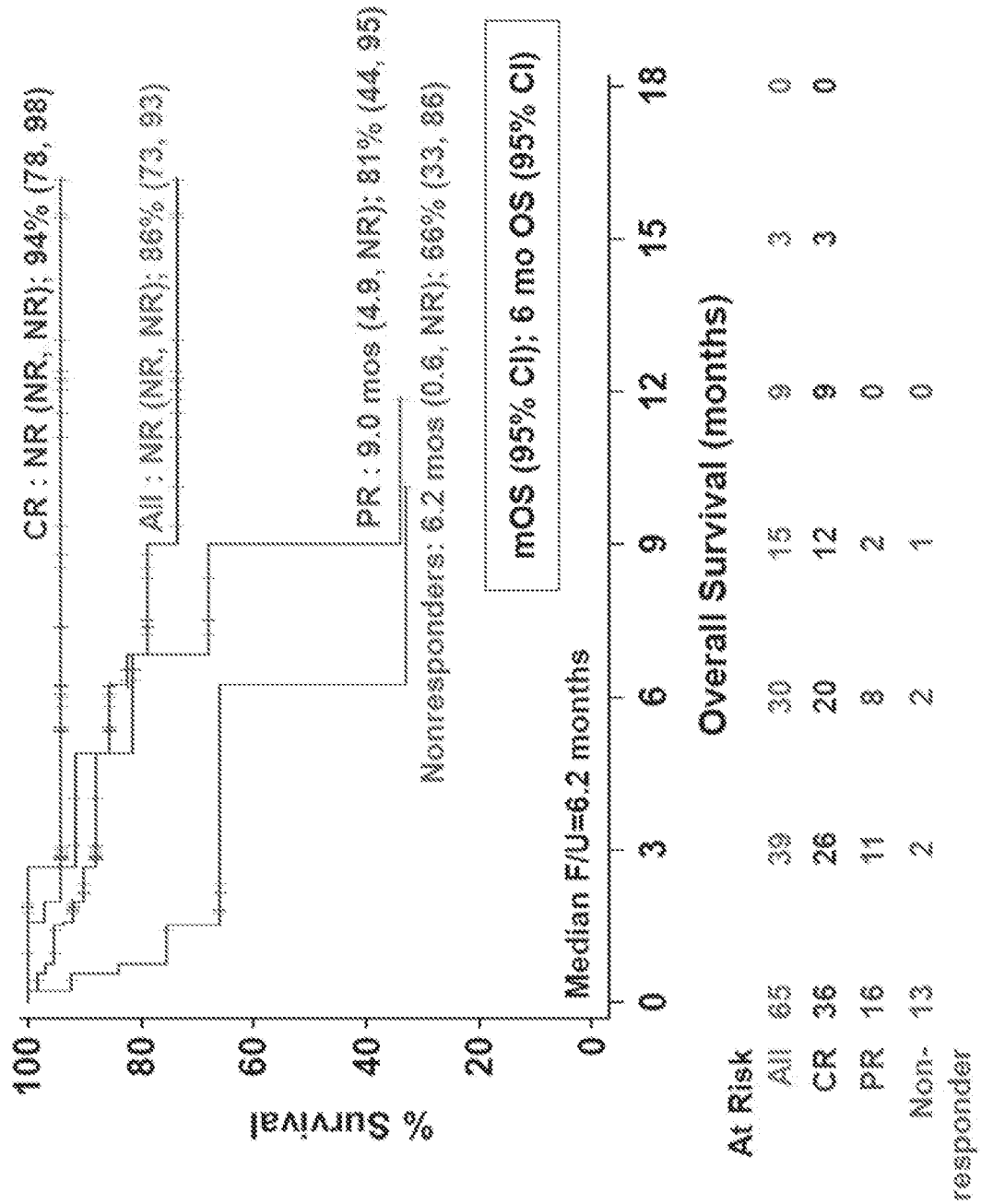

Three-month objective response rates (ORR) among various subgroups of subjects in the poor-risk DLBCL subgroups, that included all DLBCL patients treated at all dose levels in the core cohort, are shown in FIG. 22. The results showed high durable ORR in the poor-risk DLBCL subgroup.

Results for the duration of response (DOR) and overall survival (grouped by best overall response (non-responder, CR/PR, CR and/or PR)) are shown for the full cohort and the core cohort cohorts of subjects, in FIGS. 23A-23D. The results also showed 80% (16/20) of subjects with a CR at 3 months stay in CR at 6 months, and 92% (11/12) of subjects with a response (CR or PR) at 6 months continue to show a response longer term.

Figure 24:
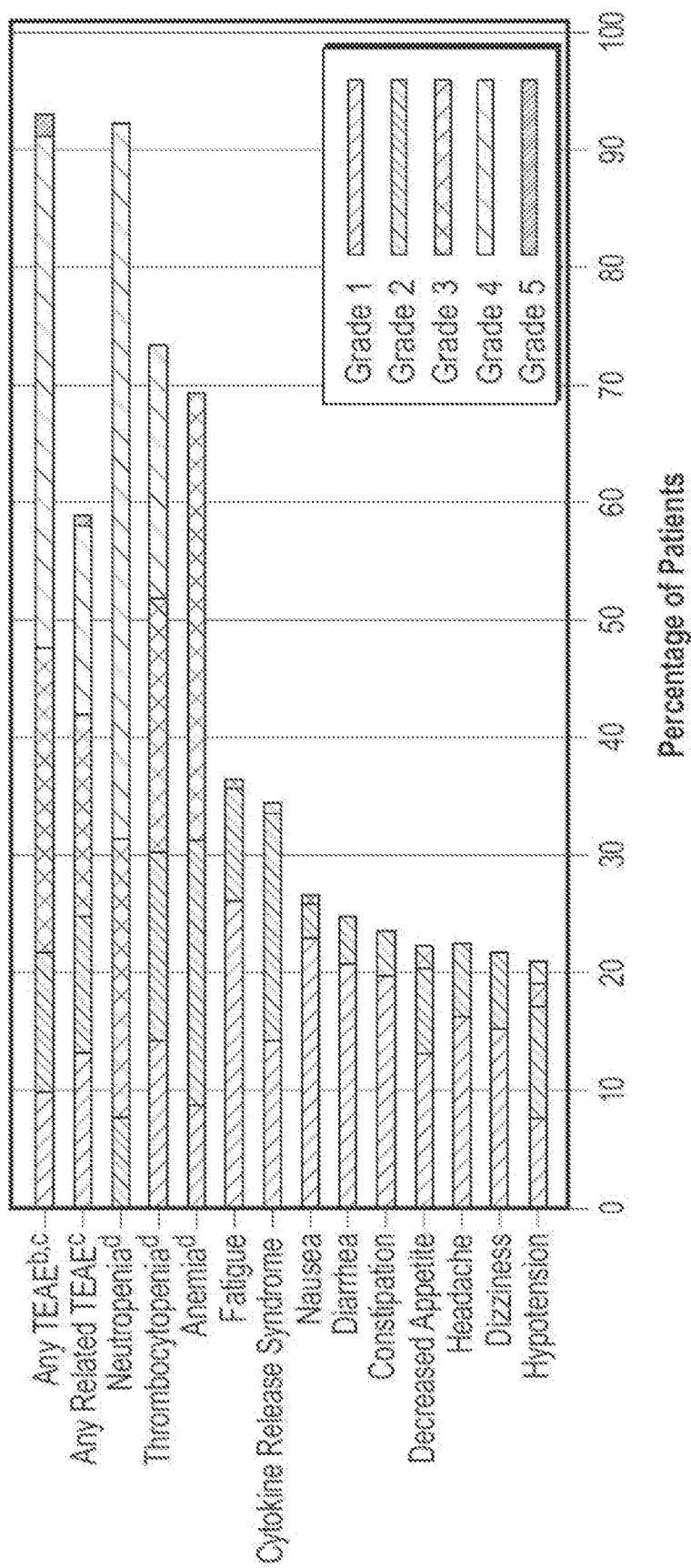
FIG. 24 shows the percentage of subjects who experienced treatment-emergent adverse events (TEAEs) in the FULL DLBCL cohort occurring in ≥20% of patients. Data for 5 patients with MCL treated with conforming product at DL1 with at least 28 days of follow-up were not included. $^b$: One grade 5 AE of septic shock unrelated to CAR$^+$ T cell administration. $^c$: One grade 5 AE of diffuse alveolar damage, investigator assessed as related to fludarabine, cyclophosphamide, and CAR$^+$ T cells, occurred on day 23 in a patient who refused mechanical ventilation for progressive respiratory failure while neutropenic on growth factors and broad-spectrum antibiotics and antifungals. $^d$: Laboratory anomalies.

FIG. 24 depicts the percentage of subjects at this timepoint who were observed to have experienced laboratory abnormalities and treatment-emergent adverse events (TEAEs) (data for 5 patients with MCL treated with conforming product at DL1 with at least 28 days of follow-up are not included). In addition to the TEAEs shown in FIG. 24, the following event terms were observed at Grade 3-4 in ≥5% of patients: encephalopathy (8%), Pancytopenia (5%) and Febrile neutropenia (7%). Eight patients (9%) had infusional toxicity, defined as AE on day of administration related to CAR+ cell administration, including flushing, headache, fever, pyrexia, chills, rigors, vomiting, rash, hives, pruritis, hypotension, wheezing, bronchospasm, shortness of breath, nausea, vomiting, back pain, cough, and infusion-related reaction. Events included chills (2), pyrexia (5), flushing (1), headache (1), hypotension (1), infusion related reaction (1), rash (1), pruritis (1), and vomiting (1), with 6 grade 1 events, 1 grade 2 (chills), and 1 grade 3 (hypotension) event. TEAE in the core cohort did not differ substantially from those in the full cohort. The most common related TEAEs in the subjects treated in the outpatient setting group were CRS, hypotension, vomiting, anemia, and dyspnea.

Table E9 sets forth the TEAEs and neurotoxicity that occurred in 25 percent or more subjects in the FULL or CORE cohort, for subjects who received DL1S and DL2S. No apparent dose-toxicity relationship was observed in the DLBCL population.

TABLE E9

TEAEs ≥25% in FULL cohort, CORE cohort, and CORE cohort by dose level.

| Term, n (%) | FULL (N = 91) | CORE[a] (n = 67) | CORE DL1S (n = 34) | CORE DL2S (n = 29) |
|---|---|---|---|---|
| Anemia[b] | 85 (93) | 63 (94) | 33 (97) | 26 (90) |
| Thrombocytopenia[b] | 64 (70) | 48 (72) | 28 (82) | 19 (66) |
| Fatigue | 48 (53) | 41 (61) | 20 (59) | 19 (66) |
| CRS | 34 (37) | 25 (37) | 11 (32) | 12 (41) |
| Nausea | 32 (35) | 24 (36) | 14 (41) | 7 (24) |
| Diarrhea | 25 (27) | 19 (28) | 12 (35) | 5 (17) |
|  | 23 (25) | 16 (24) | 7 (21) | 7 (24) |

[a]Includes 4 patients treated at dose level 1, two-dose schedule.
[b]Laboratory anomalies.

Figure 25:
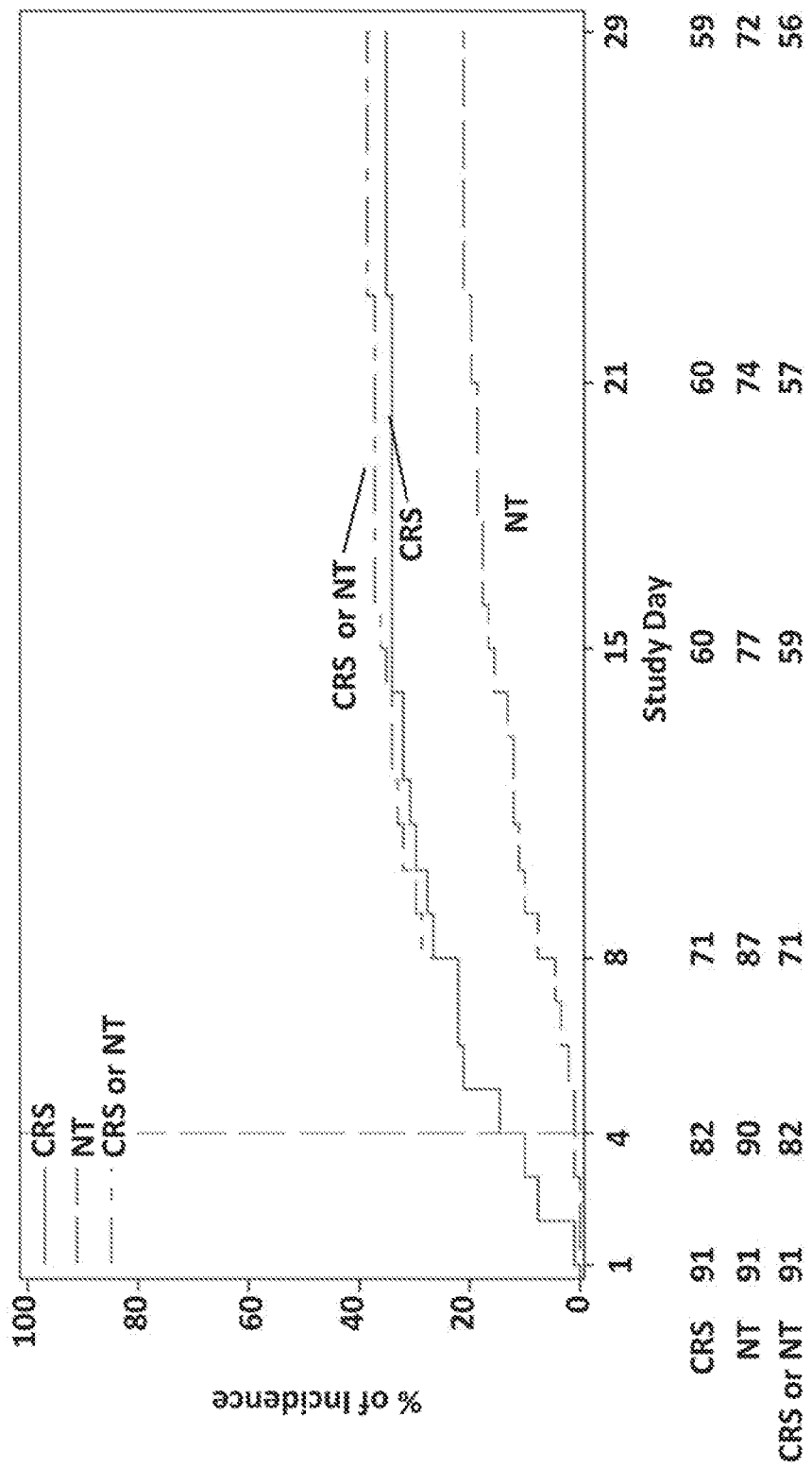
FIG. 25 shows the percentage of subjects who developed CRS or neurotoxicity over time, in the full cohort.

FIG. 25 depicts the number and percentage of subjects that were observed to have CRS and/or NT at various time points after administration of CAR+ cells. In this assessment, the median time to onset of first of CRS or NT event was observed to be 5 (range 1-14) or 10 (range 3-23) days, respectively. Within the first 72 hours after CAR+ cell administration, 1 patient had NT (grade 1), and only 14% (13 of 91) had CRS (7 grade 1; 6 grade 2). The median duration (Q1,Q3) of CRS or NT was 5 (4, 8) or 10.5 (7, 19) days, respectively. NT was preceded by CRS in 12 of 17 cases (71%). All evaluable NT events were resolved at the time of analysis except one grade 1 tremor and 2 patients died from progressive disease with ongoing NT (based on safety database of reported events including additional subjects analyzed after the analysis timepoint described in this Example).

In the full cohort (n=91), selected subjects with onset of CRS or NT were administered anti-cytokine therapy with tocilizumab and/or dexamethasone as follows: Tocilizumab alone, 4% (n=4); Dexamethasone alone, 9% (n=8); Tocilizumab and dexamethasone, 8% (n=7). The median number of dexamethasone doses was 6 (range, 2-99); and the median number of tocilizumab doses was 1 (range, 1-3).

Table E10 shows toxicity outcomes in subjects in the CORE cohort that received a single dose at DL1 or DL2. No deaths occurred from CRS or NT. The median time to onset of CRS was 5 days (range, 2-14) and NT was 11.5 days (range, 5-23). In the CORE cohort, 13% (n=9) received tocilizumab, and 18% (n=12) received dexamethasone to ameliorate toxicity. Eighteen percent of subjects (12 of 67) exhibited neurotoxicity terms consistent with encephalopathy, including encephalopathy (13%), 6% (4 of 67) had aphasia and 3% (2 of 67) had seizures. In Table E10, the number of subjects or % of total subjects (parentheses) exhibiting an indicated toxicity outcome is shown at all dose levels or specifically in subjects administered DL1 or DL2. Also shown in brackets is the upper and lower 95% confidence interval.

TABLE E10

Toxicity in Core Cohort Receiving Different Dose Levels.

|  | All Dose Levels[a] n = 67 | DL1S n = 34 | DL2S n = 29 |
|---|---|---|---|
| CRS, n (%) [95% CI] | | | |
| Any Grade | 24 (36) [24, 48] | 14 (41) [25, 59] | 7 (24) [10, 44] |
| Grade 1/2 | 23 (34) [23, 47] | 13 (38) [22, 56] | 7 (24) [10, 44] |
| Grade 3/4 (sCRS) | 1 (1) [0, 8] | 1 (3) [0, 15] | 0 |
| Neurotoxicity[b], n (%) [95% CI] | | | |
| Any Grade | 14 (21) [12, 33] | 8 (24) [11, 41] | 5 (17) [6, 36] |
| Grade 1/2 | 4 (6) [2, 15] | 1 (3) [0, 15] | 3 (10) [2, 27] |
| Grade 3/4 (sNT) | 10 (15) [7, 26] | 7 (21) [9, 38] | 2 (7) [1, 23] |
| Any, n (%) [95% CI] | | | |
| CRS or NT, n (%) | 28 (42) [30, 54] | 15 (44) [27, 62] | 10 (34) [18, 54] |
| sCRS or sNT, n (%) | 10 (15) [7, 26] | 7 (21) [9, 38] | 2 (7) [1, 23] |

[a] Four patients treated on DL1D with similar outcomes.
[b] Includes confusional state, encephalopathy, aphasia, ataxia, cerebellar syndrome, delirium, depressed level of consciousness, dizziness, flat affect, hand-eye coordination impaired, memory impairment, tremor, agitation, disturbance in attention, dysarthria, mental status changes, muscular weakness, seizure, somnolence, and urinary incontinence.

Among twelve (12) subjects receiving nonconforming products, 10 at DL1 and 2 at DL2, all had 28-day follow-up. CRS was observed in 33% of the subjects (4/12), and NT was not observed in any of the subjects. Two subjects received tocilizumab and 3 subjects received dexamethasone. The toxicity rates were comparable to those observed in the larger cohort of subjects administered conforming product. In the subjects receiving nonconforming products, pharmacokinetic (PK) expansion was higher in subjects with CRS/NT, subjects with high tumor burden or LDH levels.

C. Assessment of Outpatient Administration

Data for a total of eight (8) subjects were evaluated at this timepoint that had been treated in the outpatient setting (median age of 58.5 and ECOG of 0 or 1) at multiple clinical sites, including 3 subjects whose data was available subsequent to the time point analyzed for purposes of this Example. The mean length of hospitalization was 15.6 days for subjects treated in the inpatient setting (SD 9.6, n=86) and 9.3 days for subjects treated in the outpatient setting (SD 11.9, n=8). A 40% reduction in length of hospitalization was observed in subjects treated in the outpatient setting. The median number of days prior to hospitalization after outpatient CAR$^+$ T cell administration was 5 days (range: 4-22). None required admission to the intensive care unit (ICU) after outpatient administration.

Among those of the 8 subjects treated in the outpatient setting with more than 28-day post-administration follow-up, 1 remained outpatient throughout the duration of the dose-limiting toxicity period. Seven (7) patients were admitted with fevers (1 on study day 4, the rest on study day ≥5), 6 patients were admitted with CRS (4 grade 1, 2 grade 2) and 2 patients with grade 1 NT. No patient experienced severe CRS or NT. One (1) patient was treated with tocilizumab without dexamethasone for CRS (grade 2), and no patients were treated with dexamethasone for CRS or NT. One patient was admitted 3 days after CAR$^+$ T cell administration.

Among 91 subjects treated in the inpatient and outpatient settings, 11 subjects (12%) required ICU admission for management of toxicity; 8 subjects (9%) required ICU admission for management of CRS or NT; 2 subjects (2%) required ICU admission for management of acute respiratory events (one related to CAR$^+$ T cell administration, one unrelated). Six (6) subjects (6%) were intubated (based on safety database of reported events including additional subjects analyzed afterthe analysis timepoint described in this Example; n=94); 7 subjects (7%) received vasopressors (based on safety database of reported events, defined as exhibiting hypotension in the first 28 days after CAR$^+$ T cell administration, in the TEAE assessment); and 2 subjects (2%) underwent hemofiltration (based on safety database of reported events). The results showed that very few patients required ICU-level care and associated procedures. The results supported the feasibility of outpatient administration, with safe management of toxicity in the outpatient setting, appropriate education and outpatient monitoring.

The assessment of outpatient administration supported the feasibility of safe outpatient administration. 30% of the subjects were not re-admitted.

D. Pharmacokinetic Assessment

Numbers of CAR$^+$ T cells in peripheral blood and bone marrow at time points before administration (pre-treatment or pre-lymphodepleting chemotherapy (LDC)) and various time points post-treatment (with day of administration as day 1) in 87 subjects in the DLBCL cohort with evaluable PK, by flow cytometry using an antibody specific for the truncated receptor used as a surrogate marker, and quantitative polymerase chain reaction (qPCR) using primers specific for a woodchuck hepatitis virus post-transcriptional regulatory element (WPRE) present in the vector encoding the chimeric antigen receptor (CAR). The area under the curve plotting numbers per microliter for the indicated CAR$^+$ cell population between days 0 and 28 (AUC$_{0-28}$) and the maximum or peak blood concentration of CAR$^+$ cells (C$_{max}$; CAR$^+$ cells/μL blood) were assessed. B-cell aplasia was assessed in peripheral blood by flow cytometry, by staining with CD19. Cytokines were measured using a multiplex cytokine assay. For safety analysis, the data from all subjects receiving different dose levels were pooled. For response analysis, data were stratified by dose level. Statistical analysis was two-sided without multiplicity adjustment.

Figure 9A:
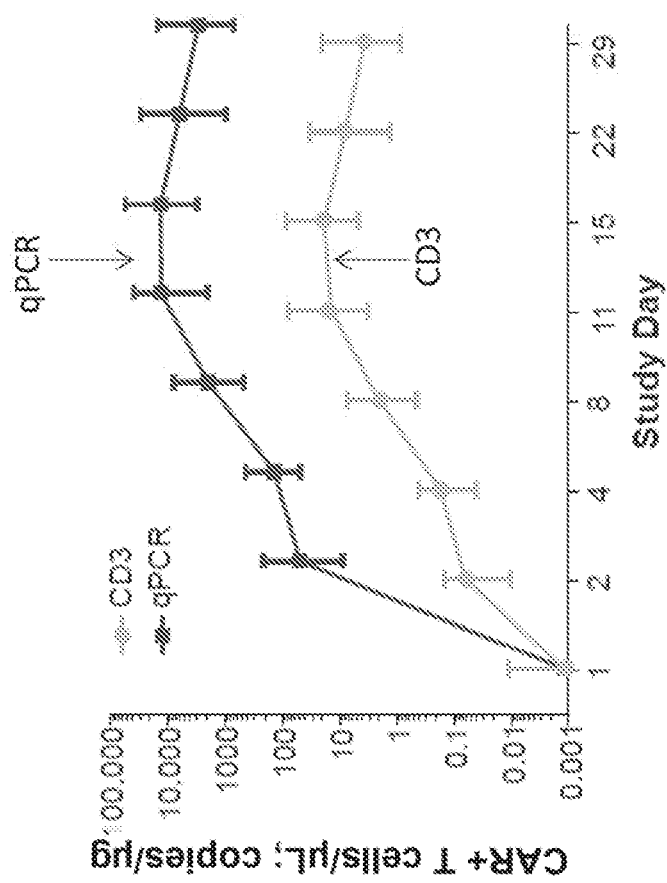
FIG. 9A depicts the median (±quartiles) number of CAR-expressing CD3$^+$ cells/μL blood, assessed by flow cytometry using an antibody specific for a truncated receptor (CD3, circle; N=87); or median (±quartiles) number of copies integrated CAR transgene/μg genomic DNA, assessed by quantitative polymerase chain reaction (qPCR) using primers specific for a woodchuck hepatitis virus post-transcriptional regulatory element (WPRE) present in the vector encoding the CAR (qPCR, square; N=85) in blood samples from 87 subjects that have been administered anti-CD19 CAR-expressing cells. The cutoff for CAR$^+$ cell detection in flow cytometry was set at ≥25 events in the CAR$^+$ gate, and limit of detection for qPCR was ≥12.5 copies of CAR transgene perm of genomic DNA.
Figure 9B:
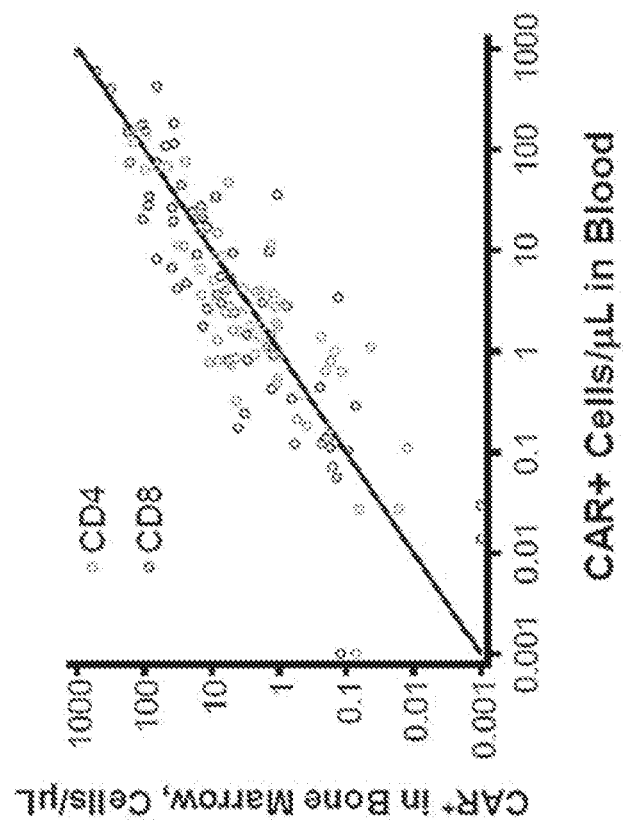
FIG. 9B depicts the relative numbers of CD4$^+$ and CD8$^+$ CAR-expressing cells/μL in blood and bone marrow samples from 67 subjects that have been administered anti-CD19 CAR-expressing cells, on day 11±3 days. The line represents the line of unity and is not a regression line.

FIG. 9A shows detected numbers of CAR T cells per microliter of blood at various indicated time-points, as assessed by qPCR or flow cytometry. FIG. 9B shows CAR$^+$ cells per microliter of blood versus microliter of bone marrow at day 11±3. As shown in FIG. 9A, levels of CAR-expressing cells in samples from subjects were observed both by flow cytometry-based assays and qPCR-based assays. As shown in FIG. 9B, all subjects (n=86 and 85 for flow cytometry and qPCR, respectively, excluding one patient that did not have flow cytometry results available and 2 patients that did not have qPCR results available) with PK results assessed, showed detectable numbers of the CAR-expressing cells in the blood and bone marrow. Results were consistent with an observation that CAR+ T cells had trafficked similarly to the bone marrow and blood.

Figure 10B:
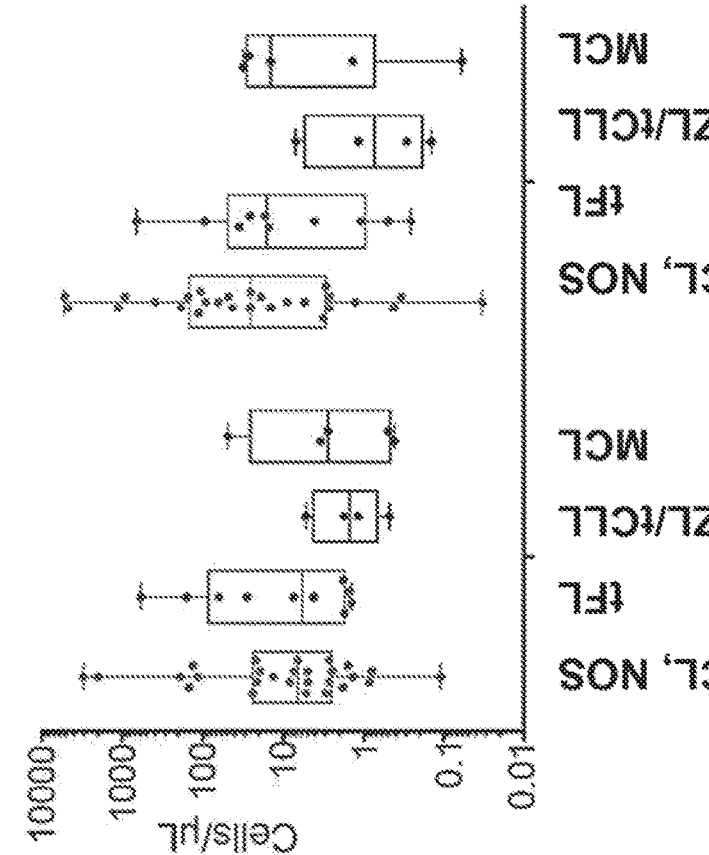
FIGS. 10A and 10B depict the median (±quartiles) area under the curve between days 0 and 28 (AUC$_{0-28}$.
Figure 10B:
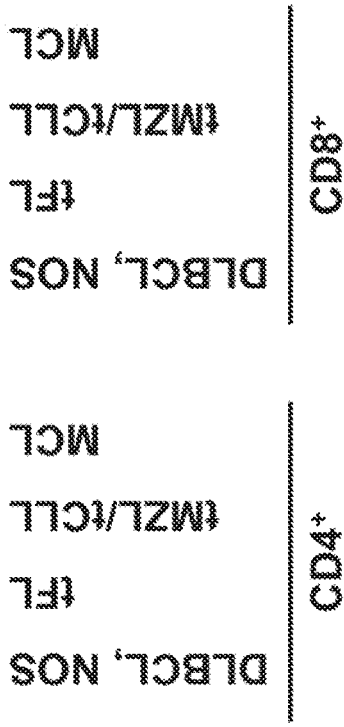
Figure 10A:
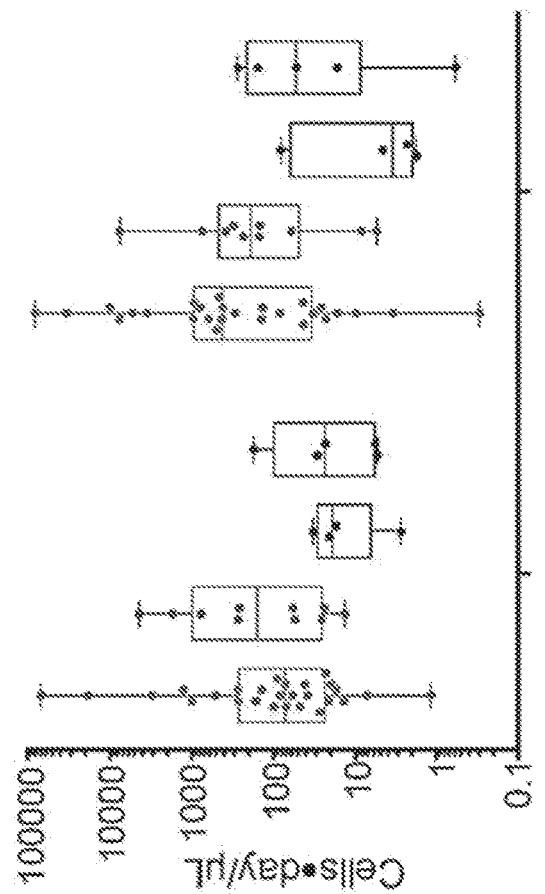
Figure 10A:
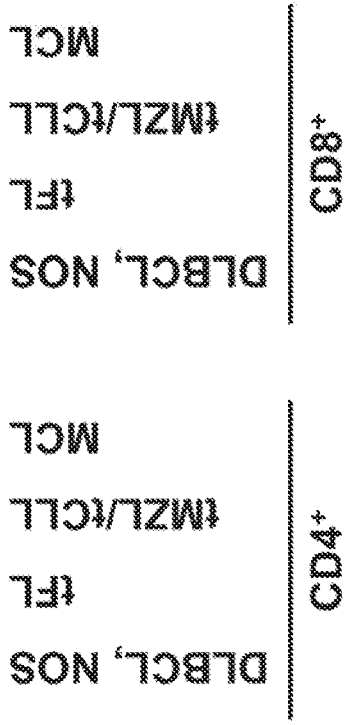

Levels over time of CD4+ and CD8+ CAR-expressing cells (as assessed by $AUC_{0-28}$ and $C_{max}$) were compared in different patient subgroups receiving dose level 1 (DL1): diffuse large B-cell lymphoma de novo (DLBCL, NOS) or transformed from follicular lymphoma (tFL) (CORE; N=32), DLBCL transformed from marginal zone lymphoma or chronic lymphocytic leukemia (tMZL/tCLL; N=4), or mantle cell lymphoma (MCL; N=5), who had received CAR-expressing T cells at DL1. As shown in FIGS. 10A and 10B, $AUC_{0-28}$ and $C_{max}$ varied among subjects in different disease subgroups, with expansion of CD4+ and CD8+ CAR-expressing cells trending lower in non-CORE subsets. PMBCL (n=2) and FL3B (n=1) not shown due to limited patient numbers. Expansion in subjects receiving DL2 was similar to in subjects receiving DL 1.

Figure 11A:
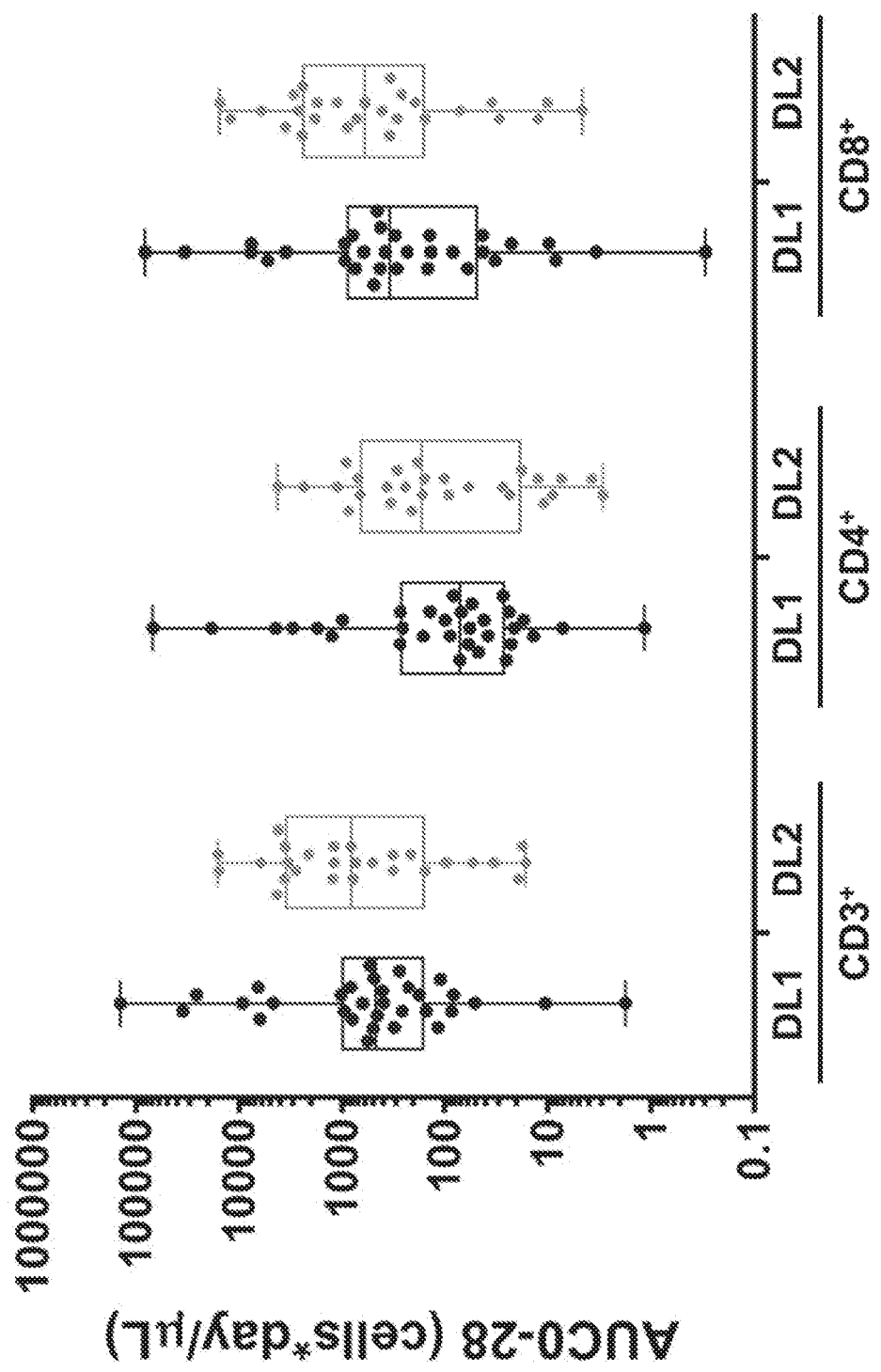
FIGS. 11A and 11B depict the median (±quartiles) area under the curve between days 0 and 28 (AUC$_{0-28}$.
Figure 11B:
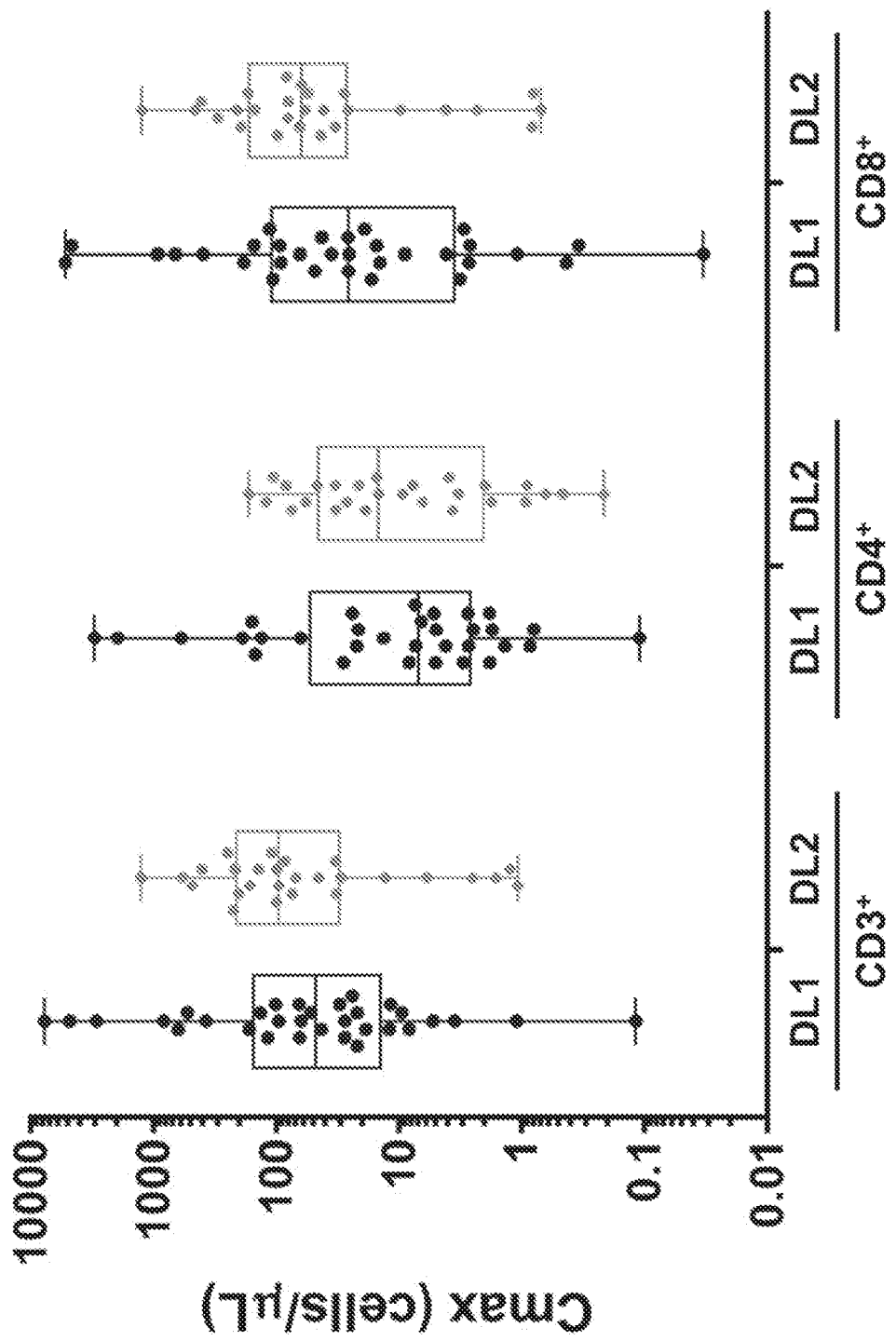
Figures 12C, 12D:
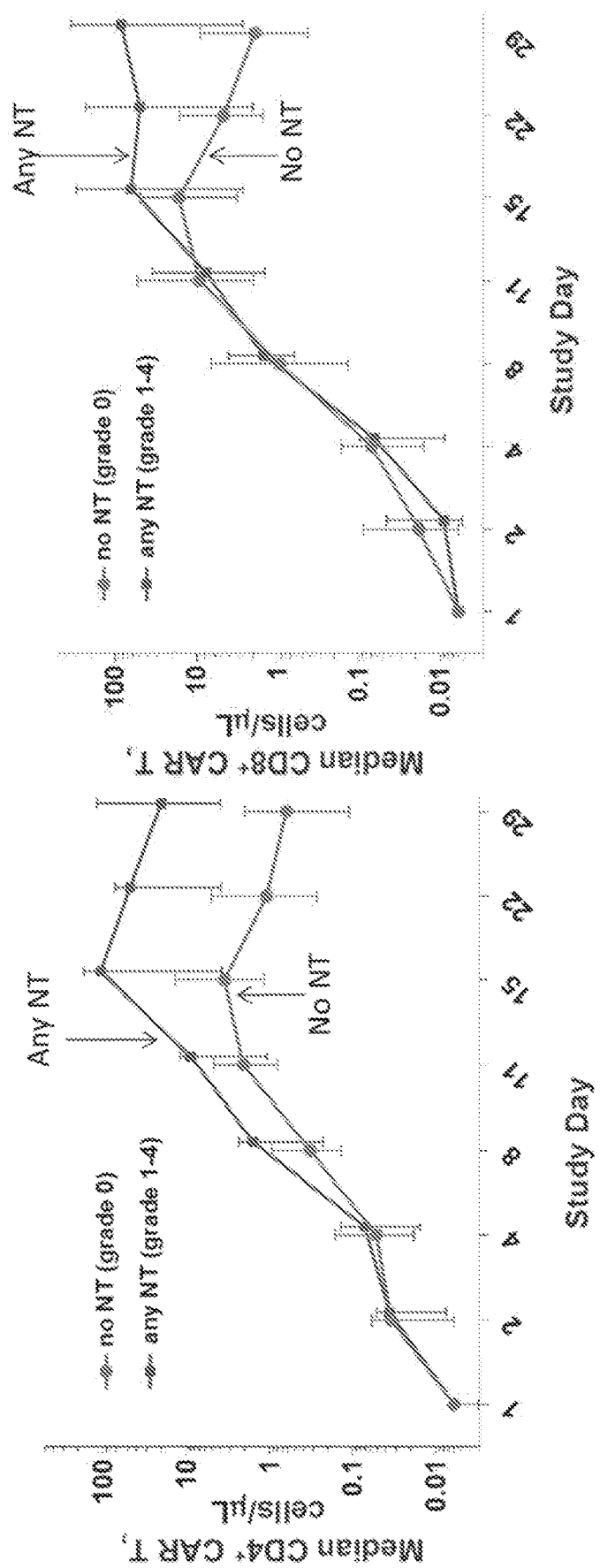

E. Pharmacokinetic Assessment by Dose Level $AUC_{0-28}$ and $C_{max}$ for CD3+, CD4+ and CD8+ CAR-expressing cells were also compared for subjects having received dose level 1 (DL1; n=32) and those having received dose level 2 (DL2; n=27), in the CORE cohort (subjects with DLBCL, NOS or high grade B-cell lymphoma (double/triple hit); N=59). As shown in FIGS. 11A and 11B and in Table E11, a higher median $AUC_{0-28}$ was observed for CD3+, CD4+ and CD8+ CAR-expressing cells was observed in subjects that received DL2, compared to subjects who had received DL 1. Similarly, a trend of higher expansion in subjects who had received DL2 was observed in the full DLBCL cohort. A higher durability of response (DOR) at 3 months also was observed among subjects who had received DL2 as compared to those having received DL1, without an increase in toxicity. The median time to $C_{max}$ ($T_{max}$) for CD4+ and CD8+ CAR+ cells was similar between subjects who received DL1 and DL2.

Increased CAR+ T cell exposure was observed in DL2 versus DL1, corresponding to an increased durability of response without increased toxicity in DL2 subjects.

TABLE E11

Pharmacokinetics in Subjects Grouped by Dose Levels in Core cohort

|  | DL1S (n = 32) | DL2S (n = 27) | Total, DL1S and DL2S (n = 59) |
|---|---|---|---|
| CD3+ | | | |
| $C_{max}$, median (cells/μL) | 48.2 | 96.2 | 65.8 |
| Q1, Q3 | 15.6, 151.3 | 30.2, 219.5 | 19.0, 204.2 |
| Min, max | 0.1, 7726.3 | 1.1, 1280.9 | 0.1, 7726.3 |
| $T_{max}$, median (days) | 14.5 | 15.0 | 15.0 |
| Q1, Q3 | 11, 15 | 11, 15 | 11, 15 |
| Min, max | 9, 24 | 8, 31 | 8, 31 |
| $AUC_{0-28}$, median (cells*day/μL) | 477.7 | 823.1 | 542.4 |
| Q1, Q3 | 165.9, 999.3 | 155.8, 3628.3 | 155.8, 3381.9 |
| Min, max | 1.8, 142816.7 | 16.5, 16087.8 | 1.8, 142816.7 |
| CD4+ | | | |
| $C_{max}$, median (cells/μL) | 7.0 | 14.9 | 7.7 |
| Q1, Q3 | 2.6, 46.0 | 2.0, 46.8 | 2.5, 46.8 |
| Min, max | 0.1, 3039.9 | 0.2, 169.4 | 0.1, 3039.9 |
| $T_{max}$, median (days) | 14.0 | 15.0 | 15.0 |
| Q1, Q3 | 11, 15 | 11, 15 | 11, 15 |
| Min, max | 8, 24 | 8, 31 | 8, 31 |
| $AUC_{0-28}$, median (cells*day/μL) | 71.1 | 166.1 | 91.5 |
| Q1, Q3 | 26.4, 274.7 | 18.1, 679.0 | 23.9, 368.8 |
| Min, max | 1.2, 68990.3 | 2.9, 4266.8 | 1.2, 68990.3 |
| CD8+ | | | |
| Cmax, median (cells/μL) | 26.1 | 62.8 | 43.6 |
| Q1, Q3 | 3.7, 111.2 | 26.2, 171.7 | 9.1, 151.6 |
| Min, max | 0.0, 5237.6 | 0.7, 1261.8 | 0.0, 5237.6 |
| $T_{max}$, median (days) | 15.0 | 15.0 | 15.0 |
| Q1, Q3 | 11, 16 | 11, 17 | 11, 16 |
| Min, max | 4, 28 | 8, 31 | 4, 31 |
| $AUC_{0-28}$, median (cells*day/μL) | 347.2 | 606.6 | 412.2 |
| Q1, Q3 | 52.1, 871.4 | 155.7, 2463.4 | 72.1, 1852.5 |
| Min, max | 0.3, 81865.9 | 4.7, 15570.0 | 0.3, 81865.9 |

F. Persistence

Persistence of CAR-expressing cells and CD19+ B cell aplasia (low numbers or absence of CD19+ B cells) was assessed at various time points in evaluable subjects with DLBCL that had been administered CAR+ T cells, based on detectable CD3+, CD4+ or CD8+ CAR-expressing cell levels and levels of CD19+ B-cells detected in the blood, respectively. The results are set forth in Table E12. Among subjects evaluated at progression (time of progression regardless of BOR; n=37), a median of 0.17 CD4+ CAR+ cells/μL (range, 0-65.5 cells/μL) and a median of 0.15 CD8+ CAR+ cells/μL (range, 0-131.8 cells/µL) were observed at progression. Among subjects evaluated at relapse (at the time of progression after achieving CR) (n=12), a median of 0.17/µL (range, 0-35.1 cells/µL) CD4+ CAR-expressing cells and a median of 0.20 cells/µL (range, 0-131.8 cells/µL) CD8+ CAR-expressing cells were observed at relapse Long-term persistence of CAR-expressing cells was observed in 75% of evaluable subjects with DLBCL at 12 months. Long-term persistence of B cell aplasia also was observed in 75% of the subjects at 12 months, and in subjects regardless of relapse status. The results are consistent with a conclusion that the anti-CD19 CAR-expressing cells exhibited long-term persistence in most subjects, and suggest the potential for ongoing, low-level disease control even in relapsed patients.

Of subjects who relapsed, 91.7% (11/12) had detectable CAR-expressing cells in the blood at the time of relapse. This result is consistent with a conclusion that a combination therapy or other intervention in some embodiments may be used to augment and/or boost CAR-expressing cells such as those that may be exhausted.

TABLE E12

CAR+ Cell Long-Term Persistence and CD19 Aplasia

| | Month 3 | Month 6 | Month 9 | Month 12 | At Progression | At Relapse |
|---|---|---|---|---|---|---|
| CAR T persistence in evaluable patients, n | 50 | 30 | 18 | 12 | 37 | 12 |
| CD3+, % | 100 | 80.0 | 77.8 | 75.0 | 91.9 | 91.7 |
| CD4+, % | 88.0 | 63.3 | 50.0 | 41.7 | 83.8 | 83.3 |
| CD8+, % | 90.0 | 70.0 | 55.6 | 50.0 | 83.8 | 75.0 |
| CD19+ B-cell aplasia (<1 cell/µL), % | 96.0 | 93.3 | 77.8 | 75.0 | 97.3 | 100 |

G Pharmacokinetic Assessment and Toxicity $AUC_{0-28}$ and $C_{max}$ of CD4+ and CD8+ CAR-expressing cells was also compared for subjects in the core cohort with any grade (in this assessment, any of grade 1-4; no grade 5 CRS or NT observed) cytokine release syndrome (CRS) or neurotoxicity (NT) to subjects that were not assessed as exhibiting any grade of CRS or NT. The median CD4+ CAR+ $AUC_{0-28}$ (Q1, Q3) was 59 (18, 210) for no CRS (grade 0; n=43), and 267 (91, 1510) for any CRS (grades 1-4; n=20) (p=0.001); the median CD8+ CAR+ $AUC_{0-28}$ (Q1, Q3) was 310 (36, 900) for no CRS (grade 0; n=43), and 605 (174, 5619) for any CRS (grades 1-4; n=20) (p=0.021); the median CD4+ CAR+ $AUC_{0-28}$ (Q1, Q3) was 71 (23, 244) for no NT (grade 0; n=50), and 1269 (184, 3057) for any NT (grades 1-4; n=13) (p=0.003); the median CD8+ CAR+ $AUC_{0-28}$ (Q1, Q3) was 304 (43, 799) for no NT (grade 0; n=50), and 2463 (607, 7691) for any NT (grades 1-4; n=13) (p=0.004). As described above and shown in FIGS. 12A-12D, higher CD4+ and CD8+ CAR-expressing cell levels over time were associated with CRS and NT.

H. Pharmacokinetic Assessment and Response

Figure 13A:
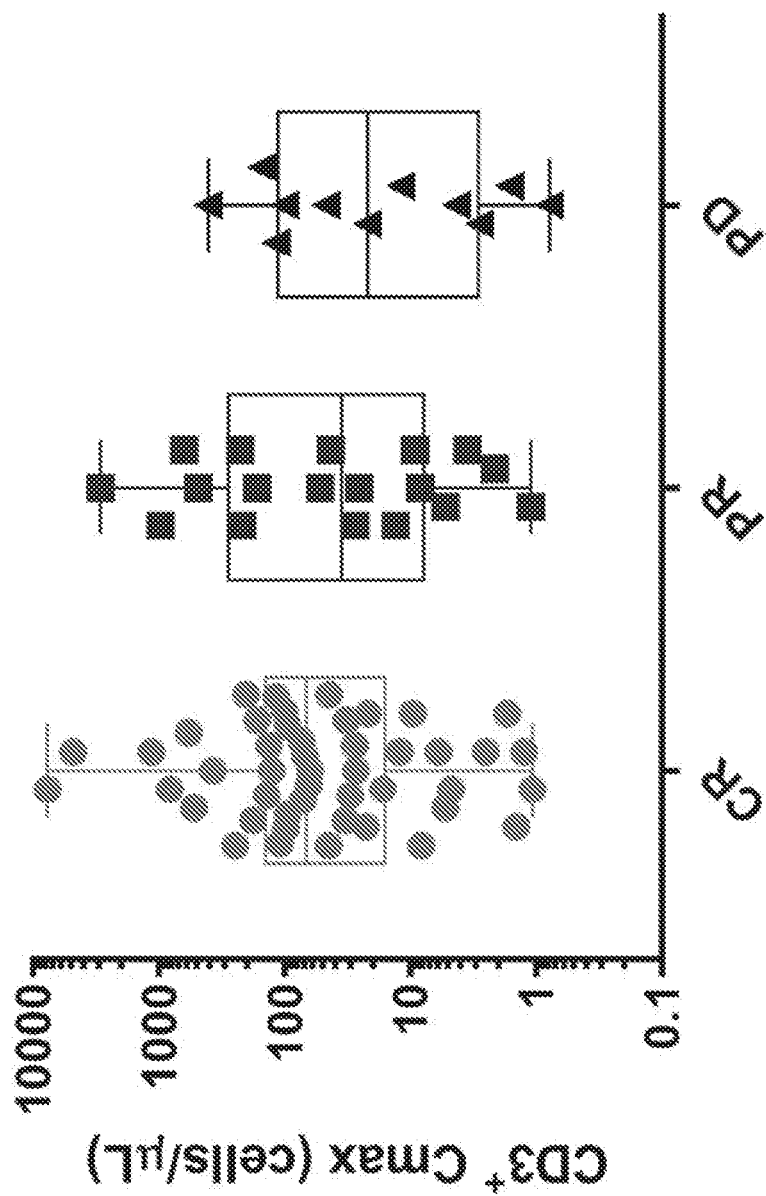
FIGS. 13A and 13B depict the number of peak CD3$^+$ CAR$^+$ cells/μL, (CD3$^+$ C$_{max}$) in subjects grouped by subjects who had the best overall response (BOR) of CR, PR or PD, or a 3-month (M3) durable response of CR, PR or PD.
Figure 13B:
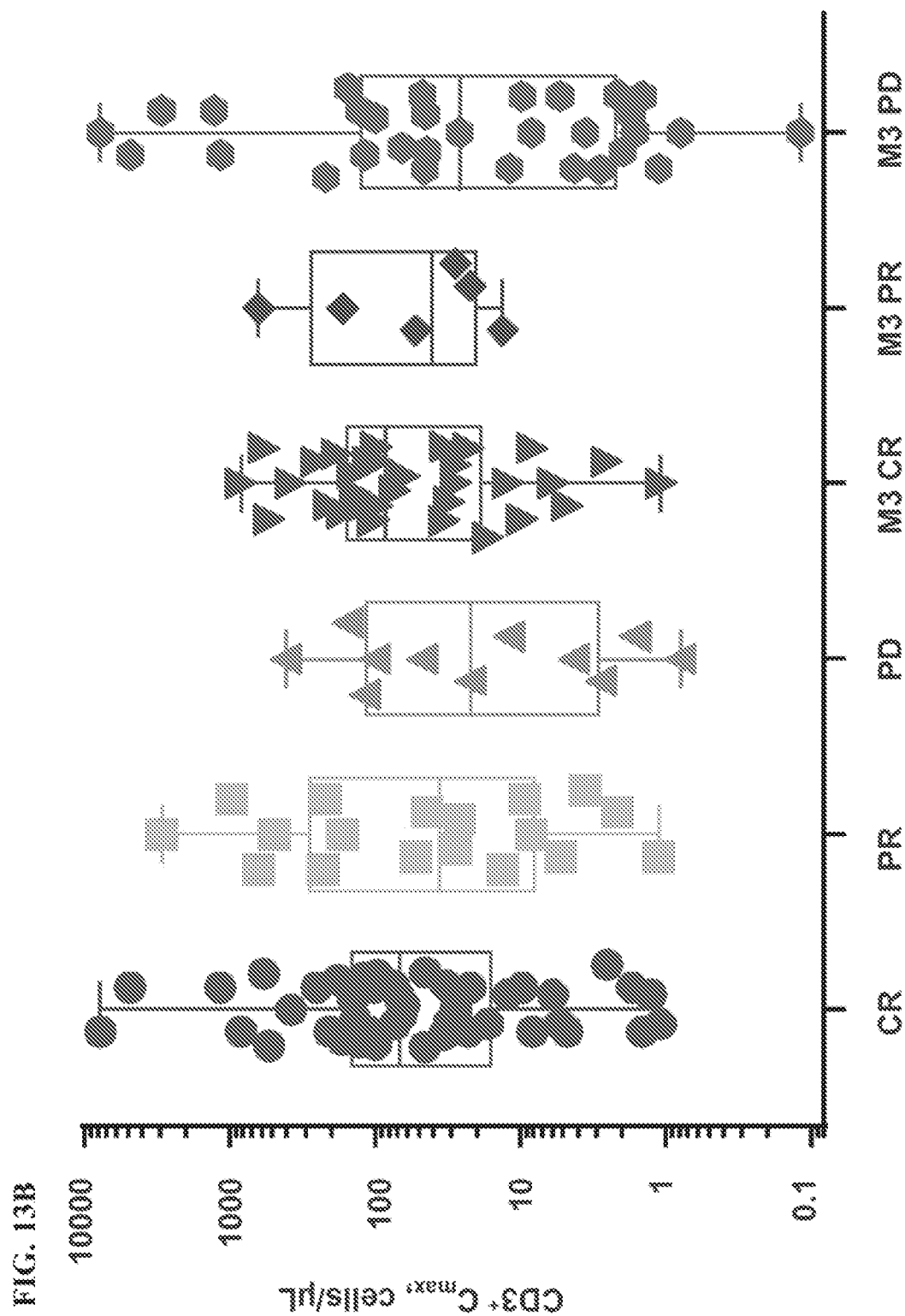

The number of peak CD3+ CAR+ cells/µL, (CD3+ $C_{max}$) was assessed over time in subjects who had a best overall response (BOR) of CR, PR or PD. As shown in FIGS. 13A and 13B, a trend towards better BOR was observed in subjects with higher expansion, with variability among subjects.

I. Pharmacokinetic Assessment by Blood Analytes and Patient Parameters

Figure 14A:
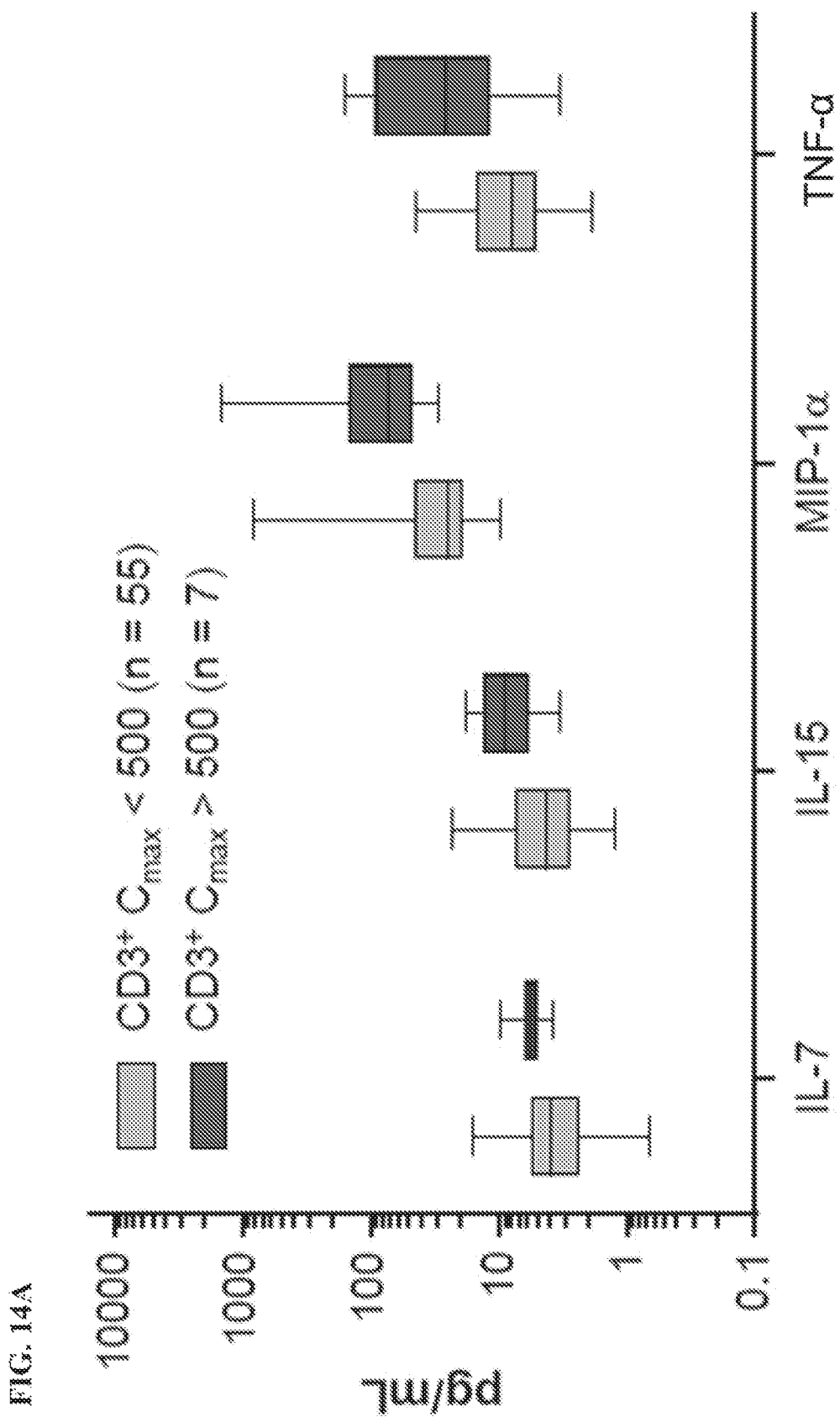
FIG. 14A depicts pre-lymphodepletionblood analyte levels in serum samples from subjects that exhibited high CAR$^+$ cell expansion (CD3$^+$ C$_{max}$>500) and subjects that exhibited low CAR$^+$ cell expansion (CD3$^+$ C$_{max}$<500).

Pre-CAR+ T cell treatment (pre-lymphodepleting chemotherapy) plasma cytokine levels, including interleukin-7 (IL-7), IL-15, macrophage inflammatory protein (MIP-1a), were assessed in subjects that exhibited a CAR+CD3+ blood $C_{max}$>500 CAR+ T cells/µL (N=55) as compared to in subjects that exhibited CAR+CD3+ blood $C_{max}$<500 CAR+ T cells/µL (N=7). As shown in FIG. 14A, elevated pre-CAR+ T cell treatment cytokine plasma levels were observed to be associated with CAR+CD3+ $C_{max}$>500 CAR+ T cells/µL (Wilcoxon P values <0.05 (without multiplicity of adjustment); except for IL-7 p=0.07).

Figure 14B:
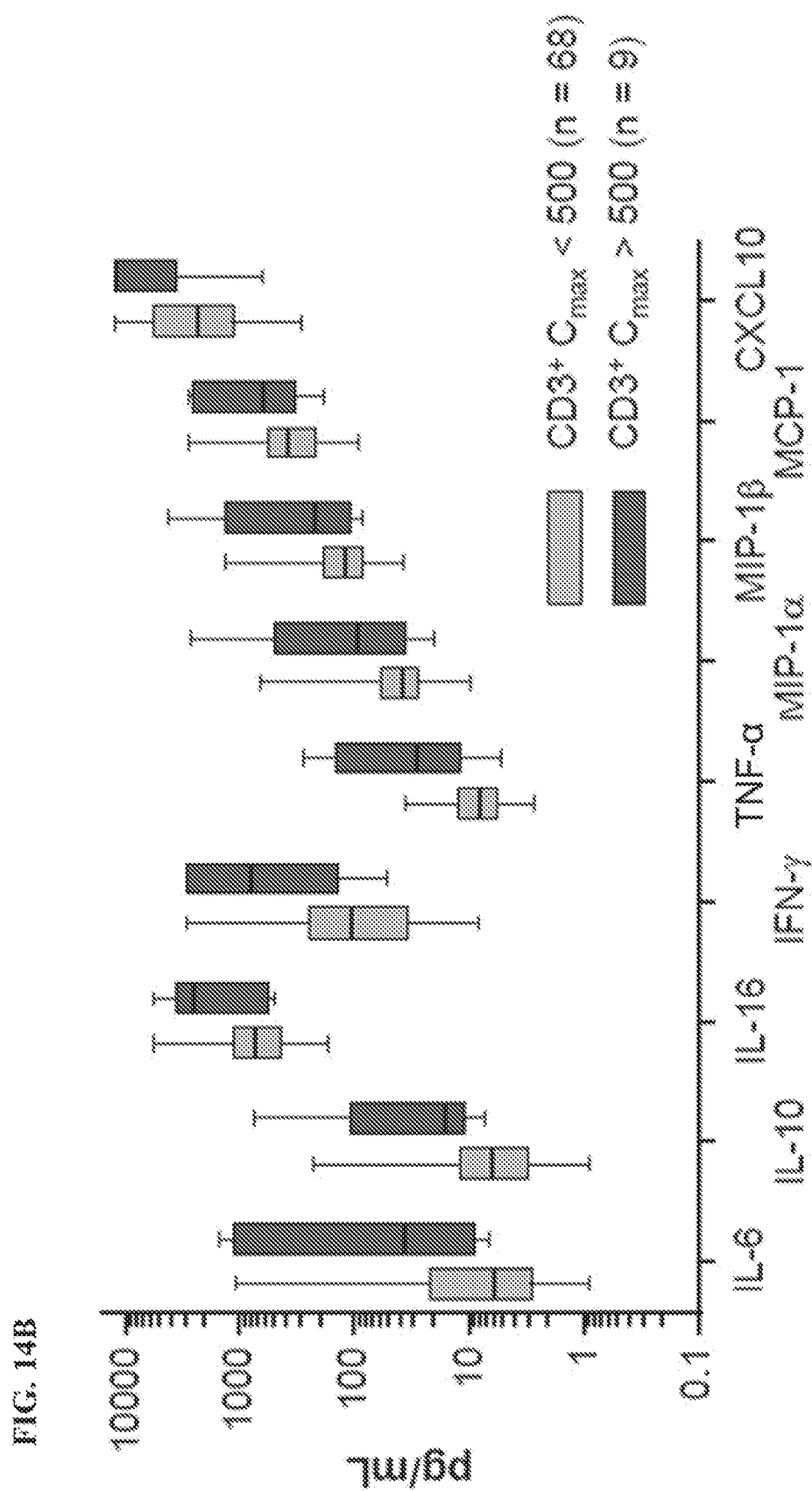
FIG. 14B depicts the peak blood analyte levels in serum samples from subjects that exhibited high CAR$^+$ cell expansion (CD3$^+$ C$_{max}$>500) and subjects that exhibited low CAR$^+$ cell expansion (CD3$^+$ C$_{max}$<500).

Peak levels of various plasma cytokines (IL-6, IL-10, IL-16, interferon gamma (IFN-γ), tumor necrosis factor alpha (TNF-α), MIP-1α, MIP-1β, Monocyte chemoattractant protein-1 (MCP-1), and C-X-C motif chemokine 10 (CXCL10)) were also assessed in subjects that exhibited CAR+ CD3+ blood $C_{max}$>500 CAR+ T cells/µL (N=68) as compared to subjects that exhibited CAR+ CD3+ blood $C_{max}$<500 CAR+ T cells/µL; N=9). As shown in FIG. 14B, higher peak cytokine levels were observed to be associated with CAR+CD3+$C_{max}$>500 CAR+ T cells/µL (Wilcoxon P values <0.05; without multiplicity of adjustment).

Figure 15:
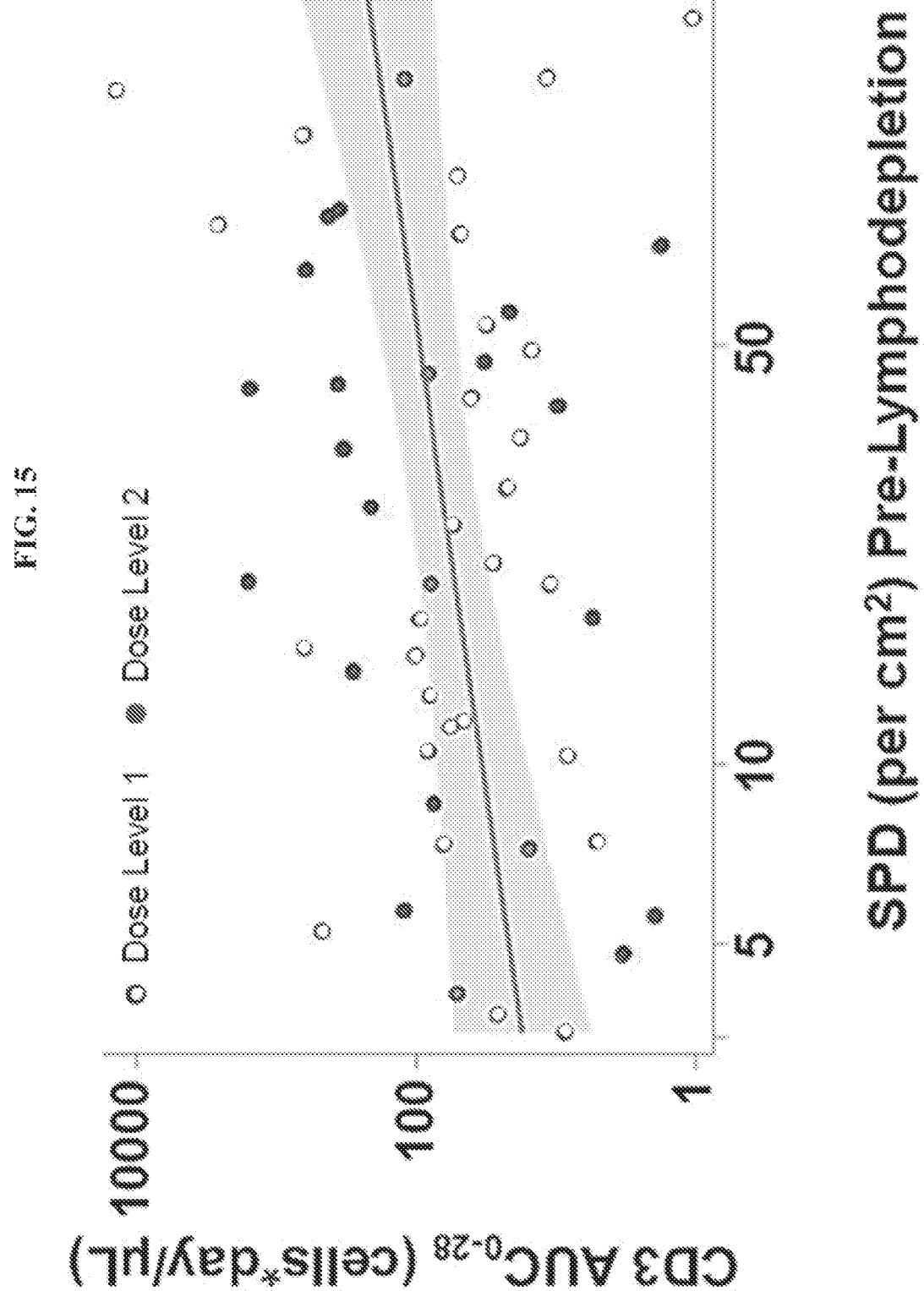
FIG. 15 depicts a plot depicting pre-lymphodepletion SPD (cm$^2$) against AUC$_{0-28}$ (cells*day/μL) of CD3$^+$ CAR$^+$ cells, for individual subjects administered DL1 or DL2 of CAR$^+$ cells.

Relationship between pre-CAR+ T cell treatment (pre-lymphodepleting chemotherapy (LDC)) volumetric tumor measurement sum of product dimensions (SPD), as an indicator of tumor burden, and $AUC_{0-28}$ of CD3+ CAR+ T cells, representing CAR+ T exposure over time, was assessed. As shown in FIG. 15, a positive correlation was observed between baseline SPD and CD3+ $AUC_{0-28}$, with a Spearman correlation of 0.32 and p=0.019.

J. Pre-Treatment Patient Parameters and Response and Toxicity Outcomes

Figure 16A:
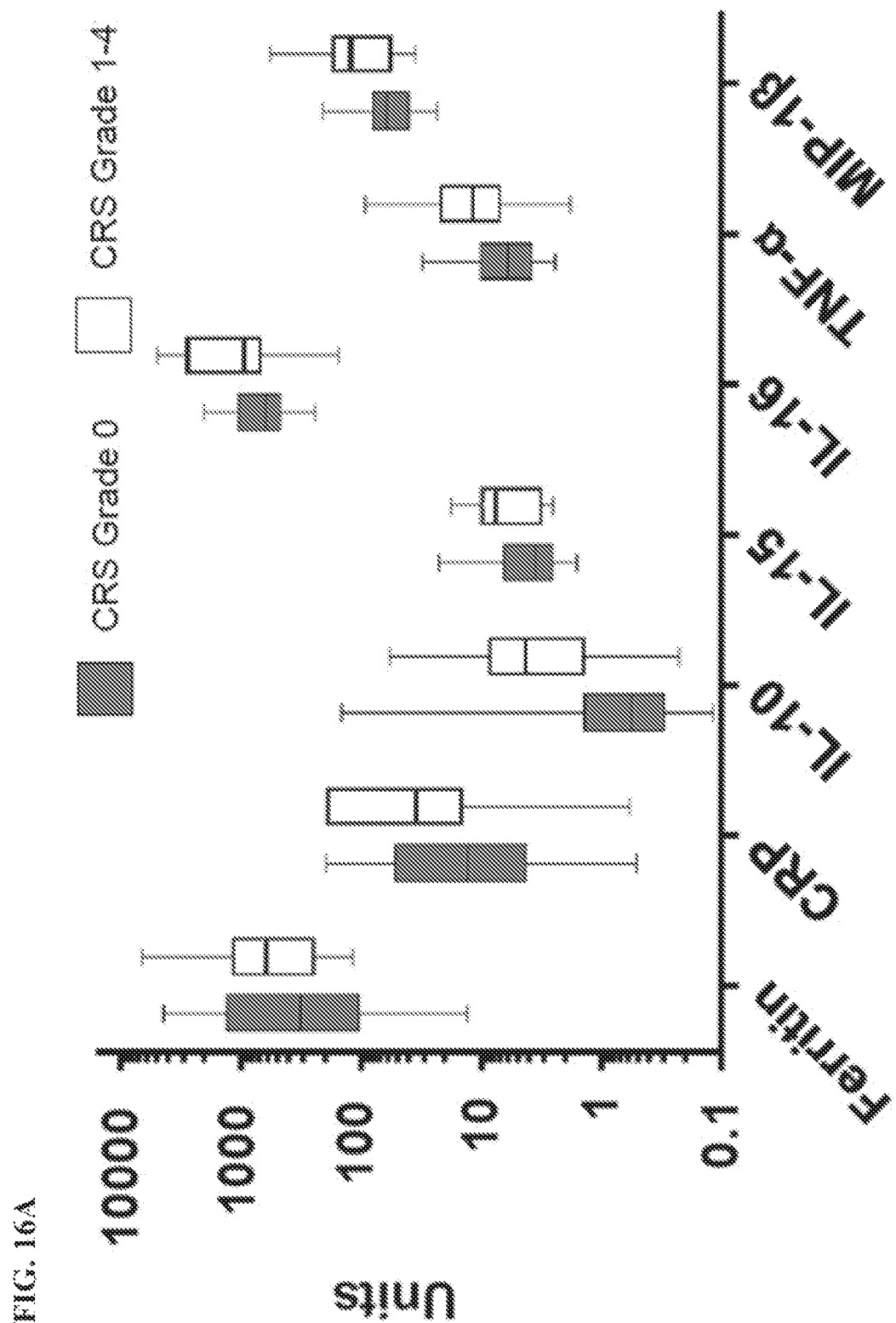
FIGS. 16A and 16B depict pre-lymphodepletion blood analyte levels in serum samples from subjects that developed cytokine release syndrome (CRS grade 1-4) compared to subjects that have not developed CRS (CRS grade 0) (FIG. 16A) or in subjects that developed neurotoxicity (NT grade 0) compared to subjects that have not developed NT (NT grade 1-4) (FIG. 16B). The units were: Ferritin and D-dimer (μg/L); CRP (mg/L) and cytokines (pg/mL).
Figure 16B:
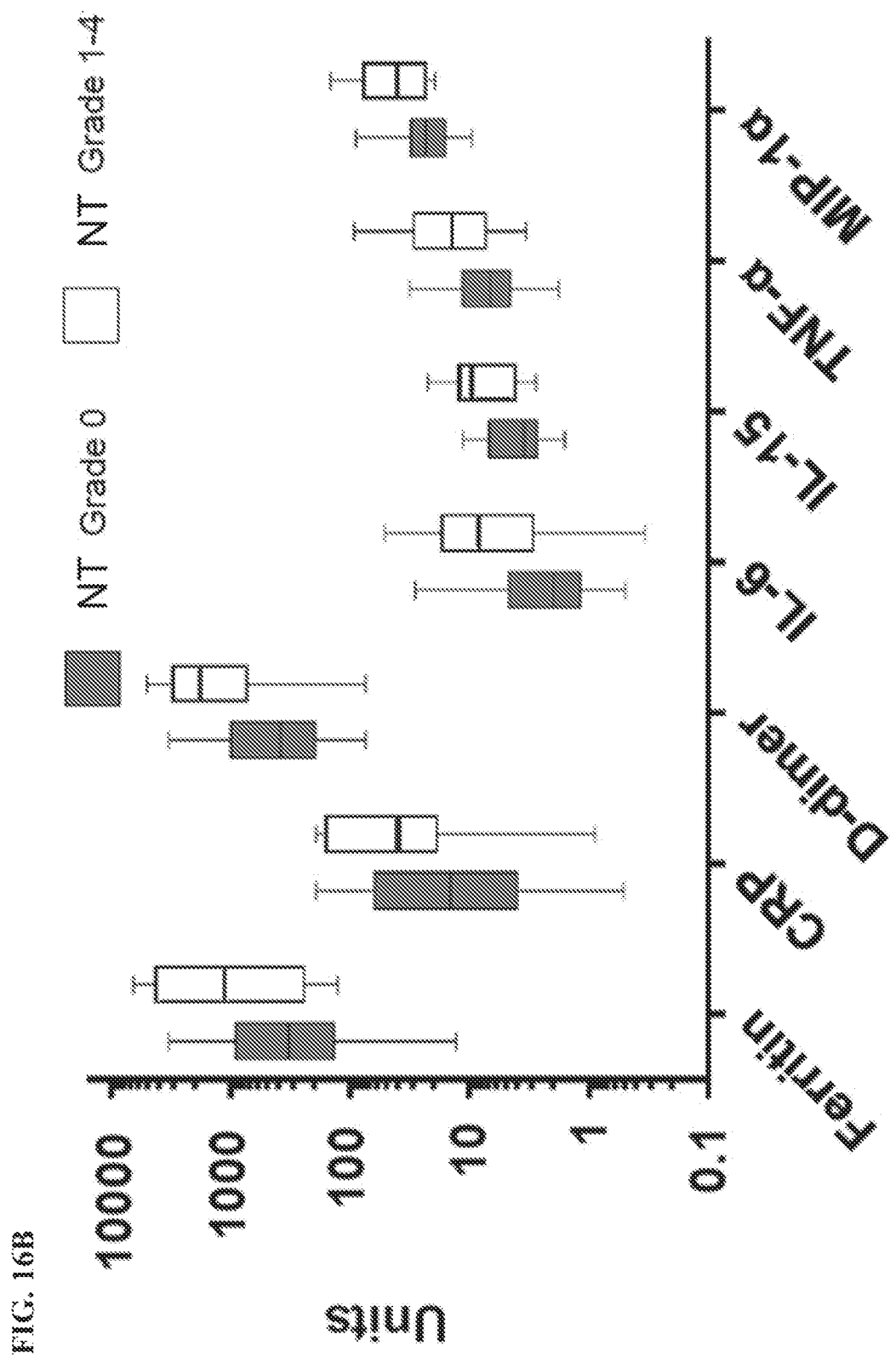

Pre-CAR+ T cell treatment (pre-LDC) analyte levels, including cytokines and inflammatory markers such as Ferritin, C-reactive protein (CRP), D-dimer (fibrin degradation product), IL-6, IL-10, IL-15, IL-16 TNF-α, MIP-1α, and MIP-1β, were compared for subjects with any grade (here, grade 1-4) cytokine release syndrome (CRS) or neurotoxicity (NT) to subjects that did not have any CRS or NT (grade 0). In this cohort, among subjects with CRS grade 1-4, all but one CRS events were determined to be grade 1 or 2. As shown in FIG. 16A (CRS) and FIG. 16B (NT), higher peak plasma cytokine levels and inflammatory marker levels were observed to be associated with CRS and NT, based on univariate analysis (Wilcoxon P values <0.05 for all analytes except ferritin for CRS (p=0.14) and CRP for CRS (p=0.09)). For CRS, after adjusting tumor burden in a multivariable analysis, MIP-1β, IL-10 and TNF had p<0.05; for NT, IL-15, IL-6, MIP-1α, and TNF had p<0.05.

Figure 17:
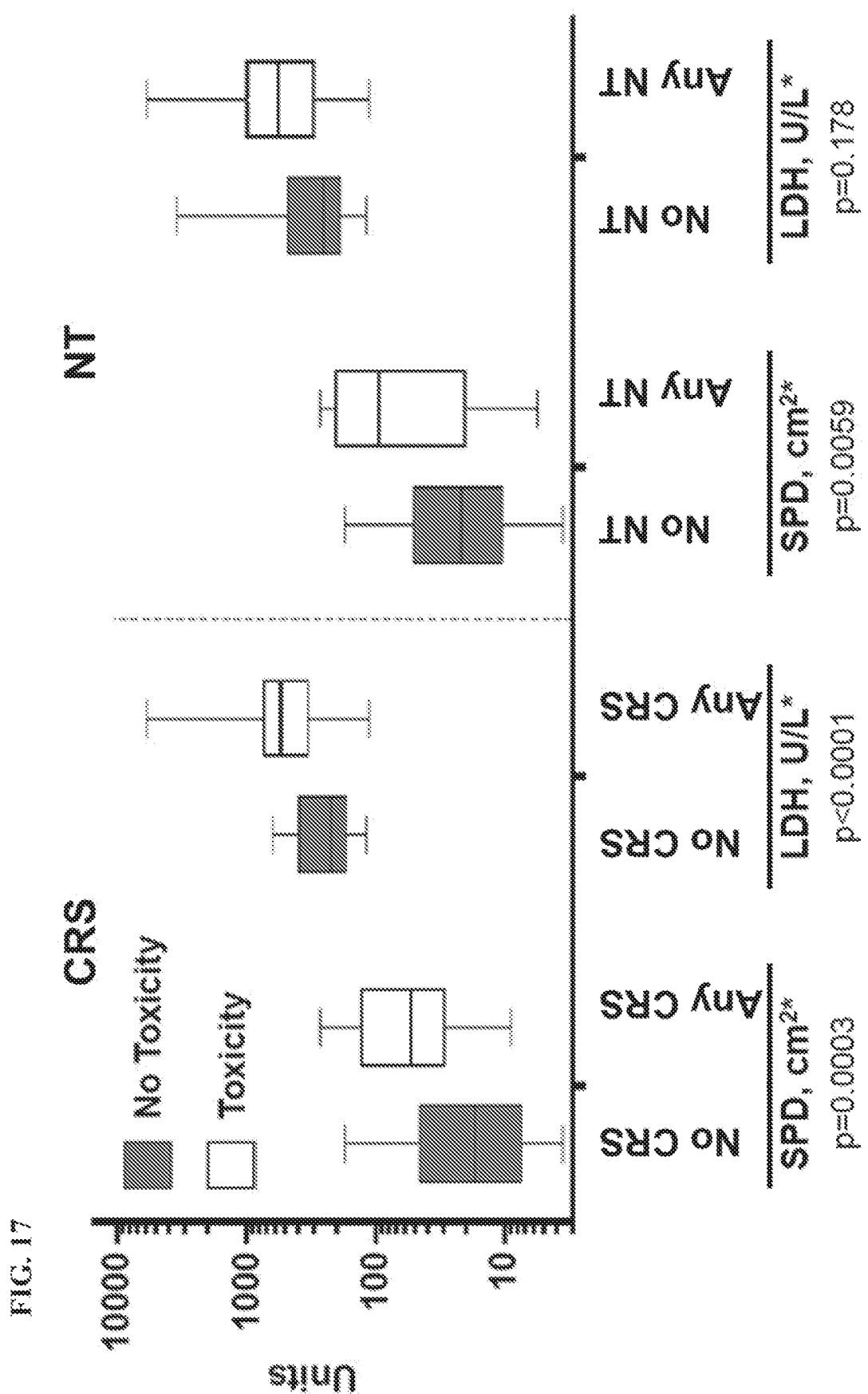
FIG. 17 depicts the assessment of pre-lymphodepletion patient parameter sum of product dimensions (SPD; cm$^2$), indicative of tumor burden, and lactate dehydrogenase (LDH; U/L) level, in subjects that developed cytokine release syndrome (any CRS) compared to subjects that have not developed CRS (no CRS) or in subjects that developed neurotoxicity (any NT) compared to subjects that have not developed NT (no NT).

Pre-treatment (pre-LDC) patient parameters, such as levels of lactate dehydrogenase (LDH) and a volumetric tumor measurement such as sum of product dimensions (SPD), as an indicator of tumor burden, were compared between subjects that were not observed to have developed CRS or neurotoxicity versus subjects that were observed to have developed CRS or NT. As shown in FIG. 17, subjects with CRS or NT exhibited higher levels of pre-treatment patient parameters such as SPD (cm²) and LDH (U/L) levels; such levels were observed to be correlated with CRS or NT, with univariate statistical analysis. Other patient parameters that were observed to be associated with CRS and NT include shorter time since diagnosis (p=0.05 and p=0.09, for CRS and NT, respectively). Patient parameters that were observed not to be associated with CRS or NT included age (p=0.19 and p=0.54, respectively) and prior numbers of therapies (p=0.67 and p=0.59, respectively), disease stage 0-2 vs 3-4 (p=0.79, p=0.51), and patient weight (p=0.35 and p=0.44, respectively).

Figure 18A:
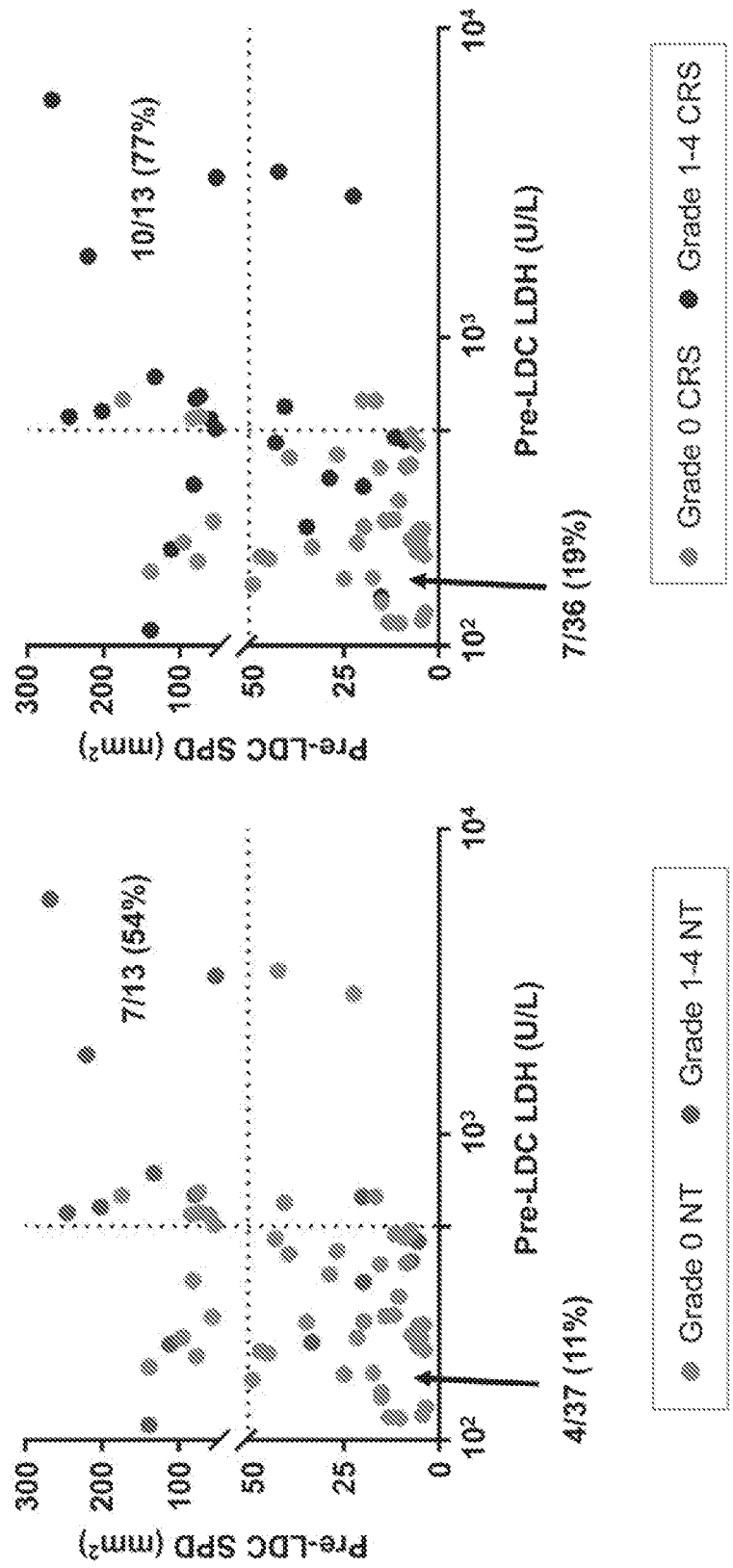
FIG. 18A is a plot depicting pre-lymphodepletion SPD (cm$^2$) against pre-lymphodepletion LDH (U/L) levels, in individuals that have developed neurotoxicity (Grade 1-4 NT) or subjects that have not developed NT (Grade 0 NT) (left panel), and in individuals that have developed CRS (Grade 1-4 CRS) or subjects that have not developed CRS (Grade 0 CRS) (right panel). Dotted lines represent levels of SPD (50 cm$^2$ or higher) or LDH (500 U/L or higher) that is associated with higher rates of CRS or NT.
Figure 18B:
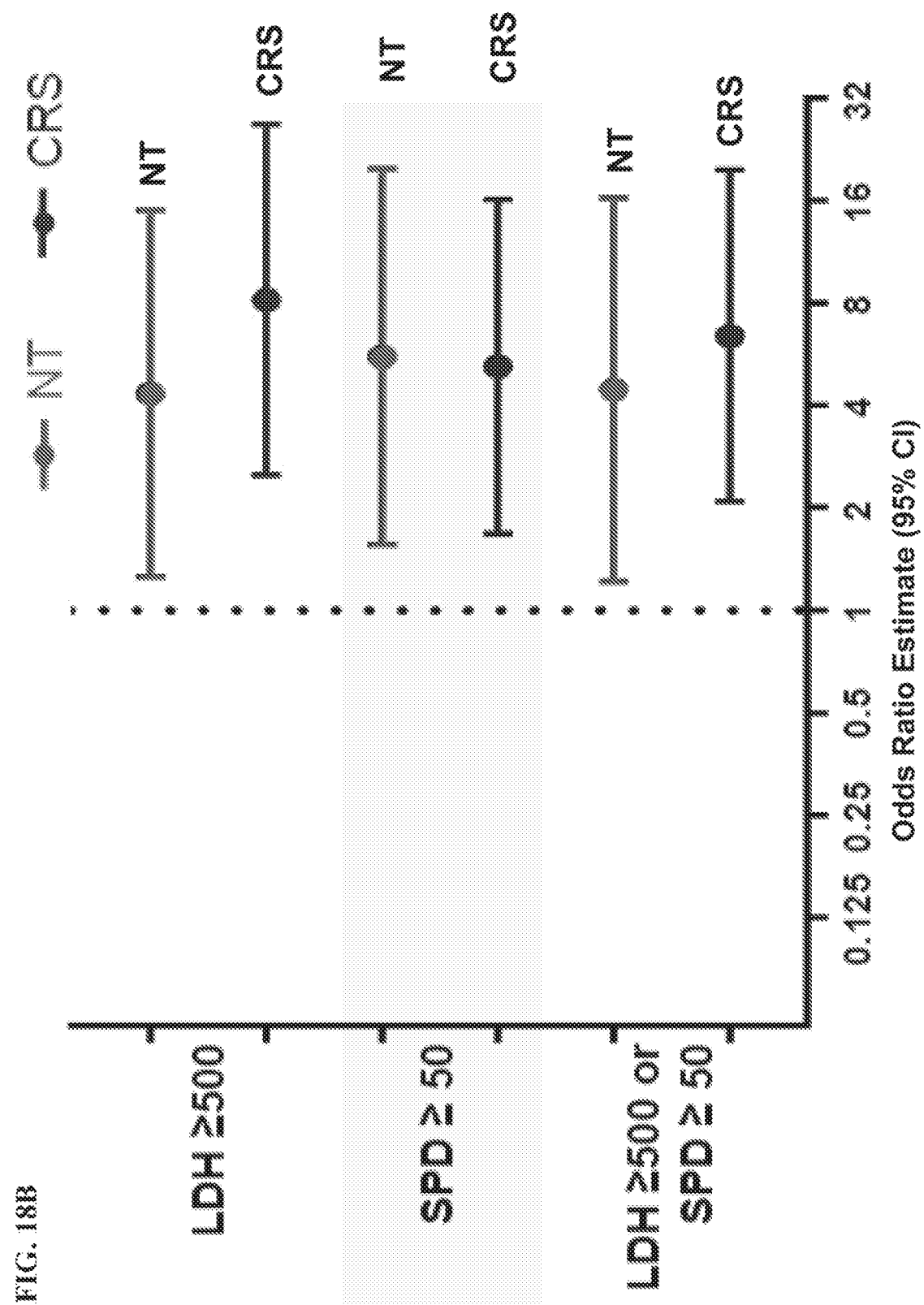
FIG. 18B depicts the odds ratio estimates for developing CRS or NT based on the levels of SPD (50 cm$^2$ or higher) or LDH (500 U/L or higher), with 95% confidence intervals (CI).
Figure 18C:
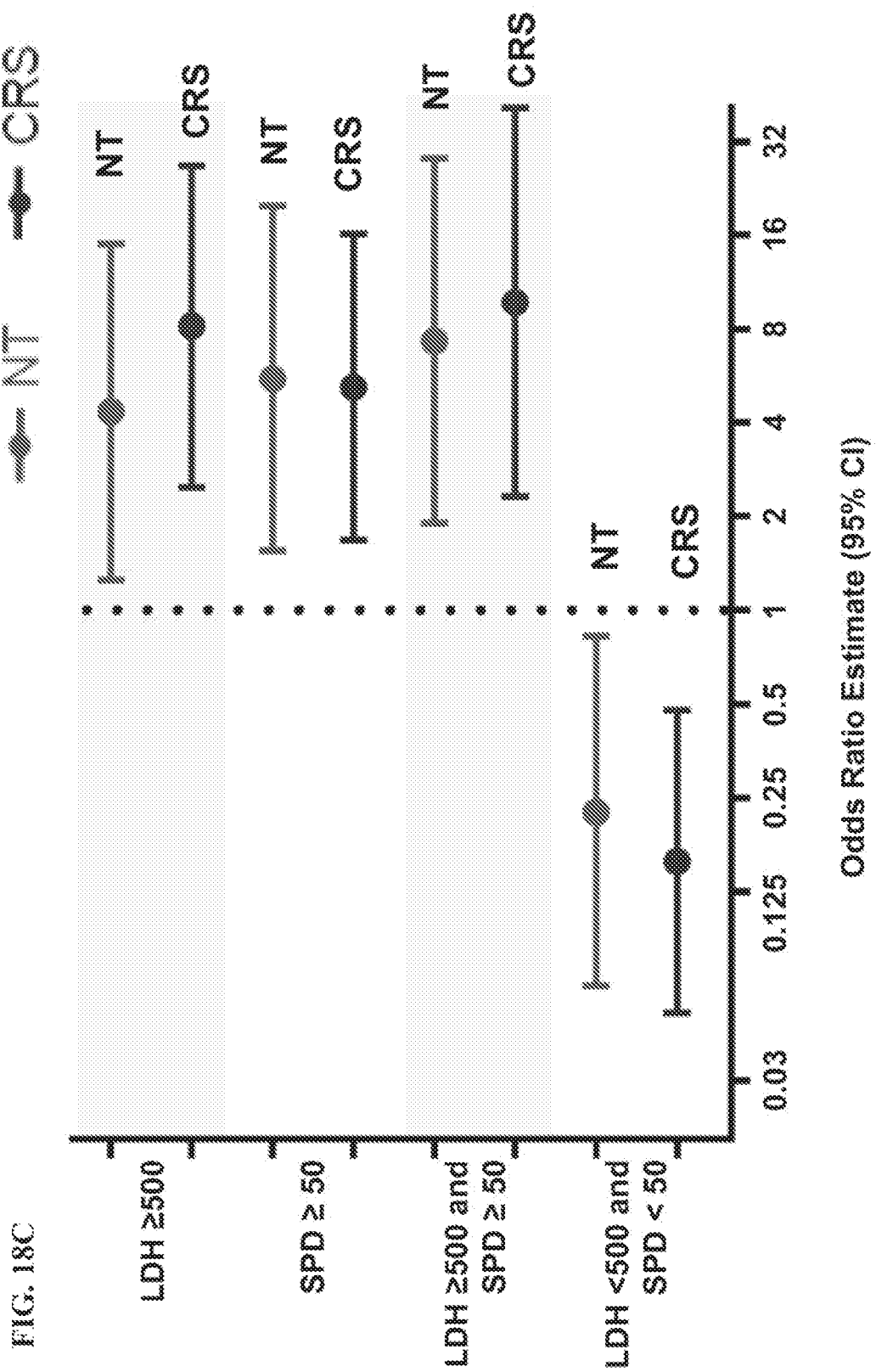
FIG. 18C depicts the odds ratio estimates for developing CRS or NT based on the levels of SPD or LDH, including the odds ratio estimates for values lower than the threshold, with 95% confidence intervals (CI).

FIG. 18A shows pre-treatment SPD and LDH levels among individual patients (dots; with shading of individual dots indicating whether the individual patients did or did and did not exhibit any grade neurotoxicity (left-hand panel) or did or did not exhibit any grade CRS (right-hand panel). In FIG. 18A, dotted lines on the y and x axes delineate SPD≥50 cm$^2$ and LDH≥500 U/L, respectively. As shown in FIG. 18A, an SPD of approximately 50 cm$^2$ or higher, and/or an LDH of approximately 500 U/L or higher, were observed to be associated with risk of NT and CRS. Calculated odds ratio estimates for developing CRS or NT in subjects above or below the SPD and LDH levels indicated by dotted lines in FIG. 18A, with 95% confidence intervals (CI), are depicted in FIGS. 18B and 18C. An odds ratio over 1 indicated an increased probability or likelihood of developing CRS or NT. As shown, SPD of 50 cm$^2$ or higher, and LDH of 500 U/L or higher, were observed to be associated with increased risk of developing CRS or NT. SPD of 50 cm$^2$ or higher and LDH of 500 U/L or higher was observed to be associated with an approximately 8-fold increased risk in developing any grade CRS and NT, and SPD of lower than 50 cm$^2$ and LDH of lower than 500 U/L showed a reduced risk of any grade CRS and NT. The results were consistent with an association of baseline patient parameters, including high tumor burden and inflammatory biomarkers, with CAR$^+$ T cell expansion and increased rates of CRS and neurotoxicity.

Figure 19:
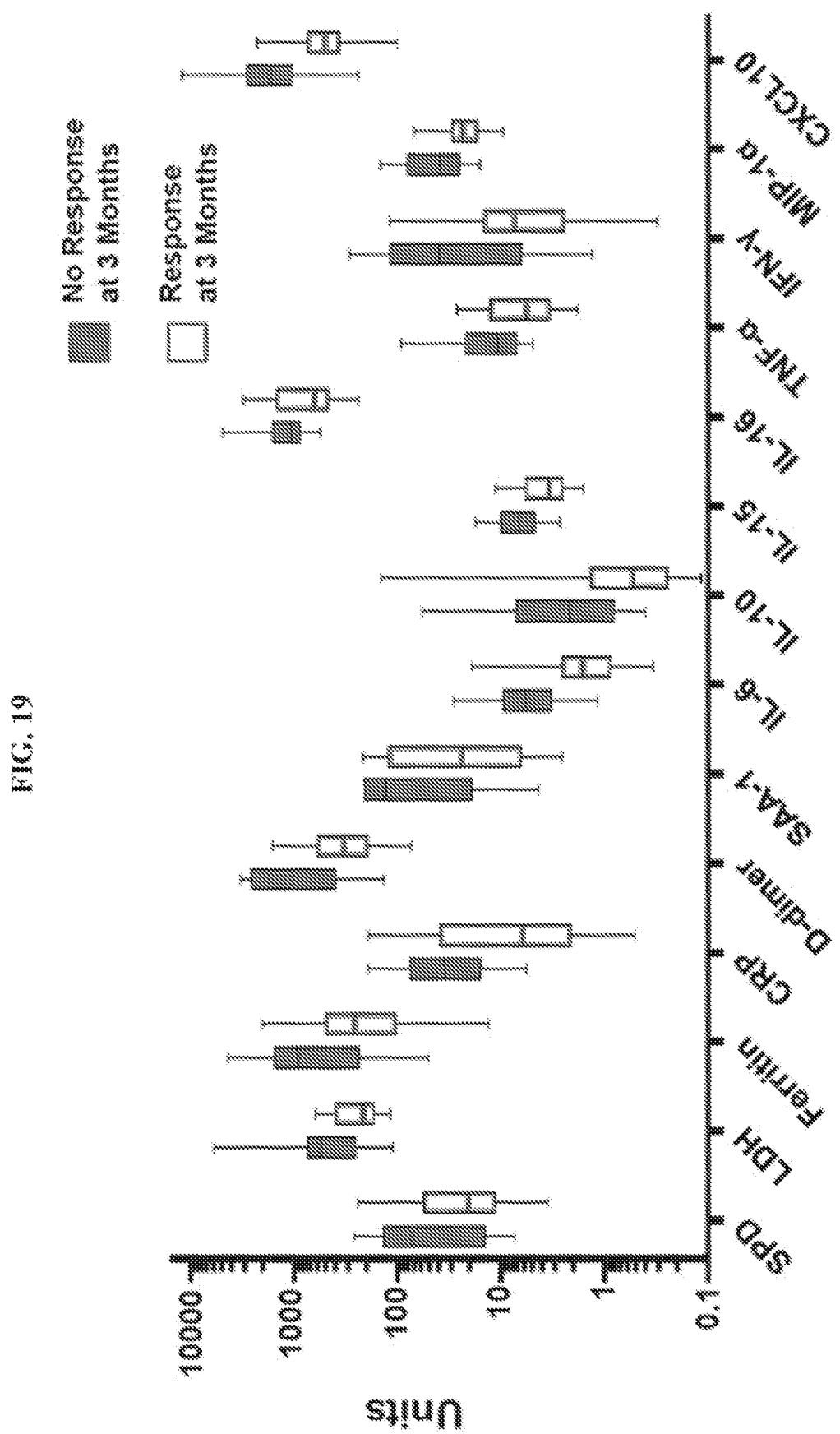
FIG. 19 depicts pre-lymphodepletion tumor burden parameter (SPD) and blood analyte levels in for subjects that had a durable response at 3 months versus for subjects that did not have a response at 3 months. The units were: Ferritin and D-dimer (μg/L); CRP and SAA-1 (mg/L) and cytokines (pg/mL).

Various pre-treatment (pre-LDC) patient parameters, including markers associated with tumor burden (SPD), inflammatory cytokines and other blood analytes, including LDH, ferritin, CRP, D-dimer, SAA-1, IL-6, IL-10, IL-15, IL-16, TNF-α, IFN-γ, MIP-1α and CXCL10, were compared for subjects with and without a durable response at 3 months, with univariate statistical analysis. As shown in FIG. 19, certain markers of tumor burden, markers of inflammation or inflammatory cytokines were observed to be lower in subjects that exhibited a durable response (p value<0.05 for all parameters except SPD (p=0.1274)). Similar results were observed in subjects receiving DL2, when analyzed alone. An inverse association of baseline patient parameters, including high tumor burden and inflammatory biomarkers, with durable response was observed. In some aspects, such inverse association may be due to higher expansion and exhaustion of CAR$^+$ T cells.

Relationships between patient factors, clinical correlates and blood analytes to developing of degrees of CRS and NT were assessed using statistical analysis based on univariate nonparametric tests. Table E13 lists the results of the univariate analysis. In this assessment, age <40 years and no prior HSCT correlated with incidence of CRS or NT. Subjects with age <40 years were not observed to have statistically different rates of higher tumor burden than older patients. Subjects with ECOG score of 2 did not have statistically different rates of higher tumor burden compared to subjects with ECOG score 0-1. Those without prior HSCT or double/triple hit or double expressor were not associated with CRS or NT.

TABLE E13

Univariate Analysis of Key Subgroups

| Variable, n (%) | CRS | | | NT | | |
|---|---|---|---|---|---|---|
| | Any Grade | Grade ½ | Grade ¾ | Any Grade | Grade ½ | Grade ¾ |
| FULL Population (N = 91) | | | | | | |
| Age | | | | | | |
| <40 years (n = 8) | 5 (63) | 4 (50) | 1 (13) | 3 (38) | 0 | 3 (38) |
| 40-64 years (n = 49) | 19 (39) | 19 (39) | 0 | 9 (18) | 5 (10) | 4 (8) |
| ≥65 years (n = 34) | 8 (24) | 8 (24) | 0 | 5 (15) | 1 (3) | 4 (12) |
| Pre-LD ECOG PS | | | | | | |
| 0-1 (n = 81) | 28 (35) | 27 (33) | 1 (1) | 15 (19) | 4 (5) | 11 (14) |
| 2 (n = 10) | 4 (40) | 4 (40) | 0 | 2 (20) | 2 (20) | 0 |
| Double/triple hit or double expressor | | | | | | |
| Yes (n = 30) | 12 (40) | 12 (40) | 0 | 6 (20) | 3 (10) | 3 (10) |
| No (n = 22) | 6 (27) | 6 (27) | 0 | 4 (18) | 2 (9) | 2 (9) |
| Prior HSCT | | | | | | |
| Yes (n = 39) | 10 (26) | 10 (26) | 0 | 5 (13) | 4 (10) | 1 (3) |
| No (n = 52) | 22 (42) | 21 (40) | 1 (2) | 12 (23) | 2 (4) | 10 (19) |

K. Peak Blood Analytes, Response and Toxicity

Figure 20A:
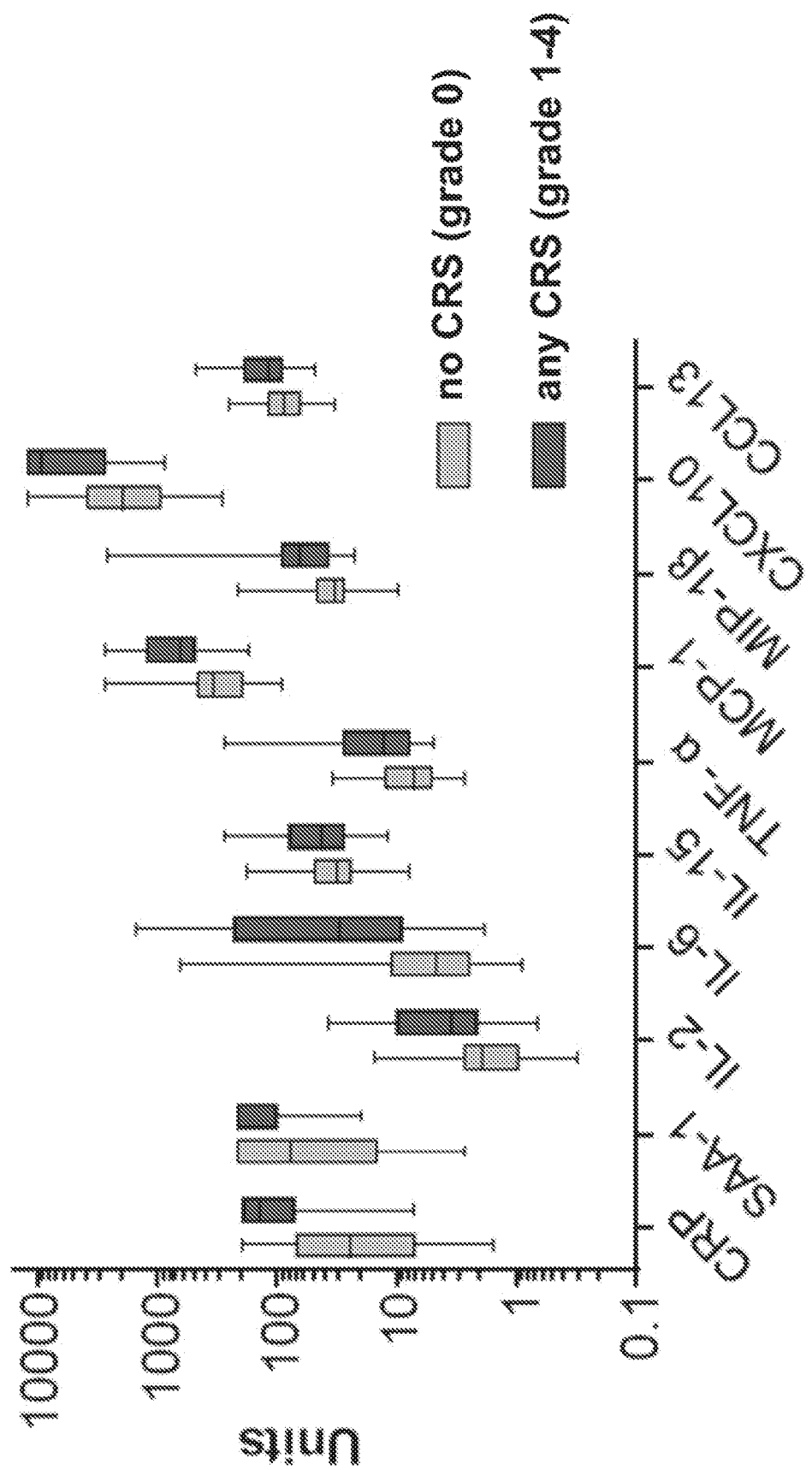
FIGS. 20A and 20B depict peak blood analyte levels in serum samples from subjects that developed cytokine release syndrome (any CRS) compared to subjects that have not developed CRS (no CRS) (FIG. 20A) or in subjects that developed neurotoxicity (any NT) compared to subjects that have not developed NT (no NT) (FIG. 20B). The units were: CRP (mg/L), SAA-1 (mg/L) and cytokines (pg/mL).
Figure 20B:
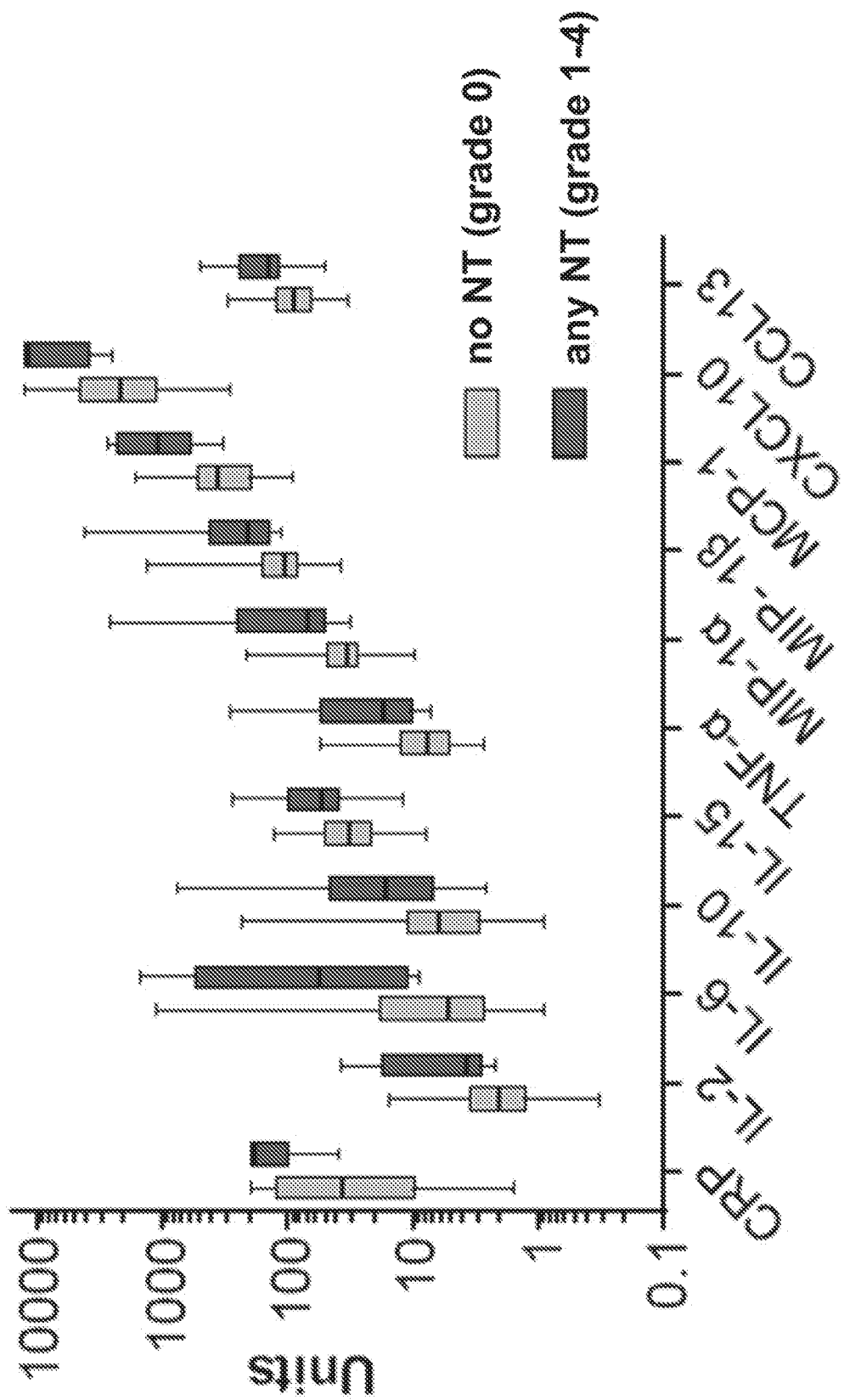

Peak post-treatment plasma levels of blood analytes, including cytokines and inflammatory markers such as CRP, Serum Amyloid A1 (SAA-1), IL-2, IL-6, IL-10, IL-15, TNF-α, MIP-1α, MIP-1β, MCP-1, CXCL10 and C-C Motif Chemokine Ligand 13 (CCL13) were compared for subjects with grade 1-4 cytokine release syndrome (CRS) or neurotoxicity (NT) to subjects that were not observed to have any CRS or NT. As shown in FIG. 20A (CRS; CRS grade 0, n=51; CRS grades 1-4, n=28) and FIG. 20B (NT; NT grade 0, n=63; NT grades 1-4, n=16), higher peak plasma cytokine levels and inflammatory marker levels were observed to be associated with CRS and NT (Wilcoxon P values<0.001 for no CRS vs. any CRS and for no NT vs. any NT, except IL-15 (P=0.05 and 0.006, respectively)).

Figure 21A:
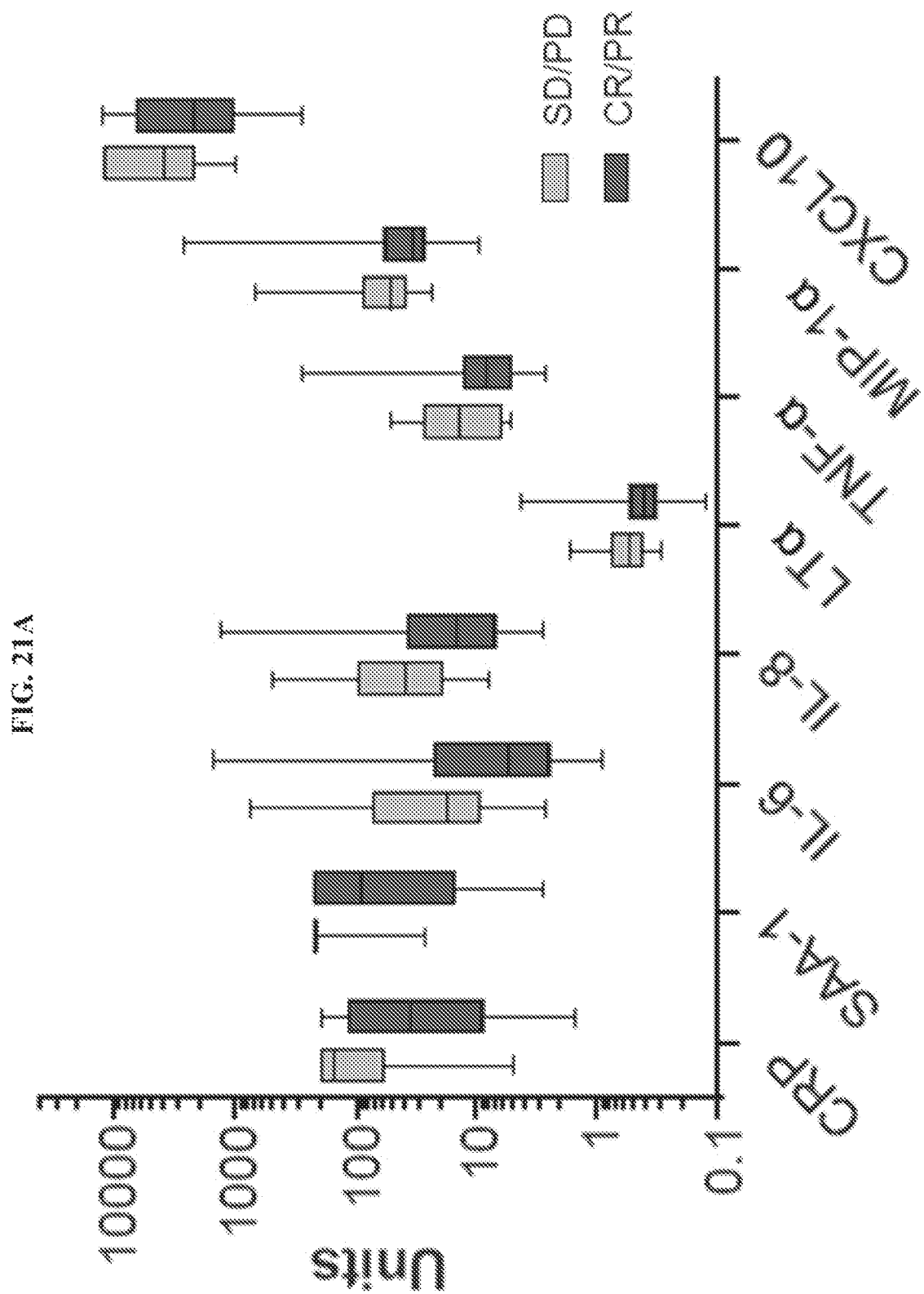
FIG. 21A depicts peak blood analyte levels in serum samples from subjects that had a best overall response (BOR) of complete response (CR) or partial response (PR) (N=57) compared to levels in subjects that had stable disease (SD) or progressive disease (PD) (N=17).
Figure 21B:
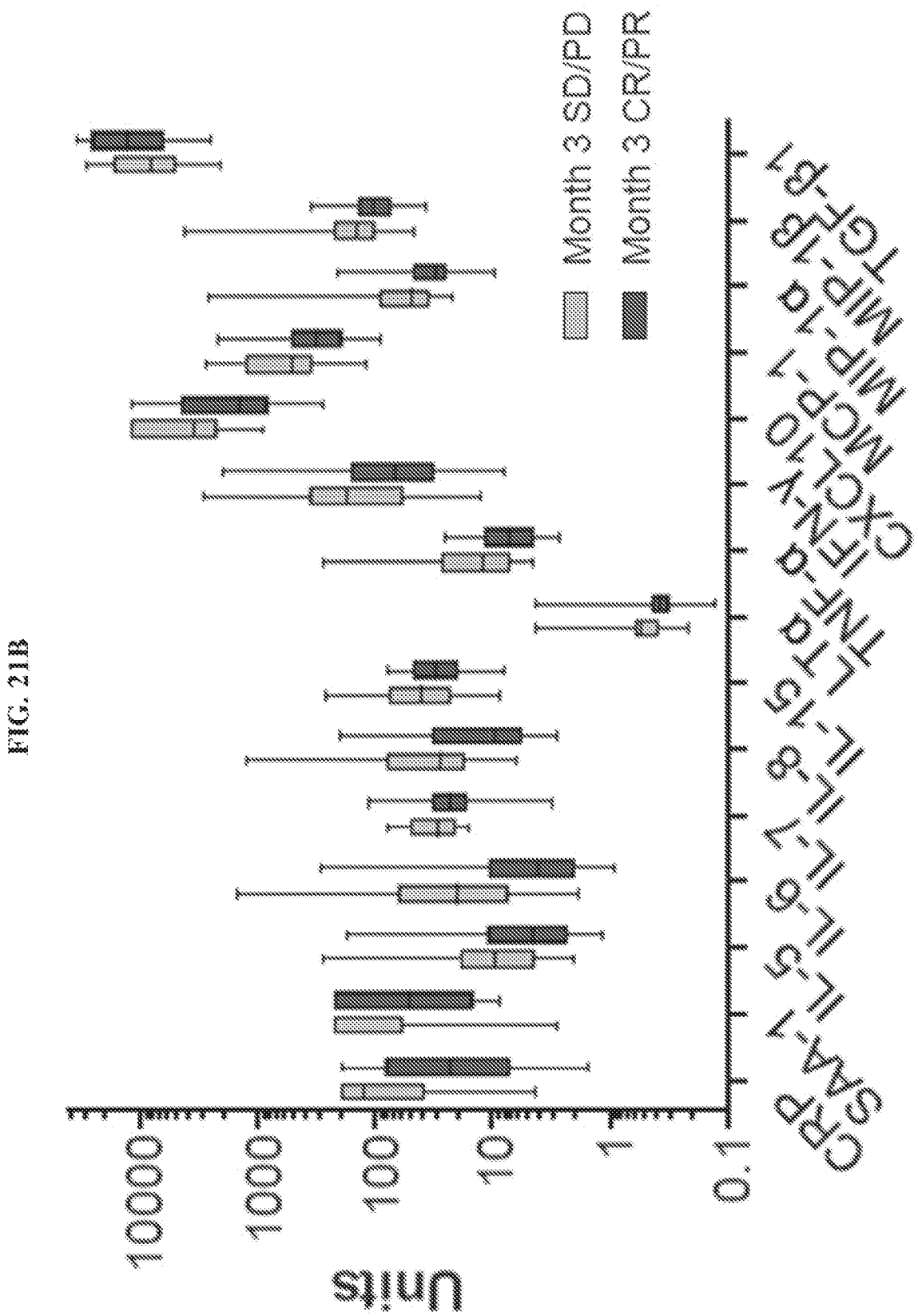
FIG. 21B depicts peak blood analyte levels in serum samples from subjects that had a 3-month response of SD/PD (N=31), compared to subjects who had a 3-month response CR/PR (N=35). The units were: CRP (mg/L), SAA-1 (mg/L) and cytokines (pg/mL).

Peak plasma levels of blood analytes, including cytokines and inflammatory markers such as CRP, SAA-1, IL-5, IL-6, IL-7, IL-8, IL-15, Lymphotoxin-alpha (LT-α), TNF-α, IFN-γ, MIP-1α, MIP-1β, MCP-1, CXCL10, and Transforming growth factor beta (TGF-β), were assessed for subjects with a best overall response (BOR) of complete response (CR) or partial response (PR) (N=57) compared to levels in subjects with stable disease (SD) or progressive disease (PD) (N=17); or for subjects with a 3-month SD or PD (SD/PD) (N=31), compared to subjects who exhibited CR/PR at 3-months (N=35). As shown in FIG. 21A (best overall response (BOR)) and FIG. 21B (month 3 response), lower peak plasma cytokine levels and inflammatory marker levels were observed to be associated with better BOR and response at month 3 (Wilcoxon P values<0.05 without multiplicity of adjustment).

In this study, administration of the anti-CD19 CAR$^+$ cell compositions was administered to subjects with relapsed/refractory aggressive non-Hodgkin lymphoma (NHL) that have poor-risk disease features. Responses, including durable responses, were observed, including 81% ORR, 63% CR at DL2, with 80% of patients in CR at 3 months remaining in CR at 6 months at all dose levels, median DOR of subjects treated at all dose levels of 9.2 months, with mediam duration of CR not having been reached at the time point of analysis in this example. The results also were consistent with manageable toxicity levels and a favorable safety profile that in some embodiments may be consistent with outpatient administration. Low rates of severe CRS (1%) and severe neurotoxicity (12%) were observed, with few events in first 72 hours. Results were consistent with feasibility of outpatient administration.

Pharmacokinetic assessments showed that higher expansion of $CAR^+$ T cells was generally associated with increased rates of CRS and NT. Subjects receiving DL2 showed higher CAR T exposure compared to subjects receiving DL2, which generally corresponded to increased durability of response without increased incidence of toxicity. In some aspects, pre-treatment, such as pre-LDC, patient factors, including homeostatic and inflammatory cytokines and tumor burden, were observed to be associated with and/or drive very high expansion and toxicity. The administered $CAR^+$ T cells were shown to expand in the blood and bone marrow of all patients, with variability among subjects and between disease types. The administered $CAR^+$ T cells also exhibited long-term persistence, with 75% (9/12) of evaluable patients having detectable CAR T cells at 12 months. CAR T cells and B cell aplasia were observed to be still present at time of relapse (11/12 and 12/12 patients, respectively), supporting that tumors may evade CAR T cell action and that combination strategies may be effective to prevent relapse or augment, boost or enhance exhausted CAR T cells. In general, a trend of higher response was observed with higher expansion, with variability among subjects, supporting that other patient factors and/or disease characteristics, e.g., tumor burden, may be contribute to determining response.

Example 4: Attributes of Therapeutic T Cell Composition for Administration and Process for Generation of Composition Exemplary therapeutic T cell compositions containing autologous T cells expressing a chimeric antigen-receptor (CAR) specific for CD19, used for administration in Examples 1 and 2 above were assessed for greater than one hundred phenotypic, functional, and cell health related attributes, using flow cytometry and in vitro assays. Therapeutic cell compositions generated for subjects enrolled in a clinical study evaluating anti-CD19 CAR-T cell therapy for treatment of relapsed/refractory B-cell non-Hodgkin lymphoma were examined (N=63; core cohort). Cells were assessed before and after engineering, for various attributes. Exemplary attributes that were assessed are set forth in Table E14. Memory and cell health phenotypes of the CAR T cells were examined using flow cytometry. T cell functionality was assessed using in vitro antigen-specific bioassays. Characterization and release testing was conducted on therapeutic T cell compositions that had undergone a representative number of freeze-thaw cycles.

TABLE E14

Representative characterization attributes measured in therapeutic cell compositions containing anti-CD19 CAR T cells

| Cell Composition Characterization Class | Representative Attribute |
|---|---|
| Cell Health | Viability |
| | Active intracellular caspase-3 |
| | Annexin V |

TABLE E14-continued

Representative characterization attributes measured in therapeutic cell compositions containing anti-CD19 CAR T cells

| Cell Composition Characterization Class | Representative Attribute |
|---|---|
| Memory phenotype | CCR7 (C-C chemokine receptor type 7) |
| Cell function | Inflammatory cytokines such as TNF-α (tumor necrosis factor α) |

For generation of cell compositions for administration, autologous cells were isolated from the subjects via leukapheresis. Leukapheresis samples were subjected to a process for generation of CAR-expressing cells. The process involved washing of cells using an automated wash and immunoaffinity based selection for purification of $CD4^+$ and $CD8^+$ T cells, resulting in two compositions, enriched for $CD8^+$ (in which a median of 99%, Inter Quartile Range (IQR) 98-100%, of cells were $CD8^+$) and $CD4^+$ (in which a median of 99%, IQR 99-100%, cells were $CD4^+$) cells, respectively.

Cells of the enriched $CD4^+$ and $CD8^+$ compositions were separately subjected to lentiviral transduction with a vector encoding an anti-CD19 CAR with a 41BB costimulatory domain. Transduced populations then were separately incubated in the presence of stimulating reagents for cell expansion. Expanded $CD8^+$ and $CD4^+$ cells were formulated and cryopreserved separately and stored prior to administration. To minimize variations, between lots and/or cell compositions derived from different patients, such as those having different patient attributes, in parameters indicative of cell health, cells were held at constant volumes across lots. Cell products exhibited a tight range of viable cell concentrations (based on an assessment of cell compositions for one group of subjects, $CD8^+$: median $31 \times 10^6$ cells/mL, IQR $28-40 \times 10^6$ cells/mL, N=38; $CD4^+$: median $35 \times 10^6$ cells/mL, IQR $31-40 \times 10^6$, N=36).

Figure 26:
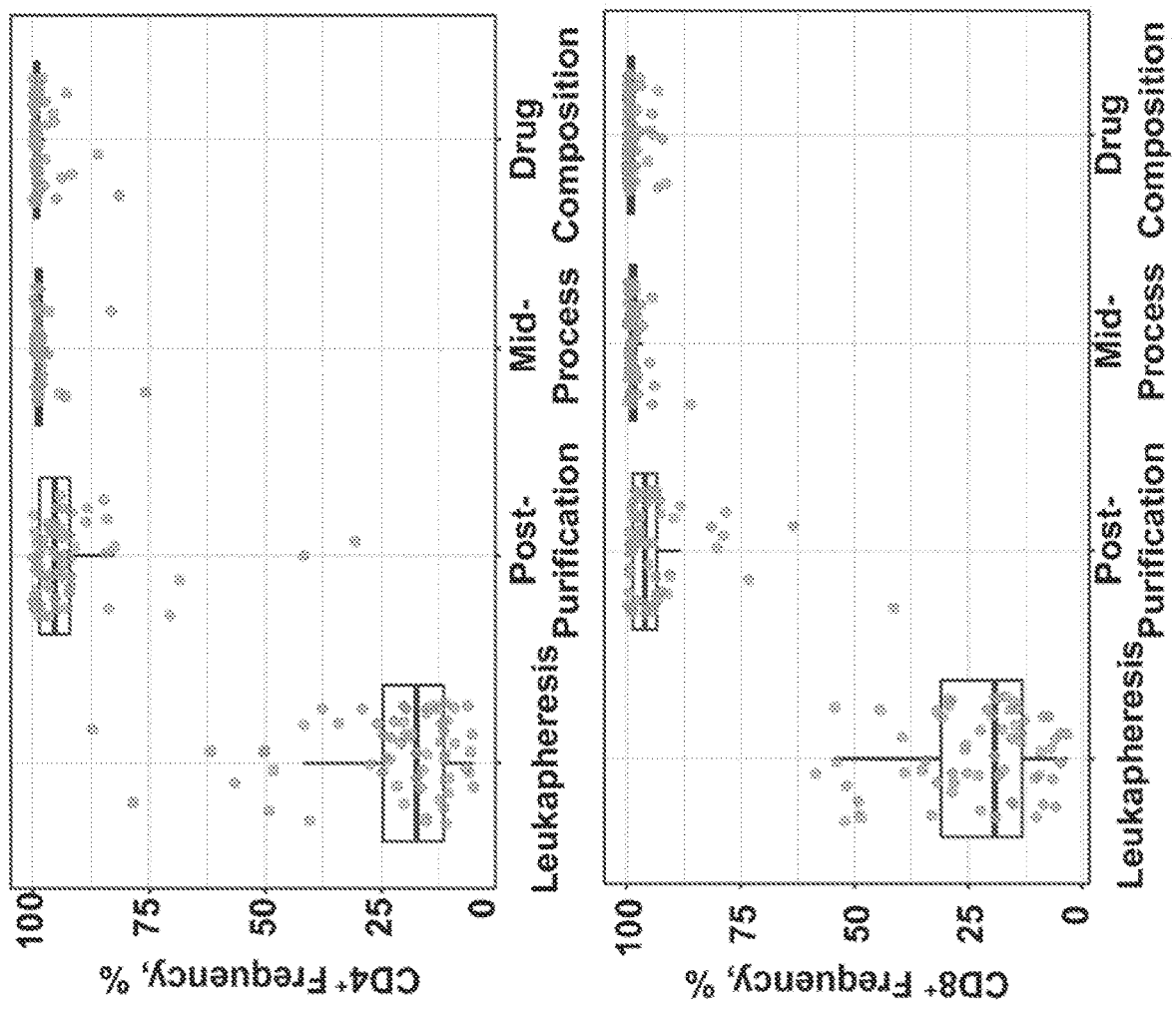
FIG. 26 shows box plots displaying the T cell purity of T cell compositions enriched for CD4$^+$ and CD8$^+$ cells at different stages of the process for generating engineered cell compositions containing CAR T cells that is described in Example 8. The frequency (% of total leukocytes) of CD4$^+$ and CD8$^+$ cells in the compositions are shown.

As shown in FIG. 26 and summarized in Table E15, the automated T cell purification resulted in pure $CD8^+$ and $CD4^+$ T cell populations. This strategy reduced the probability of transducing non-T cells and resulted in high T cell purities in therapeutic cell composition independent of the expansion duration.

TABLE E15

T cell purity (% of total leukocytes) by process step

| | | Leuka-pheresis | Post-Purification | Mid-Process | Drug Composition |
|---|---|---|---|---|---|
| $CD4^+$ T Cell frequency | Median | 17.6 | 95.3 | 98.9 | 99.2 |
| | IQR | 11.7-24.7 | 92.1-98.5 | 98.1-99.2 | 98.7-99.6 |
| $CD8^+$ T Cell frequency | Median | 19.2 | 96.0 | 98.9 | 99.3 |
| | IQR | 13.2-30.9 | 93.4-98.6 | 98.0-99.2 | 98.4-99.7 |

At the site of administration, cell compositions were thawed and administered separately, according to a target volume of each composition corresponding to the number of $CD8^+$ $CAR^+$ and $CD4^+$ $CAR^+$ cells in the appropriate dose (such as for DL1, containing $5 \times 10^7$ total CAR-expressing T cells ($2.5 \times 10^7$ each of CAR-expressing $CD4^+$ and CAR-expressing $CD8^+$ cells), or DL2, containing $1 \times 10^8$ total CAR-expressing T cells ($5 \times 10^7$ each of CAR-expressing $CD4^+$ and CAR-expressing $CD8^+$ cells)).

During the clinical trial there was a process change from a high-volume formulation to low-volume formulation. The post change therapeutic cell composition was formulated at a constant low volume, with a tightly controlled range of viable cell concentrations. In some cases, a low-volume formulation was used instead of a high-volume formulation. Parameters indicative of health of the CAR-expressing T cells in the compositions for administration were assessed, such as by measuring, post-thaw, viability, cell surface Annexin V expression and levels of active intracellular Caspase 3, in cell compositions that were formulated with high volume and low volume.

Figure 27C:
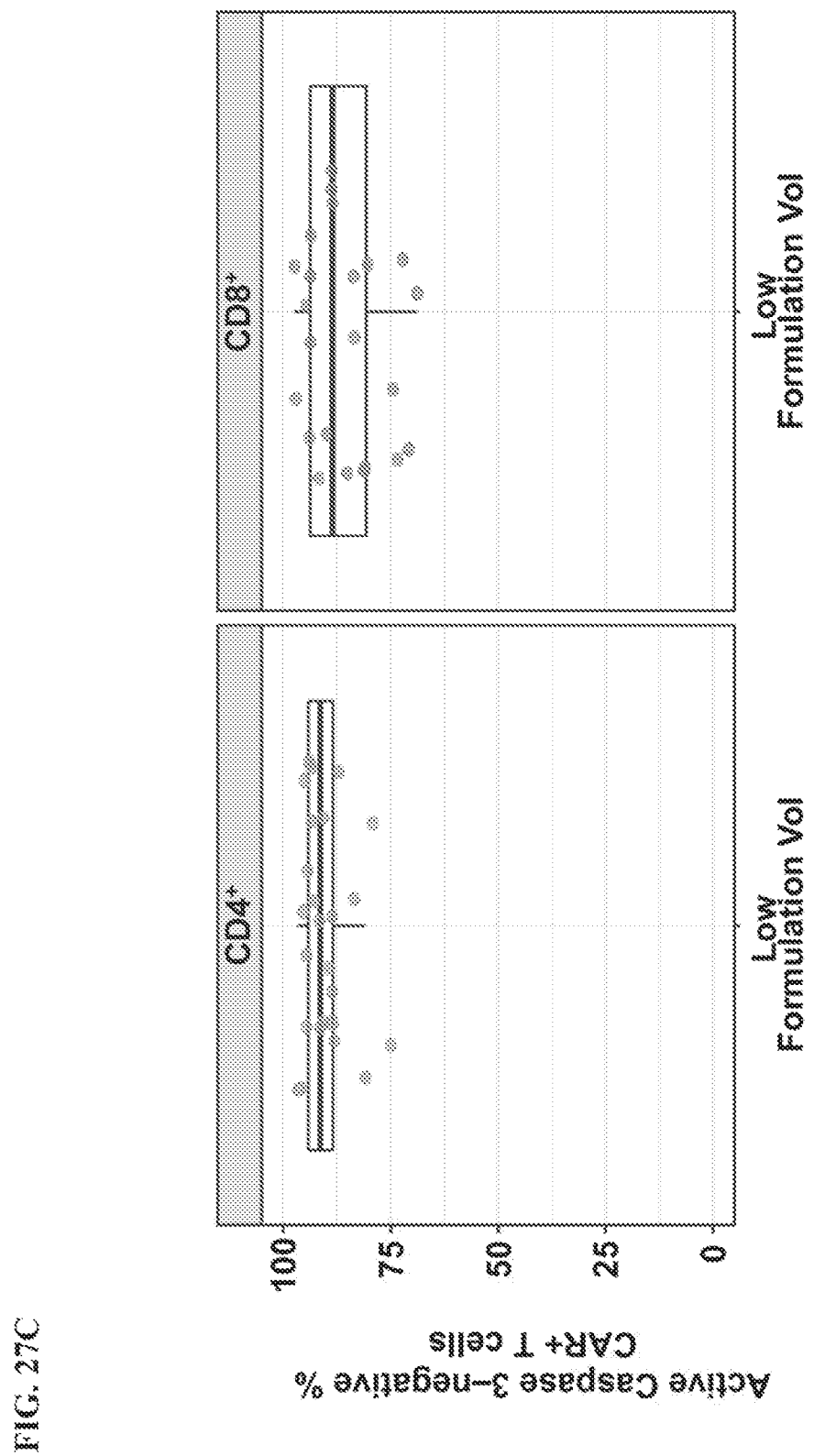

The process change from the high-volume formulation to the low-volume formulation resulted in increased process robustness and decreased variability of the cell health attributes. Values for concentration, percentage of viable cells, and percentage of active caspase-3 negative cells among $CD4^+$ and $CD8^+$ T cells from individual cell compositions are shown in FIGS. 27A-27C and are summarized in Table E16. The median percentage of Annexin V-expressing cells was 11% (IQR 9-18%; N=33) of $CD8^+$ $CAR^+$ T cells and 10% (IQR 8-17%; N=31) of $CD4^+$ $CAR^+$ T cells. Caspase 3 expression was observed to be similar to Annexin V expression. The shift to low-volume formulation resulted in increased robustness of the process and reduced the variance of cell health attributes.

TABLE E16

Cell Health Attributes

| | | $CD4^+$ | | $CD8^+$ | |
| --- | --- | --- | --- | --- | --- |
| | | High Formulation Volume | Low Formulation Volume | High Formulation Volume | Low Formulation Volume |
| Cell Concentration ×10$^6$ cells/mL | Median | 17.1 | 37.2 | 12.1 | 30.8 |
| | IQR | 15.9-19.3 | 31.7-40.4 | 10.9-15.3 | 28.5-38.0 |
| Cell viability % | Median | 82.8 | 82.5 | 72.0 | 80.3 |
| | IQR | 79.5-84.7 | 80.4-84.3 | 69.3-76.6 | 76.4-83.3 |
| % Caspase-3 negative cells | Median | | 82.8 | | 82.5 |
| | IQR | | 79.5-84.7 | | 80.4-84.3 |

The quantities of $CAR^+CD4^+$ and $CAR^+CD8^+$ T cells in the composition for administration were precisely controlled. The number of cells actually administered to an exemplary set of subjects was observed to be within 8% or less of the target number of cells for a given dose:

2.4-2.7×10$^7$ (target ±8%) $CD4^+$ $CAR^+$ T cells and 2.4-2.7×10$^7$ (target ±8%) $CD8^+$ $CAR^+$ T cells for subjects administered cells at DL1 (n=48)

4.6-5.1×10$^7$ (target ±8%) $CD4^+$ $CAR^+$ T cells or 4.6-5.1×10$^7$ (target ±8%) $CD8^+$ $CAR^+$ T cells for subjects administered cells at DL2 (n=20).

The range of administered dose was found to have low variability in a different exemplary set of subjects:

48-52×10$^6$ $CD3^+$ $CAR^+$ T cell at DL1 (n=34)

96-101×10$^6$ $CD3^+$ $CAR^+$ T cells at DL2 (n=29)

24-27×10$^6$ $CD4^+$ $CAR^+$ or $CD8^+$ $CAR^+$ T cells at DL1 (n=34)

46-51×10$^6$ $CD4^+$ $CAR^+$ or $CD8^+$ $CAR^+$ T cells at DL2 (n=29).

Figure 28A:
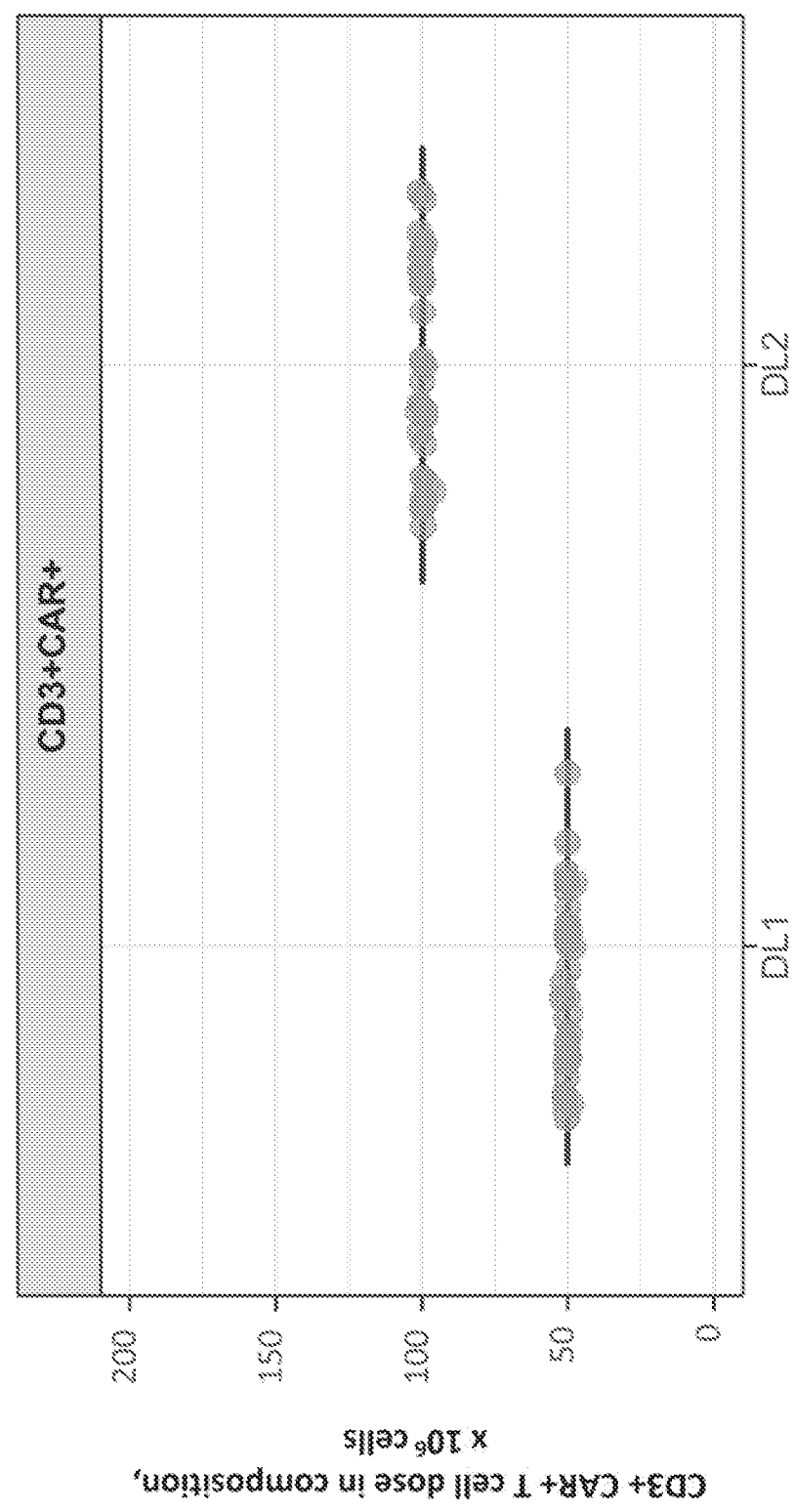
FIG. 28A shows the number of CD3$^+$ CAR$^+$ T cells present in CART cell compositions for administration at DL1 and DL2.

As shown in FIG. 28A, CAR-expressing T cell compositions administered to subjects were observed to exhibit high T cell purity and low variance between lots. In view, e.g., of process and product controls, therapeutic cell compositions containing CAR T cells were observed to have low lot-to-lot variability in cell-specific T cell function.

Figure 28B:
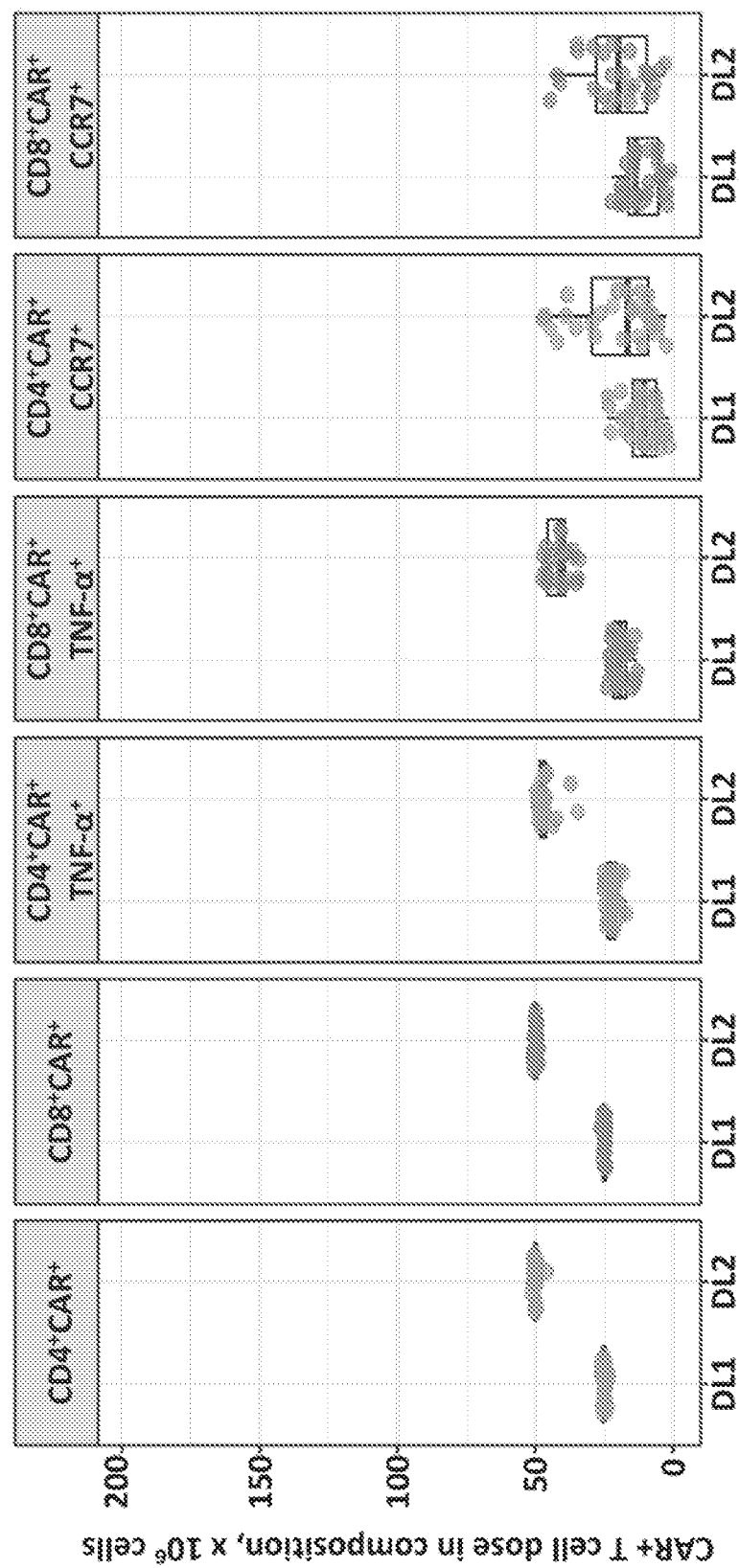
FIG. 28B shows the number of CD4$^+$ CAR$^+$ and CD8$^+$ CAR$^+$ cells, and CD4$^+$ CAR$^+$ TNF-α$^+$ cells and CD8$^+$ CAR$^+$ TNF-α$^+$ cells present in CAR T cell compositions for administration at DL1 and DL2.

In vitro antigen-specific cytokine accumulation and intracellular cytokine staining (ICS) showed a similar low variance between lots for cytokine production for multiple cytokines (IL-2, TNF-α and IFN-γ). In an exemplary ICS experiment, cells from compositions were stimulated with CD19, stained for cytokines, including TNF-α, and surface proteins, including C—C chemokine receptor type 7 (CCR7) as a memory phenotype marker, and analyzed by flow cytometry. The number of cells in the composition for administration that were positive for the cytokines or surface proteins were determined. FIG. 28B shows the number of $CD4^+CAR^+$ and $CD8^+CAR^+$ cells, $CD4^+CAR^+$ TNF-α$^+$ and $CD8^+CAR^+$ TNF-α$^+$ cells, $CD4^+CAR^+CCR7^+$ and $CD8^+CAR^+CCR7^+$ and present in CAR T cell compositions for administration at DL1 and DL2. These results are summarized in Table E17. The results show low variability in the number of $CD4^+CAR^+$ and $CD8^+CAR^+$ cells, $CD4^+CAR^+$ TNF-α$^+$ and $CD8^+CAR^+$ TNF-α$^+$ cells, $CD4^+CAR^+CCR7^+$ and $CD8^+CAR^+CCR7^+$ cells. For example, a tight range for the number of cells positive for TNF-α production was observed (n=61).

TABLE E17

Controlled dose, T cell phenotypes, and cell specific function (×10$^6$ cells)

| | $CD4^+CAR^+$ | | $CD8^+CAR^+$ | | $CD4^+CAR^+$ TNF-α$^+$ | | $CD8^+CAR^+$ TNF-α$^+$ | | $CD4^+CAR^+$ CCR7$^+$ | | $CD8^+CAR^+$ CCR7$^+$ | |
| --- | --- | --- | --- | --- | --- | --- | --- | --- | --- | --- | --- | --- |
| | DL1 | DL2 | DL1 | DL2 | DL1 | DL2 | DL1 | DL2 | DL1 | DL2 | DL1 | DL2 |
| Median | 25.1 | 50.1 | 25.0 | 50.0 | 23.0 | 47.4 | 19.9 | 41.7 | 11.1 | 15.8 | 8.9 | 15.0 |
| IQR | 24.7-25.3 | 49.6-50.0 | 24.8-25.2 | 49.6-50.4 | 21.3-23.5 | 46.6-48.5 | 18.3-21.8 | 39.9-46.0 | 5.5-14.1 | 11.0-26.0 | 3.0-14.8 | 8.6-25.3 |

A parameter indicative of production by $CAR^+$ cells of tumor necrosis factor alpha (TNFα) after stimulation with CD19 showed a narrow range among different lots, with relative standard deviation (RSD) of 37% for $CD4^+$ $CAR^+$ T cells (N=59) and 51% for $CD8^+$ $CAR^+$ T cells (N=61).

The results were consistent with an observation that a composition that contains a precise and consistent dose of $CD4^+$ and $CD8^+$ CAR T cells, control and optimization of $CD4^+$ and $CD8^+$ T cell culture conditions, low variability of cytokine production, and/or constant formulation and volume of the composition for administration can lead to consistent cell health in the composition. In provided embodiments, aspects of such manufacturing and control process contribute to low variability in attributes of such cell compositions engineered using cells from, and generated for administration to, a number of different subjects. Such aspects in some aspects include the use of a precise, consistent flat dose of administered $CD4^+$ and $CD8^+$ cells among subjects; control and optimization of $CD4^+$ and $CD8^+$ T cell culture conditions such as those that result in low between-drug product lot variability of phenotypes (e.g., CCR7) and in vitro function (e.g., IL-2, TNF-α and IFN-γ production after antigen stimulation) such as among different subjects; and the use of constant formulation and volume of drug product which can result in or contribute to consistency among therapeutic cell compositions generated by the method in attributes indicative of cell health.

Example 5: Biomarker Assessment in Pre- and Post-Administration Tumor Biopsies from Subjects with Relapsed and Refractory Non-Hodgkin's Lymphoma (NHL) for Administration of Anti-CD19 CAR-Expressing Cells Expression of several biomarkers was assessed in tumor biopsies collected from subjects before and/or after administration of CAR-expressing cells.

A. Tumor Biopsy Samples

Tumor biopsies were collected from selected subjects with relapsed or refractory (R/R) diffuse large B-cell lymphoma (DLBCL) or mantle cell lymphoma (MCL) who received treatment with therapeutic $CAR^+$ T cell compositions containing autologous T cells expressing a chimeric antigen-receptor (CAR) specific for CD19, described above in Examples 1 and 2 above, based on the time point of assessment in Example 1.A.2. Tumor biopsies were obtained prior to administration of the $CAR^+$ T cells (pre-treatment) and at 7 to 20 days after administration (post-treatment). Results are described in this example for evaluation through the time-point in Example 1.A.2, in an ongoing study. Results from 43 biopsies (26 pre-treatment; 17 post-treatment and 15 matched pairs) from 28 total subjects (25 DLBCL and 3 MCL) were examined.

B. Assessment of Biomarkers, Response and Safety Outcomes

Infiltration of $CAR^+$ T cell in the tumor biopsy was quantified using in situ hybridization (ISH) probes specific to the mRNA encoding the anti-CD19 CAR. $CAR^+$ T cells, non-CAR T cells and B cells were enumerated using multiplex immunofluorescence (IF) assays detecting for a cell surface surrogate marker for CAR-expressing cells, CD4, CD8, CD19, CD20, CD73, FOXP3, CD163, IDO and PD-L1. Tumor biopsy sections were stained with hematoxylin and eosin (H&E) and assessed for tissue quality and tumor identification. Immunofluorescence images were analyzed using an image analysis software. Potential correlations to response outcomes were assessed using statistical analysis based on univariate t-tests, and the p-values were 2-sided without multiplicity adjustment.

Subjects were assessed for response and safety outcomes, including by assessing the tumor burden at various time points after administration of the $CAR^+$ T cells, including at 3 months after administration, and determining whether the subject had progressive disease (PD), stable disease (SD), partial response (PR), or complete response (CR). Safety outcomes evaluated included neurotoxicity (neurological complications including symptoms of confusion, aphasia, encephalopathy, myoclonus seizures, convulsions, lethargy, and/or altered mental status), graded on a 1-5 scale, according to the National Cancer Institute—Common Toxicity Criteria (CTCAE) scale, version 4.03 (NCI-CTCAE v4.03).

C. Results

The observed objective response rate (ORR; including CR and PR) was 71% (20/28) in the subjects for which biopsies were assessed. Grade 1, 2 CRS was observed in 36% (10/28; grade 1, 2) of the subjects for which biopsies were assessed, and Grades 2-4 NT was observed in 18% (5/28) of the subjects for which biopsies were assessed.

Pre-treatment tumor biopsies were observed to contain varying cellular compositions: tumor cells (median: 77%; range 5-96%), $CD4^+$ cells (0.90%; 0.02-15%), and $CD8^+$ cells (1.5%; 0-23%). The results showed that subjects with a CR or PR at 3 months after $CAR^+$ T cell administration had a higher percentage of endogenous $CD4^+$ cells in pre-treatment tumors compared those with a PD (CR, PR median: 7.9%; PD median: 0.38%; p<0.0001). Percentages of $CD8^+$ cells in pre-treatment tumors did not differ between the 3 month response groups (CR, PR median: 1.9%; PD median: 0.47%; p=0.6496).

In the post-treatment biopsies, $CAR^+$ T cell were observed to have infiltrated the tumor, and constituted up to 22% of cells in the biopsy sample. The level of tumor infiltration in post-treatment samples (7 to 20 days after administration) was observed to be higher in subjects that went on to achieve a CR (median: 3.9%) or PR (median: 1.1%) compared to subjects that went on to achieve a best overall response (BOR) of SD or PD (median: 0.51%). Although both $CD4^+$ and $CD8^+$ CAR T cells were observed to have infiltrated the tumor area at the post-treatment time point (7 to 20 days after administration), subjects that went on to achieve a CR were observed to have higher ratio of $CD8^+$ $CAR^+$ T cells to $CD4^+$ $CAR^+$ T cells, at this post-treatment timepoint, as compared to subjects that went on to achieve a BOR of SD or PD (CR median: 0.83; SD, PD median: 0.14; p=0.0097).

Comparing matched pre- and post-treatment biopsies from individual subjects, results showed a trend towards subjects ultimately achieving a BOR of CR or PR having a larger post-treatment increase in $CD8^+$ cells ($CAR^+$ T and non-CAR T) in tumors, as compared to subjects ultimately achieving a BOR of SD or PD (CR, PR median change: $^+$5.3%; SD, PD median change: $^+$0.06%; p=0.1225).

Expression of immunosuppressive factors, including CD73, FOXP3, CD163, IDO and PD-L1, varied among subjects at pre-treatment (CD73 (median: 1.5%; range 0-42%), FOXP3 (0.10%; 0-1.5%), IDO (0.06%; 0-11%), CD163 (1.2%; 0-24%) and PD-L1 (0.16%; 0-56%)) and post-treatment (CD73 (1.6%; 0-53%), FOXP3 (0.09%; 0-4.3%), IDO (0.28%; 0-15%), CD163 (3.6%; 0-22%) and PD-L1 (3.3%; 0-65%)). Post-treatment increases in $CD8^+$ cells in matched biopsies were observed to be associated with post-treatment increases in IDO ($R^2$=0.64) and PD-L1 ($R^2$=0.61) expression. This result is consistent with a conclusion that infiltration of $CD8^+$ $CAR^+$ cells at the time assessed may indicate potential likelihood of achieven a degree of response or duration of response, and that the presence and/or activity of such cells may result in upregulation of TME factors.

D. Conclusion

Durable response at month 3 after $CAR^+$ T cell administration was observed to be associated with higher levels of $CD4^+$ cells in pre-treatment tumors. In post-treatment tumor cells, $CAR^+$ T cells, both $CD4^+$ and $CD8^+$, were observed to infiltrate the tumor and adjacent tissue. ORR was associated with an increase in $CAR^+$ T cells in the tumor biopsy. An increase of $CD8^+$ levels in the post-treatment tumor biopsy compared to $CD8^+$ levels in the pre-treatment tumor biopsy was associated with increased IDO and PD-L1 expression. In some embodiments, therapies targeting these pathways, such as those administered at the time of or following administration of the CAR-T cells, may enhance one or more therapeutic outcomes or duration thereof following CAR+ T cell administration.

Example 6: Further Assessment of Response and Safety Outcomes in Subjects with Relapsed and Refractory Non-Hodgkin's Lymphoma (NHL) After Administration of Anti-CD19 CAR-Expressing Cells Response and safety outcomes were assessed in patients at a subsequent point in time in the clinical study described in Examples 1 and 3 above.

A. Subjects and Treatment

The analysis at this time point presented in this example is based on assessment of a total of 102 subjects in the FULL cohort (73 in the CORE cohort) that had been administered the anti-CD19 CAR-expressing cells. The FULL cohort included subjects who had DLBCL (DLBCL, NOS de novo and transformed from follicular lymphoma; high grade B-cell lymphoma (double/triple hit); DLBCL transformed from CLL or MZL; PMBCL; and FL3B, ECOG 0-2, after 2 lines of therapy; the CORE cohort for analysis included subjects having DLBCL, NOS and transformed from follicular lymphoma (tFL) or high grade B-cell lymphoma (double/triple hit) and with Eastern Cooperative Oncology Group performance status (ECOG PS) of 0 or 1. Approximately 90% of treated patients in the FULL and the CORE cohort had at least one poor-risk disease feature predictive of short median overall survival (OS) of 3-6 months (see Crump et al., Blood (2017) 130:1800-1808 and Van de Neste et al., Bone Marrow Transplant. (2016) 51(1):51-7), such as double/triple hit expressors, primary refractory disease, refractory to 2 or more lines of therapy, never achieved CR, never received autologous stem cell transplant (ASCT) or an ECOG PS of 2.

At this time point, a total of 134 subjects had been leukapheresed, of which 2 had compositions unavailable. Product was available for 99% of apheresed subjects (132/134) in the DLBCL cohort. Of another 18 subjects whose products were available, 5 had withdrawn, and 13 had developed progressive disease or had died. A total of 114 subjects had been administered the anti-CD19 CAR-expressing cells, of which 12 received non-conforming anti-CD19 CAR-expressing cells (compositions not necessarily meeting certain specifications but deemed to be safe for administration). Subjects had received DL1 (n=45), double dose of DL1 (n=6) or DL2 (n=51). Seven (7) subjects with mantle cell lymphoma (MCL) had been administered CAR+ cells at DL1. At this time point, eight (8) subjects were treated in an outpatient setting.

The demographics and baseline characteristics of the FULL and CORE cohort subjects at the timepoint are set forth in Table E18.

TABLE E18

Patient Characteristics: DLBCL Cohort

| Characteristic | FULL (n = 102) | CORE (n = 73) |
|---|---|---|
| Median age (range), years | 61 (20-82) | 60 (20-82) |
| ≥0 (20-82) (range | 37 (36) | 24 (33) |

TABLE E18-continued

Patient Characteristics: DLBCL Cohort

| Characteristic | FULL (n = 102) | CORE (n = 73) |
|---|---|---|
| B-NHL Subtype, n (%) | | |
| DLBCL, NOS de novo | 63 (62) | 53 (73) |
| Transformed from FL (tFL) | 23 (23) | 20 (27) |
| Transformed from MZL (tMZL)/CLL (tCLL) | 6 (6)/6 (6) | 0 |
| Follicular, grade 3B/PMBCL | 1 (1)/3 (3) | 0 |
| Molecular Subtype, n (%) | | |
| Double/triple hit[a] | 19 (19) | 16 (22) |
| Patient Characteristics, n (%)L | | |
| ECOG PS 0-1 | 93 (91) | 73 (100) |
| IPI 3-5 | 43 (42) | 26 (36) |
| CNS involvement | 2 (2) | 1 (1) |
| Chemorefractory[b] | 71 (70) | 49 (67) |
| Prior lines of therapy, median (range) | 3 (1-8) | 3 (2-8) |
| Never achieved CR | 49 (48) | 36 (49) |
| Any HSCT | 41 (40) | 28 (38) |
| Prior autologous | 38 (37) | 28 (38) |
| Prior allogeneic | 5 (5) | 0 |

HSCT, hematopoietic stem cell transplant.
IPI, International Prognostic Index; SD, stable disease; WHO, World Health Organization.
[a]At trial initiation, included in DLBCL, NOS histology; based on most recent WHO criteria (Swerdlow et al., (2016) Blood 127(20): 2375-2390), are now considered high-grade B-cell lymphoma, with myc and bcl2 and/or bcl6 rearrangements with DLBCL histology (double/triple hit).
[b]SD or PD to last chemotherapy-containing regimen or relapse <12 months after autologous SCT.

B. Safety and Response Outcomes after Treatment

Table E19 shows the safety outcome of the FULL and CORE cohort. As shown, no deaths from CRS or NT were observed. In the FULL cohort, the median time to onset of CRS was 5 days (range, 2-12 days) and NT was 10 days (range, 3-23 days). In the FULL cohort, 17% (n=17) received tocilizumab and 21% (n=21) received corticosteroids as a toxicity intervention. In the CORE cohort, no increase in CRS or NT was observed at DL2, compared to DL 1.

TABLE E19

Safety OutcomesAfter CAR+ Cell Administration

| | FULL | CORE | | |
|---|---|---|---|---|
| | All Dose Levels n = 102 | All Dose Levels[a] n = 73 | DL1S n = 33 | DL2S n = 37 |
| CRS, n (%) | | | | |
| Any grade | 38 (37) | 27 (37) | 14 (42) | 11 (30) |
| Grade 1/2 | 37 (36) | 26 (36) | 13 (39) | 11 (30) |
| Grade 3/4 (sCRS) | 1 (1) | 1 (1) | 1 (3) | 0 |
| Neurotoxicity, n (%) | | | | |
| Any grade | 23 (23) | 18 (25) | 8 (24) | 9 (24) |
| Grade 1/2 | 10 (10) | 7 (10) | 1 (3) | 6 (16) |
| Grade 3/4 (sNT) | 13 (13) | 11 (15) | 7 (21) | 3 (8) |
| Any, n (%) | | | | |
| CRS or NT | 44 (43) | 32 (44) | 15 (45) | 15 (41) |
| sCRS or sNT | 13 (13) | 11 (15) | 7 (21) | 3 (8) |

[a]Three patients treated on DL1D (dose level 1, two-dose schedule) with similar outcomes.

Figure 29:
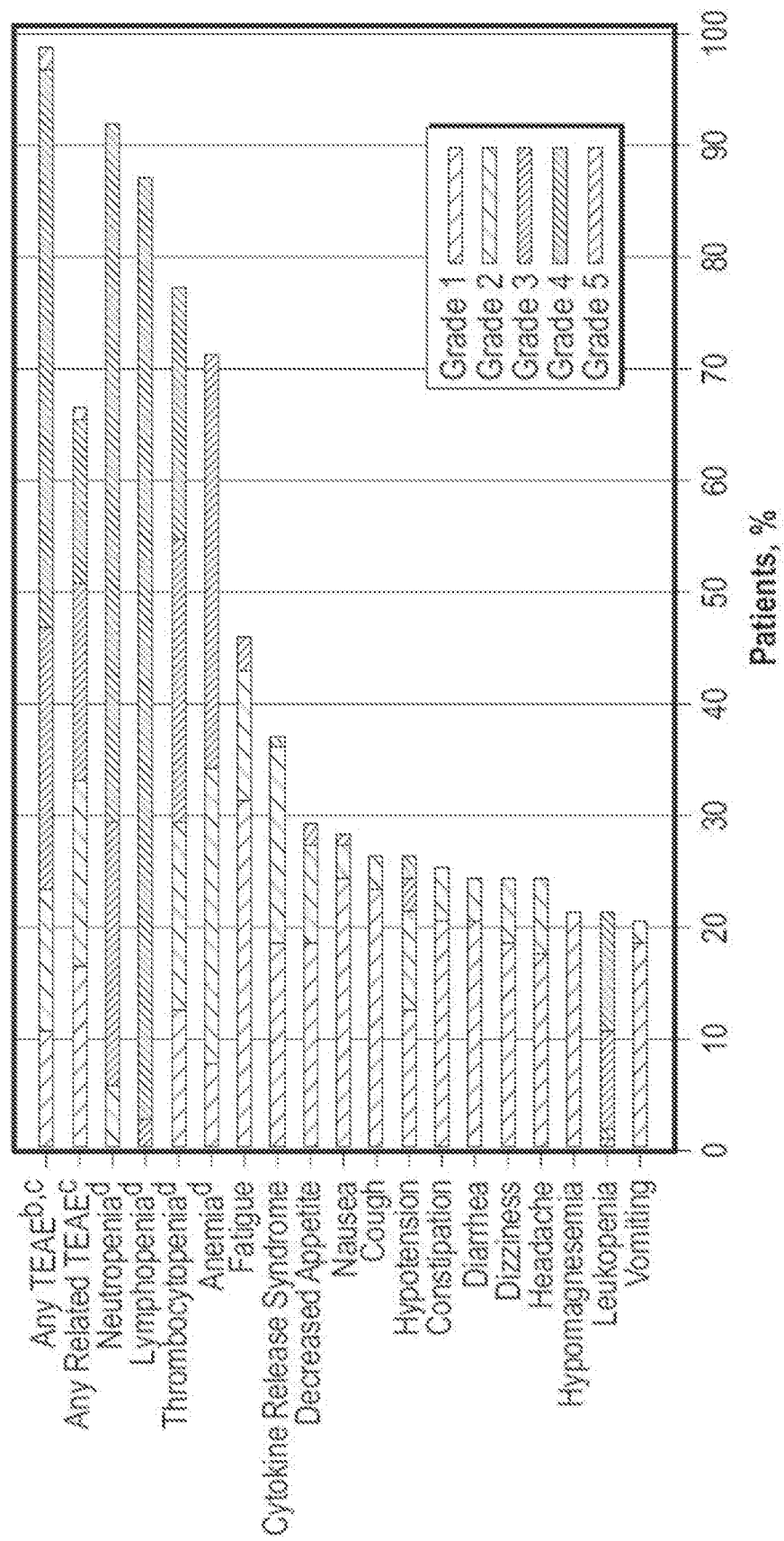
FIG. 29 shows the percentage of subjects who experienced treatment-emergent adverse events (TEAEs) in the FULL DLBCL cohort occurring in ≥20% of the subject at a study time point described in Example 6. Data for 6 subjects with MCL treated with conforming product at DL1 with at least 28 days of follow-up were not included. $^b$: One grade 5 AE of septic shock unrelated to CAR$^+$ T cell administration, occurred in the setting of disease progression. $^c$: One grade 5 AE of diffuse alveolar damage, investigator assessed as related to fludarabine, cyclophosphamide, and CAR$^+$ T cells, occurred on day 23 in a patient who refused mechanical ventilation for progressive respiratory failure while neutropenic on growth factors and broad-spectrum antibiotics and antifungals. $^d$: Laboratory anomalies.

FIG. 29 depicts the percentage of subjects in the FULL cohort at this timepoint (n=102) who were observed to have experienced laboratory abnormalities and treatment-emergent adverse events (TEAEs) (data for 6 subjects with MCL treated with conforming product at DL1 with at least 28 days of follow-up are not included; showing TEAEs and laboratory abnormalities occurring in 20% or more of the subjects).

As shown in Table E20, high rates of response was observed in subjects with relapsed or refractory (R/R) DLBCL. The results are consistent with a dose response effect on treatment outcome in the CORE cohort. Subjects with a tumor burden above a threshold (as indicated by the volumetric tumor measurement of sum of product dimensions (SPD) of more than 50 cm$^2$) was similarly distributed between subjects receiving DL1 and DL2 (approximately 1/3 of the subjects in each group).

TABLE E20

Response After CAR+ Cell Administration

|  | FULL | CORE | | |
| --- | --- | --- | --- | --- |
|  | All Dose Levels (n = 102) | All Dose Levels$^a$ (n = 73) | DL1S (n = 33) | DL2S (n = 37) |
| ORR (95% CI), % | 75 (65-83) | 80 (68-88) | 79 (61-91) | 78 (62-90) |
| CR (95% CI), % | 55 (45-65) | 59 (47-70) | 55 (36-72) | 62 (45-78) |
| 3-mo ORR (95% CI), % | 51 (41-61) | 59 (47-70) | 52 (34-69) | 65 (48-80) |
| 3-mo CR (95% CI), % | 38 (29-48) | 45 (34-57) | 36 (20-55) | 51 (34-68) |
| 6-mo ORR (95% CI), % | 40 (31-50) | 47 (35-59) | 42 (26-61) | 49 (32-66) |
| 6-mo CR (95% CI), % | 34 (25-44) | 41 (30-53) | 33 (18-52) | 46 (30-63) |

$^a$Three patients treated on DL1D (dose level 1, two-dose schedule) with similar outcomes.

Figure 30:
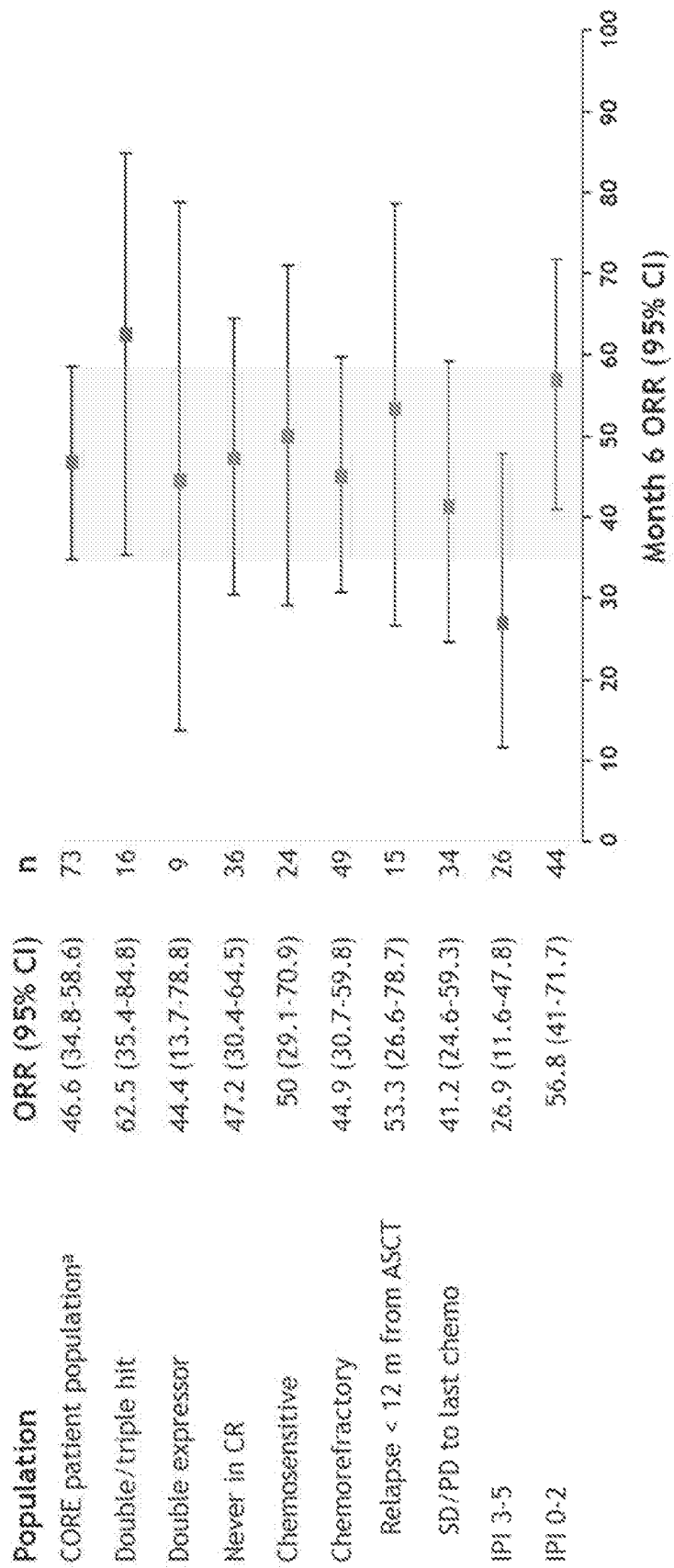
FIG. 30 depict the six (6) month objective response rates (ORR) among subgroups of treated subjects, with the 95% confidence interval. $^a$ Includes all DLBCL subjects treated at all dose levels in the CORE cohort.
Figure 31A:
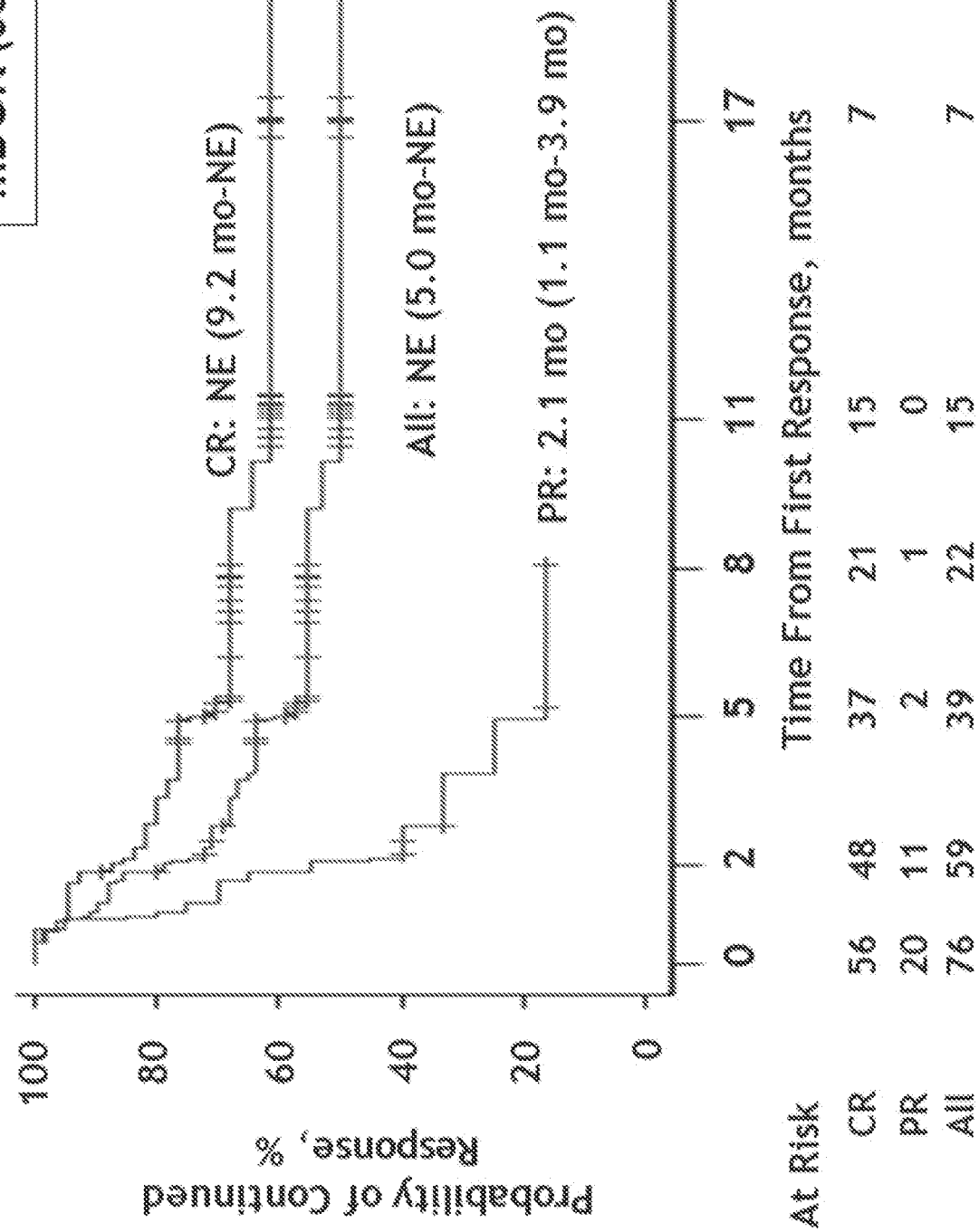
FIGS. 31A and 31B depict the duration of response (DOR) for the full cohort (FIG. 31A) and the core cohort (FIG. 31B)
Figure 31B:
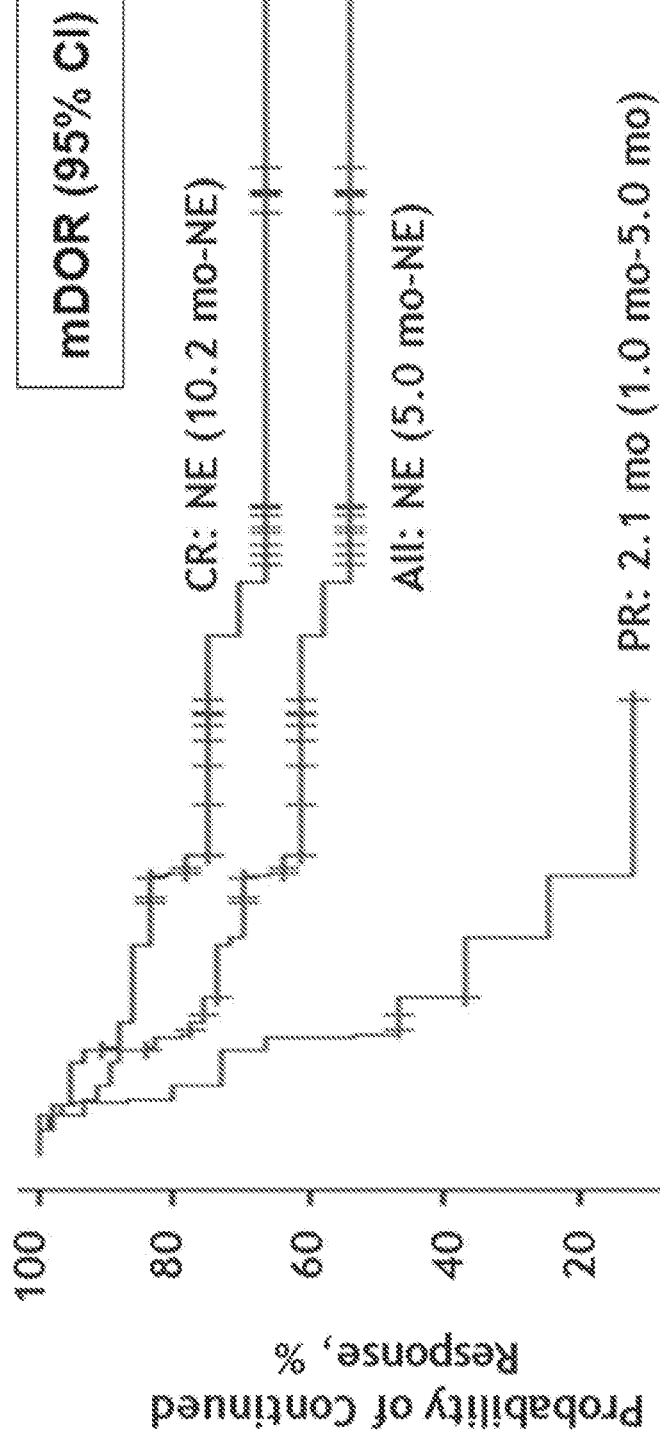
Figure 31C:
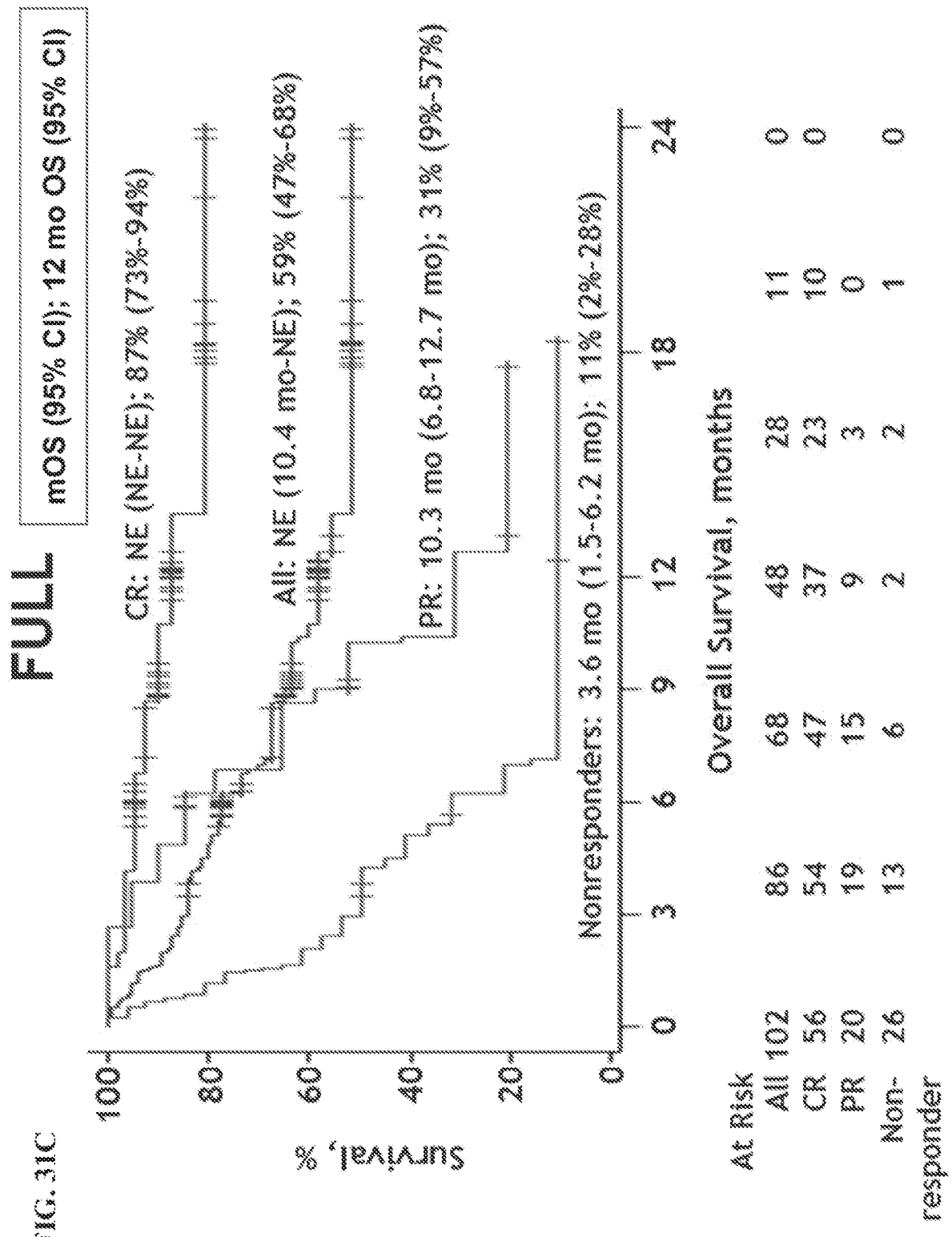

Six-month objective response rates (ORR) among various subgroups of subjects in the poor-risk DLBCL subgroups, that included all DLBCL patients treated at all dose levels in the CORE cohort, are shown in FIG. 30. The results showed high durable ORR in the poor-risk DLBCL subgroup for anti-CD19 CAR+ T cell administration.

Results for the duration of response (DOR, with median follow-up of 8 months) and overall survival (grouped by best overall response (non-responder, CR/PR, CR and/or PR), with median follow-up of 12 months) are shown for the full cohort and the core cohort cohorts of subjects, in FIGS. 31A-31D. The results showed that in the CORE cohort, 88% of subjects with CR at 3 months continued to show CR at 6 months, and 93% of subjects who exhibited CR at 6 months continued to show a response longer term.

The results were consistent with an observation that administration of anti-CD19 CAR+ cell compositions that contains a precise and consistent dose of CD4$^+$ and CD8$^+$ CAR+ T cells results in durable response in subjects with R/R aggressive NHL with poor prognosis and/or heavy pretreatment. The results showed a favorable durable response rate in the CORE cohort, with 49% ORR and 46% CR rate at 6 months, and 93% of the subjects (at all dose levels) in CR at 6 months remained in response at this time point. The results also were consistent with manageable toxicity and a favorable safety profile, including low rates of severe CRS (1%) and severe neurotoxicity (13%), which, in some aspects, supports outpatient administration.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
| --- | --- | --- |
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) homo sapiens |
| 3 | ESKYGPPCPPCPGQPREPQVYTLPPSQEEMTKNQvsLTcLvKGFYPSDIAVEWE SNGQPENNYKTTPPVLDSDGSFFLYSRLTVDKSRWQEGNVFSCSVMHEALHNHY TQKSLSLSLGK | Hinge-CH3 spacer Homo sapiens |
| 4 | ESKYGPPCPPCPAPEFLGGPSVFLFPPKPKDTLMISRTPEVTCVVVDVSQEDPE VQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHN HYTQKSLSLSLGK | Hinge-CH2-CH3 spacer Homo sapiens |
| 5 | RWPESPKAQASSVPTAQPQAEGSLAKATTAPATTRNTGRGGEEKKKEKEKEEQE ERETKTPECPSHTQPLGVYLLTPAVQDLWLRDKATFTCFVVGSDLKDAHLTWEV AGKVPTGGVEEGLLERHSNGSQSQHSRLTLPRSLWNAGTSVTCTLNHPSLPPQR LMALREPAAQAPVKLSLNLLASSDPPEAASWLLCEVSGFSPPNILLMWLEDQRE VNTSGFAPARPPPQPGSTTFWAWSVLRVPAPPSPQPATYTCVVSHEDSRTLLNA SRSLEVSYVTDH | IgD-hinge-Fc Homo sapiens |
| 6 | LEGGGEGRGSLLTCGDVEENPGPR | T2A artificial |
| 7 | MLLLVTSLLLCELPHPAFLLIPRKVCNGIGIGEFKDSLSINATNIKHFKNCTSI SGDLHILPVAFRGDSFTHTPPLDPQELDILKTVKEITGFLLIQAWPENRTDLHA FENLEIIRGRTKQHGQFSLAVVSLNITSLGLRSLKEISDGDVIISGNKNLCYAN TINWKKLFGTSGQKTKIISNRGENSCKATGQVCHALCSPEGCWGPEPRDCVSCR NVSRGRECVDKCNLLEGEPREFVENSECIQCHPECLPQAMNITCTGRGPDNCIQ | tEGFR artificial |

| SEQ ID NO. | SEQUENCE | DESCRIPTION |
|---|---|---|
| | CAHYIDGPHCVKTCPAGVMGENNTLVWKYADAGHVCHLCHPNCTYGCTGPGLEG CPTNGPKIPSIATGMVGALLLLLVVALGIGLFM | |
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKPFWVLVVVGGVLACYS LLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR | CD3 zeta *Homo sapiens* |
| 14 | RVKFSRSAEPPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR | CD3 zeta *Homo sapiens* |
| 15 | RVKFSRSADAPAYKQGQNQLYNELNLGRREEYDVLDKRRGRDpEmGGKpRRKNP QEGLYNELQKDKMAEAYSEIGMKGERRRGKGHDGLYQGLSTATKDTYDALHMQA LPPR | CD3 zeta *Homo sapiens* |
| 16 | RKVCNGIGIGEFKDSLSINATNIKHFKNCTSISGDLHILPVAFRGDSFTHTPPL DPQELDILKTVKEITGFLLIQAWPENRTDLHAFENLEIIRGRTKQHGQFSLAVV SLNITSLGLRSLKEISDGDVIISGNKNLCYANTINWKKLFGTSGQKTKIISNRG ENSCKATGQVCHALCSPEGCWGPEPRDCVSCRNVSRGRECVDKCNLLEGEPREF VENSECIQCHPECLPQAMNITCTGRGPDNCIQCAHYIDGPHCVKTCPAGVMGEN NTLVWKYADAGHVCHLCHPNCTYGCTGPGLEGCPTNGPKIPSIATGMVGALLLL LVVALGIGLFM | tEGFR artificial |
| 17 | EGRGSLLTCGDVEENPGP | T2A artificial |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | PGGG-(SGGGG)5-P- wherein P is proline, G is glycine and S is serine | linker |
| 23 | GSADDAKKDAAKKDGKS | Linker |
| 24 | GSTSGSGKPGSGEGSTKG | Linker |
| 25 | gacatccagatgacccagaccacctccagcctgagcgccagcctgggcgaccgg gtgaccatcagctgccgggccagccaggacatcagcaagtacctgaactggtat cagcagaagcccgacggcaccgtcaagctgctgatctaccacaccagccggctg cacagcggcgtgcccagccggtttagcggcagcggctccggcaccgactacagc ctgaccatctccaacctggaacaggaagatatcgccacctacttttgccagcag ggcaacacactgcccctacacctttggcggcggaacaaagctggaaatcaccggc agcacctccggcagcggcaagcctggcagcggcgagggcagcaccaagggcgag gtgaagctgcaggaaagcggccctggcctggtggcccccagccagagcctgagc gtgacctgcaccgtgagcggcgtgagcctgcccgactacggcgtgagctggatc | Sequence encoding scFv |

| SEQ ID NO. | SEQUENCE | DESCRIPTION |
|---|---|---|
| | cggcagcccccaggaagggcctggaatggctgggcgtgatctggggcagcgag accacctactacaacagcgccctgaagagccggctgaccatcatcaaggacaac agcaagagccaggtgttcctgaagatgaacagcctgcagaccgacgacaccgcc atctactactgcgccaagcactactactacggcggcagctacgccatggactac tggggccagggcaccagcgtgaccgtgagcagc | |
| 26 | x₁PPx₂P<br>x₁ is glycine, cysteine or arginine<br>X₂ is cysteine or threonine | Hinge |
| 27 | Glu Pro Lys Ser Cys Asp Lys Thr His Thr Cys Pro Pro Cys Pro | Hinge |
| 28 | Glu Arg Lys Cys Cys Val Glu Cys Pro Pro Cys Pro | Hinge |
| 29 | ELKTPLGDTHTCPRCPEPKSCDTPPPCPRCPEPKSCDTPPPCPRCPEPKSCDTP PPCPRCP | Hinge |
| 30 | Glu Ser Lys Tyr Gly Pro Pro Cys Pro Ser Cys Pro | Hinge |
| 31 | Glu Ser Lys Tyr Gly Pro Pro Cys Pro Pro Cys Pro | Hinge |
| 32 | Tyr Gly Pro Pro Cys Pro Pro Cys Pro | Hinge |
| 33 | Lys Tyr Gly Pro Pro Cys Pro Pro Cys Pro | Hinge |
| 34 | Glu Val Val Lys Tyr Gly Pro Pro Cys Pro Pro Cys Pro | Hinge |
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLEWLGVIWGS ETTYYNSALKSRTLIIKDNSKSQVFLKMNSLQTDDTAIYYCAKHYYYGGSYAMD YWGQGTSVTVSS | FMC63 VH |
| 42 | DIQMTQTTSSLSASLGDRVTISCRASQDISKYLNWYQQKPDGTVKLLIYHTSRL HSGVPSRFSGSGSGTDYSLTISNLEQEDIATYFCQQGNTLPYTFGGGTKLEIT | FMC63 VL |
| 43 | DIQMTQTTSSLSASLGDRVTISCRASQDISKYLNWYQQKPDGTVKLLIYHTSRL HSGVPSRFSGSGSGTDYSLTISNLEQEDIATYFCQQGNTLPYTFGGGTKLEITG STSGSGKPGSGEGSTKGEVKLQESGPGLVAPSQSLSVTCTVSGVSLPDYGVSWI RQPPRKGLEWLGVIWGSETTYYNSALKSRLTIIKDNSKSQVFLKMNSLQTDDTA IYYCAKHYYYGGSYAMDYWGQGTSVTVSS | FMC63 scFv |
| 44 | KASQNVGTNVA | SJ25C1 CDR L1 |
| 45 | SATYRNS | SJ25C1 CDR L2 |
| 46 | QQYNRYPYT | SJ25C1 CDR L3 |
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLEWIGQIYPG DGDTNYNGKFKGQATLTADKSSSTAYMQLSGLTSEDSAVYFCARKTISSVVDFY FDYWGQGTTVTVSS | SJ25C1 VH |
| 51 | DIELTQSPKFMSTSVGDRVSVTCKASQNVGTNVAWYQQKPGQSPKPLIYSATYR NSGVPDRFTGSGSGTDFTLTITNVQSKDLADYFCQQYNRYPYTSGGGTKLEIKR | SJ25C1 VL |
| 52 | GGGGSGGGGSGGGGS | Linker |

-continued

| SEQ ID NO. | SEQUENCE | DESCRIPTION |
|---|---|---|
| 53 | EVKLQQSGAELVRPGSSVKISCKASGYAFSSYWMNWVKQRPGQGLEWIGQIYPG DGDTNYNGKFKGQATLTADKSSSTAYMQLSGLTSEDSAVYFCARKTISSVVDFY FDYWGQGTTVTVSSGGGGSGGGGSGGGGSDIELTQSPKFMSTSVGDRVSVTCKA SQNVGTNVAWYQQKPGQSPKPLIYSATYRNSGVPDRFTGSGSGTDFTLTITNVQ SKDLADYFCQQYNRYPYTSGGGTKLEIKR | SJ25C1 scFv |
| 54 | HYYYGGSYAMDY | FMC63 HC-CDR3 |
| 55 | HTSRLHS | FMC63 LC-CDR2 |
| 56 | QQGNTLPYT | FMC63 LC-CDR3 |
| 57 | ACACGGCCTCGTGTATTACTGT | IGH primer |
| 58 | ACCTGAGGAGACGGTGACC | IGH Primer |

The invention claimed is:

1. A method of treating a subject having or suspected of having a cancer, the method comprising administering to the subject a dose of CD4$^+$ and CD8$^+$ T cells, each of the CD4$^+$ and the CD8$^+$ T cells, individually, comprising a recombinant receptor that specifically binds to a target antigen expressed by the cancer or a cell or tissue thereof and/or that is associated with the cancer, wherein the administration comprises administering a plurality of separate compositions, the plurality of separate compositions comprising a first composition comprising one of the CD4$^+$ T cells and the CD8$^+$ T cells and a second composition comprising the other of the CD4$^+$ T cells and the CD8$^+$ T cells.

2. The method of claim 1, wherein the recombinant receptor comprised by the CD4$^+$ T cells and the recombinant receptor comprised by the CD8$^+$ T cells comprises a recombinant receptor that is the same.

3. The method of claim 1, wherein
   the administration of the first composition and the administration of the second composition are carried out on the same day.

4. The method of claim 1, wherein the first composition and the second composition are administered no more than 2 hours apart.

5. The method of claim 1, wherein the first composition comprises the CD4$^+$ T cells.

6. The method of claim 1, wherein the first composition comprises the CD8$^+$ T cells.

7. The method of claim 1, wherein the initiation of the administration of the first composition is carried out prior to the initiation of the administration of the second composition.

8. The method of claim 1, wherein the dose of CD4$^+$ and CD8$^+$ T cells comprises a defined ratio of CD4$^+$ cells expressing the recombinant receptor to CD8$^+$ cells expressing the recombinant receptor, which is between approximately 1:3 and approximately 3:1.

9. The method of claim 8, wherein the defined ratio is approximately 1:1.

10. The method of claim 1, wherein the dose of CD4$^+$ and CD8$^+$ T cells comprises between at or about 1×10$^7$ and at or about 2×10$^8$ total recombinant receptor-expressing T cells, inclusive.

11. The method of claim 1, wherein the disease or condition is a B cell malignancy.

12. The method of claim 1, wherein the recombinant receptor is a chimeric antigen receptor (CAR).

13. The method of claim 2, wherein the dose of T cells comprises a defined ratio of CD4$^+$ cells expressing the recombinant receptor to CD8$^+$ cells expressing the recombinant receptor, which is between approximately 1:3 and approximately 3:1.

14. The method of claim 3, wherein the dose of T cells comprises a defined ratio of CD4$^+$ cells expressing the recombinant receptor to CD8$^+$ cells expressing the recombinant receptor, which is between approximately 1:3 and approximately 3:1.

15. The method of claim 1, wherein the subject is or has been identified as having an ECOG status of 0 or 1.

16. The method of claim 1, wherein the dose of T cells comprises between at or about 5×10$^7$ recombinant receptor-expressing T cells and 1.5×10$^8$ recombinant receptor-expressing T cells, inclusive, said dose comprising a defined ratio of CD4$^+$ cells expressing the recombinant receptor to CD8$^+$ cells expressing the recombinant receptor, which is approximately 1:1.

17. The method of claim 1, wherein
   at or prior to administration of the dose of cells, the subject is or has been identified as having a lymphoma associated with or involving central nervous system (CNS) involvement.

18. The method of claim 2, wherein the cancer is a B cell malignancy.

19. The method of claim 1, wherein the cancer is a non-Hodgkin lymphoma (NHL).

20. The method of claim 1, wherein prior to initiation of administration of the dose of cells, the subject has not been administered an agent or treatment capable of treating, preventing, delaying, reducing or attenuating the development or risk of development of a toxicity following administration of the dose of cells.

21. The method of claim 1, wherein:
   the administration and any follow up is carried out on an outpatient basis or without requiring admission to or an overnight stay at a hospital; and
   if the subject exhibits a sustained fever or a fever that is or has not been reduced by more than 1° C. after treatment with an antipyretic, the subject is admitted to a hospital or to an overnight stay at a hospital, or is administered an agent or treatment for the treatment, prevention, reduction or attenuation of a neurotoxicity or a cytokine release syndrome or risk thereof.

22. The method of claim 19, wherein the NHL is aggressive NHL.

23. The method of claim 19, wherein, at or immediately prior to the time of the administration of the dose of cells the subject has relapsed following remission after treatment with, or become refractory to, one or more prior therapies for the NHL.

24. The method of claim 1, wherein, at or prior to the administration of the dose of cells:
   the subject is or has been identified as having a double/triple hit lymphoma;
   the subject is or has been identified as having a chemorefractory lymphoma;
   the subject has not achieved complete remission (CR) in response to a prior therapy; or the subject has relapsed within 1 year or less than 1 year after receiving an autologous stem cell transplant (ASCT).

25. The method of claim 12, wherein
the CAR comprises an scFv specific for CD19, a transmembrane domain, a cytoplasmic signaling domain derived from a costimulatory molecule, a cytoplasmic signaling domain that comprises a CD3zeta signaling domain, and a spacer between the transmembrane domain and the scFv.

26. The method of claim 1, wherein, prior to the administration, the subject has been preconditioned with a lymphodepleting therapy comprising the administration of fludarabine, cyclophosphamide, or fludarabine and cyclophosphamide.

27. The method of claim 2, wherein
the first composition and second composition are administered 0 to 12 hours apart.

28. The method of claim 2, wherein the first composition and second composition are administered no more than 2 hours apart.

29. The method of claim 6, wherein the first composition is administered prior to the second composition.

30. The method of claim 2, wherein the first composition comprises the $CD8^+$ T cells.

31. The method of claim 30, wherein the first composition is administered prior to the second composition.

32. The method of claim 25, wherein the costimulatory molecule is or comprises a 4-1BB.

33. The method of claim 25, wherein the spacer consists of all or a portion of an immunoglobulin hinge and is 15 amino acids or fewer in length.

34. The method of claim 33, wherein the spacer is at or about 12 amino acids in length.

35. The method of claim 25, wherein the spacer consists of the sequence of SEQ ID NO: 1.

36. The method of claim 25, wherein the scFv comprises a CDRL1 sequence of RASQDISKYLN (SEQ ID NO: 35), a CDRL2 sequence of SRLHSGV (SEQ ID NO: 36), a CDRL3 sequence of GNTLPYTFG (SEQ ID NO: 37); a CDRH1 sequence of DYGVS (SEQ ID NO: 38), a CDRH2 sequence of VIWGSETTYYNSALKS (SEQ ID NO: 39), and a CDRH3 sequence of YAMDYWG (SEQ ID NO: 40).

37. The method of claim 25, wherein the scFv comprises the $V_H$ sequence set forth in SEQ ID NO:41 and the $V_L$ sequence set forth in SEQ ID NO:32.

38. The method of claim 25, wherein the scFv comprises the sequence set forth in SEQ ID NO:43.

39. The method of claim 1, wherein the dose of $CD4^+$ and $CD8^+$ T cells comprises between at or about $5 \times 10^7$ and at or about $1 \times 10^8$ total recombinant receptor-expressing T cells, inclusive.

40. The method of claim 1, wherein the T cells are autologous to the subject.

41. The method of claim 3, wherein the T cells are autologous to the subject.

42. The method of claim 1, wherein the subject is or has been identified as having an ECOG status of 0-2.

43. The method of claim 1, wherein the cancer is diffuse large B cell lymphoma (DLBCL).

44. The method of claim 3, wherein the cancer is diffuse large B cell lymphoma (DLBCL).

45. The method of claim 32, wherein the scFv comprises a CDRL1 sequence of RASQDISKYLN (SEQ ID NO: 35), a CDRL2 sequence of SRLHSGV (SEQ ID NO: 36), a CDRL3 sequence of GNTLPYTFG (SEQ ID NO: 37); a CDRH1 sequence of DYGVS (SEQ ID NO: 38), a CDRH2 sequence of VIWGSETTYYNSALKS (SEQ ID NO: 39), and a CDRH3 sequence of YAMDYWG (SEQ ID NO: 40).

46. The method of claim 32, wherein the scFv comprises the $V_H$ sequence set forth in SEQ ID NO:41 and the $V_L$ sequence set forth in SEQ ID NO:32.

47. The method of claim 32, wherein the scFv comprises the sequence set forth in SEQ ID NO:43.

48. The method of claim 1, wherein the target antigen is CD19.

49. The method of claim 2, wherein the target antigen is CD19.

50. The method of claim 2, wherein the recombinant receptor is a chimeric antigen receptor (CAR).

51. The method of claim 19, wherein the NHL is diffuse large B cell lymphoma (DLBCL).

52. The method of claim 19, wherein the NHL is NOS (de novo and transformed from indolent).

53. The method of claim 19, wherein the NHL is primary mediastinal large B cell lymphoma (PMBCL).

54. The method of claim 19, wherein the NHL is mantle cell lymphoma (MCL).

55. The method of claim 19, wherein the NHL is follicular lymphoma (FL).

* * * * *

UNITED STATES PATENT AND TRADEMARK OFFICE
CERTIFICATE OF CORRECTION

| | | |
|---|---|---|
| PATENT NO. | : 11,413,310 B2 | Page 1 of 1 |
| APPLICATION NO. | : 16/616938 | |
| DATED | : August 16, 2022 | |
| INVENTOR(S) | : Albertson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 248 days.

Signed and Sealed this
Twenty-first Day of January, 2025

Coke Morgan Stewart
*Acting Director of the United States Patent and Trademark Office*

SEQUENCE LISTING

<160> NUMBER OF SEQ ID NOS: 58

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge)

<400> SEQUENCE: 2
gaatctaagt acggaccgcc ctgcccccct tgccct                          36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

```
Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30
```

Thr Thr Arg Asn Thr Gly Arg Gly Gly Glu Lys Lys Glu Lys
    35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly

```
            20                  25                  30
Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
 50                  55                  60

Phe Arg Gly Asp Ser Phe Thr His Thr Pro Pro Leu Asp Pro Gln Glu
 65                  70                  75                  80

Leu Asp Ile Leu Lys Thr Val Lys Glu Ile Thr Gly Phe Leu Leu Ile
                 85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
            210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
            355

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 8

Phe Trp Val Leu Val Val Val Gly Gly Val Leu Ala Cys Tyr Ser Leu
```

```
                1               5                  10                 15
Leu Val Thr Val Ala Phe Ile Ile Phe Trp Val
                    20                  25
```

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 9

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val
65
```

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 10

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 12
<211> LENGTH: 42
<212> TYPE: PRT
<213> ORGANISM: Homo sapiens

```
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205
```

-continued

```
Leu Glu Gly Glu Pro Arg Glu Phe Val Glu Asn Ser Glu Cys Ile Gln
    210                 215                 220
Cys His Pro Glu Cys Leu Pro Gln Ala Met Asn Ile Thr Cys Thr Gly
225                 230                 235                 240
Arg Gly Pro Asp Asn Cys Ile Gln Cys Ala His Tyr Ile Asp Gly Pro
                245                 250                 255
His Cys Val Lys Thr Cys Pro Ala Gly Val Met Gly Glu Asn Asn Thr
            260                 265                 270
Leu Val Trp Lys Tyr Ala Asp Ala Gly His Val Cys His Leu Cys His
        275                 280                 285
Pro Asn Cys Thr Tyr Gly Cys Thr Gly Pro Gly Leu Glu Gly Cys Pro
    290                 295                 300
Thr Asn Gly Pro Lys Ile Pro Ser Ile Ala Thr Gly Met Val Gly Ala
305                 310                 315                 320
Leu Leu Leu Leu Leu Val Val Ala Leu Gly Ile Gly Leu Phe Met
                325                 330                 335

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15
Gly Pro

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15
Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15
Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A
```

```
<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 22
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly
1               5

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 18
<212> TYPE: PRT
<213> ORGANISM: Artificial Sequence
<220> FEATURE:
<223> OTHER INFORMATION: Linker

<400> SEQUENCE: 24

Gly Ser Thr Ser Gly Ser Gly Lys Pro Gly Ser Gly Glu Gly Ser Thr
1               5                   10                  15

Lys Gly

<210> SEQ ID NO 25
<211> LENGTH: 735
<212> TYPE: DNA
<213> ORGANISM: Artificial Sequence
<220> FEATURE:
<223> OTHER INFORMATION: scFv
```

<400> SEQUENCE: 25

```
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctggaacag   240
gaagatatcg ccacctactt ttgccagcag ggcaacacac tgccctacac ctttggcggc   300
ggaacaaagc tggaaatcac cggcagcacc tccggcagcg gcaagcctgg cagcggcgag   360
ggcagcacca agggcgaggt gaagctgcag gaaagcggcc ctggcctggt ggcccccagc   420
cagagcctga gcgtgacctg caccgtgagc ggcgtgagcc tgcccgacta cggcgtgagc   480
tggatccggc agccccccag gaagggcctg aatggctggg cgtgatctg ggcagcgag   540
accacctact acaacagcgc cctgaagagc cggctgacca tcatcaagga caacagcaag   600
agccaggtgt tcctgaagat gaacagcctg cagaccgacg acaccgccat ctactactgc   660
gccaagcact actactacgg cggcagctac gccatggact actggggcca ggcaccagc   720
gtgaccgtga gcagc                                                    735
```

<210> SEQ ID NO 26
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: (1)...(1)
<223> OTHER INFORMATION: Xaa1 = glycine, cysteine or arginine
<220> FEATURE:
<221> NAME/KEY: VARIANT
<222> LOCATION: (4)...(4)
<223> OTHER INFORMATION: Xaa4 = cysteine or threonine

<400> SEQUENCE: 26

```
Xaa Pro Pro Xaa Pro
 1               5
```

<210> SEQ ID NO 27
<211> LENGTH: 15
<212> TYPE: PRT
<213> ORGANISM: Artificial Sequence
<220> FEATURE:
<223> OTHER INFORMATION: Hinge

<400> SEQUENCE: 27

```
Glu Pro Lys Ser Cys Asp Lys Thr His Thr Cys Pro Pro Cys Pro
 1               5                  10                  15
```

<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

```
Glu Arg Lys Cys Cys Val Glu Cys Pro Pro Cys Pro
 1               5                  10
```

<210> SEQ ID NO 29
<211> LENGTH: 61
<212> TYPE: PRT

<213> ORGANISM: Artificial Sequence
<220> FEATURE:
<223> OTHER INFORMATION: Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Ser Cys Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Hinge

<400> SEQUENCE: 31

Glu Ser Lys Tyr Gly Pro Pro Cys Pro Pro Cys Pro
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Hinge

<400> SEQUENCE: 32

Tyr Gly Pro Pro Cys Pro Pro Cys Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Hinge

<400> SEQUENCE: 33

Lys Tyr Gly Pro Pro Cys Pro Pro Cys Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

```
Glu Val Val Lys Tyr Gly Pro Pro Cys Pro Pro Cys Pro
1               5                   10
```

<210> SEQ ID NO 35
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 35

```
Arg Ala Ser Gln Asp Ile Ser Lys Tyr Leu Asn
1               5                   10
```

<210> SEQ ID NO 36
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 36

```
Ser Arg Leu His Ser Gly Val
1               5
```

<210> SEQ ID NO 37
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 37

```
Gly Asn Thr Leu Pro Tyr Thr Phe Gly
1               5
```

<210> SEQ ID NO 38
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 38

```
Asp Tyr Gly Val Ser
1               5
```

<210> SEQ ID NO 39
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 39

```
Val Ile Trp Gly Ser Glu Thr Thr Tyr Tyr Asn Ser Ala Leu Lys Ser
1               5                   10                  15
```

<210> SEQ ID NO 40
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 40

Tyr Ala Met Asp Tyr Trp Gly
1               5

<210> SEQ ID NO 41
<211> LENGTH: 120
<212> TYPE: PRT
<213> ORGANISM: Artificial Sequence
<220> FEATURE:
<223> OTHER INFORMATION: FMC63 VH

<400> SEQUENCE: 41

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: FMC63 VL

<400> SEQUENCE: 42

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 43
<211> LENGTH: 245
<212> TYPE: PRT
<213> ORGANISM: Artificial Sequence
<220> FEATURE:
<223> OTHER INFORMATION: FMC63 scFv

<400> SEQUENCE: 43

Asp Ile Gln Met Thr Gln Thr Thr Ser Ser Leu Ser Ala Ser Leu Gly

```
                1               5                    10                   15
            Asp Arg Val Thr Ile Ser Cys Arg Ala Ser Gln Asp Ile Ser Lys Tyr
                            20                  25                  30

Leu Asn Trp Tyr Gln Gln Lys Pro Asp Gly Thr Val Lys Leu Leu Ile
                        35                  40                  45

Tyr His Thr Ser Arg Leu His Ser Gly Val Pro Ser Arg Phe Ser Gly
                        50                  55                  60

Ser Gly Ser Gly Thr Asp Tyr Ser Leu Thr Ile Ser Asn Leu Glu Gln
            65                  70                  75                  80

Glu Asp Ile Ala Thr Tyr Phe Cys Gln Gln Gly Asn Thr Leu Pro Tyr
                            85                  90                  95

Thr Phe Gly Gly Gly Thr Lys Leu Glu Ile Thr Gly Ser Thr Ser Gly
                            100                 105                 110

Ser Gly Lys Pro Gly Ser Gly Glu Gly Ser Thr Lys Gly Glu Val Lys
                        115                 120                 125

Leu Gln Glu Ser Gly Pro Gly Leu Val Ala Pro Ser Gln Ser Leu Ser
                        130                 135                 140

Val Thr Cys Thr Val Ser Gly Val Ser Leu Pro Asp Tyr Gly Val Ser
            145                 150                 155                 160

Trp Ile Arg Gln Pro Pro Arg Lys Gly Leu Glu Trp Leu Gly Val Ile
                            165                 170                 175

Trp Gly Ser Glu Thr Thr Tyr Tyr Asn Ser Ala Leu Lys Ser Arg Leu
                            180                 185                 190

Thr Ile Ile Lys Asp Asn Ser Lys Ser Gln Val Phe Leu Lys Met Asn
                        195                 200                 205

Ser Leu Gln Thr Asp Asp Thr Ala Ile Tyr Tyr Cys Ala Lys His Tyr
                        210                 215                 220

Tyr Tyr Gly Gly Ser Tyr Ala Met Asp Tyr Trp Gly Gln Gly Thr Ser
            225                 230                 235                 240

Val Thr Val Ser Ser
                            245

<210> SEQ ID NO 44
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 44

Lys Ala Ser Gln Asn Val Gly Thr Asn Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 45

Ser Ala Thr Tyr Arg Asn Ser
1               5

<210> SEQ ID NO 46
<211> LENGTH: 9
<212> TYPE: PRT
<213> ORGANISM: Artificial Sequence
<220> FEATURE:
```

<223> OTHER INFORMATION: SJ25C1 CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 50

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120

<210> SEQ ID NO 51
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Ser Gly Gly Gly Gly Ser
1               5                   10                  15

<210> SEQ ID NO 53
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly

```
                115                 120                 125
Gly Gly Gly Ser Gly Gly Gly Ser Asp Ile Glu Leu Thr Gln Ser
            130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245
```

<210> SEQ ID NO 54
<211> LENGTH: 12
<212> TYPE: PRT
<213> ORGANISM: Artificial Sequence
<220> FEATURE:
<223> OTHER INFORMATION: FMC63 CDR H3

<400> SEQUENCE: 54

```
His Tyr Tyr Tyr Gly Gly Ser Tyr Ala Met Asp Tyr
1               5                   10
```

<210> SEQ ID NO 55
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 55

```
His Thr Ser Arg Leu His Ser
1               5
```

<210> SEQ ID NO 56
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 56

```
Gln Gln Gly Asn Thr Leu Pro Tyr Thr
1               5
```

<210> SEQ ID NO 57
<211> LENGTH: 22
<212> TYPE: DNA
<213> ORGANISM: Artificial Sequence
<220> FEATURE:
<223> OTHER INFORMATION: IGH primer

<400> SEQUENCE: 57
acacggcctc gtgtattact gt                                          22

<210> SEQ ID NO 58

```
<211> LENGTH: 19
<212> TYPE: DNA
<213> ORGANISM: Artificial Sequence
<220> FEATURE:
<223> OTHER INFORMATION: IGH primer

<400> SEQUENCE: 58
acctgaggag acggtgacc                                                    19
```